United States Patent
Wigley et al.

(10) Patent No.: US 11,102,981 B2
(45) Date of Patent: Aug. 31, 2021

(54) AGRICULTURALLY BENEFICIAL MICROBES, MICROBIAL COMPOSITIONS, AND CONSORTIA

(71) Applicant: BIOCONSORTIA, INC., Davis, CA (US)

(72) Inventors: Peter Wigley, Parnell Auckland (NZ); Susan Turner, Davis, CA (US); Caroline George, Meadowbank Auckland (NZ); Damian Wright, Greenlane Auckland (NZ); Thomas Williams, Woodland, CA (US); Kelly Roberts, Davis, CA (US); Graham Hymus, Davis, CA (US)

(73) Assignee: BioConsortia, Inc., Davis, CA (US)

( * ) Notice: Subject to any disclaimer, the term of this patent is extended or adjusted under 35 U.S.C. 154(b) by 422 days.

(21) Appl. No.: 15/747,721

(22) PCT Filed: Jul. 25, 2016

(86) PCT No.: PCT/US2016/043933
§ 371 (c)(1),
(2) Date: Jan. 25, 2018

(87) PCT Pub. No.: WO2017/019633
PCT Pub. Date: Feb. 2, 2017

(65) Prior Publication Data
US 2019/0382714 A1    Dec. 19, 2019

Related U.S. Application Data

(60) Provisional application No. 62/196,951, filed on Jul. 25, 2015.

(51) Int. Cl.
| | | |
|---|---|---|
| *A01N 63/20* | (2020.01) |
| *C12N 1/20* | (2006.01) |
| *C12R 1/06* | (2006.01) |
| *C12R 1/38* | (2006.01) |
| *A01N 63/22* | (2020.01) |
| *A01N 63/25* | (2020.01) |
| *A01N 63/27* | (2020.01) |

(52) U.S. Cl.
CPC ............ *A01N 63/20* (2020.01); *A01N 63/22* (2020.01); *A01N 63/25* (2020.01); *A01N 63/27* (2020.01); *C12N 1/20* (2013.01); *C12R 1/06* (2013.01); *C12R 1/38* (2013.01)

(58) Field of Classification Search
CPC .......... C12N 1/20; A01N 63/20; A01N 63/22; A01N 63/25; A01N 63/27; C12R 1/06; C12R 1/38; C12R 1/01
See application file for complete search history.

(56) References Cited

U.S. PATENT DOCUMENTS

| | | | |
|---|---|---|---|
| 9,150,851 B2 * | 10/2015 | Wigley | A01N 63/00 |
| 10,602,744 B2 * | 3/2020 | Wigley | C12N 1/20 |
| 2012/0129794 A1 | 5/2012 | Dowd et al. | |
| 2014/0082770 A1 * | 3/2014 | Wigley | A01H 3/00 |
| | | | 800/298 |

FOREIGN PATENT DOCUMENTS

WO    WO-2014046553 A1 *    3/2014    ............. A01N 63/00

OTHER PUBLICATIONS

Li, A et al. Frigidibacter albus gen. nov., sp. nov., a novel member of the family Rhodobacteraceae isolated from lake water. International Journal of Systematic and Evolutionary Microbiology. 2015. 65: 1199-1206. Epub. Jan. 21, 2015. (Year: 2015).*

Bergottini, VM et al. Bio-inoculation of yerba mate seedlings (Ilex paraguariensis St. Hill.) with native plant growth-promoting rhizobacteria: a sustainable alternative to improve crop yield. Biol. Fertil. Soils. 2015. 51: 749-755. Published online Apr. 9, 2015. (Year: 2015).*

Ramirez-Bahena, M et al. Pseudomonas helmanticensis sp. nov., isolated from forest soil. International Journal of Systematic and Evolutionary Microbiology. 2014. 64: 2338-2345. Published Jul. 1, 2014. (Year: 2014).*

Ali, A et al. Characterization of plant growth promoting rhizobacteria isolated from chickpea (*Cicer arietinum*). British Microbiology Research Journal. 2015. 6(1): 32-40. Published Dec. 15, 2014. (Year: 2014).*

International Search Report and Written Opinion for corresponding International Application No. PCT/US2016/043933, dated Jan. 26, 2017 (14 pages).

Yu, X., et al.,Genbank accession FJ455451, published online Dec. 10, 2008, retrieved Jan. 30, 2018 from https://www.ncbi.nlm.nih.gov/nuccore/FJ455451 (1 page).

* cited by examiner

*Primary Examiner* — David W Berke-Schlessel
*Assistant Examiner* — Susan E. Fernandez
(74) *Attorney, Agent, or Firm* — Barnes & Thornburg LLP; Ryan L. Marshall

(57) ABSTRACT

The disclosure relates to isolated microorganisms—including novel strains of the microorganisms-microbial consortia, and agricultural compositions comprising the same. Furthermore, the disclosure teaches methods of utilizing the described microorganisms, microbial consortia, and agricultural compositions comprising the same, in methods for imparting beneficial properties to target plant species. In particular aspects, the disclosure provides methods of increasing desirable plant traits in agronomically important crop species.

7 Claims, 21 Drawing Sheets
Specification includes a Sequence Listing.

SEQUENCE LISTING

```
<160> NUMBER OF SEQ ID NOS: 307

<210> SEQ ID NO 1
<211> LENGTH: 848
<212> TYPE: DNA
<213> ORGANISM: Chryseobacterium daecheongense
<220> FEATURE:
<221> NAME/KEY: misc_feature
<222> LOCATION: (1)..(848)
<223> OTHER INFORMATION: BCI 45 16S rDNA
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t

<400> SEQUENCE: 1
```
cggtcaccga cttcaggtac cnccagactt ccatggcttg acgggcggtg tgtacaaggc    60
ccgggaacgt attcaccgcg ccatggctga tgcgcgatta ctagcgattc cagcttcata   120
gagtcgagtt gcagactcca atccgaactg agaccggctt tcgagatttg catcacatcg   180
ctgtgtagct gccctctgta ccggccattg tattacgtgt gtggcccaag cgtaagggc   240 cgtgatgatt tgacgtcatc cccaccttcc tctctacttg cgtaggcagt ctcactagag   300
tccccaactg aatgatggca actagtgaca ggggttgcgc tcgttgcagg acttaaccta   360
acacctcacg gcacgagctg acgacaacca tgcagcacct tgaaaattgc ccgaaggaag   420
gtctatttct aaaccgatca attcccattt aagccttggt aaggttcctc gcgtatcatc   480
gaattaaacc acataatcca ccgcttgtgc gggccccgt caattccttt gagtttcatt   540
cttgcgaacg tactcccag gtggctaact tatcactttc gcttagtctc tgaacccgaa   600
agcccaaaaa cgagttagca tcgtttacgg cgtggactac cagggtatct aatcctgttc   660
gctccccacg ctttcgtcca tcagcgtcag ttaanacata ntaacctgcc ttcgcaattg   720
gtgttctaag taatatctat gcatttcacc gctacactac ttattccagc tacttctacc   780
ttactcaana cctgcagtat cantggnagt gtcacagtta aactgtgaga tttcgccact   840
gacttaca                                                            848

<210> SEQ ID NO 2
<211> LENGTH: 748
<212> TYPE: DNA
<213> ORGANISM: Chryseobacterium daecheongense
<220> FEATURE:
<221> NAME/KEY: misc_feature
<222> LOCATION: (1)..(748)
<223> OTHER INFORMATION: BCI 191 16S rDNA
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t

```
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t

<400> SEQUENCE: 2
ggtacccnag acttcnntgg cttgacgggc ggtgtgtaca aggcccgggn acgtattcac      60
cgcgccatgg ctgatgcgcg attactagcg attccagctt catagagtcg agttgcagac     120
tccaatccga actgagaccg gctttcgaga tttgcatcac atcgctgtgt agctgccctc     180
tgtaccggcc attgtattac gtgtgtggcc caaggcgtaa gggccgtgat gatttgacgt     240
catccccacc ttcctctcta cttgcgtagg cagtctcact agagtcccca acttaatgat     300
ggcaactagt gacaggggtt gcgctcgttg caggacttaa cctaacacct cacggcacga     360
gctgacgaca accatgcagc accttgaaaa ttgcccgaag gaaggtctat ttctaaaccg     420
atcaattccc atttaagcct tggtaaggtt cctcgcgtat catcgaatta aaccacataa     480
tccaccgctt gtgcgggccc ccgtcaattc ctttgagttt caaacttgcg ttcgtactcc     540
ccaggtggct aacttatcac tttcgcttag tctctgaatc cgaaaaccca aaaacgagtt     600
agcatcgttt acagcgtgga ntaccagngt atctaatcct gttcgctccc cacgctttcg     660
tccntcagcg tcagttaana catagtaacc tgccttcnca attgntgttc taagnantan     720
ctatgcnttt nancgctnca ctacttan                                       748

<210> SEQ ID NO 3
<211> LENGTH: 681
<212> TYPE: DNA
<213> ORGANISM: Chryseobacterium rhizosphaerae
<220> FEATURE:
<221> NAME/KEY: misc_feature
<222> LOCATION: (1)..(681)
<223> OTHER INFORMATION: BCI 597 16S rDNA

<400> SEQUENCE: 3
cgacttcagg tacccccagac ttccatggct tgacgggcgg tgtgtacaag gcccgggaac     60
gtattcaccg cgccatggct gatgcgcgat tactagcgat tccagcttca tagagtcgag    120
ttgcagactc caatccgaac tgagaccggc tttcgagatt tgcatcacat cgctgtgtag    180
ctgccctctg taccggccat tgtattacgt gtgtggccca aggcgtaagg ccgtgatga     240
tttgacgtca tccccacctt cctctctact tgcgtaggca gtctcactag agtccccaac    300
```

```
ttaatgatgg caactagtga caggggttgc gctcgttgca ggacttaacc taacacctca    360
cggcacgagc tgacgacaac catgcagcac cttgaaaaat gtccgaagaa aagtctattt    420
ctaaacctgt catttcccat ttaagccttg gtaaggttcc tcgcgtatca tcgaattaaa    480
ccacataatc caccgcttgt gcgggcccccc gtcaattcct ttgagtttca ttcttgcgaa    540
cgtactcccc aggtggctaa cttatcactt tcgcttagtc tctgaatccg aaaacccaaa    600
aacgagttag catcgtttac ggcgtggact accagggtat ctaatcctgt tcgctcccca    660
cgctttcgtc catcagcgtc a                                              681

<210> SEQ ID NO 4
<211> LENGTH: 799
<212> TYPE: DNA
<213> ORGANISM: Chryseobacterium rhizosphaerae
<220> FEATURE:
<221> NAME/KEY: misc_feature
<222> LOCATION: (1)..(799)
<223> OTHER INFORMATION: BCI 615 16S rDNA
<220> FEATURE:
<221> NAME/KEY: misc_feature
<222> LOCATION: (5)..(5)
<223> OTHER INFORMATION: n is a, c, g, or t

<400> SEQUENCE: 4
taggnggatc tgtaagtcag tggtgaaatc tcacagctta actgtgaaac tgccattgat     60
actgcaggtc ttgagtgttg ttgaagtagc tggaataagt agtgtagcgg tgaaatgcat    120
agatattact tagaacacca attgcgaagg caggttacta agcaacaact gacgctgatg    180
gacgaaagcg tggggagcga acaggattag ataccctggt agtccacgcc gtaaacgatg    240
ctaactcgtt tttgggtttt cggattcaga gactaagcga aagtgataag ttagccacct    300
ggggagtacg ttcgcaagaa tgaaactcaa aggaattgac gggggcccgc acaagcggtg    360
gattatgtgg tttaattcga tgatacgcga ggaaccttac caaggcttaa atgggaaatg    420
acaggtttag aaatagactt ttcttcggac atttttcaag gtgctgcatg gttgtcgtca    480
gctcgtgccg tgaggtgtta ggttaagtcc tgcaacgagc gcaacccctg tcactagttg    540
ccatcattaa gttggggact ctagtgagac tgcctacgca agtagagagg aaggtgggga    600
tgacgtcaaa tcatcacggc ccttacgcct tgggccacac acgtaataca atggccggta    660
cagagggcag ctacacagcg atgtgatgca aatctcgaaa gccggtctca gttcggattg    720
gagtctgcaa ctcgactcta tgaagctgga atcgctagta atcgcgcatc agccatggcg    780
cggtgaatac gttcccggg                                                 799

<210> SEQ ID NO 5
<211> LENGTH: 618
<212> TYPE: DNA
<213> ORGANISM: Frigidibacter albus
<220> FEATURE:
<221> NAME/KEY: misc_feature
<222> LOCATION: (1)..(618)
<223> OTHER INFORMATION: BCI 712 16S rDNA

<400> SEQUENCE: 5
gcaggttggc gcaccgcctt cgggtaaacc caactcccat ggtgtgacgg gcggtgtgta     60
caaggcccgg gaacgtattc accgcgtcat gctgttacgc gattactagc gattccgact    120
tcatggggtc gagttgcaga ccccaatccg aactgagaca gctttttggg attaacccat    180
tgtcactgcc attgtagcac gtgtgtagcc caacccgtaa gggccatgag gacttgacgt    240
catccacacc ttcctccgac ttatcatcgg cagtttccct agagtgccca actgaatgct    300
```

```
ggcaactaag gacgtgggtt gcgctcgttg ccggacttaa ccgaacatct cacgacacga    360
gctgacgaca gccatgcagc acctgtgtgg tatccagccg aactgaaaga tccatctctg    420
gatccgcgat acccatgtca agggttggta aggttctgcg cgttgcttcg aattaaacca    480
catgctccac cgcttgtgcg ggcccccgtc aattcctttg agttttaatc ttgcgaccgt    540
actccccagg cggaatgctt aatccgttag gtgtgacacc gacaagcatg cttgccgacg    600
tctggcattc atcgttta                                                  618
```

```
<210> SEQ ID NO 6
<211> LENGTH: 741
<212> TYPE: DNA
<213> ORGANISM: Frigidibacter albus
<220> FEATURE:
<221> NAME/KEY: misc_feature
<222> LOCATION: (1)..(741)
<223> OTHER INFORMATION: BCI 402 16S rDNA
<220> FEATURE:
<221> NAME/KEY: misc_feature
<222> LOCATION: (3)..(3)
<223> OTHER INFORMATION: n is a, c, g, or t

<400> SEQUENCE: 6
```

```
ctnggaactg cctttgatac tgctagtcta gagttcgaga gaggtgagtg gaattccgag     60
tgtagaggtg aaattcgtag atattcggag gaacaccagt ggcgaaggcg gctcactggc    120
tcgatactga cgctgaggtg cgaaagcgtg gggagcaaac aggattagat accctggtag    180
tccacgccgt aaacgatgaa tgccagacgt cggcaagcat gcttgtcggt gtcacaccta    240
acggattaag cattccgcct ggggagtacg gtcgcaagat taaaactcaa aggaattgac    300
gggggcccgc acaagcggtg gagcatgtgg tttaattcga agcaacgcgc agaaccttac    360 caaccttga catgggtatc gcggatccag agatggatct ttcagttcgg ctggatacca    420
cacaggtgct gcatggctgt cgtcagctcg tgtcgtgaga tgttcggtta agtccggcaa    480
cgagcgcaac ccacgtcctt agttgccagc attcagttgg gcactctagg gaaactgccg    540
atgataagtc ggaggaaggt gtggatgacg tcaagtcctc atggccctta cgggttgggc    600
tacacacgtg ctacaatggc agtgacaatg ggttaatccc aaaaagctgt ctcagttcgg    660
attggggtct gcaactcgac cccatgaagt cggaatcgct agtaatcgcg taacagcatg    720
acgcggtgaa tacgttcccg g                                              741
```

```
<210> SEQ ID NO 7
<211> LENGTH: 775
<212> TYPE: DNA
<213> ORGANISM: Frigidibacter albus
<220> FEATURE:
<221> NAME/KEY: misc_feature
<222> LOCATION: (1)..(775)
<223> OTHER INFORMATION: BCI 745 16S rDNA
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (111)..(111)
```

<223> OTHER INFORMATION: n is a, c, g, or t

<400> SEQUENCE: 7

```
attagtcagt cagaggtgaa nncccagggc tcaaccttgn aactnccttt gatactgcta      60
gtctagagtt cgagagaggt gagtggaatt ccgagtgtag aggtgaaatt ngtagatatt     120
cggaggaaca ccagtggcga aggcggctca ctggctcgat actgacgctg aggtgcgaaa     180
gcgtggggag caaacaggat tagatacccct ggtagtccac gccgtaaacg atgaatgcca    240
gacgtcggca agcatgcttg tcggtgtcac acctaacgga ttaagcattc cgcctgggga    300
gtacggtcgc aagattaaaa ctcaaaggaa ttgacggggg cccgcacaag cggtggagca    360
tgtggtttaa ttcgaagcaa cgcgcagaac cttaccaacc cttgacatgg gtatcgcgga   420
tccagagatg gatctttcag ttcggctgga taccacacag gtgctgcatg gctgtcgtca    480
gctcgtgtcg tgagatgttc ggttaagtcc ggcaacgagc gcaacccacg tccttagttg    540
ccagcattca gttgggcact ctagggaaac tgccgatgat aagtcggagg aaggtgtgga    600
tgacgtcaag tcctcatggc ccttacgggt tgggctacac acgtgctaca atggcagtga    660
caatgggtta atcccaaaaa gctgtctcag ttcggattgg ggtctgcaac tcgacccccat   720
gaagtcggaa tcgctagtaa tcgcgtaaca gcatgacgcg gtgaatacgt tcccg         775
```

<210> SEQ ID NO 8
<211> LENGTH: 800
<212> TYPE: DNA
<213> ORGANISM: Arthrobacter nicotinovorans
<220> FEATURE:
<221> NAME/KEY: misc_feature
<222> LOCATION: (1)..(800)
<223> OTHER INFORMATION: BCI 717 16S rDNA
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 8

```
gtttgtcgcn tctgctgtga aagaccgggg ctcaantccg gttctgcagt gggtacgggc     60
agactagagt gcagtagggg agactggaat tcctggtgta gcggtgaaat gcgcagatat    120
caggaggaac accgatggcg aaggcaggtc tctgggctgt aactgacgct gaggagcgaa    180
agcatgggga gcgaacagga ttagataccc tggtagtcca tgccgtaaac gttgggcact    240
aggtgtgggg gacattccac gttttccgcg ccgtagctaa cgcattaagt gccccgcctg    300
gggagtacgg ccgcaaggct aaaactcaaa ggaattgacg ggggcccgca caagcggcgg    360
agcatgcgga ttaattcgat gcaacgcgaa gaaccttacc aaggcttgac atgaaccgga    420
aagacctgga aacaggtgcc ccgcttgcgg tcggtttaca ggtggtgcat ggttgtcgtc    480
agctcgtgtc gtgagatgtt gggttaagtc ccgcaacgag cgcaaccctc gttctatgtt    540
gccagcggtt cggccgggga ctcataggag actgccgggg tcaactcgga ggaaggtggg    600
gacgacgtca atcatcatg cccttatgt cttgggcttc acgcatgcta caatggccgg      660
tacaaagggt tgcgatactg tgaggtggag ctaatcccaa aaagccggtc tcagttcgga    720
ttggggtctg caactcgacc ccatgaagtc ggagtcgcta gtaatcgcag atcagcaacg    780
ctgcggtgaa tacgttcccg                                                800
```

<210> SEQ ID NO 9
<211> LENGTH: 898
<212> TYPE: DNA
<213> ORGANISM: Arthrobacter nicotinovorans
<220> FEATURE:
<221> NAME/KEY: misc_feature
<222> LOCATION: (1)..(898)
<223> OTHER INFORMATION: BCI 3189 16S rDNA

<400> SEQUENCE: 9

```
cacaagggtt aggccaccgg cttcgggtgt taccaacttt cgtgacttga cgggcggtgt      60
gtacaaggcc cgggaacgta ttcaccgcag cgttgctgat ctgcgattac tagcgactcc     120
gacttcatgg ggtcgagttg cagaccccaa tccgaactga accggctttt tgggattag     180
ctccacctca cagtatcgca acccttgta ccggccattg tagcatgcgt gaagcccaag     240
acataagggg catgatgatt tgacgtcgtc cccaccttcc tccgagttga ccccggcagt     300
ctcctatgag tccccggccg aaccgctggc aacatagaac gagggttgcg ctcgttgcgg     360
gacttaaccc aacatctcac gacacgagct gacgacaacc atgcaccacc tgtaaaccga     420
ccgcaagcgg ggcacctgtt tccaggtctt tccggttcat gtcaagcctt ggtaaggttc     480
ttcgcgttgc atcgaattaa tccgcatgct ccgccgcttg tgcgggcccc cgtcaattcc     540
tttgagtttt agccttgcgg ccgtactccc caggcggggc acttaatgcg ttagctacgg     600
cgcggaaaac gtggaatgtc ccccacacct agtgcccaac gtttacggca tggactacca     660
gggtatctaa tcctgttcgc tccccatgct ttcgctcctc agcgtcagtt acagcccaga     720
gacctgcctt cgccatcggt gttcctcctg atatctgcgc atttcaccgc tacaccagga     780
attccagtct cccctactgc actctagtct gcccgtaccc actgcagaac cggagttgag     840
ccccggtctt tcacagcaga cgcgacaaac cgcctacgag ctctttacgc ccaataat      898
```

<210> SEQ ID NO 10
<211> LENGTH: 736
<212> TYPE: DNA
<213> ORGANISM: Pseudomonas helmanticensis
<220> FEATURE:
<221> NAME/KEY: misc_feature
<222> LOCATION: (1)..(736)
<223> OTHER INFORMATION: BCI 616 16S rDNA

<400> SEQUENCE: 10

```
agactagcta cttctggtgc aacccactcc catggtgtga cgggcggtgt gtacaaggcc      60
cgggaacgta ttcaccgtga cattctgatt cacgattact agcgattccg acttcacgca     120
gtcgagttgc agactgcgat ccggactacg atcggtttta tgggattagc tccacctcgc     180
ggcttggcaa ccctttgtac cgaccattgt agcacgtgtg tagcccaggc cgtaagggcc     240
atgatgactt gacgtcatcc ccaccttcct ccggtttgtc accggcagtc tccttagagt     300
gcccaccata acgtgctggt aactaaggac aagggttgcg ctcgttacgg gacttaaccc     360
aacatctcac gacacgagct gacgacagcc atgcagcacc tgtctcaatg ttcccgaagg     420
caccaatcca tctctggaaa gttcattgga tgtcaaggcc tggtaaggtt cttcgcgttg     480
cttcgaatta aaccacatgc tccaccgctt gtgcgggccc cgtcaattc atttgagttt     540
taaccttgcg gccgtactcc ccaggcggtc aacttaatgc gttagctgcg ccactaagag     600
ctcaaggctc ccaacggcta gttgacatcg tttacggcgt ggactaccag ggtatctaat     660
cctgtttgct ccccacgctt tcgcacctca gtgtcagtat cagtccaggt ggtcgccttc     720
gccactggtg ttcctt                                                      736
```

<210> SEQ ID NO 11
<211> LENGTH: 930
<212> TYPE: DNA
<213> ORGANISM: Pseudomonas helmanticensis
<220> FEATURE:
<221> NAME/KEY: misc_feature
<222> LOCATION: (1)..(930)
<223> OTHER INFORMATION: BCI 2945 16S rDNA
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (919)..(919)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t

<400> SEQUENCE: 11
aggttagact agctacttct ggtgcaaccc actcccatgg tgtgacgggc ggtgtgtaca      60
aggcccggga acgtattcac cgtgacattc tgattcacga ttactagcga ttccgacttc     120
acgcagtcga gttgcagact gcgatccgga ctacgatcgg ttttatggga ttagctccac     180
ctcgcggctt ggcaacccctt tgtaccgacc attgtagcac gtgtgtagcc caggccgtaa    240
gggccatgat gacttgacgt catccccacc ttcctccggt ttgtcaccgg cagtctcctt     300
agagtgccca ccattacgtg ctggtaacta aggacaaggg ttgcgctcgt tacgggactt     360
aacccaacat ctcacgacac gagctgacga cagccatgca gcacctgtct caatgttccc     420
gaaggcacca atccatctct ggaaagttca ttggatgtca aggcctggta aggttcttcg     480
cgttgcttcg aattaaacca catgctccac cgcttgtgcg ggccccgtc aattcatttg      540
agttttaacc ttgcggccgt actccccagg cggtcaactt aatgcgttag ctgcgccact     600
aagagctcaa ggctcccaac ggctagttga catcgtttac ggcgtggact accagggtat     660
ctaatcctgt ttgctcccca cgctttcgca cctcagtgtc agtatcagtc caggtggtcg     720
ccttcgccac tggtgttcct tcctatatct acgcatttca ccgctacaca ngaaattcca    780
ccaccctcta ccatactcta gctcgacagt tttgaatgca gtttccaagg tngagcccgg     840
gganttcaca tccaacttaa cnaacaccta cgcgcgcttt acgaccagta attccnatta    900
acgcttgcac cctctgtant accgcngctg                                      930

<210> SEQ ID NO 12
<211> LENGTH: 822
<212> TYPE: DNA
<213> ORGANISM: Pseudomonas helmanticensis
<220> FEATURE:
<221> NAME/KEY: misc_feature

```
<222> LOCATION: (1)..(822)
<223> OTHER INFORMATION: BCI 800 16S rDNA
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 12
ggcgtaaagc gcgcgtaggt ggttcgttaa gnnggatgtg aantcccgg gctcaacctg      60
ggaactgcat tcaaaactgt cgagctagag tatggtagag ggtggtggaa tttcctgtgt    120
agcggtgaaa tgcgtagata taggaaggaa caccagtggc gaaggcgacc acctggactg    180
atactgacac tgaggtgcga aagcgtgggg agcaaacagg attagatacc ctggtagtcc    240
acgccgtaaa cgatgtcaac tagccgttgg gagccttgag ctcttagtgg cgcagctaac    300
gcattaagtt gaccgcctgg ggagtacggc cgcaaggtta aaactcaaat gaattgacgg    360
gggcccgcac aagcggtgga gcatgtggtt taattcgaag caacgcgaag aaccttacca    420
ggccttgaca tccaatgaac tttccagaga tggattggtg ccttcgggaa cattgagaca    480
ggtgctgcat ggctgtcgtc agctcgtgtc gtgagatgtt gggttaagtc ccgtaacgag    540
cgcaacccct tgtccttagtt accagcacgt tatggtgggc actctaagga gactgccggt    600
gacaaaccgg aggaaggtgg ggatgacgtc aagtcatcat ggcccttacg gcctgggcta    660
cacacgtgct acaatggtcg gtacaaaggg ttgccaagcc gcgaggtgga gctaatccca    720
taaaaccgat cgtagtccgg atcgcagtct gcaactcgac tgcgtgaagt cggaatcgct    780
agtaatcgtg aatcagaatg tcacggtgaa tacgttcccg gg                        822

<210> SEQ ID NO 13
<211> LENGTH: 894
<212> TYPE: DNA
<213> ORGANISM: Agrobacterium fabrum
<220> FEATURE:
<221> NAME/KEY: misc_feature
<222> LOCATION: (1)..(894)
<223> OTHER INFORMATION: BCI 46 16S rDNA

<400> SEQUENCE: 13
ccttgcggtt agcgcactac cttcgggtaa aaccaactcc catggtgtga cgggcggtgt      60
gtacaaggcc cgggaacgta ttcaccgcag catgctgatc tgcgattact agcgattcca    120
acttcatgca ctcgagttgc agagtgcaat ccgaactgag atggcttttg gagattagct    180
cgacatcgct gtctcgctgc ccactgtcac caccattgta gcacgtgtgt agcccagccc    240
gtaagggcca tgaggacttg acgtcatccc caccttcctc tcggcttatc accggcagtc    300
cccttagagt gcccaactaa atgctggcaa ctaagggcga gggttgcgct cgttgcggga    360
cttaacccaa catctcacga cacgagctga cgacagccat gcagcacctg ttctggggcc    420
agcctaactg aaggacatcg tctccaatgc ccatacccg aatgtcaaga gctggtaagg    480
ttctgcgcgt tgcttcgaat taaaccacat gctccaccgc ttgtgcgggc ccccgtcaat    540
tcctttgagt tttaatcttg cgaccgtact ccccaggcgg aatgtttaat gcgttagctg    600
cgccaccgaa cagtatactg cccgacggct aacattcatc gtttacggcg tggactacca    660
gggtatctaa tcctgtttgc tccccacgct ttcgcacctc agcgtcagta atggaccagt    720
aagccgcctt cgccactggt gttcctccga atatctacga atttcacctc tacactcgga    780
```

```
attccactta cctcttccat actcaagata cccagtatca aaggcagttc cgcagttgag    840
ctgcgggatt tcaccctga cttaaatatc cgcctacgtg cgctttacgc ccag           894
```

<210> SEQ ID NO 14
<211> LENGTH: 602
<212> TYPE: DNA
<213> ORGANISM: Agrobacterium fabrum
<220> FEATURE:
<221> NAME/KEY: misc_feature
<222> LOCATION: (1)..(602)
<223> OTHER INFORMATION: BCI 958 16S rDNA

<400> SEQUENCE: 14

```
cttcgggtaa aaccaactcc catggtgtga cgggcggtgt gtacaaggcc cgggaacgta     60
ttcaccgcag catgctgatc tgcgattact agcgattcca acttcatgca ctcgagttgc    120
agagtgcaat ccgaactgag atggcttttg gagattagct cgacatcgct gtctcgctgc    180
ccactgtcac caccattgta gcacgtgtgt agcccagccc gtaagggcca tgaggacttg    240
acgtcatccc caccttcctc tcggcttatc accggcagtc cccttagagt gcccaactaa    300
atgctggcaa ctaagggcga gggttgcgct cgttgcggga cttaacccaa catctcacga    360
cacgagctga cgacagccat gcagcacctg ttctggggcc agcctaactg aaggacatcg    420
tctccaatgc ccatacccg aatgtcaaga gctggtaagg ttctgcgcgt tgcttcgaat    480
taaaccacat gctccaccgc ttgtgcgggc ccccgtcaat tcctttgagt tttaatcttg    540
cgaccgtact ccccaggcgg aatgtttaat gcgttagctg cgccaccgaa cagtatactg    600
cc                                                                   602
```

<210> SEQ ID NO 15
<211> LENGTH: 600
<212> TYPE: DNA
<213> ORGANISM: Achromobacter pulmonis
<220> FEATURE:
<221> NAME/KEY: misc_feature
<222> LOCATION: (1)..(600)
<223> OTHER INFORMATION: BCI 49 16S rDNA

<400> SEQUENCE: 15

```
taggctaact acttctggta aaacccactc ccatggtgtg acgggcggtg tgtacaagac     60
ccgggaacgt attcaccgcg acatgctgat ccgcgattac tagcgattcc gacttcacgc    120
agtcgagttg cagactgcga tccggactac gatcgggttt ctgggattgg ctcccctcg    180 cgggttggcg accctctgtc ccgaccattg tatgacgtgt gaagccctac cataagggc    240 catgaggact tgacgtcatc cccaccttcc tccggtttgt caccggcagt ctcattagag    300 tgcccttcg tagcaactaa tgacaagggt tgcgctcgtt gcgggactta acccaacatc    360
tcacgacacg agctgacgac agccatgcag cacctgtgtt ccagttctct tgcgagcact    420
gccaaatctc ttcggcattc cagacatgtc aagggtaggt aaggttttc gcgttgcatc    480 gaattaatcc acatcatcca ccgcttgtgc gggtccccgt caattccttt gagttttaat    540
cttgcgaccg tactccccag gcggtcaact tcacgcgtta gctgcgctac caaggtccga    600
```

<210> SEQ ID NO 16
<211> LENGTH: 705
<212> TYPE: DNA
<213> ORGANISM: Exiguobacterium sibiricum
<220> FEATURE:
<221> NAME/KEY: misc_feature
<222> LOCATION: (1)..(705)
<223> OTHER INFORMATION: BCI 116 16S rDNA

<400> SEQUENCE: 16

```
cctcaccggc ttcgggtgtt gcaaactctc gtggtgtgac gggcggtgtg tacaagaccc      60
gggaacgtat tcaccgcagt atgctgacct gcgattacta gcgattccga cttcatgcag     120
gcgagttgca gcctgcaatc cgaactggga acggctttct gggattggct ccacctcgcg     180
gtctcgctgc cctttgtacc gtccattgta gcacgtgtgt agcccaactc ataaggggca     240
tgatgatttg acgtcatccc caccttcctc cggtttgtca ccggcagtct ccctagagtg     300
cccaactaaa tgctggcaac taaggatagg ggttgcgctc gttgcgggac ttaacccaac     360
atctcacgac acgagctgac gacaaccatg caccacctgt cacccttgtc cccgaaggga     420
aaacttgatc tctcaagcgg tcaaggggat gtcaagagtt ggtaaggttc ttcgcgttgc     480
ttcgaattaa accacatgct ccaccgcttg tgcgggtccc cgtcaattcc tttgagtttc     540
agccttgcgg ccgtactccc caggcggagt gcttaatgcg ttagcttcag cactgagggg     600
cggaaacccc ccaacaccta gcactcatcg tttacggcgt ggactaccag ggtatctaat     660
cctgtttgct ccccacgctt tcgcgcctca gcgtcagtta cagac                     705
```

<210> SEQ ID NO 17
<211> LENGTH: 796
<212> TYPE: DNA
<213> ORGANISM: Exiguobacterium sibiricum
<220> FEATURE:
<221> NAME/KEY: misc_feature
<222> LOCATION: (1)..(796)
<223> OTHER INFORMATION: BCI 718 16S rDNA
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t

<400> SEQUENCE: 17

```
tttaagtctg atgngaaagc ccccggctcn accggggagg ntcattggaa actggaaggc      60
ttgagtacag aagagaagag tggaatncca tgtgtagcgg tgaaatgcgt agagatgtgg     120
aggaacacca gtggcgaagg cgactctttg gtctgtaact gacgctgagg cgcgaaagcg     180
tggggagcaa acaggattag ataccctggt agtccacgcc gtaaacgatg agtgctaggt     240
gttgggggt ttccgcccct cagtgctgaa gctaacgcat taagcactcc gcctggggag     300
tacggccgca aggctgaaac tcaaaggaat tgacggggac ccgcacaagc ggtggagcat     360
gtggtttaat tcgaagcaac gcgaagaacc ttaccaactc ttgacatccc cttgaccgct     420
tgagagatca agtttnccct tcggggggcaa gggtgacagg tggtgcatgg ttgtcgtcag     480
ctcgtgtcgt gagatgttgg gttaagtccc gcaacgagcg caacccctat ccttagttgc     540
cagcatttag ttgggcactc tagggagact gccggtgaca aaccggagga aggtggggat     600
```

```
gacgtcaaat catcatgccc cttatgagtt gggctacaca cgtgctacaa tggacggtac      660
aaagggcagc gagaccgcga ggtggagcca atcccagaaa gccgttccca gttcggattg      720
caggctgcaa ctcgcctgca tgaagtcgga atcgctagta atcgcaggtc agcatactgc      780
ggtgaatacg ttcccg                                                      796
```

<210> SEQ ID NO 18
<211> LENGTH: 777
<212> TYPE: DNA
<213> ORGANISM: Exiguobacterium antarcticum
<220> FEATURE:
<221> NAME/KEY: misc_feature
<222> LOCATION: (1)..(777)
<223> OTHER INFORMATION: BCI 63 16S rDNA

<400> SEQUENCE: 18

```
acctcaccgg cttcgggtgt tgcaaactct cgtggtgtga cgggcggtgt gtacaagacc       60
cgggaacgta ttcaccgcag tatgctgacc tgcgattact agcgattccg acttcatgca      120
ggcgagttgc agcctgcaat ccgaactggg aacggctttc tgggattggc tccacctcgc      180
ggtctcgctg cccttttgtac cgtccattgt agcacgtgtg tagcccaact cataagggc      240 atgatgattt gacgtcatcc ccaccttcct ccggtttgtc accggcagtc tccctagagt      300
gcccaactaa atgctggcaa ctaaggatag gggttgcgct cgttgcggga cttaacccaa      360
catctcacga cacgagctga cgacaaccat gcaccacctg tcaccttgt ccccgaaggg      420 aaaacttgat ctctcaagcg gtcaagggga tgtcaagagt tggtaaggtt cttcgcgttg      480
cttcgaatta aaccacatgc tccaccgctt gtgcgggtcc ccgtcaattc ctttgagttt      540
cagccttgcg gccgtactcc ccaggcggag tgcttaatgc gttagcttca gcactgaggg      600
gcggaaaccc cccaacacct agcactcatc gtttacggcg tggactacca gggtatctaa      660
tcctgtttgc tccccacgct ttcgcgcctc agcgtcagtt acagaccaaa gagtcgcctt      720
cgccactggt gttcctccac atctctacgc atttcaccgc tacacatgga attccac        777
```

<210> SEQ ID NO 19
<211> LENGTH: 820
<212> TYPE: DNA
<213> ORGANISM: Exiguobacterium antarcticum
<220> FEATURE:
<221> NAME/KEY: misc_feature
<222> LOCATION: (1)..(820)
<223> OTHER INFORMATION: BCI 225 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t -continued

```
<400> SEQUENCE: 19
ggcgtnaagc gcgcgcnggc ggncttttaa gtntgatgtg aaagccccg gntcaaccgg      60 ggagggtcat tggaaactgg aaggcttgag tacagaagag aagagtggaa ttccatgtgt     120
agcggtgaaa tgcgtagaga tgtggaggaa caccagtggc gaaggcgact ctttngtctg     180
taactgacgc tgaggcgcga aagcgtgggg agcaaacagg attagatacc ctggtagtcc     240
acgccgtaaa cgatgagtgc taggtgttgg ggggtttccg cccctcagtg ctgaagctaa     300
cgcattaagc actccgcctg gggagtacgg ccgcaaggct gaaactcaaa ggaattgacg     360
gggacccgca caagcggtgg agcatgtggt ttaattcgaa gcaacgcgaa gaaccttacc     420
aactcttgac atccccttga ccgcttgaga gatcaagttt tcccttcggg gacaagggtg     480
acaggtggtg catggttgtc gtcagctcgt gtcgtgagat gttgggttaa gtcccgcaac     540
gagcgcaacc cctatcctta gttgccagca tttagttggg cactctaggg agactgccgg     600
tgacaaaccg gaggaaggtg gggatgacgt caaatcatca tgccccttat gagttgggct     660
acacacgtgc tacaatggac ggtacaaagg gcagcgagac cgcgaggtgg agccaatccc     720
agaaagccgt tcccagttcg gattgcaggc tgcaactcgc ctgcatgaag tcggaatcgc     780
tagtaatcgc aggtcagcat actgcggtga atacgttccc                          820

<210> SEQ ID NO 20
<211> LENGTH: 724
<212> TYPE: DNA
<213> ORGANISM: Pedobacter terrae
<220> FEATURE:
<221> NAME/KEY: misc_feature
<222> LOCATION: (1)..(724)
<223> OTHER INFORMATION: BCI 53 16S rDNA
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (108)..(109)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (353)..(353)
```

```
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (442)..(443)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (612)..(614)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (667)..(667)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
```

<222> LOCATION: (710)..(710)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t

<400> SEQUENCE: 20

```
tggnttgacg ggcggngtgt acaaggnccg ggaacgtatt caccgcgtca ttgctgatac    60
ncgattactn gcaatccaa cttcntgggg tcgagttgca naccccannc cgaactgtgn    120
acggctttgt gagattcgca tcatattgct atgtagctgc cctctgtacc gtccattgta   180
gcacgtgtgt agccccggac gtaagggcca tgatgacttg acgtcgtccc ctccttcctc   240
tctgtttgca caggcagtct gtttagagtc cccaccatta catgctggca actaaacata   300
ggggttgcgc tcgttgcggg acttaaccca acacctcacg gcacgagctg acnacagcca   360
tgcagcacct agtttcgtgt ccttgcggac tgatccatct ctggatcatt cactaacttt   420
caagcccggg naaggttcct cnngtatcat cnaattaaac canatgctcc tccgcttgtg   480
cgggccccg tcaattcctt tgagtttcac ccttgcgggc gtactcccca ggnggaacac    540
ttaacgcttt cgcttanccg ctgactgtgt atcgccnaca gcgagtgttc atcgnttang   600
gcgtggacta cnnnggnatc taatcctgtt tganccccac gcttncntgc ctcancgtca   660
ataagancat agnaagctgn cttcgcaatc ggtgttctga gacntatctn tgcntttcan   720
cgct                                                                724
```

<210> SEQ ID NO 21
<211> LENGTH: 682
<212> TYPE: DNA
<213> ORGANISM: Duganella radicis
<220> FEATURE:
<221> NAME/KEY: misc_feature
<222> LOCATION: (1)..(682)
<223> OTHER INFORMATION: BCI 31 16S rDNA

<400> SEQUENCE: 21

```
agctacctac ttctggtaaa acccgctccc atggtgtgac gggcggtgtg tacaagaccc    60
gggaacgtat tcaccgcgac atgctgatcc gcgattacta gcgattccaa cttcacgtag   120
tcgagttgca gactacgatc cggactacga tgcactttct gggattagct ccccctcgcg   180
ggttggcggc cctctgtatg caccattgta tgacgtgtga agccctaccc ataagggcca   240
tgaggacttg acgtcatccc caccttcctc cggtttgtca ccggcagtct cattagagtg   300
cccttcgta gcaactaatg acaagggttg cgctcgttgc gggacttaac ccaacatctc   360
acgacacgag ctgacgacag ccatgcagca cctgtgtatc ggttctcttt cgggcactcc   420
ccaatctctc agggattcct tccatgtcaa gggtaggtaa ggttttcgc gttgcatcga   480
attaatccac atcatccacc gcttgtgcgg gtccccgtca attcctttga gttttaatct   540
tgcgaccgta ctccccaggc ggtctacttc acgcgttagc tgcgttacca agtcaattaa   600
gacccgacaa ctagtagaca tcgtttaggg cgtggactac cagggtatct aatcctgttt   660
gctccccacg ctttcgtgca tg                                            682
```

<210> SEQ ID NO 22
<211> LENGTH: 799
<212> TYPE: DNA

```
<213> ORGANISM: Leifsonia lichenia
<220> FEATURE:
<221> NAME/KEY: misc_feature
<222> LOCATION: (1)..(799)
<223> OTHER INFORMATION: BDNZ 72243 16S rDNA

<400> SEQUENCE: 22
tccacaaggg ttaggccacc ggcttcgggt gttaccgact ttcatgactt gacgggcggt      60
gtgtacaagg cccgggaacg tattcaccgc agcgttgctg atctgcgatt actagcgact     120
ccgacttcat gaggtcgagt tgcagacctc aatccgaact gagaccggct ttttgggatt     180
cgctccacct tacggtattg cagcccttg taccggccat tgtagcatgc gtgaagccca      240
agacataagg ggcatgatga tttgacgtca tccccacctt cctccgagtt gaccccggca     300
gtctcctatg agttcccacc attacgtgct ggcaacatag aacgagggtt gcgctcgttg     360
cgggacttaa cccaacatct cacgacacga gctgacgaca accatgcacc acctgtttac     420
gagtgtccaa agagttgacc atttctggcc cgttctcgta tatgtcaagc cttggtaagg     480
ttcttcgcgt tgcatcgaat taatccgcat gctccgccgc ttgtgcgggc cccgtcaat     540 tcctttgagt tttagccttg cggccgtact ccccaggcgg ggcgcttaat gcgttagctg     600
cgacacggaa accgtggaat ggtccccaca tctagcgccc aacgtttacg gcgtggacta     660
ccagggtatc taatcctgtt cgctcccca gctttcgctc ctcagcgtca gttacggccc      720
agagaactgc cttcgccatc ggggttcctc ctgatatctg cgcattccac cgctacacca     780
ggaattccat tctcccta                                                   799

<210> SEQ ID NO 23
<211> LENGTH: 1008
<212> TYPE: DNA
<213> ORGANISM: Leifsonia lichenia
<220> FEATURE:
<221> NAME/KEY: misc_feature
<222> LOCATION: (1)..(1008)
<223> OTHER INFORMATION: BDNZ 72289 16S rDNA

<400> SEQUENCE: 23
tccacaaggg ttaggccacc ggcttcgggt gttaccgact ttcatgactt gacgggcggt      60
gtgtacaagg cccgggaacg tattcaccgc agcgttgctg atctgcgatt actagcgact     120
ccgacttcat gaggtcgagt tgcagacctc aatccgaact gagaccggct ttttgggatt     180
cgctccacct tacggtattg cagcccttg taccggccat tgtagcatgc gtgaagccca      240
agacataagg ggcatgatga tttgacgtca tccccacctt cctccgagtt gaccccggca     300
gtctcctatg agttcccacc attacgtgct ggcaacatag aacgagggtt gcgctcgttg     360
cgggacttaa cccaacatct cacgacacga gctgacgaca accatgcacc acctgtttac     420
gagtgtccaa agagttgacc atttctggcc cgttctcgta tatgtcaagc cttggtaagg     480
ttcttcgcgt tgcatcgaat taatccgcat gctccgccgc ttgtgcgggc cccgtcaat     540 tcctttgagt tttagccttg cggccgtact ccccaggcgg ggcgcttaat gcgttagctg     600
cgacacggaa accgtggaat ggtccccaca tctagcgccc aacgtttacg gcgtggacta     660
ccagggtatc taatcctgtt cgctcccca gctttcgctc ctcagcgtca gttacggccc      720
agagaactgc cttcgccatc ggtgttcctc ctgatatctg cgcattccac cgctacacca     780
ggaattccat tctcccctac cgcactctag tctgcccgta cccactgcag gcccgaggtt     840
gagcctcggg ttttcacagc agacgcgaca aaccgcctac gagctcttta cgcccaataa     900
ttccggacaa cgcttgcacc ctacgtatta ccgcggctgc tggcacgtag ttagccggtg     960
```

```
ctttttctgc aggtaccgtc actttcgctt cttccctact aaaagagg         1008
```

<210> SEQ ID NO 24
<211> LENGTH: 989
<212> TYPE: DNA
<213> ORGANISM: Tumebacillus permanentifrigoris
<220> FEATURE:
<221> NAME/KEY: misc_feature
<222> LOCATION: (1)..(989)
<223> OTHER INFORMATION: BDNZ 72229 16S rDNA

<400> SEQUENCE: 24

```
agcagttacc tcaccgactt cgggtgttac caactcccat ggtgtgacgg gcggtgtgta    60
caaggcccgg gaacgaattc accgcggcat gctgatccgc gattactagc aattccggct   120
tcatgcaggc gagttgcagc ctgcaatccg aactacgaac ggctttctgg gattggctcc   180
acctcgcggc ttcgcaaccc tttgtaccgt ccattgtagc acgtgtgtag cccaagacat   240
aaggggcatg atgatttgac gtcatccccg ccttcctccg gtttgtcacc ggcagtctgt   300
tgtaagtgct caactaaatg gtagcaacac aacataggggg ttgcgctcgt tgcgggactt   360
aacccaacat ctcacgacac gagctgacga caaccatgca ccacctgtca ccgctgcccc   420
gaagggaagc tctatctcta gaacggtcag cgggatgtca agtcttggta aggttcttcg   480
cgttgcttcg aattaaacca catgctccac tgcttgtgcg ggccccgtc aattcctttg    540
agtttcagtc ttgcgaccgt actccccagg cggagtgctt aatgcgttag cttcggcact   600
aagggggtggg cccctaaca cctagcactc atcgtttacg gcgtggacta ccagggtatc   660
taatcctgtt tgctccccac gctttcgcgc ctcagcgtca gaaatcggcc agcaaggcgc   720
cttcgccaca ggtgttcctc cacatctcta cgcatttcac cgctacacgt ggaattcccc   780
ttgcctctcc gatcctcaag tctccccgta tccaaggcaa tcccagagtt gagctctggg   840
ctttcaccccc ggacgtgaaa gaccgcctgc gcgcgcttta cgcccagtga ttccggacaa   900
cgcttgcccc ctacgtatta ccgcggctgc tggcacgtag ttagccgggg cttcctcctc   960
tgttaccgtc aggtcctgag ctttctctg                                      989
```

<210> SEQ ID NO 25
<211> LENGTH: 1021
<212> TYPE: DNA
<213> ORGANISM: Tumebacillus permanentifrigoris
<220> FEATURE:
<221> NAME/KEY: misc_feature
<222> LOCATION: (1)..(1021)
<223> OTHER INFORMATION: BDNZ 74542 16S rDNA

<400> SEQUENCE: 25

```
agcagttacc tcaccgactt cgggtgttac caactcccat ggtgtgacgg gcggtgtgta    60
caaggcccgg gaacgaattc accgcggcat gctgatccgc gattactagc aattccggct   120
tcatgcaggc gagttgcagc ctgcaatccg aactacgaac ggctttctgg gattggctcc   180
acctcgcggc ttcgcaaccc tttgtaccgt ccattgtagc acgtgtgtag cccaagacat   240
aaggggcatg atgatttgac gtcatccccg ccttcctccg gtttgtcacc ggcagtctgt   300
tgtaagtgct caactaaatg gtagcaacac aacataggggg ttgcgctcgt tgcgggactt   360
aacccaacat ctcacgacac gagctgacga caaccatgca ccacctgtca ccgctgcccc   420
gaagggaagc tctatctcta gaacggtcag cgggatgtca agtcttggta aggttcttcg   480
cgttgcttcg aattaaacca catgctccac tgcttgtgcg ggccccgtc aattcctttg    540
```
agtttcagtc ttgcgaccgt actccccagg cggagtgctt aatgcgttag cttcggcact    600
aaggggtggg cccctaaca cctagcactc atcgtttacg gcgtggacta ccagggtatc    660
taatcctgtt tgctccccac gctttcgcgc ctcagcgtca gaaatcggcc agcaaggcgc    720
cttcgccaca ggtgttcctc cacatctcta cgcatttcac cgctacacgt ggaattcccc    780
ttgcctctcc gatcctcaag tctccccgta tccaaggcaa tcccagagtt gagctctggg    840
ctttcacccc ggacgtgaaa gaccgcctgc gcgcgcttta cgcccagtga ttccggacaa    900
cgcttgcccc ctacgtatta ccgcggctgc tggcacgtag ttagccgggg cttcctcctc    960
tgttaccgtc aggtcctgag ctttctctgc acaggatggt tcttcacaga agacagagtt   1020
t                                                                   1021

<210> SEQ ID NO 26
<211> LENGTH: 989
<212> TYPE: DNA
<213> ORGANISM: Tumebacillus permanentifrigoris
<220> FEATURE:
<221> NAME/KEY: misc_feature
<222> LOCATION: (1)..(989)
<223> OTHER INFORMATION: BDNZ 72366 16S rDNA

<400> SEQUENCE: 26
agcagttacc tcaccgactt cgggtgttac caactcccat ggtgtgacgg gcggtgtgta     60
caaggcccgg gaacgaattc accgcggcat gctgatccgc gattactagc aattccggct    120
tcatgcaggc gagttgcagc ctgcaatccg aactacgaac ggctttctgg gattggctcc    180
acctcgcggt ttcgcaaccc tttgtaccgt ccattgtagc acgtgtgtag cccaagacat    240
aaggggcatg atgatttgac gtcatccccg ccttcctccg gtttgtcacc ggcagtctgt    300
tgtaagtgct caactaaatg gtagcaacac aacataggg ttgcgctcgt tgcgggactt    360
aacccaacat ctcacgacac gagctgacga caaccatgca ccacctgtca ccgctgcccc    420
gaagggaagc tctatctcta gaacggtcag cgggatgtca agtcttggta aggttcttcg    480
cgttgcttcg aattaaacca catgctccac tgcttgtgcg ggcccccgtc aattcctttg    540
agtttcagtc ttgcgaccgt actccccagg cggagtgctt aatgcgttag cttcggcact    600
aaggggtggg cccctaaca cctagcactc atcgtttacg gcgtggacta ccagggtatc    660
taatcctgtt tgctccccac gctttcgcgc ctcagcgtca gaaatcggcc agcaaggcgc    720
cttcgccaca ggtgttcctc cacatctcta cgcatttcac cgctacacgt ggaattcccc    780
ttgcctctcc gatcctcaag tctccccgta tccaaggcaa tcccagagtt gagctctggg    840
ctttcacccc ggacgtgaaa gaccgcctgc gcgcgcttta cgcccagtga ttccggacaa    900
cgcttgcccc ctacgtatta ccgcggctgc tggcacgtag ttagccgggg cttcctcctc    960
tgttaccgtc aggtcctgag ctttctctg                                      989

<210> SEQ ID NO 27
<211> LENGTH: 799
<212> TYPE: DNA
<213> ORGANISM: Bacillus asahii
<220> FEATURE:
<221> NAME/KEY: misc_feature
<222> LOCATION: (1)..(799)
<223> OTHER INFORMATION: BCI 928 16S rDNA
<220> FEATURE:
<221> NAME/KEY: misc_feature
<222> LOCATION: (416)..(418)
<223> OTHER INFORMATION: n is a, c, g, or t

<400> SEQUENCE: 27

```
tcctttaagt ctgatgtgaa agcccacggc tcaaccgtgg agggtcattg gaaactgggg      60
gacttgagtg cagaagagga gagtggaatt ccacgtgtag cggtgaaatg cgtagagatg     120
tggaggaaca ccagtggcga aggcgactct ctggtctgta actgacgctg aggcgcgaaa     180
gcgtggggag caaacaggat tagataccct ggtagtccac gccgtaaacg atgagtgcta     240
agtgttagag ggtttccgcc ctttagtgct gcagctaacg cattaagcac tccgcctggg     300
gagtacggcc gcaaggctga aactcaaagg aattgacggg ggcccgcaca agcggtggag     360
catgtggttt aattcgaagc aacgcgaaga accttaccag gtcttgacat cctctnnnaa     420
ccctagagat agggcgttcc ccttcggggg acagagtgac aggtggtgca tggttgtcgt     480
cagctcgtgt cgtgagatgt tgggttaagt cccgcaacga gcgcaaccct tgatcttagt     540
tgccagcatt cagttgggca ctctaaggtg actgccggtg acaaaccgga ggaaggtggg     600
gatgacgtca aatcatcatg cccttatga cctgggctac acacgtgcta caatggatgg     660
tacaaagagc tgcgaacccg cgagggtaag cgaatctcat aaagccattc tcagttcgga     720
ttgtaggctg caactcgcct acatgaagcc ggaatcgcta gtaatcgcgg atcagcatgc     780
cgcggtgaat acgttcccg                                                  799
```

```
<210> SEQ ID NO 28
<211> LENGTH: 763
<212> TYPE: DNA
<213> ORGANISM: Novosphingobium sediminicola
<220> FEATURE:
<221> NAME/KEY: misc_feature
<222> LOCATION: (1)..(763)
<223> OTHER INFORMATION: BCI 130 16S rDNA
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (743)..(745)
<223> OTHER INFORMATION: n is a, c, g, or t
<220> FEATURE:
```

```
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t

<400> SEQUENCE: 28
acgccttcga gtgaatccna ctcccatggt gtgacgggcg gtgtgtacaa ggcctgggaa      60
cgtattcacc gcggcatgct gatccgcgat tactagcgat tccgccttca tgctctcgag     120
ttgcagagaa caatccgaac tgagacggct tttggagatt agctacccct cgcgaggtcg     180
ctgcccactg tcaccgccat gtagcacgt gtgtagccca gcgtgtaagg gccatgagga      240
cttgacgtca tccccacctt cctccggctt atcaccggcg gtttccttag agtgcccaac     300
ttaatgatgg caactaagga cgagggttgc gctcgttgcg ggacttaacc caacatctca     360
cgacacgagc tgacgacagc catgcagcac ctgtcaccga tccagccaaa ctgaaggaaa     420
acatctctgt aatccgcgat cgggatgtca aacgctggta aggttctgcg cgttgcttcg     480
aattaaacca catgctccac cgcttgtgca ggccccgtc aattcctttg ngtttaatc       540
ttgcgaccgt actcccagg cggataactt aatgcgttag ctgcgccacc caaattccat      600
gaacccggac agctagttat catcgtttac ggcgtggant accagggtat ctaatcctgt     660
ttgctccnca cgctttcgca cctcagcgtc aatacctgtc cngtgagccg ccttcnccac     720
nngngttctt ccnaatatct acnnntttca nctctncact cgg                       763

<210> SEQ ID NO 29
<211> LENGTH: 882
<212> TYPE: DNA
<213> ORGANISM: Novosphingobium sediminicola
<220> FEATURE:
<221> NAME/KEY: misc_feature
<222> LOCATION: (1)..(882)
<223> OTHER INFORMATION: BDNZ 71628 16S rDNA

<400> SEQUENCE: 29
ctgcctccct tgcgggttag ctcaacgcct tcgagtgaat ccaactccca tggtgtgacg      60
ggcggtgtgt acaaggcctg gaacgtatt caccgcggca tgctgatccg cgattactag     120
cgattccgcc ttcatgctct cgagttgcag agaacaatcc gaactgagac ggcttttgga     180
gattagctac ccctcgcgag gtcgctgccc actgtcaccg ccattgtagc acgtgtgtag     240
cccagcgtgt aagggccatg aggacttgac gtcatcccca cttcctccg gcttatcacc     300
ggcggtttcc ttagagtgcc caacttaatg atggcaacta aggacgaggg ttgcgctcgt     360
tgcgggactt aacccaacat ctcacgacac gagctgacga cagccatgca gcacctgtca     420
ccgcgtcccc gaagggaaca ccatctctct ggtgttagcg cgggatgtca aacgctggta     480
aggttctgcg cgttgcttcg aattaaacca catgctccac cgcttgtgca ggccccgtc      540
aattcctttg agtttaatc ttgcgaccgt actcccagg cggataactt aatgcgttag      600
ctgcgccacc caaattccat gaacccggac agctagttat catcgtttac ggcgtggact     660
accagggtat ctaatcctgt ttgctcccca cgctttcgca cctcagcgtc aatacctgtc     720
cagtgagccg ccttcgccac tggtgttctt ccgaatatct acgaatttca cctctacact     780
cggaattcca ctcacctctc caggattcta gttacctagt ttcaaaggca gttccggggt     840
tgagccccgg gctttcacct ctgacttgag taaccgccta cg                        882
```

```
<210> SEQ ID NO 30
<211> LENGTH: 823
<212> TYPE: DNA
<213> ORGANISM: Novosphingobium lindaniclasticum
<220> FEATURE:
<221> NAME/KEY: misc_feature
<222> LOCATION: (1)..(823)
<223> OTHER INFORMATION: BCI 608 16S rDNA

<400> SEQUENCE: 30
ggcgtaaagc gcgcgtaggc ggttactcaa gtcagaggtg aaagcccggg gctcaacccc      60
ggaactgcct ttgaaactag gtgactagaa tcttggagag gtcagtggaa ttccgagtgt     120
agaggtgaaa ttcgtagata ttcggaagaa caccagtggc gaaggcgact gactggacaa     180
gtattgacgc tgaggtgcga aagcgtgggg agcaaacagg attagatacc ctggtagtcc     240
acgccgtaaa cgatgataac tagctgtccg gggacttggt ctttgggtgg cgcagctaac     300
gcattaagtt atccgcctgg ggagtacggt cgcaagatta aaactcaaag gaattgacgg     360
gggcctgcac aagcggtgga gcatgtggtt taattcgaag caacgcgcag aaccttacca     420
gcgtttgaca tcctcatcgc ggatttgaga gatcatttcc ttcagttcgg ctggatgagt     480
gacaggtgct gcatggctgt cgtcagctcg tgtcgtgaga tgttgggtta agtcccgcaa     540
cgagcgcaac cctcgtcctt agttgccagc atttagttgg gcactctaag gaaactgccg     600
gtgataagcc ggaggaaggt ggggatgacg tcaagtcctc atggccctta cacgctgggc     660
tacacacgtg ctacaatggc ggtgacagtg gcagcaagc aggcgactgc aagctaatct     720
ccaaaagccg tctcagttcg gattgttctc tgcaactcga gagcatgaag gcggaatcgc     780
tagtaatcgc ggatcagcat gccgcggtga atacgttccc agg                       823

<210> SEQ ID NO 31
<211> LENGTH: 930
<212> TYPE: DNA
<213> ORGANISM: Novosphingobium lindaniclasticum
<220> FEATURE:
<221> NAME/KEY: misc_feature
<222> LOCATION: (1)..(930)
<223> OTHER INFORMATION: BDNZ 71222 16S rDNA

<400> SEQUENCE: 31
cttgcgagtt agctcaacgc cttcgagtga atccaactcc catggtgtga cgggcggtgt      60
gtacaaggcc tgggaacgta ttcaccgcgg catgctgatc cgcgattact agcgattccg     120
ccttcatgct ctcgagttgc agagaacaat ccgaactgag acggcttttg gagattagct     180
tgccctcgcg cgcttgctgc ccactgtcac cgccattgta gcacgtgtgt agcccagcgt     240
gtaagggcca tgaggacttg acgtcatccc caccttcctc cggcttatca ccggcagttt     300
ccttagagtg cccaactaaa tgctggcaac taaggacgag ggttgcgctc gttgcgggac     360
ttaacccaac atctcacgac acgagctgac gacagccatg cagcacctgt cactcatcca     420
gccgaactga aggaaaagat ctctctaatc gcgatgagc atgtcaaacg ctggtaaggt     480
tctgcgcgtt gcttcgaatt aaaccacatg ctccaccgct tgtgcaggcc cccgtcaatt     540
cctttgagtt ttaatcttgc gaccgtactc cccaggcgga taacttaatg cgttagctcc     600
gccacccaag caccaagtgc ccggacagct agttatcatc gtttacggcg tggactacca     660
gggtatctaa tcctgtttgc tccccacgct ttcgcacctc agcgtcaata cttgtccagt     720
cagtcgcctt cgccactggt gttcttccga atatctacga atttcacctc tacactcgga     780
attccactga cctctccaag attctagcta cctagtttca aaggcagttc cggggttgag     840
```

```
cccgggctt tcacctctga cttgagcagc tgcatacgcg cgctttacgc ccaggaaatt    900
ccgaacaacg ctagctccct ccgtattacc                                    930

<210> SEQ ID NO 32
<211> LENGTH: 506
<212> TYPE: DNA
<213> ORGANISM: Massilia kyonggiensis
<220> FEATURE:
<221> NAME/KEY: misc_feature
<222> LOCATION: (1)..(506)
<223> OTHER INFORMATION: BCI 97 16S rDNA

<400> SEQUENCE: 32
aagacccggg aacgtattca ccgcgacatg ctgatccgcg attactagcg attccaactt    60
cacgcagtcg agttgcagac tgcgatccgg actacgatac actttctggg attagctccc   120
cctcgcgggt tggcggccct ctgtatgtac cattgtatga cgtgtgaagc cctacccata   180
agggccatga ggacttgacg tcatccccac cttcctccgg tttgtcaccg gcagtctcat   240
tagagtgccc tttcgtagca actaatgaca agggttgcgc tcgttgcggg acttaaccca   300
acatctcacg acacgagctg acgacagcca tgcagcacct gtgttcaggc tccctttcgg   360
gcactcccag atctctccag gattcctgac atgtcaaggg taggtaaggt ttttcgcgtt   420
gcatcgaatt aatccacatc atccaccgct tgtgcgggtc cccgtcaatt cctttgagtt   480
ttaatcttgc gaccgtactc cccagg                                        506

<210> SEQ ID NO 33
<211> LENGTH: 351
<212> TYPE: DNA
<213> ORGANISM: Massilia kyonggiensis
<220> FEATURE:
<221> NAME/KEY: misc_feature
<222> LOCATION: (1)..(351)
<223> OTHER INFORMATION: BCI 94 16S rDNA
<220> FEATURE:
<221> NAME/KEY: misc_feature
<222> LOCATION: (101)..(101)
<223> OTHER INFORMATION: n is a, c, g, or t

<400> SEQUENCE: 33
gaaagggagc ctgaacacag gtgctgcatg gctgtcgtca gctcgtgtcg tgagatgttg    60
ggttaagtcc cgcaacgagc gcaacccttg tcattagttg ntacgaaagg gcactctaat   120
gagactgccg gtgacaaacc ggaggaaggt ggggatgacg tcaagtcctc atggccctta   180
tgggtagggc ttcacacgtc atacaatggt acatacagag ggccgccaac ccgcgagggg   240
gagctaatcc cagaaagtgt atcgtagtcc ggatcgcagt ctgcaactcg actgcgtgaa   300
gttggaatcg ctagtaatcg cggatcagca tgccgcggtg aatacgttcc c            351

<210> SEQ ID NO 34
<211> LENGTH: 969
<212> TYPE: DNA
<213> ORGANISM: Massilia kyonggiensis
<220> FEATURE:
<221> NAME/KEY: misc_feature
<222> LOCATION: (1)..(969)
<223> OTHER INFORMATION: BDNZ 73021 16S rDNA

<400> SEQUENCE: 34
cggttaagct acctacttct ggtaaaaccc gctcccatgg tgtgacgggc ggtgtgtaca    60
agacccggga acgtattcac cgcggcatgc tgatccgcga ttactagcga ttccaacttc   120
acgcagtcga gttgcagact gcgatccgga ctacgataca ctttctggga ttagctcccc   180
```

```
ctcgcgggtt ggcggccctc tgtatgtacc attgtatgac gtgtgaagcc ctacccataa      240
gggccatgag gacttgacgt catccccacc ttcctccggt ttgtcaccgg cagtctcatt      300
agagtgctct tgcgtagcaa ctaatgacaa gggttgcgct cgttgcggga cttaacccaa      360
catctcacga cacgagctga cgacagccat gcagcacctg tgttcaggct ctctttcgag      420 cacccccga tctctcgagg gttcctgaca tgtcaagggt aggtaaggtt tttcgcgttg       480
catcgaatta atccacatca tccaccgctt gtgcgggtcc ccgtcaattc ctttgagttt      540
taatcttgcg accgtactcc ccaggcggtc tacttcacgc gttagctgcg ttaccaagtc      600
aattaagacc cgacaactag tagacatcgt ttagggcgtg gactaccagg gtatctaatc      660
ctgtttgctc cccacgcttt cgtgcatgag cgtcaatctt gacccagggg gctgccttcg      720
ccatcggtgt tcctccacat ctctacgcat ttcactgcta cacgtggaat tctaccccc       780 tctgccagat tcaagccttg cagtctccaa cgcaattccc aggttaagcc cggggctttc      840
acgtcagact tacaaaaccg cctgcgcacg ctttacgccc agtaattccg attaacgctt      900
gcaccctacg tattaccgcg gctgctggca cgtagttagc cggtgcttat tcttcaggta      960
ccgtcatta                                                              969

<210> SEQ ID NO 35
<211> LENGTH: 820
<212> TYPE: DNA
<213> ORGANISM: Rhizobium rhizoryzae
<220> FEATURE:
<221> NAME/KEY: misc_feature
<222> LOCATION: (1)..(820)
<223> OTHER INFORMATION: BCI 661 16S rDNA
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t

<400> SEQUENCE: 35
ggcgtaaagc gcacgtnggc ggacatttaa ntcaggggtg aaatcccggg gctcaacctn      60
ggnactgccn ttngatactg ggtntcttga gtgtggaaga ggtcagtgga attgcgagtg     120
tagaggtgaa attngtagat attcgcagga acaccagtgg cgaaggcggc tgactggtcc    180
```

| | |
|---|---|
| acaactgacg ctgaggtgcg aaagcgtggg gagcaaacag gattagatac cctggtagtc | 240 |
| cacgccgtaa acgatgaatg ttagccgtcg gcaagtttac ttgtcggtgg cgcagctaac | 300 |
| gcattaaaca ttccgcctgg ggagtacggt cgcaagatta aaactcaaag gaattgacgg | 360 |
| gggcccgcac aagcggtgga gcatgtggtt taattcgaag caacgcgcag aaccttacca | 420 |
| gcccttgaca tgcccggctc gccacagaga tgtggttttc ccttcgggga ccgggacaca | 480 |
| ggtgctgcat ggctgtcgtc agctcgtgtc gtgagatgtt gggttaagtc ccgcaacgag | 540 |
| cgcaaccctc gcccttagtt gccagcattt ggtgggcac tctaagggga ctgccggtga | 600 |
| taagccgaga ggaaggtggg gatgacgtca agtcctcatg gcccttacgg gctgggctac | 660 |
| acacgtgcta caatggtggt gacagtgggc agcgagcacg cgagtgtgag ctaatctcca | 720 |
| aaagccatct cagttcggat tgcactctgc aactcgagtg catgaagttg gaatcgctag | 780 |
| taatcgcgga tcagcacgcc gcggtgaata cgttcccggg | 820 |

<210> SEQ ID NO 36
<211> LENGTH: 779
<212> TYPE: DNA
<213> ORGANISM: Bosea thiooxidans
<220> FEATURE:
<221> NAME/KEY: misc_feature
<222> LOCATION: (1)..(779)
<223> OTHER INFORMATION: BCI 985 16S rDNA

<400> SEQUENCE: 36

| | |
|---|---|
| tgcggttagc gcgacgcctt cgggtaaacc caactcccat ggtgtgacgg gcggtgtgta | 60 |
| caaggcccgg gaacgtattc accgtggcat gctgatccac gattactagc gattccacct | 120 |
| tcatgtactc gagttgcaga gtacaatctg aactgagacg gcttttgggg attagctcca | 180 |
| ggtcacccct tcgctgccca ttgtcaccgc cattgtagca cgtgtgtagc ccagcctgta | 240 |
| agggccatga ggacttgacg tcatccccac cttcctcgcg gcttatcacc ggcagtcccc | 300 |
| ctagagttcc caactgaatg atggcaacta ggggcgaggg ttgcgctcgt tgcgggactt | 360 |
| aacccaacat ctcacgacac gagctgacga cagccatgca gcacctgtgt tccggccagc | 420 |
| cgaactgaag aaaggcatct ctgccgatca aaccggacat gtcaaaagct ggtaaggttc | 480 |
| tgcgcgttgc ttcgaattaa accacatgct ccaccgcttg tgcgggcccc cgtcaattcc | 540 |
| tttgagtttt aatcttgcga ccgtactccc caggcggaat gcttaaagcg ttagctgcgc | 600 |
| cactgaagag caagctcccc aacggctggc attcatcgtt tacggcgtgg actaccaggg | 660 |
| tatctaatcc tgtttgctcc ccacgctttc gcgcctcagc gtcagtatcg gaccagttgg | 720 |
| ccgccttcgc caccggtgtt cttgcgaata tctacgaatt tcacctctac actcgcagt | 779 |

<210> SEQ ID NO 37
<211> LENGTH: 311
<212> TYPE: DNA
<213> ORGANISM: Stenotrophomonas maltophilia
<220> FEATURE:
<221> NAME/KEY: misc_feature
<222> LOCATION: (1)..(311)
<223> OTHER INFORMATION: BCI 1032 16S rDNA
<220> FEATURE:
<221> NAME/KEY: misc_feature
<222> LOCATION: (37)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 37

```
tgagatgttg ggttaagtcc cgcaacgagc gcaaccnnnn tcnttagttg ccagcacgta    60
atggtgggaa ctctaaggag accgccggtg acaaaccgga ggaaggtggg gatgacgtca   120
agtcatcatg gcccttacgg ccagggctac acacgtacta caatggtagg gacagagggc   180
tgcaagccgg cgacggtaag ccaatcccag aaacccatct cagtccgga ttggagtctg    240 caactcgact ccatgaagtc ggaatcgcta gtaatcgcag atcagcattg ctgcggtgaa   300
tacgttcccg g                                                        311
```

<210> SEQ ID NO 38
<211> LENGTH: 832
<212> TYPE: DNA
<213> ORGANISM: Bosea robinae
<220> FEATURE:
<221> NAME/KEY: misc_feature
<222> LOCATION: (1)..(832)
<223> OTHER INFORMATION: BCI 1041 16S rDNA
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 38

```
ggaatcactg ggngtaaagg gcgcgtaggc ggacttttaa gtcggaggtg aaagcccagg    60
gntcaaccct ggaattgcct tcgatactgg gagtcttgag ttcggaagag gttggtggaa   120
ctgcgagtgt agaggtgaaa ttcgtagata ttcgcaagaa caccggtggc gaaggcggcc   180
aactggtccg aaactgacgc tgaggcgcga aagcgtgggg agcaaacagg attagatacc   240
ctggtagtcc acgccgtaaa cgatgaatgc cagccgttgg ggagcttgct cttcagtggc   300
gcagctaacg ctttaagcat tccgcctggg gagtacggtc gcaagattaa aactcaaagg   360
aattgacggg ggcccgcaca agcggtggag catgtggttt aattcgaagc aacgcgcaga   420
accttaccag ctttttgacat gtccggtttg atcggcagag atgcctttct tcagttcggc   480
tggccggaac acaggtgctg catggctgtc gtcagctcgt gtcgtgagat gttgggttaa   540
gtcccgcaac gagcgcaacc ctcgccccta gttgccatca ttcagttggg aactctaggg   600
ggactgccgg tgataagccg cgaggaaggt ggggatgacg tcaagtcctc atggccctta   660
caggctgggc tacacacgtg ctacaatggc ggtgacaatg ggcagcgaaa gggcgacctc   720
gagctaatcc caaaaagccg tctcagttca gattgtactc tgcaactcga gtacatgaag   780
gtggaatcgc tagtaatcgt ggatcagcat gccacggtga atacgttccc gg           832
```

<210> SEQ ID NO 39
<211> LENGTH: 740
<212> TYPE: DNA
<213> ORGANISM: Duganella radicis
<220> FEATURE:
<221> NAME/KEY: misc_feature
<222> LOCATION: (1)..(740)
<223> OTHER INFORMATION: BCI 105 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (399)..(403)
<223> OTHER INFORMATION: n is a, c, g, or t
<220> FEATURE:

<220> FEATURE:
<221> NAME/KEY: misc_feature
<222> LOCATION: (405)..(409)
<223> OTHER INFORMATION: n is a, c, g, or t
<220> FEATURE:
<221> NAME/KEY: misc_feature
<222> LOCATION: (413)..(418)
<223> OTHER INFORMATION: n is a, c, g, or t
<220> FEATURE:
<221> NAME/KEY: misc_feature
<222> LOCATION: (440)..(446)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (686)..(686)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(703)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t

<400> SEQUENCE: 39

```
naagctacct acttctggta aaacccgctc ccatggtgtg acgggcggtg tgtacaagac      60
ccgggaacgt attcaccgcg acatgctgat ccgcgattac tagcgattcc aacttcacgt     120
agtcgagttg cagactacga tccggactac gatgcacttt ctgggattag ctcccccctcg   180
cgggttggcg gccctctgta tgcaccattg tatgacgtgt gaagccctac ccataagggc    240
catgaggact tgacgtcatc cccaccttcc tccggtttgt caccggcagt ctcattagag    300
tgcccttttcg tagcaactaa tgacaagggt tgcgctcgtt gcgggactta acccaacatc   360
tcacgacacg agctgacgac agccatgcag cacctgtgnn nnngnnnnnt ttnnnnnnct    420
ccccaatctc tcagggattn nnnnnntgtc aagggtaggt aaggttttttc gcgttgcatc   480
gaattaatcc acatcatcca ccgcttgtgc gggtccccgt caattccttt gagttttaat    540
cttgcgaccg tactcccag gcggtctact tcacgcgtta gctgcgttac caagtcaatt     600
aagacccgac aactagtaga catcgtttag ggcgtggant accagggtat ctaatcctgt    660
ttgctccnna cgctttcgtg catgancgtc agttttganc cnnggggctg ccttcgccat    720
cggngttcct ccncatatct                                                740
```

<210> SEQ ID NO 40
<211> LENGTH: 696
<212> TYPE: DNA
<213> ORGANISM: Agrobacterium fabrum
<220> FEATURE:
<221> NAME/KEY: misc_feature
<222> LOCATION: (1)..(696)
<223> OTHER INFORMATION: BCI 106 16S rDNA

<400> SEQUENCE: 40

```
ccttcgggta aaaccaactc ccatggtgtg acgggcggtg tgtacaaggc ccgggaacgt      60
attcaccgca gcatgctgat ctgcgattac tagcgattcc aacttcatgc actcgagttg     120
cagagtgcaa tccgaactga gatggctttt ggagattagc tcgacatcgc tgtctcgctg     180
cccactgtca ccaccattgt agcacgtgtg tagcccagcc cgtaagggcc atgaggactt     240
gacgtcatcc ccaccttcct ctcggcttat caccggcagt ccccttagag tgcccaacta     300
aatgctggca actaagggcg agggttgcgc tcgttgcggg acttaaccca acatctcacg     360
acacgagctg acgacagcca tgcagcacct gttctgggc cagcctaact gaaggacatc      420
gtctccaatg cccataccc gaatgtcaag agctggtaag gttctgcgcg ttgcttcgaa      480
ttaaaccaca tgctccaccg cttgtgcggg ccccgtcaa ttcctttgag ttttaatctt      540
gcgaccgtac tccccaggcg gaatgtttaa tgcgttagct gcgccaccga acagtatact     600
gcccgacggc taacattcat cgtttacggc gtggactacc agggtatcta atcctgtttg     660
ctccccacgc tttcgcacct cagcgtcagt aatgga                               696
```

<210> SEQ ID NO 41
<211> LENGTH: 752
<212> TYPE: DNA
<213> ORGANISM: Kosakonia radicincitans
<220> FEATURE:
<221> NAME/KEY: misc_feature
<222> LOCATION: (1)..(752)
<223> OTHER INFORMATION: BCI 107 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (557)..(558)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t

<400> SEQUENCE: 41

```
nctacctact tcttttgnna cccactccca tggtgtgacg ggcggtgtgt acaaggcccg      60
```

```
ggaacgtatt caccgtgaca ttctgattca cgattactag cgattccgac ttcatggagt    120
cgagttgcag actccaatcc ggactacgac gcactttatg aggtccgctt gctctcgcga    180
ggtcgcttct ctttgtatgc gccattgtag cacgtgtgta gccctggtcg taagggccat    240
gatgacttga cgtcatcccc accttcctcc agtttatcac tggcagtctc ctttgagttc    300
ccggcctaac cgctggcaac aaaggataag ggttgcgctc gttgcgggac ttaacccaac    360
atttcacaac acgagctgac gacagccatg cagcacctgt ctcacagttc ccgaaggcac    420
cccggcatct ctgccaggtt ctgtggatgt caagaccagg taaggttctt cgcgttgcat    480
cgaattaaac cacatgctcc accgcttgtg cgggccccg tcaattcatt tgagttttaa     540
ccttgcggcc gtactcnnca ggcggtcgat ttaacgcgtt agctccggaa gccacgcctc    600
aagggcacaa cctccaaatc gacatcgttt acggcgtgga ntaccagggt atctaatcct    660
gtttgctccc cacgctttcg cacctgancg tcagtcttcg tccnggangc cgccttcgcc    720
accngtattc ctccngatct ctangcattt ca                                  752
```

```
<210> SEQ ID NO 42
<211> LENGTH: 650
<212> TYPE: DNA
<213> ORGANISM: Bacillus oleronius
<220> FEATURE:
<221> NAME/KEY: misc_feature
<222> LOCATION: (1)..(650)
<223> OTHER INFORMATION: BCI 1071 16S rDNA

<400> SEQUENCE: 42
```

```
cttcgggtgt tacaaactct cgtggtgtga cgggcggtgt gtacaaggcc cgggaacgta     60
ttcaccgcgg catgctgatc cgcgattact agcgattccg gcttcatgta ggcgagttgc    120
agcctacaat ccgaactgag aatggtttta tgggattggc taaacctcgc ggtcttgcag    180 cccctttgtac catccattgt agcacgtgtg tagcccaggt cataagggc atgatgattt     240 gacgtcatcc ccaccttcct ccggtttgtc accggcagtc accttagagt gcccaactga    300
atgctggcaa ctaaggtcaa gggttgcgct cgttgcggga cttaacccaa catctcacga    360
cacgagctga cgacaaccat gcaccacctg tcactcctgt ccccgaaggg aaatccctat    420
ctctagggag gtcaagagga tgtcaagacc tggtaaggtt cttcgcgttg cttcgaatta    480
aaccacatgc tccaccgctt gtgcgggccc cgtcaattc ctttgagttt cagccttgcg     540
gccgtactcc ccaggcggag tgcttaatgc gttagctgca gcactaaagg gcggaaaccc    600
tctaacactt agcactcatc gtttacggcg tggactacca gggtatctaa                650
```

```
<210> SEQ ID NO 43
<211> LENGTH: 797
<212> TYPE: DNA
<213> ORGANISM: Bacillus subtilis
<220> FEATURE:
<221> NAME/KEY: misc_feature
<222> LOCATION: (1)..(797)
<223> OTHER INFORMATION: BCI 1089 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
```

```
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t

<400> SEQUENCE: 43
tttctnaant ntgatgngaa nnccccggc tcaaccgggg agggtcattg gaaactgggg      60
aactngagtg cagaagagga gagtggaatt ccacgtgtag cgntgaaatg cgtagagatg    120
tggaggaaca ccagtggcga aggcgactct ctggtctgta actgacgctg aggagcgaaa    180
gcgtggggag cgaacaggat tagataccct ggtagtccac gccgtaaacg atgagtgcta    240
agtgttaggg ggtttccgcc ccttagtgct gcagctaacg cattaagcac tccgcctggg    300
gagtacggtc gcaagactga aactcaaagg aattgacggg ggcccgcaca agcggtggag    360
catgtggttt aattcgaagc aacgcgaaga accttaccag gtcttgacat cctctgacaa    420
tcctagagat aggacgtccc cttcgggggc agagtgacag gtggtgcatg gttgtcgtca    480
gctcgtgtcg tgagatgttg ggttaagtcc cgcaacgagc gcaacccttg atcttagttg    540
ccagcattca gttgggcact ctaaggtgac tgccggtgac aaaccggagg aaggtgggga    600
tgacgtcaaa tcatcatgcc ccttatgacc tgggctacac acgtgctaca atggacagaa    660
caaagggcag cgaaaccgcg aggttaagcc aatcccacaa atctgttctc agttcggatc    720
gcagtctgca actcgactgc gtgaagctgg aatcgctagt aatcgcggat cagcatgccg    780
cggtgaatac gttcccg                                                  797

<210> SEQ ID NO 44
<211> LENGTH: 744
<212> TYPE: DNA
<213> ORGANISM: Chitinophaga terrae
<220> FEATURE:
<221> NAME/KEY: misc_feature
<222> LOCATION: (1)..(744)
<223> OTHER INFORMATION: BCI 109 16S rDNA
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (263)..(268)
<223> OTHER INFORMATION: n is a, c, g, or t
<220> FEATURE:
<221> NAME/KEY: misc_feature
<222> LOCATION: (291)..(294)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (680)..(680)
```

```
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (715)..(716)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t

<400> SEQUENCE: 44 gntcccccg gctttnntgg cttgacgggc ggtgtgtaca aggtccggga acgtattcac      60
cgtatcattg ctgatatacg attactagcg attccagctt catgaggtcg agttgcagac     120
ctcaatccga actgagatag agtttttgag attagcagca tgttaccatg tagcagccct    180
ttgtctctac cattgtagca cgtgtgtagc cctgggcata aaggccatga tgacttgaca    240
tcatcccctc cttcctcacg tcnnnnnncg gcagtttcac tagagttccc nnnnttacgc    300
gctggcaact agtgataggg gttgcgctcg ttgcgggact taacccaaca cctcacggca    360
cgagctgacg acagccatgc agcaccttac aatctgtgta ttgctacaaa gtgaactttc    420
atccacggtc agactgcatt ctagcccagg taaggttcct cgcgtatcat cgaattaaac    480
cacatgctcc accgcttgtg cggacccccg tcaattcctt tgagtttcaa ccttgcggtc    540
gtacttccca ggtgggatac ttaatgcttt cgctcagaca cttacaatat atcgcaaatg    600
tcgagtatcc atcgtttagg gcgtgganta ccagggtatc taatcctgtt tgatccccac    660
gctttcgtgc ctcagcgtcn atagttgtgt agccngctgc cttcncnatc ggngnnctat    720
gtcatatctn ancntttcac ngct                                           744

<210> SEQ ID NO 45
<211> LENGTH: 689
<212> TYPE: DNA
<213> ORGANISM: Stenotrophomonas maltophilia
<220> FEATURE:
<221> NAME/KEY: misc_feature
<222> LOCATION: (1)..(689)
<223> OTHER INFORMATION: BCI 1092 16S rDNA
<220> FEATURE:
<221> NAME/KEY: misc_feature
<222> LOCATION: (5)..(5)
<223> OTHER INFORMATION: n is a, c, g, or t
```

```
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(52)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (85)..(86)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t

<400> SEQUENCE: 45
gtagngatcn ggaggaacnt ccanggngan ggcagctncn nggaccancn nngacantga    60
gncnngaaag cgtgggagc aaacnngatn agataccntg gtagtccacn ccctaaacga   120
```

```
tgcgaanngg atgttgggtg caatttggca cgcagtatng aagctaacgc gttaagttcg    180
ccgcctgggg agtacggtcg caagactgaa actcaaagga attgacgggg gcccgcacaa    240
gcggtggagt atgtggttta attcgatgca acgcgaagaa ccttacctgg ccttgacatg    300
tcgagaactt tccagagatg gattggtgcc ttcgggaact cgaacacagg tgctgcatgg    360
ctgtcgtcag ctcgtgtcgt gagatgttgg gttaagtccc gcaacgagcg caacccttgt    420
ccttagttgc cagcacgtaa tggtgggaac tctaaggaga ccgccggtga caaaccggag    480
gaaggtgggg atgacgtcaa gtcatcatgg cccttacggc cagggctaca cacgtactac    540
aatggtaggg acagagggct gcaagccggc gacggtaagc caatcccaga aaccctatct    600
cagtccggat tggagtctgc aactcgactc catgaagtcg gaatcgctag taatcgcaga    660
tcagcattgc tgcggtgaat acgttcccg                                      689
```

```
<210> SEQ ID NO 46
<211> LENGTH: 800
<212> TYPE: DNA
<213> ORGANISM: Stenotrophomonas maltophilia
<220> FEATURE:
<221> NAME/KEY: misc_feature
<222> LOCATION: (1)..(800)
<223> OTHER INFORMATION: BCI 1096 16S rDNA
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
```

<222> LOCATION: (239)..(239)
<223> OTHER INFORMATION: n is a, c, g, or t

<400> SEQUENCE: 46

| | | | | | |
|---|---|---|---|---|---|
| ttatttaant | ncnntgtgaa | anccctggnc | tcnacnnggg | aactgcagtg | gatacnggat | 60 |
| gactagaatg | tggtagaggg | tagcggantt | cctggtgtag | cagtgaantg | cgtagagatc | 120 |
| aggaggaaca | tccanggcga | aggcagctac | ctggaccaac | attgacactg | aggcacgaaa | 180 |
| gcgtggggag | caaacaggat | tagataccct | ggtagtccac | gccctnaacg | atgcgaacng | 240 |
| gatgttgggt | gcaatttggc | acgcagtatc | gaagctaacg | cgttaagttc | gccgcctggg | 300 |
| gagtacggtc | gcaagactga | aactcaaagg | aattgacggg | ggcccgcaca | agcggtggag | 360 |
| tatgtggttt | aattcgatgc | aacgcgaaga | accttacctg | gccttgacat | gtcgagaact | 420 |
| ttccagagat | ggattggtgc | cttcgggaac | tcgaacacag | gtgctgcatg | gctgtcgtca | 480 |
| gctcgtgtcg | tgagatgttg | ggttaagtcc | cgcaacgagc | gcaacccttg | tccttagttg | 540 |
| ccagcacgta | atggtgggaa | ctctaaggag | accgccggtg | acaaaccgga | ggaaggtggg | 600 |
| gatgacgtca | agtcatcatg | gcccttacgg | ccagggctac | acacgtacta | caatggtagg | 660 |
| gacagagggc | tgcaagccgg | cgacggtaag | ccaatcccag | aaaccctatc | tcagtccgga | 720 |
| ttggagtctg | caactcgact | ccatgaagtc | ggaatcgcta | gtaatcgcag | atcagcattg | 780 |
| ctgcggtgaa | tacgttcccg | | | | | 800 |

<210> SEQ ID NO 47
<211> LENGTH: 800
<212> TYPE: DNA
<213> ORGANISM: Agrobacterium fabrum
<220> FEATURE:
<221> NAME/KEY: misc_feature
<222> LOCATION: (1)..(800)
<223> OTHER INFORMATION: BCI 11 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (534)..(535)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (742)..(743)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:

```
<221> NAME/KEY: misc_feature
<222> LOCATION: (766)..(766)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t

<400> SEQUENCE: 47
tgnctccttg cggtnngcgn actaccttcg ggtaaaacca actcccatgg tgtgncgggc    60
ggtgtgtaca aggcccggga acgtattcac cgcagcatgc tgatctgcga ttactagcga   120
ttccaacttc atgcactcga gttgcagagt gcaatccgaa ctgagatggc ttttggagat   180
tagctcgaca tcgctgtctc gctgcccact gtcaccacca ttgtagcacg tgtgtagccc   240
agcccgtaag ggccatgagg acttgacgtc atccccacct tcctctcggc ttatcaccgg   300
cagtcccctt agagtgccca actaaatgct ggcaactaag ggcgagggtt gcgctcgttg   360
cgggacttaa cccaacatct cacgacacga gctgacgaca gccatgcagc acctgttctg   420
gggccagcct aactgaagga catcgtctcc aatgcccata ccccgaatgt caagagctgg   480
taaggttctg cgcgttgctt cgaattaaac cacatgctcc accgcttgtg cggnncccg    540 tcaattcctt tgagttttaa tcttgcgacc gtactcccca ggcggaatgt taatgcgtt    600 agctgcgcca ccgaacagta tactgcccga cggctaacat ncatcgttta cggcgtggac   660
taccagggta tctaatcctg tttgctcccc acgctttcgc acctcagcgt cagtaatgga   720
ncagtaagcc gccttcgcca cnngtgtncc tccgaatatc tacganttc acctctacac    780 tcggnattcc acttncctct                                               800

<210> SEQ ID NO 48
<211> LENGTH: 740
<212> TYPE: DNA
<213> ORGANISM: Sinorhizobium chiapanecum
<220> FEATURE:
<221> NAME/KEY: misc_feature
<222> LOCATION: (1)..(740)
<223> OTHER INFORMATION: BCI 111 16S rDNA

<400> SEQUENCE: 48
ctccttgcgg ttagcgcact accttcgggt aaaaccaact cccatggtgt gacgggcggt    60
gtgtacaagg cccgggaacg tattcaccgc ggcatgctga tccgcgatta ctagcgattc   120
caacttcatg cactcgagtt gcagagtgca atccgaactg agatggcttt tggagattag   180
ctcacactcg cgtgctcgct gcccactgtc accaccattg tagcacgtgt gtagcccagc   240
ccgtaagggc catgaggact tgacgtcatc cccaccttcc tctcggctta tcaccggcag   300
tccccttaga gtgcccaact gaatgctggc aactaagggc gagggttgcg ctcgttgcgg   360
gacttaaccc aacatctcac gacacgagct gacgacagcc atgcagcacc tgtctccggt   420
ccagccgaac tgaaggaaaa catctctgta atccgcgacc gggatgtcaa gggctggtaa   480
ggttctgcgc gttgcttcga attaaaccac atgctccacc gcttgtgcgg ccccgtca     540 attcctttga gttttaatct tgcgaccgta ctccccaggc ggaatgttta atgcgttagc   600
tgcgccaccg aacagtatac tgcccgacgg ctaacattca tcgtttacgg cgtggactac   660
cagggtatct aatcctgttt gctccccacg ctttcgcacc tcagcgtcag taatggacca   720
gtgagccgcc ttcgccactg                                               740
```

<210> SEQ ID NO 49
<211> LENGTH: 768
<212> TYPE: DNA
<213> ORGANISM: Bosea thiooxidans
<220> FEATURE:
<221> NAME/KEY: misc_feature
<222> LOCATION: (1)..(768)
<223> OTHER INFORMATION: BCI 1111 16S rDNA

<400> SEQUENCE: 49

```
gcgcgacgcc ttcgggtaaa cccaactccc atggtgtgac gggcggtgtg tacaaggccc    60
gggaacgtat tcaccgtggc atgctgatcc acgattacta gcgattccac cttcatgtac   120
tcgagttgca gagtacaatc tgaactgaga cggcttttg ggattagctc caggtcaccc   180
cttcgctgcc cattgtcacc gccattgtag cacgtgtgta gcccagcctg taagggccat   240
gaggacttga cgtcatcccc accttcctcg cggcttatca ccggcagtcc ccctagagtt   300
cccaactgaa tgatggcaac taggggcgag ggttgcgctc gttgcgggac ttaacccaac   360
atctcacgac acgagctgac gacagccatg cagcacctgt gttccggcca gccgaactga   420
agaaaggcat ctctgccgat caaaccggac atgtcaaaag ctggtaaggt tctgcgcgtt   480
gcttcgaatt aaaccacatg ctccaccgct tgtgcgggcc cccgtcaatt cctttgagtt   540
ttaatcttgc gaccgtactc cccaggcgga atgcttaaag cgttagctgc gccactgaag   600
agcaagctcc ccaacggctg gcattcatcg tttacggcgt ggactaccag ggtatctaat   660
cctgtttgct ccccacgctt tcgcgcctca gcgtcagtat cggaccagtt ggccgccttc   720
gccaccggtg ttcttgcgaa tatctacgaa tttcacctct acactcgc               768
```

<210> SEQ ID NO 50
<211> LENGTH: 708
<212> TYPE: DNA
<213> ORGANISM: Stenotrophomonas maltophilia
<220> FEATURE:
<221> NAME/KEY: misc_feature
<222> LOCATION: (1)..(708)
<223> OTHER INFORMATION: BCI 1116 16S rDNA
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (56)..(58)
<223> OTHER INFORMATION: n is a, c, g, or t
<220> FEATURE:
<221> NAME/KEY: misc_feature
<222> LOCATION: (62)..(67)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (129)..(129)

<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t

<400> SEQUENCE: 50

```
ggtgtagcag tgaantgcgt agagatcagg aggaacatcc atngcgaagg cagntnnntg    60
gnnnnnncat tgacantgag gcacgaaagc gtggggagca acaggatta gataccntgg    120
tagtccacnc cctnaacgat gcgaactgga tgttgggtgc aatttggcac gcagtatnga   180
agctaacgcg ttaagttcgc cgcntgggga gtacggtcgc aagactgaaa ctcaaaggaa   240
ttgacggggg cccgcacaag cggtggagta tgtggtttan ttcgatgcaa cgcgaagaac   300
cttacctggc cttgacatgt cgagaacttt ccagagatgg attggtgcct tcgggaactc   360
gaacacaggt gctgcatggc tgtcgtcagc tcgtgtcgtg agatgttggg ttaagtcccg   420
caacgagcgc aaccctttgtc cttagttgcc agcacgtaat ggtgggaact ctaaggagac   480
cgccggtgac aaaccggagg aaggtgggga tgacgtcaag tcatcatggc ccttacggcc   540
agggctacac acgtactaca atggtaggga cagagggctg caagccggcg acggtaagcc   600
aatcccagaa accctatctc agtccggatt ggagtctgca actcgactcc atgaagtcgg   660
aatcgctagt aatcgcagat cagcattgct gcggtgaata cgttcccg                708
```

<210> SEQ ID NO 51
<211> LENGTH: 827
<212> TYPE: DNA
<213> ORGANISM: Paenibacillus polymyxa
<220> FEATURE:
<221> NAME/KEY: misc_feature
<222> LOCATION: (1)..(827)
<223> OTHER INFORMATION: BCI 1118 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature

```
<222> LOCATION: (35)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (159)..(160)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (460)..(462)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
```

<400> SEQUENCE: 51

```
ttattnggng taanncgcgc gcnggngnct ctttnantnt gnngtttann cccgaggctc      60
aanttcgggt cgcactggaa actggggagc ttgagtgcag aagaggagag tgganttcca     120
cgtgtagcgg tgaaatgcgt agagatgtgg aggaacacnn gtggcgaagg ngactctctg     180
ggctgtaact gacgctgagg cgcgaaagcg tggggagcaa acaggattag ataccctgnt     240
agtccacgcc gtaaacgatg aatgctaggt gttaggggtt tcgatacccct tggtgccgaa    300 gttaacacat tnagcattcc gcntggggag tacggtcgca agactgaaac tcaaaggaat    360
tgacggggac ccgcacaagc agtggagtat gtggtttaat tngaagcaac gcgaagancc     420
ttaccaggtc ttgacatccc tctgaccgct gtagagatan nnctttcctt cgggacagag    480
gagacaggtg gtgcatggtt gtcgtcagct cgtgtcgtga gatgttgggt taagtcccgc     540
aacgagcgca acccttatgc ttagttgcca gcaggtcaag ctgggcactc taagcagact    600
gccggtgaca aaccggagga aggtggggat gacgtcaaat catcatgccc cttatgacnt    660
gggctacaca cgtactacaa tggccggtac aacgggaagn gaaancncga ggtggagcca    720
atcctagaaa anccggtctc agttcggatt gtaggctgca actcgcctac atgaagtcgg    780
aattgctagt aatcgcggat cagcatgccg cggtgaatac gttcccg                  827
```

```
<210> SEQ ID NO 52
<211> LENGTH: 761
<212> TYPE: DNA
<213> ORGANISM: Stenotrophomonas maltophilia
<220> FEATURE:
<221> NAME/KEY: misc_feature
<222> LOCATION: (1)..(761)
<223> OTHER INFORMATION: BCI 115 16S rDNA
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(700)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
```

```
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (734)..(737)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t

<400> SEQUENCE: 52
cctgcttctg gtgnaacaaa ctcccatggt gtgacgggcg gtgtgtacaa ggcccgggaa    60
cgtattcacc gcagcaatgc tgatctgcga ttactagcga ttccgacttc atggagtcga   120
gttgcagact ccaatccgga ctgagatagg gtttctggga ttggcttacc gtcgccggct   180
tgcagccctc tgtccctacc attgtagtac gtgtgtagcc ctggccgtaa gggccatgat   240
gacttgacgt catccccacc ttcctccggt ttgtcaccgg cggtctcctt agagttccca   300
ccattacgtg ctggcaacta aggacaaggg ttgcgctcgt tgcgggactt aacccaacat   360
ctcacgacac gagctgacga cagccatgca gcacctgtgt tcgagttccc gaaggcacca   420
atccatctct ggaaagttct cgacatgtca aggccaggta aggttcttcg cgttgcatcg   480
aattaaacca catactccac cgcttgtgcg ggccccgtc aattcctttg agtttcagtc    540
ttgcgaccgt actccccagg cggcgaactt aacgcgttag cttcgatact gcgtgccaaa   600
ttgcacccaa catccagttc gcatcgntta gggcgtggac taccagggta tctaatcctg   660
tttgctcccc acgctttcnt gcctcantgt cagtgntgnn ccangtagct gccttcgccn   720
tgnangtncc tccnnnnctc tacgnatttn actgctacnc c                       761

<210> SEQ ID NO 53
<211> LENGTH: 821
<212> TYPE: DNA
<213> ORGANISM: Mucilaginibacter gossypii
<220> FEATURE:
<221> NAME/KEY: misc_feature
<222> LOCATION: (1)..(821)
<223> OTHER INFORMATION: BCI 1156 16S rDNA

<400> SEQUENCE: 53
ttattgggtt taaagggtgc gtaggcggct ttttaagtca ggggtgaaag acggtagctc    60
aactatcgca gtgcccttga tactgaagag cttgaatgta cttgaggtag gcggaatgtg   120
acaagtagcg gtgaaatgca tagatatgtc acagaacacc aattgcgaag gcagcttact   180
aaagtatgat tgacgctgag gcacgaaagc gtggggatca acaggatta gataccctgg    240 tagtccacgc cctaaacgat gaacactcga tgttggcgat atacggtcag cgtctaagcg   300
aaagcgttaa gtgttccacc tggggagtac gcccgcaagg gtgaaactca aggaattga    360 cgggggcccg cacaagcgga ggagcatgtg gtttaattcg atgatacgcg aggaaccttac  420 cccgggcttg aaagttagtg aatgtgacag agacgtcaca gttcttcgga acacgaaact   480
aggtgctgca tggctgtcgt cagctcgtgc cgtgaggtgt tgggttaagt cccgcaacga   540
```

```
gcgcaaccccc tatgtttagt tgccagcatt taaggtgggg actctaaaca gactgcctat    600
gcaaatagag aggaaggagg ggacgacgtc aagtcatcat ggcccttacg tccggggcta    660
cacacgtgct acaatggatg gtacagaggg cagctacctg gcaacaggat gccaatctct    720
taaagccatt cacagttcgg atcggggtct gcaactcgac cccgtgaagt tggattcgct    780
agtaatcgcg tatcagcaat gacgcggtga atacgttccc g                        821

<210> SEQ ID NO 54
<211> LENGTH: 826
<212> TYPE: DNA
<213> ORGANISM: Rahnella aquatilis
<220> FEATURE:
<221> NAME/KEY: misc_feature
<222> LOCATION: (1)..(826)
<223> OTHER INFORMATION: BCI 1158 16S rDNA
<220> FEATURE:
<221> NAME/KEY: misc_feature
<222> LOCATION: (50)..(50)
<223> OTHER INFORMATION: n is a, c, g, or t

<400> SEQUENCE: 54
ttactgggcg taaagcgcac gcaggcggtt tgttaagtca gatgtgaaan ccccgcgctt     60
aacgtgggaa ctgcatttga aactggcaag ctagagtctt gtagaggggg gtagaattcc    120
aggtgtagcg gtgaaatgcg tagagatctg gaggaatacc ggtggcgaag gcggccccct    180
ggacaaagac tgacgctcag gtgcgaaagc gtggggagca acaggatta gataccctgg     240 tagtccacgc tgtaaacgat gtcgacttgg aggttgtgcc cttgaggcgt ggcttccgga    300
gctaacgcgt taagtcgacc gcctggggag tacggccgca aggttaaaac tcaaatgaat    360 tgacggggc ccgcacaagc ggtggagcat gtggtttaat tcgatgcaac gcgaagaacc     420
ttacctactc ttgacatcca cggaattcgc cagagatggc ttagtgcctt cgggaaccgt    480
gagacaggtg ctgcatggct gtcgtcagct cgtgttgtga atgttgggt taagtcccgc    540 aacgagcgca accctatcc tttgttgcca gcacgtaatg gtgggaactc aaaggagact    600
gccggtgata accggagga aggtggggat gacgtcaagt catcatggcc cttacgagta    660
gggctacaca cgtgctacaa tggcatatac aaagagaagc gaactcgcga gagcaagcgg    720
acctcataaa gtatgtcgta gtccggattg gagtctgcaa ctcgactcca tgaagtcgga    780
atcgctagta atcgtagatc agaatgctac ggtgaatacg ttcccg                    826

<210> SEQ ID NO 55
<211> LENGTH: 705
<212> TYPE: DNA
<213> ORGANISM: Exiguobacterium sibiricum
<220> FEATURE:
<221> NAME/KEY: misc_feature
<222> LOCATION: (1)..(705)
<223> OTHER INFORMATION: BCI 116 16S rDNA

<400> SEQUENCE: 55
cctcaccggc ttcgggtgtt gcaaactctc gtggtgtgac gggcggtgtg tacaagaccc     60
gggaacgtat tcaccgcagt atgctgacct gcgattacta gcgattccga cttcatgcag    120
gcgagttgca gcctgcaatc cgaactggga acggctttct gggattggct ccacctcgcg    180
gtctcgctgc cctttgtacc gtccattgta gcacgtgtgt agcccaactc ataaggggca    240
tgatgatttg acgtcatccc caccttcctc cggtttgtca ccggcagtct ccctagagtg    300
cccaactaaa tgctggcaac taaggatagg ggttgcgctc gttgcgggac ttaacccaac    360
atctcacgac acgagctgac gacaaccatg caccacctgt cacccttgtc ccgaaggga     420
```

```
aaacttgatc tctcaagcgg tcaaggggat gtcaagagtt ggtaaggttc ttcgcgttgc    480
ttcgaattaa accacatgct ccaccgcttg tgcgggtccc cgtcaattcc tttgagtttc    540
agccttgcgg ccgtactccc caggcggagt gcttaatgcg ttagcttcag cactgagggg    600
cggaaacccc ccaacaccta gcactcatcg tttacggcgt ggactaccag ggtatctaat    660
cctgtttgct ccccacgctt tcgcgcctca gcgtcagtta cagac                    705
```

<210> SEQ ID NO 56
<211> LENGTH: 705
<212> TYPE: DNA
<213> ORGANISM: Exiguobacterium sibiricum
<220> FEATURE:
<221> NAME/KEY: misc_feature
<222> LOCATION: (1)..(705)
<223> OTHER INFORMATION: BCI 116 16S rDNA

<400> SEQUENCE: 56

```
cctcaccggc ttcgggtgtt gcaaactctc gtggtgtgac gggcggtgtg tacaagaccc     60
gggaacgtat tcaccgcagt atgctgacct gcgattacta gcgattccga cttcatgcag    120
gcgagttgca gcctgcaatc cgaactggga acggctttct gggattggct ccacctcgcg    180
gtctcgctgc cctttgtacc gtccattgta gcacgtgtgt agcccaactc ataaggggca    240
tgatgatttg acgtcatccc caccttcctc cggtttgtca ccggcagtct ccctagagtg    300
cccaactaaa tgctggcaac taaggatagg ggttgcgctc gttgcgggac ttaacccaac    360
atctcacgac acgagctgac gacaaccatg caccacctgt cacccttgtc cccgaaggga    420
aaacttgatc tctcaagcgg tcaaggggat gtcaagagtt ggtaaggttc ttcgcgttgc    480
ttcgaattaa accacatgct ccaccgcttg tgcgggtccc cgtcaattcc tttgagtttc    540
agccttgcgg ccgtactccc caggcggagt gcttaatgcg ttagcttcag cactgagggg    600
cggaaacccc ccaacaccta gcactcatcg tttacggcgt ggactaccag ggtatctaat    660
cctgtttgct ccccacgctt tcgcgcctca gcgtcagtta cagac                    705
```

<210> SEQ ID NO 57
<211> LENGTH: 743
<212> TYPE: DNA
<213> ORGANISM: Rhodococcus erythropolis
<220> FEATURE:
<221> NAME/KEY: misc_feature
<222> LOCATION: (1)..(743)
<223> OTHER INFORMATION: BCI 1182 16S rDNA

<400> SEQUENCE: 57

```
ccggcttcgg gtgttaccga cttcatgac gtgacgggcg gtgtgtacaa ggcccgggaa      60
cgtattcacc gcagcgttgc tgatctgcga ttactagcga ctccgacttc acggggtcga    120
gttgcagacc ccgatccgaa ctgagaccag ctttaaggga ttcgctccac ctcacggtct    180
cgcagccctc tgtactggcc attgtagcat gtgtgaagcc ctggacataa ggggcatgat    240
gacttgacgt cgtccccacc ttcctccgag ttgaccccgg cagtctctta cgagtcccca    300
ccataacgtg ctggcaacat aagataggg ttgcgctcgt tgcgggactt aacccaacat    360
ctcacgacac gagctgacga cagccatgca ccacctgtat accgaccaca aggggggcca    420
catctctgca gctttccggt atatgtcaaa cccaggtaag gttcttcgcg ttgcatcgaa    480
ttaatccaca tgctccgccg cttgtgcggg ccccgtcaa ttcctttgag ttttagcctt    540
gcggccgtac tccccaggcg gggcgcttaa tgcgttagct acggcacgga ttccgtggaa    600
```

| | |
|---|---|
| ggaacccaca cctagcgccc accgtttacg gcgtggacta ccagggtatc taatcctgtt | 660 |
| cgctacccac gctttcgttc ctcagcgtca gttactgccc agagacccgc cttcgccacc | 720 |
| ggtgttcctc ctgatatctg cgc | 743 |

<210> SEQ ID NO 58
<211> LENGTH: 826
<212> TYPE: DNA
<213> ORGANISM: Pseudomonas oryzihabitans
<220> FEATURE:
<221> NAME/KEY: misc_feature
<222> LOCATION: (1)..(826)
<223> OTHER INFORMATION: BCI 1184 16S rDNA
<220> FEATURE:
<221> NAME/KEY: misc_feature
<222> LOCATION: (40)..(40)
<223> OTHER INFORMATION: n is a, c, g, or t

<400> SEQUENCE: 58

| | |
|---|---|
| ttactgggcg taaagcgcgc gtaggtggct tgataagttn gatgtgaaat ccccgggctc | 60 |
| aacctgggaa ctgcatccaa aactgtctgg ctagagtgcg gtagagggta gtggaatttc | 120 |
| cagtgtagcg gtgaaatgcg tagatattgg aaggaacacc agtggcgaag gcgactacct | 180 |
| ggactgacac tgacactgag gtgcgaaagc gtggggagca acaggatta gataccctgg | 240 |
| tagtccacgc cgtaaacgat gtcaactagc cgttgggatc cttgagatct tagtggcgca | 300 |
| gctaacgcat taagttgacc gcctggggag tacggccgca aggttaaaac tcaaatgaat | 360 |
| tgacggggc ccgcacaagc ggtggagcat gtggtttaat tcgaagcaac gcgaagaacc | 420 |
| ttacctggcc ttgacatgct gagaactttc cagagatgga ttggtgcctt cgggaactca | 480 |
| gacacaggtg ctgcatggct gtcgtcagct cgtgtcgtga gatgttgggt taagtcccgt | 540 |
| aacgagcgca acccttgtcc ttagttacca gcacgttatg gtgggcactc taaggagact | 600 |
| gccggtgaca aaccggagga aggtggggat gacgtcaagt catcatggcc cttacggcca | 660 |
| gggctacaca cgtgctacaa tggtcggtac aaagggttgc caagccgcga ggtggagcta | 720 |
| atcccataaa accgatcgta gtccggatcg cagtctgcaa ctcgactgcg tgaagtcgga | 780 |
| atcgctagta atcgtgaatc agaacgtcac ggtgaatacg ttcccg | 826 |

<210> SEQ ID NO 59
<211> LENGTH: 713
<212> TYPE: DNA
<213> ORGANISM: Pseudomonas oryzihabitans
<220> FEATURE:
<221> NAME/KEY: misc_feature
<222> LOCATION: (1)..(713)
<223> OTHER INFORMATION: BCI 1195 16S rDNA

<400> SEQUENCE: 59

| | |
|---|---|
| ggttagacta gctacttctg gagcaaccca ctcccatggt gtgacgggcg gtgtgtacaa | 60 |
| ggcccgggaa cgtattcacc gtgacgttct gattcacgat tactagcgat tccgacttca | 120 |
| cgcagtcgag ttgcagactg cgatccggac tacgatcggt tttatgggat tagctccacc | 180 |
| tcgcggcttg gcaacccttt gtaccgacca ttgtagcacg tgtgtagccc tggccgtaag | 240 |
| ggccatgatg acttgacgtc atccccacct tcctccggtt tgtcaccggc agtctcctta | 300 |
| gagtgcccac cataacgtgc tggtaactaa ggacaagggt tgcgctcgtt acgggactta | 360 |
| acccaacatc tcacgacacg agctgacgac agccatgcag cacctgtgtc tgagttcccg | 420 |
| aaggcaccaa tccatctctg gaaagttctc agcatgtcaa ggcaggtaa ggttcttcgc | 480 |
| gttgcttcga attaaaccac atgctccacc gcttgtgcgg gccccgtca attcatttga | 540 |

| | | |
|---|---|---|
| gttttaacct tgcggccgta ctccccaggc ggtcaactta atgcgttagc tgcgccacta | 600 | |
| agatctcaag gatcccaacg gctagttgac atcgtttacg gcgtggacta ccagggtatc | 660 | |
| taatcctgtt tgctccccac gctttcgcac ctcagtgtca gtgtcagtcc agg | 713 | |

<210> SEQ ID NO 60
<211> LENGTH: 826
<212> TYPE: DNA
<213> ORGANISM: Pseudomonas oryzihabitans
<220> FEATURE:
<221> NAME/KEY: misc_feature
<222> LOCATION: (1)..(826)
<223> OTHER INFORMATION: BCI 1199 16S rDNA
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t

<400> SEQUENCE: 60

| | |
|---|---|
| tnnctgggcg taaagcgcgc gtaggtggct tgataagtng gatgtgaaat ccccgggctc | 60 |
| aacctgggaa ctgcatccaa aactntctgg ctagagtgcg gtagagggta gtggaatttc | 120 |
| cagtgtagcg gtgaaatgcg tagatattgg aaggaacacc agtggcgaag gcgactacct | 180 |
| ggactgacac tgacactgag gtgcgaaagc gtggggagca acaggatta gataccctgg | 240 |
| tagtccacgc cgtaaacgat gtcaactagc cgttgggatc cttgagatct tagtggcgca | 300 |
| gctaacgcat taagttgacc gcctggggag tacgccgca aggttaaaac tcaaatgaat | 360 |
| tgacggggc ccgcacaagc ggtggagcat gtggtttaat tcgaagcaac gcgaagaacc | 420 |
| ttacctggcc ttgacatgct gagaactttc cagagatgga ttggtgcctt cgggaactca | 480 |
| gacacaggtg ctgcatggct gtcgtcagct cgtgtcgtga gatgttgggt taagtcccgt | 540 |
| aacgagcgca acccttgtcc ttagttacca gcacgttatg gtgggcactc taaggagact | 600 |
| gccggtgaca aaccggagga aggtggggat gacgtcaagt catcatggcc cttacggcca | 660 |
| gggctacaca cgtgctacaa tggtcggtac aaagggttgc caagccgcga ggtggagcta | 720 |
| atcccataaa accgatcgta gtccggatcg cagtctgcaa ctcgactgcg tgaagtcgga | 780 |
| atcgctagta atcgtgaatc agaacgtcac ggtgaatacg ttcccg | 826 |

<210> SEQ ID NO 61
<211> LENGTH: 741
<212> TYPE: DNA
<213> ORGANISM: Stenotrophomonas maltophilia
<220> FEATURE:
<221> NAME/KEY: misc_feature
<222> LOCATION: (1)..(741)
<223> OTHER INFORMATION: BCI 120 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (161)..(161)

```
<223> OTHER INFORMATION: n is a, c, g, or t
<220> FEATURE:
<221> NAME/KEY: misc_feature
<222> LOCATION: (523)..(524)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (725)..(726)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t

<400> SEQUENCE: 61
ncctgcttct ggtgnaacaa actcccatgg tgtgacgggc ggtgtgtaca aggcccggga    60
acgtattcac cgcagcaatg ctgatctgcg attactagcg attccgactt catggagtcg   120
agttgcagac tccaatccgg actgagatgg ggtttctggg nttggcttac cgtcgccggc   180
ttgcagccct ctgtccccac cattgtagta cgtgtgtagc cctggccgta agggccatga   240
tgacttgacg tcatccccac cttcctccgg tttgtcaccg gcggtctcct tagagttccc   300
accattacgt gctggcaact aaggacaagg gttgcgctcg ttgcgggact taacccaaca   360
tctcacgaca cgagctgacg acagccatgc agcacctgtg ttcgagttcc gaaggcacc    420 aatccatctc tggaaagttc tcgacatgtc aaggccaggt aaggttcttc gcgttgcatc   480
gaattaaacc acatactcca ccgcttgtgc gggcccccgt canntccttt gagtttcagt   540
cttgcgaccg tactcccag gcggcgaact taacgcgtta gcttcgatac tgcgtgccaa    600
attgcaccca acatccagtt cgcatcgttt anggcgtgga ntaccanggt atctaatcct   660
gtttgctccc cacgctttcg tgcctcantg tcagtgttgg nccnngtagc tgccttcncc   720
ntggnngtnc ctcccganct c                                             741
```

<210> SEQ ID NO 62
<211> LENGTH: 830
<212> TYPE: DNA
<213> ORGANISM: Pantoea agglomerans
<220> FEATURE:
<221> NAME/KEY: misc_feature
<222> LOCATION: (1)..(830)
<223> OTHER INFORMATION: BCI 1208 16S rDNA
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (96)..(97)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t

<400> SEQUENCE: 62

```
ggaattactg ggcgtaaagc gcacgcnggc ggtctgttaa gtcagatgtg aaatccccgg    60
gcttaacntg ggaactgcat ttgaaactgg caggcnngag tcttgtagan ggggtagaa   120
ttccaggtgt agcggtgaaa tgcgtagaga tctggaggaa taccggtggc gaaggcggcc   180
ccctggacaa agactgacgc tcaggtgcga aagcgtgggg agcaaacagg attagatacc   240
ctggtagtcc acgccgtaaa cgatgtcgac ttggaggttg ttcccttgag gagtggcttc   300
cggagctaac gcgttaagtc gaccgcctgg ggagtacggc cgcaaggtta aaactcaaat   360
gaattgacgg gggcccgcac aagcggtgga gcatgtggtt taattcgatg caacgcgaag   420
aaccttacct actcttgaca tccacggaat ttggcagaga tgcnttagtg ccttcgggaa   480
ccgtgagaca ggtgctgcat ggctgtcgtc agctcgtgtt gtgaaatgtt gggttaagtc   540
ccgcaacgag cgcaaccctt atcctttgtt gccagcgatt cggtcgggaa ctcaaaggag   600
actgccggtg ataaaccgga ggaaggtggg gatgacgtca agtcatcatg gcccttacga   660
gtagggctac acacgtgcta caatggcgca tacaaagaga gcgacctcg cgagagcaag   720
cggacctcac aaagtgcgtc gtagtccgga tcggagtctg caactcgact ccgtgaagtc   780
ggaatcgcta gtaatcgtgg atcagaatgc cacggtgaat acgttcccgg              830
```

<210> SEQ ID NO 63
<211> LENGTH: 825
<212> TYPE: DNA
<213> ORGANISM: Massilia niastensis
<220> FEATURE:
<221> NAME/KEY: misc_feature
<222> LOCATION: (1)..(825)
<223> OTHER INFORMATION: BCI 1217 16S rDNA
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (41)..(41)

```
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t

<400> SEQUENCE: 63
gnaattactg ggcgtaaagc gtgcgcnggc ggttttgtaa ntctgacgtg aannccccgg    60
gctcaacctg ggaantgcgt tggagactgc aaggctggag tctggcagag ggggtagaa   120 ttccacgtgt agcagtgaaa tgcgtagaga tgtggaggaa caccgatggc gaaggcagcc   180
ccctgggtca agactgacgc tcatgcacga aagcgtgggg agcaaacagg attagatacc   240
ctggtagtcc acgccctaaa cgatgtctac tagttgtcgg gtcttaattg acttggtaac   300
gcagctaacg cgtgaagtag accgcctggg gagtacggtc gcaagattaa aactcaaagg   360
aattgacggg gacccgcaca agcggtggat gatgtggatt aattcgatgc aacgcgaaaa   420
accttaccta cccttgacat gtcaggaatc ctcgagagat ngnggagtgc ccgaaaggga   480
gcctgaacac aggtgctgca tggctgtcgt cagctcgtgt cgtgagatgt tgggttaagt   540
cccgcaacga gcgcaacccct tgtcattagt tgctacgaaa gggcactcta atgagactgc   600
cggtgacaaa ccggaggaag gtggggatga cgtcaagtcc tcatggccct tatgggtagg   660
gcttcacacg tcatacaatg gtacatacag agggccgcca acccgcgagg gggagctaat   720
cccagaaagt gtatcgtagt ccggatcgca gtctgcaact cgactgcgtg aagttggaat   780
cgctagtaat cgcggatcag catgccgcgg tgaatacgtt cccgg                   825

<210> SEQ ID NO 64
<211> LENGTH: 369
<212> TYPE: DNA
<213> ORGANISM: Stenotrophomonas maltophilia
<220> FEATURE:
<221> NAME/KEY: misc_feature
<222> LOCATION: (1)..(369)
<223> OTHER INFORMATION: BCI 1224 16S rDNA
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
```

```
<222> LOCATION: (97)..(97)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t

<400> SEQUENCE: 64
attggtgcct tngggaactn gaanacaggt gctgcatggc ngtcgtcagc tcgtgtcntg    60
agatgttggg ttaagtcccg caacgagcgc aaccctngtc cttagtnncc agcacgtaat   120
ggtgggaact ctaaggagac cgccggtgac aaaccggagg aaggtgggga tgacgtcaag   180
tcatcatggc ccttacggcc agggctacac acgtactaca atggtgggga cagagggctg   240
caagccggcg acggtaagcc aatcccagaa accccatctc agtccggatt ggagtctgca   300
actcgactcc atgaagtcgg aatcgctagt aatcgcagat cagcattgct gcggtgaata   360
cgttcccgg                                                          369

<210> SEQ ID NO 65
<211> LENGTH: 619
<212> TYPE: DNA
<213> ORGANISM: Delftia lacustris
<220> FEATURE:
<221> NAME/KEY: misc_feature
<222> LOCATION: (1)..(619)
<223> OTHER INFORMATION: BCI 124 16S rDNA

<400> SEQUENCE: 65
tggcgagacc cgctcccatg gtgtgacggg cggtgtgtac aagacccggg aacgtattca    60
ccgcggcatg ctgatccgcg attactagcg attccgactt cacgcagtcg agttgcagac   120
tgcgatccgg actacgactg gttttatggg attagctccc cctcgcgggt tggcaaccct   180
ctgtaccagc cattgtatga cgtgtgtagc cccacctata agggccatga ggacttgacg   240
tcatccccac cttcctccgg tttgtcaccg gcagtctcat tagagtgctc aactgaatgt   300
agcaactaat gacaagggtt gcgctcgttg cgggacttaa cccaacatct cacgacacga   360
gctgacgaca gccatgcagc acctgtgtgc aggttctctt tcgagcacga atccatctct   420
ggaaacttcc tgccatgtca aggtgggta aggttttcg cgttgcatcg aattaaacca   480
catcatccac cgcttgtgcg ggtccccgtc aattcctttg agtttcaacc ttgcggccgt   540
actcccagg cggtcaactt cacgcgttag cttcgttact gagaaaacta attcccaaca   600
accagttgac atcgtttag                                               619

<210> SEQ ID NO 66
<211> LENGTH: 697
<212> TYPE: DNA
<213> ORGANISM: Exiguobacterium acetylicum
<220> FEATURE:
<221> NAME/KEY: misc_feature
<222> LOCATION: (1)..(697)
<223> OTHER INFORMATION: BCI 125 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (303)..(305)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
```

<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (667)..(668)
<223> OTHER INFORMATION: n is a, c, g, or t
<220> FEATURE:
<221> NAME/KEY: misc_feature
<222> LOCATION: (670)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (686)..(687)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t

<400> SEQUENCE: 66

```
nccggcttcg ggtgttgcaa actctcgtgg tgtgacgggc ggtgtgtaca agacccggga      60
acgtattcac cgcagtatgc tgacctgcga ttactagcga ttccgacttc atgcaggcga     120
gttgcagcct gcaatccgaa ctgggaacgg ctttatggga ttggctccac ctcgcggtct     180
cgctgccctt tgtaccgtcc attgtagcac gtgtgtagcc caactcataa ggggcatgat     240
gatttgacgt catccccacc ttcctccggt ttgtcaccgg cagtctccct agagtgccca     300
acnnatgct ggcaactaag gatagggtt gcgctcgttg cgggacttaa cccaacatct      360
cacgacacga gctgacgaca accatgcacc acctgtcacc attgtccccg aagggaaaac     420
ttgatctctc aagcggtcaa tgggatgtca agagttggta aggttcttcg cgttgcttcn     480
aattaaacca catgctccac cgcttgtgcg ggtccccgtc aattcctttg agtttcagcc     540
ttgcggccgt actccccagg cggagtgctt aatgcgttag cttcagcact gaggggcgga     600
anccccccna cacctagcac tcatcgttta cggcgtggac tacnanggta tctaatcctg     660
tttgctnncn ncgctttcgc ncctcnncgt cngttac                             697
```

<210> SEQ ID NO 67
<211> LENGTH: 832
<212> TYPE: DNA
<213> ORGANISM: Bosea eneae
<220> FEATURE:
<221> NAME/KEY: misc_feature
<222> LOCATION: (1)..(832)
<223> OTHER INFORMATION: BCI 1267 16S rDNA
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

```
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 67
gnantcnctg ggcgtaaagg gcgcgtaggc ggactcttaa gtcggggtg  aaagcccagg    60 gctcaaccct ggaattgcct tcgatactga gagtctngag ttcggaagag gttggtggaa   120
ctgcgagtgt agaggtgaaa ttcgtagata ttcgcaagaa caccagtggc gaaggcggcc   180
aactggtccg atactgacgc tgaggcgcga aagcgtgggg agcaaacagg attagatacc   240
ctggtagtcc acgccgtaaa cgatgaatgc cagccgttgg ggtgcatgca cttcagtggc   300
gcagctaacg ctttaagcat tccgcctggg gagtacggtc gcaagattaa aactcaaagg   360
aattgacggg ggcccgcaca agcggtggag catgtggttt aattcgaagc aacgcgcaga   420
accttaccag cttttgacat gtccggtttg atcgacagag atgtctttct tcagttcggc   480
tggccggaac acaggtgctg catggctgtc gtcagctcgt gtcgtgagat gttgggttaa   540
gtcccgcaac gagcgcaacc ctcgccccta gttgccatca ttcagttggg aactctaggg   600
ggactgccgg tgataagccg cgaggaaggt ggggatgacg tcaagtcctc atggccctta   660
caggctgggc tacacacgtg ctacaatggc ggtgacaatg ggcagcgaaa gggcgacctg   720
gagctaatcc caaaaagccg tctcagttca gattgtactc tgcaactcga gtacatgaag   780
gtggaatcgc tagtaatcgt ggatcagcat gccacggtga atacgttccc gg           832

<210> SEQ ID NO 68
<211> LENGTH: 830
<212> TYPE: DNA
<213> ORGANISM: Pantoea agglomerans
<220> FEATURE:
<221> NAME/KEY: misc_feature
<222> LOCATION: (1)..(830)
<223> OTHER INFORMATION: BCI 1274 16S rDNA
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t

<400> SEQUENCE: 68
ggaantactg ggcgtaaagc gcacgcnggc ggtctgttaa gtcagatgtg aaatccccgg    60
gcttaacntg ggaactgcat ttgaaactgg caggcttgag tcttgtagag ggggtagaa    120 ttccaggtgt agcggtgaaa tgcgtagaga tctggaggaa taccggtggc gaaggcggcc   180
ccctggacaa agactgacgc tcaggtgcga aagcgtgggg agcaaacagg attagatacc   240
ctggtagtcc acgccgtaaa cgatgtcgac ttggaggttg ttcccttgag gagtggcttc   300
cggagctaac gcgttaagtc gaccgcctgg ggagtacggc cgcaaggtta aaactcaaat   360
gaattgacgg ggggccgcac aagcggtgga gcatgtggtt taattcgatg caacgcgaag   420
aaccttacct actcttgaca tccacggaat ttggcagaga tgccttagtg ccttcgggaa   480
```

```
ccgtgagaca ggtgctgcat ggctgtcgtc agctcgtgtt gtgaaatgtt gggttaagtc    540
ccgcaacgag cgcaaccctt atcctttgtt gccagcgatt cggtcgggaa ctcaaaggag    600
actgccggtg ataaaccgga ggaaggtggg gatgacgtca agtcatcatg gcccttacga    660
gtagggctac acacgtgcta caatggcgca tacaaagaga agcgacctcg cgagagcaag    720
cggacctcac aaagtgcgtc gtagtccgga tcggagtctg caactcgact ccgtgaagtc    780
ggaatcgcta gtaatcgtgg atcagaatgc cacggtgaat acgttccgg              830
```

<210> SEQ ID NO 69
<211> LENGTH: 818
<212> TYPE: DNA
<213> ORGANISM: Stenotrophomonas maltophilia
<220> FEATURE:
<221> NAME/KEY: misc_feature
<222> LOCATION: (1)..(818)
<223> OTHER INFORMATION: BCI 1279 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (168)..(169)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t

<400> SEQUENCE: 69

```
aaagcntgcg taggtggtng tttaantntg ttgtgaaanc cctgggntca acntgggaac    60
tgcagngnaa actngacaan tagagtgtgn tagagggtag cgganttccc ggtgtagcag   120
tgaaatgcgt agagatcggg aggaacatcc atggcgaagg cagctacnng gaccaacact   180
gacantgagg cacgaaagcg tgggnagcaa acaggattag ataccctggt agtccacgcc   240
ctaaacgatg cgaactggat gttgggtgca atttggcacg cagtatcgaa gctaacgcgt   300
taagttcgcc gcctggggag tacgtcgca agactgaaac tcaaaggaat tgacggggc    360
ccgcacaagc ggtggagtat gtggtttaat tcgatgcaac gcgaagaacc ttacctggcc   420
ttgacatgtc gagaactttc cagagatgga ttggtgcctt cgggaactcg aacacaggtg   480
ctgcatggct gtcgtcagct cgtgtcgtga gatgttgggt taagtcccgc aacgagcgca   540
acccttgtcc ttagttgcca gcacgtaatg gtgggaactc taaggagacc gccggtgaca   600
aaccggagga aggtggggat gacgtcaagt catcatggcc cttacggcca gggctacaca   660
cgtactacaa tggtggggac agagggctgc aagccggcga cggtaagcca atcccagaaa   720
ccccatctca gtccggattg gagtctgcaa ctcgactcca tgaagtcgga atcgctagta   780
atcgcagatc agcattgctg cggtgaatac gttcccgg                           818
```

<210> SEQ ID NO 70
<211> LENGTH: 783
<212> TYPE: DNA
<213> ORGANISM: Novosphingobium sediminicola
<220> FEATURE:
<221> NAME/KEY: misc_feature
<222> LOCATION: (1)..(783)
<223> OTHER INFORMATION: BCI 130 16S rDNA
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:

```
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (741)..(742)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (763)..(765)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t

<400> SEQUENCE: 70
ctccnttgcg  ggtnagctnn  acgccttcga  gtgaatccna  ctcccatggt  gtgacgggcg      60
gtgtgtacaa  ggcctgggaa  cgtattcacc  gcggcatgct  gatccgcgat  tactagcgat     120
tccgccttca  tgctctcgag  ttgcagagaa  caatccgaac  tgagacggct  tttggagatt     180
agctacccct  cgcgaggtcg  ctgcccactg  tcaccgccat  gtagcacgt   gtgtagccca     240 gcgtgtaagg  gccatgagga  cttgacgtca  tccccacctt  cctccggctt  atcaccggcg     300
gtttccttag  agtgcccaac  ttaatgatgg  caactaagga  cgagggttgc  gctcgttgcg     360
ggacttaacc  caacatctca  cgacacgagc  tgacgacagc  catgcagcac  ctgtcaccga     420
tccagccaaa  ctgaaggaaa  acatctctgt  aatccgcgat  cggatgtca   aacgctggta     480 aggttctgcg  cgttgcttcg  aattaaacca  catgctccac  cgcttgtgca  ggcccccgtc     540
aattcctttg  ngttttaatc  ttgcgaccgt  actcccagg   cggataactt  aatgcgttag     600
ctgcgccacc  caaattccat  gaacccggac  agctagttat  catcgtttac  ggcgtggant     660
accagggtat  ctaatcctgt  ttgctccnca  cgctttcgca  cctcagcgtc  aatacctgtc     720
cngtgagccg  ccttcnccac  nngngttctt  ccnaatatct  acnnntttca  nctctncact     780
cgg                                                                         783

<210> SEQ ID NO 71
<211> LENGTH: 826
<212> TYPE: DNA
<213> ORGANISM: Mucilaginibacter gossypii
<220> FEATURE:
<221> NAME/KEY: misc_feature
<222> LOCATION: (1)..(826)
<223> OTHER INFORMATION: BCI 1307 16S rDNA

<400> SEQUENCE: 71
ggatttattg  ggtttaaagg  gtgcgtaggc  ggcttttaa   gtcagggtg   aaagacggta      60 gctcaactat  cgcagtgccc  ttgatactga  agagcttgaa  tgtacttgag  gtaggcggaa     120
tgtgacaagt  agcggtgaaa  tgcatagata  tgtcacagaa  caccaattgc  gaaggcagct     180
tactaaagta  tgattgacgc  tgaggcacga  aagcgtgggg  atcaaacagg  attagatacc     240
ctggtagtcc  acgccctaaa  cgatgaacac  tcgatgttgg  cgatatacgg  tcagcgtcta     300
```

```
agcgaaagcg ttaagtgttc cacctgggga gtacgcccgc aagggtgaaa ctcaaaggaa      360
ttgacggggg cccgcacaag cggaggagca tgtggtttaa ttcgatgata cgcgaggaac      420
cttacccggg cttgaaagtt agtgaatgtg acagagacgt cacagttctt cggaacacga      480
aactaggtgc tgcatggctg tcgtcagctc gtgccgtgag gtgttgggtt aagtcccgca      540
acgagcgcaa cccctatgtt tagttgccag catttaaggt ggggactcta aacagactgc      600
ctatgcaaat agagaggaag gaggggacga cgtcaagtca tcatggccct tacgtccggg      660
gctacacacg tgctacaatg gatggtacag agggcagcta cctggcaaca ggatgccaat      720
ctcataaagc cattcacagt tcggatcggg gtctgcaact cgaccccgtg aagttggatt      780
cgctagtaat cgcgtatcag caatgacgcg gtgaatacgt tcccgg                     826
```

```
<210> SEQ ID NO 72
<211> LENGTH: 953
<212> TYPE: DNA
<213> ORGANISM: Ensifer adhaerens
<220> FEATURE:
<221> NAME/KEY: misc_feature
<222> LOCATION: (1)..(953)
<223> OTHER INFORMATION: BCI 131 16S rDNA
<220> FEATURE:
<221> NAME/KEY: misc_feature
<222> LOCATION: (841)..(841)
<223> OTHER INFORMATION: n is a, c, g, or t

<400> SEQUENCE: 72
```

```
tagctgcctc cttgcggtta gcgcactacc ttcgggtaaa accaactccc atggtgtgac       60
gggcggtgtg tacaaggccc gggaacgtat tcaccgcggc atgctgatcc gcgattacta      120
gcgattccaa cttcatgcac tcgagttgca gagtgcaatc cgaactgaga tggcttttgg      180
agattagctc acactcgcgt gctcgctgcc cactgtcacc accattgtag cacgtgtgta      240
gcccagcccg taagggccat gaggacttga cgtcatcccc accttcctct cggcttatca      300
ccggcagtcc ccttagagtg cccaactgaa tgctggcaac taagggcgag ggttgcgctc      360
gttgcgggac ttaacccaac atctcacgac acgagctgac gacagccatg cagcacctgt      420
ctccggtcca gccgaactga aggaaaacat ctctgtaatc cgcgaccggg atgtcaaggg      480
ctggtaaggt tctgcgcgtt gcttcgaatt aaaccacatg ctccaccgct tgtgcgggcc      540
cccgtcaatt cctttgagtt ttaatcttgc gaccgtactc cccaggcgga atgtttaatg      600
cgttagctgc gccaccgaac agtatactgc ccgacggcta acattcatcg tttacggcgt      660
ggactaccag ggtatctaat cctgtttgct ccccacgctt tcgcacctca gcgtcagtaa      720
tggaccagta agccgccttc gccactggtg ttcctccgaa tatctacgaa tttcacctct      780
acactcggaa ttccacttac ctcttccata ctccagactt ccagtatcaa aggcagttcc      840
naggttgagc cccgggattt caccccctgac ttaaaagtcc gcctacgtgc gctttacgcc      900
cagtaattcc gaacaacgct agccccttc gtattaccgc ggctgctggc acg              953
```

```
<210> SEQ ID NO 73
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1312 16S rDNA
<220> FEATURE:
<221> NAME/KEY: misc_feature
<222> LOCATION: (28)..(29)
```

<223> OTHER INFORMATION: n is a, c, g, or t

<400> SEQUENCE: 73

```
attactgggc gtaaagcgcg cgtaggtnnt tgttaagtt ggatgtgaaa gccccgggct      60
caacctggga actgcatcca aaactggcaa gctagagtac ggtagagggt ggtggaattt     120
cctgtgtagc ggtgaaatgc gtagatatag gaaggaacac cagtggcgaa ggcgaccacc    180
tggactgata ctgacactga ggtgcgaaag cgtggggagc aaacaggatt agataccctg    240
gtagtccacg ccgtaaacga tgtcaactag ccgttggaat ccttgagatt ttagtggcgc    300
agctaacgca ttaagttgac cgcctgggga gtacggccgc aaggttaaaa ctcaaatgaa    360
ttgacggggg cccgcacaag cggtggagca tgtggtttaa ttcgaagcaa cgcgaagaac    420
cttaccaggc cttgacatgc agagaacttt ccagagatgg attggtgcct tcggaactc    480
tgacacaggt gctgcatggc tgtcgtcagc tcgtgtcgtg agatgttggg ttaagtcccg    540
taacgagcgc aacccttgtc cttagttacc agcacgttat ggtgggcact ctaaggagac    600
tgccggtgac aaaccggagg aaggtgggga tgacgtcaag tcatcatggc ccttacggcc    660
tgggctacac acgtgctaca atggtcggta cagagggttg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg          834
```

<210> SEQ ID NO 74
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1314 16S rDNA
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 74

```
attactgggc gtaaagcgcg cgtaggtggt ttgttaagtt nnatgnnaaa gccccgggct     60
caacctggga actgcatcca aaactggcaa gctagagtac agtagagggt ggtggaattt    120
cctgtgtagc ggtgaaatgc gtagatatag gaaggaacac cagtggcgaa ggcgaccacc    180
tggactgata ctgacactga ggtgcgaaag cgtggggagc aaacaggatt agataccctg    240
gtagtccacg ccgtaaacga tgtcaactag ccgttggaat ccttgagatt ttagtggcgc    300
agctaacgca ttaagttgac cgcctgggga gtacggccgc aaggttaaaa ctcaaatgaa    360
ttgacggggg cccgcacaag cggtggagca tgtggtttaa ttcgaagcaa cgcgaagaac    420
cttaccaggc cttgacatgc agagaacttt ccagagatgg attggtgcct tcggaactc    480
tgacacaggt gctgcatggc tgtcgtcagc tcgtgtcgtg agatgttggg ttaagtcccg    540
taacgagcgc aacccttgtc cttagttacc agcacgttat ggtgggcact ctaaggagac    600
tgccggtgac aaaccggagg aaggtgggga tgacgtcaag tcatcatggc ccttacggcc    660
tgggctacac acgtgctaca atggtcggta cagagggtcg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg          834
```

<210> SEQ ID NO 75
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1315 16S rDNA
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t

<400> SEQUENCE: 75

```
attactgggc gtaaagcgcg cgtaggtggt ttgttaagtt ggatgtgaaa gccccgggct      60
caacntggga actgcatcca aaactggcaa gctagagtac agtagagggt ggtggaatnt     120
cctgtgtagc ggtgaaatgc gtagatatag gaaggaacac cagtggcgaa ggcgaccacc    180
tggactgata ctgacactga ggtgcgaaag cgtggggagc aaacaggatt agataccctg    240
gtagtccacg ccgtaaacga tgtcaactag ccgttggaat ccttgagatt ttagtggcgc    300
agctaacgca ttaagttgac cgcctgggga gtacggccgc aaggttaaaa ctcaaatgaa    360
ttgacggggg cccgcacaag cggtggagca tgtggtttaa ttcgaagcaa cgcgaagaac    420
cttaccaggc cttgacatgc agagaacttt ccagagatgg attggtgcct tcgggaactc    480
tgacacaggt gctgcatggc tgtcgtcagc tcgtgtcgtg agatgttggg ttaagtcccg    540
taacgagcgc aacccttgtc cttagttacc agcacgttat ggtgggcact ctaaggagac    600
tgccggtgac aaaccggagg aaggtgggga tgacgtcaag tcatcatggc ccttacggcc    660
tgggctacac acgtgctaca atggtcggta cagagggtcg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg           834
```

<210> SEQ ID NO 76
<211> LENGTH: 837
<212> TYPE: DNA
<213> ORGANISM: Stenotrophomonas maltophilia
<220> FEATURE:
<221> NAME/KEY: misc_feature
<222> LOCATION: (1)..(837)
<223> OTHER INFORMATION: BCI 1316 16S rDNA
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:

-continued

```
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 76
attacnnggc nnaaagcgtg cgtaggtggt tgtttaantc tgttgtgaaa gcccngggct      60
caaccnnggg aactgcagtg gaaacnggac aactagagtg tggtagaggg tagcggaatt     120
cccggtgtag cagtgaantg cgtagagatc gggaggaaca tccatggcga aggcagctac     180
ctggaccaac actgacantg aggcacgaaa gcgtggggag caaacaggat tagataccct     240
ggtagtccac gccctaaacg atgcgaactg atgttgggt gcaatttggc acgcagtatc      300
gaagctaacg cgttaagttc gccgcctggg gagtacggtc gcaagactga aactcaaagg     360
aattgacggg ggcccgcaca agcggtggag tatgtggttt aattcgatgc aacgcgaaga     420
accttacctg gccttgacat gtcgagaact ttccagagat ggattggtgc cttcgggaac     480
tcgaacacag gtgctgcatg gctgtcgtca gctcgtgtcg tgagatgttg ggttaagtcc     540
cgcaacgagc gcaacccttg tccttagttg ccagcacgta atggtgggaa ctctaaggag     600
accgccggtg acaaaccgga ggaaggtggg gatgacgtca agtcatcatg gcccttacgg     660
ccagggctac acacgtacta caatggtagg gacagagggc tgcaagccgg cgacggtaag     720
ccaatcccag aaaccctatc tcagtccgga ttggagtctg caactcgact ccatgaagtc     780
ggaatcgcta gtaatcgcag atcagcattg ctgcggtgaa tacgttcccg ggccttg        837

<210> SEQ ID NO 77
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1319 16S rDNA
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t

<400> SEQUENCE: 77
attactgggn ntaaagcgcg cgtnggtggt ttgttaagtn ggatgtgaaa gccccgggct      60
caacctggga actgcatcca aaactggcaa gctagagtac ggtagagggt ggtggaattt     120
cntgtgtagc ggtgaaatgc gtagatatag gaaggaacac cagtggcgaa ggcgaccacc     180
tggactgata ctgacactga ggtgcgaaag cgtggggagc aaacaggatt agataccctg     240
gtagtccacg ccgtaaacga tgtcaactag ccgttggaat ccttgagatt ttagtggcgc     300
```

```
agctaacgca ttaagttgac cgcctgggga gtacggccgc aaggttaaaa ctcaaatgaa    360
ttgacggggg cccgcacaag cggtggagca tgtggtttaa ttcgaagcaa cgcgaagaac    420
cttaccaggc cttgacatgc agagaacttt ccagagatgg attggtgcct tcgggaactc    480
tgacacaggt gctgcatggc tgtcgtcagc tcgtgtcgtg agatgttggg ttaagtcccg    540
taacgagcgc aaccccttgtc cttagttacc agcacgtaat ggtgggcact ctaaggagac    600
tgccggtgac aaaccggagg aaggtgggga tgacgtcaag tcatcatggc ccttacggcc    660
tgggctacac acgtgctaca atggtcggta cagagggttg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg          834
```

<210> SEQ ID NO 78
<211> LENGTH: 776
<212> TYPE: DNA
<213> ORGANISM: Microbacterium oleivorans
<220> FEATURE:
<221> NAME/KEY: misc_feature
<222> LOCATION: (1)..(776)
<223> OTHER INFORMATION: BCI 132 16S rDNA
<220> FEATURE:
<221> NAME/KEY: misc_feature
<222> LOCATION: (2)..(2)
<223> OTHER INFORMATION: n is a, c, g, or t

<400> SEQUENCE: 78

```
cnccggcttc aggtgttacc gactttcatg acttgacggg cggtgtgtac aagacccggg    60
aacgtattca ccgcagcgtt gctgatctgc gattactagc gactccgact tcatgaggtc    120
gagttgcaga cctcaatccg aactgggacc ggcttttttgg gattcgctcc acctcgcggt    180
attgcagccc tttgtaccgg ccattgtagc atgcgtgaag cccaagacat aaggggcatg    240
atgatttgac gtcatcccca ccttcctccg agttgacccc ggcagtatcc catgagttcc    300
caccattacg tgctggcaac atagaacgag ggttgcgctc gttgcgggac ttaacccaac    360
atctcacgac acgagctgac gacaaccatg caccacctgt ttacgagtgt ccaaagagtt    420
gaccatttct ggcccgttct cgtatatgtc aagccttggt aaggttcttc gcgttgcatc    480
gaattaatcc gcatgctccg ccgcttgtgc gggtccccgt caattccttt gagttttagc    540
cttgcggccg tactccccag gcggggaact taatgcgtta gctgcgtcac ggaatccgtg    600
gaatggaccc cacaactagt tcccaacgtt tacggggtgg actaccaggg tatctaagcc    660
tgtttgctcc ccacccttc gctcctcagc gtcagtaacg gcccagagat ctgccttcgc    720
catcggtgtt cctcctgata tctgcgcatt ccaccgctac accaggaatt ccaatc        776
```

<210> SEQ ID NO 79
<211> LENGTH: 503
<212> TYPE: DNA
<213> ORGANISM: Stenotrophomonas maltophilia
<220> FEATURE:
<221> NAME/KEY: misc_feature
<222> LOCATION: (1)..(503)
<223> OTHER INFORMATION: BCI 1320 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:

```
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t

<400> SEQUENCE: 79
ncggtngcaa gactgaaant caaaggaatt gacgggggcc cgcacnagcg gnggagtnng      60
tggtttaatt ngntgcaacg ngaagaacnt tacntggcct tgacatgtcg agaantttcc    120
anaganggat tggtgccttc gggaactcga acacaggtgn tgcatggcng tngtcagctn    180
```

```
gngtcntgag atgttgggtt aagtcccgca acgagcgcaa cccttgtcct tagttgccag      240
cacgtaatgg tgggaactct aaggagaccg ccggtgacaa accggaggaa ggtggggatg      300
acgtcaagtc atcatggccc ttacggccag ggctacacac gtactacaat ggtagggaca      360
gagggctgca agccggcgac ggtaagccaa tcccagaaac cctatctcag tccggattgg      420
agtctgcaac tcgactccat gaagtcggaa tcgctagtaa tcgcagatca gcattgctgc      480
ggtgaatacg ttcccgggcc ttg                                              503
```

```
<210> SEQ ID NO 80
<211> LENGTH: 511
<212> TYPE: DNA
<213> ORGANISM: Stenotrophomonas maltophilia
<220> FEATURE:
<221> NAME/KEY: misc_feature
<222> LOCATION: (1)..(511)
<223> OTHER INFORMATION: BCI 1322 16S rDNA
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t

<400> SEQUENCE: 80
```

```
tggggagtac ggtcgcaaga ntgaaactca aaggaattga cggggggcccg cacaagcggt     60 ggagtatgtg gtttanttcg atgcaacgcg aagaaccttta cntggccttg acatgtcgag    120
aactttccag agatggattg gtgcnttngg gaactngaac acaggtgntg catggctgtc     180
gtcagctcgt gtcgtgagat gttgggttaa gtcccgcaac gagcgcaacc cttgtcctta    240
gttgccagca cgtaatggtg ggaactctaa ggagaccgcc ggtgacaaac cggaggaagg    300
tggggatgac gtcaagtcat catggcccctt acggccaggg ctacacacgt actacaatgg    360
tagggacaga gggctgcaag ccggcgacgg taagccaatc ccagaaaccc tatctcagtc    420
cggattggag tctgcaactc gactccatga agtcggaatc gctagtaatc gcagatcagc    480
attgctgcgg tgaatacgtt cccgggcctt g                                    511
```

```
<210> SEQ ID NO 81
<211> LENGTH: 835
<212> TYPE: DNA
<213> ORGANISM: Stenotrophomonas maltophilia
<220> FEATURE:
<221> NAME/KEY: misc_feature
<222> LOCATION: (1)..(835)
```

<223> OTHER INFORMATION: BCI 1325 16S rDNA
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (63)..(66)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t

<400> SEQUENCE: 81

| | | | | | |
|---|---|---|---|---|---|
| attactgggc | gtaaagcgtg | ngtaggtggt | ngtttaagtn | tgttgtgaaa | gccctgggnt | 60 |
| cannnnggaa | ntgcagtgga | aactggacaa | ctagagtgtg | gtagagggta | gcggaattcc | 120 |
| cggtgtagca | gtgaaatgcg | tagagatcgg | gaggaacntc | catggcgaag | gcagctacct | 180 |
| ggaccaacac | tgacantgag | gcacgaaagc | gtggggagca | aacaggatta | gataccctgg | 240 |
| tagtccacgc | cctaaacgat | gcgaactgga | tgttgggtgc | aatttggcac | gcagtatcga | 300 |
| agctaacgcg | ttaagttcgc | cgcctgggga | gtacggtcgc | aagactgaaa | ctcaaaggaa | 360 |
| ttgacggggg | cccgcacaag | cggtggagta | tgtggtttaa | ttcgatgcaa | cgcgaagaac | 420 |
| cttacctggc | cttgacatgt | cgagaacttt | ccagagatgg | attggtgcct | tcgggaactc | 480 |
| gaacacaggt | gctgcatggc | tgtcgtcagc | tcgtgtcgtg | agatgttggg | ttaagtcccg | 540 |
| caacgagcgc | aacccttgtc | cttagttgcc | agcacgtaat | ggtgggaact | ctaaggagac | 600 |
| cgccggtgac | aaaccggagg | aaggtgggga | tgacgtcaag | tcatcatggc | ccttacggcc | 660 |
| agggctacac | acgtactaca | atggtaggga | cagagggctg | caagccggcg | acggtaagcc | 720 |
| aatcccagaa | accctatctc | agtccggatt | ggagtctgca | actcgactcc | atgaagtcgg | 780 |
| aatcgctagt | aatcgcagat | cagcattgct | gcggtgaata | cgttcccggg | ccttg | 835 |

<210> SEQ ID NO 82
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1330 16S rDNA
<220> FEATURE:
<221> NAME/KEY: misc_feature
<222> LOCATION: (142)..(142)
<223> OTHER INFORMATION: n is a, c, g, or t

<400> SEQUENCE: 82

```
attactgggc gtaaagcgcg cgtaggtggt tgttaagtt ggatgtgaaa gccccgggct      60
caacctggga actgcatcca aaactggcaa gctagagtac agtagagggt ggtggaattt     120
cctgtgtagc ggtgaaatgc gnagatatag gaaggaacac cagtggcgaa ggcgaccacc    180
tggactgata ctgacactga ggtgcgaaag cgtggggagc aaacaggatt agataccctg    240
gtagtccacg ccgtaaacga tgtcaactag ccgttggaat ccttgagatt ttagtggcgc    300
agctaacgca ttaagttgac cgcctgggga gtacggccgc aaggttaaaa ctcaaatgaa    360 ttgacgggggg cccgcacaag cggtggagca tgtggtttaa ttcgaagcaa cgcgaagaac    420
cttaccagcc cttgacatgc agagaacttt ccagagatgg attggtgcct tcgggaactc    480
tgacacaggt gctgcatggc tgtcgtcagc tcgtgtcgtg agatgttggg ttaagtcccg    540
taacgagcgc aacccttgtc cttagttacc agcacgttat ggtgggcact ctaaggagac    600
tgccggtgac aaaccggagg aaggtgggga tgacgtcaag tcatcatggc ccttacggcc    660
tgggctacac acgtgctaca atggtcgta cagagggtcg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg         834

<210> SEQ ID NO 83
<211> LENGTH: 836
<212> TYPE: DNA
<213> ORGANISM: Stenotrophomonas maltophilia
<220> FEATURE:
<221> NAME/KEY: misc_feature
<222> LOCATION: (1)..(836)
<223> OTHER INFORMATION: BCI 1331 16S rDNA
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t

<400> SEQUENCE: 83
atnnctgggc gtaaagcgtg cgtaggtggt tgtttaagtc tgttgtgaaa gccctgggct     60
caacnnggga actgcagtgg aaactggaca actagagtgt ggtagagggt agcggaattc    120
ccggtgtagc agtgaaatgc gtagagatcg ggaggaacat ccatggcgaa ggcagctacc    180
tggaccaaca ctgacactga ggcacgaaag cgtggggagc aaacaggatt agataccctg    240
gtagtccacg ccctaaacga tgcgaactgg atgttgggtg caatttggca cgcagtatcg    300
aagctaacgc gttaagttcg ccgcctgggg agtacggtcg caagactgaa actcaaagga    360
attgacgggg gcccgcacaa gcggtggagt atgtggttta attcgatgca acgcgaagaa    420
ccttacctgg ccttgacatg tcgagaactt tccagagatg gattggtgcc ttcgggaact    480
cgaacacagg tgctgcatgg ctgtcgtcag ctcgtgtcgt gagatgttgg gttaagtccc    540
gcaacgagcg caacccttgt ccttagttgc cagcacgtaa tggtgggaac tctaaggaga    600
ccgccggtga caaaccggag gaaggtgggg atgacgtcaa gtcatcatgg cccttacggc    660
cagggctaca cacgtactac aatggtaggg acagagggct gcaagccggc gacggtaagc    720
caatcccaga acccctatct cagtccggat tggagtctgc aactcgactc catgaagtcg    780
gaatcgctag taatcgcaga tcagcattgc tgcggtgaat acgttcccgg gccttg        836

<210> SEQ ID NO 84
```

```
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1333 16S rDNA

<400> SEQUENCE: 84
attactgggc gtaaagcgcg cgtaggtggt ttgttaagtt ggatgtgaaa gccccgggct      60
caacctggga actgcatcca aaactggcaa gctagagtac ggtagagggt ggtggaattt     120
cctgtgtagc ggtgaaatgc gtagatatag gaaggaacac cagtggcgaa ggcgaccacc    180
tggactgata ctgacactga ggtgcgaaag cgtggggagc aaacaggatt agataccctg    240
gtagtccacg ccgtaaacga tgtcaactag ccgttggaat ccttgagatt ttagtggcgc    300
agctaacgca ttaagttgac cgcctgggga gtacggccgc aaggttaaaa ctcaaatgaa    360
ttgacggggg cccgcacaag cggtggagca tgtggtttaa ttcgaagcaa cgcgaagaac    420
cttaccaggc cttgacatgc agagaacttt ccagagatgg attggtgcct tcgggaactc    480
tgacacaggt gctgcatggc tgtcgtcagc tcgtgtcgtg agatgttggg ttaagtcccg    540
taacgagcgc aacccttgtc cttagttacc agcacgttat ggtgggcact ctaaggagac    600
tgccggtgac aaaccggagg aaggtgggga tgacgtcaag tcatcatggc ccttacggcc    660
tgggctacac acgtgctaca atggtcggta cagagggttg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg          834

<210> SEQ ID NO 85
<211> LENGTH: 765
<212> TYPE: DNA
<213> ORGANISM: Stenotrophomonas maltophilia
<220> FEATURE:
<221> NAME/KEY: misc_feature
<222> LOCATION: (1)..(765)
<223> OTHER INFORMATION: BCI 1344 16S rDNA

<400> SEQUENCE: 85
ctacctgctt ctggtgcaac aaactcccat ggtgtgacgg gcggtgtgta caaggcccgg     60
gaacgtattc accgcagcaa tgctgatctg cgattactag cgattccgac ttcatggagt    120
cgagttgcag actccaatcc ggactgagat agggtttctg ggattggctc accgtcgccg    180
gcttgcagcc ctctgtccct accattgtag tacgtgtgta gccctggccg taagggccat    240
gatgacttga cgtcatcccc accttcctcc ggtttgtcac cggcggtctc cttagagttc    300
ccaccattac gtgctggcaa ctaaggacaa gggttgcgct cgttgcggga cttaacccaa    360
catctcacga cacgagctga cgacagccat gcagcacctg tgttcgagtt cccgaaggca    420
ccaatccatc tctggaaagt tctcgacatg tcaaggccag gtaaggttct tcgcgttgca    480
tcgaattaaa ccacatactc caccgcttgt gcgggccccc gtcaattcct ttgagtttca    540
gtcttgcgac cgtactcccc aggcggcgaa cttaacgcgt tagcttcgat actgcgtgcc    600
aaattgcacc caacatccag ttcgcatcgt ttagggcgtg gactaccagg gtatctaatc    660
ctgtttgctc cccacgcttt cgtgcctcag tgtcaatgtt ggtccaggta gctgccttcg    720
ccatggatgt tcctcctgat ctctacgcat ttcactgcta cacca                     765

<210> SEQ ID NO 86
<211> LENGTH: 835
```

```
<212> TYPE: DNA
<213> ORGANISM: Stenotrophomonas maltophilia
<220> FEATURE:
<221> NAME/KEY: misc_feature
<222> LOCATION: (1)..(835)
<223> OTHER INFORMATION: BCI 1350 16S rDNA
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (71)..(73)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (95)..(100)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
```

```
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (261)..(263)
<223> OTHER INFORMATION: n is a, c, g, or t
<220> FEATURE:
<221> NAME/KEY: misc_feature
<222> LOCATION: (267)..(268)
<223> OTHER INFORMATION: n is a, c, g, or t

<400> SEQUENCE: 86
tactgggcgt aaagcgnncg taggtgnntn gnttaannnt gtngtnaaan ccnnggnntc      60 anccctgggaa nnncagngga ancnggacaa ctagnnnnnn gtagagggta gnggaattcc    120
cggtgtagca gtgaantgcg tagagatcgg gaggaacatc catggcgaag gcagntacct    180
ggaccaacac tgacantgag gcacgaaagc gtggggagca acaggatta gatacctgg      240 tagtccacgc cctaaacgnt nnnaacnnga tgttgggtgc aatttggcac gcagtatcga    300
agctaacgcg ttaagttcgc cgcctgggga gtacggtcgc aagactgaaa ctcaaaggaa    360
ttgacggggg cccgcacaag cggtggagta tgtggtttaa ttcgatgcaa cgcgaagaac    420
cttacctggc cttgacatgt cgagaacttt ccagagatgg attggtgcct tcgggaactc    480
gaacacaggt gctgcatggc tgtcgtcagc tcgtgtcgtg agatgttggg ttaagtcccg    540
caacgagcgc aacccttgtc cttagttgcc agcacgtaat ggtgggaact ctaaggagac    600
cgccggtgac aaaccggagg aaggtgggga tgacgtcaag tcatcatggc ccttacggcc    660
agggctacac acgtactaca atggtgggga cagagggctg caagccggcg acggtaagcc    720
aatcccagaa accccatctc agtccggatt ggagtctgca actcgactcc atgaagtcgg    780
aatcgctagt aatcgcagat cagcattgct gcggtgaata cgttcccggg ccttg         835

<210> SEQ ID NO 87
<211> LENGTH: 581
<212> TYPE: DNA
<213> ORGANISM: Pseudomonas putida
<220> FEATURE:
<221> NAME/KEY: misc_feature
<222> LOCATION: (1)..(581)
<223> OTHER INFORMATION: BCI 1351 16S rDNA

<400> SEQUENCE: 87
tcccatggtg tgacgggcgg tgtgtacaag gcccgggaac gtattcaccg cgacattctg     60
attcgcgatt actagcgatt ccgacttcac gcagtcgagt tgcagactgc gatccggact    120
acgatcggtt ttgtgagatt agctccacct cgcggcttgg caaccctctg taccgaccat    180
tgtagcacgt gtgtagccca ggccgtaagg gccatgatga cttgacgtca tccccacctt    240
cctccggttt gtcaccggca gtctccttag agtgcccacc ataacgtgct ggtaactaag    300
gacaagggtt gcgctcgtta cgggacttaa cccaacatct cacgacacga gctgacgaca    360
gccatgcagc acctgtgtca gagttcccga aggcaccaat ccatctctgg aaagttctct    420
gcatgtcaag gcctggtaag gttcttcgcg ttgcttcgaa ttaaaccaca tgctccaccg    480
cttgtgcggg cccccgtcaa ttcatttgag ttttaacctt gcggccgtac tccccaggcg    540
```
gtcaacttaa tgcgttagct gcgccactaa aatctcaagg a                581

<210> SEQ ID NO 88
<211> LENGTH: 834
<212> TYPE: DNA
<213> ORGANISM: Pseudomonas fluorescens
<220> FEATURE:
<221> NAME/KEY: misc_feature
<222> LOCATION: (1)..(834)
<223> OTHER INFORMATION: BCI 1352 16S rDNA
<220> FEATURE:
<221> NAME/KEY: misc_feature
<222> LOCATION: (89)..(89)
<223> OTHER INFORMATION: n is a, c, g, or t

<400> SEQUENCE: 88
attactgggc gtaaagcgcg cgtaggtggt ttgttaagtt ggatgtgaaa tccccgggct    60
caacctggga actgcatcca aaactggcna gctagagtat ggtagagggt ggtggaattt   120
cctgtgtagc ggtgaaatgc gtagatatag gaaggaacac cagtggcgaa ggcgaccacc   180
tggactgata ctgacactga ggtgcgaaag cgtggggagc aaacaggatt agataccctg   240
gtagtccacg ccgtaaacga tgtcaactag ccgttgggag ccttgagctc ttagtggcgc   300
agctaacgca ttaagttgac cgcctgggga gtacggccgc aaggttaaaa ctcaaatgaa   360
ttgacggggg cccgcacaag cggtggagca tgtggtttaa ttcgaagcaa cgcgaagaac   420
cttaccaggc cttgacatcc aatgaacttt ccagagatgg attggtgcct tcgggagcat   480
tgagacaggt gctgcatggc tgtcgtcagc tcgtgtcgtg agatgttggg ttaagtcccg   540
taacgagcgc aaccctigic cttagttacc agcacgtaat ggtgggcact ctaaggagac   600
tgccggtgac aaaccggagg aaggtgggga tgacgtcaag tcatcatggc ccttacggcc   660
tgggctacac acgtgctaca atggtcggta caaagggttg ccaagccgcg aggtggagct   720
aatcccataa aaccgatcgt agtccggatc gcagtctgca actcgactgc gtgaagtcgg   780
aatcgctagt aatcgcgaat cagaatgtcg cggtgaatac gttcccgggc cttg          834

<210> SEQ ID NO 89
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1353 16S rDNA

<400> SEQUENCE: 89
attactgggc gtaaagcgcg cgtaggtggt ttgttaagtt ggatgtgaaa gccccgggct    60
caacctggga actgcatcca aaactggcaa gctagagtac ggtagagggt ggtggaattt   120
cctgtgtagc ggtgaaatgc gtagatatag gaaggaacac cagtggcgaa ggcgaccacc   180
tggactgata ctgacactga ggtgcgaaag cgtggggagc aaacaggatt agataccctg   240
gtagtccacg ccgtaaacga tgtcaactag ccgttggaat ccttgagatt ttagtggcgc   300
agctaacgca ttaagttgac cgcctgggga gtacggccgc aaggttaaaa ctcaaatgaa   360
ttgacggggg cccgcacaag cggtggagca tgtggtttaa ttcgaagcaa cgcgaagaac   420
cttaccaggc cttgacatgc agagaacttt ccagagatgg attggtgcct tcgggaactc   480
tgacacaggt gctgcatggc tgtcgtcagc tcgtgtcgtg agatgttggg ttaagtcccg   540
taacgagcgc aaccctigic cttagttacc agcacgttat ggtgggcact ctaaggagac   600

```
tgccggtgac aaaccggagg aaggtgggga tgacgtcaag tcatcatggc ccttacggcc    660
tgggctacac acgtgctaca atggtcggta cagagggttg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg          834
```

```
<210> SEQ ID NO 90
<211> LENGTH: 833
<212> TYPE: DNA
<213> ORGANISM: Pantoea agglomerans
<220> FEATURE:
<221> NAME/KEY: misc_feature
<222> LOCATION: (1)..(833)
<223> OTHER INFORMATION: BCI 1355 16S rDNA
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (442)..(443)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (479)..(480)
<223> OTHER INFORMATION: n is a, c, g, or t

<400> SEQUENCE: 90
attactgggc gtaaagcgca cgcaggcgnt ctgttaantc agatgtgaaa ncccggnct     60 taacctggga actgcatttg aaactggcag gcttgagtct tgtagagggg ggtagaattc    120
caggtgtagc ggtgaaatgc gtagagatct ggaggaatac cggtggcgaa ggcggcccc    180 tggacaaaga ctgacgctca ggtgcgaaag cgtggggagc aaacaggatt agataccctg    240
gtagtccacg ccgtaaacga tgtcgacttg gaggttgttc ccttgaggag tggcttccgg    300
agctaacgcg ttaagtcgac cgcctgggga gtacggccgc aaggttaaaa ctcaaatgaa    360
ttgacggggg cccgcacaag cggtggagca tgtggtttaa ttcgatgcaa cgcgaagaac    420
cttacctact cttgacatcc anngaanttn gcagagatgc nttngtgcct tcgggaacnn    480
tgagacaggt gctgcatggc tgtcgtcagc tcgtgttgtg aaatgttggg ttaagtcccg    540
caacgagcgc aacccttatc ctttgttgcc agcgattcgg tcgggaactc aaaggagact    600
```

```
gccggtgata aaccggagga aggtggggat gacgtcaagt catcatggcc cttacgagta      660
gggctacaca cgtgctacaa tggcgcatac aaagagaagc gacctcgcga gagcaagcgg      720
acctcacaaa gtgcgtcgta gtccggatcg gagtctgcaa ctcgactccg tgaagtcgga      780
atcgctagta atcgtggatc agaatgccac ggtgaatacg ttcccgggcc ttg             833
```

```
<210> SEQ ID NO 91
<211> LENGTH: 523
<212> TYPE: DNA
<213> ORGANISM: Pseudomonas putida
<220> FEATURE:
<221> NAME/KEY: misc_feature
<222> LOCATION: (1)..(523)
<223> OTHER INFORMATION: BCI 1356 16S rDNA
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t

<400> SEQUENCE: 91
taagttgncc gcntggggag nncggccgca aggttaaaac tcaaangaat tgacggggc       60 ccgcacaagc ggtggagcat gtggtttaat tngaagcaac gngaagancc ttnccagncc     120
ttgacatgca gagaactttc cagagatgga ttggtgcctt cgggaactct gacacaggtg    180
ctgcatggct gtcgtcagct cgtgtcgtga gatgttgggt taagtcccgt aacgagcgca    240
acccttgtcc ttagttacca gcncgttatg gtgggcactc taaggagact gccggtgaca    300
aaccggagga aggtggggat gacgtcaagt catcatggcc cttacggcct gggctacaca    360
cgtgctacaa tggtcggtac agagggttgc caagccgcga ggtggagcta atctcacaaa    420
accgatcgta gtccggatcg cagtctgcaa ctcgactgcg tgaagtcgga atcgctagta    480
atcgcgaatc agaatgtcgc ggtgaatacg ttcccgggcc ttg                      523
```

<210> SEQ ID NO 92
<211> LENGTH: 836
<212> TYPE: DNA
<213> ORGANISM: Stenotrophomonas maltophilia
<220> FEATURE:
<221> NAME/KEY: misc_feature
<222> LOCATION: (1)..(836)
<223> OTHER INFORMATION: BCI 1357 16S rDNA
<220> FEATURE:
<221> NAME/KEY: misc_feature
<222> LOCATION: (31)..(31)
<223> OTHER INFORMATION: n is a, c, g, or t

<400> SEQUENCE: 92

```
attactgggc gtaaagcgtg cgtaggtggt ngtttaagtc tgttgtgaaa gccctgggct    60
caacctggga actgcagtgg aaactggacg actagagtgt ggtagagggt agcggaattc   120
ccggtgtagc agtgaaatgc gtagagatcg ggaggaacat ccatggcgaa ggcagctacc   180
tggaccaaca ctgacactga ggcacgaaag cgtggggagc aaacaggatt agataccctg   240
gtagtccacg ccctaaacga tgcgaactgg atgttgggtg caatttggca cgcagtatcg   300
aagctaacgc gttaagttcg ccgcctgggg agtacggtcg caagactgaa actcaaagga   360
attgacgggg cccgcacaa gcggtggagt atgtggttta attcgatgca acgcgaagaa   420
ccttacctgg ccttgacatg tcgagaactt ccagagatg gattggtgcc ttcgggaact   480
cgaacacagg tgctgcatgg ctgtcgtcag ctcgtgtcgt gagatgttgg gttaagtccc   540
gcaacgagcg caaccettgt ccttagttgc cagcacgtaa tggtgggaac tctaaggaga   600
ccgccggtga caaccggag gaaggtgggg atgacgtcaa gtcatcatgg cccttacggc   660
cagggctaca cacgtactac aatggtgggg acagagggct gcaagccggc gacggtaagc   720
caatcccaga aaccccatct cagtccggat tggagtctgc aactcgactc catgaagtcg   780
gaatcgctag taatcgcaga tcagcattgc tgcggtgaat acgttccgg ccttg         836
```

<210> SEQ ID NO 93
<211> LENGTH: 833
<212> TYPE: DNA
<213> ORGANISM: Pseudomonas putida
<220> FEATURE:
<221> NAME/KEY: misc_feature
<222> LOCATION: (1)..(833)
<223> OTHER INFORMATION: BCI 1358 16S rDNA
<220> FEATURE:
<221> NAME/KEY: misc_feature
<222> LOCATION: (117)..(119)
<223> OTHER INFORMATION: n is a, c, g, or t

<400> SEQUENCE: 93

```
attactgggc gtaaagcgcg cgtaggtggt ttgttaagtt ggatgtgaaa gccccgggct    60
caacctggga actgcatcca aaactggcaa gctagagtac ggtagagggt ggtggannnc   120
ctgtgtagcg gtgaaatgcg tagatatagg aaggaacacc agtggcgaag gcgaccacct   180
ggactgatac tgacactgag gtgcgaaagc gtggggagca acaggatta gataccctgg    240
tagtccacgc cgtaaacgat gtcaactagc cgttggaatc cttgagattt agtggcgca    300
gctaacgcat taagttgacc gcctggggag tacggccgca aggttaaaac tcaaatgaat   360
tgacggggc ccgcacaagc ggtggagcat gtggtttaat tcgaagcaac gcgaagaacc   420
ttaccaggcc ttgacatgca gagaactttc cagagatgga ttggtgcctt cgggaactct   480
gacacaggtg ctgcatggct gtcgtcagct cgtgtcgtga gatgttgggt taagtcccgt   540
aacgagcgca accettgtcc ttagttacca gcacgttatg gtgggcactc taaggagact   600
```

-continued

```
gccggtgaca aaccggagga aggtggggat gacgtcaagt catcatggcc cttacggcct      660
gggctacaca cgtgctacaa tggtcggtac agagggttgc caagccgcga ggtggagcta      720
atctcacaaa accgatcgta gtccggatcg cagtctgcaa ctcgactgcg tgaagtcgga      780
atcgctagta atcgcgaatc agaatgtcgc ggtgaatacg ttcccgggcc ttg             833
```

```
<210> SEQ ID NO 94
<211> LENGTH: 782
<212> TYPE: DNA
<213> ORGANISM: Novosphingobium sediminicola
<220> FEATURE:
<221> NAME/KEY: misc_feature
<222> LOCATION: (1)..(782)
<223> OTHER INFORMATION: BCI 136 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (685)..(686)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (767)..(767)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
```

<221> NAME/KEY: misc_feature
<222> LOCATION: (781)..(781)
<223> OTHER INFORMATION: n is a, c, g, or t

<400> SEQUENCE: 94

```
ccnttgcggg tnngctnnac gccttcgagt gaatccnact cccatggtgt gacgggcggt      60
gtgtacaagg cctgggaacg tattcaccgc ggcatgctga tccgcgatta ctagcgattc     120
cgccttcatg ctctcgagtt gcagagaaca atccgaactg agacggcttt tggagattag     180
ctacccctcg cgaggtcgct gcccactgtc accgccattg tagcacgtgt gtagcccagc     240
gtgtaagggc catgaggact tgacgtcatc cccaccttcc tccggcttat caccggcggt     300
ttccttagag tgcccaactt aatgatggca actaaggacg agggttgcgc tcgttgcggg     360
acttaaccca acatctcacg acacgagctg acgacagcca tgcagcacct gtcaccgatc     420
cagccaaact gaaggaaaac atctctgtaa tccgcgatcg ggatgtcaaa cgctggtaag     480
gttctgcgcg ttgcttcgaa ttaaaccaca tgctccaccg cttgtgcagg cccccgtcaa     540
ttcctttgng ttttaatctt gcgaccgtac tccccaggcg gataacttaa tgcgttagct     600
gcgccaccca aattccatga acccggacag ctagttatca tcgtttacgg cgtggantac     660
cagggtatct aatcctgttt gctcnncacg ctttcgcacc tcagcgtcna tanctgtccn     720
gtgagccgcc ttcgccactn gtgttcttcc naatatctac gantttnanc tctacactcg     780
na                                                                    782
```

<210> SEQ ID NO 95
<211> LENGTH: 836
<212> TYPE: DNA
<213> ORGANISM: Stenotrophomonas maltophilia
<220> FEATURE:
<221> NAME/KEY: misc_feature
<222> LOCATION: (1)..(836)
<223> OTHER INFORMATION: BCI 1362 16S rDNA
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t

<400> SEQUENCE: 95

```
attnctgggc gtaaagcgtg cgtaggtgnt ngtttangtc tgttgtgaaa gccctgggct      60
cancntggga actgcagtgg aaactgnaca actagagtgt ggtagagggt agcggaattc     120
ccggtgtagc agtgaaatgc gtagagatcg ggaggaacat ccatggcgaa ggcagctacc     180
```

```
tggaccaaca ctgacactga ggcacgaaag cgtggggagc aaacaggatt agatacccctg    240 gtagtccacg ccctaaacga tgcgaactgg atgttgggtg caatttggca cgcagtatcg    300
aagctaacgc gttaagttcg ccgcctgggg agtacggtcg caagactgaa actcaaagga    360
attgacgggg gcccgcacaa gcggtggagt atgtggttta attcgatgca acgcgaagaa    420
ccttacctgg ccttgacatg tcgagaactt ccagagatg gattggtgcc ttcgggaact     480
cgaacacagg tgctgcatgg ctgtcgtcag ctcgtgtcgt gagatgttgg gttaagtccc    540
gcaacgagcg caacccttgt ccttagttgc cagcacgtaa tggtgggaac tctaaggaga    600
ccgccggtga caaaccggag gaaggtgggg atgacgtcaa gtcatcatgg cccttacggc    660
cagggctaca cacgtactac aatggtaggg acagagggct gcaagccggc gacggtaagc    720
caatcccaga aaccctatct cagtccggat tggagtctgc aactcgactc catgaagtcg    780
gaatcgctag taatcgcaga tcagcattgc tgcggtgaat acgttcccgg gccttg        836
```

```
<210> SEQ ID NO 96
<211> LENGTH: 834
<212> TYPE: DNA
<213> ORGANISM: Pseudomonas putida
<220> FEATURE:
<221> NAME/KEY: misc_feature
<222> LOCATION: (1)..(834)
<223> OTHER INFORMATION: BCI 1363 16S rDNA
<220> FEATURE:
<221> NAME/KEY: misc_feature
<222> LOCATION: (40)..(40)
<223> OTHER INFORMATION: n is a, c, g, or t

<400> SEQUENCE: 96
```

```
attactgggc gtaaagcgcg cgtaggtggt ttgttaagtn ggatgtgaaa gccccgggct    60
caacctggga actgcatcca aaactggcaa gctagagtac ggtagagggt ggtggaattt    120
cctgtgtagc ggtgaaatgc gtagatatag gaaggaacac cagtggcgaa ggcgaccacc    180
tggactgata ctgacactga ggtgcgaaag cgtggggagc aaacaggatt agatacccctg   240 gtagtccacg ccgtaaacga tgtcaactag ccgttggaat ccttgagatt ttagtggcgc    300
agctaacgca ttaagttgac cgcctgggga gtacggccgc aaggttaaaa ctcaaatgaa    360
ttgacggggg cccgcacaag cggtggagca tgtggtttaa ttcgaagcaa cgcgaagaac    420
cttaccaggc cttgacatgc agagaacttt ccagagatgg attggtgcct tcgggaactc    480
tgacacaggt gctgcatggc tgtcgtcagc tcgtgtcgtg agatgttggg ttaagtcccg    540
taacgagcgc aacccttgtc cttagttacc agcacgttat ggtgggcact caaggagac    600 tgccggtgac aaaccggagg aaggtgggga tgacgtcaag tcatcatggc ccttacggcc    660
tgggctacac acgtgctaca atggtcgta cagaggttg ccaagccgcg aggtggagct    720
aatctcacaa aaccgatcgt agtccggatc gcagtctgca actcgactgc gtgaagtcgg    780
aatcgctagt aatcgcgaat cagaatgtcg cggtgaatac gttcccgggc cttg          834
```

```
<210> SEQ ID NO 97
<211> LENGTH: 746
<212> TYPE: DNA
<213> ORGANISM: Variovorax ginsengisoli
<220> FEATURE:
<221> NAME/KEY: misc_feature
<222> LOCATION: (1)..(746)
<223> OTHER INFORMATION: BCI 137 16S rDNA
<220> FEATURE:
<221> NAME/KEY: misc_feature
<222> LOCATION: (17)..(17)
```

<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (709)..(710)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t

<400> SEQUENCE: 97

| | | | | | |
|---|---|---|---|---|---|
| agctaactac | ttctggnaga | acccgctccc | atggtgtgac | gggcggtgtg | tacaagaccc | 60 |
| gggaacgtat | tcaccgtgac | attctgatcc | acgattacta | gcgattccga | cttcacgcag | 120 |
| tcgagttgca | gactgcgatc | cggactacga | ctggttttat | gggattagct | ccccctcgcg | 180 |
| ggttggcaac | cctttgtacc | agccattgta | tgacgtgtgt | agccccacct | ataagggcca | 240 |
| tgaggacttg | acgtcatccc | caccttcctc | cggtttgtca | ccggcagtct | cattagagtg | 300 |
| cccaactgaa | tgtagcaact | aatgacaagg | gttgcgctcg | ttgcgggact | taacccaaca | 360 |
| tctcacgaca | cgagctgacg | acagccatgc | agcacctgtg | ttacggttct | ctttcgagca | 420 |
| ctaagccatc | tctggcaaat | tccgtacatg | tcaaaggtgg | gtaaggtttt | tcgcgttgca | 480 |
| tcgaattaaa | ccacatcatc | caccgcttgt | gcgggtcccc | gtcaattcct | ttgagtttca | 540 |
| accttgcggc | cgtactcccc | aggcggtcaa | cttcacgcgt | tagcttcgtt | actgagtcag | 600 |
| tgaagaccca | acaaccagtt | gacatcgttt | agggcgtgga | ctaccagggt | atctaatcct | 660 |
| gtttgctccc | cacgctttcg | tgcatgagcg | tcagtacagg | nccnggggnn | tgccttcgcc | 720 |
| ntcngngttc | ctccncatat | ctacnc | | | | 746 |

<210> SEQ ID NO 98
<211> LENGTH: 859
<212> TYPE: DNA
<213> ORGANISM: Mucilaginibacter gossypii
<220> FEATURE:
<221> NAME/KEY: misc_feature
<222> LOCATION: (1)..(859)
<223> OTHER INFORMATION: BCI 142 16S rDNA

<400> SEQUENCE: 98

| | | | | | |
|---|---|---|---|---|---|
| aggcacttcc | agcttccatg | gcttgacggg | cggtgtgtac | aaggcccggg | aacgtattca | 60 |
| ccgcgtcatt | gctgatacgc | gattactagc | gaatccaact | tcacgggtc | gagttgcaga | 120 |
| ccccgatccg | aactgtgaat | ggctttaaga | gattggcatc | ctgttgccag | gtagctgccc | 180 |

```
tctgtaccat ccattgtagc acgtgtgtag ccccggacgt aagggccatg atgacttgac    240
gtcgtcccct ccttcctctc tatttgcata ggcagtctgt ttagagtccc cacct taaat    300 gctggcaact aaacataggg gttgcgctcg ttgcgggact taacccaaca cctcacggca    360
cgagctgacg acagccatgc agcacctagt ttcgtgttcc gaagaactgt gacgtctctg    420
tcacattcac taactttcaa gcccgggtaa ggttcctcgc gtatcatcga attaaaccac    480
atgctcctcc gcttgtgcgg gccccgtca attcctttga gtttcaccct tgcgggcgta    540
ctccccaggt ggaacactta acgctttcgc ttagacgctg accgtatatc gccaacatcg    600
agtgttcatc gtttagggcg tggactacca gggtatctaa tcctgtttga tccccacgct    660
ttcgtgcctc agcgtcaatc atactttagt aagctgcctt cgcaattggt gttctgtgac    720
atatctatgc atttcaccgc tacttgtcac attccgccta cctcaagtac attcaagctc    780
ttcagtatca agggcactgc gatagttgag ctaccgtctt tcacccctga cttaaaaagc    840
cgcctacgca ccctttaaa                                                 859
```

<210> SEQ ID NO 99
<211> LENGTH: 859
<212> TYPE: DNA
<213> ORGANISM: Mucilaginibacter gossypii
<220> FEATURE:
<221> NAME/KEY: misc_feature
<222> LOCATION: (1)..(859)
<223> OTHER INFORMATION: BCI 142 16S rDNA

<400> SEQUENCE: 99

```
aggcacttcc agcttccatg gcttgacggg cggtgtgtac aaggcccggg aacgtattca     60
ccgcgtcatt gctgatacgc gattactagc gaatccaact tcacggggtc gagttgcaga    120
ccccgatccg aactgtgaat ggctttaaga gattggcatc ctgttgccag gtagctgccc    180
tctgtaccat ccattgtagc acgtgtgtag ccccggacgt aagggccatg atgacttgac    240
gtcgtcccct ccttcctctc tatttgcata ggcagtctgt ttagagtccc cacct taaat    300 gctggcaact aaacataggg gttgcgctcg ttgcgggact taacccaaca cctcacggca    360
cgagctgacg acagccatgc agcacctagt ttcgtgttcc gaagaactgt gacgtctctg    420
tcacattcac taactttcaa gcccgggtaa ggttcctcgc gtatcatcga attaaaccac    480
atgctcctcc gcttgtgcgg gccccgtca attcctttga gtttcaccct tgcgggcgta    540
ctccccaggt ggaacactta acgctttcgc ttagacgctg accgtatatc gccaacatcg    600
agtgttcatc gtttagggcg tggactacca gggtatctaa tcctgtttga tccccacgct    660
ttcgtgcctc agcgtcaatc atactttagt aagctgcctt cgcaattggt gttctgtgac    720
atatctatgc atttcaccgc tacttgtcac attccgccta cctcaagtac attcaagctc    780
ttcagtatca agggcactgc gatagttgag ctaccgtctt tcacccctga cttaaaaagc    840
cgcctacgca ccctttaaa                                                 859
```

<210> SEQ ID NO 100
<211> LENGTH: 773
<212> TYPE: DNA
<213> ORGANISM: Pseudomonas putida
<220> FEATURE:
<221> NAME/KEY: misc_feature
<222> LOCATION: (1)..(773)
<223> OTHER INFORMATION: BCI 159 16S rDNA
<220> FEATURE:
<221> NAME/KEY: misc_feature
<222> LOCATION: (2)..(2)

```
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t

<400> SEQUENCE: 100
tngctacttc tggtgcaacc cactccnntg gtgtgacggg cggtgtgtac aaggcccggg      60
aacgtattca ccgcgacatt ctgattcgcg attactagcg attccgactt cacgcagtcg     120
agttgcagac tgcgatccgg actacgatcg gttttgtgag attagctcca cctcgcggct     180
tggcaaccct ctgtaccgac cattgtagca cgtgtgtagc ccaggccgta agggccatga     240
tgacttgacg tcatccccac cttcctccgg tttgtcaccg gcagtctcct tagagtgccc     300
accataacgt gctggtaact aaggacaagg gttgcgctcg ttacgggact taacccaaca     360
tctcacgaca cgagctgacg acagccatgc agcacctgtg tcagagttcc cgaaggcacc     420
aatccatctc tggaaagttc tctgcatgtc aaggcctggt aaggttcttc gcgttgcttc     480
gaattaaacc acatgctcca ccgcttgtgc gggcccccgt caattcattt gagttttaac     540
cttgcggccg tactccccag gcggtcaact taatgcgtta gctgcgccac taaaatctca     600
```

-continued

```
aggattccaa cggctagttg acatcgttta cggcgtggan taccagggta tctaatcctg      660
tttgctcccc acgctttcgc acctcagtgt cagtatcagt ccaggnggtc gccttcgcca      720
ctngngtncc ttccnatatc tacncatttc ncngctncnc angaaattcc ncc             773
```

<210> SEQ ID NO 101
<211> LENGTH: 694
<212> TYPE: DNA
<213> ORGANISM: Herbaspirillum chlorophenolicum
<220> FEATURE:
<221> NAME/KEY: misc_feature
<222> LOCATION: (1)..(694)
<223> OTHER INFORMATION: BCI 162 16S rDNA

<400> SEQUENCE: 101

```
ccacttctgg taaaacccgc tcccatggtg tgacgggcgg tgtgtacaag acccgggaac       60
gtattcaccg cgacatgctg atccgcgatt actagcgatt ccaacttcat ggagtcgagt      120
tgcagactcc aatccggact acgatacact ttctgggatt agctcccccct cgcgggttgg     180 cggccctctg tatgtaccat tgtatgacgt gtgaagccct acccataagg gccatgagga     240
cttgacgtca tccccacctt cctccggttt gtcaccggca gtctcattag agtgccctt      300 cgtagcaact aatgacaagg gttgcgctcg ttgcgggact aacccaaca tctcacgaca       360 cgagctgacg acagccatgc agcacctgtg tgatggttct ctttcgagca ctcccaaatc      420
tcttcaggat tccatccatg tcaagggtag gtaaggtttt tcgcgttgca tcgaattaat      480
ccacatcatc caccgcttgt gcgggtcccc gtcaattcct ttgagtttta atcttgcgac      540
cgtactcccc aggcggtcta cttcacgcgt tagctgcgtt accaagtcaa ttaagacccg      600
acaactagta gacatcgttt agggcgtgga ctaccagggt atctaatcct gtttgctccc      660
cacgctttcg tgcatgagcg tcagtgttat ccca                                  694
```

<210> SEQ ID NO 102
<211> LENGTH: 726
<212> TYPE: DNA
<213> ORGANISM: Stenotrophomonas maltophilia
<220> FEATURE:
<221> NAME/KEY: misc_feature
<222> LOCATION: (1)..(726)
<223> OTHER INFORMATION: BCI 164 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (707)..(707)

<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t

<400> SEQUENCE: 102

```
naagctacct gcttctggtg caacaaactc ccatggtgtg acgggcggtg tgtacaaggc    60
ccgggaacgt attaccgca gcaatgctga tctgcgatta ctagcgattc cgacttcatg   120
gagtcgagtt gcagactcca atccggactg agatagggtt tctgggattg gcttaccgtc   180
gccggcttgc agccctctgt ccctaccatt gtagtacgtg tgtagccctg ccgtaaggg    240
ccatgatgac ttgacgtcat ccccaccttc ctccggtttg tcaccggcgg tctccttaga   300
gttcccacca ttacgtgctg gcaactaagg acaaggttg cgctcgttgc gggacttaac    360
ccaacatctc acgacacgag ctgacgacag ccatgcagca cctgtgttcg agttcccgaa   420
ggcaccaatc catctctgga aagttctcga catgtcaagg ccaggtaagg ttcttcgcgt   480
tgcatcgaat taaaccacat actccaccgc ttgtgcgggc cccgncaat tcctttgagt    540
ttcagtcttg cgaccgtact ccccaggcgg cgaacttaac gcgttagctt cgatactgcg   600
tgccaaattg cacccaacat ccagttngca tcgttnaggg cgtggantac canggtatct   660
aatcctgttt gctccccacg ctttcgtgcc tcagtgtcag tgttggnccn ggtagctgcc   720
ttcncc                                                              726
```

<210> SEQ ID NO 103
<211> LENGTH: 717
<212> TYPE: DNA
<213> ORGANISM: Stenotrophomonas maltophilia
<220> FEATURE:
<221> NAME/KEY: misc_feature
<222> LOCATION: (1)..(717)
<223> OTHER INFORMATION: BCI 171 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (688)..(689)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t

<400> SEQUENCE: 103

```
ncctgcttct ggtgcaacaa actcccatgg tgtgacgggc ggtgtgtaca aggcccggga    60
acgtattcac cgcagcaatg ctgatctgcg attactagcg attccgactt catggagtcg   120
agttgcagac tccaatccgg actgagatag ggtttctggg attggcttac cgtcgccggc   180
ttgcagccct ctgtccctac cattgtagta cgtgtgtagc cctggccgta agggccatga   240
tgacttgacg tcatccccac cttcctccgg tttgtcaccg gcggtctcct tagagttccc   300
accattacgt gctggcaact aaggacaagg gttgcgctcg ttgcgggact taacccaaca   360
tctcacgaca cgagctgacg acagccatgc agcacctgtg ttcgagttcc cgaaggcacc   420
aatccatctc tggaaagttc tcgacatgtc aaggccaggt aaggttcttc gcgttgcatc   480
gaattaaacc acatactcca ccgcttgtgc gggccccgt caattccttn gagtttcagt    540
cttgcgaccg tactccccag gcggcgaact taacgcgtta gcttcgatac tgcgtgccaa   600
attgcaccca acatccagtt ngcatcgttn anggcgtgga ntaccagggt atctaatcct   660
gtttgctccc cacgctttcg tgcctcanng tcaatgntgg tccnggtagc tgccttn     717
```

<210> SEQ ID NO 104
<211> LENGTH: 772
<212> TYPE: DNA
<213> ORGANISM: Pseudomonas putida
<220> FEATURE:
<221> NAME/KEY: misc_feature
<222> LOCATION: (1)..(772)
<223> OTHER INFORMATION: BCI 178 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (701)..(702)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (731)..(731)

```
<223> OTHER INFORMATION: n is a, c, g, or t
<220> FEATURE:
<221> NAME/KEY: misc_feature
<222> LOCATION: (734)..(735)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (755)..(756)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (760)..(761)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t

<400> SEQUENCE: 104
ngctacttct ggtgcnaccc actcccatgg tgtgacgggc ggtgtgtaca aggcccggga      60
acgtattcac cgcgacattc tgattcgcga ttactagcga ttccgacttc acgcagtcga     120
gttgcagact gcgatccgga ctacgatcgg ttttgtgaga ttagctccac ctcgcggctt     180
ggcaaccctc tgtaccgacc attgtagcac gtgtgtagcc caggccgtaa gggccatgat     240
gacttgacgt catccccacc ttcctccggt ttgtcaccgg cagtctcctt agagtgccca     300
ccataacgtg ctggtaacta aggacaaggg ttgcgctcgt tacgggactt aacccaacat     360
ctcacgacac gagctgacga cagccatgca gcacctgtgt cagagttccc gaaggcacca     420
atccatctct ggaaagttct ctgcatgtca aggcctggta aggttcttcg cgttgcttcg     480
aattaaacca catgctccac cgcttgtgcg ggccccgtc aattcatttg agttttaacc      540
ttgcggccgt actccccagg cggtcaactt aatgcgttag ctgcgccact aaaatctcaa     600
ngattccaac ggctagttga catcgtttac ggcgtggact accanggtat ctaatcctgt     660
ttgctcccca cgctttcgca cctcagngtc agtatcagtc nnggnggtcg ccttcgccac     720
tngtgttcct nccnntatct acncatttcn ccgcnncncn ngaaattccn cc            772

<210> SEQ ID NO 105
<211> LENGTH: 724
<212> TYPE: DNA
<213> ORGANISM: Stenotrophomonas maltophilia
<220> FEATURE:
<221> NAME/KEY: misc_feature
<222> LOCATION: (1)..(724)
<223> OTHER INFORMATION: BCI 181 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
```

```
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (74)..(77)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t

<400> SEQUENCE: 105
ganggnagcg nanntnnngn tgtagcagtg aantgnntag nnntcaggan naacatccat      60
ggngaaggca gctnnnngga ncaacattga cactgaggca cganagcgtg gggagcaaac     120
aggattagat accntggtag tncacnccct aaacgatgcg aactggatgt tgggtgcaat     180
ttggcacgca gtatcgaagc taacgcgtta agttcgccgc ctggggagta cggtcgcaag     240
actgaaactc aaaggaattg acggggggccc gcacaagcgg tggagtatgt ggtttaattc     300
gatgcaacgc gaagaacctt acctggcctt gacatgtcga gaactttcca gagatggatt     360
ggtgccttcg ggaactcgaa cacaggtgct gcatggctgt cgtcagctcg tgtcgtgaga     420
tgttgggtta agtcccgcaa cgagcgcaac ccttgtcctt agttgccagc acgtaatggt     480
gggaactcta aggagaccgc cggtgacaaa ccggaggaag gtgggatgac gtcaagtca     540 tcatggccct tacggccagg gctacacacg tactacaatg gtagggacag agggctgcaa     600
```

| | |
|---|---|
| gccggcgacg gtaagccaat cccagaaacc ctatctcagt ccggattgga gtctgcaact | 660 |
| cgactccatg aagtcggaat cgctagtaat cgcagatcag cattgctgcg gtgaatacgt | 720 |
| tccc | 724 |

<210> SEQ ID NO 106
<211> LENGTH: 774
<212> TYPE: DNA
<213> ORGANISM: Ramlibacter henchirensis
<220> FEATURE:
<221> NAME/KEY: misc_feature
<222> LOCATION: (1)..(774)
<223> OTHER INFORMATION: BCI 1959 16S rDNA

<400> SEQUENCE: 106

| | |
|---|---|
| cttctggcag aacccgctcc catggtgtga cgggcggtgt gtacaagacc cgggaacgta | 60 |
| ttcaccgcga cattctgatc cgcgattact agcgattccg acttcacgca gtcgagttgc | 120 |
| agactgcgat ccggactacg actggtttta tgggattagc tcccctcgc gggttggcaa | 180 |
| ccctctgtac cagccattgt atgacgtgtg tagccccacc tataagggcc atgaggactt | 240 |
| gacgtcatcc ccaccttcct ccggtttgtc accggcagtc tcattagagt gcctttcgt | 300 |
| agcaactaat gacaagggtt gcgctcgttg cgggacttaa cccaacatct cacgacacga | 360 |
| gctgacgaca gccatgcagc acctgtgttc tggttctctt tcgagcactc ccacgtctct | 420 |
| gcgggattcc agacatgtca aaggtgggta aggttttcg cgttgcatcg aattaaacca | 480 |
| catcatccac cgcttgtgcg ggtccccgtc aattcctttg agtttcaacc ttgcggccgt | 540 |
| actcccagg cggtcaactt cacgcgttag cttcgttact gatccagtga aggaccaaca | 600 |
| accagttgac atcgtttagg gcgtggacta ccagggtatc taatcctgtt tgctccccac | 660 |
| gctttcgtgc atgagcgtca gtgcaggcc aggggattgc cttcgccatc ggtgttcctc | 720 |
| cgcatatcta cgcatttcac tgctacacgc ggaattccat ccccctctgc cgca | 774 |

<210> SEQ ID NO 107
<211> LENGTH: 1085
<212> TYPE: DNA
<213> ORGANISM: Duganella violaceinigra
<220> FEATURE:
<221> NAME/KEY: misc_feature
<222> LOCATION: (1)..(1085)
<223> OTHER INFORMATION: BCI 2204 16S rDNA

<400> SEQUENCE: 107

| | |
|---|---|
| agcgccctcc ttgcggttag ctacctactt ctggtaaaac ccgctcccat ggtgtgacgg | 60 |
| gcggtgtgta caagacccgg gaacgtattc accgcgacat gctgatccgc gattactagc | 120 |
| gattccaact tcatgtagtc gagttgcaga ctacaatccg gactacgata cactttctgg | 180 |
| gattagctcc ccctcgcggg ttggcggccc tctgtatgta ccattgtatg acgtgtgaag | 240 |
| ccctacccat aagggccatg aggacttgac gtcatcccca ccttcctccg gtttgtcacc | 300 |
| ggcagtctca ttagagtgct cttgcgtagc aactaatgac aagggttgcg ctcgttgcgg | 360 |
| gacttaaccc aacatctcac gacacgagct gacgacagcc atgcagcacc tgtgtgcagg | 420 |
| ttctctttcg agcactccca gatctctcca ggattcctgc catgtcaagg gtaggtaagg | 480 |
| tttttcgcgt tgcatcgaat taatccacat catccaccgc ttgtgcgggt ccccgtcaat | 540 |
| tcctttgagt tttaatcttg cgaccgtact ccccaggcgg tctacttcac gcgttagctg | 600 |
| cgttactaag tcaattaaga cccaacaact agtagacatc gtttagggcg tggactacca | 660 |
| gggtatctaa tcctgtttgc tccccacgct ttcgtgcatg agcgtcagtt tgacccagg | 720 |

```
gggctgcctt cgccatcggt gttcctccac atctctacgc atttcactgc tacacgtgga    780
attctacccc cctctgccaa actctagcct cgcagtctcc atcgccattc ccaggttaag    840
cccggggatt tcacgacaga cttacgaaac cgcctgcgca cgctttacgc ccagtaattc    900
cgattaacgc ttgcacccta cgtattaccg cggctgctgg cacgtagtta gccggtgctt    960
attcttcagg taccgtcagc agtcgtggat attagccacg accttttctt ccctgacaaa   1020
agagctttac aacccgaagg ccttcttcac tcacgcggca ttgctggatc agggttgccc   1080
ccatt                                                               1085
```

<210> SEQ ID NO 108
<211> LENGTH: 687
<212> TYPE: DNA
<213> ORGANISM: Exiguobacterium acetylicum
<220> FEATURE:
<221> NAME/KEY: misc_feature
<222> LOCATION: (1)..(687)
<223> OTHER INFORMATION: BCI 23 16S rDNA

<400> SEQUENCE: 108

```
ttcgggtgtt gcaaactctc gtggtgtgac gggcggtgtg tacaagaccc gggaacgtat     60
tcaccgcagt atgctgacct gcgattacta gcgattccga cttcatgcag gcgagttgca    120
gcctgcaatc cgaactggga acggctttat gggattggct ccacctcgcg gtctcgctgc    180
cctttgtacc gtccattgta gcacgtgtgt agcccaactc ataaggggca tgatgatttg    240
acgtcatccc caccttcctc cggtttgtca ccggcagtct ccctagagtg cccaactaaa    300
tgctggcaac taaggatagg ggttgcgctc gttgcgggac ttaacccaac atctcacgac    360
acgagctgac gacaaccatg caccacctgt caccattgtc cccgaaggga aaacttgatc    420
tctcaagcgg tcaatgggat gtcaagagtt ggtaaggttc ttcgcgttgc ttcgaattaa    480
accacatgct ccaccgcttg tgcgggtccc cgtcaattcc tttgagtttc agccttgcgg    540
ccgtactccc caggcggagt gcttaatgcg ttagcttcag cactgagggg cggaaacccc    600
ccaacaccta gcactcatcg tttacggcgt ggactaccag ggtatctaat cctgtttgct    660
ccccacgctt tcgcgcctca gcgtcag                                        687
```

<210> SEQ ID NO 109
<211> LENGTH: 768
<212> TYPE: DNA
<213> ORGANISM: Pseudomonas putida
<220> FEATURE:
<221> NAME/KEY: misc_feature
<222> LOCATION: (1)..(768)
<223> OTHER INFORMATION: BCI 234 16S rDNA

<400> SEQUENCE: 109

```
ggttagacta gctacttctg gtgcaaccca ctcccatggt gtgacgggcg gtgtgtacaa     60
ggcccgggaa cgtattcacc gcgacattct gattcgcgat tactagcgat tccgacttca    120
cgcagtcgag ttgcagactg cgatccggac tacgatcggt tttgtgagat tagctccacc    180
tcgcggcttg gcaaccctct gtaccgacca ttgtagcacg tgtgtagccc aggccgtaag    240
ggccatgatg acttgacgtc atccccacct tcctccggtt tgtcaccggc agtctcctta    300
gagtgcccac cataacgtgc tggtaactaa ggacaagggt tgcgctcgtt acgggactta    360
acccaacatc tcacgacacg agctgacgac agccatgcag cacctgtgtc agagttcccg    420
aaggcaccaa tccatctctg gaaagttctc tgcatgtcaa ggcctggtaa ggttcttcgc    480
```

| | |
|---|---|
| gttgcttcga attaaaccac atgctccacc gcttgtgcgg gccccgtca attcatttga | 540 |
| gttttaacct tgcggccgta ctccccaggc ggtcaactta atgcgttagc tgcgccacta | 600 |
| aaatctcaag gattccaacg gctagttgac atcgtttacg gcgtggacta ccagggtatc | 660 |
| taatcctgtt tgctcccac gctttcgcac ctcagtgtca gtatcagtcc aggtggtcgc | 720 |
| cttcgccact ggtgttcctt cctatatcta cgcatttcac cgctacac | 768 |

<210> SEQ ID NO 110
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 235 16S rDNA
<220> FEATURE:
<221> NAME/KEY: misc_feature
<222> LOCATION: (39)..(39)
<223> OTHER INFORMATION: n is a, c, g, or t

<400> SEQUENCE: 110

| | |
|---|---|
| ttactgggcg taaagcgcgc gtaggtggtt tgttaagtng gatgtgaaag ccccgggctc | 60 |
| aacctgggaa ctgcatccaa aactggcaag ctagagtacg gtagagggtg gtggaatttc | 120 |
| ctgtgtagcg gtgaaatgcg tagatatagg aaggaacacc agtggcgaag gcgaccacct | 180 |
| ggactgatac tgacactgag gtgcgaaagc gtggggagca acaggatta gataccctgg | 240 |
| tagtccacgc cgtaaacgat gtcaactagc cgttggaatc cttgagattt tagtggcgca | 300 |
| gctaacgcat taagttgacc gcctggggag tacggccgca aggttaaaac tcaaatgaat | 360 |
| tgacgggggc ccgcacaagc ggtggagcat gtggtttaat tcgaagcaac gcgaagaacc | 420 |
| ttaccaggcc ttgacatgca gagaactttc cagagatgga ttggtgcctt cgggaactct | 480 |
| gacacaggtg ctgcatggct gtcgtcagct cgtgtcgtga gatgttgggt taagtcccgt | 540 |
| aacgagcgca acccttgtcc ttagttacca gcacgttatg gtgggcactc taaggagact | 600 |
| gccggtgaca aaccggagga aggtggggat gacgtcaagt catcatggcc cttacggcct | 660 |
| gggctacaca cgtgctacaa tggtcggtac agagggttgc caagccgcga ggtgagcta | 720 |
| atctcacaaa accgatcgta gtccggatcg cagtctgcaa ctcgactgcg tgaagtcgga | 780 |
| atcgctagta atcgcgaatc agaatgtcgc ggtgaatacg ttccc | 825 |

<210> SEQ ID NO 111
<211> LENGTH: 897
<212> TYPE: DNA
<213> ORGANISM: Delftia lacustris
<220> FEATURE:
<221> NAME/KEY: misc_feature
<222> LOCATION: (1)..(897)
<223> OTHER INFORMATION: BCI 2350 16S rDNA

<400> SEQUENCE: 111

| | |
|---|---|
| gctagctcct tacggttact ccaccgactt cgggtgttac aaactctcgt ggtgtgacgg | 60 |
| gcggtgtgta caaggcccgg gaacgtattc accgcggcat gctgatccgc gattactagc | 120 |
| gattccagct tcatgtaggc gagttgcagc ctacaatccg aactgagaat ggttttatgg | 180 |
| gattggcttg acctcgcggt cttgcagccc tttgtaccat ccattgtagc acgtgtgtag | 240 |
| cccaggtcat aaggggcatg atgatttgac gtcatcccca ccttcctccg gtttgtcacc | 300 |
| ggcagtcacc ttagagtgcc caactaaatg ctggcaacta agatcaaggg ttgcgctcgt | 360 |
| tgcgggactt aacccaacat ctcacgacac gagctgacga caaccatgca ccacctgtca | 420 |

```
ctctgtcccc cgaagggaa cgctctatct ctagagttgt cagaggatgt caagacctgg      480
taaggttctt cgcgttgctt cgaattaaac cacatgctcc accgcttgtg cgggccccccg   540 tcaattcctt tgagtttcag tcttgcgacc gtactcccca ggcggagtgc ttaatgcgtt    600
agctgcagca ctaaagggcg aaaccctct aacacttagc actcatcgtt tacggcgtgg    660
actaccaggg tatctaatcc tgtttgctcc ccacgctttc gcgcctcagc gtcagttaca   720
gaccaaaaag ccgccttcgc cactggtgtt cctccacatc tctacgcatt tcaccgctac   780
acgtggaatt ccgctttct cttctgcact caagttcccc agtttccaat gaccctccac    840
ggttgagccg tgggctttca catcagactt aagaaaccgc ctgcgcgcgc tttacgc      897
```

```
<210> SEQ ID NO 112
<211> LENGTH: 827
<212> TYPE: DNA
<213> ORGANISM: Pseudomonas putida
<220> FEATURE:
<221> NAME/KEY: misc_feature
<222> LOCATION: (1)..(827)
<223> OTHER INFORMATION: BCI 244 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t

<400> SEQUENCE: 112
ntactgggcg taaagcgcgc gtaggtggtt tnttaagttn gnatgtgaaa gccccgggct     60
caacctggga actgcatncn aaaactggca agctagagta cggtagaggg tggtggaatt   120
tcntgtgtag cggtgaaatg cgtagatata ggaaggaaca ccagtggcga aggcgaccac   180
ctggactgat actgacactg aggtgcgaaa gcgtgggag caaacaggat tagataccct    240
ggtagtccac gccgtaaacg atgtcaacta gccgttggaa tccttgagat tttagtggcg   300
cagctaacgc attaagttga ccgcctgggg agtacggccg caaggttaaa actcaaatga   360
attgacgggg gcccgcacaa gcggtggagc atgtggttta attcgaagca acgcgaagaa   420
ccttaccagg ccttgacatg cagagaactt tccagagatg gattggtgcc ttcgggaact   480
ctgacacagg tgctgcatgg ctgtcgtcag ctcgtgtcgt gagatgttgg gttaagtccc   540
gtaacgagcg caaccccttgt ccttagttac cagcacgtta tggtgggcac tctaaggaga   600
ctgccggtga caaaccggag gaaggtgggg atgacgtcaa gtcatcatgg cccttacggc   660
```

```
ctgggctaca cacgtgctac aatggtcggt acagagggtt gccaagccgc gaggtggagc      720
taatctcaca aaaccgatcg tagtccggat cgcagtctgc aactcgactg cgtgaagtcg      780
gaatcgctag taatcgcgaa tcagaatgtc gcggtgaata cgttccc                   827
```

<210> SEQ ID NO 113
<211> LENGTH: 826
<212> TYPE: DNA
<213> ORGANISM: Bacillus megaterium
<220> FEATURE:
<221> NAME/KEY: misc_feature
<222> LOCATION: (1)..(826)
<223> OTHER INFORMATION: BCI 251 16S rDNA
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t

<400> SEQUENCE: 113

```
ttannggcg taaagcgcgc gcnggcggtt tcttaagtct gatgtgaaag cccncggntc       60
aaccgtggag ggtcattgga aactggggaa cttgagtgca gaagagaaaa gcggaattcc     120
acgtgtagcg gtgaaatgcg tagagatgtg gaggaacacc agtggcgaag gcggcttttt     180
ggtctgtaac tgacgctgag gcgcgaaagc gtggggagca acaggatta gataccctgg      240 tagtccacgc cgtaaacgat gagtgctaag tgttagaggg tttccgccct ttagtgctgc     300
agctaacgca ttaagcactc cgcctgggga gtacggtcgc aagactgaaa ctcaaaggaa     360
ttgacggggg cccgcacaag cggtggagca tgtggtttaa ttcgaagcaa cgcgaagaac     420
cttaccaggt cttgacatcc tctgacaact ctagagatag gcgttcccc ttcggggac      480 agagtgacag gtggtgcatg gttgtcgtca gctcgtgtcg tgagatgttg ggttaagtcc     540
cgcaacgagc gcaacccttg atcttagttg ccagcattna gttgggcact ctaaggtgac     600
tgccggtgac aaaccggagg aaggtgggga tgacgtcaaa tcatcatgcc ccttatgacc     660
tgggctacac acgtgctaca atggatggta caaagggctg caagaccgcg aggtcaagcc     720
aatcccataa aaccattctc agttcggatt gtaggctgca actcgcctac atgaagctgg     780
aatcgctagt aatcgcggat cagcatgccg cggtgaatac gttccc                   826
```

<210> SEQ ID NO 114
<211> LENGTH: 826
<212> TYPE: DNA
<213> ORGANISM: Bacillus megaterium
<220> FEATURE:
<221> NAME/KEY: misc_feature
<222> LOCATION: (1)..(826)
<223> OTHER INFORMATION: BCI 255 16S rDNA
<220> FEATURE:
<221> NAME/KEY: misc_feature
<222> LOCATION: (23)..(23)
<223> OTHER INFORMATION: n is a, c, g, or t

```
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t

<400> SEQUENCE: 114
ttattgggcg taaagcgcgc gcnggcggtt tcttaantnt gatgtgaaag cccncggntc      60
naccgtggag ggtcattgga aactggggaa cttgagtgca gaagagaaaa gcgganttcc     120
acgtgtagcg gtgaaatgcg tagagatgtg gaggaacacc agtggcgaag gcggctttt     180 ggtctgtaac tgacgctgag gcgcgaaagc gtggggagca acaggatta gatacctgg      240 tagtccacgc cgtaaacgat gagtgctaag tgttagaggg tttccgccct ttagtgctgc    300
agctaacgca ttaagcactc cgcctgggga gtacggtcgc aagactgaaa ctcaaaggaa    360
ttgacggggg cccgcacaag cggtggagca tgtggtttaa ttcgaagcaa cgcgaagaac    420
cttaccaggt cttgacatcc tctgacaact ctagagatag agcgttcccc ttcgggggac    480
agagtgacag gtggtgcatg gttgtcgtca gctcgtgtcg tgagatgttg ggttaagtcc    540
cgcaacgagc gcaaccttg atcttagttg ccagcattta gttgggcact ctaaggtgac     600
tgccggtgac aaaccggagg aaggtgggga tgacgtcaaa tcatcatgcc ccttatgacc    660
tgggctacac acgtgctaca atggatggta caaagggctg caagaccgcg aggtcaagcc    720
aatcccataa aaccattctc agttcggatt gtaggctgca actcgcctac atgaagctgg    780
aatcgctagt aatcgcggat cagcatgccg cggtgaatac gttccc                   826

<210> SEQ ID NO 115
<211> LENGTH: 826
<212> TYPE: DNA
<213> ORGANISM: Bacillus megaterium
<220> FEATURE:
<221> NAME/KEY: misc_feature
<222> LOCATION: (1)..(826)
<223> OTHER INFORMATION: BCI 262 16S rDNA
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (54)..(54)
```

<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t

<400> SEQUENCE: 115

```
ttatngggcg taaagcgcgc gcnggcgntt tcttaagtct gatgtgaaag cccncggctc      60
naccgtggag ggtcattgga aactggggaa cttgagtgca gaagagaaaa gcgnaattcc     120
acgtgtagcg gtgaaatgcg tagagatgtg gaggaacacc agtggcgaag gcggcttttt    180
ggtctgtaac tgacgctgag gcgcgaaagc gtggggagca aacaggatta gataccctgg    240
tagtccacgc cgtaaacgat gagtgctaag tgttagaggg tttccgccct ttagtgctgc    300
agctaacgca ttaagcactc cgcctgggga gtacggtcgc aagactgaaa ctcaaaggaa    360
ttgacggggg cccgcacaag cggtggagca tgtggtttaa ttcgaagcaa cgcgaagaac    420
cttaccaggt cttgacatcc tctgacaact ctagagatag agcgttcccc ttcggggggac   480 agagtgacag gtggtgcatg gttgtcgtca gctcgtgtcg tgagatgttg ggttaagtcc    540
cgcaacgagc gcaacccttg atcttagttg ccagcattta gttgggcact ctaaggtgac    600
tgccggtgac aaaccggagg aaggtgggga tgacgtcaaa tcatcatgcc ccttatgacc    660
tgggctacac acgtgctaca atggatggta caaagggctg caagaccgcg aggtcaagcc    720
aatcccataa aaccattctc agttcggatt gtaggctgca actcgcctac atgaagctgg    780
aatcgctagt aatcgcggat cagcatgccg cggtgaatac gttccc                   826
```

<210> SEQ ID NO 116
<211> LENGTH: 826
<212> TYPE: DNA
<213> ORGANISM: Bacillus megaterium
<220> FEATURE:
<221> NAME/KEY: misc_feature
<222> LOCATION: (1)..(826)
<223> OTHER INFORMATION: BCI 264 16S rDNA
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 116

```
ttattgggcg taaagcgcgc gcnggcgntt tcttaagtnt gatgtgaaag cccncggntc      60
aaccgtggag ggtcattgga aactggggaa cttgagtgca gaagagaaaa gcggaattcc    120
acgtgtagcg gtgaaatgcg tagagatgtg gaggaacacc agtggcgaag gcggcttttt    180
ggtctgtaac tgacgctgag gcgcgaaagc gtggggagca aacaggatta gataccctgg    240
```

-continued

```
tagtccacgc cgtaaacgat gagtgctaag tgttagaggg tttccgccct ttagtgctgc        300
agctaacgca ttaagcactc cgcctgggga gtacggtcgc aagactgaaa ctcaaaggaa        360
ttgacggggg cccgcacaag cggtggagca tgtggtttaa ttcgaagcaa cgcgaagaac        420
cttaccaggt cttgacatcc tctgacaact ctagagatag agcgttcccc ttcggggac         480 agagtgacag gtggtgcatg gttgtcgtca gctcgtgtcg tgagatgttg ggttaagtcc        540
cgcaacgagc gcaaccttg atcttagttg ccagcattta gttgggcact ctaaggtgac         600
tgccggtgac aaaccggagg aaggtgggga tgacgtcaaa tcatcatgcc ccttatgacc        660
tgggctacac acgtgctaca atggatggta caagggctg caagaccgcg aggtcaagcc         720
aatcccataa aaccattctc agttcggatt gtaggctgca actcgcctac atgaagctgg       780
aatcgctagt aatcgcggat cagcatgccg cggtgaatac gttccc                      826
```

<210> SEQ ID NO 117
<211> LENGTH: 382
<212> TYPE: DNA
<213> ORGANISM: Stenotrophomonas maltophilia
<220> FEATURE:
<221> NAME/KEY: misc_feature
<222> LOCATION: (1)..(382)
<223> OTHER INFORMATION: BCI 271 16S rDNA

<400> SEQUENCE: 117

```
agctacctgc ttctggtgca acaaactccc atggtgtgac gggcggtgtg tacaaggccc        60
gggaacgtat tcaccgcagc aatgctgatc tgcgattact agcgattccg acttcatgga      120
gtcgagttgc agactccaat ccggactgag atagggtttc tgggattggc ttaccgtcgc      180
cggcttgcag ccctctgtcc ctaccattgt agtacgtgtg tagccctggc cgtaagggcc      240
atgatgactt gacgtcatcc ccaccttcct ccggtttgtc accggcggtc tccttagagt      300
tcccaccatt acgtgctggc aactaaggac aagggttgcg ctcgttgcgg gacttaaccc      360
aacatctcac gacacgagct ga                                                382
```

<210> SEQ ID NO 118
<211> LENGTH: 782
<212> TYPE: DNA
<213> ORGANISM: Rahnella aquatilis
<220> FEATURE:
<221> NAME/KEY: misc_feature
<222> LOCATION: (1)..(782)
<223> OTHER INFORMATION: BCI 29 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (728)..(728)

<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (757)..(758)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (767)..(767)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t

<400> SEQUENCE: 118

```
tangctacct acttcttttg nnacccactc ccatggtgtg acgggcggtg tgtacaaggc    60
ccgggaacgt attcaccgta gcattctgat ctacgattac tagcgattcc gacttcatgg   120
agtcgagttg cagactccaa tccggactac gacatacttt atgaggtccg cttgctctcg   180
cgagttcgct tctctttgta tatgccattg tagcacgtgt gtagccctac tcgtaagggc   240
catgatgact tgacgtcatc cccaccttcc tccggtttat caccggcagt ctcctttgag   300
ttcccaccat tacgtgctgg caacaaagga taagggttgc gctcgttgcg ggacttaacc   360
caacatttca caacacgagc tgacgacagc catgcagcac ctgtctcacg gttcccgaag   420
gcactaagcc atctctggcg aattccgtgg atgtcaagag taggtaaggt tcttcgcgtt   480
gcatcgaatt aaaccacatg ctccaccgct tgtgcgggcc ccgtcaatt catttgagtt    540
ttaaccttgc ggccgtactc cccaggcggt cgacttaacg cgttagctcc ggaagccacg   600
cctcaaggnc acaacctcca agtcgacatc gtttacagcg tggactacca gggtatctaa   660
tcctgtttgc tccccacgct ttcgcacctg ancgtcagtc tttgtccngg gggccgcctt   720
cgccaccngt nttcctccng anctctncgc atttcanngc tncnccngna antcnacccc   780
cc                                                                  782
```

<210> SEQ ID NO 119
<211> LENGTH: 860

<212> TYPE: DNA
<213> ORGANISM: Variovorax ginsengisoli
<220> FEATURE:
<221> NAME/KEY: misc_feature
<222> LOCATION: (1)..(860)
<223> OTHER INFORMATION: BCI 3078 16S rDNA

<400> SEQUENCE: 119

```
tgcggttagg ctaactactt ctggcagaac ccgctcccat ggtgtgacgg gcggtgtgta      60
caagacccgg gaacgtattc accgtgacat tctgatccac gattactagc gattccgact     120
tcacgcagtc gagttgcaga ctgcgatccg gactacgact ggttttatgg gattagctcc     180
ccctcgcggg ttggcaaccc tttgtaccag ccattgtatg acgtgtgtag ccccaccctat    240
aagggccatg aggacttgac gtcatcccca ccttcctccg gtttgtcacc ggcagtctca     300
ttagagtgcc caactaaatg tagcaactaa tgacaagggt tgcgctcgtt gcgggactta     360
acccaacatc tcacgacacg agctgacgac agccatgcag cacctgtgtt acggttctct     420
ttcgagcact aaaccatctc tggtaaattc gtacatgtc aaaggtgggt aaggtttttc      480
gcgttgcatc gaattaaacc acatcatcca ccgcttgtgc gggtccccgt caattccttt     540
gagtttcaac cttgcggccg tactccccag gcggtcaact tcacgcgtta gcttcgttac     600
tgagtcagtg aagacccaac aaccagttga catcgtttag ggcgtggact accagggtat     660
ctaatcctgt ttgctcccca cgctttcgtg catgagcgtc agtacaggtc caggggattg     720
ccttcgccat cggtgttcct ccgcatatct acgcatttca ctgctacacg cggaattcca     780
tccccctcta ccgtactcta gctatgcagt cacagatgca attcccaggt tgagcccggg     840
ggatttcaca actgtcttac                                                 860
```

<210> SEQ ID NO 120
<211> LENGTH: 682
<212> TYPE: DNA
<213> ORGANISM: Duganella radicis
<220> FEATURE:
<221> NAME/KEY: misc_feature
<222> LOCATION: (1)..(682)
<223> OTHER INFORMATION: BCI 31 16S rDNA

<400> SEQUENCE: 120

```
agctacctac ttctggtaaa acccgctccc atggtgtgac gggcggtgtg tacaagaccc      60
gggaacgtat tcaccgcgac atgctgatcc gcgattacta gcgattccaa cttcacgtag     120
tcgagttgca gactacgatc cggactacga tgcactttct gggattagct ccccctcgcg     180
ggttggcggc cctctgtatg caccattgta tgacgtgtga agcccctaccc ataagggcca    240
tgaggacttg acgtcatccc caccttcctc cggtttgtca ccggcagtct cattagagtg     300
ccctttcgta gcaactaatg acaagggttg cgctcgttgc gggacttaac ccaacatctc     360
acgacacgag ctgacgacag ccatgcagca cctgtgtatc ggttctcttt cgggcactcc     420
ccaatctctc agggattcct tccatgtcaa gggtaggtaa ggttttttcgc gttgcatcga    480
attaatccac atcatccacc gcttgtgcgg gtccccgtca attcctttga gttttaatct     540
tgcgaccgta ctccccaggc ggtctacttc acgcgttagc tgcgttacca agtcaattaa     600
gacccgacaa ctagtagaca tcgtttaggg cgtggactac cagggtatct aatcctgttt     660
gctccccacg ctttcgtgca tg                                              682
```

<210> SEQ ID NO 121
<211> LENGTH: 687
<212> TYPE: DNA

```
<213> ORGANISM: Rhizobium lemnae
<220> FEATURE:
<221> NAME/KEY: misc_feature
<222> LOCATION: (1)..(687)
<223> OTHER INFORMATION: BCI 34 16S rDNA

<400> SEQUENCE: 121
gccttcgggt aaaaccaact cccatggtgt gacgggcggt gtgtacaagg cccgggaacg      60
tattcaccgc ggcgtgctga tccgcgatta ctagcgattc caacttcatg cactcgagtt     120
gcagagtgca atccgaactg agatggcttt tggagattag ctcacactcg cgtgctcgct     180
gcccactgtc accaccattg tagcacgtgt gtagcccagc ccgtaagggc catgaggact     240
tgacgtcatc cccaccttcc tctcggctta tcaccggcag tccccttaga gtgcccaacc     300
aaatgctggc aactaagggc gagggttgcg ctcgttgcgg gacttaaccc aacatctcac     360
gacacgagct gacgacagcc atgcagcacc tgtgtcccgg tccccgaagg gaaaaccaca     420
tctctgtggc gagccgggca tgtcaagggc tggtaaggtt ctgcgcgttg cttcgaatta     480
aaccacatgc tccaccgctt gtgcgggccc ccgtcaattc ctttgagttt taatcttgcg     540
accgtactcc ccaggcggaa tgtttaatgc gttagctgcg ccaccgacaa gtaaacttgc     600
cgacggctaa cattcatcgt ttacggcgtg gactaccagg gtatctaatc ctgtttgctc     660
cccacgcttt cgcacctcag cgtcagt                                         687

<210> SEQ ID NO 122
<211> LENGTH: 823
<212> TYPE: DNA
<213> ORGANISM: Stenotrophomonas maltophilia
<220> FEATURE:
<221> NAME/KEY: misc_feature
<222> LOCATION: (1)..(823)
<223> OTHER INFORMATION: BCI 343 16S rDNA
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 122
ttactgggcg taaagcgtgc gcnggcgntt atataagaca gatgtgaant ccccgggctc      60
aacntgggaa ctgcatttgt gactgtatag ctagagtacg gtagaggggg atggaattcc     120
gcgtgtagca gtgaaatgcg tagatatgcg gaggaacacc gatggcgaag gcaatccct     180 ggacctgtac tgacgctcat gcacgaaagc gtggggagca acaggatta gataccctgg     240 tagtccacgc cctaaacgat gtcaactggt tgttgggtct tcactgactc agtaacgaag     300
ctaacgcgtg aagttgaccg cctggggagt acggccgcaa ggttgaaact caaaggaatt     360
gacggggacc cgcacaagcg gtggatgatg tggtttaatt cgatgcaacg cgaaaaacct     420
tacccacctt tgcatgtgac ggaatccttt agagatagag gagtgctcga agagaaccg     480 taacacaggt gctgcatggc tgtcgtcagc tcgtgtcgtg agatgttggg ttaagtcccg     540
caacgagcgc aacccttgtc attagttgct acatttagtt gggcactcta atgagactgc     600
```

```
cggtgacaaa ccggaggaag gtggggatga cgtcaagtcc tcatggccct tataggtggg      660
gctacacacg tcatacaatg gctggtacag agggttgcca acccgcgagg gggagccaat      720
cccataaagc cagtcgtagt ccggatcgca gtctgcaact cgactgcgtg aagtcggaat      780
cgctagtaat cgcggatcag aatgtcgcgg tgaatacgtt ccc                        823
```

```
<210> SEQ ID NO 123
<211> LENGTH: 823
<212> TYPE: DNA
<213> ORGANISM: Stenotrophomonas maltophilia
<220> FEATURE:
<221> NAME/KEY: misc_feature
<222> LOCATION: (1)..(823)
<223> OTHER INFORMATION: BCI 344 16S rDNA
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 123
```

```
ttactgggcg taaagcgtgc gcnggcgntt atataagaca gatgtgaant ccccgggctc       60
aacntgggaa ctgcatttgt gactgtatag ctagagtacg gtagaggggg atggaattcc      120
gcgtgtagca gtgaaatgcg tagatatgcg gaggaacacc gatggcgaag gcaatcccct     180
ggacctgtac tgacgctcat gcacgaaagc gtggggagca acaggatta gatacctgg       240 tagtccacgc cctaaacgat gtcaactggt tgttgggtct tcactgactc agtaacgaag    300
ctaacgcgtg aagttgaccg cctggggagt acggccgcaa ggttgaaact caaaggaatt     360
gacggggacc cgcacaagcg gtggatgatg tggtttaatt cgatgcaacg cgaaaaacct     420
tacccacctt tgacatgtac ggaatccttt agagatagag gagtgctcga agagaaccg      480 taacacaggt gctgcatggc tgtcgtcagc tcgtgtcgtg agatgttggg ttaagtcccg     540
caacgagcgc aacccttgtc attagttgct acatttagtt gggcactcta atgagactgc     600
cggtgacaaa ccggaggaag gtggggatga cgtcaagtcc tcatggccct tataggtggg    660
gctacacacg tcatacaatg gctggtacag agggttgcca acccgcgagg gggagccaat     720
cccataaagc cagtcgtagt ccggatcgca gtctgcaact cgactgcgtg aagtcggaat     780
cgctagtaat cgcggatcag aatgtcgcgg tgaatacgtt ccc                       823
```

```
<210> SEQ ID NO 124
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 357 16S rDNA
<220> FEATURE:
<221> NAME/KEY: misc_feature
<222> LOCATION: (64)..(64)
<223> OTHER INFORMATION: n is a, c, g, or t
<220> FEATURE:
```

```
<221> NAME/KEY: misc_feature
<222> LOCATION: (86)..(86)
<223> OTHER INFORMATION: n is a, c, g, or t

<400> SEQUENCE: 124
ttactgggcg taaagcgcgc gtaggtggtt tgttaagttg gatgtgaaag ccccgggctc     60
aacntgggaa ctgcatccaa aactgncaag ctagagtacg gtagagggtg gtggaatttc    120
ctgtgtagcg gtgaaatgcg tagatatagg aaggaacacc agtggcgaag gcgaccacct    180
ggactgatac tgacactgag gtgcgaaagc gtggggagca acaggatta gataccctgg     240 tagtccacgc cgtaaacgat gtcaactagc cgttggaatc cttgagattt tagtggcgca    300
gctaacgcat taagttgacc gcctggggag tacggccgca aggttaaaac tcaaatgaat    360 tgacggggc ccgcacaagc ggtggagcat gtggtttaat tcgaagcaac gcgaagaacc     420
ttaccaggcc ttgacatgca gagaactttc cagagatgga ttggtgcctt cgggaactct    480
gacacaggtg ctgcatggct gtcgtcagct cgtgtcgtga gatgttgggt taagtcccgt    540
aacgagcgca acccttgtcc ttagttacca gcacgttatg gtgggcactc taaggagact    600
gccggtgaca aaccggagga aggtgggat gacgtcaagt catcatggcc cttacggcct     660
gggctacaca cgtgctacaa tggtcggtac agagggttgc caagccgcga ggtggagcta    720
atctcacaaa accgatcgta gtccggatcg cagtctgcaa ctcgactgcg tgaagtcgga    780
atcgctagta atcgcgaatc agaatgtcgc ggtgaatacg ttccc                    825

<210> SEQ ID NO 125
<211> LENGTH: 819
<212> TYPE: DNA
<213> ORGANISM: Massilia kyonggiensis
<220> FEATURE:
<221> NAME/KEY: misc_feature
<222> LOCATION: (1)..(819)
<223> OTHER INFORMATION: BCI 36 16S rDNA
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t

<400> SEQUENCE: 125
ttactgggcg taaagcgtgc gcnggcggtt ttgtaantct gacgtgaant ccccgggctt    60
aacctgggaa ttgcgttgga gactgcaagg ctggantctg gcagagggg gtagaattcc    120 acgtgtagca gtgaaatgcg tagagatgtg gaggaacacc gatggcgaag gcagccccnt    180
gggtcaagac tgacgctcat gcacgaaagc gtggggagca acaggatta gataccctgg    240 tagtccacgc cctaaacgat gtctactagt tgtcgggtct taattgactt ggtaacgcag    300
ctaacgcgtg aagtagaccg cctggggagt acgtcgcaa gattaaaact caaaggaatt    360 gacgggga ccgcacaagc ggtggatgatg tggattaatt cgatgcaacg cgaaaaacct     420
```

```
tacctaccct tgacatgtca ggaaccttgg agagatctga gggtgcccga aagggagcct    480
gaacacaggt gctgcatggc tgtcgtcagc tcgtgtcgtg agatgttggg ttaagtcccg    540
caacgagcgc aacccttgtc attagttgct acgaaagggc actctaatga gactgccggt    600
gacaaaccgg aggaaggtgg ggatgacgtc aagtcctcat ggcccttatg ggtagggctt    660
cacacgtcat acaatggtac atacagaggg ccgccaaccc gcgaggggga gctaatccca    720
gaaagtgtat cgtagtccgg atcgcagtct gcaactcgac tgcgtgaagt tggaatcgct    780
agtaatcgcg gatcagcatg tcgcggtgaa tacgttccc                          819
```

```
<210> SEQ ID NO 126
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 360 16S rDNA

<400> SEQUENCE: 126
ttactgggcg taaagcgcgc gtaggtggtt tgttaagttg gatgtgaaag ccccgggctc     60
aacctgggaa ctgcatccaa aactggcaag ctagagtacg gtagagggtg gtggaatttc    120
ctgtgtagcg gtgaaatgcg tagatatagg aaggaacacc agtggcgaag gcgaccacct    180
ggactgatac tgacactgag gtgcgaaagc gtggggagca acaggatta gataccctgg     240 tagtccacgc cgtaaacgat gtcaactagc cgttggaatc cttgagattt tagtggcgca    300
gctaacgcat taagttgacc gcctggggag tacggccgca aggttaaaac tcaaatgaat    360 tgacggggggc ccgcacaagc ggtggagcat gtggtttaat tcgaagcaac gcgaagaacc    420
ttaccaggcc ttgacatgca gagaactttc cagagatgga ttggtgcctt cgggaactct    480
gacacaggtg ctgcatggct gtcgtcagct cgtgtcgtga gatgtgggt taagtcccgt     540 aacgagcgca acccttgtcc ttagttacca gcacgttatg gtgggcactc taaggagact    600
gccggtgaca aaccggagga aggtgggat gacgtcaagt catcatggcc cttacggcct     660
gggctacaca cgtgctacaa tggtcggtac agagggttgc caagccgcga ggtggagcta    720
atctcacaaa accgatcgta gtccggatcg cagtctgcaa ctcgactgcg tgaagtcgga    780
atcgctagta atcgcgaatc agaatgtcgc ggtgaatacg ttccc                    825
```

```
<210> SEQ ID NO 127
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 363 16S rDNA
<220> FEATURE:
<221> NAME/KEY: misc_feature
<222> LOCATION: (20)..(20)
<223> OTHER INFORMATION: n is a, c, g, or t

<400> SEQUENCE: 127
ttactgggcg taaagcgcgn gtaggtggtt tgttaagttg gatgtgaaag ccccgggctc     60
aacctgggaa ctgcatccaa aactggcaag ctagagtacg gtagagggtg gtggaatttc    120
ctgtgtagcg gtgaaatgcg tagatatagg aaggaacacc agtggcgaag gcgaccacct    180
ggactgatac tgacactgag gtgcgaaagc gtggggagca acaggatta gataccctgg     240
```

```
tagtccacgc cgtaaacgat gtcaactagc cgttggaatc cttgagattt tagtggcgca      300
gctaacgcat taagttgacc gcctggggag tacggccgca aggttaaaac tcaaatgaat      360 tgacggggc ccgcacaagc ggtggagcat gtggtttaat tcgaagcaac gcgaagaacc       420
ttaccaggcc ttgacatgca gagaactttc cagagatgga ttggtgcctt cgggaactct      480
gacacaggtg ctgcatggct gtcgtcagct cgtgtcgtga gatgttgggt taagtcccgt      540
aacgagcgca acccttgtcc ttagttacca gcacgttatg gtgggcactc taaggagact     600
gccggtgaca aaccggagga aggtggggat gacgtcaagt catcatggcc cttacggcct     660
gggctacaca cgtgctacaa tggtcggtac agagggttgc caagccgcga ggtgagcta      720 atctcacaaa accgatcgta gtccggatcg cagtctgcaa ctcgactgcg tgaagtcgga     780
atcgctagta atcgcgaatc agaatgtcgc ggtgaatacg ttccc                     825

<210> SEQ ID NO 128
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 365 16S rDNA
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (162)..(163)
<223> OTHER INFORMATION: n is a, c, g, or t

<400> SEQUENCE: 128
ttactgggcg taaagcgcgc gtaggtgnnn gttaagntgg atgtgaaagc cccgggctca      60
acnngggaac tgcatccaaa actgncaagn tagagtncgg tagagggtgg tggaatttcc     120
tgngtagcgg tgaaatgcgt agatataggr aggaacncca gnnggcgaag cgaccacct      180 ggactgatac tgacactgag gtgcgaaagc gtggggagca aacaggatta gataccctgg     240
tagtccacgc cgtaaacgat gtcaactagc cgttggaatc cttgagattt tagtggcgca     300
gctaacgcat taagttgacc gcctggggag tacggccgca aggttaaaac tcaaatgaat     360
```

```
tgacggggc  ccgcacaagc  ggtggagcat  gtggtttaat  tcgaagcaac  gcgaagaacc      420
ttaccaggcc  ttgacatgca  gagaactttc  cagagatgga  ttggtgcctt  cgggaactct      480
gacacaggtg  ctgcatggct  gtcgtcagct  cgtgtcgtga  gatgttgggt  taagtcccgt      540
aacgagcgca  accctgtcc   ttagttacca  gcacgttatg  gtgggcactc  taaggagact      600
gccggtgaca  aaccggagga  aggtggggat  gacgtcaagt  catcatggcc  cttacggcct      660
gggctacaca  cgtgctacaa  tggtcggtac  agagggttgc  caagccgcga  ggtgagcta       720 atctcacaaa  accgatcgta  gtccggatcg  cagtctgcaa  ctcgactgcg  tgaagtcgga      780
atcgctagta  atcgcgaatc  agaatgtcgc  ggtgaatacg  ttccc                      825
```

<210> SEQ ID NO 129
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 367 16S rDNA

<400> SEQUENCE: 129

```
ttactgggcg  taaagcgcgc  gtaggtggtt  tgttaagttg  gatgtgaaag  ccccgggctc      60
aacctgggaa  ctgcatccaa  aactggcaag  ctagagtacg  gtagagggtg  gtggaatttc     120
ctgtgtagcg  gtgaaatgcg  tagatatagg  aaggaacacc  agtggcgaag  gcgaccacct     180
ggactgatac  tgacactgag  gtgcgaaagc  gtggggagca  aacaggatta  gataccctgg     240
tagtccacgc  cgtaaacgat  gtcaactagc  cgttggaatc  cttgagattt  tagtggcgca     300
gctaacgcat  taagttgacc  gcctggggag  tacggccgca  aggttaaaac  tcaaatgaat     360 tgacggggc  ccgcacaagc  ggtggagcat  gtggtttaat  tcgaagcaac  gcgaagaacc      420
ttaccaggcc  ttgacatgca  gagaactttc  cagagatgga  ttggtgcctt  cgggaactct      480
gacacaggtg  ctgcatggct  gtcgtcagct  cgtgtcgtga  gatgttgggt  taagtcccgt      540
aacgagcgca  accctgtcc   ttagttacca  gcacgttatg  gtgggcactc  taaggagact      600
gccggtgaca  aaccggagga  aggtggggat  gacgtcaagt  catcatggcc  cttacggcct      660
gggctacaca  cgtgctacaa  tggtcggtac  agagggttgc  caagccgcga  ggtgagcta       720 atctcacaaa  accgatcgta  gtccggatcg  cagtctgcaa  ctcgactgcg  tgaagtcgga      780
atcgctagta  atcgcgaatc  agaatgtcgc  ggtgaatacg  ttccc                      825
```

<210> SEQ ID NO 130
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 368 16S rDNA
<220> FEATURE:
<221> NAME/KEY: misc_feature
<222> LOCATION: (88)..(88)
<223> OTHER INFORMATION: n is a, c, g, or t

<400> SEQUENCE: 130

```
ttactgggcg  taaagcgcgc  gtaggtggtt  tgttaagttg  gatgtgaaag  ccccgggctc      60
aacctgggaa  ctgcatccaa  aactggcnag  ctagagtacg  gtagagggtg  gtggaatttc     120
ctgtgtagcg  gtgaaatgcg  tagatatagg  aaggaacacc  agtggcgaag  gcgaccacct     180
```

```
ggactgatac tgacactgag gtgcgaaagc gtggggagca acaggatta gatacctgg    240 tagtccacgc cgtaaacgat gtcaactagc cgttggaatc cttgagattt tagtggcgca   300
gctaacgcat taagttgacc gcctggggag tacggccgca aggttaaaac tcaaatgaat   360 tgacggggc ccgcacaagc ggtggagcat gtggtttaat tcgaagcaac gcgaagaacc   420
ttaccaggcc ttgacatgca gagaacttc cagagatgga ttggtgcctt cgggaactct    480
gacacaggtg ctgcatggct gtcgtcagct cgtgtcgtga gatgttgggt taagtcccgt   540
aacgagcgca acccttgtcc ttagttacca gcacgttatg gtgggcactc taaggagact   600
gccggtgaca accggagga aggtggggat gacgtcaagt catcatggcc cttacggcct    660
gggctacaca cgtgctacaa tggtcggtac agagggttgc caagccgcga ggtggagcta   720
atctcacaaa accgatcgta gtccggatcg cagtctgcaa ctcgactgcg tgaagtcgga   780
atcgctagta atcgcgaatc agaatgtcgc ggtgaatacg ttccc                   825
```

<210> SEQ ID NO 131
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 369 16S rDNA
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t

<400> SEQUENCE: 131

```
ttactgggcg taaagcgcgc gtaggtggtt tgttaagtng gatgtgaaag ccccgggctc    60 aaccnggaa ctgcatccaa aactggcaag ctagagtacg gtagagggtg gtggantttc   120
ctgtgtagcg gtgaaatgcg tagatatagg aaggaacacc agtggcgaag gcgaccacct   180
ggactgatac tgacactgag gtgcgaaagc gtggggagca acaggatta gatacctgg    240 tagtccacgc cgtaaacgat gtcaactagc cgttggaatc cttgagattt tagtggcgca   300
gctaacgcat taagttgacc gcctggggag tacggccgca aggttaaaac tcaaatgaat   360 tgacggggc ccgcacaagc ggtggagcat gtggtttaat tcgaagcaac gcgaagaacc   420
ttaccaggcc ttgacatgca gagaacttc cagagatgga ttggtgcctt cgggaactct    480
gacacaggtg ctgcatggct gtcgtcagct cgtgtcgtga gatgttgggt taagtcccgt   540
aacgagcgca acccttgtcc ttagttacca gcacgttatg gtgggcactc taaggagact   600
gccggtgaca accggagga aggtggggat gacgtcaagt catcatggcc cttacggcct    660
gggctacaca cgtgctacaa tggtcggtac agagggttgc caagccgcga ggtggagcta   720
atctcacaaa accgatcgta gtccggatcg cagtctgcaa ctcgactgcg tgaagtcgga   780
atcgctagta atcgcgaatc agaatgtcgc ggtgaatacg ttccc                   825
```

<210> SEQ ID NO 132
<211> LENGTH: 825
<212> TYPE: DNA
<213> ORGANISM: Pseudomonas putida

```
<220> FEATURE:
<221> NAME/KEY: misc_feature
<222> LOCATION: (1)..(825)
<223> OTHER INFORMATION: BCI 370 16S rDNA
<220> FEATURE:
<221> NAME/KEY: misc_feature
<222> LOCATION: (65)..(65)
<223> OTHER INFORMATION: n is a, c, g, or t

<400> SEQUENCE: 132
ttactgggcg taaagcgcgc gtaggtggtt tgttaagttg gatgtgaaag ccccgggctc      60
aaccngggaa ctgcatccaa aactggcaag ctagagtacg gtagagggtg gtggaatttc     120
ctgtgtagcg gtgaaatgcg tagatatagg aaggaacacc agtggcgaag gcgaccacct     180
ggactgatac tgacactgag gtgcgaaagc gtggggagca acaggatta gatacccctgg    240 tagtccacgc cgtaaacgat gtcaactagc cgttggaatc cttgagattt tagtggcgca     300
gctaacgcat taagttgacc gcctggggag tacggccgca aggttaaaac tcaaatgaat     360
tgacgggggc ccgcacaagc ggtggagcat gtggtttaat tcgaagcaac gcgaagaacc     420
ttaccaggcc ttgacatgca gagaactttc cagagatgga ttggtgcctt cgggaactct     480
gacacaggtg ctgcatggct gtcgtcagct cgtgtcgtga tgttgggt taagtcccgt      540 aacgagcgca accttgtcc ttagttacca gcacgttatg gtgggcactc taaggagact     600
gccggtgaca aaccggagga aggtgggggat gacgtcaagt catcatggcc cttacggcct     660
gggctacaca cgtgctacaa tggtcggtac agagggttgc caagccgcga ggtggagcta     720
atctcacaaa accgatcgta gtccggatcg cagtctgcaa ctcgactgcg tgaagtcgga     780
atcgctagta atcgcgaatc agaatgtcgc ggtgaatacg ttccc                     825

<210> SEQ ID NO 133
<211> LENGTH: 882
<212> TYPE: DNA
<213> ORGANISM: Novosphingobium resinovorum
<220> FEATURE:
<221> NAME/KEY: misc_feature
<222> LOCATION: (1)..(882)
<223> OTHER INFORMATION: BCI 3709 16S rDNA

<400> SEQUENCE: 133
gggttagctc aacgccttcg agtgaatcca actcccatgg tgtgacgggc ggtgtgtaca      60
aggcctggga acgtattcac cgcggcatgc tgatccgcga ttactagcga ttccgccttc     120
atgctctcga gttgcagaga acaatccgaa ctgagacggc ttttggagat tagctcacac     180
tcgcgtgctt gctgcccact gtcaccgcca ttgtagcacg tgtgtagccc agcgtgtaag     240
ggccatgagg acttgacgtc atccccacct tcctccggct tatcaccggc agtttcctta     300
gagtgcccaa ctaaatgctg gcaactaagg acgagggttg cgctcgttgc gggacttaac     360
ccaacatctc acgacacgag ctgacgacag ccatgcagca cctgtgcacg gtccagccga     420
actgaaggaa atggtctccc aaatccgcga ccggcatgtc aaacgctggt aaggttctgc     480
gcgttgcttc gaattaaacc acatgctcca ccgcttgtgc aggccccgt caattccttt      540 gagtttttaat cttgcgaccg tactccccag gcggataact taatgcgtta gctgcgccac     600
ccaagtacca agtacccgga cagctagtta tcatcgttta cggcgtggac taccagggta     660
tctaatcctg tttgctcccc acgctttcgc acctcagcgt caatacttgt ccagtcagtc     720
gccttcgcca ctggtgttct tccgaatatc tacgaatttc acctctacac tcggaattcc     780
actgacctct ccaagattct agtcacctag tttcaaaggc agttccgggg ttgagccccg     840
```
ggctttcacc tctgacttga gtaaccgcct acgcgcgctt ta  882

<210> SEQ ID NO 134
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 372 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t

<400> SEQUENCE: 134
ntnctgggcg taaagcgcgc gtaggtgntt tgttaagttg gatgtgaaag ccccgggctc  60
aacntgggaa ctgcatncaa aactggcaag ctagagtacg gtagagggtg gtggaatttc  120
ctgtgtagcg gtgaaatgcg tagatatagg aaggaacacc agtggcgaag gcgaccacct  180
ggactgatac tgacactgag gtgcgaaagc gtggggagca acaggatta gatacctgg  240
tagtccacgc cgtaaacgat gtcaactagc cgttggaatc cttgagattt tagtggcgca  300
gctaacgcat taagttgacc gcctggggag tacggccgca aggttaaaac tcaaatgaat  360
tgacggggc ccgcacaagc ggtggagcat gtggtttaat tcgaagcaac gcgaagaacc  420
ttaccaggcc ttgacatgca gagaactttc cagagatgga ttggtgcctt cgggaactct  480
gacacaggtg ctgcatggct gtcgtcagct cgtgtcgtga gatgttgggt taagtcccgt  540
aacgagcgca acccttgtcc ttagttacca gcacgttatg gtgggcactc taaggagact  600
gccggtgaca aaccggagga aggtggggat gacgtcaagt catcatggcc cttacggcct  660
gggctacaca cgtgctacaa tggtcggtac agagggttgc caagccgcga ggtgagcta  720
atctcacaaa accgatcgta gtccggatcg cagtctgcaa ctcgactgcg tgaagtcgga  780
atcgctagta atcgcgaatc agaatgtcgc ggtgaatacg ttccc  825

<210> SEQ ID NO 135
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 375 16S rDNA
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t

<400> SEQUENCE: 135

```
ttactgggcg taaagcgcgc gtaggtggtt tgttaagttg gatgtgaaag ccccgggctc    60
aaccngggaa ctgcatccaa aactggcaag ctagagtacg gtagagggtg gtggaatttc   120
ntgtgtagcg gtgaaatgcg tagatatagg aaggaacacc agtggcgaag gcgaccacct   180
ggactgatac tgacactgag gtgcgaaagc gtggggagca acaggatta gatacctgg     240
tagtccacgc cgtaaacgat gtcaactagc cgttggaatc cttgagattt tagtggcgca   300
gctaacgcat taagttgacc gcctggggag tacggccgca aggttaaaac tcaaatgaat   360
tgacgggggc ccgcacaagc ggtggagcat gtggtttaat tcgaagcaac gcgaagaacc   420
ttaccaggcc ttgacatgca gagaactttc cagagatgga ttggtgcctt cgggaactct   480
gacacaggtg ctgcatggct gtcgtcagct cgtgtcgtga gatgttgggt taagtcccgt   540
aacgagcgca acccttgtcc ttagttacca gcacgttatg gtgggcactc taaggagact   600
gccggtgaca aaccggagga aggtgggat gacgtcaagt catcatggcc cttacggcct    660
gggctacaca cgtgctacaa tggtcggtac agagggttgc caagccgcga ggtggagcta   720
atctcacaaa accgatcgta gtccggatcg cagtctgcaa ctcgactgcg tgaagtcgga   780
atcgctagta atcgcgaatc agaatgtcgc ggtgaatacg ttccc                  825
```

<210> SEQ ID NO 136
<211> LENGTH: 827
<212> TYPE: DNA
<213> ORGANISM: Stenotrophomonas maltophilia
<220> FEATURE:
<221> NAME/KEY: misc_feature
<222> LOCATION: (1)..(827)
<223> OTHER INFORMATION: BCI 380 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t

<400> SEQUENCE: 136

```
ntactnggng taaagcgtgc gtaggtggtt atttaantcn nttgtgaaag ccntgggctc      60
ancntgggaa ctgcagtgga tactggatga ctagaatgtg gtagagggta gcggaattcc     120
tggtgtagca gtgaaatgcg tagagatcag gaggaacatc catggcgaag gcagctacct    180
ggaccaacat tgacactgag gcacgaaagc gtgnggagca acaggatta gataccctgg     240 tagtccacgc cctaaacgat gcgaactgga tgttgggtgc aatttggcac gcagtatcga    300
agctaacgcg ttaagttcgc cgcctgggga gtacggtcgc aagactgaaa ctcaaaggaa    360
ttgacggggg cccgcacaag cggtggagta tgtggtttaa ttcgatgcaa cgcgaagaac    420
cttacctggc cttgacatgt cgagaacttt ccagagatgg atgggtgcct tcgggaactc    480
gaacacaggt gctgcatggc tgtcgtcagc tcgtgtcgtg agatgttggg ttaagtcccg    540
caacgagcgc aacccttgtc cttagttgcc agcacgtaat ggtgggaact ctaaggagac    600
cgccggtgac aaaccggagg aaggtgggga tgacgtcaag tcatcatggc ccttacggcc    660
agggctacac acgtactaca atggtaggga cagagggctg caagccggcg acggtaagcc    720
aatcccagaa accctatctc agtccggatt ggagtctgca actcgactcc atgaagtcgg    780
aatcgctagt aatcgcagat cagcattgct gcggtgaata cgttccc                 827

<210> SEQ ID NO 137
<211> LENGTH: 695
<212> TYPE: DNA
<213> ORGANISM: Achromobacter spanius
<220> FEATURE:
<221> NAME/KEY: misc_feature
<222> LOCATION: (1)..(695)
<223> OTHER INFORMATION: BCI 385 16S rDNA

<400> SEQUENCE: 137
acttctggta aaacccactc ccatggtgtg acgggcggtg tgtacaagac ccgggaacgt      60
attcaccgcg acatgctgat ccgcgattac tagcgattcc gacttcacgc agtcgagttg    120
cagactgcga tccggactac gatcgggttt ctgggattgg ctcccccctcg cgggttggcg   180 accctctgtc ccgaccattg tatgacgtgt gaagccctac ccataagggc catgaggact    240
tgacgtcatc cccaccttcc tccggtttgt caccggcagt ctcattagag tgcccttcg    300 tagcaactaa tgacaagggt tgcgctcgtt gcgggactta acccaacatc tcacgacacg    360
agctgacgac agccatgcag cacctgtgtt ccggttctct tgcgagcact tccaaatctc    420
ttcggaattc cagacatgtc aagggtaggt aaggtttttc gcgttgcatc gaattaatcc    480
acatcatcca ccgcttgtgc gggtccccgt caattccttt gagttttaat cttgcgaccg    540
tactccccag gcggtcaact tcacgcgtta gctgcgctac caaggcccga aggccccaac    600
agctagttga catcgtttag ggcgtggact accagggtat ctaatcctgt ttgctcccca    660
cgctttcgtg catgagcgtc agtgttatcc cagga                               695

<210> SEQ ID NO 138
<211> LENGTH: 824
<212> TYPE: DNA
<213> ORGANISM: Bacillus subtilis
<220> FEATURE:
<221> NAME/KEY: misc_feature
<222> LOCATION: (1)..(824)
<223> OTHER INFORMATION: BCI 395 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
```

```
<222> LOCATION: (34)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 138
aantattggg cgtaaagggc tcgcaggcgg tttnttaagt ntgatgtgaa agcccccggc      60
tcaaccgggg agggtcattg gaaactgggg aacttgagtg cagaagagga gagtggaatt     120
ccacgtgtag cggtgaaatg cgtagagatg tggaggaaca ccagtggcga aggcgactct     180
ctggtctgta actgacgctg aggagcgaaa gcgtggggag cgaacaggat tagataccct     240
ggtagtccac gccgtaaacg atgagtgcta agtgttaggg ggtttccgcc ccttagtgct     300
gcagctaacg cattaagcac tccgcctggg gagtacggtc gcaagactga aactcaaagg     360
aattgacggg ggcccgcaca agcggtggag catgtggttt aattcgaagc aacgcgaaga     420
accttaccag gtcttgacat cctctgacaa tcctagagat aggacgtccc cttcgggggc     480
agagtgacag gtggtgcatg gttgtcgtca gctcgtgtcg tgagatgttg ggttaagtcc     540
cgcaacgagc gcaaccttg atcttagttg ccagcattca gttgggcact ctaaggtgac      600
tgccggtgac aaaccggagg aaggtgggga tgacgtcaaa tcatcatgcc ccttatgacc     660
tgggctacac acgtgctaca atggacagaa caaagggcag cgaaaccgcg aggttaagcc     720
aatcccacaa atctgttctc agttcggatc gcagtctgca actcgactgc gtgaagctgg     780
aatcgctagt aatcgcggat cagcatgccg cggtgaatac gttc                      824

<210> SEQ ID NO 139
<211> LENGTH: 897
<212> TYPE: DNA
<213> ORGANISM: Flavobacterium glaciei
<220> FEATURE:
<221> NAME/KEY: misc_feature
<222> LOCATION: (1)..(897)
<223> OTHER INFORMATION: BCI 4005 16S rDNA

<400> SEQUENCE: 139
tgtacaaggc ccgggaacgt attcaccgca gcaatgctga tctgcgatta ctagcgattc      60
cgacttcatg gagtcgagtt gcagactcca atccggactg agattaggtt tctgggattg     120
gcttactctc gcgagtttgc agccctctgt cctaaccatt gtagtacgtg tgtagccctg     180
gtcgtaaggg ccatgatgac ttgacgtcat ccccaccttc ctccggtttg tcaccggcgg     240
tctccttaga gttcccacca ttacgtgctg gcaactaagg acaagggttg cgctcgttgc     300
gggacttaac ccaacatctc acgacacgag ctgacgacag ccatgcagca cctgtctcac     360
ggttcccgaa ggcaccaatc catctctgga aagttccgtg gatgtcaaga ccaggtaagg     420
ttcttcgcgt tgcatcgaat taaaccacat actccaccgc ttgtgcgggc cccgtcaat     480
tcctttgagt ttcagtcttg cgaccgtact ccccaggcgg cgaacttaac gcgttagctt     540
cgatactgcg tgccaagttg cacccaacat ccagttcgca tcgtttaggg cgtggactac     600
cagggtatct aatcctgttt gctccccacg ctttcgtgcc tcagtgtcag tgttggtcca     660
gatggccgcc ttcgccacag atgttcctcc cgatctctac gcatttcact gctacaccgg     720
gaattccgcc atcctctacc acactctagt tgcccagtat ccactgcaat tcccaggttg     780
agcccagggc tttcacaacg gacttaaaca accacctacg cacgctttac gcccagtaat     840
tccgagtaac gcttgcaccc ttcgtattac cgcggctgct ggcacgaagt tagccgg       897
```

<210> SEQ ID NO 140
<211> LENGTH: 823
<212> TYPE: DNA
<213> ORGANISM: Sphingopyxis alaskensis
<220> FEATURE:
<221> NAME/KEY: misc_feature
<222> LOCATION: (1)..(823)
<223> OTHER INFORMATION: BCI 412 16S rDNA

<400> SEQUENCE: 140

| | | | | | |
|---|---|---|---|---|---|
| ggcgtaaagc | gcgcgtaggc | ggtttttttaa | gtcagaggtg | aaagcccagt | gctcaacact | 60 |
| ggaactgcct | ttgaaactgg | aaaacttgaa | tcttggagag | gtcagtggaa | ttccgagtgt | 120 |
| agaggtgaaa | ttcgtagata | ttcggaagaa | caccagtggc | gaaggcgact | gactggacaa | 180 |
| gtattgacgc | tgaggtgcga | aagcgtgggg | agcaaacagg | attagatacc | ctggtagtcc | 240 |
| acgccgtaaa | cgatgataac | tagctgtccg | ggttcataga | acttgggtgg | cgcagctaac | 300 |
| gcattaagtt | atccgcctgg | ggagtacggt | cgcaagatta | aaactcaaag | gaattgacgg | 360 |
| gggcctgcac | aagcggtgga | gcatgtgtt | taattcgaag | caacgcgcag | aaccttacca | 420 |
| gcgtttgaca | tcctgatcgc | ggattagaga | gatcttttcc | ttcagttcgg | ctggatcagt | 480 |
| gacaggtgct | gcatggctgt | cgtcagctcg | tgtcgtgaga | tgttgggtta | agtcccgcaa | 540 |
| cgagcgcaac | cctcatccct | agttgccatc | attcagttgg | gcactctaag | gaaactgccg | 600 |
| gtgataagcc | ggaggaaggt | ggggatgacg | tcaagtcctc | atggccctta | cgcgctgggc | 660 |
| tacacacgtg | ctacaatggc | aactacagtg | ggcagcaacc | tcgcgagggg | tagctaatct | 720 |
| ccaaaagttg | tctcagttcg | gattgttctc | tgcaactcga | gagcatgaag | gcggaatcgc | 780 |
| tagtaatcgc | ggatcagcat | gccgcggtga | atacgttccc | agg | | 823 |

<210> SEQ ID NO 141
<211> LENGTH: 649
<212> TYPE: DNA
<213> ORGANISM: Paenibacillus glycanilyticus
<220> FEATURE:
<221> NAME/KEY: misc_feature
<222> LOCATION: (1)..(649)
<223> OTHER INFORMATION: BCI 418 16S rDNA

<400> SEQUENCE: 141

| | | | | | |
|---|---|---|---|---|---|
| cttggtgccg | aagttaacac | attaagcatt | ccgcctgggg | agtacggtcg | caagactgaa | 60 |
| actcaaagga | attgacgggg | acccgcacaa | gcagtggagt | atgtggttta | attcgaagca | 120 |
| acgcgaagaa | ccttaccagg | tcttgacatc | cctctgaatc | cactagagat | agtggcggcc | 180 |
| ttcgggacag | aggagacagg | tggtgcatgg | ttgtcgtcag | ctcgtgtcgt | gagatgttgg | 240 |
| gttaagtccc | gcaacgagcg | caacccttga | tcttagttgc | cagcattttg | gatgggcact | 300 |
| ctaggatgac | tgccggtgac | aaaccggagg | aaggtgggga | tgacgtcaaa | tcatcatgcc | 360 |
| ccttatgacc | tgggctacac | acgtactaca | atggccgata | caacgggaag | cgaaaccgcg | 420 |
| aggtggagcc | aatcctatca | aagtcggtct | cagttcggat | tgcaggctgc | aactcgcctg | 480 |
| catgaagtcg | gaattgctag | taatcgcgga | tcagcatgcc | gcggtgaata | cgttcccggg | 540 |
| tcttgtacac | accgcccgtc | acaccacgag | agtttacaac | acccgaagcc | ggtggggtaa | 600 |
| ccgcaaggag | ccagccgtcg | aaggtggggt | agatgattgg | ggtgaagtc | | 649 |

<210> SEQ ID NO 142
<211> LENGTH: 776
<212> TYPE: DNA
<213> ORGANISM: Kosakonia radicincitans

```
<220> FEATURE:
<221> NAME/KEY: misc_feature
<222> LOCATION: (1)..(776)
<223> OTHER INFORMATION: BCI 44 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (710)..(711)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (738)..(739)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t

<400> SEQUENCE: 142
tangctacct acttctttg caaccnactc ccatggtgtg acgggcggtg tgtacaaggc      60
ccgggaacgt attcaccgtg acattctgat tcacgattac tagcgattcc gacttcatgg    120
agtcgagttg cagactccaa tccggactac gacgcacttt atgaggtccg cttgctctcg    180
cgaggtcgct tctctttgta tgcgccattg tagcacgtgt gtagccctgg tcgtaagggc    240
catgatgact tgacgtcatc cccaccttcc tccagtttat cactggcagt ctcctttgag    300
ttcccggcct aaccgctggc aacaaaggat aagggttgcg ctcgttgcgg gacttaaccc    360
aacatttcac aacacgagct gacgacagcc atgcagcacc tgtctcacag ttcccgaagg    420 cacccggca tctctgccag gttctgtgga tgtcaagacc aggtaaggtt cttcgcgttg    480
```

```
catcgaatta aaccacatgc tccaccgctt gtgcgggccc ccgtcaattc atttgagttt      540
taaccttgcg gccgtactcc ccaggcggtc gatttaacgc gttagctccg gaagccacgc      600
ctcaagggca caacctccaa atcgacatcg tttacggcgt ggactaccag gntatctaat      660
cctgtttgct ccncacgctt tcgcacctga gcgtcagtct tcgtccaggn ngccgncttc      720
gccaccggtn ttcctncnna nctctacgca tttcancgct ncncctggaa ntctac          776
```

```
<210> SEQ ID NO 143
<211> LENGTH: 689
<212> TYPE: DNA
<213> ORGANISM: Chryseobacterium daecheongense
<220> FEATURE:
<221> NAME/KEY: misc_feature
<222> LOCATION: (1)..(689)
<223> OTHER INFORMATION: BCI 45 16S rDNA
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (96)..(101)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (115)..(117)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (127)..(129)
<223> OTHER INFORMATION: n is a, c, g, or t
```

```
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (148)..(152)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t

<400> SEQUENCE: 143
cgnngaaatg catagatatt antnagaaca ccaatngcga aggcaggtta ntatgtntta      60
actgacgnng atggangaaa gngtggggan cgaacnnnnn nagataccnt ggtannncac     120
nccgtannng atgctaactn gtttttgnnn nntngggttc agagactaag cgaaagtgat     180
aagttagcca cctggggagt acgttngcaa gaatgaaact caaaggaatt gacggggggcc    240 cgcacaagcg gtggattatg tggtttaatt cgatgatacg cgaggaacct taccaaggct    300
taaatgggaa ttgatcggtt tagaaataga ccttccttcg ggcaatttc aaggtgctgc     360 atggttgtcg tcagctcgtg ccgtgaggtg ttaggttaag tcctgcaacg agcgcaaccc    420
ctgtcactag ttgccatcat tcagttgggg actctagtga gactgcctac gcaagtagag    480
aggaaggtgg ggatgacgtc aaatcatcac ggcccttacg ccttgggcca cacacgtaat    540
acaatggccg gtacagaggg cagctacaca gcgatgtgat gcaaatctcg aaagccggtc    600
tcagttcgga ttggagtctg caactcgact ctatgaagct ggaatcgcta gtaatcgcgc    660
atcagccatg gcgcggtgaa tacgttccc                                      689

<210> SEQ ID NO 144
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 458 16S rDNA
<220> FEATURE:
<221> NAME/KEY: misc_feature
<222> LOCATION: (116)..(116)
<223> OTHER INFORMATION: n is a, c, g, or t

<400> SEQUENCE: 144
aattactggg cgtaaagcgc gcgtaggtgg tttgttaagt tggatgtgaa agccccgggc     60
tcaacctgga aactgcatcc aaaactggca agctagagta cggtagaggg tggtgnaatt    120
tcctgtgtag cggtgaaatg cgtagatata ggaaggaaca ccagtggcga aggcgaccac    180
ctggactgat actgacactg aggtgcgaaa gcgtggggag caaacaggat tagataccct    240
ggtagtccac gccgtaaacg atgtcaacta gccgttggaa tccttgagat tttagtggcg    300
cagctaacgc attaagttga ccgcctgggg agtacggccg caaggttaaa actcaaatga    360
attgacgggg gcccgcacaa gcggtggagc atgtggttta attcgaagca acgcgaagaa    420
ccttaccagg ccttgacatg cagagaactt tccagagatg gattggtgcc ttcgggaact    480
ctgacacagg tgctgcatgg ctgtcgtcag ctcgtgtcgt gagatgttgg gttaagtccc    540
gtaacgagcg caaccctttgt ccttagttac cagcacgtta tggtgggcac tctaaggaga    600
```

```
ctgccggtga caaaccggag gaaggtgggg atgacgtcaa gtcatcatgg cccttacggc      660
ctgggctaca cacgtgctac aatggtcggt acagagggtt gccaagccgc gaggtggagc      720
taatctcaca aaaccgatcg tagtccggat cgcagtctgc aactcgactg cgtgaagtcg      780
gaatcgctag taatcgcgaa tcagaatgtc gcggtgaata cgttc                      825

<210> SEQ ID NO 145
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 459 16S rDNA

<400> SEQUENCE: 145
aattactggg cgtaaagcgc gcgtaggtgg tttgttaagt tggatgtgaa agccccgggc       60
tcaacctggg aactgcatcc aaaactggca agctagagta cggtagaggg tggtggaatt     120
tcctgtgtag cggtgaaatg cgtagatata ggaaggaaca ccagtggcga aggcgaccac     180
ctggactgat actgacactg aggtgcgaaa gcgtggggag caaacaggat tagataccct     240
ggtagtccac gccgtaaacg atgtcaacta gccgttggaa tccttgagat tttagtggcg     300
cagctaacgc attaagttga ccgcctgggg agtacggccg caaggttaaa actcaaatga     360
attgacgggg gcccgcacaa gcggtggagc atgtggttta attcgaagca acgcgaagaa     420
ccttaccagg ccttgacatg cagagaactt tccagagatg gattggtgcc ttcgggaact     480
ctgacacagg tgctgcatgg ctgtcgtcag ctcgtgtcgt gagatgttgg gttaagtccc     540
gtaacgagcg caacccttgt ccttagttac cagcacgtta tggtgggcac tctaaggaga     600
ctgccggtga caaaccggag gaaggtgggg atgacgtcaa gtcatcatgg cccttacggc     660
ctgggctaca cacgtgctac aatggtcggt acagagggtt gccaagccgc gaggtggagc     720
taatctcaca aaaccgatcg tagtccggat cgcagtctgc aactcgactg cgtgaagtcg     780
gaatcgctag taatcgcgaa tcagaatgtc gcggtgaata cgttc                      825

<210> SEQ ID NO 146
<211> LENGTH: 894
<212> TYPE: DNA
<213> ORGANISM: Agrobacterium fabrum
<220> FEATURE:
<221> NAME/KEY: misc_feature
<222> LOCATION: (1)..(894)
<223> OTHER INFORMATION: BCI 46 16S rDNA

<400> SEQUENCE: 146
ccttgcggtt agcgcactac cttcgggtaa aaccaactcc catggtgtga cgggcggtgt       60
gtacaaggcc cgggaacgta ttcaccgcag catgctgatc tgcgattact agcgattcca     120
acttcatgca ctcgagttgc agagtgcaat ccgaactgag atggcttttg gagattagct     180
cgacatcgct gtctcgctgc ccactgtcac caccattgta gcacgtgtgt agcccagccc     240
gtaagggcca tgaggacttg acgtcatccc caccttcctc tcggcttatc accggcagtc     300
cccttagagt gcccaactaa atgctggcaa ctaaggggga gggttgcgct cgttgcggga     360
cttaacccaa catctcacga cacgagctga cgacagccat gcagcacctg ttctggggcc     420
agcctaactg aaggacatcg tctccaatgc ccatacccccg aatgtcaaga gctggtaagg     480
ttctgcgcgt tgcttcgaat taaaccacat gctccaccgc ttgtgcgggc cccgtcaat      540 tccttttgagt tttaatcttg cgaccgtact ccccaggcgg aatgtttaat gcgttagctg     600
```

-continued

```
cgccaccgaa cagtatactg cccgacggct aacattcatc gtttacggcg tggactacca      660
gggtatctaa tcctgtttgc tccccacgct ttcgcacctc agcgtcagta atggaccagt      720
aagccgcctt cgccactggt gttcctccga atatctacga atttcacctc tacactcgga      780
attccactta cctcttccat actcaagata cccagtatca aaggcagttc cgcagttgag      840
ctgcgggatt tcaccccctga cttaaatatc cgcctacgtg cgctttacgc ccag          894
```

<210> SEQ ID NO 147
<211> LENGTH: 827
<212> TYPE: DNA
<213> ORGANISM: Pseudomonas putida
<220> FEATURE:
<221> NAME/KEY: misc_feature
<222> LOCATION: (1)..(827)
<223> OTHER INFORMATION: BCI 460 16S rDNA
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t

<400> SEQUENCE: 147

```
aattactggg cgtaaagcgc gcgtaggtgg tttgttaagt tggatgtgaa agccccgggc       60
tcaacctggg aactgcatnc caaaactggc nagctagagt acggtagagg ggtggtggaa      120
tttcctgtgt agcggtgaaa tgcgtagata taggaaggaa caccagtggc gaaggcgacc      180
acctggactg atactgacac tgaggtgcga aagcgtgggg agcaaacagg attagatacc      240
ctggtagtcc acgccgtaaa cgatgtcaac tagccgttgg aatccttgag atttagtgg       300 cgcagctaac gcattaagtt gaccgcctgg ggagtacggc cgcaaggtta aaactcaaat      360
gaattgacgg gggcccgcac aagcggtgga gcatgtggtt taattcgaag caacgcgaag      420
aaccttacca ggccttgaca tgcagagaac tttccagaga tggattggtg ccttcgggaa      480
ctctgacaca ggtgctgcat ggctgtcgtc agctcgtgtc gtgagatgtt gggttaagtc      540
ccgtaacgag cgcaacccct tgtccttagt taccagcacgt tatggtgggc actctaagga    600
gactgccggt gacaaaccgg aggaaggtgg ggatgacgtc aagtcatcat ggcccttacg     660
gcctgggcta cacacgtgct acaatggtcg gtacagaggg ttgccaagcc gcgaggtgga    720
gctaatctca caaaaccgat cgtagtccgg atcgcagtct gcaactcgac tgcgtgaagt    780
cggaatcgct agtaatcgcg aatcagaatg tcgcggtgaa tacgttc                  827
```

<210> SEQ ID NO 148
<211> LENGTH: 764
<212> TYPE: DNA
<213> ORGANISM: Pseudomonas putida
<220> FEATURE:
<221> NAME/KEY: misc_feature
<222> LOCATION: (1)..(764)
<223> OTHER INFORMATION: BCI 461 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t

<400> SEQUENCE: 148

| | |
|---|---|
| ntgggaactg catccaaaac tggcaagcta gagtacggta gagggtggtg gaatttcctg | 60 |
| tgtagcggtg aaatgngtag atataggaag gaacaccagt ggcgaaggcg accacctgga | 120 |
| ctgatactga cactgaggtg cgaaagcgtg gggagcaaac aggattagat accctggtag | 180 |
| tccacgccgt aaacgatgtc aactagccgt tggaatcctt gagattttag tggcgcagct | 240 |
| aacgcattaa gttgaccgcc tggggagtac ggccgcaagg ttaaaactca aatgaattga | 300 |
| cgggggcccg cacaagcggt ggagcatgtg gtttaattcg aagcaacgcg aagaaccttt a | 360 |
| ccaggccttg acatgcagag aactttccag agatggattg gtgccttcgg gaactctgac | 420 |
| acaggtgctg catggctgtc gtcagctcgt gtcgtgagat gttgggttaa gtcccgtaac | 480 |
| gagcgcaacc cttgtcctta gttaccagca cgttatggtg gcactctaa ggagactgcc | 540 |
| ggtgacaaac cggaggaagg tggggatgac gtcaagtcat catggccctt acggcctggg | 600 |
| ctacacacgt gctacaatgg tcggtacaga gggttgccaa gccgcgaggt ggagctaatc | 660 |
| tcacaaaacc gatcgtagtc cggatcgcag tctgcaactc gactgcgtga agtcggaatc | 720 |
| gctagtaatc gcgaatcaga atgtcgcggt gaatacgttc ccgg | 764 |

<210> SEQ ID NO 149
<211> LENGTH: 825
<212> TYPE: DNA
<213> ORGANISM: Pseudomonas putida
<220> FEATURE:
<221> NAME/KEY: misc_feature
<222> LOCATION: (1)..(825)
<223> OTHER INFORMATION: BCI 462 16S rDNA
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t

<400> SEQUENCE: 149

| | |
|---|---|
| aattnctggg cgtaaagcgc gngtaggtgg tttgttnagt tggatgtgaa agccccgggc | 60 |
| tcaacntggg aactgcatcc aaaactggca agctagagta cggtagaggg tggtggaatt | 120 |
| tcctgtgtag cggtgaaatg ngtagatata ggaaggaaca ccagtggcga aggcgaccac | 180 |
| ctggactgat actgacactg aggtgcgaaa gcgtggggag caaacaggat tagataccct | 240 |
| ggtagtccac gccgtaaacg atgtcaacta gccgttggaa tccttgagat tttagtggcg | 300 |
| cagctaacgc attaagttga ccgcctgggg agtacggccg caaggttaaa actcaaatga | 360 |
| attgacgggg gcccgcacaa gcggtggagc atgtggttta attcgaagca acgcgaagaa | 420 |
| ccttaccagg ccttgacatg cagagaactt tccagagatg gattggtgcc ttcgggaact | 480 |
| ctgacacagg tgctgcatgg ctgtcgtcag ctcgtgtcgt gagatgttgg gttaagtccc | 540 |
| gtaacgagcg caacccttgt ccttagttac cagcacgtta tggtgggcac tctaaggaga | 600 |
| ctgccggtga caaaccggag gaaggtgggg atgacgtcaa gtcatcatgg cccttacggc | 660 |

```
ctgggctaca cacgtgctac aatggtcggt acagagggtt gccaagccgc gaggtggagc    720
taatctcaca aaaccgatcg tagtccggat cgcagtctgc aactcgactg cgtgaagtcg    780
gaatcgctag taatcgcgaa tcagaatgtc gcggtgaata cgttc                    825
```

<210> SEQ ID NO 150
<211> LENGTH: 764
<212> TYPE: DNA
<213> ORGANISM: Pseudomonas putida
<220> FEATURE:
<221> NAME/KEY: misc_feature
<222> LOCATION: (1)..(764)
<223> OTHER INFORMATION: BCI 467 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t

<400> SEQUENCE: 150

```
ntgggaactg catccaaaac tggcaagcta gagtacgnna gagggtggtg gaatttcctg     60
tgtagcggtg aaatgcgtag atataggaag gaacaccagt ggcgnaggcg accacctgga   120
ctgatactga cantgaggtg cgaaagcgtg gggagcaaac aggattagat accctggtag   180
tccacgccgt aaacgatgtc aactagccgt tggaatcctt gagattttag tggcgcagct   240
aacgcattaa gttgaccgcc tggggagtac ggccgcaagg ttaaaactca aatgaattga   300
cgggggcccg cacaagcggt ggagcatgtg gtttaattng aagcaacgcg aagaacctta   360
ccaggccttg acatgcagag aactttccag agatggattg gtgccttcgg gaactctgac   420
acaggtgntg catggctgtc gtcagctcgt gtcgtgagat gttgggttaa gtcccgtaac   480
gagcgcaacc cttgtcctta gttaccagca cgttatggtg ggcactntaa ggagactgcc   540
ggtgacaaac cggaggaagg tggggatgac gtcaagtcat catggccctt acggcctggg   600
ctacacacgt gctacaatgg tcggtacaga gggttgccaa gccgcgaggt ggagctaatc   660
tcacaaaacc gatcgtagtc cggatcgcag tctgcaactc gactgcgtga agtcggaatc   720
gctagtaatc gcgaatcaga atgtcgcggt gaatacgttc ccgg                    764
```

<210> SEQ ID NO 151
<211> LENGTH: 763
<212> TYPE: DNA
<213> ORGANISM: Pseudomonas putida
<220> FEATURE:

<221> NAME/KEY: misc_feature
<222> LOCATION: (1)..(763)
<223> OTHER INFORMATION: BCI 469 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t

<400> SEQUENCE: 151

```
ggnaactgca tncnaaaact ggcaagntag agtacggtag agggtggngn nntttcctgt      60
gtagcggtna aatnngtaga tataggaagg aacnccagtg gcgaaggcga ccacctggac     120
tgatactgac antgaggtgc gaaagcgtgg ggagcaaaca ggattagata ccctggtagt     180
ncacgccgta aacgatgtca actagccgtn ggaatccttg agattttagt ggcgcagcta     240
acgcattaag ttgaccgcct ggggagtacg gccgcaaggt taaaactcaa atgaattgac     300
gggggcccgc acaagcggtg gagcatgtgg tttaattcga agcaacgcga agaaccttac     360
caggccttga catgcagaga actttccaga gatggattgg tgccttcggg aactctgaca     420
caggtgctgc atggctgtcg tcagctcgtg tcgtgagatg ttgggttaag tcccgtaacg     480
agcgcaaccc ttgtccttag ttaccagcac gttatggtgg gcactntaag gagactgccg     540
gtgacaaacc ggaggaaggt ggggatgacg tcaagtcatc atggccctta cggcctgggc     600
tacacacgtg ctacaatggt cggtacagag ggttgccaag ccgcgaggtg gagctaatct     660
```

```
cacaaaaccg atcgtagtcc ggatcgcagt ctgcaactcg actgcgtgaa gtcggaatcg    720
ctagtaatcg cgaatcagaa tgtcgcggtg aatacgttcc cgg                      763
```

<210> SEQ ID NO 152
<211> LENGTH: 764
<212> TYPE: DNA
<213> ORGANISM: Pseudomonas putida
<220> FEATURE:
<221> NAME/KEY: misc_feature
<222> LOCATION: (1)..(764)
<223> OTHER INFORMATION: BCI 470 16S rDNA
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (511)..(511)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t

<400> SEQUENCE: 152

```
ctgggaactg cntccaaaac nggcaagcta gagtncngta gagggtggtg gaatttcctg     60
tgtagcggtg aaatgcgtag atataggaag gaacaccagt ggcgaaggcg accacctgga   120
ctgatactga cantgaggtg cgaaagcgtg gggagcaaac aggattagat accctggtag   180
tccacgccgt aaacgatgtc aactagccgt tggaatcctt gagattttag tggcgcagct   240
aacgcattaa gttgaccgcc tggggagtac ggccgcaagg ttaaaactca aatgaattga   300
cgggggcccg cacaagcggt ggagcatgtg gtttaattcg aagcaacgcg aagaacctta   360
ccaggccttg acatgcagag aactttccag agatggattg tgccttcgg gaactctgac   420 acaggtgctg catggctgtc gtcagctcgt gtcgtgagat gttgggttaa gtcccgtaac   480
gagcgcaacc cttgtcctta gttaccagca ngtnatggtg ggcactctaa ggagactgcc   540
ggtgacaaac cggaggaagg tggggatgac gtcaagtcat catggccctt acggcctggg   600
ctacacacgt gctacaatgg tcggtacaga gggttgccaa gccgcgaggt ggagctaatc   660
tcacaaaacc gatcgtagtc cggatcgcag tctgcaactc gactgcgtga agtcggaatc   720
gctagtaatc gcgaatcaga atgtcgcggt gaatacgttc ccgg                    764
```

<210> SEQ ID NO 153
<211> LENGTH: 963
<212> TYPE: DNA
<213> ORGANISM: Bacillus niacini
<220> FEATURE:
<221> NAME/KEY: misc_feature
<222> LOCATION: (1)..(963)

<223> OTHER INFORMATION: BCI 4718 16S rDNA

<400> SEQUENCE: 153

| | |
|---|---|
| gtgttacaaa ctctcgtggt gtgacgggcg gtgtgtacaa ggcccgggaa cgtattcacc | 60 |
| gcggcatgct gatccgcgat tactagcgat tccggcttca tgcaggcgag ttgcagcctg | 120 |
| caatccgaac tgagaatggt tttatgggat tggctaaacc tcgcggtctt gcagccctt | 180 |
| gtaccatcca ttgtagcacg tgtgtagccc aggtcataag gggcatgatg atttgacgtc | 240 |
| atccccacct tcctccggtt tgtcaccggc agtctcctta gagtgcccaa ctgaatgctg | 300 |
| gcaactaaga acaagggttg cgctcgttgc gggacttaac ccaacatctc acgacacgag | 360 |
| ctgacgacaa ccatgcacca cctgtcactc tgtccccga aggggaacgt cctatctcta | 420 |
| ggagtgtcag aggatgtcaa gacctggtaa ggttcttcgc gttgcttcga attaaaccac | 480 |
| atgctccacc gcttgtgcgg gccccgtca attcctttga gtttcagcct tgcggccgta | 540 |
| ctccccaggc ggagtgctta atgcgttagc tgcagcacta aagggcggaa accctctaac | 600 |
| acttagcact catcgtttac ggcgtggact accagggtat ctaatcctgt ttgctcccca | 660 |
| cgctttcgcg cctcagcgtc agttacagac cagaaagccg ccttcgccac tggtgttcct | 720 |
| ccacatctct acgcatttca ccgctacacg tggaattccg ctttcctctt ctgtactcaa | 780 |
| gtcccccagt ttccaatgac cctccacggt tgagccgtgg gctttcacat cagacttaaa | 840 |
| ggaccgcctg cgcgcgcttt acgcccaata attccggaca acgcttgcca cctacgtatt | 900 |
| accgcggctg ctggcacgta gttagccgtg gctttctggt taggtaccgt caaggtaccg | 960 |
| gca | 963 |

<210> SEQ ID NO 154
<211> LENGTH: 600
<212> TYPE: DNA
<213> ORGANISM: Achromobacter pulmonis
<220> FEATURE:
<221> NAME/KEY: misc_feature
<222> LOCATION: (1)..(600)
<223> OTHER INFORMATION: BCI 49 16S rDNA

<400> SEQUENCE: 154

| | |
|---|---|
| taggctaact acttctggta aaacccactc ccatggtgtg acgggcggtg tgtacaagac | 60 |
| ccgggaacgt attcaccgcg acatgctgat ccgcgattac tagcgattcc gacttcacgc | 120 |
| agtcgagttg cagactgcga tccggactac gatcgggttt ctgggattgg ctccccctcg | 180 |
| cggggttggcg accctctgtc ccgaccattg tatgacgtgt gaagccctac ccataagggc | 240 |
| catgaggact tgacgtcatc cccaccttcc tccggtttgt caccggcagt ctcattagag | 300 |
| tgcccttcg tagcaactaa tgacaagggt tgcgctcgtt gcgggactta acccaacatc | 360 |
| tcacgacacg agctgacgac agccatgcag cacctgtgtt ccagttctct tgcgagcact | 420 |
| gccaaatctc ttcggcattc cagacatgtc aagggtaggg aaggtttttc gcgttgcatc | 480 |
| gaattaatcc acatcatcca ccgcttgtgc gggtccccgt caattccttt gagttttaat | 540 |
| cttgcgaccg tactccccag gcggtcaact tcacgcgtta gctgcgctac caaggtccga | 600 |

<210> SEQ ID NO 155
<211> LENGTH: 609
<212> TYPE: DNA
<213> ORGANISM: Exiguobacterium aurantiacum
<220> FEATURE:
<221> NAME/KEY: misc_feature
<222> LOCATION: (1)..(609)
<223> OTHER INFORMATION: BCI 50 16S rDNA

<400> SEQUENCE: 155

```
ggtgttacaa actctcgtgg tgtgacgggc ggtgtgtaca agacccggga acgtattcac    60
cgcagtatgc tgacctgcga ttactagcga ttccgacttc atgcaggcga gttgcagcct   120
gcaatccgaa ctgagaacgg ctttctggga ttggctccac ctcgcggctt cgctgccctt   180
tgtaccgtcc attgtagcac gtgtgtagcc caactcataa ggggcatgat gatttgacgt   240
catccccacc ttcctccggt ttgtcaccgg cagtctcctt agagtgccca acttaatgct   300
ggcaactaag gacaagggtt gcgctcgttg cgggacttaa cccaacatct cacgacacga   360
gctgacgaca accatgcacc acctgtcacc cctgccccg aaggggaagg tacatctctg    420
caccggtcag ggggatgtca agagttggta aggttcttcg cgttgcttcg aattaaacca   480
catgctccac cgcttgtgcg ggtccccgtc aattcctttg agtttcagcc ttgcgaccgt   540
actccccagg cggagtgctt aatgcgttag cttcagcact gaagggcgga aaccctccaa   600
cacctagca                                                           609
```

<210> SEQ ID NO 156
<211> LENGTH: 767
<212> TYPE: DNA
<213> ORGANISM: Pedobacter terrae
<220> FEATURE:
<221> NAME/KEY: misc_feature
<222> LOCATION: (1)..(767)
<223> OTHER INFORMATION: BCI 53 16S rDNA
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:

```
<221> NAME/KEY: misc_feature
<222> LOCATION: (126)..(127)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (460)..(461)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (575)..(575)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (630)..(632)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
```

```
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (743)..(744)
<223> OTHER INFORMATION: n is a, c, g, or t
<220> FEATURE:
<221> NAME/KEY: misc_feature
<222> LOCATION: (752)..(755)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t

<400> SEQUENCE: 156
angtaccccc ngntnnnntg gnttgacggg cggngtgtac aaggnccggg aacgtattca      60
ccgcgtcatt gctgatacnc gattactngc gaatccaact tcntgggtc gagttgcana     120 ccccannccg aactgtgnac ggctttgtga gattcgcatc atattgctat gtagctgccc    180
tctgtaccgt ccattgtagc acgtgtgtag ccccggacgt aagggccatg atgacttgac    240
gtcgtcccct ccttcctctc tgttttgcaca ggcagtctgt ttagagtccc caccattaca   300
tgctggcaac taaacatagg ggttgcgctc gttgcgggac ttaacccaac acctcacggc    360
acgagctgac nacagccatg cagcacctag tttcgtgtcc ttgcggactg atccatctct    420
ggatcattca ctaactttca gcccgggna aggttcctcn ngtatcatcn aattaaacca     480
natgctcctc cgcttgtgcg ggccccgtc aattcctttg agtttcaccc ttgcgggcgt     540 actcccagg nggaacactt aacgctttcg cttanccgct gactgtgtat cgccnacagc     600
gagtgttcat cgnttanggc gtggactacn nnggnatcta atcctgtttg anccccacgc    660
ttncntgcct cancgtcaat aagancatag naagctgnct tcgcaatcgg tgttctgaga    720
cntatctntg cntttcancg ctnnttgtct cnnnncncct ncctcta                  767

<210> SEQ ID NO 157
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 539 16S rDNA
<220> FEATURE:
<221> NAME/KEY: misc_feature
<222> LOCATION: (34)..(34)
<223> OTHER INFORMATION: n is a, c, g, or t
<220> FEATURE:
```

<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (47)..(49)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 157

```
ggcgtaaagc gtgcgtaggt ggttatttaa gtcngttgtg aaanccnnng gctcaaccctn    60
ggaactgcag tggatactgg atgactagaa tgtgntagag ggtagcggaa ttcctggtgt   120
agcagtgaaa tgcgtagaga tcaggaggaa catccatggc gaaggcagct acctggacca   180
acattgacac tgaggcacga aagcgtgggg agcaaacagg attagatacc ctggtagtcc   240
acgccctaaa cgatgcgaac tggatgttgg gtgcaatttg gcacgcagta tcgaagctaa   300
cgcgttaagt tcgccgcctg gggagtacgg tcgcaagact gaaactcaaa ggaattgacg   360
ggggcccgca caagcggtgg agtatgtggt ttaattcgat gcaacgcgaa gaaccttacc   420
tggccttgac atgtcgagaa ctttccagag atggattggg gccttcggga actcgaacac   480
aggtgctgca tggctgtcgt cagctcgtgt cgtgagatgt tgggttaagt cccgcaacga   540
gcgcaaccct tgtccttagt tgccagcacg taatggtggg aactctaagg agaccgccgg   600
tgacaaaccg gaggaaggtg gggatgacgt caagtcatca tggcccttac ggccagggct   660
acacacgtac tacaatggta gggacagagg gctgcaagcc ggcgacggta agccaatccc   720
agaaacccta tctcagtccg gattggagtc tgcaactcga ctccatgaag tcggaatcgc   780
tagtaatcgc agatcagcat tgctgcggtg aatacgttcc cggg                     824
```

<210> SEQ ID NO 158
<211> LENGTH: 820
<212> TYPE: DNA
<213> ORGANISM: Stenotrophomonas maltophilia
<220> FEATURE:
<221> NAME/KEY: misc_feature
<222> LOCATION: (1)..(820)
<223> OTHER INFORMATION: BCI 545 16S rDNA
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t

<400> SEQUENCE: 158

```
taaagcgtgc gtaggtggtt atttaantcc gttgtgaaag ncnngggctc aacctgggaa    60
ctgcagtgga tactgatga ctagaatgtg gtagagggta gcggaattcc tggtgtagca   120
gtgaaatgcg tagagatcag gaggaacatc catggcgaag gcagctacct ggaccaacat   180
```

```
tgacantgag gcacgaaagc gtggggagca aacaggatta gatacctctgg tagtccacgc    240 cctaaacgat gcgaactgga tgttgggtgc aatttggcac gcagtatcga agctaacgcg    300
ttaagttcgc cgcctgggga gtacggtcgc aagactgaaa ctcaaaggaa ttgacggggg    360
cccgcacaag cggtggagta tgtggtttaa ttcgatgcaa cgcgaagaac cttacctggc    420
cttgacatgt cgagaacttt ccagagatgg attggtgcct tcgggaactc gaacacaggt    480
gctgcatggc tgtcgtcagc tcgtgtcgtg agatgttggg ttaagtcccg caacgagcgc    540
aacccttgtc cttagttgcc agcacgtaat ggtgggaact ctaaggagac cgccggtgac    600
aaaccggagg aaggtgggga tgacgtcaag tcatcatggc ccttacggcc agggctacac    660
acgtactaca atggtaggga cagagggctg caagccggcg acggtaagcc aatcccagaa    720
accctatctc agtccggatt ggagtctgca actcgactcc atgaagtcgg aatcgctagt    780
aatcgcagat cagcattgct gcggtgaata cgttcccggg                          820
```

```
<210> SEQ ID NO 159
<211> LENGTH: 368
<212> TYPE: DNA
<213> ORGANISM: Stenotrophomonas maltophilia
<220> FEATURE:
<221> NAME/KEY: misc_feature
<222> LOCATION: (1)..(368)
<223> OTHER INFORMATION: BCI 551 16S rDNA
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (88)..(88)
```

```
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t

<400> SEQUENCE: 159
attggtncct tngngaactn gaacacaggn gnngcanggc ngtngtcagc tcgtgtnntg      60
agangttggg ttaagtcccg caacgagngc aanccttgtc cttagttgcc agcacgtant    120
ggtgggaact ctaaggagac cgccggtgac aaacnggagg aaggtgggga tgacgtcaag    180
tcatcatggc ccttacggcc agggctacac acgtactaca atggtaggga cagagggctg    240
caagccggng acggtaagcc aatcccagaa accctatctc agtccggatt ggagtctgca    300
actcgactcc atgaagtngg aatcgctagt aatcgcagat cagcattgnt cggtgaata    360
cgttcccg                                                             368

<210> SEQ ID NO 160
<211> LENGTH: 659
<212> TYPE: DNA
<213> ORGANISM: Novosphingobium resinovorum
<220> FEATURE:
<221> NAME/KEY: misc_feature
<222> LOCATION: (1)..(659)
<223> OTHER INFORMATION: BCI 557 16S rDNA

<400> SEQUENCE: 160
cgccttcgag tgaatccaac tcccatggtg tgacgggcgg tgtgtacaag gcctgggaac      60
gtattcaccg cggcatgctg atccgcgatt actagcgatt ccgccttcat gctctcgagt    120
tgcagagaac aatccgaact gagacggctt ttggagatta gctcacactc gcgtgcttgc    180
tgcccactgt caccgccatt gtagcacgtg tgtagcccag cgtgtaaggg ccatgaggac    240
ttgacgtcat ccccaccttc ctccggctta tcaccggcag tttccttaga gtgcccaact    300
aaatgctggc aactaaggac gagggttgcg ctcgttgcgg gacttaaccc aacatctcac    360
gacacgagct gacgacagcc atgcagcacc tgtgcacggt ccagccgaac tgaaggaaat    420
ggtctcccaa atccgcgacc ggcatgtcaa acgctggtaa ggttctgcgc gttgcttcga    480
attaaaccac atgctccacc gcttgtgcag gccccgtca attcctttga gttttaatct    540
tgcgaccgta ctccccaggc ggataactta atgcgttagc tgcgccaccc aagtaccaag    600
tacccggaca gctagttatc atcgtttacg gcgtggacta ccagggtatc taatcctgt    659

<210> SEQ ID NO 161
<211> LENGTH: 751
```

```
<212> TYPE: DNA
<213> ORGANISM: Duganella radicis
<220> FEATURE:
<221> NAME/KEY: misc_feature
<222> LOCATION: (1)..(751)
<223> OTHER INFORMATION: BCI 57 16S rDNA
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (398)..(400)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t

<400> SEQUENCE: 161
gctncctact tctggtaaaa cccgctccca tggtgtgncg ggcggtgtgt acaagacccg      60
ggaacgtatt caccgcgaca tgctgatccg cgattactag cgattccaac ttcacgtagt    120
cgagttgcag actacgatcc ggactacgat gcactttctg ggattagctc ccctcgcgg     180 gttggcggcc ctctgtatgc accattgtat gacgtgtgaa gccctaccca taagggccat    240
gaggacttga cgtcatcccc accttcctcc ggtttgtcac cggcagtctc attagagtgc    300
cctttcgtag caactaatga caagggttgc gctcgttgcg ggacttaacc caacatctca    360
cgacacgagc tgacgacagc catgcagcac ctgtgnannn gntctctttc nagcactccc    420
caatctctca gggattccna ccatgtcaag ggtaggtaag gttttcgcg ttgcatcgaa     480 ttaatccaca tcatccaccg cttgtgcggg tccccgtcaa ttcctttgag ttttaatctt    540
```

-continued

```
gcgaccgtac tccccaggcg gtctacttca cgcgttagct gcgttaccaa gtcaattaag    600
acccgacaac tagtagacat cgtttagggc gtggactacc agggtatcta atcctgtttg    660
ctccccacgc tttcgtgcat gancgtcagt tttgacccag ggggctgcct tcgccntcgg    720
ngttcctccn catatctacn catttnactg c                                   751
```

<210> SEQ ID NO 162
<211> LENGTH: 822
<212> TYPE: DNA
<213> ORGANISM: Pseudomonas putida
<220> FEATURE:
<221> NAME/KEY: misc_feature
<222> LOCATION: (1)..(822)
<223> OTHER INFORMATION: BCI 571 16S rDNA
<220> FEATURE:
<221> NAME/KEY: misc_feature
<222> LOCATION: (2)..(2)
<223> OTHER INFORMATION: n is a, c, g, or t

<400> SEQUENCE: 162

```
gncgtaaagc gcgcgtaggt ggtttgttaa gttggatgtg aaagccccgg gctcaacctg     60
ggaactgcat ccaaaactgg caagctagag tacggtagag ggtggtggaa tttcctgtgt    120
agcggtgaaa tgcgtagata taggaaggaa caccagtggc gaaggcgacc acctggactg    180
atactgacac tgaggtgcga aagcgtgggg agcaaacagg attagatacc ctggtagtcc    240
acgccgtaaa cgatgtcaac tagccgttgg aatccttgag attttagtgg cgcagctaac    300
gcattaagtt gaccgcctgg ggagtacggc cgcaaggtta aaactcaaat gaattgacgg    360
gggcccgcac aagcggtgga gcatgtggtt taattcgaag caacgcgaag aaccttacca    420
ggccttgaca tgcagagaac tttccagaga tggattggtg ccttcgggaa ctctgacaca    480
ggtgctgcat ggctgtcgtc agctcgtgtc gtgagatgtt gggttaagtc ccgtaacgag    540
cgcaacccct gtccttagtt accagcacgt tatggtgggc actctaagga gactgccggt    600
gacaaaccgg aggaaggtgg ggatgacgtc aagtcatcat ggcccttacg gcctgggcta    660
cacacgtgct acaatggtcg gtacagaggg ttgccaagcc gcgaggtgga gctaatctca    720
caaaaccgat cgtagtccgg atcgcagtct gcaactcgac tgcgtgaagt cggaatcgct    780
agtaatcgcg aatcagaatg tcgcggtgaa tacgttcccg gg                      822
```

<210> SEQ ID NO 163
<211> LENGTH: 476
<212> TYPE: DNA
<213> ORGANISM: Stenotrophomonas maltophilia
<220> FEATURE:
<221> NAME/KEY: misc_feature
<222> LOCATION: (1)..(476)
<223> OTHER INFORMATION: BCI 574 16S rDNA
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature

```
<222> LOCATION: (147)..(147)
<223> OTHER INFORMATION: n is a, c, g, or t

<400> SEQUENCE: 163
aaggaattga cggggccccg cacaagcggt ggagtangtg gtttaattcg atgcaacgng      60
aagaaccttA cntgnccttg acatgtcgag aactttccag agatggattg gtgccttcgg    120
gaactcgaac acaggtgctg catggcngtc gtcagctcgt gtcgtgagat gttgggttaa    180
gtcccgcaac gagcgcaacc cttgtcctta gttgccagca cgtaatggtg ggaactctaa    240
ggagaccgcc ggtgacaaac cggaggaagg tggggatgac gtcaagtcat catggccctt    300
acggccaggg ctacacacgt actacaatgg tagggacaga gggctgcaag ccggcgacgg    360
taagccaatc ccagaaaccc tatctcagtc cggattggag tctgcaactc gactccatga    420
agtcggaatc gctagtaatc gcagatcagc attgctgcgg tgaatacgtt cccggg        476

<210> SEQ ID NO 164
<211> LENGTH: 773
<212> TYPE: DNA
<213> ORGANISM: Herbaspirillum chloropenolicum
<220> FEATURE:
<221> NAME/KEY: misc_feature
<222> LOCATION: (1)..(773)
<223> OTHER INFORMATION: BCI 58 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
```

<400> SEQUENCE: 164

```
nccttgcggt nnggntaccn ncttctggta aaacccgctc ccntggtgtg acgggcggtg      60
tgtacaagac ccgggaacgt attcaccgcg acatgctgat ccgcgattac tagcgattcc     120
aacttcatgg agtcgagttg cagactccaa tccggactac gatacacttt ctggattag     180
ctcccctcg cggttggcg gccctctgta tgtaccattg tatgacgtgt gaagccctac       240
ccataagggc catgaggact tgacgtcatc cccaccttcc tccggtttgt caccggcagt     300
ctcattagag tgccctttcg tagcaactaa tgacaagggt tgcgctcgtt gcgggactta     360
acccaacatc tcacgacacg agctgacgac agccatgcag cacctgtgtg atggttctct     420
ttcgagcact cccaaatctc ttcaggattc catccatgtc aagggtaggt aaggtttttc     480
gcgttgcatc gaattaatcc acatcatcca ccgcttgtgc gggtcccgt caattccttt      540
gagttttnat cttgcgaccg tactccccag gcggtctant tcacgcgtta gctgcgttac     600
caagtcaatt aagacccgac aactagtaga catcgtttag ggcgtggact accagggtat     660
ctaatcctgt ttgctcccca cgctttcgtg catgancgtc agtgttatcc canggggctg     720
ccttcgccat cggnattcct ccacatatct acgcatttca cngctacacg ngg            773
```

<210> SEQ ID NO 165
<211> LENGTH: 763
<212> TYPE: DNA
<213> ORGANISM: Stenotrophomonas maltophilia
<220> FEATURE:
<221> NAME/KEY: misc_feature
<222> LOCATION: (1)..(763)
<223> OTHER INFORMATION: BCI 588 16S rDNA
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (52)..(57)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(78)
<223> OTHER INFORMATION: n is a, c, g, or t
<220> FEATURE:
<221> NAME/KEY: misc_feature

```
<222> LOCATION: (99)..(99)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 165
gganntgcag tggatactgg atgantagan ngtggtagag gntagnggan tnnnnnngta      60
gcagtnaant gcgtnnnnat caggaggaac atccatggng aaggcagcta cnnggaccan     120
cattgacant gaggcangaa agcgtgggga gcaaacagga ttagataccc tggtagtcca     180
cgccctaaac gatgcgaact ggatgttggg tgcaatttgg cacgcagtat cgaagctaac     240
gcgttaagtt cgccgcctgg ggagtacggt cgcaagactg aaactcaaag gaattgacgg     300
gggcccgcac aagcggtgga gtatgtggtt taattcgatg caacgcgaag aaccttacct     360
ggccttgaca tgtcgagaac tttccagaga tggattggtg ccttcgggaa ctcgaacaca     420
ggtgctgcat ggctgtcgtc agctcgtgtc gtgagatgtt gggttaagtc ccgcaacgag     480
cgcaacccct tgtccttagtt gccagcacgt aatggtggga actctaagga accgccggt     540 gacaaaccgg aggaaggtgg ggatgacgtc aagtcatcat ggcccttacg gccagggcta     600
cacacgtact acaatggtag ggacagaggg ctgcaagccg gcgacggtaa gccaatccca     660
gaaaccctat ctcagtccgg attggagtct gcaactcgac tccatgaagt cggaatcgct     720
agtaatcgca gatcagcatt gctgcggtga atacgttccc ggg                      763

<210> SEQ ID NO 166
<211> LENGTH: 708
<212> TYPE: DNA
<213> ORGANISM: Arthrobacter cupressi
<220> FEATURE:
<221> NAME/KEY: misc_feature
<222> LOCATION: (1)..(708)
<223> OTHER INFORMATION: BCI 59 16S rDNA

<400> SEQUENCE: 166
gttaggccac cggcttcggg tgttaccaac tttcgtgact tgacgggcgg tgtgtacaag      60
gcccgggaac gtattcaccg cagcgttgct gatctgcgat tactagcgac tccgacttca     120
tggggtcgag ttgcagaccc caatccgaac tgagaccggc tttttgggat tagctccacc     180
tcacagtatc gcaacccttt gtaccggcca ttgtagcatg cgtgaagccc aagacataag     240
gggcatgatg atttgacgtc gtccccacct tcctccgagt tgaccccggc agtctcccat     300
gagtccccgg cactacccgc tggcaacatg gaacgagggt tgcgctcgtt gcgggactta     360
acccaacatc tcacgacacg agctgacgac aaccatgcac cacctgtaaa ccaaccccaa     420
aggggaagga ctgtttccag cccggtctgg ttcatgtcaa gccttggtaa ggttcttcgc     480
gttgcatcga attaatccgc atgctccgcc gcttgtgcgg gccccgtca attcctttga     540 gttttagcct tgcggccgta ctccccaggc ggggcactta atgcgttagc tacggcgcgg     600
```

```
aaaacgtgga atgtccccca cacctagtgc ccaacgttta cggcatggac taccagggta    660
tctaatcctg ttcgctcccc atgctttcgc tcctcagcgt cagttaat                 708
```

<210> SEQ ID NO 167
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 590 16S rDNA
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (58)..(60)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t

<400> SEQUENCE: 167

```
ggcgtaaagc gtgcgtaggt ggttatttaa ntccgttgtg aaagccctgg gctcnacnnn    60
ggaactgcag tggatactgg atgactagaa tgtggtagag ggtagcggaa ttcctggtgt   120
agcagtgaaa tgcgtagaga tcaggaggaa catccatggc gaaggcagct acctggacca   180
acattgacan tgaggcacga aagcgtgggg agcaaacagg attagatacc ctggtagtcc   240
acgccctaaa cgatgcgaac tggatgttgg gtgcaatttg gcacgcagta tcgaagctaa   300
cgcgttaagt tcgccgcctg gggagtacgg tcgcaagact gaaactcaaa ggaattgacg   360
ggggcccgca caagcggtgg agtatgtggt ttaattcgat gcaacgcgaa gaaccttacc   420
tggccttgac atgtcgagaa cttttccagag atggattggt gccttcggga actcgaacac   480
aggtgctgca tggctgtcgt cagctcgtgt cgtgagatgt tgggttaagt cccgcaacga   540
gcgcaaccct tgtccttagt tgccagcacg taatggtggg aactctaagg agaccgccgg   600
tgacaaaccg gaggaaggtg gggatgacgt caagtcatca tggcccttac ggccagggct   660
acacacgtac tacaatggta gggacagagg gctgcaagcc ggcgacggta agccaatccc   720
agaaacccta tctcagtccg gattggagtc tgcaactcga ctccatgaag tcggaatcgc   780
tagtaatcgc agatcagcat tgctgcggtg aatacgttcc cggg                    824
```

<210> SEQ ID NO 168
<211> LENGTH: 822
<212> TYPE: DNA
<213> ORGANISM: Pseudomonas putida
<220> FEATURE:
<221> NAME/KEY: misc_feature
<222> LOCATION: (1)..(822)
<223> OTHER INFORMATION: BCI 593 16S rDNA
<220> FEATURE:
<221> NAME/KEY: misc_feature
<222> LOCATION: (2)..(3)
<223> OTHER INFORMATION: n is a, c, g, or t

<400> SEQUENCE: 168

```
gnngtaaagc gcgcgtaggt ggtttgttaa gttggatgtg aaagccccgg gctcaacctg    60
ggaactgcat ccaaaactgg caagctagag tacggtagag ggtggtggaa tttcctgtgt   120
```

```
agcggtgaaa tgcgtagata taggaaggaa caccagtggc gaaggcgacc acctggactg    180
atactgacac tgaggtgcga aagcgtgggg agcaaacagg attagatacc ctggtagtcc    240
acgccgtaaa cgatgtcaac tagccgttgg aatccttgag attttagtgg cgcagctaac    300
gcattaagtt gaccgcctgg ggagtacggc cgcaaggtta aaactcaaat gaattgacgg    360
gggcccgcac aagcggtgga gcatgtggtt taattcgaag caacgcgaag aaccttacca    420
ggccttgaca tgcagagaac tttccagaga tggattggtg ccttcgggaa ctctgacaca    480
ggtgctgcat ggctgtcgtc agctcgtgtc gtgagatgtt gggttaagtc ccgtaacgag    540
cgcaaccctt gtccttagtt accagcacgt tatggtgggc actctaagga gactgccggt    600
gacaaaccgg aggaaggtgg ggatgacgtc aagtcatcat ggcccttacg gcctgggcta    660
cacacgtgct acaatggtcg gtacagaggg ttgccaagcc gcgaggtgga gctaatctca    720
caaaaccgat cgtagtccgg atcgcagtct gcaactcgac tgcgtgaagt cggaatcgct    780
agtaatcgcg aatcagaatg tcgcggtgaa tacgttcccg gg                      822
```

```
<210> SEQ ID NO 169
<211> LENGTH: 664
<212> TYPE: DNA
<213> ORGANISM: Pedobacter rhizosphaerae
<220> FEATURE:
<221> NAME/KEY: misc_feature
<222> LOCATION: (1)..(664)
<223> OTHER INFORMATION: BCI 598 16S rDNA

<400> SEQUENCE: 169
tggcttgacg ggcggtgtgt acaaggcccg ggaacgtatt caccgcgtca ttgctgatac     60
gcgattacta gcgaatccaa cttcaagagg tcgagttgca gacctctatc cgaactgtga    120
tcggcttttt gagattggca ttccattgct ggatagctgc cctctgtacc gaccattgta    180
gcacgtgtgt agccccggac gtaagggcca tgatgacttg acgtcgtccc ctccttcctc    240
tctgtttgca caggcagtct gtctagagtc cccaccatta catgctggca actagacata    300
ggggttgcgc tcgttgcggg acttaaccca acacctcacg gcacgagctg acgacagcca    360
tgcagcacct agtttcgtgt gattgctcac tgtgccatct ctggcacatt cactaacttt    420
caagcccggg taaggttcct cgcgtatcat cgaattaaac cacatgctcc tccgcttgtg    480
cgggcccccg tcaattcctt tgagtttcac ccttgcgggc gtactcccca ggtggaacac    540
ttaacgcttt cgcttagccg ctgactgtat atcgccaaca gcgagtgttc atcgtttagg    600
gcgtggacta ccagggtatc taatcctgtt tgatccccac gctttcgtgc ctcagcgtca    660
atat                                                                664
```

```
<210> SEQ ID NO 170
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 601 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
```

```
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t

<400> SEQUENCE: 170
ggngtnaagc gtgcgtaggt nntnnttnan ntctgtngtg aaancectgg gntcnacnng      60 ggaactgcag tggaaactgg acaactagag tgtggtagag ggtagcggan ntcccggtgt     120
agcagtgaan tgcgtagaga tcgggaggaa catccatggc gaaggcagct acctggacca    180
acactgacan tgaggcacga aagcgtgggg agcaaacagg attagatacc ctggtagtcc    240
acgccctaaa cgatgcgaac tggatgttgg gtgcaatttg gcacgcagta tcgaagctaa    300
cgcgttaagt tcgccgcctg gggagtacgg tcgcaagact gaaactcaaa ggaattgacg    360
ggggcccgca caagcggtgg agtatgtggt ttaattcgat gcaacgcgaa gaaccttacc    420
tggccttgac atgtcgagaa ctttccagag atgattggt gccttcggga actcgaacac    480
aggtgctgca tggctgtcgt cagctcgtgt cgtgagatgt tgggttaagt cccgcaacga    540
gcgcaaccct tgtccttagt tgccagcacg taatggtggg aactctaagg agaccgccgg    600
tgacaaaccg gaggaaggtg gggatgacgt caagtcatca tggcccttac ggccagggct    660
acacacgtac tacaatggtg gggacagagg gctgcaagcc ggcgacggta agccaatccc    720 agaaaccca tctcagtccg gattggagtc tgcaactcga ctccatgaag tcggaatcgc    780
tagtaatcgc agatcagcat tgctgcggtg aatacgttcc cggg                     824
```

-continued

```
<210> SEQ ID NO 171
<211> LENGTH: 327
<212> TYPE: DNA
<213> ORGANISM: Stenotrophomonas maltophilia
<220> FEATURE:
<221> NAME/KEY: misc_feature
<222> LOCATION: (1)..(327)
<223> OTHER INFORMATION: BCI 602 16S rDNA
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (152)..(155)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (207)..(208)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (244)..(244)
```

<223> OTHER INFORMATION: n is a, c, g, or t
<220> FEATURE:
<221> NAME/KEY: misc_feature
<222> LOCATION: (255)..(256)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t

<400> SEQUENCE: 171
gtcgtcagct ngtgtcgtga gatgttgggt taagtcnngc aacgagcgca acccttgtcn      60
ttagttgcca gcangtaatg gtgggaantn taaggagacc gccggtgaca aaccggagga    120
aggtggggat gangtcaagt catcatgncc cnnnngncca gggntacaca cgtactacaa    180
tggtagggac agagggntgc aagcngnnga cggtaagcca atnccagaaa ccntatntca    240
gtcnggattg gagtnngcaa ctngactcca ngaagtngga atcgctagta atcgcagatc    300
agcattgntg cggtgaatac gttcccg                                        327

<210> SEQ ID NO 172
<211> LENGTH: 816
<212> TYPE: DNA
<213> ORGANISM: Stenotrophomonas maltophilia
<220> FEATURE:
<221> NAME/KEY: misc_feature
<222> LOCATION: (1)..(816)
<223> OTHER INFORMATION: BCI 606 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (69)..(71)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (105)..(107)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t

<400> SEQUENCE: 172
gcgtgngtng gtggttattt anntnngttg nnaaanccnn gggctcnncn tgggannntgc    60 agnggatann ngatgantag aatgtggtag agggtagcgg aattnnnggt gtagcantga   120
antgngtaga gatcaggagg aacatccatg gngaaggcag ctacctggac caacatngac   180
antgaggcac ganagcgtgg ggagcaaaca ggattagata ccntggtagt ccacgccctn   240
aacgatgcga acnggatgtt gggtgcaatt tggcacgcag tatngaagct aacgcgttaa   300

```
gttcgccgcc tgggagtac ggtcgcaaga ctgaaactca aaggaattga cgggggcccg    360
cacaagcggt ggagtatgtg gtttaattcg atgcaacgcg aagaaccta cctggccttg    420 acatgtcgag aactttccag agatggattg gtgccttcgg gaactcgaac acaggtgctg    480
catggctgtc gtcagctcgt gtcgtgagat gttgggttaa gtcccgcaac gagcgcaacc    540
cttgtcctta gttgccagca cgtaatggtg ggaactctaa ggagaccgcc ggtgacaaac    600
cggaggaagg tggggatgac gtcaagtcat catggccctt acggccaggg ctacacacgt    660
actacaatgg tagggacaga gggctgcaag ccggcgacgg taagccaatc ccagaaaccc    720
tatctcagtc cggattggag tctgcaactc gactccatga agtcggaatc gctagtaatc    780
gcagatcagc attgctgcgg tgaatacgtt cccggg                              816

<210> SEQ ID NO 173
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 607 16S rDNA

<400> SEQUENCE: 173
ggcgtaaagc gtgcgtaggt ggttatttaa gtccgttgtg aaagccctgg gctcaacctg     60
ggaactgcag tggatactgg atgactagaa tgtggtagag ggtagcggaa ttcctggtgt    120
agcagtgaaa tgcgtagaga tcaggaggaa catccatggc gaaggcagct acctggacca    180
acattgacac tgaggcacga aagcgtgggg agcaaacagg attagatacc ctggtagtcc    240
acgccctaaa cgatgcgaac tggatgttgg gtgcaatttg gcacgcagta tcgaagctaa    300
cgcgttaagt tcgccgcctg gggagtacgg tcgcaagact gaaactcaaa ggaattgacg    360
ggggcccgca caagcggtgg agtatgtggt taattcgat gcaacgcgaa gaaccttacc    420
tggccttgac atgtcgagaa cttccagag atggattggg ccttcggga actcgaacac    480 aggtgctgca tggctgtcgt cagctcgtgt cgtgagatgt tgggttaagt cccgcaacga    540
gcgcaaccct tgtccttagt tgccagcacg taatggtggg aactctaagg agaccgccgg    600
tgacaaaccg gaggaaggtg gggatgacgt caagtcatca tggcccttac ggccagggct    660
acacacgtac tacaatggta gggacagagg gctgcaagcc ggcgacggta agccaatccc    720 agaaaccta tctcagtccg gattggagtc tgcaactcga ctccatgaag tcggaatcgc    780
tagtaatcgc agatcagcat tgctgcggtg aatacgttcc cggg                    824

<210> SEQ ID NO 174
<211> LENGTH: 823
<212> TYPE: DNA
<213> ORGANISM: Novosphingobium lindaniclasticum
<220> FEATURE:
<221> NAME/KEY: misc_feature
<222> LOCATION: (1)..(823)
<223> OTHER INFORMATION: BCI 608 16S rDNA

<400> SEQUENCE: 174
ggcgtaaagc gcgcgtaggc ggttactcaa gtcagaggtg aaagcccggg gctcaacccc     60
ggaactgcct ttgaaactag gtgactagaa tcttggagag gtcagtggaa ttccgagtgt    120
agaggtgaaa ttcgtagata ttcggaagaa caccagtggc gaaggcgact gactggacaa    180
gtattgacgc tgaggtgcga aagcgtgggg agcaaacagg attagatacc ctggtagtcc    240
acgccgtaaa cgatgataac tagctgtccg gggacttggt cttggtgg cgcagctaac    300
```

```
gcattaagtt atccgcctgg ggagtacggt cgcaagatta aaactcaaag gaattgacgg      360
gggcctgcac aagcggtgga gcatgtggtt taattcgaag caacgcgcag aaccttacca      420
gcgtttgaca tcctcatcgc ggatttgaga gatcatttcc ttcagttcgg ctggatgagt      480
gacaggtgct gcatggctgt cgtcagctcg tgtcgtgaga tgttgggtta agtcccgcaa      540
cgagcgcaac cctcgtcctt agttgccagc atttagttgg cactctaag gaaactgccg       600 gtgataagcc ggaggaaggt ggggatgacg tcaagtcctc atggcccta cacgctgggc       660 tacacacgtg ctacaatggc ggtgacagtg gcagcaagc aggcgactgc aagctaatct       720
ccaaaagccg tctcagttcg gattgttctc tgcaactcga gagcatgaag gcggaatcgc      780
tagtaatcgc ggatcagcat gccgcggtga atacgttccc agg                        823
```

<210> SEQ ID NO 175
<211> LENGTH: 410
<212> TYPE: DNA
<213> ORGANISM: Agrobacterium fabrum
<220> FEATURE:
<221> NAME/KEY: misc_feature
<222> LOCATION: (1)..(410)
<223> OTHER INFORMATION: BCI 609 16S rDNA

<400> SEQUENCE: 175

```
aactgagatg gcttttggag attagctcga catcgctgtc tcgctgccca ctgtcaccac       60
cattgtagca cgtgtgtagc ccagcccgta agggccatga ggacttgacg tcctccccac      120
cttcctctcg gcttatcacc ggcagtcccc ttagagtgcc caactaaatg ctggcaacta      180
agggcgaggg ttgcgctcgt tgcgggactt aacccaacat ctcacgacac gagctgacga      240
cagccatgca gcacctgttc tggggccagc ctaactgaag gacatcgtct ccaatgccca      300
taccccgaat gtcaagagct ggtaaggttc tgcgcgttgc ttcgaattaa accacatgct      360
ccaccgcttg tgcgggcccc cgtcaattcc tttgagtttt aatcttgcga                 410
```

<210> SEQ ID NO 176
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 610 16S rDNA
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 176

```
ggcgtaaagc gtgcgtaggn nnntgtttaa gtctgttgtg aaagccctgg gntcaacntg       60
ggaactgcag tggaaactgg acaactagag tgtggtagag ggtagcggaa ttcccggtgt      120
agcagtgaaa tgcgtagaga tcgggaggaa catccatggc gaaggcagct acctggacca      180
acactgacac tgaggcacga aagcgtgggg agcaaacagg attagatacc ctggtagtcc      240
acgccctaaa cgatgcgaac tggatgttgg gtgcaatttg gcacgcagta tcgaagctaa      300
```

```
cgcgttaagt tcgccgcctg gggagtacgg tcgcaagact gaaactcaaa ggaattgacg      360
ggggcccgca caagcggtgg agtatgtggt ttaattcgat gcaacgcgaa gaaccttacc      420
tggccttgac atgtcgagaa ctttccagag atggattggt gccttcggga actcgaacac      480
aggtgctgca tggctgtcgt cagctcgtgt cgtgagatgt tgggttaagt cccgcaacga      540
gcgcaaccct tgtccttagt tgccagcacg taatggtggg aactctaagg agaccgccgg      600
tgacaaaccg gaggaaggtg gggatgacgt caagtcatca tggcccttac ggccagggct      660
acacacgtac tacaatggtg gggacagagg gctgcaagcc ggcgacggta agccaatccc      720
agaaacccca tctcagtccg gattggagtc tgcaactcga ctccatgaag tcggaatcgc      780
tagtaatcgc agatcagcat tgctgcggtg aatacgttcc cggg                      824
```

<210> SEQ ID NO 177
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 617 16S rDNA
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 177

```
ggcgtaaagc gtgcgtaggt ggttatttaa ntccgttgtg aaagccctgg gctcaacntg      60
ggaactgcag tggatactgg atgactagaa tgtggtagag ggtagcggaa ttcctggtgt      120
agcagtgaaa tgcgtagaga tcaggaggaa catccatggc gaaggcagct acctggacca      180
acattgacac tgaggcacga aagcgtgggg agcaaacagg attagatacc ctggtagtcc      240
acgccctaaa cgatgcgaac tggatgttgg gtgcaatttg gcacgcagta tcgaagctaa      300
cgcgttaagt tcgccgcctg gggagtacgg tcgcaagact gaaactcaaa ggaattgacg      360
ggggcccgca caagcggtgg agtatgtggt ttaattcgat gcaacgcgaa gaaccttacc      420
tggccttgac atgtcgagaa ctttccagag atggatgggt gccttcggga actcgaacac      480
aggtgctgca tggctgtcgt cagctcgtgt cgtgagatgt tgggttaagt cccgcaacga      540
gcgcaaccct tgtccttagt tgccagcacg taatggtggg aactctaagg agaccgccgg      600
tgacaaaccg gaggaaggtg gggatgacgt caagtcatca tggcccttac ggccagggct      660
acacacgtac tacaatggta gggacagagg gctgcaagcc ggcgacggta agccaatccc      720
agaaacccta tctcagtccg gattggagtc tgcaactcga ctccatgaag tcggaatcgc      780
tagtaatcgc agatcagcat tgctgcggtg aatacgttcc cggg                      824
```

<210> SEQ ID NO 178
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 618 16S rDNA

<400> SEQUENCE: 178

```
ggcgtaaagc gtgcgtaggt ggttgtttaa gtctgttgtg aaagccctgg gctcaacctg      60
```

```
ggaactgcag tggaaactgg acaactagag tgtggtagag ggtagcgaaa ttcccggtgt    120
agcagtgaaa tgcgtagaga tcgggaggaa catccatggc gaaggcagct acctggacca    180
acactgacac tgaggcacga aagcgtgggg agcaaacagg attagatacc ctggtagtcc    240
acgccctaaa cgatgcgaac tggatgttgg gtgcaatttg gcacgcagta tcgaagctaa    300
cgcgttaagt tcgccgcctg gggagtacgg tcgcaagact gaaactcaaa ggaattgacg    360
ggggcccgca caagcggtgg agtatgtggt ttaattcgat gcaacgcgaa gaaccttacc    420
tggccttgac atgtcgagaa ctttccagag atggattggt gccttcggga actcgaacac    480
aggtgctgca tggctgtcgt cagctcgtgt cgtgagatgt tgggttaagt cccgcaacga    540
gcgcaaccct tgtccttagt tgccagcacg taatggtggg aactctaagg agaccgccgg    600
tgacaaaccg gaggaaggtg gggatgacgt caagtcatca tggcccttac ggccagggct    660
acacacgtac tacaatggtg gggacagagg gctgcaagcc ggcgacggta agccaatccc    720
agaaacccca tctcagtccg gattggagtc tgcaactcga ctccatgaag tcggaatcgc    780
tagtaatcgc agatcagcat tgctgcggtg aatacgttcc cggg                    824
```

```
<210> SEQ ID NO 179
<211> LENGTH: 805
<212> TYPE: DNA
<213> ORGANISM: Stenotrophomonas maltophilia
<220> FEATURE:
<221> NAME/KEY: misc_feature
<222> LOCATION: (1)..(805)
<223> OTHER INFORMATION: BCI 619 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (112)..(112)
```

```
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t

<400> SEQUENCE: 179
tgnttgttta antcnnttgt gaaagccctg ggctcancnt gggaactgca gtggaaacng      60
gacaantaga gtgtnntaga gggtagcgna attcccggtg tagcagtgna angngtagag     120
atcgggaggn acntccatgg cgaaggcagc tacctggacc aacactgaca ntgaggcacg     180
aaagcgtggg gagcaaacag gattagatac cctggtagtc cacgccctaa acgatgcgaa     240
ctggatgttg ggtgcaattt ggcacgcagt atcgaagcta acgcgttaag ttcgccgcct     300
ggggagtacg gtcgcaagac tgaaactcaa aggaattgac ggggccccgc acaagcggtg     360
gagtatgtgg tttaattcga tgcaacgcga agaaccttac ctggccttga catgtcgaga     420
actttccaga gatggattgg tgccttcggg aactcgaaca caggtgctgc atggctgtcg     480
tcagctcgtg tcgtgagatg ttgggttaag tcccgcaacg agcgcaaccc ttgtccttag     540
ttgccagcac gtaatggtgg gaactctaag gagaccgccg gtgacaaacc ggaggaaggt     600
ggggatgacg tcaagtcatc atggccctta cggccagggc tacacacgta ctacaatggt     660
ggggacagag ggctgcaagc cggcgacggt aagccaatcc cagaaacccc atctcagtcc     720
ggattggagt ctgcaactcg actccatgaa gtcggaatcg ctagtaatcg cagatcagca     780
ttgctgcggt gaatacgttc ccggg                                           805

<210> SEQ ID NO 180
<211> LENGTH: 829
<212> TYPE: DNA
<213> ORGANISM: Arthrobacter cupressi
<220> FEATURE:
<221> NAME/KEY: misc_feature
<222> LOCATION: (1)..(829)
<223> OTHER INFORMATION: BCI 62 16S rDNA
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
```

<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

<400> SEQUENCE: 180

```
ttattgggcg taaagagntc gtaggcggtt tgtcgcntct gccgtgaaag tccggggctc      60
aantncngna tntgcggtgg gtacgggcag actagagtga tgtaggggag actgnaattc     120
ctggtgtagc ggtgaaatgc gcagatatca ggaggaacac cgatggcgaa ggcaggtctc     180
tgggcattaa ctgacgctga ggagcgaaag catggggagc gaacaggatt agataccctg     240
gtagtccatg ccgtaaacgt tgggcactag gtgtgggga cattccacgt tttccgcgcc     300
gtagctaacg cattaagtgc cccgcctggg gagtacggcc gcaaggctaa aactcaaagg     360
aattgacggg ggcccgcaca agcggcggag catgcggatt aattcgatgc aacgcgaaga    420
accttaccaa ggcttgacat gaaccagacc gggctgaaaa cagtccttcc cctttgggt     480
tggtttacag gtggtgcatg gttgtcgtca gctcgtgtcg tgagatgttg ggttaagtcc    540
cgcaacgagc gcaaccctcg ttccatgttg ccagcgggta gtccgggga ctcatgggag      600
actgccgggg tcaactcgga ggaaggtggg gacgacgtca atcatcatg ccccttatgt      660
cttgggcttc acgcatgcta caatggccgg tacaaagggt tgcgatactg tgaggtggag    720
ctaatcccaa aaagccggtc tcagttcgga ttggggtctg caactcgacc ccatgaagtc    780
ggagtcgcta gtaatcgcag atcagcaacg ctgcggtgaa tacgttccc                 829
```

<210> SEQ ID NO 181
<211> LENGTH: 784
<212> TYPE: DNA
<213> ORGANISM: Stenotrophomonas maltophilia
<220> FEATURE:
<221> NAME/KEY: misc_feature
<222> LOCATION: (1)..(784)
<223> OTHER INFORMATION: BCI 620 16S rDNA
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:

<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t

<400> SEQUENCE: 181

```
aaagccctgg nntnnacntn gnaantgcag tggaaacngg acaactagag tgtggtagag      60
ggtagcgnaa ttcccggtgt agcagtgaaa ngcgtagaga tcgggaggaa catccanggc     120
gaaggcagnt acctggacca acactgacan tgaggcacga aagcgtgggg agcaaacagg     180
attagatacc ctggtagtcc acgccctnaa cgatgcgaac nggatgttgg gtgcaatttg     240
gcacgcagta tcgaagctaa cgcgttaagt tcgccgcctg gggagtacgg tcgcaagact     300
gaaactcaaa ggaattgacg ggggcccgca caagcgtgg agtatgtggt ttaattcgat     360
gcaacgcgaa gaaccttacc tggccttgac atgtcgagaa ctttccagag atggattggt     420
gccttcggga actcgaacac aggtgctgca tggctgtcgt cagctcgtgt cgtgagatgt     480
tgggttaagt cccgcaacga gcgcaaccct tgtccttagt tgccagcacg taatggtggg     540
aactctaagg agaccgccgg tgacaaaccg gaggaaggtg gggatgacgt caagtcatca     600
tggcccttac ggccagggct acacacgtac tacaatggtg gggacagagg gctgcaagcc     660
ggcgacggta agccaatccc agaaacccca tctcagtccg gattggagtc tgcaactcga     720
ctccatgaag tcggaatcgc tagtaatcgc agatcagcat tgctgcggtg aatacgttcc     780
cggg                                                                 784
```

<210> SEQ ID NO 182
<211> LENGTH: 823
<212> TYPE: DNA
<213> ORGANISM: Stenotrophomonas maltophilia
<220> FEATURE:
<221> NAME/KEY: misc_feature
<222> LOCATION: (1)..(823)
<223> OTHER INFORMATION: BCI 623 16S rDNA
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (129)..(130)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t

<400> SEQUENCE: 182

| | | | | | |
|---|---|---|---|---|---|
| ggcgtaaagc | ntgngtaggt | ggttgttnaa | gtntgttgtg | aaancccdng | gctcaacntg | 60 |
| gnaactgcag | tggaaactgg | acaactagag | tgtggtagag | ggtagcggaa | ttcccggtgt | 120 |
| agcagtgann | gcgtagagat | cgggaggaac | atccatggcg | aaggcagcta | cctggaccaa | 180 |
| cactgacant | gaggcacgaa | agcgtgggga | gcaaacagga | ttagatacco | tggtagtcca | 240 |
| cgccctaaac | gatgcgaacn | ggatgttggg | tgcaatttgg | cacgcagtat | cgaagctaac | 300 |
| gcgttaagtt | cgccgcctgg | ggagtacggt | cgcaagactg | aaactcaaag | gaattgacgg | 360 |
| gggcccgcac | aagcggtgga | gtatgtggtt | taattcgatg | caacgcgaag | aaccttacct | 420 |
| ggccttgaca | tgtcgagaac | tttccagaga | tggattggtg | ccttcgggaa | ctcgaacaca | 480 |
| ggtgctgcat | ggctgtcgtc | agctcgtgtc | gtgagatgtt | gggttaagtc | ccgcaacgag | 540 |
| cgcaaccctt | gtccttagtt | gccagcacgt | aatggtggga | actctaagga | gaccgccggt | 600 |
| gacaaaccgg | aggaaggtgg | ggatgacgtc | aagtcatcat | ggcccttacg | gccagggcta | 660 |
| cacacgtact | acaatggtgg | ggacagaggg | ctgcaagccg | cgacggtaa | gccaatccca | 720 |
| gaaaccccat | ctcagtccgg | attggagtct | gcaactcgac | tccatgaagt | cggaatcgct | 780 |
| agtaatcgca | gatcagcatt | gctgcggtga | atacgttccc | ggg | | 823 |

<210> SEQ ID NO 183
<211> LENGTH: 720
<212> TYPE: DNA
<213> ORGANISM: Stenotrophomonas maltophilia
<220> FEATURE:
<221> NAME/KEY: misc_feature
<222> LOCATION: (1)..(720)
<223> OTHER INFORMATION: BCI 64 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (16)..(16)

<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t

<400> SEQUENCE: 183

```
ncctgcttct ggtgcnacaa actcccatgg tgtgacgggc ggtgtgtaca aggcccggga      60
acgtattcac cgcagcaatg ctgatctgcg attactagcg attccgactt catggagtcg     120
agttgcagac tccaatccgg actgagatag ggtttctggg attggcttac cgtcgccggc     180
ttgcagccct ctgtccctac cattgtagta cgtgtgtagc cctggccgta agggccatga     240
tgacttgacg tcatccccac cttcctccgg tttgtcaccg gcggtctcct tagagttccc     300
accattacgt gctggcaact aaggacaagg gttgcgctcg ttgcgggact aacccaaca      360
tctcacgaca cgagctgacg acagccatgc agcacctgtg ttcgagttcc cgaaggcacc     420
aatcnatctc tggaaagttc tcgacatgtc aaggccaggt aaggttcttc gcgttgcatc     480
gaattaaacc acatactcca ccgcttgtgc gggcccccgt caattccttt gagtttcagt     540
cttgcgaccg tactccccag gcggcgaact aacgcgtta gcttcnatac tgcgtgccaa      600
attgcaccca acatccagtt cgcatcgttt anggcgtgga ctaccagggt atctaatcct     660
gtntgctccc cacgctttcg tgcctcagtg tcngtgttgg nccnngnagc tgccttngcc     720
```

<210> SEQ ID NO 184
<211> LENGTH: 816
<212> TYPE: DNA
<213> ORGANISM: Acidovorax soli
<220> FEATURE:
<221> NAME/KEY: misc_feature
<222> LOCATION: (1)..(816)
<223> OTHER INFORMATION: BCI 648 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature

```
<222> LOCATION: (17)..(18)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t

<400> SEQUENCE: 184
ggcgtnaagc gtgcgcnngc ggttatataa gacagatgtg aanncccgg gctcancnng      60 ggaactgcat ttgtgantgt atagctagag tnnggcagag ggggatggaa ttccgcgtgt    120
agcagtgaaa tgcgtagata tgcggaggaa caccgatggc gaaggcantc ccctgggcct    180
gtactgacgc tcatgcacga aagcgtgggg agcaaacagg attagatacc ctggtagtcc    240
acgccctaaa cgatgtcaac tggttgttgg gtcttcactg actcagtaac gaagctaacg    300
cgtgaagttg accgcctggg gagtacggcc gcaaggttga aactcaaagg aattgacggg    360
gacccgcaca agcggtggat gatgtggttt aattcgatgc aacgcgaaaa accttaccca    420
cctttgacat gtatggaatc ctttagagat agaggagtgc tcgaaagaga gccataacac    480
aggtgctgca tggctgtcgt cagctcgtgt cgtgagatgt tgggttaagt cccgcaacga    540
gcgcaaccct tgccattagt tgctacgaaa gggcactcta atgggactgc cggtgacaaa    600
ccggaggaag gtgggatga cgtcaagtcc tcatggccct tataggtggg gctacacacg    660
tcatacaatg gctggtacag agggttgcca acccgcgagg gggagccaat cccataaagc    720
cagtcgtagt ccggatcgca gtctgcaact cgactgcgtg aagtcggaat cgctagtaat    780
cgcggatcag aatgtcgcgg tgaatacgtt cccggg                              816

<210> SEQ ID NO 185
<211> LENGTH: 836
<212> TYPE: DNA
<213> ORGANISM: Stenotrophomonas maltophilia
<220> FEATURE:
<221> NAME/KEY: misc_feature
<222> LOCATION: (1)..(836)
<223> OTHER INFORMATION: BCI 665 16S rDNA

<400> SEQUENCE: 185
attactgggc gtaaagcgtg cgtaggtggt tatttaagtc cgttgtgaaa gccctgggct     60
caacctggga actgcagtgg atactggatg actagaatgt ggtagagggt agcggaattc    120
ctggtgtagc agtgaaatgc gtagagatca ggaggaacat ccatggcgaa ggcagctacc    180
tggaccaaca ttgacactga ggcacgaaag cgtggggagc aaacaggatt agataccctg    240
gtagtccacg ccctaaacga tgcgaactgg atgttgggtg caatttggca cgcagtatcg    300
```

| aagctaacgc gttaagttcg ccgcctgggg agtacggtcg caagactgaa actcaaagga | 360 |
| attgacgggg gcccgcacaa gcggtggagt atgtggttta attcgatgca acgcgaagaa | 420 |
| ccttacctgg ccttgacatg tcgagaactt tccagagatg gattggtgcc ttcgggaact | 480 |
| cgaacacagg tgctgcatgg ctgtcgtcag ctcgtgtcgt gagatgttgg gttaagtccc | 540 |
| gcaacgagcg caaccctgt ccttagttgc cagcacgtaa tggtgggaac tctaaggaga | 600 |
| ccgccggtga caaaccggag gaaggtgggg atgacgtcaa gtcatcatgg ccttacggc | 660 |
| cagggctaca cacgtactac aatggtaggg acagagggct gcaagccggc gacggtaagc | 720 |
| caatcccaga aaccctatct cagtccggat tggagtctgc aactcgactc catgaagtcg | 780 |
| gaatcgctag taatcgcaga tcagcattgc tgcggtgaat acgttcccgg gccttg | 836 |

<210> SEQ ID NO 186
<211> LENGTH: 730
<212> TYPE: DNA
<213> ORGANISM: Dyadobacter soli
<220> FEATURE:
<221> NAME/KEY: misc_feature
<222> LOCATION: (1)..(730)
<223> OTHER INFORMATION: BCI 68 16S rDNA

<400> SEQUENCE: 186

| gtctccccga ctcccatggc ttgacgggcg gtgtgtacaa ggtccgggaa cgtattcacc | 60 |
| gcgtcatagc tgatacgcga ttactagcga ttccagcttc atagagtcga gttgcagact | 120 |
| ccaatccgaa ctgagaacgg cttttgga ttggcatcac atcgctgtgt agcaaccctc | 180 |
| tgtaccgccc attgtagcac gtgtgttgcc ctggacgtaa gggccatgat gacttgacgt | 240 |
| cgtcccctcc ttcctctctg tttgcacagg cagtctggct agagtcccca ccattacgtg | 300 |
| ctggcaacta accataggg ttgcgctcgt tgcgggactt aacccaacat ctcacgacac | 360 |
| gagctgacga cagccatgca gcaccttcaa acaggccatt gctggcttac acatttctgc | 420 |
| ataattcctg tctgatttag cccaggtaag gttcctcgcg tatcatcgaa ttaaaccaca | 480 |
| tgctccaccg cttgtgcgga cccccgtcaa ttcctttgag tttcaccgtt gccggcgtac | 540 |
| tccccaggtg gaggacttaa cggttttccct aagtcgctca gcattgctgc caaacaacga | 600 |
| gtcctcatcg tttacagcat ggactaccag ggtatctaat cctgtttgct ccccatgctt | 660 |
| tcgtgcctca gtgtcaaaca aatcgtagcc acctgccttc gcaatcggtg ttctggatga | 720 |
| tatctatgca | 730 |

<210> SEQ ID NO 187
<211> LENGTH: 690
<212> TYPE: DNA
<213> ORGANISM: Arthrobacter pascens
<220> FEATURE:
<221> NAME/KEY: misc_feature
<222> LOCATION: (1)..(690)
<223> OTHER INFORMATION: BCI 682 16S rDNA

<400> SEQUENCE: 187

| tcgggtgtta ccaactttcg tgacttgacg ggcggtgtgt acaaggcccg ggaacgtatt | 60 |
| caccgcagcg ttgctgatct gcgattacta gcgactccga cttcatgggg tcgagttgca | 120 |
| gaccccaatc cgaactgaga ccggctttt gggattagct ccacctcaca gtatcgcaac | 180 |
| cctttgtacc ggccattgta gcatgcgtga agcccaagac ataagggca tgatgatttg | 240 |
| acgtcgtccc caccttcctc cgagttgacc ccggcagtct cctatgagtc cccgccataa | 300 |
| cgcgctggca acatagaacg agggttgcgc tcgttgcggg acttaaccca acatctcacg | 360 |

```
acacgagctg acgacaacca tgcaccacct gtgaaccagc cccaaagggg aaaccacatt    420
tctgcagcga tccagtccat gtcaagcctt ggtaaggttc ttcgcgttgc atcgaattaa    480
tccgcatgct ccgccgcttg tgcgggcccc cgtcaattcc tttgagttt agccttgcgg    540 ccgtactccc caggcggggc acttaatgcg ttagctacgg cgcggaaaac gtggaatgtc    600
ccccacacct agtgcccaac gtttacggca tggactacca gggtatctaa tcctgttcgc    660
tccccatgct ttcgctcctc agcgtcagtt                                    690
```

<210> SEQ ID NO 188
<211> LENGTH: 719
<212> TYPE: DNA
<213> ORGANISM: Novosphingobium lindaniclasticum
<220> FEATURE:
<221> NAME/KEY: misc_feature
<222> LOCATION: (1)..(719)
<223> OTHER INFORMATION: BCI 684 16S rDNA

<400> SEQUENCE: 188

```
gccttcgggt gaaaccaact cccatggtgt gacgggcggt gtgtacaagg cctgggaacg     60
tattcaccgc ggcatgctga tccgcgatta ctagcgattc cgccttcatg ctctcgagtt    120
gcagagaaca atccgaactg agacggcttt tggagattag cttgcagtcg cctgcttgct    180
gcccactgtc accgccattg tagcacgtgt gtagcccagc gtgtaagggc catgaggact    240
tgacgtcatc cccaccttcc tccggcttat caccggcagt ttccttagag tgcccaacta    300
aatgctggca actaaggacg agggttgcgc tcgttgcggg acttaaccca acatctcacg    360
acacgagctg acgacagcca tgcagcacct gtcactcatc cagccgaact gaaggaaatc    420
atctctgaaa tccgcgatga ggatgtcaaa cgctggtaag gttctgcgcg ttgcttcgaa    480
ttaaaccaca tgctccaccg cttgtgcagg cccccgtcaa ttcctttgag ttttaatctt    540
gcgaccgtac tccccaggcg gataacttaa tgcgttagct cgccaccca aagaccaagt    600 ccccggacag ctagttatca tcgtttacgg cgtggactac cagggtatct aatcctgttt    660
gctccccacg ctttcgcacc tcagcgtcaa tacttgtcca gtcagtcgcc ttcgccact    719
```

<210> SEQ ID NO 189
<211> LENGTH: 824
<212> TYPE: DNA
<213> ORGANISM: Microbacterium sp.
<220> FEATURE:
<221> NAME/KEY: misc_feature
<222> LOCATION: (1)..(824)
<223> OTHER INFORMATION: BCI 688 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 189

```
ggcgtnaaga gctngtaggc ggtttgtcgc gtctgntgng aaatccggag gctcaacntc    60
cggcctgcag tgggtacggg cagactagag tgcggtaggg gagattggaa ttcctggtgt   120
agcggtggaa tgcgcagata tcaggaggaa caccgatggc gaaggcagat ctctgggccg   180
taactgacgc tgaggagcga aagggtgggg agcaaacagg cttagatacc ctggtagtcc   240
accccgtaaa cgttgggaac tagttgtggg gtccattcca cggattccgt gacgcagcta   300
acgcattaag ttccccgcct ggggagtacg gccgcaaggc taaaactcaa aggaattgac   360
ggggacccgc acaagcggcg gagcatgcgg attaattcga tgcaacgcga agaaccttac   420
caaggcttga catatacgag aacgggccag aaatggtcaa ctctttggac actcgtaaac   480
aggtggtgca tggttgtcgt cagctcgtgt cgtgagatgt tgggttaagt cccgcaacga   540
gcgcaaccct cgttctatgt tgccagcacg taatggtggg aactcatggg atactgccgg   600
ggtcaactcg aggaaggtg gggatgacgt caaatcatca tgccccttat gtcttgggct   660
tcacgcatgc tacaatggcc ggtacaaagg gctgcaatac cgcgaggtgg agcgaatccc   720
aaaaagccgg tcccagttcg gattgaggtc tgcaactcga cctcatgaag tcggagtcgc   780
tagtaatcgc agatcagcaa cgctgcggtg aatacgttcc cggg                    824
```

<210> SEQ ID NO 190
<211> LENGTH: 699
<212> TYPE: DNA
<213> ORGANISM: Bosea robiniae
<220> FEATURE:
<221> NAME/KEY: misc_feature
<222> LOCATION: (1)..(699)
<223> OTHER INFORMATION: BCI 689 16S rDNA

<400> SEQUENCE: 190

```
gacgccttcg ggtaaaccca actcccatgg tgtgacgggc ggtgtgtaca aggcccggga    60
acgtattcac cgtggcatgc tgatccacga ttactagcga ttccaccttc atgcactcga   120
gttgcagagt gcaatctgaa ctgagacggc ttttgggat tagctcgagg tcgccctttc   180
gctgcccatt gtcaccgcca ttgtagcacg tgtgtagccc agcctgtaag ggccatgagg   240
acttgacgtc atccccacct tcctcgcggc ttatcaccgg cagtccccct agagttccca   300
acttaatgat ggcaactagg ggcgagggtt gcgctcgttg cgggacttaa cccaacatct   360
cacgacacga gctgacgaca gccatgcagc acctgtgttc cggccagccg aactgaagaa   420
aggcatctct gccgatcaaa ccggacatgt caaaagctgg taaggttctg cgcgttgctt   480
cgaattaaac cacatgctcc accgcttgtg cgggccccg tcaattcctt tgagttttaa   540
tcttgcgacc gtactcccca ggcggaatgc ttaaagcgtt agctgcgcca ctgaagagca   600
agctccccaa cggctggcat tcatcgttta cggcgtggac taccagggta tctaatcctg   660
tttgctcccc acgctttcgc gcctcagcgt cagtttcgg                          699
```

<210> SEQ ID NO 191
<211> LENGTH: 816
<212> TYPE: DNA
<213> ORGANISM: Acidovorax soli
<220> FEATURE:
<221> NAME/KEY: misc_feature
<222> LOCATION: (1)..(816)
<223> OTHER INFORMATION: BCI 690 16S rDNA

<400> SEQUENCE: 191

```
ggcgtaaagc gtgcgcaggc ggttatataa gacagatgtg aaatccccgg gctcaacctg    60
```

```
ggaactgcat tgtgactgt atagctagag tacggcagag ggggatggaa ttccgcgtgt    120
agcagtgaaa tgcgtagata tgcggaggaa caccgatggc gaaggcaatc ccctgggcct   180
gtactgacgc tcatgcacga aagcgtgggg agcaaacagg attagatacc ctggtagtcc   240
acgccctaaa cgatgtcaac tggttgttgg gtcttcactg actcagtaac gaagctaacg   300
cgtgaagttg accgcctggg gagtacggcc gcaaggttga aactcaaagg aattgacggg   360
gacccgcaca gcggtggat gatgtggttt aattcgatgc aacgcgaaaa accttaccca    420
cctttgacat gtatggaatc ctttagagat agaggagtgc tcgaaagaga gccataacac   480
aggtgctgca tggctgtcgt cagctcgtgt cgtgagatgt tgggttaagt cccgcaacga   540
gcgcaaccct tgccattagt tgctacgaaa gggcactcta atgggactgc cggtgacaaa   600
ccggaggaag gtggggatga cgtcaagtcc tcatggccct tataggtggg gctacacacg   660
tcatacaatg gctggtacag agggttgcca acccgcgagg gggagccaat cccataaagc   720
cagtcgtagt ccggatcgca gtctgcaact cgactgcgtg aagtcggaat cgctagtaat   780
cgcggatcag aatgtcgcgg tgaatacgtt cccggg                             816
```

<210> SEQ ID NO 192
<211> LENGTH: 715
<212> TYPE: DNA
<213> ORGANISM: Rhizobium grahamii
<220> FEATURE:
<221> NAME/KEY: misc_feature
<222> LOCATION: (1)..(715)
<223> OTHER INFORMATION: BCI 691 16S rDNA

<400> SEQUENCE: 192

```
ctaccttcgg gtaaaaccaa ctcccatggt gtgacgggcg gtgtgtacaa ggcccgggaa    60
cgtattcacc gcggcatgct gatccgcgat tactagcgat tccaacttca tgcactcgag   120
ttgcagagtg caatccgaac tgagatggct tttggagatt agctgacat cgctgtctcg    180 ctgcccactg tcaccaccat gtagcacgt gtgtagccca gcccgtaagg gccatgagga    240
cttgacgtca tcccaccttt cctctcggct tatcaccggc agtcccctta gagtgcccaa   300
ccaaatgctg gcaactaagg gcgagggttg cgctcgttgc gggacttaac ccaacatctc   360
acgacacgag ctgacgacag ccatgcagca cctgtgttcc ggtccccgaa gggaaccttg   420
catctctgca agtagccgga catgtcaagg gctggtaagg ttctgcgcgt tgcttcgaat   480
taaaccacat gctccaccgc ttgtgcgggc ccccgtcaat cctttgagt tttaatcttg    540 cgaccgtact ccccaggcgg aatgtttaat gcgttagctg cgccaccgaa cagtatactg   600
cccgacggct aacattcatc gtttacggcg tggactacca gggtatctaa tcctgtttgc   660
tccccacgct ttcgcacctc agcgtcagta atggaccagt gagccgcctt cgcca         715
```

<210> SEQ ID NO 193
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 693 16S rDNA
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (62)..(62)

<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t

<400> SEQUENCE: 193

```
ggcgtaaagc gtgcgtaggt ggttgtttaa gtctgttgtg aaagcccngg gctcaacctg      60
gnaactgcag tggaaactgg acaactagag tgtggtagag ggtagcggaa ttcccggtgt     120
agcagtgaaa tgcgtagaga tcgggaggaa catccatggc gaaggcagct acctggacca    180
acactgacac tgaggcacga aagcgtgggg agcaaacagg attagatacc ctggtagtcc    240
acgcccctnaa cgatgcgaac tggatgttgg gtgcaatttg gcacgcagta tcgaagctaa    300
cgcgttaagt tcgccgcctg gggagtacgg tcgcaagact gaaactcaaa ggaattgacg    360
ggggcccgca caagcggtgg agtatgtggt ttaattcgat gcaacgcgaa gaaccttacc    420
tggccttgac atgtcgagaa ctttccagag atggattggt gccttcggga actcgaacac    480
aggtgctgca tggctgtcgt cagctcgtgt cgtgagatgt tgggttaagt cccgcaacga    540
gcgcaaccct tgtccttagt tgccagcacg taatggtggg aactctaagg agaccgccgg    600
tgacaaaccg gaggaaggtg gggatgacgt caagtcatca tggcccttac ggccagggct    660
acacacgtac tacaatggtg gggacagagg gctgcaagcc ggcgacggta agccaatccc    720
agaaacccca tctcagtccg gattggagtc tgcaactcga ctccatgaag tcggaatcgc    780
tagtaatcgc agatcagcat tgctgcggtg aatacgttcc cggg                     824
```

<210> SEQ ID NO 194
<211> LENGTH: 735
<212> TYPE: DNA
<213> ORGANISM: Stenotrophomonas maltophilia
<220> FEATURE:
<221> NAME/KEY: misc_feature
<222> LOCATION: (1)..(735)
<223> OTHER INFORMATION: BCI 7 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t

<400> SEQUENCE: 194

```
ncctgcttct ggtgcaacaa actcccatnn tgtgacgggc ggtgtgtaca aggcccggga    60
acgtattcac cgcagcaatg ctgatctgcg attactagcg attccgactt catggagtcg   120
agttgcagac tccaatccgg actgagatgg ggtttctggg attggcttac cgtcgccggc   180
ttgcagccct ctgtccccac cattgtagta cgtgtgtagc cctggccgta agggccatga   240
tgacttgacg tcatccccac cttcctccgg tttgtcaccg gcggtctcct tagagttccc   300
accattacgt gctggcaact aaggacaagg gttgcgctcg ttgcgggact taacccaaca   360
tctcacgaca cgagctgacg acagccatgc agcacctgtg ttcgagttcc cgaaggcacc   420
aatccatctc tggaaagttc tcgacatgtc aaggccaggt aaggttcttc gcgttgcatc   480
gaattaaacc acatactcca ccgcttgtgc gggccccgt caattccttt gagtttcagt    540
cttgcgaccg tactcccag gcggcgaact taacgcgtta gcttcgatac tgcgtgccaa    600
attgcacccn acatccagtt cgcatcgttt agggcgtgga ctaccagggt atctaatcct   660
gtttgctccc cacgctttcg tgcctcagtg tcagtgttgg tccangnagc tgccttcgcc   720
ntngatgntc ctccc                                                    735

<210> SEQ ID NO 195
<211> LENGTH: 824
<212> TYPE: DNA
<213> ORGANISM: Arthrobacter mysorens
<220> FEATURE:
<221> NAME/KEY: misc_feature
<222> LOCATION: (1)..(824)
<223> OTHER INFORMATION: BCI 700 16S rDNA
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t

<400> SEQUENCE: 195
ggcgtaaaga gntngtaggc ggtttgtcgc ntctgccgtg aaantccgag gctcaacntn    60
ggatntgcgg tgggtacggg cagactagag tgatgtaggg gagactggaa ttcctggtgt   120
agcggtgaaa tgcgcagata tcaggaggaa caccgatggc gaaggcaggt ctctgggcat   180
ttactgacgc tgaggagcga aagcatgggg agcgaacagg attagatacc ctggtagtcc   240
atgccgtaaa cgttgggcac taggtgtggg ggacattcca cgttttccgc gccgtagcta   300
acgcattaag tgccccgcct ggggagtacg gccgcaaggc taaaactcaa aggaattgac   360
```

```
gggggcccgc acaagcggcg gagcatgcgg attaattcga tgcaacgcga agaaccttac      420
caaggcttga catgtgccag accgctccag agatggggtt tcccttcggg gctggttcac      480
aggtggtgca tggttgtcgt cagctcgtgt cgtgagatgt tgggttaagt cccgcaacga      540
gcgcaaccct cgttccatgt tgccagcacg tagtggtggg gactcatggg agactgccgg      600
ggtcaactcg gaggaaggtg gggatgacgt caaatcatca tgccccttat gtcttgggct      660
tcacgcatgc tacaatggcc ggtacaatgg gttgcgatac tgtgaggtgg agctaatccc      720
taaaagccgg tctcagttcg gattggggtc tgcaactcga ccccatgaag tcggagtcgc      780
tagtaatcgc agatcagcaa cgctgcggtg aatacgttcc cggg                      824
```

<210> SEQ ID NO 196
<211> LENGTH: 720
<212> TYPE: DNA
<213> ORGANISM: Bosea thiooxidans
<220> FEATURE:
<221> NAME/KEY: misc_feature
<222> LOCATION: (1)..(720)
<223> OTHER INFORMATION: BCI 703 16S rDNA

<400> SEQUENCE: 196

```
tgtacaaggc ccgggaacgt attcaccgtg gcatgctgat ccacgattac tagcgattcc       60
accttcatgt actcgagttg cagagtacaa tctgaactga gacggctttt tgggattagc      120
tccaggtcac cccttcgctg cccattgtca ccgccattgt agcacgtgtg tagcccagcc      180
tgtaagggcc atgaggactt gacgtcatcc ccaccttcct cgcggcttat caccggcagt      240 cccccctagag ttcccaactg aatgatgcaa actaggggcg agggttgcgc tcgttgcggg      300
acttaaccca acatctcacg acacgagctg acgacagcca tgcagcacct gtgttccggc      360
cagccgaact gaagaaaggc atctctgccg atcaaaccgg acatgtcaaa agctggtaag      420
gttctgcgcg ttgcttcgaa ttaaaccaca tgctccaccg cttgtgcggg ccccccgtcaa      480 ttccttttgag tttttaatctt gcgaccgtac tccccaggcg gaatgcttaa agcgttagct      540
gcgccactga agagcaagct ccccaacggc tggcattcat cgtttacggc gtggactacc      600
agggtatcta atcctgtttg ctccccacgc tttcgcgcct cagcgtcagt atcggaccag      660
ttggccgcct tcgccaccgg tgttcttgcg aatatctacg aatttcacct ctacactcgc      720
```

<210> SEQ ID NO 197
<211> LENGTH: 650
<212> TYPE: DNA
<213> ORGANISM: Bacillus sp.
<220> FEATURE:
<221> NAME/KEY: misc_feature
<222> LOCATION: (1)..(650)
<223> OTHER INFORMATION: BCI 715 16S rDNA

<400> SEQUENCE: 197

```
gttaccccac cgacttcggg tgttacaaac tctcgtggtg tgacgggcgg tgtgtacaag       60
gcccgggaac gtattcaccg cggcatgctg atccgcgatt actagcgatt ccagcttcat      120
gtaggcgagt tgcagcctac aatccgaact gagaacggtt ttatgagatt agctccacct      180
cgcggtcttg cagctctttg taccgtccat tgtagcacgt gtgtagccca ggtcataagg      240
ggcatgatga tttgacgtca tccccacctt cctccggttt gtcaccggca gtcaccttag      300
agtgcccaac ttaatgatgg caactaagat caagggttgc gctcgttgcg ggacttaacc      360
caacatctca cgacacgagc tgacgacaac catgcaccac ctgtcactct gctcccgaag      420
gagaagccct atctctaggg ttttcagagg atgtcaagac ctggtaaggt tcttcgcgtt      480
```

-continued

```
gcttcgaatt aaaccacatg ctccaccgct tgtgcgggcc cccgtcaatt cctttgagtt    540
tcagccttgc ggccgtactc cccaggcgga gtgcttaatg cgttaacttc agcactaaag    600
ggcggaaacc ctctaacact tagcactcat cgtttacggc gtggactacc              650
```

<210> SEQ ID NO 198
<211> LENGTH: 798
<212> TYPE: DNA
<213> ORGANISM: Pseudomonas putida
<220> FEATURE:
<221> NAME/KEY: misc_feature
<222> LOCATION: (1)..(798)
<223> OTHER INFORMATION: BCI 731 16S rDNA
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t

<400> SEQUENCE: 198

```
tttgttaagt nggatgtgaa agccccnggc tcaaccnngg aactgcatcc aaaactggca     60
agctagagta cggtagaggg tggtggaatt tcctgtgtag cggtgaaatg ngtagatata    120
ggaaggaaca ccagtggcga aggcgaccac ctggactgat actgacactg aggtgcgaaa    180
gcgtggggag caaacaggat tagataccct ggtagtccac gccgtaaacg atgtcaacta    240
gccgttggaa tccttgagat tttagtggcg cagctaacgc attaagttga ccgcctgggg    300
agtacggccg caaggttaaa actcaaatga attgacgggg gcccgcacaa gcggtggagc    360
atgtggttta attcgaagca acgcgaagaa ccttaccagg ccttgacatg cagagaactt    420
tccagagatg gattggtgcc ttcgggaact ctgacacagg tgctgcatgg ctgtcgtcag    480
ctcgtgtcgt gagatgttgg gttaagtccc gtaacgagcg caaccccttgt ccttagttac    540 cagcacgtta tggtgggcac tctaaggaga ctgccggtga caaacggag gaaggtgggg    600 atgacgtcaa gtcatcatgg cccttacggc ctgggctaca cacgtgctac aatggtcggt    660
acagagggtt gccaagccgc gaggtggagc taatctcaca aaaccgatcg tagtccggat    720
cgcagtctgc aactcgactg cgtgaagtcg gaatcgctag taatcgcgaa tcagaatgtc    780
gcggtgaata cgttcccg                                                  798
```

<210> SEQ ID NO 199
<211> LENGTH: 791
<212> TYPE: DNA
<213> ORGANISM: Ramlibacter henchirensis
<220> FEATURE:
<221> NAME/KEY: misc_feature
<222> LOCATION: (1)..(791)
<223> OTHER INFORMATION: BCI 739 16S rDNA
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (12)..(13)

<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (26)..(28)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t

<400> SEQUENCE: 199

```
tttgtaanac anntgtgaan ncccnnnct tnacntggga actgcatttg tgactgcaag      60
gctggagtgc ggcagagggg gatggaattc cgcgtgtagc agtgaaatgc gtagatatgc    120
ggaggaacac cgatggcgaa ggcantcccc tgggcctgca ctgacgctca tgcacgaaag    180
cgtgggagc aaacaggatt agataccctg gtagtccacg ccctaaacga tgtcaactgg    240
ttgttggtcc ttcactggat cagtaacgaa gctaacgcgt gaagttgacc gcctggggag    300
tacggccgca aggttgaaac tcaaaggaat tgacgggac ccgcacaagc ggtggatgat    360
gtggtttaat tcgatgcaac gcgaaaaacc ttacctaccc ttgacatgtc tggaattgcg    420
cagagatgtg caagtgcccg aaagggagcc agaacacagg tgctgcatgg ctgtcgtcag    480
ctcgtgtcgt gagatgttgg gttaagtccc gcaacgagcg caacccttgc cattagttgc    540
tacgaaaggg cactctaatg ggactgccgg tgacaaaccg gaggaaggtg gggatgacgt    600
caagtcctca tggcccttat gggtagggct acacacgtca tacaatggct ggtacagagg    660
gttgccaacc cgcgaggggg agctaatccc ataaaaccag tcgtagtccg gatcgtagtc    720
tgcaactcga ctgcgtgaag tcggaatcgc tagtaatcgc ggatcagcat gtcgcggtga    780
atacgttccc g                                                        791
```

<210> SEQ ID NO 200
<211> LENGTH: 799
<212> TYPE: DNA
<213> ORGANISM: Bosea robiniae
<220> FEATURE:
<221> NAME/KEY: misc_feature
<222> LOCATION: (1)..(799)
<223> OTHER INFORMATION: BCI 765 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t

<400> SEQUENCE: 200

```
actttnaagt nggaggngaa agcccaggnn tcaacccngg aattgcnttc gatactggga    60
gtcttgagtt cggaagaggt nggnggaact gcgagtgtag aggtgaaatt ngtagatatt   120
cgcaagaaca cnggtggnga aggcgnccaa ctggtccgaa actgacgctg aggcgcgaaa   180
gcgtggggag caaacaggat tagataccct ggtagtccac gcngtaaacg atgaatgcca   240
gccgttgggg agcttgctct tcagtggcgc agctaacgct ttaagcattc cgcctgggga   300
gtacggtcgc aagattaaaa ctcaaaggaa ttgacggggg cccgcacaag cggtggagca   360
tgtggtttaa ttcgaagcaa cgcgcagaac cttaccagct tttgacatgt ccggtttgat   420
cggcagagat gcctttcttc agttcggctg gccggaacac aggtgctgca tggctgtcgt   480
cagctcgtgt cgtgagatgt tgggttaagt cccgcaacga gcgcaaccct cgcccctagt   540
tgccatcatt aagttgggaa ctctaggggg actgccggtg ataagccgcg aggaaggtgg   600
ggatgacgtc aagtcctcat ggcccttaca ggctgggcta cacacgtgct acaatggcgg   660
tgacaatggg cagcgaaagg gcgacctcga gctaatccca aaagccgtc tcagttcaga   720
ttgcactctg caactcgagt gcatgaaggt ggaatcgcta gtaatcgtgg atcagcatgc   780
cacggtgaat acgttcccg                                              799
```

<210> SEQ ID NO 201
<211> LENGTH: 796
<212> TYPE: DNA
<213> ORGANISM: Stenotrophomonas maltophilia
<220> FEATURE:
<221> NAME/KEY: misc_feature
<222> LOCATION: (1)..(796)
<223> OTHER INFORMATION: BCI 77 16S rDNA
<220> FEATURE:
<221> NAME/KEY: misc_feature
<222> LOCATION: (2)..(2)
<223> OTHER INFORMATION: n is a, c, g, or t
<220> FEATURE:

```
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (767)..(768)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (782)..(783)
<223> OTHER INFORMATION: n is a, c, g, or t
<220> FEATURE:
<221> NAME/KEY: misc_feature
<222> LOCATION: (785)..(786)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t

<400> SEQUENCE: 201
anctacctgc ttctggtgca acaaactccc atggtgtgac gggcggtgtg tacaaggccc     60
gggaacgtat tcaccgcagc aatgctgatc tgcgattact agcgattccg acttcatgga    120
gtcgagttgc agactccaat ccggactgag atggggtttc tgggattggc ttaccgtcgc    180
cggcttgcag ccctctgtcc ccaccattgt agtacgtgtg tagccctggc cgtaagggcc    240
atgatgactt gacgtcatcc ccaccttcct ccggtttgtc accggcggtc tccttagagt    300
tcccaccatt acgtgctggc aactaaggac aagggttgcg ctcgttgcgg gacttaaccc    360
aacatctcac gacacgagct gacgacagcc atgcagcacc tgtgttcgag ttcccgaagg    420
caccaatcca tctctggaaa gttctcgaca tgtcaaggcc aggtaaggtt cttcgcgttg    480
catcgaatta aaccacatac tccaccgctt gtgcgggccc ccgtcaattc ctttgagttt    540
cagtcttgcg accgtactcc ccaggcggcg aacttaacgc gttagcttcg atactgcgtg    600
ccaaattgca cccaacatcc agttcgcatc gtttagggcg tggantacca gggtatctaa    660
tcctgtttgc tccccacgct ttcgtgcctc agtgtcagtg ttggtccagg tagctgcctt    720
cgccatggan gttcctcccg atctctacnc atttcactgc tncaccnnga antccgctnc    780
cnncnnccac actcna                                                    796

<210> SEQ ID NO 202
<211> LENGTH: 824
<212> TYPE: DNA
<213> ORGANISM: Stenotrophomonas maltophilia
<220> FEATURE:
<221> NAME/KEY: misc_feature
<222> LOCATION: (1)..(824)
<223> OTHER INFORMATION: BCI 787 16S rDNA
```

```
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (130)..(131)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t

<400> SEQUENCE: 202
```

```
gncgtaaagc nngnntangt nntnntttan ntctnttgtg aaagccnngg gctcnacnng    60
ggaantgcag tggaaactgg acaactagag tgtggtagag gntagcggaa ttccnngtgt   120
agcagtgaan ngcgtagaga tcggnaggaa catccatggc gaaggcagct acntggacca  180
acactgacan tgaggcacga aagcgtgggg agcaaacagg attagatacc ntggtagtcc  240
acgccctaaa cgatgcgaac tggatgttgg gtgcaatttg gcacgcagta tcgaagctaa  300
cgcgttaagt tcgccgcctg gggagtacgg tcgcaagact gaaactcaaa ggaattgacg  360
ggggcccgca caagcggtgg agtatgtggt ttaattcgat gcaacgcgaa gaaccttacc  420
tggccttgac atgtcgagaa ctttccagag atggattggt gccttcggga actcgaacac  480
aggtgctgca tggctgtcgt cagctcgtgt cgtgagatgt tgggttaagt cccgcaacga  540
gcgcaaccct tgtccttagt tgccagcacg taatggtggg aactctaagg agaccgccgg  600
tgacaaaccg gaggaaggtg gggatgacgt caagtcatca tggcccttac ggccagggct  660
acacacgtac tacaatggtg gggacagagg gctgcaagcc ggcgacggta agccaatccc  720
agaaacccca tctcagtccg gattggagtc tgcaactcga ctccatgaag tcggaatcgc  780
tagtaatcgc agatcagcat tgctgcggtg aatacgttcc cggg                   824
```

<210> SEQ ID NO 203
<211> LENGTH: 647
<212> TYPE: DNA
<213> ORGANISM: Chitinophaga terrae
<220> FEATURE:
<221> NAME/KEY: misc_feature
<222> LOCATION: (1)..(647)
<223> OTHER INFORMATION: BCI 79 16S rDNA

<400> SEQUENCE: 203

```
gtcccccgg ctttcatggc ttgacgggcg gtgtgtacaa ggtccgggaa cgtattcacc    60
gtatcattgc tgatatacga ttactagcga ttccagcttc atgaggtcga gttgcagacc  120
tcaatccgaa ctgagataga gttttttgaga ttagcagcat gttaccatgt agcagccctt  180
tgtctctacc attgtagcac gtgtgtagcc ctgggcataa aggccatgat gacttgacat  240
catcccctcc ttcctcgcgt cttacgacgg cagtttcact agagttccca ccattacgcg  300
ctggcaacta gtgatagggg ttgcgctcgt tgcgggactt aacccaacac ctcacggcac  360
gagctgacga cagccatgca gcaccttaca atctgtgtat tgctacaaag tgaactttca  420
tccacggtca gactgcattc tagcccaggt aaggttcctc gcgtatcatc gaattaaacc  480
acatgctcca ccgcttgtgc ggaccccgt caattccttt gagtttcaac cttgcggtcg   540
tacttcccag gtgggatact taatgctttc gctcagacac ttacaatata tcgcaaatgt  600
cgagtatcca tcgtttaggg cgtggactac cagggtatct aatcctg                 647
```

<210> SEQ ID NO 204
<211> LENGTH: 590
<212> TYPE: DNA
<213> ORGANISM: Stenotrophomonas maltophilia
<220> FEATURE:
<221> NAME/KEY: misc_feature
<222> LOCATION: (1)..(590)
<223> OTHER INFORMATION: BCI 790 16S rDNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

```
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (33)..(35)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (261)..(262)
<223> OTHER INFORMATION: n is a, c, g, or t

<400> SEQUENCE: 204
```

```
gtngtncacg ccntnannga tgngaanngg atnnngggtg caatttgncn ngcagnatnn     60
aagctaacgc gttaanttcg cngcntgggg agtncggtcg caagantgaa actcaaagga   120
attgacgggg gcccgcacaa gcggtggagt atgtggttta nttngntgca acgcgaagaa   180
ccttacctgg ccttgacatg tcgagaactt tccagagatg gattggtgcc ttcgggaact   240
cgaacacagg tgctgcatgg nntcgtcagc tcgtgtcgtg agatgttggg ttaagtcccg   300
caacgagcgc aacccttgtc cttagttgcc agcacgtaat ggtgggaact ctaaggagac   360
cgccggtgac aaaccggagg aaggtgggga tgacgtcaag tcatcatggc ccttacggcc   420
agggctacac acgtactaca atggtgggga cagagggctg caagccggcg acggtaagcc   480
aatcccagaa accccatctc agtccggatt ggagtctgca actcgactcc atgaagtcgg   540
aatcgctagt aatcgcagat cagcattgct gcggtgaata cgttcccggg              590
```

```
<210> SEQ ID NO 205
<211> LENGTH: 822
<212> TYPE: DNA
<213> ORGANISM: Pseudomonas putida
<220> FEATURE:
<221> NAME/KEY: misc_feature
<222> LOCATION: (1)..(822)
<223> OTHER INFORMATION: BCI 791 16S rDNA
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t

<400> SEQUENCE: 205
```

```
ggcgtaaagc gcgcgtaggt ggtttgttaa gtnggatgtg aaagcccccgg gctcaaccng    60 ggaactgcat ccaaaactgg caagctagag tacggtagag ggtggtggaa tttcctgtgt   120
agcggtgaaa tgcgtagata taggaaggaa caccagtggc gaaggcgacc acctggactg   180
atactgacac tgaggtgcga aagcgtgggg agcaaacagg attagatacc ctggtagtcc   240
acgccgtaaa cgatgtcaac tagccgttgg aatccttgag attttagtgg cgcagctaac   300
gcattaagtt gaccgcctgg ggagtacggc cgcaaggtta aaactcaaat gaattgacgg   360
gggcccgcac aagcggtgga gcatgtggtt taattcgaag caacgcgaag aaccttacca   420
ggccttgaca tgcagagaac tttccagaga tggattggtg ccttcgggaa ctctgacaca   480
ggtgctgcat ggctgtcgtc agctcgtgtc gtgagatgtt gggttaagtc cgtaacgag    540 cgcaacccct tgtccttagtt accagcacgt tatggtgggc actctaagga gactgccggt   600
gacaaaccgg aggaaggtgg ggatgacgtc aagtcatcat ggcccttacg gcctgggcta   660
cacacgtgct acaatggtcg gtacagaggg ttgccaagcc gcgaggtgga gctaatctca   720
caaaaccgat cgtagtccgg atcgcagtct gcaactcgac tgcgtgaagt cggaatcgct   780
agtaatcgcg aatcagaatg tcgcggtgaa tacgttcccg gg                      822
```

```
<210> SEQ ID NO 206
<211> LENGTH: 836
<212> TYPE: DNA
<213> ORGANISM: Stenotrophomonas maltophilia
<220> FEATURE:
<221> NAME/KEY: misc_feature
<222> LOCATION: (1)..(836)
<223> OTHER INFORMATION: BCI 793 16S rDNA
<220> FEATURE:
<221> NAME/KEY: misc_feature
```

<222> LOCATION: (18)..(18)
<223> OTHER INFORMATION: n is a, c, g, or t

<400> SEQUENCE: 206

```
attactgggc gtaaagcntg cgtaggtggt tgtttaagtc tgttgtgaaa gccctgggct    60
caacctggga actgcagtgg aaactggaca actagagtgt ggtagagggt agcggaattc   120
ccggtgtagc agtgaaatgc gtagagatcg ggaggaacat ccatggcgaa ggcagctacc   180
tggaccaaca ctgacactga ggcacgaaag cgtggggagc aaacaggatt agataccctg   240
gtagtccacg ccctaaacga tgcgaactgg atgttgggtg caatttggca cgcagtatcg   300
aagctaacgc gttaagttcg ccgcctgggg agtacggtcg caagactgaa actcaaagga   360
attgacgggg gcccgcacaa gcggtggagt atgtggttta attcgatgca acgcgaagaa   420
ccttacctgg ccttgacatg tcgagaactt tccagagatg gattggtgcc ttcgggaact   480
cgaacacagg tgctgcatgg ctgtcgtcag ctcgtgtcgt gagatgttgg gttaagtccc   540
gcaacgagcg caacccttgt ccttagttgc cagcacgtaa tggtgggaac tctaaggaga   600
ccgccggtga caaaccggag gaaggtgggg atgacgtcaa gtcatcatgg cccttacggc   660
cagggctaca cacgtactac aatggtgggg acagagggct gcaagccggc gacggtaagc   720
caatcccaga accccatct cagtccggat tggagtctgc aactcgactc catgaagtcg   780
gaatcgctag taatcgcaga tcagcattgc tgcggtgaat acgttcccgg gccttg       836
```

<210> SEQ ID NO 207
<211> LENGTH: 836
<212> TYPE: DNA
<213> ORGANISM: Stenotrophomonas maltophilia
<220> FEATURE:
<221> NAME/KEY: misc_feature
<222> LOCATION: (1)..(836)
<223> OTHER INFORMATION: BCI 795 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 207

```
nttactgggc gtaaagcgtg cgtaggtngt ngtttaagtc tgttgtgaaa gccctgggct    60
caacntggga actgcagtgg aaactggaca actagagtgt ggtagagggt agcggaattc   120
ccggtgtagc agtgaantgc gtagagatcg ggaggaacat ccatggcgaa ggcagctacc   180
tggaccaaca ctgacactga ggcacgaaag cgtggggagc aaacaggatt agataccctg   240
gtagtccacg ccctaaacga tgcgaactgg atgttgggtg caatttggca cgcagtatcg   300
aagctaacgc gttaagttcg ccgcctgggg agtacggtcg caagactgaa actcaaagga   360
attgacgggg gcccgcacaa gcggtggagt atgtggttta attcgatgca acgcgaagaa   420
```

```
ccttacctgg ccttgacatg tcgagaactt tccagagatg gattggtgcc ttcgggaact    480
cgaacacagg tgctgcatgg ctgtcgtcag ctcgtgtcgt gagatgttgg gttaagtccc    540
gcaacgagcg caaccccttgt ccttagttgc cagcacgtaa tggtgggaac tctaaggaga    600
ccgccggtga caaaccggag gaaggtgggg atgacgtcaa gtcatcatgg cccttacggc    660
cagggctaca cacgtactac aatggtgggg acagagggct gcaagccggc gacggtaagc    720
caatcccaga acccatct cagtccggat tggagtctgc aactcgactc catgaagtcg    780
gaatcgctag taatcgcaga tcagcattgc tgcggtgaat acgttcccgg gccttg        836
```

```
<210> SEQ ID NO 208
<211> LENGTH: 822
<212> TYPE: DNA
<213> ORGANISM: Pseudomonas putida
<220> FEATURE:
<221> NAME/KEY: misc_feature
<222> LOCATION: (1)..(822)
<223> OTHER INFORMATION: BCI 802 16S rDNA
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 208
```

```
ggcgtaaagc gcgcgtaggt ggtttgttaa gnnngatgtg aaagccccgg gctcaacntg    60
ggaactgcat ccaaaactgg caagctagag tacggtagag ggtggtggaa tttcctgtgt   120
agcggtgaaa tgcgtagata taggaaggaa caccagtggc gaaggcgacc acctggactg   180
atactgacac tgaggtgcga aagcgtgggg agcaaacagg attagatacc ctggtagtcc   240
acgccgtaaa cgatgtcaac tagccgttgg aatccttgag attttagtgg cgcagctaac   300
gcattaagtt gaccgcctgg ggagtacggc cgcaaggtta aaactcaaat gaattgacgg   360
gggcccgcac aagcggtgga gcatgtggtt taattcgaag caacgcgaag aaccttacca   420
ggccttgaca tgcagagaac tttccagaga tggattggtg ccttcgggaa ctctgacaca   480
ggtgctgcat ggctgtcgtc agctcgtgtc gtgagatgtt gggttaagtc ccgtaacgag   540
cgcaaccctt gtccttagtt accagcacgt tatggtgggc actctaagga gactgccggt   600
gacaaaccgg aggaaggtgg ggatgacgtc aagtcatcat ggcccttacg gcctgggcta   660
cacacgtgct acaatggtcg gtacagaggg ttgccaagcc gcgaggtgga gctaatctca   720
caaaaccgat cgtagtccgg atcgcagtct gcaactcgac tgcgtgaagt cggaatcgct   780
agtaatcgcg aatcagaatg tcgcggtgaa tacgttcccg gg                      822
```

```
<210> SEQ ID NO 209
<211> LENGTH: 656
<212> TYPE: DNA
<213> ORGANISM: Pseudomonas jinjuensis
<220> FEATURE:
<221> NAME/KEY: misc_feature
<222> LOCATION: (1)..(656)
<223> OTHER INFORMATION: BCI 804 16S rDNA

<400> SEQUENCE: 209
```

```
ggagcaaccc actcccatgg tgtgacgggc ggtgtgtaca aggcccggga acgtattcac    60
cgtgacattc tgattcacga ttactagcga ttccgacttc acgcagtcga gttgcagact   120
gcgatccgga ctacgatcgg ttttctggga ttagctccac ctcgcggctt ggcaaccctc   180
```

-continued

```
tgtaccgacc attgtagcac gtgtgtagcc ctggccgtaa gggccatgat gacttgacgt    240
catccccacc ttcctccggt ttgtcaccgg cagtctcctt agagtgccca ccttaacgtg    300
ctggtaacta aggacaaggg ttgcgctcgt tacgggactt aacccaacat ctcacgacac    360
gagctgacga cagccatgca gcacctgtgt tccgattccc gaaggcactc ccgcatctct    420
gcaggattcc ggacatgtca aggccaggta aggttcttcg cgttgcttcg aattaaacca    480
catgctccac cgcttgtgcg ggccccgtc aattcatttg agttttaacc ttgcggccgt     540
actccccagg cggtcgactt atcgcgttag ctgcgccact aagatctcaa ggatcccaac    600
ggctagtcga catcgtttac ggcgtggact accagggtat ctaatcctgt ttgctc        656

<210> SEQ ID NO 210
<211> LENGTH: 798
<212> TYPE: DNA
<213> ORGANISM: Pseudomonas putida
<220> FEATURE:
<221> NAME/KEY: misc_feature
<222> LOCATION: (1)..(798)
<223> OTHER INFORMATION: BCI 805 16S rDNA
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (33)..(37)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
```

<400> SEQUENCE: 210

```
tttnttaant nggatgtgaa agccccgggc tcnnnnnggg aacngcatcc aaaacnggcn      60
agctagagta cggtagaggg tggtggaatt cctgngtag cggnnaaatg cgtagatata     120
ggaaggaaca ccagtggcga aggcgaccac cnggactgat actgacactg aggtgcgaaa    180
gcgtgnggag caaacaggat tagataccct ggtagtccac gcngtaaacg atgtcaacta    240
gccgtnggaa tccttgagat tttagtggcg cagctaacgc attaagttga ccgcctgggg    300
agtacggccg caaggttaaa actcaaatga attgacgggg gcccgcacaa gcggtggagc    360
atgtggttta attcgaagca acgcgaagaa ccttaccagg ccttgacatg cagagaactt    420
tccagagatg gattggtgcc ttcgggaact ctgacacagg tgctgcatgg ctgtcgtcag    480
ctcgtgtcgt gagatgttgg gttaagtccc gtaacgagcg caaccttgt ccttagttac     540
cagcacgtta tggtgggcac tctaaggaga ctgccggtga caaaccggag aaggtgggg     600
atgacgtcaa gtcatcatgg cccttacggc ctgggctaca cacgtgctac aatggtcggt    660
acagagggtt gccaagccgc gaggtggagc taatctcaca aaaccgatcg tagtccggat    720
cgcagtctgc aactcgactg cgtgaagtcg gaatcgctag taatcgcgaa tcagaatgtc    780
gcggtgaata cgttcccg                                                  798
```

<210> SEQ ID NO 211
<211> LENGTH: 798
<212> TYPE: DNA
<213> ORGANISM: Pseudomonas putida
<220> FEATURE:
<221> NAME/KEY: misc_feature
<222> LOCATION: (1)..(798)
<223> OTHER INFORMATION: BCI 806 16S rDNA
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 211

```
tttgttaagt nngatgtgaa agccccgggc tcaacctggg aactgcatcc aaaacnggca     60
agctagagta cggtagaggg tggtggaatt cctgtgtag cggtgaaatg cgtagatata    120
ggaaggaaca ccagtggcga aggcgaccac ctggactgat actgacactg aggtgcgaaa   180
gcgtggggag caaacaggat tagataccct ggtagtccac gccgtaaacg atgtcaacta   240
gccgttggaa tccttgagat tttagtggcg cagctaacgc attaagttga ccgcctgggg   300
agtacggccg caaggttaaa actcaaatga attgacgggg gcccgcacaa gcggtggagc   360
atgtggttta attcgaagca acgcgaagaa ccttaccagg ccttgacatg cagagaactt   420
tccagagatg gattggtgcc ttcgggaact ctgacacagg tgctgcatgg ctgtcgtcag   480
ctcgtgtcgt gagatgttgg gttaagtccc gtaacgagcg caaccttgt ccttagttac    540
cagcacgtta tggtgggcac tctaaggaga ctgccggtga caaaccggag aaggtgggg    600
atgacgtcaa gtcatcatgg cccttacggc ctgggctaca cacgtgctac aatggtcggt   660
acagagggtt gccaagccgc gaggtggagc taatctcaca aaaccgatcg tagtccggat   720
cgcagtctgc aactcgactg cgtgaagtcg gaatcgctag taatcgcgaa tcagaatgtc   780
gcggtgaata cgttcccg                                                 798
```

```
<210> SEQ ID NO 212
<211> LENGTH: 524
<212> TYPE: DNA
<213> ORGANISM: Stenotrophomonas maltophilia
<220> FEATURE:
<221> NAME/KEY: misc_feature
<222> LOCATION: (1)..(524)
<223> OTHER INFORMATION: BCI 808 16S rDNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (27)..(29)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (58)..(61)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t

<400> SEQUENCE: 212
aacgcnttaa nttngcngcn nngggannnc ggtngcangn ntgaaantca aggaatnnn      60 nggggggcccg cacnagcggt ggagtatgtg gtttaattcg atgcaacgcg aagaacctta  120
cctggccttg acatgtcgag aactttccan agatggattg gtgccttcgg gaactcgaac  180
acaggtgctg catggcngtn gtcagctcgt gtcgtgagat gttgggttaa gtcccgcaac  240
```

-continued

| | |
|---|---|
| gagcgcaacc cttgtcctta gttgccagca cgtaatggtg ggaactctaa ggagaccgcc | 300 |
| ggtgacaaac cggaggaagg tggggatgac gtcaagtcat catggccctt acggccaggg | 360 |
| ctacacacgt actacaatgg tggggacaga gggctgcaag ccggcgacgg taagccaatc | 420 |
| ccagaaaccc catctcagtc cggattggag tctgcaactc gactccatga agtcggaatc | 480 |
| gctagtaatc gcagatcagc attgctgcgg tgaatacgtt cccg | 524 |

```
<210> SEQ ID NO 213
<211> LENGTH: 798
<212> TYPE: DNA
<213> ORGANISM: Pseudomonas putida
<220> FEATURE:
<221> NAME/KEY: misc_feature
<222> LOCATION: (1)..(798)
<223> OTHER INFORMATION: BCI 809 16S rDNA
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
```

<400> SEQUENCE: 213

| | |
|---|---|
| tttgttaagt nggatgtgaa agccccgggc tcaacntggg aactgcatcc aaaacnggca | 60 |
| agctagagta cggtagaggg tggtggaatt tcctgtgtag cggtgaaatg cgtagatata | 120 |
| ggaaggaaca ccagtggcga aggcgaccac ctggactgat actgacactg aggtgcgaaa | 180 |
| gcgtggggag caaacaggat tagataccct ggtagtccac gccgtaaacg atgtcaacta | 240 |
| gccgttggaa tccttgagat tttagtggcg cagctaacgc attaagttga ccgcctgggg | 300 |
| agtacggccg caaggttaaa actcaaatga attgacgggg gcccgcacaa gcggtggagc | 360 |
| atgtggttta attcgaagca acgcgaagaa ccttaccagg ccttgacatg cagagaactt | 420 |
| tccagagatg gattggtgcc ttcgggaact ctgacacagg tgctgcatgg ctgtcgtcag | 480 |
| ctcgtgtcgt gagatgttgg gttaagtccc gtaacgagcg caaccccttgt ccttagttac | 540 |
| cagcacgtta tggtgggcac tctaaggaga ctgccggtga caaaccggag gaaggtgggg | 600 |
| atgacgtcaa gtcatcatgg cccttacggc ctgggctaca cacgtgctac aatggtcggt | 660 |
| acagagggtt gccaagccgc gaggtggagc taatctcaca aaaccgatcg tagtccggat | 720 |
| cgcagtctgc aactcgactg cgtgaagtcg gaatcgctag taatcgcgaa tcagaatgtc | 780 |
| gcggtgaata cgttcccg | 798 |

```
<210> SEQ ID NO 214
<211> LENGTH: 644
<212> TYPE: DNA
<213> ORGANISM: Exiguobacterium sp.
<220> FEATURE:
<221> NAME/KEY: misc_feature
<222> LOCATION: (1)..(644)
<223> OTHER INFORMATION: BCI 81 16S rDNA
```

<400> SEQUENCE: 214

| | |
|---|---|
| ccgacttcgg gtgttgcaaa ctctcgtggt gtgacgggcg gtgtgtacaa gacccgggaa | 60 |
| cgtattcacc gcagtatgct gacctgcgat tactagcgat tccgacttca tgcaggcgag | 120 |
| ttgcagcctg caatccgaac tgagaacggc tttctgggat tggctccacc tcgcggcttc | 180 |

```
gctgcccttt gtaccgtcca ttgtagcacg tgtgtagccc aactcataag gggcatgatg    240
atttgacgtc atccccacct tcctccggtt tgtcaccggc agtctcccta gagtgcccaa    300
ccaaatgctg gcaactaagg acaagggttg cgctcgttgc gggacttaac ccaacatctc    360
acgacacgag ctgacgacaa ccatgcacca cctgtcaccc ctgcccccga aggggaaggt    420
acatctctgt accggtcagg ggatgtcaa gagttggtaa ggttcttcgc gttgcttcga     480
attaaaccac atgctccacc gcttgtgcgg gtccccgtca attcctttga gtttcagcct    540
tgcgaccgta ctccccaggc ggagtgctta atgcgttagc ttcagcactg aagggcggaa    600
accctccaac acctagcact catcgtttac ggcgtggact acca                    644

<210> SEQ ID NO 215
<211> LENGTH: 766
<212> TYPE: DNA
<213> ORGANISM: Novosphingobium sediminicola
<220> FEATURE:
<221> NAME/KEY: misc_feature
<222> LOCATION: (1)..(766)
<223> OTHER INFORMATION: BCI 82 16S rDNA

<400> SEQUENCE: 215
cgccttcgag tgaatccaac tcccatggtg tgacgggcgg tgtgtacaag gcctgggaac     60
gtattcaccg cggcatgctg atccgcgatt actagcgatt ccgccttcat gctctcgagt    120
tgcagagaac aatccgaact gagacggctt ttggagatta gctacccctc gcgaggtcgc    180
tgcccactgt caccgccatt gtagcacgtg tgtagcccag cgtgtaaggg ccatgaggac    240
ttgacgtcat ccccaccttc ctccggctta tcaccggcgg tttccttaga gtgcccaact    300
taatgatggc aactaaggac gagggttgcg ctcgttgcgg gacttaaccc aacatctcac    360
gacacgagct gacgacagcc atgcagcacc tgtcaccgat ccagccaaac tgaaggaaaa    420
catctctgta atccgcgatc gggatgtcaa acgctggtaa ggttctgcgc gttgcttcga    480
attaaaccac atgctccacc gcttgtgcag gccccgtca attcctttga gttttaatct     540
tgcgaccgta ctccccaggc ggataactta atgcgttagc tgcgccaccc aaattccatg    600
aacccggaca gctagttatc atcgtttacg gcgtggacta ccagggtatc taatcctgtt    660
tgctccccac gctttcgcac ctcagcgtca atacctgtcc agtgagccgc cttcgccact    720
ggtgttcttc cgaatatcta cgaatttcac ctctacactc ggaatt                   766

<210> SEQ ID NO 216
<211> LENGTH: 761
<212> TYPE: DNA
<213> ORGANISM: Exiguobacterium acetylicum
<220> FEATURE:
<221> NAME/KEY: misc_feature
<222> LOCATION: (1)..(761)
<223> OTHER INFORMATION: BCI 83 16S rDNA

<400> SEQUENCE: 216
ccggcttcgg gtgttgcaaa ctctcgtggt gtgacgggcg gtgtgtacaa gacccgggaa     60
cgtattcacc gcagtatgct gacctgcgat tactagcgat tccgacttca tgcaggcgag    120
ttgcagcctg caatccgaac tgggaacggc tttatggat tggctccacc tcgcggtctc     180
gctgcccttt gtaccgtcca ttgtagcacg tgtgtagccc aactcataag gggcatgatg    240
atttgacgtc atccccacct tcctccggtt tgtcaccggc agtctcccta gagtgcccaa    300
ctcaatgctg gcaactaagg ataggggttg cgctcgttgc gggacttaac ccaacatctc    360
```

```
acgacacgag ctgacgacaa ccatgcacca cctgtcacca ttgtccccga agggaaaact    420
tgatctctca agcggtcaat gggatgtcaa gagttggtaa ggttcttcgc gttgcttcga    480
attaaaccac atgctccacc gcttgtgcgg gtccccgtca attcctttga gtttcagcct    540
tgcggccgta ctccccaggc ggagtgctta atgcgttagc ttcagcactg aggggcggaa    600
accccccaac acctagcact catcgtttac ggcgtggact accagggtat ctaatcctgt    660
ttgctcccca cgctttcgcg cctcagcgtc agttacagac caaagagtcg ccttcgccac    720
tggtgttcct ccacatctct acgcatttca ccgctacacg t                       761

<210> SEQ ID NO 217
<211> LENGTH: 760
<212> TYPE: DNA
<213> ORGANISM: Herbaspirillum huttinese
<220> FEATURE:
<221> NAME/KEY: misc_feature
<222> LOCATION: (1)..(760)
<223> OTHER INFORMATION: BCI 9 16S rDNA
<220> FEATURE:
<221> NAME/KEY: misc_feature
<222> LOCATION: (671)..(671)
<223> OTHER INFORMATION: n is a, c, g, or t

<400> SEQUENCE: 217
acttctggta aaacccgctc ccatggtgtg acgggcggtg tgtacaagac ccgggaacgt    60
attcaccgcg acatgctgat ccgcgattac tagcgattcc aacttcatgg agtcgagttg    120
cagactccaa tccggactac gatacacttt ctgggattag ctcccctcg cgggttggcg    180 gccctctgta tgtaccattg tatgacgtgt gaagccctac ccataagggc catgaggact    240
tgacgtcatc cccaccttcc tccggtttgt caccggcagt ctcattagag tgcccttttcg   300 tagcaactaa tgcaagggt tgcgctcgtt gcgggactta acccaacatc tcacgacacg    360
agctgacgac agccatgcag cacctgtgtg atggttctct ttcgagcact cccaaatctc    420
ttcgggattc catccatgtc aagggtaggt aaggttttc gcgttgcatc gaattaatcc    480
acatcatcca ccgcttgtgc gggtccccgt caattccttt gagttttaat cttgcgaccg    540
tactccccag gcggtctact tcacgcgtta gctgcgttac caagtcaatt aagacccgac    600
aactagtaga catcgtttag ggcgtggact accagggtat ctaatcctgt ttgctcccca    660
cgctttcgtg natgagcgtc agtgttatcc caggggggctg ccttcgccat cggtattcct    720
ccacatatct acgcatttca ctgctacacg tggaattcta                         760

<210> SEQ ID NO 218
<211> LENGTH: 829
<212> TYPE: DNA
<213> ORGANISM: Stenotrophomonas maltophilia
<220> FEATURE:
<221> NAME/KEY: misc_feature
<222> LOCATION: (1)..(829)
<223> OTHER INFORMATION: BCI 903 16S rDNA
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
```

```
<222> LOCATION: (51)..(51)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t

<400> SEQUENCE: 218
attactnggc gtaaagcntg cgtaggtggt tatttaantc cgttgtgaaa nccnnggget       60 caacctggna actgcagtgg atacnggatg actagaatgt ggtagagggt agcggaattc      120
ntggtgtagc agtgaantgc gtagagatca ggaggaacat ccatggcgaa ggcagctacc      180
tggaccaaca ttgacactga ggcacgaaag cgtggggagc aaacaggatt agataccctg      240
gtagtccacg ccctaaacga tgcgaactgg atgttgggtg caatttggca cgcagtatcg      300
aagctaacgc gttaagttcg ccgcctgggg agtacggtcg caagactgaa actcaaagga      360
attgacgggg gcccgcacaa gcggtggagt atgtggttta attcgatgca acgcgaagaa      420
ccttacctgg ccttgacatg tcgagaactt tccagagatg gattggtgcc ttcgggaact      480
cgaacacagg tgctgcatgg cngtcgtcag ctcgtgtcgt gagatgttgg gttaagtccc      540
gcaacgagcg caacccttgt ccttagttgc cagcacgtaa tggtgggaac tctaaggaga      600
ccgccggtga caaaccggag gaaggtgggg atgacgtcaa gtcatcatgg cccttacggc      660
cagggctaca cacgtactac aatggtaggg acagagggct gcaagccggc gacggtaagc      720
caatcccaga aaccctatct cagtccggat tggagtctgc aactcgactc catgaagtcg      780
gaatcgctag taatcgcaga tcagcattgc tgcggtgaat acgttcccg                  829

<210> SEQ ID NO 219
<211> LENGTH: 628
<212> TYPE: DNA
<213> ORGANISM: Stenotrophomonas maltophilia
<220> FEATURE:
<221> NAME/KEY: misc_feature
<222> LOCATION: (1)..(628)
<223> OTHER INFORMATION: BCI 908 16S rDNA

<400> SEQUENCE: 219
tacctgcttc tggtgcaaca aactcccatg gtgtgacggg cggtgtgtac aaggcccggg       60
aacgtattca ccgcagcaat gctgatctgc gattactagc gattccgact tcatggagtc      120
gagttgcaga ctccaatccg gactgagata gggtttctgg gattggctta ccgtcgccgg      180
cttgcagccc tctgtcccta ccattgtagt acgtgtgtag ccctggccgt aagggccatg      240
atgacttgac gtcatcccca ccttcctccg gtttgtcacc ggcggtctcc ttagagttcc      300
```

-continued

| | |
|---|---|
| caccattacg tgctggcaac taaggacaag ggttgcgctc gttgcgggac ttaacccaac | 360 |
| atctcacgac acgagctgac gacagccatg cagcacctgt gttcgagttc ccgaaggcac | 420 |
| caatccatct ctggaaagtt ctcgacatgt caaggccagg taaggttctt cgcgttgcat | 480 |
| cgaattaaac cacatactcc accgcttgtg cgggcccccg tcaattcctt tgagtttcag | 540 |
| tcttgcgacc gtactcccca ggcggcgaac ttaacgcgtt agcttcgata ctgcgtgcca | 600 |
| aattgcaccc aacatccagt tcgcatcg | 628 |

<210> SEQ ID NO 220
<211> LENGTH: 744
<212> TYPE: DNA
<213> ORGANISM: Pedobacter terrae
<220> FEATURE:
<221> NAME/KEY: misc_feature
<222> LOCATION: (1)..(744)
<223> OTHER INFORMATION: BCI 91 16S rDNA

<400> SEQUENCE: 220

| | |
|---|---|
| accccccagct tccatggctt gacgggcggt gtgtacaagg cccgggaacg tattcaccgc | 60 |
| gtcattgctg atacgcgatt actagcgaat ccaacttcat ggggtcgagt tgcagacccc | 120 |
| aatccgaact gtgaacggct ttgtgagatt cgcatcatat tgctatgtag ctgccctctg | 180 |
| taccgtccat tgtagcacgt gtgtagcccc ggacgtaagg gccatgatga cttgacgtcg | 240 |
| tcccctcctt cctctctgtt tgcacaggca gtctgtttag agtccccacc attacatgct | 300 |
| ggcaactaaa catagggggtt gcgctcgttg cgggacttaa cccaacacct cacggcacga | 360 |
| gctgacgaca gccatgcagc acctagtttc gtgtccttgc ggactgatcc atctctggat | 420 |
| cattcactaa ctttcaagcc cgggtaaggt tcctcgcgta tcatcgaatt aaaccacatg | 480 |
| ctcctccgct tgtgcgggcc ccgtcaatt cctttgagtt tcacccttgc gggcgtactc | 540 |
| cccaggtgga acacttaacg ctttcgctta gccgctgact gtgtatcgcc aacagcgagt | 600 |
| gttcatcgtt tagggcgtgg actaccaggg tatctaatcc tgtttgatcc ccacgctttc | 660 |
| gtgcctcagc gtcaataaga ccatagtaag ctgccttcgc aatcggtgtt ctgagacata | 720 |
| tctatgcatt tcaccgctac ttgt | 744 |

<210> SEQ ID NO 221
<211> LENGTH: 783
<212> TYPE: DNA
<213> ORGANISM: Sphingopyxis alaskensis
<220> FEATURE:
<221> NAME/KEY: misc_feature
<222> LOCATION: (1)..(783)
<223> OTHER INFORMATION: BCI 914 16S rDNA
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t

<400> SEQUENCE: 221

```
gaaanccngg ggctcaaccc cngnaattgc ctttgaaacn ggaaaantng antctnggag      60
aggtcagngg aattccgagt gtagaggtga aattngtaga tattcggaag aacaccagng    120
gngaaggcga ctgactngac aagtatngac gctgaggtgc gaaagcgtgg ggagcaaaca    180
ggattagata ccctggtagt ccacgccgta acgatgata  actagctgtc cgggttcatg    240
gaacttgggt ggcgcagcta acgcattaag ttatccgcct ggggagtacg gtcgcaagat    300
taaaactcaa aggaattgac gggggcctgc acaagcggtg gagcatgtgg tttaattcga    360
agcaacgcgc agaaccttac cagcgtttga catcctgatc gcggattaga gagatctttt    420
ccttcagttc ggctggatca gtgacaggtg ctgcatggct gtcgtcagct cgtgtcgtga    480
gatgttgggt taagtcccgc aacgagcgca accctcatcc ctagttgcca tcattcagtt    540
gggcactcta aggaaactgc cggtgataag ccggaggaag gtggggatga cgtcaagtcc    600
tcatggccct tacgcgctgg gctacacacg tgctacaatg gcaactacag tgggcagcaa    660
cctcgcgagg ggtagctaat ctccaaaagt tgtctcagtt cggattgttc tctgcaactc    720
gagagcatga aggcggaatc gctagtaatc gcggatcagc atgccgcggt gaatacgttc    780
cca                                                                  783
```

<210> SEQ ID NO 222
<211> LENGTH: 764
<212> TYPE: DNA
<213> ORGANISM: Dyadobacter soli
<220> FEATURE:
<221> NAME/KEY: misc_feature
<222> LOCATION: (1)..(764)

<223> OTHER INFORMATION: BCI 96 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (747)..(748)
<223> OTHER INFORMATION: n is a, c, g, or t
<220> FEATURE:
<221> NAME/KEY: misc_feature
<222> LOCATION: (751)..(753)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t

<400> SEQUENCE: 222

```
nggtctcccc gactcccatg gcttgacggg cggtgtgtac aaggtccggg aacgtattca      60
ccgcgtcata gctgatacgc gattactagc gattccagct tcatagagtc gagttgcaga     120
ctccaatccg aactgagaat ggcttttttgg gattggcatc acctcgcagt gtagctaccc    180
tctgtaccat ccattgtagc acgtgtgttg ccctggacgt aagggccatg atgacttgac     240
gtcgtcccct ccttcctctc tgtttgcaca ggcagtctgg ctagagtccc caccattacg    300
tgctggcaac taaccatagg ggttgcgctc gttgcgggac ttaacccaac atctcacgac    360
acgagctgac gacagccatg cagcaccttc aaacaggcca ttgctggctt acacatttct    420
gcataattcc tgtctgattt agcccaggta aggttcctcg cgtatcatcg aattaaacca    480
catgctccac cgcttgtgcg gaccccgtc aattcctttg agtttcaccg ttgccggcgt     540
actccccagg tggaggactt aacggtttcc ctaagtcgct cagctctgca gccaaacaac    600
gagtcctcat cgtttacagc atggactacc agggtatcta atcctgtttg ctccccatgc    660
tttcgtgcct cagtgtcaaa caaatcgtag ccacctgcct tcgcaatcgg ngttctggan   720
gatatctatg catttcancg ctncncnntc nnntccggcn gcct                     764
```

<210> SEQ ID NO 223
<211> LENGTH: 506
<212> TYPE: DNA
<213> ORGANISM: Massilia kyonggiensis
<220> FEATURE:
<221> NAME/KEY: misc_feature
<222> LOCATION: (1)..(506)
<223> OTHER INFORMATION: BCI 97 16S rDNA

<400> SEQUENCE: 223

```
aagacccggg aacgtattca ccgcgacatg ctgatccgcg attactagcg attccaactt     60
```

```
cacgcagtcg agttgcagac tgcgatccgg actacgatac actttctggg attagctccc    120
cctcgcgggt tggcggccct ctgtatgtac cattgtatga cgtgtgaagc cctacccata    180
agggccatga ggacttgacg tcatccccac cttcctccgg tttgtcaccg gcagtctcat    240
tagagtgccc tttcgtagca actaatgaca agggttgcgc tcgttgcggg acttaaccca    300
acatctcacg acacgagctg acgacagcca tgcagcacct gtgttcaggc tccctttcgg    360
gcactcccag atctctccag gattcctgac atgtcaaggg taggtaaggt ttttcgcgtt    420
gcatcgaatt aatccacatc atccaccgct tgtgcgggtc cccgtcaatt cctttgagtt    480
ttaatcttgc gaccgtactc cccagg                                         506
```

<210> SEQ ID NO 224
<211> LENGTH: 808
<212> TYPE: DNA
<213> ORGANISM: Stenotrophomonas maltophilia
<220> FEATURE:
<221> NAME/KEY: misc_feature
<222> LOCATION: (1)..(808)
<223> OTHER INFORMATION: BCI 970 16S rDNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (62)..(65)
<223> OTHER INFORMATION: n is a, c, g, or t
<220> FEATURE:

```
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (99)..(100)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (217)..(219)
<223> OTHER INFORMATION: n is a, c, g, or t

<400> SEQUENCE: 224
ntnggtggtt attnanntcn gttgtnanag ccctngnctc nacctnggaa ntgcagtgga      60
tnnnnganga ntngaatgtg ntngagggta gcggaattnn tggtgtagca ntgaaatgng    120
tagagatcag naggaacatc catggngaag gcagctacct ggaccaacat tgacanngag    180
gcacgaaagc gtggggagca aacaggatta gataccnnng tagtccacgc cctaaacgat    240
gcgaactgga tgttgggtgc aatttggcac gcagtatcga agctaacgcg ttaagttcgc    300
cgcctgggga gtacggtcgc aagactgaaa ctcaaaggaa ttgacggggg cccgcacaag    360
cggtggagta tgtggtttaa ttcgatgcaa cgcgaagaac cttacctggc cttgacatgt    420
cgagaacttt ccagagatgg attggtgcct tcgggaactc gaacacaggt gctgcatggc    480
tgtcgtcagc tcgtgtcgtg agatgttggg ttaagtcccg caacgagcgc aacccttgtc    540
cttagttgcc agcacgtaat ggtgggaact ctaaggagac cgccggtgac aaaccggagg    600
aaggtgggga tgacgtcaag tcatcatggc ccttacggcc agggctacac acgtactaca    660
atggtaggga cagagggctg caagccggcg acggtaagcc aatcccagaa accctatctc    720
agtccggatt ggagtctgca actcgactcc atgaagtcgg aatcgctagt aatcgcagat    780
cagcattgct gcggtgaata cgttcccg                                       808
```

-continued

```
<210> SEQ ID NO 225
<211> LENGTH: 787
<212> TYPE: DNA
<213> ORGANISM: Bacillus subtilis
<220> FEATURE:
<221> NAME/KEY: misc_feature
<222> LOCATION: (1)..(787)
<223> OTHER INFORMATION: BCI 989 16S rDNA
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t

<400> SEQUENCE: 225
tgatgtgaaa gcccccggct caaccgggga gggtcattgg aaactgggnn acttgagtgc      60
agaagaggag agtgganntn cnacgtgtag cggtgaaatg cgtagagatg nggaggaaca     120
ccagtggcga aggcgactct ctggtctgta actgacgctg aggagcgaaa gcgtggggag     180
cgaacaggat tagataccct ggtagtccac gccgtaaacg atgagtgcta agtgttaggg     240
ggtttccgcc ccttagtgct gcagctaacg cattaagcac tccgcctggg gagtacggtc     300
gcaagactga aactcaaagg aattgacggg ggcccgcaca gcggtggag catgtggttt     360 aattcgaagc aacgcgaaga accttaccag gtcttgacat cctctgacaa tcctagagat     420
aggacgtccc cttcgggggc agagtgacag gtggtgcatg gttgtcgtca gctcgtgtcg     480
tgagatgttg ggttaagtcc cgcaacgagc gcaacccttg atcttagttg ccagcattca     540
gttgggcact ctaaggtgac tgccggtgac aaaccggagg aaggtgggga tgacgtcaaa     600
tcatcatgcc ccttatgacc tgggctacac acgtgctaca atggacagaa caaagggcag     660
cgaaaccgcg aggttaagcc aatcccacaa atctgttctc agttcggatc gcagtctgca     720
actcgactgc gtgaagctgg aatcgctagt aatcgcggat cagcatgccg cggtgaatac     780
gttcccg                                                               787

<210> SEQ ID NO 226
<211> LENGTH: 327
<212> TYPE: DNA
<213> ORGANISM: Stenotrophomonas maltophilia
<220> FEATURE:
<221> NAME/KEY: misc_feature
<222> LOCATION: (1)..(327)
<223> OTHER INFORMATION: BCI 996 16S rDNA
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (37)..(37)
```

```
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t

<400> SEQUENCE: 226
nngtcagctc gtgtcntgag atgttgggtt aagtccngca acgagcgcaa cccttgtcct      60
tagttgccan cangtaatgg tgggaantnt aaggagaccg ccggtgacaa accggaggaa     120
ggtggggatg acgtcaagtc atcatggccc ttacggccag ggctacacac gtactacaat    180
ggtagggaca gagggctgca agccggcgac ggtaagccaa tcccagaaac cctatctcag    240
tccggattgg agtctgcaac tcgactccat gaagtcggaa tcgctagtaa tcgcagatca    300
gcattgctgc ggtgaatacg ttcccgg                                         327

<210> SEQ ID NO 227
<211> LENGTH: 719
<212> TYPE: DNA
<213> ORGANISM: Stenotrophomonas maltophilia
<220> FEATURE:
<221> NAME/KEY: misc_feature
<222> LOCATION: (1)..(719)
<223> OTHER INFORMATION: BCI 997 16S rDNA
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (23)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
```

```
<222> LOCATION: (73)..(73)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (98)..(100)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (154)..(156)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (162)..(164)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
```

<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t

<400> SEQUENCE: 227

```
gaatttcnng gngtagcagt gannnnngna gagatcagnn ggaacatncc ntggcgaagg    60
cagctncnng gancancatn gacantnngg cangaaannn tgggagcaa acaggattag    120
atacccctggt agtncacgcc ctaancgatg cgannnngnat gnnnggtgca atnnggcacg  180
cagtatcgaa gctaacgngt taagttcgcn ncntggggag tacggtcgnc aagantgana   240
ntcaaaggaa ttgacggggg cccgcacaag cggtggagta tgtggtttaa ttcgatgcaa   300
cgcgaagaac cttacntggc cttgacatgt cgagaacttt ccagagatgg attggtgcct   360
tngggaactc gaacacaggt gctgcatggc tgtcgtcagc tcgtgtcgtg agatgttggg   420
ttaagtcccg caacgagcgc aaccttgtc cttagttgcc agcacgtaat ggtgggaact    480
ctaaggagac cgccggtgac aaaccggagg aaggtgggga tgacgtcaag tcatcatggc   540
ccttacggcc agggctacac acgtactaca atggtaggga cagagggctg caagccggcg   600
acggtaagcc aatcccagaa accctatctc agtccggatt ggagtctgca actcgactcc   660
atgaagtcgg aatcgctagt aatcgcagat cagcattgct gcggtgaata cgttcccgg   719
```

<210> SEQ ID NO 228
<211> LENGTH: 500
<212> TYPE: DNA
<213> ORGANISM: Stenotrophomonas rhizophila
<220> FEATURE:
<221> NAME/KEY: misc_feature
<222> LOCATION: (1)..(500)
<223> OTHER INFORMATION: BDNZ 45125 16S rDNA

<400> SEQUENCE: 228

```
cggcagcaca gtaagagctt gctcttatgg gtggcgagtg gaggacgggt gaggaataca    60
tcggaatcta ccttttcgtg ggggattacg tagggaaact tacgctaata ccgcatacga   120
ccttcgggtg aaagcagggg accttcgggc cttgcctctt gtgaaaagag ccgatgtcgg   180
attagctagt tggcggggta aaggcccacc aaggcgacga tccgtagctg gtctgagagg   240
atgatcagcc acactggaac tgagacacgg tccagactcc tacgggaggc agcagtgggg   300
aatattggac aatgggcgca agcctgatcc agccataccg cgtgggtgaa gaaggccttc   360
gggttgtaaa gccctttttgt tgggaaagaa aagcagtcga ttaatactcg gttgttctga   420
cggtacccaa agaataagca ccggctaact tcgtgccagc agccgcggta atacgaaggg   480
tgcaagcgtt actcggaatt                                             500
```

<210> SEQ ID NO 229
<211> LENGTH: 500
<212> TYPE: DNA
<213> ORGANISM: Stenotrophomonas rhizophila
<220> FEATURE:
<221> NAME/KEY: misc_feature
<222> LOCATION: (1)..(500)
<223> OTHER INFORMATION: BDNZ 46012 16S rDNA

<400> SEQUENCE: 229

```
cacagtaaga gcttgctctt atgggtggcg agtggggacg ggtgaggaat acatcggaat      60 ctacctttc gtgggggata acgtaggaa acttacgcta ataccgcata cgaccttcgg      120
gtgaaagcag gggaccttcg ggccttgcgc cctattcaag agccgatgtc ggattagcta     180
gttggcgggg taaaggccca ccaaggcgac gatccgtagc tggtctgaga ggatgatcag     240
ccacactgga actgagacac ggtccagact cctacgggag gcagcagtgg ggaatattgg     300
acaatgggcg caagcctgat ccagccatac cgcgtgggtg aagaaggcct tcggttgta     360 aagcccttt gttgggaaag aaaagcagtc gattaatact cggttgttct gacggtaccc      420
aaagaataag caccggctaa cttcgtgcca gcagccgcgg taatacgaag ggtgcaagcg     480
ttactcggaa ttactgggcg                                                 500

<210> SEQ ID NO 230
<211> LENGTH: 876
<212> TYPE: DNA
<213> ORGANISM: Stenotrophomonas rhizophila
<220> FEATURE:
<221> NAME/KEY: misc_feature
<222> LOCATION: (1)..(876)
<223> OTHER INFORMATION: BDNZ 46120 16S rDNA

<400> SEQUENCE: 230
ctcggtgata gtgggtcata gctaaatgca gtcgacggag cacagtacga gcttgctctt      60
atgggtggcg agtgttggat gggtgaggaa tacatcggaa tctacctttt cgtgggggat    120
aacgtaggga aacttacgct aataccgcat acgaccttcg ggtgaaagca ggggaccttc    180
gggccttgcg cggtttaaag agacgatgtc ggattagcta gttggcgggg taaaggccca    240
ccaaggcgac gatccgtagc tggtctgaga ggatgatcag ccacactgga actgagacac    300
ggtccagact cctacgggag gcagcagtgg ggaatattgg acaatgggcg caagcctgat    360
ccagccatac cgcgtgggtg aagaaggcct tcggttgta aagcccttt gttgggaaag     420 aaaagcagtc gattaatact cggttgttct gacggtaccc aaagaataag caccggctaa    480
cttcgtgcca gcagccgcgg taatacgaag ggtgcaagcg ttactcggaa ttactgggcg    540
taaagcgtgc gtaggtggtt gtttaagtct gttgtgaaag ccctgggctc aacctggaa    600 ttgcagtgga tactgggcga ctagagtgtg gtagagggta gtggaattcc cggtgtagca    660
gtgaaatgcg tagagatcgg gaggaacatc catggcgaaa gcagctacct ggaccaacac    720
tgacactgag gcacgaaagc gtggggagca acaggatta gatacctgg tagtccacgc    780 cctaaacgat gcgaactgga tgttgggtgc aatttggcac gcagtatcga agctaacgcg    840
ttaagttccg ccgcctgggg agtacgtccc aaaact                               876

<210> SEQ ID NO 231
<211> LENGTH: 500
<212> TYPE: DNA
<213> ORGANISM: Stenotrophomonas rhizophila
<220> FEATURE:
<221> NAME/KEY: misc_feature
<222> LOCATION: (1)..(500)
<223> OTHER INFORMATION: BDNZ 46856 16S rDNA

<400> SEQUENCE: 231
ccatgcagtc gaacggcagc acaggagagc ttgctctctg ggtggcgagt ggcggacggg      60
tgaggaatac atcggaatct accttttcgt gggggataac gtaggaaac ttacgctaat     120 accgcatacg accttcgggt gaaagcaggg gaccttcggg ccttgcgcgg atagatgagc    180
```

-continued

| | |
|---|---|
| cgatgtcgga ttagctagtt ggcggggtaa aggcccacca aggcgacgat ccgtagctgg | 240 |
| tctgagagga tgatcagcca cactggaact gagacacggt ccagactcct acgggaggca | 300 |
| gcagtgggga atattggaca atgggcgcaa gcctgatcca gccataccgc gtgggtgaag | 360 |
| aaggccttcg ggttgtaaag ccctttttgtt gggaaagaaa agcagccgat taatactcgg | 420 |
| ttgttctgac ggtacccaaa gaataagcac cggctaactt cgtgccagca gccgcggtaa | 480 |
| tacgaagggt gcaagcgtta | 500 |

<210> SEQ ID NO 232
<211> LENGTH: 500
<212> TYPE: DNA
<213> ORGANISM: Stenotrophomonas chelatiphaga
<220> FEATURE:
<221> NAME/KEY: misc_feature
<222> LOCATION: (1)..(500)
<223> OTHER INFORMATION: BDNZ 47207 16S rDNA

<400> SEQUENCE: 232

| | |
|---|---|
| tgcagtcgaa cggcagcaca gtaagagctt gctcttatgg gtggcgagtg gcggacgggt | 60 |
| gaggaataca tcggaatcta cttttttcgtg ggggataacg tagggaaact tacgctaata | 120 |
| ccgcatacga ccttcgggtg aaagcagggg accttcgggc cttgcgcgat tgaatgagcc | 180 |
| gatgtcggat tagctagttg gcggggtaaa ggcccaccaa ggcgacgatc cgtagctggt | 240 |
| ctgagaggat gatcagccac actggaactg agacacggtc cagactccta cgggaggcag | 300 |
| cagtggggaa tattggacaa tgggcgcaag cctgatccag ccataccgcg tgggtgaaga | 360 |
| aggccttcgg gttgtaaagc ccttttgttg ggaaagaaaa gcagcgggct aataccttgc | 420 |
| tgttctgacg gtacccaaag aataagcacc ggctaacttc gtgccagcag ccgcggtaat | 480 |
| acgaagggtg caagcgttac | 500 |

<210> SEQ ID NO 233
<211> LENGTH: 500
<212> TYPE: DNA
<213> ORGANISM: Stenotrophomonas rhizophila
<220> FEATURE:
<221> NAME/KEY: misc_feature
<222> LOCATION: (1)..(500)
<223> OTHER INFORMATION: BDNZ 48183 16S rDNA

<400> SEQUENCE: 233

| | |
|---|---|
| gcagtcgacg gcagcacagt aagagcttgc tcttatgggt ggcgagtggc ggacgggtga | 60 |
| ggaatacatc ggaatctacc ttttcgtggg ggataacgta gggaaactta cgctaatacc | 120 |
| gcatacgacc ttcgggtgaa agcaggggac cttcgggcct tgcgcggata gatgagccga | 180 |
| tgtcggatta gctagttggc ggggtaaagg cccaccaagg cgacgatccg tagctggtct | 240 |
| gagaggatga tcagccacac tggaactgag acacggtcca gactcctacg ggaggcagca | 300 |
| gtggggaata ttggacaatg ggcgcaagcc tgatccagcc ataccgcgtg gtgaagaag | 360 |
| gccttcgggt tgtaaagccc ttttgtttggg aaagaaaagc agtcgattaa tactcggttg | 420 |
| ttctgacggt acccaaagaa taagcaccgg ctaacttcgt gccagcagcc gcggtaatac | 480 |
| gaagggtgca agcgttactc | 500 |

<210> SEQ ID NO 234
<211> LENGTH: 500
<212> TYPE: DNA
<213> ORGANISM: Herbaspirillum frisingense
<220> FEATURE:
<221> NAME/KEY: misc_feature

```
<222> LOCATION: (1)..(500)
<223> OTHER INFORMATION: BDNZ 50525 16S rDNA

<400> SEQUENCE: 234
gcagtcgacg gcagcatagg agcttgctcc tgatggcgag tggcgaacgg gtgagtaata      60
tatcggaacg tgccctagag tgggggataa ctagtcgaaa gattagctaa taccgcatac     120
gatctaagga tgaaagtggg ggatcgcaag acctcatgct cctggagcgg ccgatatctg     180
attagctagt tggtgaggta aaagctcacc aaggcgacga tcagtagctg gtctgagagg     240
acgaccagcc acactgggac tgagacacgg cccagactcc tacgggaggc agcagtgggg     300
aattttggac aatgggggca accctgatcc agcaatgccg cgtgagtgaa gaaggccttc     360
gggttgtaaa gctcttttgt cagggaagaa acggttctgg ataataccta gagctaatga     420
cggtacctga agaataagca ccggctaact acgtgccagc agccgcggta atacgtaggg     480
tgcaagcgtt aatcggaatt                                                 500

<210> SEQ ID NO 235
<211> LENGTH: 1046
<212> TYPE: DNA
<213> ORGANISM: Luteibacter yeojuensis
<220> FEATURE:
<221> NAME/KEY: misc_feature
<222> LOCATION: (1)..(1046)
<223> OTHER INFORMATION: BDNZ 57549 16S rDNA

<400> SEQUENCE: 235
cccttgcggt tagactaacg gcttctggag cagctcactc ccatggtgtg acgggcggtg      60
tgtacaaggc ccgggaacgt attcaccgca gcatagctga tctgcgatta ctagcgattc     120
cgacttcatg gagtcgagtt gcagactcca atccggactg ggatcggctt tctgggatta     180
gctccacctc gcggtcttgc aaccctctgt accgaccatt gtagtacgtg tgtagccctg     240
gccgtaaggg ccatgatgac ttgacgtcat ccccaccttc ctccggtttg tcaccggcag     300
tctccttaga gttcccgact ttactcgctg gcaactaagg acaagggttg cgctcgttgc     360
gggacttaac ccaacatctc acgacacgag ctgacgacag ccatgcagca cctgtgttcc     420
gattcccgaa ggcactcccg catctctgca ggattccgga catgtcaagg ccaggtaagg     480
ttcttcgcgt tgcatcgaat taaaccacat actccaccgc ttgtgcgggc ccccgtcaat     540
tcctttgagt ttcagtcttg cgaccgtact ccccaggcgg cgaacttaac gcgttagctt     600
cgacactgat ctccgagttg agaccaacat ccagttcgca tcgtttaggg cgtggactac     660
cagggtatct aatcctgttt gctccccacg ctttcgtgcc tcagcgtcag tgttgatcca     720
gatggccgcc ttcgccactg atgttcctcc cgatctctac gcatttcacc gctacaccgg     780
gaattccacc atcctctatc acactctagc tcgccagtat ccactgccat tcccaggttg     840
agcccggggc tttcacagca gacttaacga accgcctacg cacgctttac gcccagtaat     900
tccgattaac gcttgcaccc tccgtattac cgcggctgct ggcacggagt tagccggtgc     960
ttattcctca ggtaccgtca gactgcatgg gtattagccc tgcagatttc gctcctgata    1020
aaagtgcttt acaacccgaa ggcctt                                         1046

<210> SEQ ID NO 236
<211> LENGTH: 500
<212> TYPE: DNA
<213> ORGANISM: Stenotrophomonas rhizophila
<220> FEATURE:
<221> NAME/KEY: misc_feature
<222> LOCATION: (1)..(500)
```

<223> OTHER INFORMATION: BDNZ 50839 16S rDNA

<400> SEQUENCE: 236

```
gcagtcgacg gcagcacagt aagagcttgc tcttatgggt ggcgagtggc ggacgggtga      60
ggaatacatc ggaatctacc ttttcgtggg ggataacgta gggaaactta cgctaatacc     120
gcatacgacc ttcgggtgaa agcaggggac cttcgggcct gcgcggata datgagccga     180
tgtcggatta gctagttggc ggggtaaagg cccaccaagg cgacgatccg tagctggtct     240
gagaggatga tcagccacac tggaactgag acacggtcca gactcctacg ggaggcagca     300
gtggggaata ttggacaatg ggcgcaagcc tgatccagcc ataccgcgtg ggtgaagaag     360
gccttcgggt tgtaaagccc ttttgttggg aaagaaaagc agtcgattaa tactcggttg     420
ttctgacggt acccaaagaa taagcaccgg ctaacttcgt gccagcagcc gcggtaatac     480
gaagggtgca agcgttactc                                                 500
```

<210> SEQ ID NO 237
<211> LENGTH: 650
<212> TYPE: DNA
<213> ORGANISM: Stenotrophomonas rhizophila
<220> FEATURE:
<221> NAME/KEY: misc_feature
<222> LOCATION: (1)..(650)
<223> OTHER INFORMATION: BDNZ 51718 16S rDNA

<400> SEQUENCE: 237

```
acggcagcac agtaagagct tgctcttatg ggtggcgagt ggcggacggg tgaggaatac      60
atcggaatct acctttttcgt gggggataac gtagggaaac ttacgctaat accgcatacg    120
accttcgggt gaaagcaggg gaccttcggg ccttgcgcgg atagatgagc cgatgtcgga    180
ttagctagtt ggcggggtaa aggcccacca aggcgacgat ccgtagctgg tctgagagga    240
tgatcagcca cactggaact gagacacggt ccagactcct acgggaggca gcagtgggga    300
atattggaca atgggcgcaa gcctgatcca gccataccgc gtgggtgaag aaggccttcg    360
ggttgtaaag cccttttgtt gggaaagaaa agcagtcgat taatactcgg ttgttctgac    420
ggtacccaaa gaataagcac cggctaactt cgtgccagca gccgcggtaa tacgaagggt    480
gcaagcgtta ctcggaatta ctgggcgtaa agcgtgcgta ggtggttgtt taagtctgtt    540
gtgaaagccc tgggctcaac ctgggaattg cagtggatac tgggcgacta gagtgtggta    600
gagggtagtg gaattcccgg tgtagcagtg aaatgcgtag agatcgggag                650
```

<210> SEQ ID NO 238
<211> LENGTH: 499
<212> TYPE: DNA
<213> ORGANISM: Frateuria sp.
<220> FEATURE:
<221> NAME/KEY: misc_feature
<222> LOCATION: (1)..(499)
<223> OTHER INFORMATION: BDNZ 52707 16S rDNA

<400> SEQUENCE: 238

```
acggcagcac agcagagctt gctctgtggg tggcgagtgg cggacgggtg agtaatgcat      60
cgggacctac ctagacgtgg gggataacgt agggaaactt acgctaatac cgcacacatc    120
ctacgggaga aagcagggga ccttcgggcc ttgcgcggtt agacggaccg atgttcgatt    180
agcttgttgg tgaggtaatg gctcaccaag cgacgatcg atagctggtc tgagaggatg    240
atcagccaca ctggaactga gacacggtcc agactcctac gggaggcagc agtgggaat    300
attggacaat gggcgcaagc ctgatccagc aatgccgcgt gtgtgaagaa ggccttcggg    360
```

```
ttgtaaagca cttttatcag gagcgaaata ctaccggcta atatccggtg gggctgacgg    420
tacctgagga ataagcaccg gctaacttcg tgccagcagc cgcggtaata cgaagggtgc    480
aagcgttaat cggaattac                                                 499
```

```
<210> SEQ ID NO 239
<211> LENGTH: 1237
<212> TYPE: DNA
<213> ORGANISM: Janthinobacterium sp.
<220> FEATURE:
<221> NAME/KEY: misc_feature
<222> LOCATION: (1)..(1237)
<223> OTHER INFORMATION: BDNZ 54456 16S rDNA

<400> SEQUENCE: 239
```

```
tcagattgaa cgctggcggc atgctttaca catgcaagtc gaacggcagc gcggggcaac     60
ctggcggcga gtggcgaacg ggtgagtaat acatcggaac gtacccagaa gtggggggata   120 acgtagcgaa agttacgcta ataccgcata cgttctacgg aagaaagtgg gggaccttcg   180
ggcctcatgc ttttggagcg gccgatgtct gattagctag ttggtgaggt aaaggctcac   240
caaggcgacg atcagtagct ggtctgagag gacgaccagc cacactggga ctgagacacg   300
gcccagactc ctacgggagg cagcagtggg gaattttgga caatgggcgc aagcctgatc   360
cagcaatgcc gcgtgagtga agaaggcctt cgggttgtaa agctcttttg tcagggaaga   420
aacggctgag gataataccct tcggctaatg acggtacctg aagaataagc accggctaac   480
tacgtgccag cagccgcggt aatacgtagg gtgcaagcgt taatcggaat tactgggcgt   540
aaagcgtgcg caggcggttt tgtaagtctg acgtgaaatc cccgggctca acctgggaat   600
tgcgttggag actgcaaggc tggagtctgg cagaggggggt agaattcca cgtgtagcag   660 tgaaatgcgt agagatgtgg aggaacaccg atggcgaagg cagccccctg ggtcaagact   720
gacgctcatg cacgaaagcg tggggagcaa acaggattag ataccctggt agtccacgcc   780
ctaaacgatg tctactagtt gtcgggtctt aattgacttg gtaacgcagc taacgcgtga   840
agtagaccgc ctggggagta cggtcgcaag attaaaactc aaaggaattg acggggaccc   900
gcacaagcgg tggatgatgt ggattaattc gatgcaacgc gaaaaacctt acctacccctt   960 gacatgtcag gaatcctgga gagatctagg agtgcccgaa agggagcctg aacacaggtg  1020
ctgcatggct gtcgtcagct cgtgtcgtga gatgttgggt taagtcccgc aacgagcgca  1080
acccttgtca ttagttgcta cgaaagggca ctctaatgag actgccggtg acaaaccgga  1140
ggaaggtggg gatgacgtca gtcctcatg gcccttatgg gtagggcttc acacgtcata  1200
caatggtaca tacagagggc cgccaacccg cgagggg                            1237
```

```
<210> SEQ ID NO 240
<211> LENGTH: 1346
<212> TYPE: DNA
<213> ORGANISM: Bosea thiooxidans
<220> FEATURE:
<221> NAME/KEY: misc_feature
<222> LOCATION: (1)..(1346)
<223> OTHER INFORMATION: BDNZ 54522 16S rDNA

<400> SEQUENCE: 240
```

```
gtcgaacggg cacttcggtg ctagtggcag acgggtgagt aacgcgtggg aacgtgcctt     60
tcggttcgga ataatccagg gaaacttgga ctaataccgg atacgccctt cgggggaaag   120
atttatcgcc gaaagatcgg cccgcgtctg attagctagt tggtgaggta aaggctcacc   180
```

| | |
|---|---|
| aaggcgacga tcagtagctg gtctgagagg atgatcagcc acattgggac tgagacacgg | 240 |
| cccaaactcc tacgggaggc agcagtgggg aatattggac aatgggcgaa agcctgatcc | 300 |
| agccatgccg cgtgagtgat gaaggcctta gggttgtaaa gctcttttgt ccgggaagat | 360 |
| aatgactgta ccggaagaat aagccccggc taacttcgtg ccagcagccg cggtaatacg | 420 |
| aaggggcta gcgttgctcg gaatcactgg gcgtaaaggg cgcgtaggcg gacttttaag | 480 |
| tcggaggtga agcccaggg ctcaaccctg gaattgcctt cgatactggg agtcttgagt | 540 |
| tcggaagagg ttggtggaac tgcgagtgta gaggtgaaat tcgtagatat tcgcaagaac | 600 |
| accggtggcg aaggcggcca actggtccga aactgacgct gaggcgcgaa agcgtgggga | 660 |
| gcaaacagga ttagataccc tggtagtcca cgccgtaaac gatgaatgcc agccgttggg | 720 |
| gagcttgctc ttcagtggcg cagctaacgc tttaagcatt ccgcctgggg agtacggtcg | 780 |
| caagattaaa actcaaagga attgacgggg cccgcacaa gcggtggagc atgtggttta | 840 |
| attcgaagca acgcgcagaa ccttaccagc ttttgacatg tccggtttga tcggcagaga | 900 |
| tgcctttctt cagttcggct ggccggaaca caggtgctgc atggctgtcg tcagctcgtg | 960 |
| tcgtgagatg tttgggttaag tcccgcaacg agcgcaaccc tcgcccctag ttgccatcat | 1020 |
| tcagttggga actctagggg gactgccggt gataagccgc gaggaaggtg gggatgacgt | 1080 |
| caagtcctca tggcccttac aggctgggct acacacgtgc tacaatggcg gtgacaatgg | 1140 |
| gcagcgaaag ggcgacctcg agctaatccc aaaaagccgt ctcagttcag attgtactct | 1200 |
| gcaactcgag tacatgaagg tggaatcgct agtaatcgtg gatcagcatg ccacggtgaa | 1260 |
| tacgttcccg ggccttgtac acaccgcccg tcacaccatg ggagttgggt ttacccgaag | 1320 |
| gcgtcgcgct aaccgcaagg aggcag | 1346 |

<210> SEQ ID NO 241
<211> LENGTH: 1012
<212> TYPE: DNA
<213> ORGANISM: Stenotrophomonas rhizophila
<220> FEATURE:
<221> NAME/KEY: misc_feature
<222> LOCATION: (1)..(1012)
<223> OTHER INFORMATION: BDNZ 54841 16S rDNA

<400> SEQUENCE: 241

| | |
|---|---|
| tactccggtt acgggcggca cgtgcagcgc ctccgaggtt agctacctgc ttctggtgca | 60 |
| acaaactccc atggtgtgac gggcggtgtg tacaaggccc gggaacgtat tcaccgcagc | 120 |
| aatgctgatc tgcgattact agcgattccg acttcatgga gtcgagttgc agactccaat | 180 |
| ccggactgag atagggtttc tgggattggc ttgccctcgc gggtttgcag ccctctgtcc | 240 |
| ctaccattgt agtacgtgtg tagccctggt cgtaagggcc atgatgactt gacgtcatcc | 300 |
| ccaccttcct ccggtttgtc accggcggtc tccttagagt tcccaccatt acgtgctggc | 360 |
| aactaaggac aagggttgcg ctcgttgcgg gacttaaccc aacatctcac gacacgagct | 420 |
| gacgacagcc atgcagcacc tgtgttcgag ttcccgaagg caccaatcca tctctggaaa | 480 |
| gttctcgaca tgtcaagacc aggtaaggtt cttcgcgttg catcgaatta aaccacatac | 540 |
| tccaccgctt gtgcgggccc ccgtcaattc ctttgagttt cagtcttgcg accgtactcc | 600 |
| ccaggcggcg aacttaacgc gttagcttcg atactgcgtg ccaaattgca cccaacatcc | 660 |
| agttcgcatc gtttagggcg tgcactacca cggtatctaa tcctgtttgc tccccacgct | 720 |
| ttcgtgcctc agtgtcagtg ttggtccagg tagctgcctt cgccatggat gttcctcccg | 780 |
| atctctacgc attcactgct acaccgggaa ttccactacc ctctaccaca ctctagtcgc | 840 |

```
cagtatccac tgcattccca ggttgagcca gggcttcaca cagacttaaa caaccaccta      900
cgcagcttac gccagtatcc gagtaacgct gcacccttcg tattaccggc gctgctgcac      960
gagttagcgg gcttatctta gatacggtcc gaacaacccg gatataagtt ca            1012
```

<210> SEQ ID NO 242
<211> LENGTH: 1016
<212> TYPE: DNA
<213> ORGANISM: Stenotrophomonas rhizophila
<220> FEATURE:
<221> NAME/KEY: misc_feature
<222> LOCATION: (1)..(1016)
<223> OTHER INFORMATION: BDNZ 54850 16S rDNA

<400> SEQUENCE: 242

```
ttgtttgggg ttcggggatg gacgtgcagc gcctccgaag gttagctacc tgcttctggt       60
gcaacaaact cccatggtgt gacgggcggt gtgtacaagg cccgggaacg tattcaccgc      120
agcaatgctg atctgcgatt actagcgatt ccgacttcat ggagtcgagt tgcagactcc      180
aatccggact gagatagggt ttctgggatt ggcttgccct cgcgggtttg cagccctctg      240
tccctaccat tgtagtacgt gtgtagccct ggtcgtaagg gccatgatga cttgacgtca      300
tccccacctt cctccggttt gtcaccggcg gtctccttag agttcccacc attacgtgct      360
ggcaactaag gacaagggtt gcgctcgttg cgggacttaa cccaacatct cacgacacga      420
gctgacgaca gccatgcagc acctgtgttc gagttcccga aggcaccaat ccatctctgg      480
aaagttctcg acatgtcaag accaggtaag gttcttcgcg ttgcatcgaa ttaaaccaca      540
tactccaccg cttgtgcggg ccccgtcaa ttcctttgag tttcagtctt gcgaccgtac       600
tccccaggcg gcgaacttaa cgcgttagct tcgatactgc gtgccaaatt gcacccaaca      660
tccagttcgc atcgtttagg gcgtgactac caggtatcta atcctgtttg ctccccacgc      720
tttcgtgcct cagtgtcagt gttggtccag gtagctgcct tcgccatgat gttcctcccg      780
atctctacgc atttcactgc tacaccggga attccactac cctctaccac aactctagtc      840
gccagtatca ctgcaattcc aaggttgagc cagggctttc acacagactt aacaccacct      900
acgccacgct tacgccaagt aatcgagtac ctgcacgtcg tataccgcg cctgctgcac       960 gagtagccgg agcttattct ttggtaccgt ccgaacaacc cgagatatta tatctc         1016
```

<210> SEQ ID NO 243
<211> LENGTH: 1019
<212> TYPE: DNA
<213> ORGANISM: Stenotrophomonas chelatiphaga
<220> FEATURE:
<221> NAME/KEY: misc_feature
<222> LOCATION: (1)..(1019)
<223> OTHER INFORMATION: BDNZ 54952 16S rDNA

<400> SEQUENCE: 243

```
tccctttgca agcaggcacg tacagcgcct ccgaggttaa gctacctgct tctggtgcaa       60
caaactccca tggtgtgacg ggcggtgtgt acaaggcccg gaacgtatt caccgcagca      120 atgctgatct gcgattacta gcgattccga cttcatggag tcgagttgca gactccaatc      180
cggactgaga tagggtttct gggattggct taccgtcgcc ggcttgcagc cctctgtccc      240
taccattgta gtacgtgtgt agccctggcc gtaagggcca tgatgacttg acgtcatccc      300
caccttcctc cggtttgtca ccggcggtct ccttagagtt cccaccatta cgtgctggca      360
actaaggaca agggttgcgc tcgttgcggg acttaaccca acatctcacg acacgagctg      420
```

| | |
|---|---|
| acgacagcca tgcagcacct gtgttcgagt tcccgaaggc accaatccat ctctggaaag | 480 |
| ttctcgacat gtcaaggcca ggtaaggttc ttcgcgttgc atcgaattaa accacatact | 540 |
| ccaccgcttg tgcgggcccc cgtcaattcc tttgagtttc agtcttgcga ccgtactccc | 600 |
| caggcggcga acttaacgcg ttagcttcga tactgcgtgc caaagtgcac caacatcca | 660 |
| gttcgcatcg tttagggcgt ggactaccag ggtatctaat cctgtttgct ccccacgctt | 720 |
| tcgtgcctca gtgtcagtgt tggtccaggt agctgcctcc gccatggatg ttcctcccga | 780 |
| tctctacgca tttcactgct acacgggaat tccgctaccc tctacacact tctagtcgtc | 840 |
| cagtttccac tgcagttcca aggttgagcc cagggctttt acaaacagac ttaaacgacc | 900 |
| acctacgcac gcttttacgc tcagttattt cgagatacgc ttgcacccct tcgattaccg | 960 |
| cggctgctgt ccgaagatta gcgggtgcta atctttgcta cccgttctaa cagcaggat | 1019 |

<210> SEQ ID NO 244
<211> LENGTH: 985
<212> TYPE: DNA
<213> ORGANISM: Stenotrophomonas rhizophila
<220> FEATURE:
<221> NAME/KEY: misc_feature
<222> LOCATION: (1)..(985)
<223> OTHER INFORMATION: BDNZ 54999 16S rDNA

<400> SEQUENCE: 244

| | |
|---|---|
| tagcgcgagg aggggcgca cgtacagcgc ctccgaggtt aagctacctg cttctggtgc | 60 |
| aacaaactcc catggtgtga cgggcggtgt gtacaaggcc cgggaacgta ttcaccgcag | 120 |
| caatgctgat ctgcgattac tagcgattcc gacttcatgg agtcgagttg cagactccaa | 180 |
| tccggactga gatagggttt ctgggattgg cttgccctcg cgggtttgca gccctctgtc | 240 |
| cctaccattg tagtacgtgt gtagccctgg tcgtaagggc catgatgact tgacgtcatc | 300 |
| cccaccttcc tccggtttgt caccggcggt ctccttagag ttcccaccat tacgtgctgg | 360 |
| caactaagga caagggttgc gctcgttgcg ggacttaacc caacatctca cgacacgagc | 420 |
| tgacgacagc catgcagcac ctgtgttcga gttcccgaag gcaccaatcc atctctggaa | 480 |
| agttctcgac atgtcaagac caggtaaggt tcttcgcgtt gcatcgaatt aaaccacata | 540 |
| ctccaccgct tgtgcgggcc ccgtcaatt cctttgagtt tcagtcttgc gaccgtactc | 600 |
| cccaggcggc gaacttaacg cgttagcttc gatactgcgt gccaaattgc acccaacatc | 660 |
| cagttcgcat cgtttagggc gtgcactacc agggtatcta atcctgtttg ctccccacgc | 720 |
| tttcgtgcct cagtgtcagt gttggtccag gtagctgcct cgccatgga tgttcctccc | 780 |
| gatctctacg catttcactg ctacaccggg gaattccact accctctacc acactctagt | 840 |
| cgcccagtat ccactgcaat tcccaggtga gccaggcttt ccacacagac taaacaacca | 900 |
| cctaccgcac gcttacgccc agtattcgag taacgctgca cccatcgatt accgcgctgc | 960 |
| tgcacgaagt tagccggtgc taatc | 985 |

<210> SEQ ID NO 245
<211> LENGTH: 1400
<212> TYPE: DNA
<213> ORGANISM: Stenotrophomonas rhizophilia
<220> FEATURE:
<221> NAME/KEY: misc_feature
<222> LOCATION: (1)..(1400)
<223> OTHER INFORMATION: BDNZ 56181 16S rDNA

<400> SEQUENCE: 245

| | |
|---|---|
| gcagtcgacg gcagcacagt aagagcttgc tcttatgggt ggcgagtggc ggacgggtga | 60 |

```
ggaatacatc ggaatctacc ttttcgtggg ggataacgta gggaaactta cgctaatacc      120
gcatacgacc ttcgggtgaa agcagggggac cttcgggcct tgcgcggata gatgagccga     180
tgtcggatta gctagttggc ggggtaaagg cccaccaagg cgacgatccg tagctggtct      240
gagaggatga tcagccacac tggaactgag acacggtcca gactcctacg ggaggcagca     300
gtggggaata ttggacaatg ggcgcaagcc tgatccagcc ataccgcgtg ggtgaagaag      360
gccttcgggt tgtaaagccc ttttgttggg aaagaaaagc agtcgattaa tactcggttg     420
ttctgacggt acccaaagaa taagcaccgg ctaacttcgt gccagcagcc gcggtaatac     480
gaagggtgca agcgttactc ggaattactg ggcgtaaagc gtgcgtaggt ggttgtttaa     540
gtctgttgtg aaagccctgg gctcaacctg gaattgcag tggatactgg gcgactagag       600
tgtggtagag ggtagtggaa ttccgggtgt agcagtgaaa tgcgtagaga tcggaggaa       660 catccatggc gaaggcagct acctggacca acactgacac tgaggcacga aagcgtgggg     720
agcaaacagg attagatacc tggtagtcca cgccctaaac gatgcgaact ggatgttggg     780
tgcaatttgg cacgcagtat cgaagctaac gcgttaagtt cgccgcctgg ggagtacggt     840
cgcaagactg aaactcaaag gaattgacgg gggcccgcac aagcggtgga gtatgtggtt     900
taattcgatg caacgcgaag aaccttacct ggtcttgaca tgtcgagaac tttccagaga     960
tggattggtg ccttcgggaa ctcgaacaca ggtgctgcat ggctgtcgtc agctcgtgtc     1020
gtgagatgtt gggttaagtc cgcaacgag cgcaaccctt gtccttagtt gccagcacgt     1080
aatggtggga actctaagga gaccgccggt gacaaaccgg aggaaggtgg ggatgacgtc     1140
aagtcatcat ggcccttacg accagggcta cacacgtact acaatggtag ggacagaggg     1200
ctgcaaaccc gcgagggcaa gccaatccca gaaaccytat ctcagtccgg attggagtct     1260
gcaactcgac tccatgaagt cggaatcgct agtaatcgca gatcagcatt gctgcggtga     1320
atacgttccc gggccttgta cacaccgccc gtcacaccat gggagtttgt tgcaccagaa     1380
gcaggtagct taacctcgga                                                  1400
```

<210> SEQ ID NO 246
<211> LENGTH: 985
<212> TYPE: DNA
<213> ORGANISM: Chitinophaga arvensicola
<220> FEATURE:
<221> NAME/KEY: misc_feature
<222> LOCATION: (1)..(985)
<223> OTHER INFORMATION: BDNZ 56343 16S rDNA

<400> SEQUENCE: 246

```
gcggttcctt gcggttgccg acttcaggtc cccccggctt tcatggcttg acgggcggtg      60
tgtacaaggt ccgggaacgt attcaccgta tcattgctga tatacgatta ctagcgattc     120
cagcttcatg aggtcgagtt gcagacctca atccgaactg agatgggatt tttgagatta    180
gcagcctgtt accagggagc agcccttttgt tcccaccatt gtagcacgtg tgtagccctg    240
ggcataaagg ccatgatgac ttgacatcat cccctccttc ctcgcgtctt acgacggcag    300
tttcactaga gttcccacct tgacgtgctg gcaactagtg ataggggttg cgtcgttgc     360 gggacttaac ccaacaccct acggcacgag ctgacgacag ccatgcagca ccttacaatc    420
tgtgtattgc tacaaagaca cctttcagca tcggtcagac tgcattctag cccaggtaag    480
gttcctcgcg tatcatcgaa ttaaaccaca tgctccaccg cttgtgcgga cccccgtcaa    540
ttcctttgag tttcaacctt gcggtcgtac ttcccaggtg gattacttaa tgctttcgct    600
```

```
cagacacaca ctgtgtatcg cgtatgtcga gtaatcatcg tttagggcgt ggactaccag    660
ggtatctaat cctgtttgat ccccacgctt cgtgcctca gcgtcaatat ttgtgtagcc    720
agctgccttc gcaattggtg ttctatgtca tatctatgca tttcaccgct acatgacata    780
ttccgctaac ctccacaaca ttcaagacat atagtatcca tggcagtttc cgagttaagc    840
tcggagattt caccacggac ttacacgtcc gcctacgcac cctttaaacc cagtgaatcc    900
ggataacgct tgcaccctcc gtattaccgc ggctgctggc acggagttag ccggtgctta    960
ttcacctggt accgtcaagc tcctt                                         985
```

<210> SEQ ID NO 247
<211> LENGTH: 1044
<212> TYPE: DNA
<213> ORGANISM: Stenotrophomonas chelatiphaga
<220> FEATURE:
<221> NAME/KEY: misc_feature
<222> LOCATION: (1)..(1044)
<223> OTHER INFORMATION: BDNZ 58264 16S rDNA

<400> SEQUENCE: 247

```
gccctcccga aggttaagct acctgcttct ggtgcaacaa actcccatgg tgtgacgggc    60
ggtgtgtaca aggcccggga acgtattcac cgcagcaatg ctgatctgcg attactagcg    120
attccgactt catggagtcg agttgcagac tccaatccgg actgagatag ggtttctggg    180
attggcttac cgtcgccggc ttgcagccct ctgtccctac cattgtagta cgtgtgtagc    240
cctggccgta agggccatga tgacttgacg tcatccccac cttcctccgg tttgtcaccg    300
gcggtctcct tagagttccc accattacgt gctggcaact aaggacaagg gttgcgctcg    360
ttgcgggact aacccaaca tctcacgaca cgagctgacg acagccatgc agcacctgtg    420
ttcgagttcc cgaaggcacc aatccatctc tggaaagttc tcgacatgtc aaggccaggt    480
aaggttcttc gcgttgcatc gaattaaacc acatactcca ccgcttgtgc gggccccgt    540 caattccttt gagtttcagt cttgcgaccg tactccccag gcggcgaact taacgcgtta    600
gcttcgatac tgcgtgccaa attgcaccca acatccagtt cgcatcgttt agggcgtgga    660
ctaccagggt atctaatcct gtttgctccc cacgctttcg tgcctcagtg tcagtgttgg    720
tccaggtagc tgccttcgcc atggatgttc ctcccgatct ctacgcattt cactgctaca    780 ccggaattc cgctaccctc taccacactc tagtcatcca gtttccactg cagttcccag    840
gttgagccca gggctttcac aacagactta acaaccacc tacgcacgct ttacgcccag    900
taattccgag taacgcttgc acccttcgta ttaccgcggc tgctggcacg aagttagccg    960
gtgcttattc tttgggtacc gtcagaacag ctgggtatta gcccgctgct tttcttccc    1020 aacaaagggg ctttacaacc cgaa                                         1044
```

<210> SEQ ID NO 248
<211> LENGTH: 853
<212> TYPE: DNA
<213> ORGANISM: Duganella violaceinigra
<220> FEATURE:
<221> NAME/KEY: misc_feature
<222> LOCATION: (1)..(853)
<223> OTHER INFORMATION: BDNZ 58291 16S rDNA

<400> SEQUENCE: 248

```
agcgccctcc ttgcggttaa gctacctact tctggtaaaa cccgctccca tggtgtgacg    60
ggcggtgtgt acaagacccg ggaacgtatt caccgcgaca tgctgatccg cgattactag    120
cgattccaac ttcatgtagt cgagttgcag actacaatcc ggactacgat acactttctg    180
```

```
ggattagctc ccctcgcgg gttggcggcc ctctgtatgt accattgtat gacgtgtgaa      240
gccctaccca taagggccat gaggacttga cgtcatcccc accttcctcc ggtttgtcac      300
cggcagtctc attagagtgc tcttgcgtag caactaatga caagggttgc gctcgttgcg      360
ggacttaacc caacatctca cgacacgagc tgacgacagc catgcagcac ctgtgtgatg      420
gttctctttc gagcactccc aaatctctcc gggattccat ccatgtcaag ggtaggtaag      480
gtttttcgcg ttgcatcgaa ttaatccaca tcatccaccg cttgtgcggg tccccgtcaa      540
ttcctttgag ttttaatctt gcgaccgtac tccccaggcg gtctacttca cgcgttagct      600
gcgttactaa gtcaattaag acccaacaac tagtagacat cgtttagggc gtggactacc      660
agggtatcta atcctgtttg ctccccacgc tttcgtgcat gagcgtcagt tttgacccag      720
ggggctgcct tcgccatcgg tgttcctcca catctctacg catttcactg ctacacgtgg      780
aattctaccc ccctctggca aactctagcc tcgcagtctc catcgccatt cccaggttaa      840 gcccgggaa ttt                                                         853
```

<210> SEQ ID NO 249
<211> LENGTH: 1056
<212> TYPE: DNA
<213> ORGANISM: Frateuria sp.
<220> FEATURE:
<221> NAME/KEY: misc_feature
<222> LOCATION: (1)..(1056)
<223> OTHER INFORMATION: BDNZ 60517 16S rDNA

<400> SEQUENCE: 249

```
cgtcgtcccc ttgcggttag actaacggct tctggagcaa ctcactccca tggtgtgacg       60
ggcggtgtgt acaaggcccg ggaacgtatt caccgcagca tagctgatct gcgattacta      120
gcgattccga cttcacgaag tcgagttgca gacttcgatc cggactggga tcggctttct      180
gggattggct ccacctcgcg gtattgcaac cctctgtacc gaccattgta gtacgtgtgt      240
agccctggcc gtaagggcca tgatgacttg acgtcatccc caccttcctc cggtttgtca      300
ccggcagtct ccttagagtt ccaccattta cgtgctggca actaaggaca agggttgcgc      360
tcgttgcggg acttaaccca acatctcacg acacgagctg acgacagcca tgcagcacct      420
gtgttccgat tcccgaaggc actcccgcat ctctgcagga ttccggacat gtcaaggcca      480
ggtaaggttc ttcgcgttgc atcgaattaa accacatact ccaccgcttg tgcgggcccc      540
cgtcaattcc tttgagtttc agtcttgcga ccgtactccc caggcggcga acttaacgcg      600
ttagcttcga cactgatctc cgagttgaga ccaacatcca gttcgcatcg tttagggcgt      660
ggactaccag ggtatctaat cctgtttgct ccccacgctt tcgtgcctca gcgtcagtgt      720
tgtcccagat ggccgccttc gccactgatg ttcctcccga tctctacgca tttcaccgct      780
acaccgggaa ttccaccatc ctctgacaca ctctagcttg ccagtatcca ctgccattcc      840
caggttgagc ccggggattt cacagcagac ttaacaaacc gcctacgcac gctttacgcc      900
cagtaattcc gattaacgct tgcacccttc gtattaccgc ggctgctggc acgaagttag      960
ccggtgctta ttcctcaggt accgtcagcc ccaccggata ttagccggta gtatttcgct     1020
cctgataaaa gtgctttaca acccgaaggc cttctt                               1056
```

<210> SEQ ID NO 250
<211> LENGTH: 1025
<212> TYPE: DNA
<213> ORGANISM: Leifsonia shinshuensis
<220> FEATURE:

```
<221> NAME/KEY: misc_feature
<222> LOCATION: (1)..(1025)
<223> OTHER INFORMATION: BDNZ 61433 16S rDNA

<400> SEQUENCE: 250
ccaagggttg ggccaccggc ttcgggtgtt accgactttc atgacttgac gggcggtgtg      60
tacaaggccc gggaacgtat tcaccgcagc gttgctgatc tgcgattact agcgactccg     120
acttcatgag gtcgagttgc agacctcaat ccgaactgag accggctttt tgggattcgc     180
tccaccttac ggtattgcag ccctttgtac cggccattgt agcatgcgtg aagcccaaga     240
cataaggggc atgatgattt gacgtcatcc ccaccttcct ccgagttgac cccggcagtc     300
tcctatgagt tcccaccatt acgtgctggc aacatagaac gagggttgcg ctcgttgcgg     360
gacttaaccc aacatctcac gacacgagct gacgacaacc atgcaccacc tgtttacgag     420
tgtccaaaga gttgaccatt tctggcccgt tctcgtatat gtcaagcctt ggtaaggttc     480
ttcgcgttgc atcgaattaa tccgcatgct ccgccgcttg tgcgggcccc cgtcaattcc     540
tttgagtttt agccttgcgg ccgtactccc caggcggggc gcttaatgcg ttagctgcga     600
cacggaaacc gtggaatggt ccccacatct agcgcccaac gtttacggcg tggactacca     660
gggtatctaa tcctgttcgc tccccacgct ttcgctcctc agcgtcagtt acggcccaga     720
gaactgcctt cgccatcggt gttcctcctg atatctgcgc attccaccgc tacaccagga     780
attccattct cccctaccgc actctagtct gcccgtaccc actgcaggcc cgaggttgag     840
cctcgggttt tcacagcaga cgcgacagac cgcctacgag ctctttacgc ccaataattc     900
cggacaacgc tcgcacccta cgtattaccg cggctgctgg cacgtagtta gccggtgctt     960
tttctgcagg taccgtcact ttcgcttctt ccctactaaa agaggtttac aacccgaagg    1020
ccgtc                                                                1025

<210> SEQ ID NO 251
<211> LENGTH: 696
<212> TYPE: DNA
<213> ORGANISM: Sphingobium chlorophenolicum
<220> FEATURE:
<221> NAME/KEY: misc_feature
<222> LOCATION: (1)..(696)
<223> OTHER INFORMATION: BDNZ 61473 16S rDNA

<400> SEQUENCE: 251
ctcttgcggt tagcgcacag ccttcgggtg aaaccaactc ccatggtgtg acgggcggtg      60
tgtacaaggc ctgggaacgt attcaccgcg gcatgctgat ccgcgattac tagcgattcc     120
gccttcatgc tctcgagttg cagagaacaa tccgaactga dacgactttt ggagattagc     180
ttccactcgc atggtcgctg cccactgtag tcgccattgt agcacgtgtg tagcccaacg     240
cgtaagggcc atgaggactt gacgtcatcc ccaccttcct ccggcttatc accggcggtt     300
cctttagagt acccaactaa atgatggcaa ctaaaggcga gggttgcgct cgttgcggga     360
cttaacccaa catctcacga cacgagctga cgacagccat gcagcacctg tcacctatcc     420
agccgaactg aaggaaagtg tctccacgat ccgcgatagg gatgtcaaac gttggtaagg     480
ttctgcgcgt tgcttcgaat taaaccacat gctccaccgc ttgtgcaggc cccgtcaat      540
tcctttgagt tttaatcttg cgaccgtact ccccaggcgg ataacttaat gcgttagctg     600
cgccactgaa atgccatgca ccccagcagc tagttatcat cgtttacggc gtgactacca     660
gggtatctaa tcctgtttgc tccccacgct ttcgca                               696
```

<210> SEQ ID NO 252
<211> LENGTH: 1041
<212> TYPE: DNA
<213> ORGANISM: Janthinobacterium sp.
<220> FEATURE:
<221> NAME/KEY: misc_feature
<222> LOCATION: (1)..(1041)
<223> OTHER INFORMATION: BDNZ 63491 16S rDNA

<400> SEQUENCE: 252

| | | | | |
|---|---|---|---|---|
| agcgccctcc | ttgcggttaa | gctacctact | tctggtaaaa | cccgctccca | tggtgtgacg | 60 |
| ggcggtgtgt | acaagacccg | ggaacgtatt | caccgcggca | tgctgatccg | cgattactag | 120 |
| cgattccaac | ttcacgcagt | cgagttgcag | actgcgatcc | ggactacgat | gcactttctg | 180 |
| ggattagctc | ccctcgcgg | gttggcggcc | ctctgtatgc | accattgtat | gacgtgtgaa | 240 |
| gccctaccca | taagggccat | gaggacttga | cgtcatcccc | accttcctcc | ggtttgtcac | 300 |
| cggcagtctc | attagagtgc | cctttcgtag | caactaatga | caagggttgc | gctcgttgcg | 360 |
| ggacttaacc | caacatctca | cgacacgagc | tgacgacagc | catgcagcac | ctgtgttcag | 420 |
| gctccctttc | gggcacccyy | caatctctcg | arggttcctg | acatgtcaag | ggtaggtaag | 480 |
| gtttttcgcg | ttgcatcgaa | ttaatccaca | tcatccaccg | cttgtgcggg | tccccgtcaa | 540 |
| ttcctttgag | ttttaatctt | gcgaccgtac | tccccaggcg | gtctacttca | cgcgttagct | 600 |
| gcgttaccaa | gtcaattaag | acccgacaac | tagtagacat | cgtttagggc | gtggactacc | 660 |
| agggtatcta | atcctgtttg | ctccccacgc | tttcgtgcat | gagcgtcagt | cttgacccag | 720 |
| ggggctgcct | tcgccatcgg | tgttcctcca | catctctacg | catttcactg | ctacacgtgg | 780 |
| aattctaccc | ccctctgcca | gactccagcc | ttgcagtctc | caatgcaatt | cccaggttaa | 840 |
| gcccggggat | ttcacatcag | acttacaaaa | ccgcctgcgc | acgctttacg | cccagtaatt | 900 |
| ccgattaacg | cttgcaccct | acgtattacc | gcggctgctg | cacgtagtt | agccggtgct | 960 |
| tattcttcag | gtaccgtcat | taggcccagg | tattaaccwg | gccgtttct | tccctgacaa | 1020 |
| aararcttta | caacccgaag | g | | | | 1041 |

<210> SEQ ID NO 253
<211> LENGTH: 824
<212> TYPE: DNA
<213> ORGANISM: Stenotrophomonas chelatiphaga
<220> FEATURE:
<221> NAME/KEY: misc_feature
<222> LOCATION: (1)..(824)
<223> OTHER INFORMATION: BDNZ 64212 16S rDNA

<400> SEQUENCE: 253

| | | | | |
|---|---|---|---|---|
| cgtggcagcg | ccctcccgaa | ggttaagcta | cctgcttctg | gtgcaacaaa | ctcccatggt | 60 |
| gtgacgggcg | gtgtgtacaa | ggcccgggaa | cgtattcacc | gcagcaatgc | tgatctgcga | 120 |
| ttactagcga | ttccgacttc | atggagtcga | gttgcagact | ccaatccgga | ctgagatagg | 180 |
| gtttctggga | ttggcttacc | gtcgccggct | tgcagccctc | tgtccctacc | attgtagtac | 240 |
| gtgtgtagcc | ctggccgtaa | gggccatgat | gacttgacgt | catccccacc | ttcctccggt | 300 |
| ttgtcaccgg | cggtctcctt | agagttccca | ccattacgtg | ctggcaacta | aggacaaggg | 360 |
| ttgcgctcgt | tgcgggactt | aacccaacat | ctcacgacac | gagctgacga | cagccatgca | 420 |
| gcacctgtgt | tcgagttccc | gaaggcacca | atccatctct | ggaaagttct | cgacatgtca | 480 |
| aggccaggta | aggttcttcg | cgttgcatcg | aattaaacca | catactccac | cgcttgtgcg | 540 |
| ggcccccgtc | aattcctttg | agtttcagtc | ttgcgaccgt | actccccagg | cggcgaactt | 600 |

| | |
|---|---|
| aacgcgttag cttcgatact gcgtgccaaa gtgcacccaa catccagttc gcatcgttta | 660 |
| gggcgtggac taccagggta tctaatcctg tttgctcccc acgctttcgt gcctcagtgt | 720 |
| cagtgttggt ccaggwagct gccttcgcca tggatgttcc tcccgatctc tacgcatttc | 780 |
| actgctacac cggggaattc cgctaccctc taccacactc tagt | 824 |

<210> SEQ ID NO 254
<211> LENGTH: 930
<212> TYPE: DNA
<213> ORGANISM: Lysinibacillus fusiformis
<220> FEATURE:
<221> NAME/KEY: misc_feature
<222> LOCATION: (1)..(930)
<223> OTHER INFORMATION: BDNZ 63466 16S rDNA

<400> SEQUENCE: 254

| | |
|---|---|
| gttacctcac cgacttcggg tgttacaaac tctcgtggtg tgacgggcgg tgtgtacaag | 60 |
| gcccgggaac gtattcaccg cggcatgctg atccgcgatt actagcgatt ccggcttcat | 120 |
| gtaggcgagt tgcagcctac aatccgaact gagaacgact ttatcggatt agctccctct | 180 |
| cgcgagttgg caaccgtttg tatcgtccat tgtagcacgt gtgtagccca ggtcataagg | 240 |
| ggcatgatga tttgacgtca tccccacctt cctccggttt gtcaccggca gtcaccttag | 300 |
| agtgcccaac taaatgatgg caactaagat caagggttgc gctcgttgcg ggacttaacc | 360 |
| caacatctca cgacacgagc tgacgacaac catgcaccac ctgtcaccgt tgccccgaa | 420 |
| ggggaaacta tatctctaca gtggtcaacg ggatgtcaag acctggtaag gttcttcgcg | 480 |
| ttgcttcgaa ttaaaccaca tgctccaccg cttgtgcggg ccccgtcaa ttcctttgag | 540 |
| tttcagtctt gcgaccgtac tccccaggcg gagtgcttaa tgcgttagct gcagcactaa | 600 |
| ggggcggaaa ccccctaaca cttagcactc atcgtttacg cgtggacta ccagggtatc | 660 |
| taatcctgtt tgctccccac gctttcgcgc ctcagtgtca gttacagacc agatagtcgc | 720 |
| cttcgccact ggtgttcctc caaatctcta cgcatttcac cgctacactt ggaattccac | 780 |
| tatcctcttc tgcactcaag tctcccagtt tccaatgacc ctccacggtt gagccgtggg | 840 |
| ctttcacatc agacttaaga aaccacctgc gcgcgcttta cgcccaataa ttccggacaa | 900 |
| cgcttgccac ctacgtatta ccgcggctgc | 930 |

<210> SEQ ID NO 255
<211> LENGTH: 881
<212> TYPE: DNA
<213> ORGANISM: Luteibacter rhizovicinus
<220> FEATURE:
<221> NAME/KEY: misc_feature
<222> LOCATION: (1)..(881)
<223> OTHER INFORMATION: BDNZ 65069 16S rDNA

<400> SEQUENCE: 255

| | |
|---|---|
| caaggcccgg gaacgtattc accgcagcat agctgatctg cgattactag cgattccgac | 60 |
| ttcatggagt cgagttgcag actccaatcc ggactgggat cggctttctg ggattagctc | 120 |
| cacctcgcgg tcttgcaacc ctctgtaccg accattgtag tacgtgtgta gccctggccg | 180 |
| taagggccat gatgacttga cgtcatcccc accttcctcc ggtttgtcac cggcagtctc | 240 |
| cttagagttc ccaccattac gtgctggcaa ctaaggacaa gggttgcgct cgttgcggga | 300 |
| cttaacccaa catctcacga cacgagctga cgacagccat gcagcacctg tgttccgatt | 360 |
| cccgaaggca ctcctgcatc tctgctggat tccgacatg tcaaggccag gtaaggttct | 420 |
| tcgcgttgca tcgaattaaa ccacatactc caccgcttgt gcgggccccc gtcaattcct | 480 |

```
ttgagtttca gtcttgcgac cgtactcccc aggcggcgaa cttaacgcgt tagcttcgac    540
actgatctcc gagttgagac caacatccag ttcgcatcgt ttagggcgtg gactaccagg    600
gtatctaatc ctgtttgctc cccacgcttt cgtgcctcag cgtcagtgtt gatccagatg    660
gccgccttcg ccactgatgt tcctcccgat ctctacgcat tcaccgcta caccgggaat    720 tccaccatcc tctatcacac tctagctcgc cagtatccat tgccattccc aggttgagcc    780
cggggctttc acaacagact taacgaaccg cctacgcacg ctttacgccc agtaattccg    840
attaacgctt gcaccctccg tattaccgcg gctgctggca c                        881

<210> SEQ ID NO 256
<211> LENGTH: 925
<212> TYPE: DNA
<213> ORGANISM: Rhizobium miluonense
<220> FEATURE:
<221> NAME/KEY: misc_feature
<222> LOCATION: (1)..(925)
<223> OTHER INFORMATION: BDNZ 65070 16S rDNA

<400> SEQUENCE: 256
ctaccttcgg gtaaaaccaa ctcccatggt gtgacgggcg gtgtgtacaa ggcccgggaa     60
cgtattcacc gcggcatgct gatccgcgat tactagcgat tccaacttca tgcactcgag    120
ttgcagagtg caatccgaac tgagatggct tttggagatt agctcacact cgcgtgctcg    180
ctgcccactg tcaccaccat tgtagcacgt gtgtagccca gcccgtaagg gccatgagga    240
cttgacgtca tccccacctt cctctcggct tatcaccggc agtcccctta gagtgcccaa    300
ctaaatgctg gcaactaagg gcgagggttg cgctcgttgc gggacttaac ccaacatctc    360
acgacacgag ctgacgacag ccatgcagca cctgtctctg cgccaccgaa gtggaccccc    420
tatctctacg ggtaacacag gatgtcaagg gctggtaagg ttctgcgcgt tgcttcgaat    480
taaaccacat gctccaccgc ttgtgcgggc cccgtcaat tcctttgagt tttaatcttg    540
cgaccgtact ccccaggcgg aatgtttaat gcgttagctg cgccaccgaa cagtatactg    600
cccgacggct aacattcatc gtttacggcg tggactacca gggtatctaa tcctgtttgc    660
tccccacgct ttcgcacctc agcgtcagta atggaccagt gagccgcctt cgccactggt    720
gttcctccga atatctacga atttcacctc tacactcgga attccactca cctcttccat    780
actccagatc gacagtatca aaggcagttc cagggttgag ccctgggatt tcaccctga    840 ctgatcgatc cgcctacgtg cgctttacgc ccagtaattc cgaacaacgc tagccccctt    900
cgtattaccg cggctgctgg cacga                                          925

<210> SEQ ID NO 257
<211> LENGTH: 1048
<212> TYPE: DNA
<213> ORGANISM: Stenotrophomonas rhizophila
<220> FEATURE:
<221> NAME/KEY: misc_feature
<222> LOCATION: (1)..(1048)
<223> OTHER INFORMATION: BDNZ 65303 16S rDNA

<400> SEQUENCE: 257
ggcagcgccc tcccgaaggt taagctacct gcttctggtg caacaaactc ccatggtgtg     60
acgggcggtg tgtacaaggc ccgggaacgt attcaccgca gcaatgctga tctgcgatta    120
ctagcgattc cgacttcatg gagtcgagtt gcagactcca atccggactg agataggggtt    180 tctgggattg gcttgccctc gcgggtttgc agccctctgt ccctaccatt gtagtacgtg    240
```

```
tgtagccctg gtcgtaaggg ccatgatgac ttgacgtcat ccccaccttc ctccggtttg    300
tcaccggcgg tctccttaga gttcccacca ttacgtgctg gcaactaagg acaagggttg    360
cgctcgttgc gggacttaac ccaacatctc acgacacgag ctgacgacag ccatgcagca    420
cctgtgttcg agttcccgaa ggcaccaatc catctctgga aagttctcga catgtcaaga    480
ccaggtaagg ttcttcgcgt tgcatcgaat taaaccacat actccaccgc ttgtgcgggc    540
ccccgtcaat tcctttgagt ttcagtcttg cgaccgtact ccccaggcgg cgaacttaac    600
gcgttagctt cgatactgcg tgccaaattg cacccaacat ccagttcgca tcgtttaggg    660
cgtggactac cagggtatct aatcctgttt gctccccacg ctttcgtgcc tcagtgtcag    720
tgttggtcca ggtagctgcc ttcgccatgg atgttcctcc cgatctctac gcatttcact    780
gctacaccgg gaattccact accctctacc acactctagt cgcccagtat ccactgcaat    840
tcccaggttg agcccagggc tttcacaaca gacttaaaca accacctacg cacgctttac    900
gcccagtaat tccgagtaac gcttgcaccc ttcgtattac cgcggctgct ggcacgaagt    960
tagccggtgc ttattctttg ggtaccgtca gaacaaccga gtattaatcg actgcttttc   1020
tttcccaaca aagggctttt acaacccg                                      1048

<210> SEQ ID NO 258
<211> LENGTH: 707
<212> TYPE: DNA
<213> ORGANISM: Novosphingobium rosa
<220> FEATURE:
<221> NAME/KEY: misc_feature
<222> LOCATION: (1)..(707)
<223> OTHER INFORMATION: BDNZ 65589 16S rDNA

<400> SEQUENCE: 258
gtcgcctgcc tcccttgcgg gttagctcaa cgccttcgag tgaatccaac tcccatggct     60
gtgacgggcg gtgtgtacaa ggcctgggaa cgtattcacc gcggcatgct gatccgcgat    120
tactagcgat tccgccttca tgctctcgag ttgcagagaa caatccgaac tgagacggct    180
tttggagatt agctcacact cgcgtgcttg ctgcccactg tcaccgccat tgtagcacgt    240
gtgtagccca cgcgtgtaagg gccatgagga cttgacgtca tccccacctt cctccggctt    300
atcaccggcg gtttccttag agtgcccaac ttaatgatgg caactaagga cgagggttgc    360
gctcgttgcg ggacttaacc caacatctca cgacacgagc tgacgacagc catgcagcac    420
ctgtcactca tccagccgaa ctgaagaaat ccatctctgg aaatcgcgat gaggatgtca    480
aacgctggta aggttctgcg cgttgcttcg aattaaacca catgctccac cgcttgtgca    540 ggccccccgtc aattcctttg agttttaatc ttgcgaccgt actccccagg cggataactt    600
aatgcgttag ctgcgccacc ccagcaccat gtgcccggac agctagttat catcgtttta    660
cggcgtggac taccagggta tctaatcctg tttgctcccc acgcttt               707

<210> SEQ ID NO 259
<211> LENGTH: 834
<212> TYPE: DNA
<213> ORGANISM: Novosphingobium rosa
<220> FEATURE:
<221> NAME/KEY: misc_feature
<222> LOCATION: (1)..(834)
<223> OTHER INFORMATION: BDNZ 65619 16S rDNA

<400> SEQUENCE: 259
ccttgcgggt tagctcaacg ccttcgagtg aatccaactc ccatggtgtg acgggcggtg     60
tgtacaaggc ctgggaacgt attcaccgcg gcatgctgat ccgcgattac tagcgattcc    120
```

```
gccttcatgc tctcgagttg cagagaacaa tccgaactga gacggctttt ggagattagc    180
tcacactcgc gtgcttgctg cccactgtca ccgccattgt agcacgtgtg tagcccagcg    240
tgtaagggcc atgaggactt gacgtcatcc ccaccttcct ccggcttatc accggcggtt    300
tccttagagt gcccaactta atgatggcaa ctaaggacga gggttgcgct cgttgcggga    360
cttaacccaa catctcacga cacgagctga cgacagccat gcagcacctg tcactcatcc    420
agccgaactg aagaaatcca tctctggaaa tcgcgatgag gatgtcaaac gctggtaagg    480
ttctgcgcgt tgcttcgaat taaaccacat gctccaccgc ttgtgcaggc cccgtcaat     540 tcctttgagt tttaatcttg cgaccgtact ccccaggcgg ataacttaat gcgttagctg    600
cgccacccaa gcaccatgtg cccggacagc tagttatcat cgtttacggc gtggactacc    660
agggtatcta atcctgtttg ctccccacgc tttcgcacct cagcgtcaat acttgtccag    720
cgggccgcct tcgccactgg tgttcttccg aatatctacg aatttcacct ctacactcgg    780
aattccaccc gcctctccaa gattctagta cactagtttc aagggcagtt ccgg          834
```

<210> SEQ ID NO 260
<211> LENGTH: 1380
<212> TYPE: DNA
<213> ORGANISM: Rhizobium pisi
<220> FEATURE:
<221> NAME/KEY: misc_feature
<222> LOCATION: (1)..(1380)
<223> OTHER INFORMATION: BDNZ 66326 16S rDNA

<400> SEQUENCE: 260

```
gctgcctcct tgcggttagc gcactacctt cgggtaaaac caactcccat ggtgtgacgg    60
gcggtgtgta caaggcccgg gaacgtattc accgcggcat gctgatccgc gattactagc    120
gattccaact tcatgcactc gagttgcaga gtgcaatccg aactgagatg cttttggag    180 attagctcac actcgcgtgc tgctgcccca ctgtcaccac cattgtagca cgtgtgtagc    240
ccagcccgta agggccatga ggacttgacg tcatccccac cttcctctcg gcttatcacc    300
ggcagtcccc ttagagtgcc caactgaatg ctggcaacta agggcgaggg ttgcgctcgt    360
tgcgggactt aacccaacat ctcacgacac gagctgacga cagccatgca gcacctgtgt    420
cccggtcccc gaagggaacc ttgcatctct gcaagtagcc gggcatgtca agggctggta    480
aggttctgcg cgttgcttcg aattaaacca catgctccac cgcttgtgcg gccccgtc     540 aattcctttg agttttaatc ttgcgaccgt actccccagg cggaatgttt aatgcgttag    600
ctgcgccacc gaacagtata ctgcccgacg gctaacatta tcgtttacg gcgtggacta    660 ccagggtatc taatcctgtt tgctccccac gctttcgcac ctcagcgtca gtaatggacc    720
agtgagccgc cttcgccact ggtgttcctc gaatatcta cgaatttcac ctctacactc    780
ggaattccac tcacctcttc catactccag atcgacagta tcaaaggcag ttccagggtt    840
gagccctggg atttcacccc tgactgatcg atccgcctac gtgcgcttta cgcccagtaa    900
ttccgaacaa cgctagcccc cttcgtatta ccgcggctgc tggcacgaag ttagccgggg    960
cttcttctcc ggataccgtc attatcttct ccggtgaaag agctttacaa ccctagggcc    1020
ttcatcactc acgcggcatg gctggatcag gcttgcgccc attgtccaat attccccact    1080
gctgcctccc gtaggagttt gggccgtgtc tcagtcccaa tgtggctgat catcctctca    1140
gaccagctat ggatcgtcgc cttggtaggc ctttaccccca ccaactagct aatccaacgc    1200
gggccgatcc tttaccgata aatctttccc ccaaagggca catacggtat tagcacaagt    1260
```

```
ttccctgcgt tattccgtag taaagggtac gttcccacgc gttactcacc cgtctgccgc   1320
tccccttgcg gggcgctcga cttgcatgtg ttaagcctgc cgccagcgtt cgttctgagc   1380
```

<210> SEQ ID NO 261
<211> LENGTH: 1429
<212> TYPE: DNA
<213> ORGANISM: Ramlibacter henchirensis
<220> FEATURE:
<221> NAME/KEY: misc_feature
<222> LOCATION: (1)..(1429)
<223> OTHER INFORMATION: BDNZ 66331 16S rDNA

<400> SEQUENCE: 261

```
atcgccctcc ttgcggttag gctaactact tctggcagaa cccgctccca tggtgtgacg     60
ggcggtgtgt acaagacccg ggaacgtatt caccgcgaca tgctgatccg cgattactag    120
cgattccgac ttcacgcagt cgagttgcag actgcgatcc ggactacgac tggttttatg    180
ggattagctc ccctcgcgg gttggcaacc ctctgtacca gccattgtat gacgtgtgta    240
gccctaccca taagggccat gaggacttga cgtcatcccc accttcctcc ggtttgtcac    300
cggcagtctc attagagtgc cctttcgtag caactaatga caagggttgc gctcgttgcg    360
ggacttaacc caacatctca cgacacgagc tgacgacagc catgcagcac ctgtgttctg    420
gctctctttc gagcactccc acatctctgc gggattccag acatgtcaag ggtaggtaag    480 gttttttcgcg ttgcatcgaa ttaaaccaca tcatccaccg cttgtgcggg tccccgtcaa    540
ttcctttgag tttcaacctt gcggccgtac tccccaggcg gtcaacttca cgcgttagct    600
tcgttactga gtcagtgaag acccaacaac cagttgacat cgtttagggc gtggactacc    660
agggtatcta atcctgtttg ctccccacgc tttcgtgcat gagcgtcagt gcaggcccag    720
gggattgcct tcgccatcgg tgttcctccg catatctacg catttcactg ctacacgcgg    780
aattccatcc ccctctgccg cactccagcg atgcagtcac aaatgcagtt cccaggttaa    840
gcccggggat ttcacacctg tcttacatca ccgcctgcgc acgctttacg cccagtaatt    900
ccgattaacg cttgcaccct acgtattacc gcggctgctg gcacgtagtt agccggtgct    960
tattcttacg gtaccgtcat gagccctctg tattagagaa agcctttcg ttccgtacaa   1020 aagcagttta caacccgagg gccttcatcc tgcacgcgga atggctggat caggcttgcg   1080
cccattgtcc aaaattcccc actgctgcct cccgtaggag tctgggccgt gtctcagtcc   1140
cagtgtggct ggtcgtcctc tcagaccagc tacagatcgt cggcttggtg agcctttacc   1200
ccaccaacta cctaatctgc catcggccgc tccaattgcg cgaggtcttg cgatcccccg   1260
ctttcaacct cagttcgtat gcggtattag cgtagctttc gctacgttat cccccacaac   1320
tgggcacgtt ccgatgtatt actcacccgt tcgccactcg ccaccagggt tgccccgtg   1380 ctgccgttcg acttgcatgt gtaaagcatt ccgccagcgt tcaatctga               1429
```

<210> SEQ ID NO 262
<211> LENGTH: 1098
<212> TYPE: DNA
<213> ORGANISM: Caulobacter henricii
<220> FEATURE:
<221> NAME/KEY: misc_feature
<222> LOCATION: (1)..(1098)
<223> OTHER INFORMATION: BDNZ 66341 16S rDNA

<400> SEQUENCE: 262

```
cctgcctctc ttgcgagtta gcgcagcgcc ttcgggtaaa gccaactccc atggtgtgac     60
gggcggtgtg tacaaggccc gggaacgtat tcaccgcggc atgctgatcc gcgattacta    120
```

```
gcgattccaa cttcatgcac tcgagttgca gagtgcaatc cgaactgaga cgactttag      180 ggattggctc ccctcgcgg gattgcagcc ctctgtagtc gccattgtag cacgtgtgta      240
gcccaccttg taagggccat gaggacttga cgtcatcccc accttcctcc gaattaactt    300
cggcagtact attagagtgc ccagccaaac ctgatggcaa ctaatagcga gggttgcgct    360
cgttgcggga cttaacccaa catctcacga cacgagctga cgacagccat gcagcacctg   420
tgtcccagtc cccgaaggga aagccgcatc tctgcggcgg tccgggcatg tcaaaaggtg   480
gtaaggttct gcgcgttgct tcgaattaaa ccacatgctc caccgcttgt gcgggccccc   540
gtcaattcct ttgagtttta atcttgcgac cgtactcccc aggcggagtg cttaatgcgt   600
tagctgcgtc accgacaggc atgcctgccg acaactagca ctcatcgttt acagcgtgga   660
ctaccagggt atctaatcct gtttgctccc cacgctttcg agcctcagcg tcagtaacgg   720
accagtatgt cgccttcgcc actggtgttc ttccgaatat ctacgaattt cacctctaca   780
ctcggagttc cacatacctc ttccgtactc aagatagcca gtatcaaagg caattccaag   840
gttgagccct gggctttcac ctctgactaa actatccgcc tacgctccct ttacgcccag   900
taattccgag caacgctagc ccccttcgta ttaccgcggc tgctggcacg aagttagccg   960
gggcttcttc tccgggtacc gtcattatcg tccccggtga aagaatttta caatcctaag  1020
accttcatca ttcacgcggc atggctgcgt caggctttcg cccattgcgc aagattcccc  1080
actgctgcct cccgtagg                                                 1098

<210> SEQ ID NO 263
<211> LENGTH: 1450
<212> TYPE: DNA
<213> ORGANISM: Bacillus subtilis
<220> FEATURE:
<221> NAME/KEY: misc_feature
<222> LOCATION: (1)..(1450)
<223> OTHER INFORMATION: BDNZ 66347 16S rDNA

<400> SEQUENCE: 263
cggcggctgg ctcctaaagg ttacctcacc gacttcgggt gttacaaact ctcgtggtgt       60
gacgggcggt gtgtacaagg cccgggaacg tattcaccgc ggcatgctga tccgcgatta     120
ctagcgattc cagcttcacg cagtcgagtt gcagactgcg atccgaactg agaacagatt     180
tgtgggattg gcttaacctc gcggtttcgc tgcccttgtg tctgtccatt gtagcacgtg    240
tgtagcccag gtcataaggg gcatgatgat ttgacgtcat ccccaccttc ctccggtttg    300
tcaccggcag tcaccttaga gtgcccaact gaatgctggc aactaagatc aagggttgcg    360
ctcgttgcgg gacttaaccc aacatctcac gacacgagct gacgacaacc atgcaccacc    420
tgtcactctg cccccgaagg ggacgtccta tctctaggat tgtcagagga tgtcaagacc    480
tggtaaggtt cttcgcgttg cttcgaatta aaccacatgc tccaccgctt gtgcgggccc    540
ccgtcaattc ctttgagttt cagtcttgcg accgtactcc ccaggcggag tgcttaatgc    600
gttagctgca gcactaaggg gcggaaaccc cctaacactt agcactcatc gtttacggcg    660
tggactacca gggtatctaa tcctgttcgc tccccacgct ttcgctcctc agcgtcagtt    720
acagaccaga gagtcgcctt cgccactggt gttcctccac atctctacgc atttcaccgc    780
tacacgtgga attccactct cctcttctgc actcaagttc cccagtttcc aatgaccctc    840
cccggttgag ccgggggctt tcacatcaga cttaagaaac cgcctgcgag cccttacgc    900 ccaataattc cggacaacgc ttgccaccta cgtattaccg cggctgctgg cacgtagtta    960
```

| | |
|---|---|
| gccgtggctt tctggttagg taccgtcaag gtaccgccct attcgaacgg tacttgttct | 1020 |
| tccctaacaa cagagcttta cgatccgaaa accttcatca ctcacgcggc gttgctccgt | 1080 |
| cagactttcg tccattgcgg aagattccct actgctgcct cccgtaggag tctgggccgt | 1140 |
| gtctcagtcc cagtgtggcc gatcaccctc tcaggtcggc tacgcatcgt tgccttggtg | 1200 |
| agccgttacc tcaccaacta gctaatgcgc cgcgggtcca tctgtaagtg gtagccraag | 1260 |
| ccacctttta tgtttgaacc atgcggttca acaaccatc cggtattagc cccggtttcc | 1320 |
| cggagttatc ccagtcttac aggcaggtta cccacgtgtt actcacccgt ccgccgctaa | 1380 |
| catcagggag caagctccca tctgtccgct cgacttgcat gtattaggca cgccgccagc | 1440 |
| gttcgtcctg | 1450 |

<210> SEQ ID NO 264
<211> LENGTH: 933
<212> TYPE: DNA
<213> ORGANISM: Bosea minatitlanensis
<220> FEATURE:
<221> NAME/KEY: misc_feature
<222> LOCATION: (1)..(933)
<223> OTHER INFORMATION: BDNZ 66354 16S rDNA

<400> SEQUENCE: 264

| | |
|---|---|
| cgcctgcctc cttgcggtta gcgcgacgcc ttcgggtaaa cccaactccc atggtgtgac | 60 |
| gggcggtgtg tacaaggccc gggaacgtat tcaccgtggc atgctgatcc acgattacta | 120 |
| gcgattccac cttcatgcac tcgagttgca gagtgcaatc tgaactgaga cggcttttg | 180 |
| ggattagctc gaggtcgccc tttcgctgcc cattgtcacc gccattgtag cacgtgtgta | 240 |
| gcccagcctg taagggccat gaggacttga cgtcatcccc accttcctcg cggcttatca | 300 |
| ccggcagtcc ccctagagtt cccaacttaa tgatggcaac taggggcgag ggttgcgctc | 360 |
| gttgcgggac ttaacccaac atctcacgac acgagctgac gacagccatg cagcacctgt | 420 |
| gttccggcca gccgaactga agaaaggcat ctctgccgat caaaccggac atgtcaaaag | 480 |
| ctggtaaggt tctgcgcgtt gcttcgaatt aaaccacatg ctccaccgct tgtgcgggcc | 540 |
| cccgtcaatt cctttgagtt ttaatcttgc gaccgtactc cccaggcgga atgcttaaag | 600 |
| cgttagctgc gccactgaag agcaagctcc ccaacggctg gcattcatcg tttacggcgt | 660 |
| ggactaccag ggtatctaat cctgtttgct ccccacgctt tcgcgcctca gcgtcagttt | 720 |
| cggaccagtt ggccgccttc gccaccggtg ttcttgcgaa tatctacgaa tttcacctct | 780 |
| acactcgcag ttccaccaac ctctttccga actcaagact ccccagtatc gaaaggcaat | 840 |
| ttccaggggt tgagcccctg ggcttttcc cctcccgact ttaaaagtcc cccctacgcc | 900 |
| gcccttttac gccccagttg atttccgagc aac | 933 |

<210> SEQ ID NO 265
<211> LENGTH: 640
<212> TYPE: DNA
<213> ORGANISM: Duganella violaceinigra
<220> FEATURE:
<221> NAME/KEY: misc_feature
<222> LOCATION: (1)..(640)
<223> OTHER INFORMATION: BDNZ 66361 16S rDNA

<400> SEQUENCE: 265

| | |
|---|---|
| gcgccctcct tgcggttaag ctacctactt ctggtaaacc cgctcccatg gtgtgacggg | 60 |
| cggtgtgtac aagacccggg aacgtattca ccgcgacatg ctgatccgcg attactagcg | 120 |
| attccaactt catgtagtcg agttgcagac tacaatccgg actacgatac actttctggg | 180 |

```
attagctccc cctcgcgggt tggcggccct ctgtatgtac cattgtatga cgtgtgaagc    240
cctacccata agggccatga ggacttgacg tcatccccac cttcctccgg tttgtcaccg    300
gcagtctcat tagagtgctc ttgcgtagca actaatgaca agggttgcgc tcgttgcggg    360
acttaaccca acatctcacg acacgagctg acgacagccc tgcagcacct gtgtgatggt    420
tctctttcga gcactcccaa atctctccgg gattccatcc atgtcaaggg taggtaaggt    480
ttttcgcgtt gcatcgaatt aatccacatc atccaccgct tgtgcgggtc cccgtcaatt    540
cctttgagtt ttaatcttgc gaccgtactc cccaggcggt ctacttcacg cgttagctgc    600
gttactaagt caattaagac ccaacaacta gtagacatcg                          640
```

<210> SEQ ID NO 266
<211> LENGTH: 1064
<212> TYPE: DNA
<213> ORGANISM: Polaromonas ginsengisoli
<220> FEATURE:
<221> NAME/KEY: misc_feature
<222> LOCATION: (1)..(1064)
<223> OTHER INFORMATION: BDNZ 66373 16S rDNA

<400> SEQUENCE: 266

```
cgccctcctt gcggttaggc taactacttc tggcagaacc cgctcccatg gtgtgacggg    60
cggtgtgtac aagacccggg aacgtattca ccgcgacatt ctgatccgcg attactagcg    120
attccgactt cacgtagtcg agttgcagac tacgatccgg actacgactg gttttatggg    180
attagctccc cctcgcgggt tggcaaccct ctgtaccagc cattgtatga cgtgtgtagc    240
cctacctata agggccatga ggacttgacg tcatccccac cttcctccgg tttgtcaccg    300
gcagtctcat tagagtgccc aactaaatgt agcaactaat gacaagggtt gcgctcgttg    360
cgggacttaa cccaacatct cacgacacga gctgacgaca gccatgcagc acctgtgtta    420
cggttctctt tcgagcacta agccatctct ggcgaattcc gtacatgtca aggtaggta    480 aggtttttcg cgttgcatcg aattaaacca catcatccac cgcttgtgcg ggtccccgtc    540
aattcctttg agtttcaacc ttgcggccgt actcccagg cggtcaactt cacgcgttag    600
cttcgttact gagtactaat gcacccaaca accagttgac atcgtttagg gcgtggacta    660
ccagggtatc taatcctgtt tgctccccac gctttcgtgc atgagcgtca gtacaggtcc    720
aggggattgc cttcgccatc ggtgttcctc cgcatatcta cgcatttcac tgctacacgc    780
ggaattccat ccccctctac cgtactctag ctatacagtc acagatgcaa ttcccaggtt    840
gagcccgggg atttcacaac tgtcttatat aaccgcctgc gcacgcttta cgcccagtaa    900
ttccgattaa cgctcgcacc ctacgtatta ccgcggctgc tggcacgtag ttagccggtg    960
cttattctta cggtaccgtc attagccctc tttattagaa agagccgttt cgttccgtac    1020
aaaagcagtt tacaacccga aggccttctt cctgcacgcg gcat                    1064
```

<210> SEQ ID NO 267
<211> LENGTH: 1060
<212> TYPE: DNA
<213> ORGANISM: Rhodoferax ferrireducens
<220> FEATURE:
<221> NAME/KEY: misc_feature
<222> LOCATION: (1)..(1060)
<223> OTHER INFORMATION: BDNZ 66374 16S rDNA

<400> SEQUENCE: 267

```
cgccctcctt gcggttaggc taactacttc tggcagaacc cgctcccatg gtgtgacggg    60
```

```
cggtgtgtac aagacccggg aacgtattca ccgtgacatt ctgatccacg attactagcg    120
attccgactt cacgcagtcg agttgcagac tgcgatccgg actacgactg gttttatggg    180
attagctccc cctcgcgggt tggcaaccct ttgtaccagc cattgtatga cgtgtgtagc    240
cccacctata agggccatga ggacttgacg tcatccccac cttcctccgg tttgtcaccg    300
gcagtctcac tagagtgccc aactaaatgt agcaactaat gacaagggtt gcgctcgttg    360
cgggacttaa cccaacatct cacgacacga gctgacgaca gccatgcagc acctgtgtta    420
cggctctctt tcgagcacga agctatctct agcgacttcc gtacatgtca aggtgggta    480 aggttttcg cgttgcatcg aattaaacca catcatccac cgcttgtgcg ggtccccgtc    540
aattcctttg agtttcaacc ttgcggccgt actccccagg cggtcaactt cacgcgttag    600
cttcgttact gagtcagtga agacccaaca accagttgac atcgtttagg gcgtggacta    660
ccagggtatc taatcctgtt tgctccccac gctttcgtgc atgagcgtca gtacaggtcc    720
aggggattgc cttcgccatc ggtgttcctc cgcatatcta cgcatttcac tgctacacgc    780
ggaattccat cccctctac cgtactctag ctatgcagtc acaaatgcag gtcccaggtt    840
gagcccgggg atttcacatc tgtcttacat aaccgcctgc gcacgcttta cgcccagtaa    900
ttccgattaa cgctcgcacc ctacgtatta ccgcggctgc tggcacgtag ttagccggtg    960
cttattctta cggtaccgtc attagcccac cgtattaggg cagaccgttt cgttccgtac    1020
aaaagcagtt tacaaccccg aaggccttca tcctgcacgc                          1060
```

<210> SEQ ID NO 268
<211> LENGTH: 924
<212> TYPE: DNA
<213> ORGANISM: Stenotrophomonas rhizophila
<220> FEATURE:
<221> NAME/KEY: misc_feature
<222> LOCATION: (1)..(924)
<223> OTHER INFORMATION: BDNZ 66478 16S rDNA

<400> SEQUENCE: 268

```
cctgcttctg gtgcacaaac tcccatggtg tgacgggcgg tgtgtacaag gcccgggaac     60
gtattcaccg cagcaatgct gatctgcgat tactagcgat tccgacttca tggagtcgag    120
ttgcagactc caatccggac tgagataggg tttctgggat tggcttgccc tcgcgggttt    180
gcagccctct gtccctacca ttgtagtacg tgtgtagccc tggccgtaag ggccatgatg    240
acttgacgtc atccccacct tcctccggtt tgtcaccggc ggtctcctta gagttcccac    300
cattacgtgc tggcaactaa ggacaagggt tgcgctcgtt gcgggactta acccaacatc    360
tcacgacacg agctgacgac agccatgcag cacctgtgtt cgagttcccg aaggcaccaa    420
tccatctctg gaaagttctc gacatgtcaa ggccaggtaa ggttcttcgc gttgcatcga    480
attaaaccac atactccacc gcttgtgcgg gccccgtca attcctttga gtttcagtct    540
tgcgaccgta ctccccaggc ggcgaactta acgcgttagc ttcgatactg cgtgccaaat    600
tgcacccaac atccagttcg catcgtttag ggcgtggact accagggtat ctaatcctgt    660
ttgctcccca cgctttcgtg cctcagtgtc agtgttggtc caggtagctg ccttcgccat    720
ggatgttcct cctgatctct acgcatttca ctgctacacc aggaattcca ctaccctcta    780
ccacactcta gtcgtccagt atccactgca attcccaggt tgagcccagg ctttcacaa    840 cagacttaaa caaccaccta cgcacgcttt acgcccagta attccgagta acgcttgcac    900
ccttcgtatt accgcggctg ctgg                                           924
```

<210> SEQ ID NO 269
<211> LENGTH: 1057
<212> TYPE: DNA
<213> ORGANISM: Sphingobium quisquiliarum
<220> FEATURE:
<221> NAME/KEY: misc_feature
<222> LOCATION: (1)..(1057)
<223> OTHER INFORMATION: BDNZ 66576 16S rDNA

<400> SEQUENCE: 269

```
ctgcctccct tgcgggttag ctcaacgcct tcgagtgaat ccaactccca tggtgtgacg      60
ggcggtgtgt acaaggcctg ggaacgtatt caccgcggca tgctgatccg cgattactag     120
cgattccgcc ttcatgctct cgagttgcag agaacaatcc gaactgagac gactttgga      180
gattagcttc cactcgcatg gtcgctgccc actgtagtcg ccattgtagc acgtgtgtag     240
cccaacgcgt aagggccatg aggacttgac gtcatcccca ccttcctccg gcttatcacc     300
ggcggttcct ttagagtacc caactaaatg atggcaacta aaggcgaggg ttgcgctcgt     360
tgcgggactt aacccaacat ctcacgacac gagctgacga cagccatgca gcacctgtca     420
cctatccagc cgaactgaag gaaagtgtct ccacgatccg cgatagggat gtcaaacgtt     480
ggtaaggttc tgcgcgttgc ttcgaattaa accacatgct ccaccgcttg tgcaggcccc     540
cgtcaattcc tttgagtttt aatcttgcga ccgtactccc caggcggata acttaatgcg     600
ttagctgcgc cactgaaatg ccatgcaccc cagcagctag ttatcatcgt ttacggcgtg     660
gactaccagg gtatctaatc ctgtttgctc cccacgcttt cgcacctcag cgtcaacaat     720
cgtccagtga gccgccttcg ccactggtgt tcttccgaat atctacgaat ttcacctcta     780
cactcggaat tccactcacc tctccgatgt tcaagcaatc cagtctcaaa ggcagttccg     840
gggttgagcc ccgggctttc acctctgact taaatcgccg cctacgtgcg ctttacgccc     900
agtaattccg aacaacgcta gccccctccg tattaccgcg gctgctggca cggagttagc     960
cggggcttat tctcccggta ctgtcattat catcccgggg taaaagagct ttacaaccct    1020
aaggccttca tcactcacgc ggcattgctg gatcagg                             1057
```

<210> SEQ ID NO 270
<211> LENGTH: 1066
<212> TYPE: DNA
<213> ORGANISM: Polaromonas ginsengisoli
<220> FEATURE:
<221> NAME/KEY: misc_feature
<222> LOCATION: (1)..(1066)
<223> OTHER INFORMATION: BDNZ 66821 16S rDNA

<400> SEQUENCE: 270

```
cgccctcctt gcggttaggc taactacttc tggcagaacc cgctcccatg gtgtgacggg      60
cggtgtgtac aagacccggg aacgtattca ccgcgacatt ctgatccgcg attactagcg     120
attccgactt cacgtagtcg agttgcagac tacgatccgg actacgactg gttttatggg     180
attagctccc cctcgcgggt tggcaaccct ctgtaccagc cattgtatga cgtgtgtagc     240
cctacctata agggccatga ggacttgacg tcatcccac cttcctccgg tttgtcaccg     300
gcagtctcat tagagtgccc aactaaatgt agcaactaat gacaagggtt gcgctcgttg     360
cgggacttaa cccaacatct cacgacacga gctgacgaca gccatgcagc acctgttta     420
cggttctctt tcgagcacta agccatctct ggcgaattcc gtacatgtca aggtaggta     480
aggtttttcg cgttgcatcg aattaaacca catcatccac cgcttgtgcg ggtccccgtc     540
aattcctttg agtttcaacc ttgcggccgt actccccagg cggtcaactt cacgcgttag     600
```

| | |
|---|---|
| cttcgttact gagtactaat gcacccaaca accagttgac atcgtttagg gcgtggacta | 660 |
| ccagggtatc taatcctgtt tgctccccac gctttcgtgc atgagcgtca gtacaggtcc | 720 |
| aggggattgc cttcgccatc ggtgttcctc cgcatatcta cgcatttcac tgctacacgc | 780 |
| ggaattccat cccctctac cgtactctag ctatacagtc acagatgcaa ttcccaggtt | 840 |
| gagcccgggg atttcacaac tgtcttatat aaccgcctgc gcacgcttta cgcccagtaa | 900 |
| ttccgattaa cgctcgcacc ctacgtatta ccgcggctgc tggcacgtag ttagccggtg | 960 |
| cttattctta cggtaccgtc attagccctc tttattagaa aagagccgtt tcgttccgta | 1020 |
| caaaagcagt ttacaacccg gaaggccttc ttcctgcacg cggcat | 1066 |

<210> SEQ ID NO 271
<211> LENGTH: 979
<212> TYPE: DNA
<213> ORGANISM: Stenotrophomonas terrae
<220> FEATURE:
<221> NAME/KEY: misc_feature
<222> LOCATION: (1)..(979)
<223> OTHER INFORMATION: BDNZ 68599 16S rDNA

<400> SEQUENCE: 271

| | |
|---|---|
| ggttaagcta cctgcttctg gtgcaacaaa ctcccatggt gtgacgggcg gtgtgtacaa | 60 |
| ggcccgggaa cgtattcacc gcagcaatgc tgatctgcga ttactagcga ttccgacttc | 120 |
| atggagtcga gttgcagact ccaatccgga ctgagatagg gttctgggat tggcttacc | 180 |
| gtcgccggct tgcagccctc tgtccccacc attgtagtac gtgtgtagcc ctggccgtaa | 240 |
| gggccatgat gacttgacgt catccccacc ttcctccggt ttgtcaccgg cggtctcctt | 300 |
| agagttccca ccattacgtg ctggcaacta aggacaaggg ttgcgctcgt tgcgggactt | 360 |
| aacccaacat ctcacgacac gagctgacga cagccatgca gcacctgtgt tcgcgttccc | 420 |
| gaaggcacca atccatctct ggaaagttcg cgacatgtca aggccaggta aggttcttcg | 480 |
| cgttgcatcg aattaaacca catactccac cgcttgtgcg ggccccgtc aattcctttg | 540 |
| agtttcagtc ttgcgaccgt actccccagg cggcgaactt aacgcgttag cttcgatact | 600 |
| gcgtgccaaa ttgcacccaa catccagttc gcatcgttta gggcgtggac taccagggta | 660 |
| tctaatcctg tttgctcccc acgctttcgt gcctcagtgt cagtgttggc ccagacagtc | 720 |
| gccttcgcca cggatgttcc tcctgatctc tacgcatttc actgctacac caggaattcc | 780 |
| actatcctct gccacactct agtcgcccag tttccatcgc aattcccagg ttgagcccag | 840 |
| ggctttcacg acagacttaa acaaccacct acgcacgctt tacgcccagt aattccgagt | 900 |
| aacgcttgca cccttcgtat taccgcggct gctggcacga agttagccgg tgcttattct | 960 |
| ttgggtaccg tcagaacaa | 979 |

<210> SEQ ID NO 272
<211> LENGTH: 1086
<212> TYPE: DNA
<213> ORGANISM: Stenotrophomonas terrae
<220> FEATURE:
<221> NAME/KEY: misc_feature
<222> LOCATION: (1)..(1086)
<223> OTHER INFORMATION: BDNZ 68741 16S rDNA

<400> SEQUENCE: 272

| | |
|---|---|
| gcagcgccct cccgaaggtt aagctacctg cttctggtgc aacaaactcc catggtgtga | 60 |
| cgggcggtgt gtacaaggcc cgggaacgta ttcaccgcag caatgctgat ctgcgattac | 120 |
| tagcgattcc gacttcatgg agtcgagttg cagactccaa tccggactga gatagggttt | 180 |

```
ctgggattgg cttaccgtcg ccggcttgca gccctctgtc cccaccattg tagtacgtgt    240
gtagccctgg ccgtaagggc catgatgact tgacgtcatc cccaccttcc tccggtttgt    300
caccggcggt ctccttagag ttcccaccat tacgtgctgg caactaagga caagggttgc    360
gctcgttgcg ggacttaacc caacatctca cgacacgagc tgacgacagc catgcagcac    420
ctgtgttcgc gttcccgaag gcaccaatcc atctctggaa agttcgcgac atgtcaaggc    480
caggtaaggt tcttcgcgtt gcatcgaatt aaaccacata ctccaccgct tgtgcgggcc    540
cccgtcaatt cctttgagtt tcagtcttgc gaccgtactc cccaggcggc gaacttaacg    600
cgttagcttc gatactgcgt gccaaattgc acccaacatc cagttcgcat cgtttagggc    660
gtggactacc agggtatcta atcctgtttg ctccccacgc tttcgtgcct cagtgtcagt    720 gttgcccag acagtcgcct cgccacgga tgttcctcct gatctctacg catttcactg    780
ctacaccagg aattccacta tcctctgcca cactctagtc gcccagtttc catcgcaatt    840
cccaggttga gcccagggct ttcacgacag acttaaacaa ccacctacgc acgctttacg    900
cccagtaatt ccgagtaacg cttgcaccct tcgtattacc gcggctgctg cacgaagtt    960 agccggtgct tattctttgg gtaccgtcag aacaaccggg tattaaccag ctgcttttct    1020
ttcccaacaa aagggcttta caacccgaag gccttcttca cccacgcggt atggctggat    1080
caggct                                                                1086

<210> SEQ ID NO 273
<211> LENGTH: 1393
<212> TYPE: DNA
<213> ORGANISM: Stenotrophomonas maltophilia
<220> FEATURE:
<221> NAME/KEY: misc_feature
<222> LOCATION: (1)..(1393)
<223> OTHER INFORMATION: BDNZ54073 16S rDNA

<400> SEQUENCE: 273
ccgaaggtta agctacctgc ttctggtgca acaaactccc atggtgtgac gggcggtgtg     60
tacaaggccc gggaacgtat tcaccgcagc aatgctgatc tgcgattact agcgattccg    120
acttcatgga gtcgagttgc agactccaat ccggactgag atagggtttc tgggattggc    180
ttaccgtcgc cggcttgcag ccctctgtcc ctaccattgt agtacgtgtg tagccctggc    240
cgtaagggcc atgatgactt gacgtcatcc ccaccttcct ccggtttgtc accggcggtc    300
tccttagagt tcccaccatt acgtgctggc aactaaggac aagggttgcg ctcgttgcgg    360
gacttaaccc aacatctcac gacacgagct gacgacagcc atgcagcacc tgtgttcgag    420
ttcccgaagg caccaatcca tctctggaaa gttctcgaca tgtcaaggcc aggtaaggtt    480
cttcgcgttg catcgaatta aaccacatac tccaccgctt gtgcgggccc cgtcaattc    540 ctttgagttt cagtcttgcg accgtactcc ccaggcggcg aacttaacgc gttagcttcg    600
atactgcgtg ccaaattgca cccaacatcc agttcgcatc gtttagggcg tggactacca    660
gggtatctaa tcctgtttgc tccccacgct ttcgtgcctc agtgtcagtg ttggtccagg    720
tagctgcctt cgccatggat gttcctcccg atctctacgc atttcactgc tacaccggga    780
attccgctac cctctaccac actctagttg tccagtttcc actgcagttc ccaggttgag    840
cccagggctt tcacaacaga cttaaacaac cacctacgca cgctttacgc ccagtaattc    900
cgagtaacgc ttgcacccct tcgtattaccg cggctgctgg cacgaagtta gccggtgctt    960
attctttggg taccgtcatc ccaaccaggt attagccggc tggatttctt tcccaacaaa   1020
```

```
agggctttac aacccgaagg ccttcttcac ccacgcggta tggctggatc aggcttgcgc    1080
ccattgtcca atattcccca ctgctgcctc ccgtaggagt ctggaccgtg tctcagttcc    1140
agtgtggctg atcatcctct cagaccagct acggatcgtc gccttggtgg gcctttaccc    1200
cgccaactag ctaatccgac atcggctcat tcaatcgcgc aaggtccgaa gatccctgc     1260 tttcacccgt aggtcgtatg cggtattagc gtaagtttcc ctacgttatc ccccacgaaa    1320
aagtagattc cgatgtattc ctcacccgtc cgccactcgc cacccataag agcaagctct    1380
tactgtgctg ccg                                                       1393

<210> SEQ ID NO 274
<211> LENGTH: 1415
<212> TYPE: DNA
<213> ORGANISM: Rhodococcus erythropolis
<220> FEATURE:
<221> NAME/KEY: misc_feature
<222> LOCATION: (1)..(1415)
<223> OTHER INFORMATION: BDNZ54093 16S rDNA

<400> SEQUENCE: 274
tccctcccac aagggggttaa gccaccggct tcgggtgtta ccgactttca tgacgtgacg     60
ggcggtgtgt acaaggcccg ggaacgtatt caccgcagcg ttgctgatct gcgattacta    120
gcgactccga cttcacgggg tcgagttgca gaccccgatc cgaactgaga ccagctttaa    180
gggattcgct ccacctcacg gtctcgcagc cctctgtact ggccattgta gcatgtgtga    240
agccctggac ataaggggca tgatgacttg acgtcgtccc accttcctc cgagttgacc     300 ccggcagtct cttacgagtc cccaccataa cgtgctggca acataagata ggggttgcgc    360
tcgttgcggg acttaaccca acatctcacg acacgagctg acgacagcca tgcaccacct    420
gtataccgac cacaagggg gccacatctc tgcagctttc cggtatatgt caaacccagg    480
taaggttctt cgcgttgcat cgaattaatc cacatgctcc gccgcttgtg cgggcccccg    540
tcaattcctt tgagttttag ccttgcggcc gtactcccca ggcggggcgc ttaatgcgtt    600
agctacggca cggattccgt ggaaggaacc cacacctagc gcccaccgtt tacggcgtgg    660
actaccaggt tatctaatcc tgttcgctac ccacgctttc gttcctcagc gtcagttact    720
gcccagagac ccgccttcgc caccggtgtt cctcctgata tctgcgcatt tcaccgctac    780
accaggaatt ccagtctccc ctgcagtact caagtctgcc cgtatcgcct gcaagccagc    840
agttgagctg ctggttttca caaacgacgc gacaaaccgc ctacgaactc tttacgccca    900
gtaattccgg acaacgcttg caccctacgt attaccgcgg ctgctggcac gtagttagcc    960
ggtgcttctt ctgcaggtac cgtcacttgc gcttcgtccc tgctgaaaga ggtttacaac   1020
ccgaaggccg tcatccctca cgcggcgtcg ctgcatcagg cttttcgccca ttgtgcaata   1080 ttccccactg ctgcctcccg taggagtctg ggccgtgtct cagtcccagt gtggccggtc   1140
accctctcag gtcggctacc cgtcgtcgcc ttggtaggcc attacccccac caacaagctg   1200 ataggccgcg ggcccatcct gcaccgataa atctttccac cacccaccat gcgataggag   1260
gtcatatccg gtattagacc cagtttccca ggcttatccc gaagtgcagg gcagatcacc   1320
cacgtgttac tcacccgttc gccgctcgtg taccccgaaa ggccttaccg ctcgacttgc   1380
atgtgttaag cacgccgcca gcgttcgtcc tgagc                              1415

<210> SEQ ID NO 275
<211> LENGTH: 1406
<212> TYPE: DNA
<213> ORGANISM: Rhodococcus erythropolis
```

```
<220> FEATURE:
<221> NAME/KEY: misc_feature
<222> LOCATION: (1)..(1406)
<223> OTHER INFORMATION: BDNZ54299 16S rDNA

<400> SEQUENCE: 275
caaggggtta agccaccggc ttcgggtgtt accgactttc atgacgtgac gggcggtgtg      60
tacaaggccc gggaacgtat tcaccgcagc gttgctgatc tgcgattact agcgactccg     120
acttcacggg gtcgagttgc agaccccgat ccgaactgag accagcttta agggattcgc     180
tccacctcac ggtctcgcag ccctctgtac tggccattgt agcatgtgtg aagccctgga     240 cataagggggc atgatgactt gacgtcgtcc caccttcct ccgagttgac cccggcagtc     300
tcttacgagt ccccaccata acgtgctggc aacataagat aggggttgcg ctcgttgcgg     360
gacttaaccc aacatctcac gacacgagct gacgacagcc atgcaccacc tgtataccga     420
ccacaagggg ggccacatct ctgcagcttt ccggtatatg tcaaacccag gtaaggttct     480
tcgcgttgca tcgaattaat ccacatgctc cgccgcttgt gcgggccccc gtcaattcct     540
ttgagtttta gccttgcggc cgtactcccc aggcggggcg cttaatgcgt tagctacggc     600
acggattccg tggaaggaac ccacacctag cgcccaccgt ttacgcgtg gactaccagg      660 gtatctaatc ctgttcgcta cccacgcttt cgttcctcag cgtcagttac tgcccagaga     720
cccgccttcg ccaccggtgt tcctcctgat atctgcgcat ttcaccgcta caccaggaat     780
tccagtctcc cctgcagtac tcaagtctgc ccgtatcgcc tgcaagccag cagttgagct     840
gctggttttc acaaacgacg cgacaaaccg cctacgaact cttacgcccc agtaattccg     900
gacaacgctt gcaccctacg tattaccgcg gctgctggca cgtagttagc cggtgcttct     960
tctgcaggta ccgtcacttg cgcttcgtcc ctgctgaaag aggtttacaa cccgaaggcc    1020
gtcatccctc acgcggcgtc gctgcatcag gctttcgccc attgtgcaat attccccact    1080
gctgcctccc gtaggagtct gggccgtgtc tcagtcccag tgtggccggt caccctctca    1140
ggtcggctac ccgtcgtcgc cttggtaggc cattacccca ccaacaagct gataggccgc    1200
gggcccatcc tgcaccgata aatctttcca ccacccacca tgcgatagga gtcatatcc    1260 ggtattagac ccagtttccc aggcttatcc cgaagtgcag ggcagatcac ccacgtgtta    1320
ctcacccgtt cgccgctcgt gtaccccgaa aggccttacc gctcgacttg catgtgttaa    1380
gcacgccgcc agcgttcgtc ctgagc                                         1406

<210> SEQ ID NO 276
<211> LENGTH: 1426
<212> TYPE: DNA
<213> ORGANISM: Pseudomonas fluorescens
<220> FEATURE:
<221> NAME/KEY: misc_feature
<222> LOCATION: (1)..(1426)
<223> OTHER INFORMATION: BDNZ54480 16S rDNA

<400> SEQUENCE: 276
aggttagact agctacttct ggtgcaaccc actcccatgg tgtgacgggc ggtgtgtaca      60
aggcccggga acgtattcac cgcgacattc tgattcgcga ttactagcga ttccgacttc     120
acgcagtcga gttgcagact gcgatccgga ctacgatcgt ttttatggga ttagctccac     180
ctcgcggctt ggcaaccctt gtaccgacc attgtagcac gtgtgtagcc caggccgtaa     240
gggccatgat gacttgacgt catccccacc ttcctccggt ttgtcaccgg cagtctcctt     300
agagtgccca ccattacgtg ctggtaacta aggacaaggg ttgcgctcgt tacgggactt     360
```

| | |
|---|---|
| aacccaacat ctcacgacac gagctgacga cagccatgca gcacctgtct caatgttccc | 420 |
| gaaggcacca atccatctct ggaaagttca ttggatgtca aggcctggta aggttcttcg | 480 |
| cgttgcttcg aattaaacca catgctccac cgcttgtgcg ggccccgtc aattcatttg | 540 |
| agttttaacc ttgcggccgt actcccagg cggtcaactt aatgcgttag ctgcgccact | 600 |
| aagagctcaa ggctcccaac ggctagttga catcgtttac ggcgtggact accagggtat | 660 |
| ctaatcctgt ttgctcccca cgctttcgca cctcagtgtc agtatcagtc caggtggtcg | 720 |
| ccttcgccac tggtgttcct tcctatatct acgcatttca ccgctacaca ggaaattcca | 780 |
| ccaccctcta ccatactcta gctcgccagt tttggatgca gttcccaggt tgagcccggg | 840 |
| gatttcacat ccaacttaac gaaccaccta cgcgcgcttt acgcccagta attccgatta | 900 |
| acgcttgcac cctctgtatt accgcggctg ctggcacaga gttagccggt gcttattctg | 960 |
| tcggtaacgt caaaattgca gagtattaat ctacaaccct tcctcccaac ttaaagtgct | 1020 |
| ttacaatccg aagaccttct tcacacacgc ggcatggctg gatcaggctt tcgcccattg | 1080 |
| tccaatattc cccactgctg cctcccgtag gagtctggac cgtgtctcag ttccagtgtg | 1140 |
| actgatcatc ctctcagacc agttacggat cgtcgccttg gtgagccatt acctcaccaa | 1200 |
| ctagctaatc cgacctaggc tcatctgata gcgcaaggcc cgaaggtccc ctgctttctc | 1260 |
| ccgtaggacg tatgcggtat tagcgttcct ttcgaaacgt tgtcccccac taccaggcag | 1320 |
| attcctaggc attactcacc cgtccgccgc tgaatccggg agcaagctcc cttcatccgc | 1380 |
| tcgacttgca tgtgttaggc ctgccgccag cgttcaatct gagcga | 1426 |

<210> SEQ ID NO 277
<211> LENGTH: 1183
<212> TYPE: DNA
<213> ORGANISM: Herbaspirillum huttiense
<220> FEATURE:
<221> NAME/KEY: misc_feature
<222> LOCATION: (1)..(1183)
<223> OTHER INFORMATION: BDNZ54487 16S rDNA

<400> SEQUENCE: 277

| | |
|---|---|
| tcagattgaa cgctggcggc atgccttaca catgcaagtc gaacggcagc ataggagctt | 60 |
| gctcctgatg gcgagtggcg aacgggtgag taatatatcg gaacgtgccc tagagtgggg | 120 |
| gataactagt cgaaagacta gctaataccg catacgatct acggatgaaa gtggggatc | 180 |
| gcaagacctc atgctcctgg agcggccgat atctgattag ctagttggtg gggtaaaagc | 240 |
| ctaccaaggc aacgatcagt agctggtctg agaggacgac cagccacact gggactgaga | 300 |
| cacggcccag actcctacgg gaggcagcag tggggaattt tggacaatgg gggcaaccct | 360 |
| gatccagcaa tgccgcgtga gtgaagaagg ccttcgggtt gtaaagctct tttgtcaggg | 420 |
| aagaaacggt agtagcgaat aactattact aatgacggta cctgaagaat aagcaccggc | 480 |
| taactacgtg ccagcagccg cggtaatacg tagggtgcaa gcgttaatcg gaattactgg | 540 |
| gcgtaaagcg tgcgcaggcg gttgtgtaag tcagatgtga atccccggg ctcaacctgg | 600 |
| gaattgcatt tgagactgca cggctagagt gtgtcagagg ggggtagaat tccacgtgta | 660 |
| gcagtgaaat gcgtagatat gtggaggaat accgatggcg aaggcagccc ctgggataa | 720 |
| cactgacgct catgcacgaa agcgtgggga gcaaacagga ttagataccc tggtagtcca | 780 |
| cgccctaaac gatgtctact agttgtcggg tcttaattga cttggtaacg cagctaacgc | 840 |
| gtgaagtaga ccgcctgggg agtacggtcg caagattaaa actcaaagga attgacgggg | 900 |
| acccgcacaa gcggtggatg atgtggatta attcgatgca acgcgaaaaa ccttacctac | 960 |

```
ccttgacatg gatggaatcc cgaagagatt tgggagtgct cgaaagagaa ccatcacaca    1020
ggtgctgcat ggctgtcgtc agctcgtgtc gtgagatgtt gggttaagtc ccgcaacgag    1080
cgcaaccctt gtcattagtt gctacgaaag ggcactctaa tgagactgcc gggtgacaaa    1140 ccggaggaa ggtgggggat gacgtcaagt cctcatggcc ctt                       1183
```

<210> SEQ ID NO 278
<211> LENGTH: 1302
<212> TYPE: DNA
<213> ORGANISM: Pantoea agglomerans
<220> FEATURE:
<221> NAME/KEY: misc_feature
<222> LOCATION: (1)..(1302)
<223> OTHER INFORMATION: BDNZ54499 16S rDNA

<400> SEQUENCE: 278

```
gggggataac cactggaaaa cggtggctaa taccgcataa cgtcgcaaga ccaaagaggg     60
ggaccttcgg gcctctcact atcggatgaa cccagatggg attagctagt aggcggggta   120
atggcccacc taggcgacga tccctagctg gtctgagagg atgaccagcc acactggaac   180
tgagacacgg tccagactcc tacgggaggc agcagtgggg aatattgcac aatgggcgca   240
agcctgatgc agccatgccg cgtgtatgaa gaaggccttc gggttgtaaa gtactttcag   300
cggggaggaa ggcgacgggg ttaataaccg ygtcgattga cgttacccgc agaagaagca   360
ccggctaact ccgtgccagc agccgcggta atacggaggg tgcaagcgtt aatcggaatt   420
actgggcgta aagcgcacgc aggcggtctg ttaagtcaga tgtgaaatcc ccgggcttaa   480
cctgggaact gcatttgaaa ctggcaggct tgagtcttgt agaggggggt agaattccag   540
gtgtagcggt gaaatgcgta gagatctgga ggaataccgg tggcgaaggc ggcccccctgg  600 acaaagactg acgctcaggt gcgaaagcgt ggggagcaaa caggattaga taccctggta   660
gtccacgccg taaacgatgt cgacttggag gttgttccct tgaggagtgg cttccggagc   720
taacgcgtta agtcgaccgc ctgggagta cggccgcaag gttaaaactc aaatgaattg    780 acggggggccc gcacaagcgg tggagcatgt ggtttaattc gatgcaacgc gaagaacctt   840
acctactctt gacatccacg gaatttggca gagatgcctt agtgccttcg ggaaccgtga   900
gacaggtgct gcatggctgt cgtcagctcg tgttgtgaaa tgttgggtta agtcccgcaa   960
cgagcgcaac ccttatcctt tgttgccagc gattcggtcg ggaactcaaa ggagactgcc  1020
ggtgataaac cggaggaagg tgggatgac gtcaagtcat catggccctt acgagtaggg  1080
ctacacacgt gctacaatgg cgcatacaaa gagaagcgac ctcgcgagag caagcggacc  1140
tcacaaagtg cgtcgtagtc cggatcggag tctgcaactc gactccgtga agtcggaatc  1200
gctagtaatc gtggatcaga atgccacggt gaatacgttc ccgggccttg tacacaccgc  1260
ccgtcacacc atgggagtgg gttgcaaaag aagtaggtag ct                    1302
```

<210> SEQ ID NO 279
<211> LENGTH: 1452
<212> TYPE: DNA
<213> ORGANISM: Bacillus megaterium
<220> FEATURE:
<221> NAME/KEY: misc_feature
<222> LOCATION: (1)..(1452)
<223> OTHER INFORMATION: BDNZ55076 16S rDNA

<400> SEQUENCE: 279

```
gcggctagct ccttacggtt actccaccga cttcgggtgt tacaaactct cgtggtgtga    60
```

| | |
|---|---|
| cgggcggtgt gtacaaggcc cgggaacgta ttcaccgcgg catgctgatc cgcgattact | 120 |
| agcgattcca gcttcatgta ggcgagttgc agcctacaat ccgaactgag aatggtttta | 180 |
| tgggattggc ttgacctcgc ggtcttgcag ccctttgtac catccattgt agcacgtgtg | 240 |
| tagcccaggt cataagggc atgatgattt gacgtcatcc ccaccttcct ccggtttgtc | 300 |
| accggcagtc accttagagt gcccaactra atgctggcaa ctaagatcaa gggttgcgct | 360 |
| cgttgcggga cttaacccaa catctcacga cacgagctga cgacaaccat gcaccacctg | 420 |
| tcactctgtc ccccgaaggg gaacgctcta tctctagagt tgtcagagga tgtcaagacc | 480 |
| tggtaaggtt cttcgcgttg cttcgaatta aaccacatgc tccaccgctt gtgcgggccc | 540 |
| ccgtcaattc ctttgagttt cagtcttgcg accgtactcc ccaggcggag tgcttaatgc | 600 |
| gttagctgca gcactaaagg gcggaaaccc tctaacactt agcactcatc gtttacggcg | 660 |
| tggactacca gggtatctaa tcctgtttgc tccccacgct ttcgcgcctc agcgtcagtt | 720 |
| acagaccaaa aagccgcctt cgccactggt gttcctccac atctctacgc atttcaccgc | 780 |
| tacacgtgga attccgcttt tctcttctgc actcaagttc cccagtttcc aatgaccctc | 840 |
| cacggttgag ccgtgggctt tcacatcaga cttaagaaac cgcctgcgcg cgctttacgc | 900 |
| ccaataattc cggataacgc ttgccaccta cgtattaccg cggctgctgg cacgtagtta | 960 |
| gccgtggctt tctggttagg taccgtcaag gtacgagcag ttactctcgt acttgttctt | 1020 |
| ccctaacaac agagttttac gacccgaaag ccttcatcac tcacgcggcg ttgctccgtc | 1080 |
| agactttcgt ccattgcgga agattcccta ctgctgcctc ccgtaggagt ctgggccgtg | 1140 |
| tctcagtccc agtgtggccg atcaccctct caggtcggct atgcatcgtt gccttggtga | 1200 |
| gccgttacct caccaactag ctaatgcacc gcgggcccat ctgtaagtga tagccgaaac | 1260 |
| catctttcaa tcatctccca tgaaggagaa gatcctatcc ggtattagct tcggtttccc | 1320 |
| gaagttatcc cagtcttaca ggcaggttgc ccacgtgtta ctcacccgtc cgccgctaac | 1380 |
| gtcatagaag caagcttcta atcagttcgc tcgacttgca tgtattaggc acgccgccag | 1440 |
| cgttcatcct ga | 1452 |

<210> SEQ ID NO 280
<211> LENGTH: 1448
<212> TYPE: DNA
<213> ORGANISM: Paenibacillus polymyxa
<220> FEATURE:
<221> NAME/KEY: misc_feature
<222> LOCATION: (1)..(1448)
<223> OTHER INFORMATION: BDNZ55146 16S rDNA

<400> SEQUENCE: 280

| | |
|---|---|
| ccttgcgggt tccccaccga cttcgggtgt tgtaaactct cgtggtgtga cgggcggtgt | 60 |
| gtacaagacc cgggaacgta ttcaccgcgg catgctgatc cgcgattact agcaattccg | 120 |
| acttcatgta ggcgagttgc agcctacaat ccgaactgag accggctttt ctaggattgg | 180 |
| ctccacctcg cggcttcgct tcccgttgta ccggccattg tagtacgtgt gtagcccagg | 240 |
| tcataagggg catgatgatt tgacgtcatc cccaccttcc tccggtttgt caccggcagt | 300 |
| ctgcttagag tgcccagctt gacctgctgg caactaagca taagggttgc gctcgttgcg | 360 |
| ggacttaacc caacatctca cgacacgagc tgacgacaac catgcaccac ctgtctcctc | 420 |
| tgtcccgaag gaaagccata tctctacagc ggtcagaggg atgtcaagac ctggtaaggt | 480 |
| tcttcgcgtt gcttcgaatt aaaccacata ctccactgct gtgcgggtc cccgtcaatt | 540 |
| cctttgagtt tcagtcttgc gaccgtactc cccaggcgga atgcttaatg tgttaacttc | 600 |

```
ggcaccaagg gtatcgaaac ccctaacacc tagcattcat cgtttacggc gtggactacc      660
agggtatcta atcctgtttg ctccccacgc tttcgcgcct cagcgtcagt tacagcccag      720
agagtcgcct tcgccactgg tgttcctcca catctctacg catttcaccg ctacacgtgg      780
aattccactc tcctcttctg cactcaagct ccccagtttc cagtgcgacc cgaagttgag      840
cctcgggatt aaacaccaga cttaaagagc cgcctgcgcg cgctttacgc ccaataattc      900
cggacaacgc ttgcccccta cgtattaccg cggctgctgg cacgtagtta gccgggcctt      960
tcttctcagg taccgtcact cttgtagcag ttactctaca agacgttctt ccctggcaac     1020
agagctttac gatccgaaaa ccttcatcac tcacgcggcg ttgctccgtc aggctttcgc     1080
ccattgcgga agattcccta ctgctgcctc ccgtaggagt ctgggccgtg tctcagtccc     1140
agtgtggccg atcaccctct caggtcggct acgcatcgtc gccttggtag gcctttaccc     1200
caccaactag ctaatgcgcc gcaggcccat ccacaagtga cagattgctc cgtctttcct     1260
ccttcgccca tgcaggaaaa ggatgtatcg ggtattagct accgtttccg gtagttatcc     1320
ctgtcttgtg ggcaggttgc ctacgtgtta ctcacccgtc cgccgctagg ttatttagaa     1380
gcaagcttct aaataacccc gctcgacttg catgtattag gcacgccgcc agcgttcgtc     1440
ctgagcga                                                              1448

<210> SEQ ID NO 281
<211> LENGTH: 1424
<212> TYPE: DNA
<213> ORGANISM: Massilia niastensis
<220> FEATURE:
<221> NAME/KEY: misc_feature
<222> LOCATION: (1)..(1424)
<223> OTHER INFORMATION: BDNZ55184 16S rDNA

<400> SEQUENCE: 281
cctccttgcg gttagctacc tacttctggt aaaacccgct cccatggtgt gacgggcggt       60
gtgtacaaga cccgggaacg tattcaccgc gacatgctga tccgcgatta ctagcgattc      120
caacttcacg cagtcgagtt gcagactgcg atccggacta cgatacactt tctgggatta      180 gctcccctc gcgggttggc ggccctctgt atgtaccatt gtatgacgtg tgaagcccta       240
cccataaggg ccatgaggac ttgacgtcat ccccaccttc ctccggtttg tcaccggcag      300
tctcattaga gtgccctttc gtagcaacta atgacaaggg ttgcgctcgt tgcgggactt      360
aacccaacat ctcacgacac gagctgacga cagccatgca gcacctgtgt tcaggctccc      420
tttcgggcac tcyccgatct ctcgaagatt cctgacatgt caagggtagg taaggttttt      480
cgcgttgcat cgaattaatc cacatcatcc accgcttgtg cgggtccccg tcaattcctt      540
tgagttttaa tcttgcgacc gtactcccca ggcggtctac ttcacgcgtt agctgcgtta      600
ccaagtcaat taagacccga caactagtag acatcgttta gggcgtggac taccagggta      660
tctaatcctg tttgctcccc acgctttcgt gcatgagcgt cagtcttgac ccaggggct      720 gccttcgcca tcggtgttcc tccacatctc tacgcatttc actgctacac gtggaattct      780
acccccctct gccagactcc agccttgcag tctccaacgc aattcccagg ttgagcccgg      840
ggatttcacg tcagacttac aaaaccgcct gcgcacgctt tacgcccagt aattccgatt      900
aacgcttgca ccctacgtat taccgcggct gctggcacgt agttagccgg tgcttattct      960
tcaggtaccg tcattagccg aggatattag ccccaaccgt tcttccctg acaaaagagc     1020 tttacaaccc gaaggccttc ttcactcacg cggcattgct ggatcaggct tgcgcccatt     1080
```

-continued

```
gtccaaaatt ccccactgct gcctcccgta ggagtctggg ccgtgtctca gtcccagtgt    1140
ggctggtcgt cctctcagac cagctactga tcgtcgcctt ggtgagcctt acctcacca     1200 actagctaat cagacatcgg ccgctccaaa agcatgaggt cttgcgatcc cccactttct    1260
tccgtagaac gtatgcggta ttagcgtaac tttcgctacg ttatccccca cttctgggta    1320
cgttccgatg tattactcac ccgttcgcca ctcgccgcca ggttgccccg cgctgccgtt    1380
cgacttgcat gtgtaaagca tgccgccagc gttcaatctg agcg                    1424
```

<210> SEQ ID NO 282
<211> LENGTH: 1357
<212> TYPE: DNA
<213> ORGANISM: Pantoea vagans
<220> FEATURE:
<221> NAME/KEY: misc_feature
<222> LOCATION: (1)..(1357)
<223> OTHER INFORMATION: BDNZ55529 16S rDNA

<400> SEQUENCE: 282

```
ggttaagcta cctacttctt ttgcaaccca ctcccatggt gtgacgggcg gtgtgtacaa      60
ggcccgggaa cgtattcacc gtggcattct gatccacgat tactagcgat tccgacttca    120
cggagtcgag ttgcagactc cgatccggac tacgacgcac tttgtgaggt ccgcttgctc    180
tcgcgaggtc gcttctcttt gtatgcgcca ttgtagcacg tgtgtagccc tactcgtaag    240
ggccatgatg acttgacgtc atccccacct tcctccggtt tatcaccggc agtctccttt    300
gagttcccga ccgaatcgct ggcaacaaag gataagggtt gcgctcgttg cgggacttaa    360
cccaacattt cacaacacga gctgacgaca gccatgcagc acctgtctca gcgttcccga    420
aggcaccaaa gcatctctgc taagttcgct ggatgtcaag agtaggtaag gttcttcgcg    480
ttgcatcgaa ttaaaccaca tgctccaccg cttgtgcggg cccccgtcaa ttcatttgag    540
ttttaacctt gcggccgtac tccccaggcg gtcgacttaa cgcgttagct ccggaagcca    600
ctcctcaagg gaacaacctc caagtcgaca tcgtttacgg cgtggactac cagggtatct    660
aatcctgttt gctccccacg ctttcgcacc tgagcgtcag tctttgtcca gggggccgcc    720
ttcgccaccg gtattcctcc agatctctac gcatttcacc gctacacctg gaattctacc    780
cccctctaca agactcaagc ctgccagttt caaatgcagt tcccaggtta agcccgggga    840
tttcacatct gacttaacag accgcctgcg tgcgctttac gcccagtaat tccgattaac    900
gcttgcaccc tccgtattac cgcggctgct ggcacggagt tagccggtgc ttcttctgcg    960
ggtaacgtca atcgacaggg ttattaaccc cgtcgccttc ctccccgctg aaagtacttt   1020
acaacccgaa ggccttcttc atacacgcgg catggctgca tcaggcttgc gcccattgtg   1080
caatattccc cactgctgcc tcccgtagga gtctggaccg tgtctcagtt ccagtgtggc   1140
tggtcatcct ctcagaccag ctagggatcg tcgcctaggt gggccattac cccgcctact   1200
agctaatccc atctgggttc atccgatagt gagaggcccg aaggtccccc tctttggtct   1260
tgcgacgtta tgcggtatta gccaccgttt ccagtggtta tccccctcta tcgggcagat   1320
ccccagacat tactcacccg tccgccactc gtcaccc                              1357
```

<210> SEQ ID NO 283
<211> LENGTH: 1400
<212> TYPE: DNA
<213> ORGANISM: Pseudomonas oryzihabitans
<220> FEATURE:
<221> NAME/KEY: misc_feature
<222> LOCATION: (1)..(1400)
<223> OTHER INFORMATION: BDNZ55530 16S rDNA

<400> SEQUENCE: 283

```
cgagggttag actagctact tctggagcaa cccactccca tggtgtgacg ggcggtgtgt      60
acaaggcccg ggaacgtatt caccgtgacg ttctgattca cgattactag cgattccgac     120
ttcacgcagt cgagttgcag actgcgatcc ggactacgat cggttttatg ggattagctc     180
cacctcgcgg cttggcaacc ctttgtaccg accattgtag cacgtgtgta gccctggccg     240
taagggccat gatgacttga cgtcatcccc accttcctcc ggtttgtcac cggcagtctc     300
cttagagtgc ccaccataac gtgctggtaa ctaaggacaa gggttgcgct cgttacggga     360
cttaacccaa catctcacga cacgagctga cgacagccat gcagcacctg tgtctgagtt     420
cccgaaggca ccaatccatc tctggaaagt tctcagcatg tcaaggccag gtaaggttct     480
tcgcgttgct tcgaattaaa ccacatgctc caccgcttgt gcgggccccc gtcaattcat     540
ttgagttttta accttgcggc cgtactcccc aggcggtcaa cttaatgcgt tagctgcgcc     600
actaagatct caaggatccc aacggctagt tgacatcgtt tacggcgtgg actaccaggg     660
tatctaatcc tgtttgctcc ccacgctttc gcacctcagt gtcagtgtca gtccaggtag     720
tcgccttcgc cactggtgtt ccttccaata tctacgcatt tcaccgctac actggaaatt     780
ccactaccct ctaccgcact ctagccagac agttttggat gcagttccca ggttgagccc     840
ggggatttca catccaactt atcaagccac ctacgcgcgc tttacgccca gtaattccga     900
ttaacgcttg caccttcgt attaccgcgg ctgctggcac gaagttagcc ggtgcttatt     960
ctgttggtaa cgtcaaaact cacaggtatt cgctatgagc ccttcctccc aacttaaagt    1020
gctttacgac ccgaaggcct tcttcacaca cgcggcatgg ctggatcagg ctttcgccca    1080
ttgtccaata ttccccactg ctgcctcccg taggagtctg gaccgtgtct cagttccagt    1140
gtgactgatc atcctctcag accagttacg gatcgtcgcc ttggtaggcc tttaccctac    1200
caactagcta atccgaccta ggctcatcta atagcgtgag gtccgaagat cccccacttt    1260
ctcccgtagg acgtatgcgg tattagcgtt cctttcgaaa cgttgtcccc cactactagg    1320
cagattccta ggcattactc acccgtccgc cgctgaatcg aagagcaagc tcctctcatc    1380
cgctcgactt gcatgtgtta                                                 1400
```

<210> SEQ ID NO 284
<211> LENGTH: 974
<212> TYPE: DNA
<213> ORGANISM: Pseudomonas fluorescens
<220> FEATURE:
<221> NAME/KEY: misc_feature
<222> LOCATION: (1)..(974)
<223> OTHER INFORMATION: BDNZ56249 16S rDNA

<400> SEQUENCE: 284

```
ggttagacta gctacttctg gtgcaaccca ctcccatggt gtgacgggcg gtgtgtacaa      60
ggcccgggaa cgtattcacc gcgacattct gattcgcgat tactagcgat tccgacttca     120
cgcagtcgag ttgcagactg cgatccggac tacgatcggt tttatgggat tagctccacc     180
tcgcggcttg caacccttt gtaccgacca ttgtagcacg tgtgtagccc aggccgtaag     240
ggccatgatg acttgacgtc atccccacct tcctccggtt tgtcaccggc agtctcctta     300
gagtgcccac cattacgtgc tggtaactaa ggacaagggt tgcgctcgtt acgggactta     360
acccaacatc tcacgacacg agctgacgac agccatgcag cacctgtctc aatgttcccg     420
aaggcaccaa tccatctctg gaaagttcat tggatgtcaa ggcctggtaa ggttcttcgc     480
```

```
gttgcttcga attaaaccac atgctccacc gcttgtgcgg gcccccgtca attcatttga        540
gttttaacct tgcggccgta ctccccaggc ggtcaactta atgcgttagc tgcgccacta        600
agagctcaag gctcccaacg gctagttgac atcgtttacg gcgtggacta ccagggtatc        660
taatcctgtt tgctccccac gctttcgcac ctcagtgtca gtatcagtcc aggtggtcgc        720
cttcgccact ggtgttcctt cctatatcta cgcatttcac cgctacacag gaaattccac        780
caccctctac catactctag ctcgccagtt ttggatgcag ttcccaggtt gagcccgggg        840
atttcacatc caacttaacg aaccacctac gcgcgcttta cgcccagtaa ttccgattaa        900
cgcttgcacc ctctgtatta ccgcggctgc tggcacagag ttagccggtg cttattctgt        960
cggtaacgtc aaaa                                                         974

<210> SEQ ID NO 285
<211> LENGTH: 974
<212> TYPE: DNA
<213> ORGANISM: Pseudomonas fluorescens
<220> FEATURE:
<221> NAME/KEY: misc_feature
<222> LOCATION: (1)..(974)
<223> OTHER INFORMATION: BDNZ56530 16S rDNA

<400> SEQUENCE: 285
ggttagacta gctacttctg gtgcacccca ctcccatggt gtgacgggcg gtgtgtacaa         60
ggcccgggaa cgtattcacc gcgacattct gattcgcgat tactagcgat tccgacttca        120
cgcagtcgag ttgcagactg cgatccggac tacgatcggt tttatgggat tagctccacc        180
tcgcggcttg gcaaccctct gtaccgacca ttgtagcacg tgtgtagccc aggccgtaag        240
ggccatgatg acttgacgtc atccccacct tcctccggtt tgtcaccggc agtctcctta        300
gagtgcccac cataacgtgc tggtaactaa ggacaagggt tgcgctcgtt acgggactta        360
acccaacatc tcacgacacg agctgacgac agccatgcag cacctgtctc aatgttcccg        420
aaggcaccaa tctatctcta gaaagttcat ggatgtcaa ggcctggtaa ggttcttcgc        480
gttgcttcga attaaaccac atgctccacc gcttgtgcgg gcccccgtca attcatttga        540
gttttaacct tgcggccgta ctccccaggc ggtcaactta atgcgttagc tgcgccacta        600
aaagctcaag gcttccaacg gctagttgac atcgtttacg gcgtggacta ccagggtatc        660
taatcctgtt tgctccccac gctttcgcac ctcagtgtca gtattagtcc aggtggtcgc        720
cttcgccact ggtgttcctt cctatatcta cgcatttcac cgctacacag gaaattccac        780
caccctctac catactctag tcagtcagtt ttgaatgcag ttcccaggtt gagcccgggg        840
atttcacatc caacttaaca aaccacctac gcgcgcttta cgcccagtaa ttccgattaa        900
cgcttgcacc ctctgtatta ccgcggctgc tggcacagag ttagccggtg cttattctgt        960
cggtaacgtc aaaa                                                         974

<210> SEQ ID NO 286
<211> LENGTH: 968
<212> TYPE: DNA
<213> ORGANISM: Rahnella aquatilis
<220> FEATURE:
<221> NAME/KEY: misc_feature
<222> LOCATION: (1)..(968)
<223> OTHER INFORMATION: BDNZ56532 16S rDNA

<400> SEQUENCE: 286
gctacctact tcttttgcaa cccactccca tggtgtgacg ggcggtgtgt acaaggcccg         60
ggaacgtatt caccgtagca ttctgatcta cgattactag cgattccgac ttcatggagt        120
```

```
cgagttgcag actccaatcc ggactacgac atactttatg aggtccgctt gctctcgcga    180
gttcgcttct ctttgtatat gccattgtag cacgtgtgta gccctactcg taagggccat    240
gatgacttga cgtcatcccc accttcctcc ggtttatcac cggcagtctc ctttgagttc    300
ccaccattac gtgctggcaa caaaggataa gggttgcgct cgttgcggga cttaacccaa    360
catttcacaa cacgagctga cgacagccat gcagcacctg tctcacggtt cccgaaggca    420
ctaagccatc tctggcgaat tccgtggatg tcaagagtag gtaaggttct tcgcgttgca    480
tcgaattaaa ccacatgctc accgcttgt gcgggccccc gtcaattcat ttgagtttta    540
accttgcggc cgtactcccc aggcggtcga cttaacgcgt tagctccgga agccacgcct    600
caagggcaca acctccaagt cgacatcgtt tacagcgtgg actaccaggg tatctaatcc    660
tgtttgctcc ccacgctttc gcacctgagc gtcagtcttt gtccaggggg ccgcttcgc    720
caccggtatt cctccagatc tctacgcatt tcaccgctac acctggaatt ctacccccct    780
ctacaagact ctagcttgcc agtttcaaat gcagttccca cgttaagcgc ggggatttca    840
catctgactt aacaaaccgc ctgcgtgcgc tttacgccca gtaattccga ttaacgcttg    900
caccctccgt attaccgcgg ctgctggcac ggagttagcc ggtgcttctt ctgcgagtaa    960
cgtcaatc                                                             968
```

<210> SEQ ID NO 287
<211> LENGTH: 986
<212> TYPE: DNA
<213> ORGANISM: Rahnella aquatilis
<220> FEATURE:
<221> NAME/KEY: misc_feature
<222> LOCATION: (1)..(986)
<223> OTHER INFORMATION: BDNZ57157 16S rDNA

<400> SEQUENCE: 287

```
gcgccctccc gaaggttaag ctacctactt cttttgcaac ccactcccat ggtgtgacgg    60
gcggtgtgta caaggcccgg gaacgtattc accgtagcat tctgatctac gattactagc   120
gattccgact tcatggagtc gagttgcaga ctccaatccg gactacgaca tactttatga   180
ggtccgcttg ctctcgcgag ttcgcttctc tttgtatatg ccattgtagc acgtgtgtag   240
ccctactcgt aagggccatg atgacttgac gtcatcccca ccttcctccg gtttatcacc   300
ggcagtctcc tttgagttcc caccattacg tgctggcaac aaaggataag ggttgcgctc   360
gttgcgggac ttaacccaac atttcacaac acgagctgac gacagccatg cagcacctgt   420
ctcacggttc ccgaaggcac taagccatct ctggcgaatt ccgtggatgt caagagtagg   480
taaggttctt cgcgttgcat cgaattaaac cacatgctcc accgcttgtg cgggccccccg    540
tcaattcatt tgagttttaa ccttgcggcc gtactcccca ggcggtcgac ttaacgcgtt   600
agctccggaa gccacgcctc aagggcacaa cctccaagtc gacatcgttt acagcgtgga   660
ctaccagggt atctaatcct gtttgctccc cacgctttcg cacctgagcg tcagtctttg   720
tccaggggc cgccttcgcc accggtattc ctccagatct ctacgcattt caccgctaca   780
cctggaattc taccccctc tacaagactc tagcttgcca gtttcaaatg cagttcccac   840
gttaagcgcg gggatttcac atctgactta acaaaccgcc tgcgtgcgct ttacgcccag   900
taattccgat taacgcttgc accctccgta ttaccgcggc tgctggcacg gagttagccg   960
gtgcttcttc tgcgagtaac gtcaat                                        986
```

<210> SEQ ID NO 288

```
<211> LENGTH: 987
<212> TYPE: DNA
<213> ORGANISM: Pantoea agglomerans
<220> FEATURE:
<221> NAME/KEY: misc_feature
<222> LOCATION: (1)..(987)
<223> OTHER INFORMATION: BDNZ57547 16S rDNA

<400> SEQUENCE: 288
agcgccctcc cgaaggttaa gctacctact tcttttgcaa cccactccca tggtgtgacg      60
ggcggtgtgt acaaggcccg ggaacgtatt caccgtggca ttctgatcca cgattactag     120
cgattccgac ttcatggagt cgagttgcag actccaatcc ggactacgac atactttatg     180
aggtccgctt gctctcgcga ggtcgcttct ctttgtatat gccattgtag cacgtgtgta     240
gccctggtcg taagggccat gatgacttga cgtcatcccc accttcctcc agtttatcac     300
tggcagtctc ctttgagttc ccggccggac cgctggcaac aaaggataag ggttgcgctc     360
gttgcgggac ttaacccaac atttcacaac acgagctgac gacagccatg cagcacctgt     420
ctcacggttc ccgaaggcac taaggcatct ctgccaaatt ccgtggatgt caagaccagg     480
taaggttctt cgcgttgcat cgaattaaac cacatgctcc accgcttgtg cgggccccg      540
tcaattcatt tgagttttaa ccttgcggcc gtactcccca ggcggtcgac ttaacgcgtt     600
agctccggaa gccacgcctc aagggcacaa cctccaagtc gacatcgttt acggcgtgga     660
ctaccagggt atctaatcct gtttgctccc cacgctttcg cacctgagcg tcagtctttg     720
tccaggggc cgccttcgcc accggtattc ctccagatct ctacgcattt caccgctaca     780
cctggaattc tacccccctc tacaagactc aagcctgcca gtttcgaatg cagttcccag     840
gttgagcccg gggatttcac atccgacttg acagaccgcc tgcgtgcgct ttacgcccag     900
taattccgat taacgcttgc accctccgta ttaccgcggc tgctggcacg gagttagccg     960
gtgcttcttc tgcgggtaac gtcaatc                                         987

<210> SEQ ID NO 289
<211> LENGTH: 1103
<212> TYPE: DNA
<213> ORGANISM: Azotobacter chroococcum
<220> FEATURE:
<221> NAME/KEY: misc_feature
<222> LOCATION: (1)..(1103)
<223> OTHER INFORMATION: BDNZ57597 16S rDNA

<400> SEQUENCE: 289
cccgaaggtt agactagcta cttctggagc aacccactcc catggtgtga cgggcggtgt      60
gtacaaggcc cgggaacgta ttcaccgcga cattctgatt cgcgattact agcgattccg     120
acttcacgca gtcgagttgc agactgcgat ccgactacg atcggttttc tgggattggc     180
tccgcctcgc gacttggcaa ccctctgtac cgaccattgt agcacgtgtg tagccctggc     240
cgtaagggcc atgatgactt gacgtcatcc ccaccttcct ccggtttgtc accggcagtc     300
tccttagagt gcccacccga ggtgctggta actaaggaca agggttgcgc tcgttacggg     360
acttaaccca acatctcacg acacgagctg acgacagcca tgcagcacct gtgtctgagt     420
tcccgaaggc accaatccat ctctggaaag ttctcagcat gtcaaggcca ggtaaggttc     480
ttcgcgttgc ttcgaattaa accacatgct ccaccgcttg tgcgggcccc cgtcaattca     540
tttgagtttt aaccttgcgg ccgtactccc caggcggtcg acttaatgcg ttagctgcgc     600
cactaagctc tcaaggagcc caacggctag tcgacatcgt ttacgcgtgt gactaccagg     660
gtatctaatc ctgtttgctc cccacgcttt cgcacctcag tgtcagtatc agtccaggtg     720
```

-continued

```
gtcgccttcg ccactggtgt tccttcctat atctacgcat ttcaccgcta cacaggaaat    780
tccaccaccc tctaccgtac tctagtcagg cagttttgga tgcagttccc aggttgagcc    840
cggggctttc acatccaact taccaaacca cctacgcgcg ctttacgccc agtaattccg    900
attaacgctt gcacccttcg tattaccgcg gctgctggca cgaagttagc cggtgcttat    960
tctgtcggta acgtcaaaac tgcaaggtat tcgcttacag cccttcctcc caacttaaag   1020
tgctttacaa tccgaagacc ttcttcacac acgcggcatg gctggatcag gctttcgccc   1080
attgtccaat attccccact gct                                           1103
```

<210> SEQ ID NO 290
<211> LENGTH: 1018
<212> TYPE: DNA
<213> ORGANISM: Paenibacillus chondroitinus
<220> FEATURE:
<221> NAME/KEY: misc_feature
<222> LOCATION: (1)..(1018)
<223> OTHER INFORMATION: BDNZ57634 16S rDNA

<400> SEQUENCE: 290

```
cccgaaggtt agactagcta cttctggtgc aacccactcc catggtgtga cgggcggtgt     60
gtacaaggcc cgggaacgta ttcaccgcga cattctgatt cgcgattact agcgattccg    120
acttcacgca gtcgagttgc agactgcgat ccggactacg atcggttttg tgggattagc    180
tccacctcgc ggcttggcaa ccctctgtac cgaccattgt agcacgtgtg tagcccaggc    240
cgtaagggcc atgatgactt gacgtcatcc ccaccttcct ccggtttgtc accggcagtc    300
tccttagagt gcccaccatg acgtgctggt aactaaggac aagggttgcg ctcgttacgg    360
gacttaaccc aacatctcac gacacgagct gacgacagcc atgcagcacc tgtctcaatg    420
ttcccgaagg caccaatcca tctctggaaa gttcattgga tgtcaaggcc tggtaaggtt    480
cttcgcgttg cttcgaatta aaccacatgc tccaccgctt gtgcgggccc cgtcaattc    540 atttgagttt taaccttgcg gccgtactcc ccaggcggtc aacttaatgc gttagctgcg    600
ccactaagag ctcaaggctc ccaacggcta gttgacatcg tttacggcgt ggactaccag    660
ggtatctaat cctgtttgct ccccacgctt tcgcacctca gtgtcagtat cagtccaggt    720
ggtcgccttc gccactggtg ttccttccta tatctacgca tttcaccgct acacaggaaa    780
ttccaccacc ctctaccata ctctagcttg gcagttttga atgcagttcc caggttgagc    840
ccggggcttt cacatccaac ttaacaaacc cctacgcgc gctttacgcc cagtaattcc    900
gattaacgct tgcaccctct gtattaccgc ggctgctggc acagagttag ccggtgctta    960
ttctgtcggt acgtcaaaca ctaacgtatt agggtaatgc cctcctccca acttaaag    1018
```

<210> SEQ ID NO 291
<211> LENGTH: 1055
<212> TYPE: DNA
<213> ORGANISM: Azospirillum lipoferum
<220> FEATURE:
<221> NAME/KEY: misc_feature
<222> LOCATION: (1)..(1055)
<223> OTHER INFORMATION: BDNZ57661 16S rDNA

<400> SEQUENCE: 291

```
agtcgaacga aggcttcggc cttagtggcg cacgggtgag taacacgtgg gaacctgcct     60
ttcggttcgg aataacgttt ggaaacgaac gctaacaccg gatacgccct tcggggggaaa  120 gttcacgccg agagaggggc ccgcgtcgga ttaggtagtt ggtgaggtaa tggctcacca    180
```

```
agccttcgat ccgtagctgg tctgagagga tgatcagcca cactgggact gagacacggc    240
ccagactcct acgggaggca gcagtgggga atattggaca atgggcgcaa gcctgatcca    300
gcaatgccgc gtgagtgatg aaggccttag ggttgtaaag ctctttcgca cgcgacgatg    360
atgacggtag cgtgagaaga agccccggct aacttcgtgc cagcagccgc ggtaatacga    420
agggggctag cgttgttcgg aattactggg cgtaaagggc gcgtaggcgg cctgtttagt    480
cagaagtgaa agccccgggc tcaacctggg aatagctttt gatactggca ggcttgagtt    540
ccggagagga tggtggaatt cccagtgtag aggtgaaatt cgtagatatt gggaagaaca    600
ccggtggcga aggcggccat ctggacggac actgacgctg aggcgcgaaa gcgtggggag    660
caaacaggat tagataccct ggtagtccac gccgtaaacg atgaatgcta gacgtcgggg    720
tgcatgcact tcggtgtcgc cgctaacgca ttaagcattc cgcctgggga gtacggccgc    780
aaggttaaaa ctcaaaggaa ttgacggggg cccgcacaag cggtggagca tgtggtttaa    840
ttcgaagcaa cgcgcagaac cttaccaacc cttgacatgt ccattatggg ctcgagagat    900
caggtccttc agttcggctg ggtggaacac aggtgctgca tggctgtcgt cagctcgtgt    960
cgtgagatgt tggggttaag tcccgcaacg agcgcaaccc ctaccgtcag ttgccatcat   1020
tcagttgggc actctggtgg aaccgccggt gacaa                              1055
```

<210> SEQ ID NO 292
<211> LENGTH: 1087
<212> TYPE: DNA
<213> ORGANISM: Sphingomonas yanoikuyae
<220> FEATURE:
<221> NAME/KEY: misc_feature
<222> LOCATION: (1)..(1087)
<223> OTHER INFORMATION: BDNZ57662 16S rDNA

<400> SEQUENCE: 292

```
ctgcctcctt acggttagct caacgccttc gagtgaatcc aactcccatg gtgcgatggg     60
cggtgtgtac aaggcctggg aacgtattca ccgcggcatg ctgatccgcg attactagcg    120
attccgcctt cacgctctcg agttgcagag aacgatccga actgagacga cttttggaga    180
ttagctccct ctcgcgaggt ggctgcccac tgtagtcgcc attgtagcac gtgtgtagcc    240
caacgcgtaa gggccatgag gacttgacgt catccccacc ttcctccggc ttatcaccgg    300
cggttccttt agagtaccca actaaatgct ggcaactaaa ggcgagggtt gcgctcgttg    360
cgggacttaa cccaacatct cacgacacga gctgacgaca gccatgcagc acctgtcacc    420
tatccagccg aactgaagga aagtgtctcc acgatccgcg atagggatgt caaacgttgg    480
taaggttctg cgcgttgctt cgaattaaac cacatgctcc accgcttgtg caggccccg     540 tcaattcctt tgagttttaa tcttgcgacc gtactcccca ggcggataac ttaatgcgtt    600
agctgcgcca ccaaaacacc atgtgccctg acagctagtt atcatcgttt acggcgtgga    660 ctaccgggt atctaatcct gtttgctccc cacgctttcg cacctcagcg tcaataccag    720
tccagtgagc cgccttcgcc actggtgttc ttccgaatat ctacgaattt cacctctaca    780
ctcggaattc cactcaccct cctggattc aagctatcta gtttcaaagg cagttccggg    840
gttgagcccc gggctttcac ctctgacttg aatagccgcc tacgtgcgct ttacgcccag    900
taattccgaa caacgctagc tccctccgta ttaccgcggc tgctggcacg gagttagccg    960
gagcttattc tcccggtact gtcattatca tcccggggta aaagagcttt acaaccctaa   1020
aggccttcat cactcacgcg gcattgctgg gatcaggctt cgcccattg gccaatattc   1080 cctactg                                                            1087
```

<210> SEQ ID NO 293
<211> LENGTH: 1000
<212> TYPE: DNA
<213> ORGANISM: Rahnella aquatilis
<220> FEATURE:
<221> NAME/KEY: misc_feature
<222> LOCATION: (1)..(1000)
<223> OTHER INFORMATION: BDNZ58013 16S rDNA

<400> SEQUENCE: 293

```
agcgccctcc cgaaggttaa gctacctact tcttttgcaa cccactccca tggtgtgacg      60
ggcggtgtgt acaaggcccg ggaacgtatt caccgtagca ttctgatcta cgattactag     120
cgattccgac ttcatggagt cgagttgcag actccaatcc ggactacgac atactttatg     180
aggtccgctt gctctcgcga gttcgcttct ctttgtatat gccattgtag cacgtgtgta     240
gccctactcg taagggccat gatgacttga cgtcatcccc accttcctcc ggtttatcac     300
cggcagtctc ctttgagttc ccaccattac gtgctggcaa caaggataaa gggttgcgct     360
cgttgcggga cttaacccaa catttcacaa cacgagctga cgacagccat gcagcacctg     420
tctcacggtt cccgaaggca ctaagccatc tctggcgaat ccgtggatg tcaagagtag      480
gtaaggttct tcgcgttgca tcgaattaaa ccacatgctc caccgcttgt gcgggcccccc    540
gtcaattcat ttgagtttta accttgcggc cgtactcccc aggcggtcga cttaacgcgt     600
tagctccgga agccacgcct caagggcaca acctccaagt cgacatcgtt tacagcgtgg     660
actaccaggg tatctaatcc tgtttgctcc ccacgctttc gcacctgagc gtcagtcttt     720
gtccaggggg ccgccttcgc caccggtatt cctccagatc tctacgcatt tcaccgctac     780
acctggaatt ctaccccccct ctacaagact ctagcttgcc agtttcaaat gcagttccca    840
cgttaagcgc ggggatttca catctgactt aacaaaccgc ctgcgtgcgc tttacgccca     900
gtaattccga ttaacgcttg caccctccgt attaccgcgg ctgctggcac ggagttagcc     960
ggtgcttctt ctgcgagtaa cgtcaatcac cacacgtatt                          1000
```

<210> SEQ ID NO 294
<211> LENGTH: 1052
<212> TYPE: DNA
<213> ORGANISM: Pseudomonas putida
<220> FEATURE:
<221> NAME/KEY: misc_feature
<222> LOCATION: (1)..(1052)
<223> OTHER INFORMATION: BDNZ60303 16S rDNA

<400> SEQUENCE: 294

```
gtcctcccga aggttagact agctacttct ggtgcaaccc actcccatgg tgtgacgggc      60
ggtgtgtaca aggcccggga acgtattcac cgcgacattc tgattcgcga ttactagcga     120
ttccgacttc acgcagtcga gttgcagact gcgatccgga ctacgatcgg ttttgtgaga     180
ttagctccac ctcgcggctt ggcaaccctc tgtaccgacc attgtagcac gtgtgtagcc     240
caggccgtaa gggccatgat gacttgacgt catccccacc ttcctccggt tgtcaccgg      300
cagtctcctt agagtgccca ccattacgtg ctggtaacta aggacaaggg ttgcgctcgt     360
tacgggactt aacccaacat ctcacgacac gagctgacga cagccatgca gcacctgtgt     420
cagagttccc gaaggcacca atccatctct ggaaagttct ctgcatgtca aggcctggta     480
aggttcttcg cgttgcttcg aattaaacca catgctccac cgcttgtgcg ggccccgtc      540
aattcatttg agttttaacc ttgcggccgt actccccagg cggtcaactt aatgcgttag     600
```

```
ctgcgccact aaaatctcaa ggattccaac ggctagttga catcgtttac ggcgtggact      660
accagggtat ctaatcctgt ttgctcccca cgctttcgca cctcagtgtc agtatcagtc      720
caggtggtcg ccttcgccac tggtgttcct tcctatatct acgcatttca ccgctacaca      780
ggaaattcca ccaccctcta ccgtactcta gcttgccagt tttggatgca gttcccaggt      840
tgagcccggg gctttcacat ccaacttaac aaaccaccta cgcgcgcttt acgcccagta      900
attccgatta acgcttgcac cctctgtatt accgcggctg ctggcacaga gttagccggt      960
gcttattctg tcggtaacgt caaaacagca agggattaac ttactggcct tcctcccaac     1020
ttaaagggct ttacaatccg aaaaacttct tt                                   1052

<210> SEQ ID NO 295
<211> LENGTH: 1389
<212> TYPE: DNA
<213> ORGANISM: Rhizobium etli
<220> FEATURE:
<221> NAME/KEY: misc_feature
<222> LOCATION: (1)..(1389)
<223> OTHER INFORMATION: BDNZ60473 16S rDNA

<400> SEQUENCE: 295
gtggttagct gcctccttgc ggttagcgca ctaccttcgg gtaaaaccaa ctcccatggt       60
gtgacgggcg gtgtgtacaa ggcccgggaa cgtattcacc gcggcatgct gatccgcgat      120
tactagcgat tccaacttca tgcactcgag ttgcagagtg caatccgaac tgagatggct      180
tttggagatt agctcgacat cgctgtctcg ctgcccactg tcaccaccat tgtagcacgt      240
gtgtagccca gcccgtaagg gccatgagga cttgacgtca tccccacctt cctctcggct      300
tatcaccggc agtcccctta gagtgcccaa ctaaatgctg gcaactaagg gcgagggttg      360
cgctcgttgc gggacttaac ccaacatctc acgacacgag ctgacgacag ccatgcagca      420
cctgtgttcc ggtccccgaa gggaacacta catctctgta gctggccgga catgtcaagg      480
gctggtaagg ttctgcgcgt tgcttcgaat taaaccacat gctccaccgc ttgtgcgggc      540
ccccgtcaat tcctttgagt tttaatcttg cgaccgtact ccccaggcgg aatgtttaat      600
gcgttagctg cgccaccgaa cagtatactg cccgacggc aacattcatc gtttacggcg       660
tggactacca gggtatctaa tcctgttttgc tccccacgct ttcgcacctc agcgtcagta      720
atggaccagt gagccgcctt cgccactggt gttcctccga atatctacga atttcacctc      780
tacactcgga attccactca cctcttccat actccagatc gacagtatca aaggcagttc      840
cagggttgag ccctgggatt tcacccctga ctgatcgatc cgcctacgtg cgctttacgc      900
ccagtaaatc cgaacaacgc tagccccctt cgtattaccg cggctgctgg cacgaagtta      960
gccgggcgtt cttctccggt taccgtcatt atcttcaccg gtgaaagagc tttacaaccc     1020
taaggccttc atcactcacg cggcatggct ggatcaggct tgcgcccatt gtccaatatt     1080
ccccactgct gcctccgta ggagtttggg ccgtgtctca gtcccaatgt ggctgatcat      1140
cctctcagac cagctatgga tcgtcgcctt ggtaggcctt tacccccacca actagctaat     1200 ccaacgcggg ctcatccttt gccgataaat cttcccccca aagggcacat acggtattag     1260
cacacgtttc catgcgttat ccgtagcaa aaggtagatt cccacgcgtt actcacccgt      1320
ctgccgctcc ccttgcgggg cgctcgactt gcatgtgtta agcctgccgc cagcgttcgt     1380
tctgagcga                                                             1389

<210> SEQ ID NO 296
<211> LENGTH: 1073
```

```
<212> TYPE: DNA
<213> ORGANISM: Paenibacillus amylolyticus
<220> FEATURE:
<221> NAME/KEY: misc_feature
<222> LOCATION: (1)..(1073)
<223> OTHER INFORMATION: BDNZ66316 16S rDNA

<400> SEQUENCE: 296
ctccttgcgg ttaccccacc gacttcgggt gttataaact ctcgtggtgt gacgggcggt      60
gtgtacaaga cccgggaacg tattcaccgc ggcatgctga tccgcgatta ctagcaattc     120
cgacttcatg caggcgagtt gcagcctgca atccgaactg agaccggctt tgttgggatt     180
ggctccatct cgcgatttcg cagcccgttg taccggccat tgtagtacgt gtgtagccca     240
ggtcataagg ggcatgatga tttgacgtca tccccacctt cctccggttt gtcaccggca     300
gtctatctag agtgcccacc cgaagtgctg caaactaaat ataagggttg cgctcgttgc     360
gggacttaac ccaacatctc acgacacgag ctgacgacaa ccatgcacca cctgtcttga     420
atgttccgaa gaaaaggtac atctctgtac cggtcattca gatgtcaaga cctggtaagg     480
ttcttcgcgt tgcttcgaat taaaccacat actccactgc ttgtgcgggt ccccgtcaat     540
tcctttgagt ttcagtcttg cgaccgtact ccccaggcgg agtgcttaat gtgttaactt     600
cggcaccaag ggtatcgaaa cccctaacac ctagcactca tcgtttacgg cgtggactac     660
cagggtatct aatcctgttt gctccccacg ctttcgcgcc tcagcgtcag ttacagccca     720
gagagtcgcc ttcgccactg gtgttcctcc acatatctac gcatttcacc gctacacgtg     780
gaattccact ctcctcttct gcactcaagt cacccagttt ccagtgcgat ccggggttga     840
gccccgggat taaacaccag acttaaatga ccgcctgcgc gcgctttacg cccaataatt     900
ccggacaacg cttgccccct acgtattacc gcggctgctg gcacgtagtt agccggggct     960
ttcttctcag gtaccgtcac cttgagagca gttactctcc caagcgttct tccctggcaa    1020
cagagcttta cgatccgaaa accttcatca ctcacgcggc attgctccgt cag           1073

<210> SEQ ID NO 297
<211> LENGTH: 1420
<212> TYPE: DNA
<213> ORGANISM: Mucilaginibacter gossypii
<220> FEATURE:
<221> NAME/KEY: misc_feature
<222> LOCATION: (1)..(1420)
<223> OTHER INFORMATION: BDNZ66321 16S rDNA

<400> SEQUENCE: 297
acgctccttg cggttacgca cttcaggcac ttccagcttc catggcttga cgggcggtgt      60
gtacaaggcc cgggaacgta ttcaccgcgt cattgctgat acgcgattac tagcgaatcc     120
aacttcacgg ggtcgagttg cagacccga tccgaactgt gaatggcttt gagagattgg     180
catcctgttg ccaggtagct gccctctgta ccatccattg tagcacgtgt gtagccccgg     240
acgtaagggc catgatgact tgacgtcgtc ccctccttcc tctctatttg cataggcagt     300
ctgtttagag tccccacctt aaatgctggc aactaaacat aggggttgcg ctcgttgcgg     360
gacttaaccc aacacctcac ggcacgagct gacgacagcc atgcagcacc tagtttcgtg     420
ttccgaagaa ctgtgacgtc tctgtcacat tcactaactt tcaagcccgg gtaaggttcc     480
tcgcgtatca tcgaattaaa ccacatgctc ctccgcttgt gcgggccccc gtcaattcct     540
ttgagtttca cccttgcggg cgtactcccc aggtggaaca cttaacgctt tcgcttagac     600
gctgaccgta tatcgccaac atcgagtgtt catcgtttag ggcgtggact accagggtat     660
```

| | |
|---|---|
| ctaatcctgt ttgatcccca cgctttcgtg cctcagcgtc aatcatactt tagtaagctg | 720 |
| ccttcgcaat tggtgttctg tgacatatct atgcatttca ccgctacttg tcacattccg | 780 |
| cctacctcaa gtacattcaa gctcttcagt atcaagggca ctgcgatagt tgagctaccg | 840 |
| tctttcaccc ctgacttaaa aagccgccta cgcacccttt aaaccaata aatccggata | 900 |
| acgcttggat cctccgtatt accgcggctg ctggcacgga gttagccgat ccttattctt | 960 |
| accgtacatt caacccgatt cacgaatcgg ggtttattcc ggtacaaaag cagtttacaa | 1020 |
| cccgtagggc cgtcttcctg cacgcggcat ggctggttca gacttccgtc cattgaccaa | 1080 |
| tattccttac tgctgcctcc cgtaggagtc tggtccgtgt ctcagtacca gtgtgggggg | 1140 |
| tcatcctctc agatccccta aacatcgtag ccttggtatg ccgttaccac accaactagc | 1200 |
| taatgttgcg catgcccatc ttagtcctat aaatatttga ttatcctgcg atgccacaaa | 1260 |
| ataatgttat gcggtcttaa tctctctttc gagaggctat ccccctgact aaggtaggtt | 1320 |
| acatacgtgt tacgcacccg tgcgccactc tcaagaaaag caagctcttc tatcccgtcc | 1380 |
| gacttgcatg tattaggcct gccgctagcg ttcatcctga | 1420 |

<210> SEQ ID NO 298
<211> LENGTH: 1098
<212> TYPE: DNA
<213> ORGANISM: Caulobacter henricii
<220> FEATURE:
<221> NAME/KEY: misc_feature
<222> LOCATION: (1)..(1098)
<223> OTHER INFORMATION: BDNZ66341 16S rDNA

<400> SEQUENCE: 298

| | |
|---|---|
| cctgcctctc ttgcgagtta gcgcagcgcc ttcgggtaaa gccaactccc atggtgtgac | 60 |
| gggcggtgtg tacaaggccc gggaacgtat tcaccgcggc atgctgatcc gcgattacta | 120 |
| gcgattccaa cttcatgcac tcgagttgca gagtgcaatc cgaactgaga cgacttttag | 180 |
| ggattggctc cccctcgcgg gattgcagcc ctctgtagtc gccattgtag cacgtgtgta | 240 |
| gcccaccttg taagggccat gaggacttga cgtcatcccc accttcctcc gaattaactt | 300 |
| cggcagtact attagagtgc ccagccaaac ctgatggcaa ctaatagcga gggttgcgct | 360 |
| cgttgcggga cttaacccaa catctcacga cacgagctga cgacagccat gcagcacctg | 420 |
| tgtcccagtc cccgaaggga aagccgcatc tctgcggcgg tccgggcatg tcaaaaggtg | 480 |
| gtaaggttct gcgcgttgct tcgaattaaa ccacatgctc caccgcttgt gcgggccccc | 540 |
| gtcaattcct ttgagtttta atcttgcgac cgtactcccc aggcggagtg cttaatgcgt | 600 |
| tagctgcgtc accgacaggc atgcctgccg acaactagca ctcatcgttt acagcgtgga | 660 |
| ctaccagggt atctaatcct gtttgctccc cacgctttcg agcctcagcg tcagtaacgg | 720 |
| accagtatgt cgccttcgcc actggtgttc ttccgaatat ctacgaattt cacctctaca | 780 |
| ctcggagttc cacataccct ttccgtactc aagatagcca gtatcaaagg caattccaag | 840 |
| gttgagccct gggctttcac ctctgactaa actatccgcc tacgctccct ttacgcccag | 900 |
| taattccgag caacgctagc ccccttcgta ttaccgcggc tgctggcacg aagttagccg | 960 |
| gggcttcttc tccgggtacc gtcattatcg tccccgtgta aagaattta caatcctaag | 1020 |
| accttcatca ttcacgcggc atggctgcgt caggctttcg cccattgcgc aagattcccc | 1080 |
| actgctgcct cccgtagg | 1098 |

<210> SEQ ID NO 299
<211> LENGTH: 640

```
<212> TYPE: DNA
<213> ORGANISM: Duganella violaceinigra
<220> FEATURE:
<221> NAME/KEY: misc_feature
<222> LOCATION: (1)..(640)
<223> OTHER INFORMATION: BDNZ66361 16S rDNA

<400> SEQUENCE: 299
gcgccctcct tgcggttaag ctacctactt ctggtaaacc cgctcccatg gtgtgacggg      60
cggtgtgtac aagacccggg aacgtattca ccgcgacatg ctgatccgcg attactagcg     120
attccaactt catgtagtcg agttgcagac tacaatccgg actacgatac actttctggg     180
attagctccc cctcgcgggt tggcggccct ctgtatgtac cattgtatga cgtgtgaagc     240
cctacccata agggccatga ggacttgacg tcatccccac cttcctccgg tttgtcaccg     300
gcagtctcat tagagtgctc ttgcgtagca actaatgaca agggttgcgc tcgttgcggg     360
acttaaccca acatctcacg acacgagctg acgacagcca tgcagcacct gtgtgatggt     420
tctctttcga gcactcccaa atctctccgg gattccatcc atgtcaaggg taggtaaggt     480
ttttcgcgtt gcatcgaatt aatccacatc atccaccgct tgtgcgggtc cccgtcaatt     540
cctttgagtt ttaatcttgc gaccgtactc cccaggcggt ctacttcacg cgttagctgc     600
gttactaagt caattaagac ccaacaacta gtagacatcg                            640

<210> SEQ ID NO 300
<211> LENGTH: 1385
<212> TYPE: DNA
<213> ORGANISM: Azospirillum lipoferum
<220> FEATURE:
<221> NAME/KEY: misc_feature
<222> LOCATION: (1)..(1385)
<223> OTHER INFORMATION: BDNZ66460 16S rDNA

<400> SEQUENCE: 300
gctgcctccc gttgccgggt tagcgcacca ccttcgggta aaaccaactc ccatggtgtg      60
acgggcggtg tgtacaaggc ccgggaacgt attcaccgcg gcgtgctgat ccgcgattac     120
tagcgattcc aacttcacgc actcgagttg cagagtgcga tccgaactga gacggctttt     180
ggggatttgc tccatctcgc gacttcgctt cccactgtca ccgccattgt agcacgtgtg     240
tagcccaacc cataagggcc atgaggactt gacgtcatcc ccgccttcct ccggcttgtc     300
accggcggtt ccaccagagt gcccaactga atgatgcaa ctgacggtag gggttgcgct     360
cgttgcggga cttaacccaa catctcacga cacgagctga cgacagccat gcagcacctg     420
tgttccaccc agccgaactg aaggacctga tctctsaagc ccaaagtgga catgtcaagg     480
gttggtaagg ttctgcgcgt tgcttcgaat aaaccacat gctccaccgc ttgtgcgggc     540
ccccgtcaat tcctttgagt tttaaccttg cggccgtact cccaggcgg aatgcttaat     600 gcgttagcgg cgacaccgaa gtgcatgcac cccgacgtct agcattcatc gtttacggcg     660
tggactacca gggtatctaa tcctgtttgc tccccacgct ttcgcgcctc agcgtcagtg     720
tccgtccaga tggccgcctt cgccaccggt gttcttccca atatctacga atttcacctc     780
tacactggga attccaccat cctctccgga actcaagcct gccagtatca aaagctattc     840
ccaggttgag cccggggctt tcacttctga ctaaacaggc cgcctacgcg cccttttacgc    900 ccagtaattc cgaacaacgc tagccccctt cgtattaccg cggctgctgg cacgaagtta     960
gccggggctt cttctcacgc taccgtcatc atcgtcgcgt gcgaaagagc tttacaaccc    1020
taaggccttc atcactcacg cggcattgct ggatcaggct tgcgcccatt gtccaatatt    1080
```

```
ccccactgct gcctcccgta ggagtctggg ccgtgtctca gtcccagtgt ggctgatcat    1140
cctctcagac cagctacgga tcgaaggctt ggtgagccat tacctcacca actacctaat    1200
ccgacgcggg cccctctctc ggcgtaaact tcccccaaa gggcgtatcc ggtgttagcg     1260
ttcgtttcca aacgttattc cgaaccgaaa ggcaggttcc cacgtgttac tcacccgtgc    1320
gccactaagg ccgaagcctt cgttcgactt gcatgtgtta ggcatgccgc cagcgttcgt    1380
tctga                                                                1385
```

<210> SEQ ID NO 301
<211> LENGTH: 1415
<212> TYPE: DNA
<213> ORGANISM: Flavobacterium glaciei
<220> FEATURE:
<221> NAME/KEY: misc_feature
<222> LOCATION: (1)..(1415)
<223> OTHER INFORMATION: BDNZ66487 16S rDNA

<400> SEQUENCE: 301

```
gcagctcctt gcggtcccga cttcaggcac cccagcttc catggcttga cgggcggtgt      60
gtacaaggcc cgggaacgta ttcaccggat catggctgat atccgattac tagcgattcc    120
agcttcacgg agtcgagttg cagactccga tccgaactgt gaccggtttt atagattcgc    180
tcctggtcgc ccagtggctg ctctctgtac cggccattgt agcacgtgtg tagcccaagg    240
cgtaagggcc gtgatgattt gacgtcatcc ccaccttcct cacagtttgc actggcagtc    300
ttgttagagt tcccgacttg actcgctggc aactaacaac aggggttgcg ctcgttatag    360
gacttaacct gacacctcac ggcacgagct gacgacaacc atgcagcacc ttgtaaattg    420
tcttgcgaaa gttctgtttc caaaacggtc aatctacatt taagccttgg taaggttcct    480
cgcgtatcat cgaattaaac cacatgctcc accgcttgtg cgggccccg  tcaattcctt    540 tgagtttcat tcttgcgaac gtactcccca ggtgggatac ttatcacttt cgcttagcca    600
ctgaaattgc ttccaacagc tagtatccat cgtttacggc gtggactacc agggtatcta    660
atcctgttcg ctacccacgc tttcgtccat cagcgtcaat ccattagtag taacctgcct    720 tgcaattgg tattccatgt aatctctaag catttcaccg ctacactaca tattctagtt    780
acttcctaat aattcaagtc ctgcagtatc aatggccgtt ccatcgttga gcgatgggct    840
ttcaccactg acttacaaga ccgcctacgg acccttttaaa cccaatgatt ccggataacg    900
cttggatcct ccgtattacc gcggctgctg gcacggagtt agccgatcct tattctcaca    960
gtaccgtcaa gctcggacac gtccgagtgt tcttcctgt gcaaaagcag tttacaatcc    1020
ataggaccgt catcctgcac gcggcatggc tggatcaggc ttgcgcccat tgtccaatat    1080
tcctcactgc tgcctcccgt aggagtctgg tccgtgtctc agtaccagtg tggggggatct   1140 ccctctcagg acccctaccc atcgtagcct tggtaagccg ttaccttacc aacaagctaa    1200
tgggacgcat gctcatcttt caccgttgtg actttaatta taaagtgatg ccactccata    1260
atactatgag gtattaatcc aaatttctct gggctatccc tctgtgaaag gcagattgca    1320
tacgcgttac gcaccegtgc gccggtctct atatccgaag acatatacccc ctcgacttgc    1380 atgtgttaag cctgccgcta gcgttcatcc tgagc                               1415
```

<210> SEQ ID NO 302
<211> LENGTH: 1415
<212> TYPE: DNA
<213> ORGANISM: Duganella zoogloeoides
<220> FEATURE:
<221> NAME/KEY: misc_feature
<222> LOCATION: (1)..(1415)
<223> OTHER INFORMATION: BDNZ66500 16S rDNA

<400> SEQUENCE: 302

```
ggttaagcta cctacttctg gtaaaacccg ctcccatggt gtgacgggcg gtgtgtacaa      60
gacccgggaa cgtattcacc gcgacatgct gatccgcgat tactagcgat tccaacttca     120
tgcagtcgag ttgcagacta caatccggac tacgatacac tttctgggat tagctccccc     180
tcgcggggttg gcggccctct gtatgtacca ttgtatgacg tgtgaagccc tacccataag    240
ggccatgagg acttgacgtc atccccacct tcctccggtt tgtcaccggc agtctcatta    300
gagtgccctt tcgtagcaac taatgacaag ggttgcgctc gttgcgggac ttaacccaac    360
atctcacgac acgagctgac gacagccatg cagcacctgt gtaatggttc tctttcgagc    420
actcccaat ctctcaggga ttccatccat gtcaagggta ggtaaggttt ttcgcgttgc     480
atcgaattaa tccacatcat ccaccgcttg tgcgggtccc cgtcaattcc tttgagtttt    540
aatcttgcga ccgtactccc caggcggtct acttcacgcg ttagctgcgt taccaagtca    600
attaagaccc gacaactagt agacatcgtt tagggcgtgg actaccaggg tatctaatcc    660
tgtttgctcc ccacgctttc gtgcatgagc gtcagttttg acccaggggg ctgccttcgc    720
catcggtgtt cctccacata tctacgcatt tcactgctac acgtggaatt ctacccccct    780
ctgccaaact ctagccttgc agtcaccatc gccattccca ggttgagccc ggggattt ca   840
cgacagtctt acaaaaccgc ctgcgcacgc tttacgccca gtaattccga ttaacgcttg    900
caccctacgt attaccgcgg ctgctggcac gtagttagcc ggtgcttatt cttcaggtac    960
cgtcattagc araggatatt agcctycacc gtttcttccc tgacaaaaga gctttacaac   1020
ccgaaggcct tcttcactca cgcggcattg ctggatcagg cttgcgccca ttgtccaaaa   1080
ttccccactg ctgcctcccg taggagtctg gaccgtgtct cagttccagt gtggctggtc   1140
gtcctctcag accagctact gatcgatgcc ttggtgggcc tttacccac  caactagcta   1200
atcagatatc ggccgctcca ggagcacaag gccttgcggt cccctgcttt catccttgga   1260
tcgtatgcgg tattagcgta actttcgcta cgttatcccc cactccaggg tacgttccga   1320
tatattactc acccgttcgc cactcgccgc caggttgccc cgcgctgccg ttcgacttgc   1380
atgtgtaagg catgccgcca gcgttcaatc tgagc                              1415
```

<210> SEQ ID NO 303
<211> LENGTH: 1443
<212> TYPE: DNA
<213> ORGANISM: Bacillus psychrosaccharolyticus
<220> FEATURE:
<221> NAME/KEY: misc_feature
<222> LOCATION: (1)..(1443)
<223> OTHER INFORMATION: BDNZ66518 16S rDNA

<400> SEQUENCE: 303

```
ggctccttgc ggttacctca ccgacttcgg gtgttacaaa ctctcgtggt gtgacgggcg      60
gtgtgtacaa ggcccgggaa cgtattcacc gcggcatgct gatccgcgat tactagcgat    120
tccggcttca tgcaggcgag ttgcagcctg caatccgaac tgagaatggc tttatgagat    180
tcgcttaccc tcgcgagttt gcagctcttt gtaccatcca ttgtagcacg tgtgtagccc    240
aggtcataag gggcatgatg atttgacgtc atccccacct tcctccggtt tatcaccggc    300
agtcaccttca gagtgcccaa ctgaatgctg caactaaga tcaagggttg cgctcgttgc    360
gggacttaac ccaacatctc acgacacgag ctgacgacaa ccatgcacca cctgtcactc    420
```

```
tgtccccga agggaacgt cctatctcta ggagtgtcag aggatgtcaa gacctggtaa    480
ggttcttcgc gttgcttcga attaaaccac atgctccacc gcttgtgcgg gccccgtca    540 attcctttga gtttcagcct tgcggccgta ctccccaggc ggagtgctta atgcgttagc    600
tgcagcacta aagggcggaa accctctaac acttagcact catcgtttac ggcgtggact    660
accagggtat ctaatcctgt ttgctcccca cgctttcgcg cctcagtgtc agttatagac    720
cagaaagtcg ccttcgccac tggtgttcct ccacatctct acgcatttca ccgctacacg    780
tggaattcca ctttcctctt ctacactcaa gttccccagt ttccaatgac cctccccggt    840
tgagccgggg gctttcacat cagacttaag gaaccacctg cgcgcgcttt acgcccaata    900
attccggata acgcttgcca cctacgtatt accgcggctg ctggcacgta gttagccgtg    960
gctttctggt taggtaccgt caaggtacca gcagttactc tggtacttgt tcttccctaa   1020
caacagaact ttacgacccg aaagccttca tcgttcacgc ggcgttgctc cgtcagactt   1080
tcgtccattg cggaagattc cctactgctg cctcccgtag gagtctgggc cgtgtctcag   1140
tcccagtgtg gccgatcacc ctctcaggtc ggctacgcat cgttgccttg gtgagccatt   1200
acctcaccaa ctagctaatg cgccgcgggc ccatctataa gtgacagcga gacgccgtct   1260
ttccatcttt tctcatgcaa aaaagaacaa tatccggtat tagctccggt ttcccgaagt   1320
tatcccagtc ttataggcag gttgcccact tgttactcac ccgtccgccg ctaattgttg   1380
agtaaactca caattcgct caacttgcat gtattaggca cgccgccagc gttcatcctg    1440
agc                                                                1443
```

<210> SEQ ID NO 304
<211> LENGTH: 1439
<212> TYPE: DNA
<213> ORGANISM: Paenibacillus polymyxa
<220> FEATURE:
<221> NAME/KEY: misc_feature
<222> LOCATION: (1)..(1439)
<223> OTHER INFORMATION: BDNZ66545 16S rDNA

<400> SEQUENCE: 304

```
ccccaccgac ttcgggtgtt gtaaactctc gtggtgtgac gggcggtgtg tacaagaccc     60
gggaacgtat tcaccgcggc atgctgatcc gcgattacta gcaattccga cttcatgtag    120
gcgagttgca gcctacaatc cgaactgaga ccggcttttc taggattggc tccacctcgc    180
ggcttcgctt cccgttgtac cggccattgt agtacgtgtg tagcccaggt cataaggggc    240
atgatgattt gacgtcatcc ccaccttcct ccggtttgtc accggcagtc tgcttagagt    300
gcccagcttg acctgctggc aactaagcat aagggttgcg ctcgttgcgg gacttaaccc    360
aacatctcac gacacgagct gacgacaacc atgcaccacc tgtctcctct gtcccgaagg    420
aaagccatat ctctacagcg gtcagaggga tgtcaagacc tggtaaggtt cttcgcgttg    480
cttcgaatta aaccacatac tccactgctt gtgcgggtcc ccgtcaattc ctttgagttt    540
cagtcttgcg accgtactcc ccaggcggaa tgcttaatgt gttaacttcg gcaccaaggg    600
tatcgaaacc cctaacacct agcattcatc gtttacggcg tggactacca gggtatctaa    660
tcctgtttgc tccccacgct ttcgcgcctc agtcagtt acagcccaga gagtcgcctt    720
cgccactggt gttcctccac atctctacgc atttcaccgc tacacgtgga attccactct    780
cctcttctgc actcaagctc ccagttttcc agtgcgaccc gaagttgagc ctcgggatta    840 aacaccgac ttaaagagcc gcctgcgcgc gcttacgcc caataattcc ggacaacgct    900
tgccccctac gtattaccgc ggctgctggc acgtagttag ccggggctttc cttctcaggt    960
```

```
accgtcactc ttgtagcagt tactctacaa dacgttcttc cctggcaaca gagctttacg      1020
atccgaaaac cttcatcact cacgcggcgt tgctccgtca ggctttcgcc cattgcggaa      1080
gattccctac tgctgcctcc cgtaggagtc tgggccgtgt ctcagtccca gtgtggccga      1140
tcaccctctc aggtcggcta cgcatcgtcg ccttggtagg cctttacccc accaactagc      1200
taatgcgccg caggcccatc cacaagtgac agattgctcc gtctttcctc cttcgcccat      1260
gcaggaaaag gatgtatcgg gtattagcta ccgtttccgg tagttatccc tgtcttgtgg      1320
gcaggttgcc tacgtgttac tcaccegtcc gccgctaggt tatttagaag caagcttcta      1380
aataaccccg ctcgacttgc atgtattagg cacgccgcca gcgttcgtcc tgagcgaga       1439

<210> SEQ ID NO 305
<211> LENGTH: 1060
<212> TYPE: DNA
<213> ORGANISM: Stenotrophomonas chelatiphaga
<220> FEATURE:
<221> NAME/KEY: misc_feature
<222> LOCATION: (1)..(1060)
<223> OTHER INFORMATION: BNDZ 64208 16S rDNA

<400> SEQUENCE: 305
agcgccctcc cgaaggttaa gctacctgct tctggtgcaa caaactccca tggtgtgacg      60
ggcggtgtgt acaaggcccg ggaacgtatt caccgcagca atgctgatct gcgattacta    120
gcgattccga cttcatggag tcgagttgca gactccaatc cggactgaga tagggtttct    180
gggattggct taccgtcgcc ggcttgcagc cctctgtccc taccattgta gtacgtgtgt    240
agccctggcc gtaagggcca tgatgacttg acgtcatccc caccttcctc cggtttgtca    300
ccggcggtct ccttagagtt cccaccatta cgtgctggca actaaggaca agggttgcgc    360
tcgttgcggg acttaaccca acatctcacg acacgagctg acgacagcca tgcagcacct    420
gtgttcgagt tcccgaaggc accaatccat ctctggaaag ttctcgacat gtcaaggcca    480
ggtaaggttc ttcgcgttgc atcgaattaa accacatact ccaccgcttg tgcgggcccc    540
cgtcaattcc tttgagtttc agtcttgcga ccgtactccc caggcggcga acttaacgcg    600
ttagcttcga tactgcgtgc caaagtgcac ccaacatcca gttcgcatcg tttagggcgt    660
ggactaccag ggtatctaat cctgtttgct ccccacgctt tcgtgcctca gtgtcagtgt    720
tggtccaggt agctgccttc gccatggatg ttcctcccga tctctacgca tttcactgct    780
acaccgggaa ttccgctacc ctctaccaca ctctagtcat ccagtttcca ctgcagttcc    840
caggttgagc ccagggcttt cacaacagac ttaaacaacc acctacgcac gctttacgcc    900
cagtaattcc gagtaacgct tgcacccttc gtattaccgc ggctgctggc acgaagttag    960
ccggtgctta ttctttgggt accgtcagaa cagcaaggta ttagcccgct gcttttcttt     1020
cccaacaaaa gggctttaca acccgaaggc cttcttcacc                           1060

<210> SEQ ID NO 306
<211> LENGTH: 1243
<212> TYPE: DNA
<213> ORGANISM: Bacillus psychrosaccharolyticus
<220> FEATURE:
<221> NAME/KEY: misc_feature
<222> LOCATION: (1)..(1243)
<223> OTHER INFORMATION: BDNZ66544 16S rDNA

<400> SEQUENCE: 306
ggctccttgc ggttcctcac cgacttcggg tgttacaaac tctcgtggtg tgacgggcgg      60
```

```
tgtgtacaag gcccgggaac gtattcaccg cggcatgctg atccgcgatt actagcgatt    120
ccggcttcat gcaggcgagt tgcagcctgc aatccgaact gagaatggct ttatgagatt    180
cgcttaccct cgcgagtttg cagctctttg taccatccat tgtagcacgt gtgtagccca    240
ggtcataagg ggcatgatga tttgacgtca tccccacctt cctccggttt atcaccggca    300
gtcaccttag agtgcccaac tgaatgctgg caactaagat caagggttgc gctcgttgcg    360
ggacttaacc caacatctca cgacacgagc tgacgacaac catgcaccac ctgtcactct    420
gtcccccgaa ggggaacgtc ctatctctag gagtgtcaga ggatgtcaag acctggtaag    480
gttcttcgcg ttgcttcgaa ttaaaccaca tgctccaccg cttgtgcggg ccccgtcaa    540 ttcctttgag tttcagcctt gcggccgtac tccccaggcg gagtgcttaa tgcgttagct    600
gcagcactaa agggcggaaa ccctctaaca cttagcactc atcgtttacg gcgtggacta    660
ccagggtatc taatcctgtt tgctccccac gctttcgcgc ctcagtgtca gttatagacc    720
agaaagtcgc cttcgccact ggtgttcctc cacatctcta cgcatttcac cgctacacgt    780
ggaattccac tttcctcttc tacactcaag ttccccagtt ccaatgacc ctccccggtt    840 gagccggggg ctttcacatc agacttaagg aaccacctgc gcgcgcttta cgcccaataa    900
ttccggataa cgcttgccac ctacgtatta ccgcggctgc tggcacgtag ttagccgtgg    960
ctttctggtt aggtaccgtc aaggtaccag cagttactct ggtacttgtt cttccctaac   1020
aacagaactt tacgacccga aagccttcat cgttcacgcg cgttgctcc gtcagacttt   1080 cgtccattgc ggaagattcc ctactgctgc ctcccgtagg agtctgggcc gtgtctcagt   1140
cccagtgtgg ccgatcaccc tctcaggtcg gctacgcatc gttgccttgg tgagccatta   1200
cctcaccaac tagctaatgc gccgcgggcc catctataag tga                     1243
```

<210> SEQ ID NO 307
<211> LENGTH: 989
<212> TYPE: DNA
<213> ORGANISM: Tumebacillus permanentifrigoris
<220> FEATURE:
<221> NAME/KEY: misc_feature
<222> LOCATION: (1)..(989)
<223> OTHER INFORMATION: BDNZ 72287 16S rDNA

<400> SEQUENCE: 307

```
agcagttacc tcaccgactt cgggtgttac caactcccat ggtgtgacgg gcggtgtgta     60
caaggcccgg gaacgaattc accgcggcat gctgatccgc gattactagc aattccggct    120
tcatgcaggc gagttgcagc ctgcaatccg aactacgaac ggctttctgg gattggctcc    180
acctcgcggc ttcgcaaccc tttgtaccgt ccattgtagc acgtgtgtag cccaagacat    240
aaggggcatg atgatttgac gtcatccccg ccttcctccg gtttgtcacc ggcagtctgt    300
tgtaagtgct caactaaatg gtagcaacac aacataggg ttgcgctcgt tgcgggactt    360
aacccaacat ctcacgacac gagctgacga caaccatgca ccacctgtca ccgctgcccc    420
gaagggaagc tctatctcta gaacggtcag cgggatgtca agtcttggta aggttcttcg    480
cgttgcttcg aattaaacca catgctccac tgcttgtgcg ggccccgtc aattcctttg    540 agtttcagtc ttgcgaccgt actccccagg cggagtgctt aatgcgttag cttcggcact    600
aaggggtggg ccccctaaca cctagcactc atcgtttacg gcgtggacta ccagggtatc    660
taatcctgtt tgctccccac gctttcgcgc ctcagcgtca gaaatcggcc agcaaggcgc    720
cttcgccaca ggtgttcctc cacatctcta cgcatttcac cgctacacgt ggaattcccc    780
ttgcctctcc gatcctcaag tctccccgta tccaaggcaa tcccagagtt gagctctggg    840
```

```
ctttcacccc ggacgtgaaa gaccgcctgc gcgcgcttta cgcccagtga ttccggacaa    900
cgcttgcccc ctacgtatta ccgcggctgc tggcacgtag ttagccgggg cttcctcctc    960
tgttaccgtc aggtcctgag ctttctctg                                      989
```

AGRICULTURALLY BENEFICIAL MICROBES, MICROBIAL COMPOSITIONS, AND CONSORTIA

CROSS REFERENCE TO RELATED APPLICATIONS

This application is a 371 national phase of PCT International Patent Application No. PCT/US2016/043933, filed Jul. 25, 2016, claiming the benefit of priority to U.S. Provisional Patent Application No. 62/196,951, filed on Jul. 25, 2015, which is hereby incorporated by reference in its entirety for all purposes. The following applications are generally related to the instant disclosure, U.S. Provisional Patent Application No. 62/113,792, filed on Feb. 9, 2015, and U.S. Provisional Patent Application No. 62/165,620, filed on May 22, 2015, and U.S. Provisional Patent Application No. 62/280,503, filed on Jan. 19, 2016, each of which is hereby incorporated by reference in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BICO_005_02WO_SeqList_ST25.txt, date recorded Jul. 22, 2016, file size 477 kilobytes).

FIELD

The present disclosure relates to isolated and biologically pure microorganisms that have application, inter alia, in agriculture. The disclosed microorganisms can be utilized in their isolated and biologically pure states, as well as being formulated into agriculturally acceptable compositions. Further, the disclosure provides agriculturally beneficial microbial consortia, containing at least two members of the disclosed microorganisms, as well as methods of utilizing said consortia in agricultural applications.

BACKGROUND

According to the United Nations World Food Program, there are close to 900 million malnourished people in the world. The malnourishment epidemic is particularly striking in the developing nations of the world, where one in six children is underweight. The paucity of available food can be attributed to many socioeconomic factors; however, regardless of ultimate cause, the fact remains that there is a shortage of food available to feed a growing world population, which is expected to reach 9 billion people by 2050. The United Nations estimates that agricultural yields must increase by 70-100% to feed the projected global population in 2050.

These startling world population and malnutrition figures highlight the importance of agricultural efficiency and productivity, in sustaining the world's growing population. The technological advancements achieved by modern row crop agriculture, which has led to never before seen crop yields, are impressive. However, despite the advancements made by technological innovations such as genetically engineered crops and new novel pesticidal and herbicidal compounds, there is a need for improved crop performance, in order to meet the demands of an exponentially increasing global population.

Scientists have estimated that if the global agricultural "yield gap" (which is the difference between the best observed yield and results elsewhere) could be closed, then worldwide crop production would rise by 45-70%. That is, if all farmers, regardless of worldwide location, could achieve the highest attainable yield expected for their respective regions, then a great majority of the deficiencies in worldwide food production could be addressed. However, solving the problem of how to achieve higher yields across a heterogenous worldwide landscape are difficult.

Often, yield gaps can be explained by inadequate water, substandard farming practices, inadequate fertilizers, and the non-availability of herbicides and pesticides. However, to vastly increase the worldwide use of water, fertilizers, herbicides, and pesticides, would not only be economically infeasible for most of the world, but would have negative environmental consequences.

Thus, meeting global agricultural yield expectations, by simply scaling up current high-input agricultural systems-utilized in most of the developed world—is simply not feasible.

There is therefore an urgent need in the art for improved methods of increasing crop performance and imparting beneficial traits to desired plant species.

SUMMARY OF THE DISCLOSURE

The present disclosure addresses this important issue of how to improve crop performance, thereby closing the worldwide yield gap, along with providing ways of imparting other beneficial traits to plant species.

The solution to increasing crop performance and increasing yield proffered by the present disclosure is not detrimental to the earth's resources, as it does not rely upon increased water consumption or increased input of synthetic chemicals into a system. Rather, the present disclosure utilizes microbes to impart beneficial properties, including increased yields, to desirable plants.

The disclosure therefore offers an environmentally sustainable solution that allows farmers to increase yields of important crops, which is not reliant upon increased utilization of synthetic herbicides and pesticides.

In embodiments, the disclosure provides for an efficient and broadly applicable agricultural platform utilizing microbes and microbial consortia that promote one or more desirable plant properties.

In some embodiments, a single microbe is utilized. In some aspects, the single microbe is isolated and purified. In some aspects, the single microbe is a taxonomic species of bacteria. In some aspects, the single microbe is an identifiable strain of a taxonomic species of bacteria. In some aspects, the single microbe is a novel, newly discovered strain of a taxonomic species of bacteria.

In some embodiments, a single microbe from Table 1 is utilized. In other embodiments, a single microbe from Table 2 is utilized. In yet other embodiments, a single microbe from Table 3 is utilized. In additional embodiments, a single microbe from Table 4 is utilized.

In some embodiments, a microbe from the genus *Bosea* is utilized.

In some aspects, the single microbe—whether a taxonomically identifiable species or strain—is combined with one or more other microbes of a different species or strain. In certain aspects, the combination of two or more microbes forms a consortia or consortium. The terms consortia and consortium are utilized interchangeably.

In certain aspects, the disclosure provides for the development of highly functional microbial consortia that help promote the development and expression of a desired phenotypic or genotypic plant trait. In some embodiments, the consortia of the present disclosure possess functional attributes that are not found in nature, when the individual microbes are living alone. That is, in various embodiments, the combination of particular microbial species into consortia, leads to the microbial combination possessing functional attributes that are not possessed by any one individual member of the consortia when considered alone.

In some embodiments, this functional attribute possessed by the microbial consortia is the ability to impart one or more beneficial properties to a plant species, for example: increased growth, increased yield, increased nitrogen utilization efficiency, increased stress tolerance, increased drought tolerance, increased photosynthetic rate, enhanced water use efficiency, increased pathogen resistance, modifications to plant architecture that don't necessarily impact plant yield, but rather address plant functionality, etc.

The ability to impart these beneficial properties upon a plant is not possessed, in some embodiments, by the individual microbes as they would occur in nature. Rather, in some embodiments, it is by the hand of man combining these microbes into consortia that a functional composition is developed, said functional composition possessing attributes and functional properties that do not exist in nature.

However, in other embodiments, the disclosure provides for individual isolated and biologically pure microbes that are able to impart beneficial properties upon a desired plant species, without the need to combine said microbes into consortia.

In embodiments, the microbial consortia can be any combination of individual microbes from Table 1. In other embodiments, the microbial consortia can be any combination of individual microbes from Table 2. In yet other embodiments, the microbial consortia can be any combination of individual microbes from Table 3. In additional embodiments, the microbial consortia can be any combination of individual microbes from Table 4. In yet other embodiments, the microbial consortia can be any combination of individual microbes from any of Tables 1-4. In certain embodiments, the microbial consortia comprise two microbes, or three microbes, or four microbes, or five microbes, or six microbes, or seven microbes, or eight microbes, or nine microbes, or 10 microbes, or more than 10 microbes.

Another object of the disclosure relates to the use of the isolated microbes and microbial consortia as plant growth promoters. In other aspects, the isolated microbes and microbial consortia function as growth modifiers, which can, e.g. subvert normal senescence that leads to increased biomass.

Yet another object of the disclosure relates to the use of the isolated microbes and microbial consortia as soil health enhancers and plant health enhancers.

Another object of the disclosure is to design a microbial consortium, which is able to perform multidimensional activities in common. In certain aspects, the microbes comprising the consortium act synergistically. In aspects, the effect that the microbial consortium has on a certain plant characteristic is greater than the effect that would be observed had any one individual microbial member of the consortium been utilized singularly. That is, in some aspects, the consortium exhibit a greater than additive effect upon a desired plant characteristic, as compared to the effect that would be found if any individual member of the consortium had been utilized by itself.

In some aspects, the consortia lead to the establishment of other plant-microbe interactions, e.g. by acting as primary colonizers or founding populations that set the trajectory for the future microbiome development.

In embodiments, the disclosure is directed to synergistic combinations (or mixtures) of microbial isolates.

In some aspects, the consortia taught herein provide a wide range of agricultural applications, including: improvements in yield of grain, fruit, and flowers; improvements in growth of plant parts; improved resistance to disease; improved survivability in extreme climate; and improvements in other desired plant phenotypic characteristics. Significantly, these benefits to plants can be obtained without any hazardous side effects to the environment.

In some aspects, the individual microbes of the disclosure, or consortia comprising same, can be combined into an agriculturally acceptable composition.

In some embodiments, the agricultural compositions of the present disclosure include, but are not limited to: wetters, compatibilizing agents, antifoam agents, cleaning agents, sequestering agents, drift reduction agents, neutralizing agents, buffers, corrosion inhibitors, dyes, odorants, spreading agents, penetration aids, sticking agents, binders, dispersing agents, thickening agents, stabilizers, emulsifiers, freezing point depressants, antimicrobial agents, fertilizers, pesticides, herbicides, inert carriers, polymers, and the like.

In one embodiment of the present disclosure, the microbes (including isolated single species, or strains, or consortia), are supplied in the form of seed coatings or other applications to the seed. In embodiments, the seed coating may be applied to a naked and untreated seed. In other embodiments, the seed coating may be applied as a seed overcoat to a previously treated seed.

In some embodiments, the applied microbes may become endophytic and consequently will be present in the growing plant that was treated and its subsequent offspring. In other embodiments the microbes might be applied at the same time as a co-treatment with seed treatments.

In one embodiment of the present disclosure, the microbes are supplied in the form of granules, or plug, or soil drench that is applied to the plant growth media. In other embodiments, the microbes are supplied in the form of a foliar application, such as a foliar spray or liquid composition. The foliar spray or liquid application may be applied to a growing plant or to a growth media, e.g. soil.

In embodiments, the agricultural compositions of the disclosure can be formulated as: (1) solutions; (2) wettable powders; (3) dusting powders; (4) soluble powders; (5) emulsions or suspension concentrates; (6) seed dressings, (7) tablets; (8) water-dispersible granules; (9) water soluble granules (slow or fast release); (10) microencapsulated granules or suspensions; and (11) as irrigation components, among others. In certain aspects, the compositions may be diluted in an aqueous medium prior to conventional spray application. The compositions of the present disclosure can be applied to the soil, plant, seed, rhizosphere, rhizosheath, or other area to which it would be beneficial to apply the microbial compositions.

Still another object of the disclosure relates to the agricultural compositions being formulated to provide a high colony forming units (CFU) bacterial population or consortia. In some aspects, the agricultural compositions have adjuvants that provide for a pertinent shelf life. In embodiments, the CFU concentration of the taught agricultural compositions is higher than the concentration at which the microbes would exist naturally, outside of the disclosed methods. In another embodiment, the agricultural composition contains the microbial cells in a concentration of $10^3$-$10^{12}$ CFU per gram of the carrier or $10^5$-$10^9$ CFU per gram of the carrier. In an aspect, the microbial cells are applied as a seed coat directly to a seed at a concentration of $10^5$-$10^9$ CFU. In other aspects, the microbial cells are applied as a seed overcoat on top of another seed coat at a concentration of $10^5$-$10^9$ CFU. In other aspects, the microbial cells are applied as a co-treatment together with another seed treatment at a rate of $10^5$-$10^9$ CFU.

In aspects, the disclosure is directed to agricultural microbial formulations that promote plant growth. In aspects, the disclosure provides for the taught isolated microbes, and consortia comprising same, to be formulated as an agricultural bioinoculant. The taught bioinoculants can be applied to plants, seeds, or soil. Suitable examples of formulating bioinoculants comprising isolated microbes can be found in U.S. Pat. No. 7,097,830, which is herein incorporated by reference.

The disclosed polymicrobial formulations can: lower the need for nitrogen containing fertilizers, solubilize minerals, protect plants against pathogens, and make available to the plant valuable nutrients, such as phosphate, thus reducing and eliminating the need for using chemical pesticides and chemical fertilizers.

In some embodiments, the isolated and biologically pure microbes of the present disclosure can be utilized, in a method of imparting one or more beneficial properties or traits to a desired plant species.

In some embodiments, the agriculturally acceptable composition containing isolated and biologically pure microbes of the present disclosure can be utilized, in a method of imparting one or more beneficial properties or traits to a desired plant species.

In some embodiments, the consortia of the present disclosure can be utilized, in a method of imparting one or more beneficial properties or traits to a desired plant species.

In some embodiments, the agriculturally acceptable composition containing consortia of the present disclosure can be utilized, in a method of imparting one or more beneficial properties or traits to a desired plant species.

In some aspects, the isolated and biologically pure microbes of the present disclosure, and/or the consortia of the present disclosure, are derived from an accelerated microbial selection process ("AMS" process). The AMS process utilized in some aspects of the present disclosure is described, for example, in: (1) International Patent Application No. PCT/NZ2012/000041, published on Sep. 20, 2012, as International Publication No. WO 2012125050 A1, and (2) International Patent Application No. PCT/NZ2013/000171, published on Mar. 27, 2014, as International Publication No. WO 2014046553 A1, each of these PCT Applications is herein incorporated by reference in their entirety for all purposes. The AIMS process is described in the present disclosure, for example, in FIGS. 1-4.

However, in other embodiments, the microbes of the present disclosure are not derived from an accelerated microbial selection process. In some aspects, the microbes utilized in embodiments of the disclosure are chosen from amongst members of microbes present in a database. In particular aspects, the microbes utilized in embodiments of the disclosure are chosen from microbes present in a database based upon particular characteristics of said microbes.

The present disclosure provides that a plant element or plant part can be effectively augmented, by coating said plant element or plant part with an isolated microbe or microbial consortia, in an amount that is not normally found on the plant element or plant part Some embodiments described herein are methods for preparing an agricultural seed composition, or seed coating, comprising: contacting the surface of a seed with a formulation comprising a purified microbial population that comprises at least one isolated microbe that is heterologous to, or rarely present on the seed. Further embodiments entail preparing an agricultural plant composition, comprising: contacting the surface of a plant with a formulation comprising a purified microbial population that comprises at least one isolated microbe that is heterologous to the plant.

In some aspects, applying an isolated microbe, microbial consortia, and/or agricultural composition of the disclosure to a seed or plant modulates a trait of agronomic importance. The trait of agronomic importance can be, e.g., disease resistance, drought tolerance, heat tolerance, cold tolerance, salinity tolerance, metal tolerance, herbicide tolerance, chemical tolerance, improved water use efficiency, improved nitrogen utilization, improved resistance to nitrogen stress, improved nitrogen fixation, pest resistance, herbivore resistance, pathogen resistance, increased yield, increased yield under water limited conditions, health enhancement, vigor improvement, growth improvement, photosynthetic capability improvement, nutrition enhancement, altered protein content, altered oil content, increased biomass, increased shoot length, increased root length, improved root architecture, increased seed weight, faster seed germination, altered seed carbohydrate composition, altered seed oil composition, number of pods, delayed senescence, stay-green, and altered seed protein composition. In some aspects, at least 2, 3, 4, or more traits of agronomic importance are modulated. In some aspects, the modulation is a positive effect on one of the aforementioned agronomic traits.

In some aspects, the isolated microbes, consortia, and/or agricultural compositions of the disclosure can be applied to a plant, in order to modulate or alter a plant characteristic such as altered oil content, altered protein content, altered seed carbohydrate composition, altered seed oil composition, altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, decreased biomass, increased root length, decreased root length, increased seed weight, increased shoot length, decreased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome relative to a reference plant.

In some embodiments, the agricultural formulations taught herein comprise at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient The methods described herein can include contacting a seed or plant with at least 100 CFU or spores, at least 300 CFU or spores, at least 1,000 CFU or spores, at least 3,000 CFU or spores, at least 10,000 CFU or spores, at least 30,000 CFU or spores, at least 100,000 CFU or spores, at least 300,000 CFU or spores, at least 1,000,000 CFU or spores or more, of the microbes taught herein.

In some embodiments of the methods described herein, an isolated microbe of the disclosure is present in a formulation in an amount effective to be detectable within and/or on a target tissue of an agricultural plant. For example, the microbe is detected in an amount of at least 100 CFU or spores, at least 300 CFU or spores, at least 1,000 CFU or spores, at least 3,000 CFU or spores, at least 10,000 CFU or spores, at least 30,000 CFU or spores, at least 100,000 CFU or spores, at least 300,000 CFU or spores, at least 1,000,000 CFU or spores, or more, in and/or on a target tissue of a plant. Alternatively or in addition, the microbes of the disclosure may be present in a formulation in an amount effective to increase the biomass and/or yield of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied. Alternatively or in addition, the microbes of the disclosure may be present in a formulation in an amount effective to detectably modulate an agronomic trait of interest of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied.

In some embodiments, the agricultural compositions taught herein are shelf-stable. In some aspects, the microbes taught herein are freeze dried. Also described herein are a plurality of isolated microbes confined within an object selected from the group consisting of: bottle, jar, ampule, package, vessel, bag, box, bin, envelope, carton, container, silo, shipping container, truck bed, and case.

In some aspects, combining a selected plant species with a disclosed microbe-operational taxonomic unit (OTU), strain, or composition comprising any of the aforementioned-leads to improved yield from crops and generation of products thereof. Therefore, in one aspect, the present disclosure provides a synthetic combination of a seed of a first plant and a preparation of a microbe(s) that is coated onto the surface of the seed of the first plant, such that the microbe is present at a higher level on the surface of the seed, than is present on the surface of an uncoated reference seed. In another aspect, the present disclosure provides a synthetic combination of a part of a first plant and a preparation of a microbe(s) that is coated onto the surface of the part of the first plant, such that the microbe is present at a higher level on the surface of the part of the first plant, than is present on the surface of an uncoated reference plant part. The aforementioned methods can be used alone, or in parallel with plant breeding and transgenic technologies.

In some embodiments, an isolated bacterial strain may be selected from the group consisting of *Chryseobacterium daecheongense* deposited as NRRL Accession Deposit No. NRRL B-67291; *Chryseobacterium rhizosphaerae* deposited as NRRL Accession Deposit No. NRRL B-67288; *Chryseobacterium rhizosphaerae* deposited as NRRL Accession Deposit No. NRRL B-67287; *Frigidibacter albus* deposited as NRRL Accession Deposit No. NRRL B-67285; *Frigidibacter albus* deposited as NRRL Accession Deposit No. NRRL B-67283; *Frigidibacter albus* deposited as NRRL Accession Deposit No. NRRL B-67284; *Arthrobacter nicotinovorans* deposited as NRRL Accession Deposit No. NRRL B-67289; *Arthrobacter nicotinovorans* deposited as NRRL Accession Deposit No. NRRL B-67209; *Pseudomonas helmanticensis* deposited as NRRL Accession Deposit No. NRRL B-67295; *Pseudomonas helmanticensis* deposited as NRRL Accession Deposit No. NRRL B-97296; *Pseudomonas helmanticensis* deposited as NRRL Accession Deposit No. NRRL B-67297; *Agrobacterium fabrum* deposited as NRRL Accession Deposit No. NRRL B-67286; *Exiguobacterium sibiricum* deposited as NRRL Accession Deposit No. NRRL B-67294; *Exiguobacterium antarcticum* deposited as NRRL Accession Deposit No. NRRL B-67292; *Exiguobacterium antarcticum* deposited as NRRL Accession Deposit No. NRRL B-67293; *Leifsonia lichenia* deposited as NRRL Accession Deposit No. NRRL B-67298; *Leifsonia lichenia* deposited as NRRL Accession Deposit No. NRRL B-67299; *Tumebacillus permanentifrigoris* deposited as NRRL Accession Deposit No. NRRL B-67302; *Tumebacillus permanentifrigoris* deposited as NRRL Accession Deposit No. NRRL B-67300; *Tumebacillus permanentifrigoris* deposited as NRRL Accession Deposit No. NRRL B-67303; and *Tumebacillus permanentifrigoris* deposited as NRRL Accession Deposit No. NRRL B-67301.

In some embodiments, the isolated bacterial strain has substantially similar morphological and physiological characteristics as an isolated bacterial strain of the present disclosure. In some embodiments, the isolated bacterial strain has substantially similar genetic characteristics as an isolated bacterial strain of the present disclosure. In some embodiments, an isolated bacterial strain of the present disclosure is in substantially pure culture.

In some embodiments, progeny and/or mutants of an isolated bacterial strain of the present disclosure are contemplated. In some embodiments, an isolated bacterial strain of the present disclosure comprises a polynucleotide sequence sharing at least 97% sequence identity with any one of SEQ ID Nos: 1-307. In other embodiments, an isolate bacterial strain of the present disclosure comprises a polynucleotide sequence sharing at least 97% sequence identity with any one of SEQ ID NOs: 2-13, 14, 17-19, 22-27, 29, 31, 33, and 34.

In some embodiments, a cell-free or inactivated preparation of an isolated bacterial strain of the present disclosure is contemplated, or a mutant of said isolated bacterial strain. In some embodiments, a metabolite produced by an isolated bacterial strain of the present disclosure is contemplated, or a mutant of said isolated bacterial strain.

In some embodiments, an agricultural composition comprises an isolated bacterial strain and an agriculturally acceptable carrier. The isolated bacterial strain may be present in the composition at $1\times10^3$ to $1\times10^{12}$ bacterial cells per gram. The agricultural composition may be formulated as a seed coating.

In some embodiments, a method of imparting at least one beneficial train upon a plant species comprises applying an isolated bacterial strain to the plant or to a growth medium in which said plant is located. In some embodiments, a method of imparting at least one beneficial trait upon a plant species comprises applying an agricultural composition of the present disclosure to the plant or to a growth medium in which the plant is located.

In some embodiments a microbial consortium comprises at least two microbes selected from the groups consisting of: A) *Stenotrophomonas maltophilia, Rhodococcus erythropolis, Pantoea vagans, Pseudomonas oryzihabitans, Rahnella aquatilis, Duganella radicis, Exiguobacterium acetylicum, Arthrobacter pascens, Pseudomonas putida, Bacillus megatarium, Bacillus aryabhattai, Bacillus cereus, Novosphingobium sediminicola, Rhizobium etli, Ensifer adhaerens, Chitinophaga terrae, Variovorax ginsengisoli, Pedobacter terrae, Massilia albidiflava, Dyadobacter soli, Bosea robiniae, Microbacterium maritypicum, Microbacterium azadirachtae, Sphingopyxis alaskensis, Arthrobacter pascens, Chryseobacterium rhizosphaerae, Variovorax paradoxus, Hydrogenophaga atypica*, and *Microbacterium oleivorans*; and/or B) *Chryseobacterium daecheongense, Chryseobacterium rhizosphaerae, Frigidibacter albus, Arthrobacter nicotinovorans, Pseudomonas helmanticensis, Agrobacterium fabrum, Achromobacter pulmonis, Exiguobacterium sibiricum, Exiguobacterium antarcticum, Leifsonia lichenia, Tumebacillus permanentifrigoris, Novosphingobium lindaniclasticum*, and *Massilia kyonggiensis*; and combinations thereof, and wherein at least one microbe from B) is selected.

In some embodiments, the microbial consortium has substantially similar morphological and physiological characteristics as a microbial consortium of the present disclosure. In some embodiments, the microbial consortium has substantially similar genetic characteristics as a microbial consortium of the present disclosure. In some embodiments, the microbial consortium is in substantially pure culture. In some embodiments, a subsequent generation of any microbe of the microbial consortium is contemplated. In some embodiments, a mutant of any microbe of microbial consortium is contemplated. In some embodiments, a cell-free or inactivated preparation of the microbial consortium, or a mutant of any microbe in the microbial consortium, is contemplated. In some embodiments, a metabolite produced by the microbial consortium, or a mutant of any microbe in the microbial consortium, is contemplated.

In some embodiments, an agricultural composition comprises a microbial consortium and an agriculturally acceptable carrier. The microbial consortium of the agricultural composition may be present in the composition at $1\times10^3$ to $1\times10^{12}$ bacterial cells per gram. In some embodiments, the agricultural composition is formulated as a seed coating. In some embodiments, a method of imparting at least one beneficial train upon a plant species comprises applying a microbial consortium to said plant, or to a growth medium in which said plant is located. In some embodiments, a method of imparting at least one beneficial trait upon a plant species, comprising applying the agricultural composition to the plant, or to a growth medium in which said plant is located.

In some embodiments, a microbial consortium comprises at least two microbes selected from the group consisting of *Chryseobacterium daecheongense* deposited as NRRL Accession Deposit No. NRRL B-67291; *Chryseobacterium rhizosphaerae* deposited as NRRL Accession Deposit No. NRRL B-67288; *Chryseobacterium rhizosphaerae* deposited as NRRL Accession Deposit No. NRRL B-67287; *Frigidibacter albus* deposited as NRRL Accession Deposit No. NRRL B-67285; *Frigidibacter albus* deposited as NRRL Accession Deposit No. NRRL B-67283; *Frigidibacter albus* deposited as NRRL Accession Deposit No. NRRL B-67284; *Arthrobacter nicotinovorans* deposited as NRRL Accession Deposit No. NRRL B-67289; *Arthrobacter nicotinovorans* deposited as NRRL Accession Deposit No. NRRL B-67290; *Pseudomonas helmanticensis* deposited as NRRL Accession Deposit No. NRRL B-67295; *Pseudomonas helmanticensis* deposited as NRRL Accession Deposit No. NRRL B-67296; *Pseudomonas helmanticensis* deposited as NRRL Accession Deposit No. NRRL B-67297; *Agrobacterium fabrum* deposited as NRRL Accession Deposit No. NRRL B-67286; *Exiguobacterium sibiricum* deposited as NRRL Accession Deposit No. NRRL B-67294; *Exiguobacterium antarcticum* deposited as NRRL Accession Deposit No. NRRL B-67292; *Exiguobacterium antarcticum* deposited as NRRL Accession Deposit No. NRRL B-67293; *Leifsonia lichenia* deposited as NRRL Accession Deposit No. NRRL B-67298; *Leifsonia lichenia* deposited as NRRL Accession Deposit No. NRRL B-67299; *Tumebacillus permanentifrigoris* deposited as NRRL Accession Deposit No. NRRL B-67302; *Tumebacillus permanentifrigoris* deposited as NRRL Accession Deposit No. NRRL B-67300; *Tumebacillus permanentifrigoris* deposited as NRRL Accession Deposit No. NRRL B-67303; *Tumebacillus permanentifrigoris* deposited as NRRL Accession Deposit No. NRRL B-67301; and combinations thereof.

In one embodiment, the microbial consortium comprises *Leifsonia lichenia* deposited as NRRL Accession Deposit No. NRRL B-67298, *Tumebacillus permanentifrigoris* deposited as NRRL Accession Deposit No. NRRL B-67301, *Chryseobacterium rhizosphaerae* deposited as NRRL Accession Deposit No. NRRL B-67288, and *Frigidibacter albus* deposited as NRRL Accession Deposit No. NRRL B-67285. In another embodiment, the microbial consortium comprises *Exiguobacterium sibiricum* deposited as NRRL Accession Deposit No. NRRL B-67294, and *Massilia kyonggiensis* deposited as NRRL Accession Deposit No. NRRL B-67198. In another embodiment, the microbial consortium comprises *Chryseobacterium rhizosphaerae* deposited as NRRL Accession Deposit No. NRRL B-67288, *Frigidibacter albus* deposited as NRRL Accession Deposit No. NRRL B-67285, and *Arthrobacter nicotinovorans* deposited as NRRL Accession Deposit No. NRRL B-67289.

In some embodiments, a method of imparting at least one beneficial train upon a plant species comprises applying at least one isolated bacterial species to the plant, or to a growth medium in which the plant is located, wherein the at least one isolated bacterial species is selected from the group consisting of: *Agrobacterium fabrum, Novosphingobium lindaniclasticum, Pedobacter terrae, Chryseobacterium daecheongense, Chryseobacterium rhizosphaerae, Frigidibacter albus, Arthrobacter nicotinovorans, Pseudomonas helmanticensis, Agrobacterium fabrum, Achromobacter pulmonis, Exiguobacterium sibiricum, Exiguobacterium antarcticum, Pedobacter terrae, Leifsonia lichenia, Massilia kyongiensis, Tumebacillus permanentifrigoris*, and combinations thereof. In a further embodiment, the at least one isolated bacterial species is a strain selected from the group consisting of: *Chryseobacterium daecheongense* deposited as NRRL Accession Deposit No. NRRL B-67291; *Chryseobacterium rhizosphaerae* deposited as NRRL Accession Deposit No. NRRL B-67288; *Chryseobacterium rhizosphaerae* deposited as NRRL Accession Deposit No. NRRL B-67287; *Frigidibacter albus* deposited as NRRL Accession Deposit No. NRRL B-67285; *Frigidibacter albus* deposited as NRRL Accession Deposit No. NRRL B-67283; *Frigidibacter albus* deposited as NRRL Accession Deposit No. NRRL B-67284; *Arthrobacter nicotinovorans* deposited as NRRL Accession Deposit No. NRRL B-67289; *Arthrobacter nicotinovorans deposited as NRRL Accession Deposit No. NRRL B-67290; *Pseudomonas helmanticensis* deposited as NRRL Accession Deposit No. NRRL B-67295; *Pseudomonas helmanticensis* deposited as NRRL Accession Deposit No. NRRL B-67296; *Pseudomonas helmanticensis* deposited as NRRL Accession Deposit No. NRRL B-67297; *Agrobacterium fabrum* deposited as NRRL Accession Deposit No. NRRL B-67286; *Exiguobacterium sibiricum* deposited as NRRL Accession Deposit No. NRRL B-67294; *Exiguobacterium antarcticum* deposited as NRRL Accession Deposit No. NRRL B-67292; *Exiguobacterium antarcticum* deposited as NRRL Accession Deposit No. NRRL B-67293; *Leifsonia lichenia* deposited as NRRL Accession Deposit No. NRRL B-67298; *Leifsonia lichenia* deposited as NRRL Accession Deposit No. NRRL B-67299; *Tumebacillus permanentifrigoris* deposited as NRRL Accession Deposit No. NRRL B-67302; *Tumebacillus permanentifrigoris* deposited as NRRL Accession Deposit No. NRRL B-67300; *Tumebacillus permanentifrigoris* deposited as NRRL Accession Deposit No. NRRL B-67303; and *Tumebacillus permanentifrigoris* deposited as NRRL Accession Deposit No. NRRL B-67301.

In some embodiments, an isolated bacterial strain is selected from Table 4. In some embodiments, an isolated bacterial strain is contemplated having substantially similar morphological and physiological characteristics as an isolated bacterial strain selected from Table 4. In some embodiments, an isolated bacterial strain is contemplated having substantially similar genetic characteristics as an isolated bacterial strain from Table 4. In some embodiments, a substantially pure culture is contemplated of an isolated bacterial strain from Table 4. In some embodiments, a progeny or a mutant of an isolated bacterial strain from Table 4 is contemplated. In some embodiments, a cell-free or inactivated preparation is contemplated from an isolated bacterial strain, or a mutant thereof, from Table 4. In some embodiments, a metabolite produced by an isolated bacterial strain, or a mutant thereof, from Table 4.

In some embodiments, an agricultural composition comprises an isolated bacterial strain from Table 4 and an agriculturally acceptable carrier. In some embodiments, the isolated bacterial strain is present in the agricultural composition at $1 \times 10^3$ to $1 \times 10^{12}$ bacterial cells per gram. In some embodiments, the agricultural composition is formulated as a seed coating. In some embodiments, a method of imparting at least one beneficial train upon a plant species comprises applying an isolated bacterial strain from Table 4 to the plant, or to a growth medium in which said plant is located. In some embodiments, a method of imparting at least one beneficial trait upon a plant species comprises applying an agricultural composition of the present disclosure to the plant, or to a growth medium in which said plant is located.

In some embodiments, a microbial consortium comprises at least two microbes selected from those listed in Table 4. In some embodiments, a microbial consortium is selected from the consortia listed in Table 5, wherein the consortium comprises at least one microbe listed in Table 4. In some embodiments, a microbial consortium is selected from the consortia listed in Table 6, wherein the consortium comprises at least one microbe listed in Table 4. In some embodiments, a microbial consortium is selected from the consortia listed in Table 7, wherein the consortium comprises at least one microbe listed in Table 4. In some embodiments, a microbial consortium is selected from the consortia listed in Table 8, wherein the consortium comprises at least one microbe listed in Table 4. In some embodiments, a microbial consortium is selected from the consortia listed in Table 9, wherein the consortium comprises at least one microbe listed in Table 4. In some embodiments, a microbial consortium is selected from the consortia listed in Table 10, wherein the consortium comprises at least one microbe listed in Table 4. In some embodiments, a microbial consortium is selected from the consortia listed in Table 11, wherein the consortium comprises at least one microbe listed in Table 4.

In some embodiments, a plant seed enhanced with a microbial seed coating comprises a plant seed and a seed coating applied onto said plant seed, wherein the seed coating comprises at least two microbes as listed in Tables 1-4, and wherein at least one microbe is selected from Table 4. In a further embodiment, the seed coating comprises a consortium of microbes as listed in Tables 5-11. In a further embodiment, the seed coating comprises at least one microbe as listed in Table 4 at a concentration of $1 \times 10^5$ to $1 \times 10^9$ bacterial cells per seed. In some embodiments, a microbe selected from Table 4 is used in agriculture. In some embodiments, a synthetic combination of a plant and microbe comprises at least one plant and at least one microbe selected from Table 4.

In some embodiments, a method of increasing or promoting a desirable phenotypic trait of a plant species comprises applying at least one bacteria selected from Table 4 to said plant, or to a growth medium in which said plant is located. In a further embodiment, the method of applying the at least one bacteria occurs by coating a plant seed with said bacteria, coating a plant part with said bacteria, spraying said bacteria onto a plant part, spraying said bacteria into a furrow into which a plant or seed will be placed, drenching said bacteria onto a plant part or into an area into which a plant will be placed, spreading said bacteria onto a plant part or into an area into which a plant will be placed, broadcasting said bacteria onto a plant part or into an area into which a plant will be placed, and combinations thereof.

In any of the methods, the microbe can include a 16S nucleic acid sequence having at least 97% sequence identity to a 16S nucleic acid sequence of a bacteria selected from a genus provided in Table 4.

Figure 1:
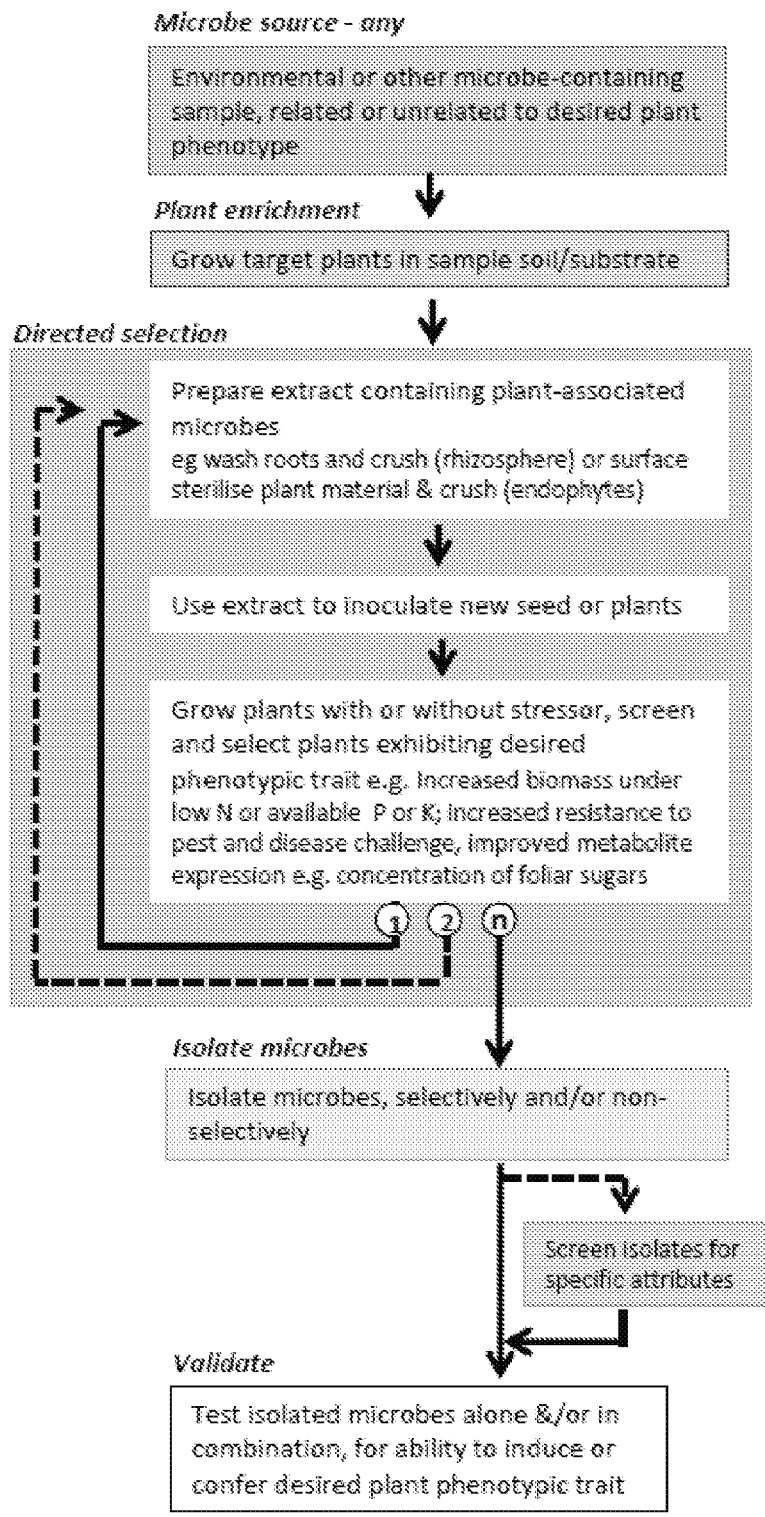
FIG. 1 shows a generalized process schematic of a disclosed method of accelerated microbial selection (AMS), also referred to herein as directed microbial selection. When the process is viewed in the context of a microbial consortium, the schematic is illustrative of a process of directed evolution of a microbial consortium. The process is one method, by which the beneficial microbes of the present disclosure were obtained.
Figure 2:
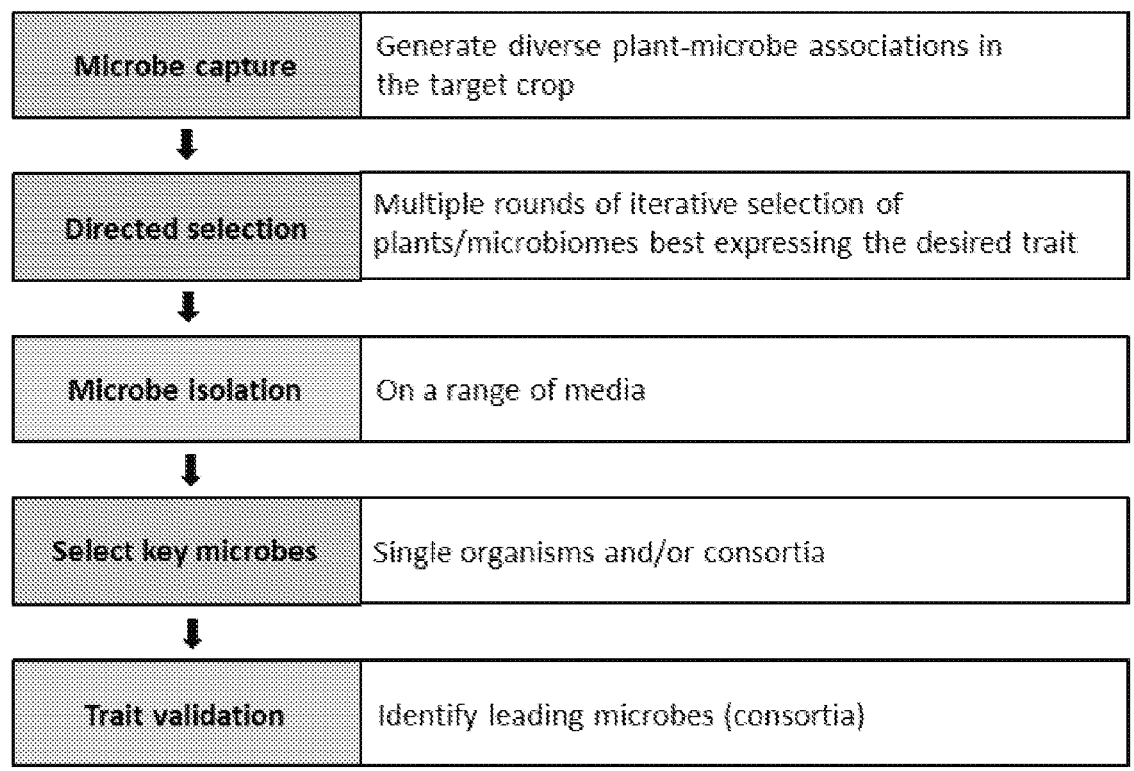
FIG. 2 shows a generalized process flow chart of an embodiment, by which the beneficial microbes of the present disclosure were obtained.
Figure 3:
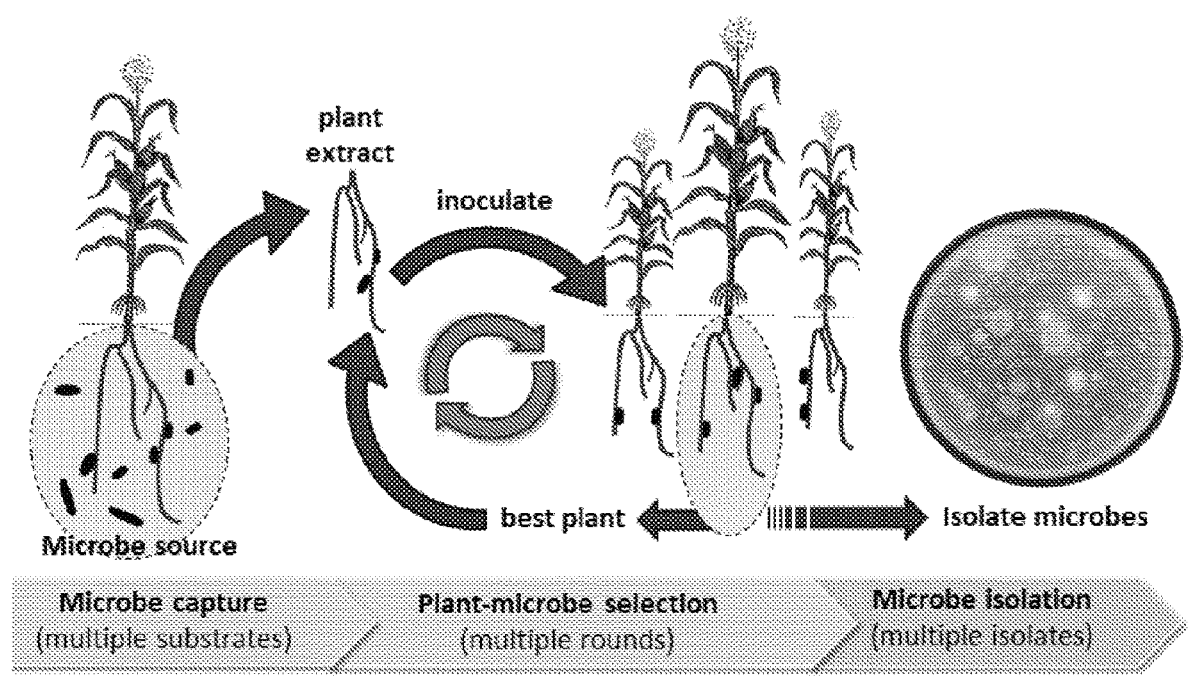
FIG. 3 shows a graphic representation and associated flow chart of an embodiment, by which the beneficial microbes of the present disclosure were obtained.
Figure 4:
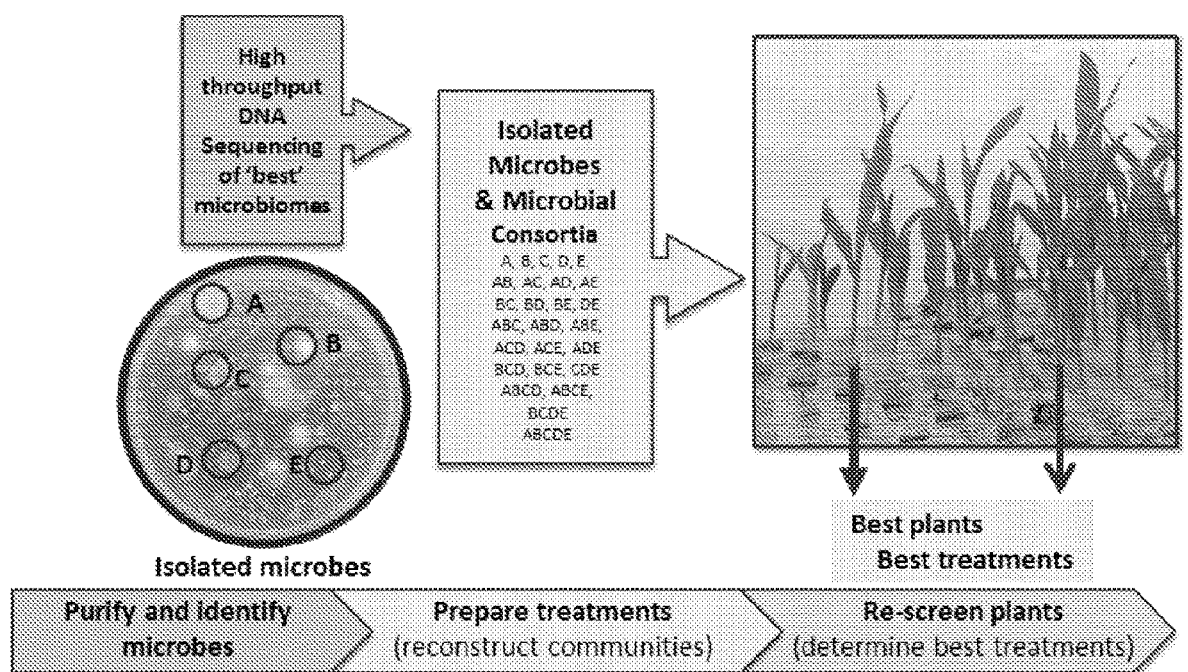
FIG. 4 shows a graphic representation and associated flow chart of an embodiment, by which the beneficial microbes of the present disclosure were obtained.

BUDAPEST TREATY ON THE INTERNATIONAL RECOGNITION OF THE DEPOSIT OF MICROORGANISMS FOR THE PURPOSE OF PATENT PROCEDURES

The microorganisms described in this Application were deposited with the Agricultural Research Service Culture Collection (NRRL), which is an International Depositary Authority, located at 1815 North University Street, Peoria, Ill. 61604, USA.

The deposits were made under the terms of the Budapest Treaty on the International Recognition of the Deposit of Microorganisms for the Purposes of Patent Procedure.

The deposits were made in accordance with, and to satisfy, the criteria set forth in 37 C.F.R. §§ 1.801-1.809 and the Manual of Patent Examining Procedure §§ 2402-2411.05.

The NRRL accession numbers, dates of deposit, and descriptions for the aforementioned Budapest Treaty deposits are provided in Tables 1-4.

TABLE 1

| Microbial Species | Strains | Origin | Budapest Treaty International Depositary Authority Accession No. & Date of Deposit | Representative Deposited Species Available to the Public | SEQ ID No. |
|---|---|---|---|---|---|
| 1. *Azotobacter chroococcum* | BDNZ 57597 | NZ | | DSM-2286* | 289 |
| 2. *Pantoea agglomerans* | BDNZ 54499 | NZ | NRRL B-67224 | | 278 |
| (recently reassigned to | BDNZ 55529 | | Jan. 29, 2016 | | 289 |
| *Pantoea vagans*) | BDNZ 57547 | | | | 288 |
| 3. *Pantoea agglomerans* | BCI 1208 | US | | DSM-23078* | 62 |
| (recently reassigned to | BCI 1274 | | | | 68 |
| *Pantoea vagans*) | BCI 1355 | | | | 90 |
| 4. *Pseudomonas fluorescens* | BDNZ 54480 | NZ | | DSM-50090* | 276 |
| | BDNZ 56530 | | | | 285 |
| | BDNZ 56249 | | | | 284 |
| 5. *Pseudomonas fluorescens* | BCI 1352 | US | | DSM-50090* | 88 |
| 6. *Pseudomonas oryzihabitans* | BDNZ 55530 | NZ | NRRL B-67225 Jan. 29, 2016 | | 283 |
| 7. *Pseudomonas oryzihabitans* | BCI 1184 | US | | DSM-6835* | 58 |
| | BCI 1195 | | | | 59 |
| | BCI 1199 | | | | 60 |
| 8. *Pseudomonas putida* | BDNZ 60303 | NZ | | DSM-291* | 294 |
| 9. *Pseudomonas putida* | BCI 159 | US | | DSM-291* | 100 |
| | BCI 178 | | | | 104 |
| | BCI 234 | | | | 109 |
| | BCI 235 | | | | 110 |
| | BCI 244 | | | | 112 |
| | BCI 357 | | | | 124 |
| | BCI 360 | | | | 126 |
| | BCI 363 | | | | 127 |
| | BCI 365 | | | | 128 |
| | BCI 367 | | | | 129 |
| | BCI 368 | | | | 130 |
| | BCI 369 | | | | 131 |
| | BCI 370 | | | | 132 |
| | BCI 372 | | | | 134 |
| | BCI 375 | | | | 135 |
| | BCI 458 | | | | 144 |
| | BCI 459 | | | | 145 |
| | BCI 460 | | | | 147 |
| | BCI 461 | | | | 148 |
| | BCI 462 | | | | 149 |
| | BCI 467 | | | | 150 |
| | BCI 469 | | | | 151 |
| | BCI 470 | | | | 152 |
| | BCI 571 | | | | 162 |
| | BCI 593 | | | | 168 |
| | BCI 731 | | | | 198 |
| | BCI 791 | | | | 205 |
| | BCI 802 | | | | 208 |
| | BCI 805 | | | | 210 |
| | BCI 806 | | | | 211 |
| | BCI 809 | | | | 213 |
| | BCI 1312 | | | | 73 |
| | BCI 1314 | | | | 74 |
| | BCI 1315 | | | | 75 |
| | BCI 1319 | | | | 77 |
| | BCI 1330 | | | | 82 |
| | BCI 1333 | | | | 84 |
| | BCI 1351 | | | | 87 |
| | BCI 1353 | | | | 89 |
| | BCI 1356 | | | | 91 |
| | BCI 1358 | | | | 93 |
| | BCI 1363 | | | | 96 |
| 10. *Rahnella aquatilis* | BDNZ 56532 | NZ | NRRL B-67228 Jan. 29, 2016 | | 286 |
| | BDNZ 57157 | | | | 287 |
| | BDNZ 58013 | | NRRL B-67229 Jan. 29, 2016 | | 293 |

TABLE 1-continued

| Microbial Species | Strains | Origin | Budapest Treaty International Depositary Authority Accession No. & Date of Deposit | Representative Deposited Species Available to the Public | SEQ ID No. |
|---|---|---|---|---|---|
| 11. *Rahnella aquatilis* | BCI 29 | US | NRRL B-67165 |  | 118 |
|  | BCI 1158 |  | Dec. 18, 2015 |  | 54 |
| 12. *Rhizobium etli* | BDNZ 60473 | NZ |  | DSM-11541* | 295 |
| 13. *Rhodococcus erythropolis* | BDNZ 54093 | NZ | NRRL B-67227 |  | 274 |
|  | BDNZ 54299 |  | Jan. 29, 2016 |  | 275 |
| 14. *Rhodococcus erythropolis* | BCI 1182 | US |  | DSM-43066* | 57 |
| 15. *Stenotrophomonas maltophilia* | BDNZ 54073 | NZ | NRRL B-67226 Jan. 29, 2016 |  | 273 |
| 16. *Stenotrophomonas maltophilia* | BCI 7 | US |  | DSM-50170* | 194 |
|  | BCI 64 |  |  |  | 183 |
|  | BCI 77 |  |  |  | 201 |
|  | BCI 115 |  |  |  | 52 |
|  | BCI 120 |  |  |  | 61 |
|  | BCI 164 |  |  |  | 102 |
|  | BCI 171 |  |  |  | 103 |
|  | BCI 181 |  |  |  | 105 |
|  | BCI 271 |  |  |  | 114 |
|  | BCI 343 |  |  |  | 122 |
|  | BCI 344 |  |  |  | 123 |
|  | BCI 380 |  |  |  | 136 |
|  | BCI 539 |  |  |  | 157 |
|  | BCI 545 |  |  |  | 158 |
|  | BCI 551 |  |  |  | 159 |
|  | BCI 574 |  |  |  | 163 |
|  | BCI 588 |  |  |  | 165 |
|  | BCI 590 |  |  |  | 167 |
|  | BCI 601 |  |  |  | 170 |
|  | BCI 602 |  |  |  | 171 |
|  | BCI 606 |  |  |  | 172 |
|  | BCI 607 |  |  |  | 173 |
|  | BCI 610 |  |  |  | 176 |
|  | BCI 617 |  |  |  | 177 |
|  | BCI 618 |  |  |  | 178 |
|  | BCI 619 |  |  |  | 179 |
|  | BCI 620 |  |  |  | 181 |
|  | BCI 623 |  |  |  | 182 |
|  | BCI 665 |  |  |  | 185 |
|  | BCI 693 |  |  |  | 193 |
|  | BCI 787 |  |  |  | 202 |
|  | BCI 790 |  |  |  | 204 |
|  | BCI 793 |  |  |  | 206 |
|  | BCI 795 |  |  |  | 207 |
|  | BCI 808 |  |  |  | 212 |
|  | BCI 903 |  |  |  | 218 |
|  | BCI 908 |  |  |  | 219 |
|  | BCI 970 |  |  |  | 224 |
|  | BCI 996 |  |  |  | 226 |
|  | BCI 997 |  |  |  | 227 |
|  | BCI 1032 |  |  |  | 37 |
|  | BCI 1092 |  |  |  | 45 |
|  | BCI 1096 |  |  |  | 46 |
|  | BCI 1116 |  |  |  | 50 |
|  | BCI 1224 |  |  |  | 64 |
|  | BCI 1279 |  |  |  | 69 |
|  | BCI 1316 |  |  |  | 76 |
|  | BCI 1320 |  |  |  | 79 |
|  | BCI 1322 |  |  |  | 80 |
|  | BCI 1325 |  |  |  | 81 |
|  | BCI 1331 |  |  |  | 83 |
|  | BCI 1344 |  |  |  | 85 |
|  | BCI 1350 |  |  |  | 86 |
|  | BCI 1357 |  |  |  | 92 |
|  | BCI 1362 |  |  |  | 95 |

*Denotes a microbial species that has been deposited and is available to the public, but said species is not a deposit of the exact BCI or BDNZ strain.

TABLE 2

| Microbial Species | Strain | Origin | Budapest Treaty International Depositary Authority Accession No. & Date of Deposit | Representative Deposited Species Available to the Public | SEQ ID No. |
|---|---|---|---|---|---|
| 1. *Azospirillum lipoferum* | BDNZ57661 | NZ | | DSM-1838* | 291 |
| | BDNZ66460 | | | | 300 |
| 2. *Bacillus megaterium* | BDNZ55076 | NZ | | DSM-32* | 279 |
| 3. *Bacillus megaterium* | BCI 251 | US | | DSM-32* | 113 |
| | BCI 255 | | | | 114 |
| | BCI 262 | | | | 115 |
| | BCI 264 | | | | 116 |
| 4. *Bacillus psychrosaccharolyticus* | BDNZ 66518 | NZ | | DSM-13778* | 303 |
| | BDNZ 66544 | | | | 306 |
| 5. *Duganella zoogloeoides* | BDNZ 66500 | NZ | | DSM-16928* | 302 |
| 6. *Herbaspirillum huttiense* | BDNZ 54487 | NZ | | DSM-10281* | 277 |
| 7. *Herbaspirillum huttiense* | BCI 9 | US | | DSM-10281* | 217 |
| 8. *Paenibacillus chondroitinus* | BDNZ 57634 | NZ | | DSM-5051* | 290 |
| 9. *Paenibacillus polymyxa* | BDNZ 55146 | NZ | | DSM-36* | 280 |
| | BDNZ 66545 | | | | 304 |
| 10. *Paenibacillus polymyxa* | BCI 1118 | US | | D5M-36* | 51 |

*Denotes a microbial species that has been deposited and is available to the public, but said species is not a deposit of the exact BCI or BDNZ strain.

TABLE 3

| Microbial Species | Strain | Origin | Budapest Treaty International Depositary Authority Accession No. & Date of Deposit | Representative Deposited Species Available to the Public | SEQ ID No. |
|---|---|---|---|---|---|
| 1. *Flavobacterium glaciei* | BDNZ 66487 | NZ | | DSM-19728* | 301 |
| 2. *Massilia niastensis* | BDNZ 55184 | NZ | NRRL B-67235 Feb. 8, 2016 | | 281 |
| | BCI 1217 | US | NRRL B-67199 Dec. 29, 2015 | | 63 |
| 3. *Massilia kyonggiensis* (*Massilia albidiflava*) | BCI 36 | US | | DSM-17472* | 125 |
| 4. *Sphingobium yanoikuyae* | BDNZ 57662 | NZ | | DSM-7462* | 292 |
| 5. *Bacillus subtilis* | BDNZ 66347 | NZ | | DSM-1088* | 263 |
| 6. *Bacillus subtilis* | BCI 395 | US | | DSM-1088* | 138 |
| | BCI 989 | | | | 225 |
| | BCI 1089 | | | | 43 |
| 7. *Bosea minatitlanensis* | BDNZ 66354 | NZ | | DSM-13099* | 264 |
| 8. *Bosea thiooxidans* | BDNZ 54522 | NZ | | DSM-9653* | 240 |
| 9. *Bosea thiooxidans* | BCI 703 | US | NRRL B-67187 Dec. 29, 2015 | | 196 |
| | BCI 985 | | | | 36 |
| | BCI 1111 | | | | 49 |
| 10. *Bosea robinae* | BCI 1041 | US | NRRL B-67186 Dec. 29, 2015 | | 38 |
| | BCI 689 | | | | 190 |
| | BCI 765 | | | | 200 |
| 11. *Bosea eneae* | BCI 1267 | US | NRRL B-67185 Dec. 29, 2015 | | 67 |
| 12. *Caulobacter henrici* | BDNZ 66341 | NZ | | DSM-4730* | 262 |
| 13. *Pseudoduganella violaceinigra* | BDNZ 66361 | NZ | | DSM-15887* | 265 |
| 14. *Luteibacter yeojuensis* | BDNZ 57549 | NZ | | DSM-17673* | 235 |
| 15. *Mucilaginibacter gossypii* | BDNZ66321 | NZ | | | 297 |
| 16. *Mucilaginibacter gossypii* | BCI 142 | US | | | 99 |
| | BCI 1156 | | | | 53 |
| | BCI 1307 | | | | 71 |
| 17. *Paenibacillus amylolyticus* | BDNZ 66316 | NZ | | DSM-11730* | 296 |
| 18. *Polaromonas ginsengisoli* | BDNZ 66373 | NZ | NRRL B-67231 Feb. 8, 2016 | DSM-14656* | 266 |
| | BDNZ 66821 | NZ | NRRL B-67234 Feb. 8, 2016 | | 270 |

TABLE 3-continued

| | Microbial Species | Strain | Origin | Budapest Treaty International Depositary Authority Accession No. & Date of Deposit | Representative Deposited Species Available to the Public | SEQ ID No. |
|---|---|---|---|---|---|---|
| 19. | Ramlibacter henchirensis | BDNZ 66331 | NZ | | DSM-14656* | 261 |
| 20. | Ramlibacter henchirensis | BCI 739 | US | NRRL B-67208 Dec. 29, 2015 | | 199 |
| 21. | Leifsonia shinshuensis (previously Rhizobium leguminosarum bv. trifolii) | BDNZ 61433 | NZ | | DSM-15165* | 250 |
| 22. | Rhizobium pisi | BDNZ 66326 | NZ | | DSM-30132* | 260 |
| 23. | Rhodoferax ferrireducens | BDNZ 66374 | NZ | | DSM-15236* | 267 |
| 24. | Sphingobium chlorophenolicum | BDNZ 61473 | NZ | | DSM-24952* | 251 |
| 25. | Sphingobium quisquiliarum | BDNZ 66576 | NZ | | DSM-24952* | 269 |
| 26. | Herbaspirillum frisingense | BDNZ 50525 | NZ | | DSM-13128* | 234 |
| 27. | Caulibacter henrici | BDNZ 66341 | NZ | | DSM-4730* | 262 |
| 28. | Chitinophaga arvensicola | BDNZ 56343 | NZ | | DSM-3695* | 246 |
| 29. | Duganella violaceinigra | BDNZ 66361 | NZ | NRRL B-67232 Feb. 8, 2016 | DSM-15887* | 265 |
| | | BDNZ 58291 | NZ | NRRL B-67233 Feb. 8, 2016 | | 248 |
| 30. | Frateuria sp. | BDNZ 52707 | NZ | | DSM-6220* (Frateuria aurantia) | 238 |
| | | BDNZ 60517 | | | DSM-26515* (Frateuria terrea) | 249 |
| 31. | Janthinobacterium sp. | BDNZ 54456 | NZ | | | 239 |
| | | BDNZ 63491 | | | | 252 |
| 32. | Luteibacter rhizovicinus | BDNZ 65069 | NZ | | DSM-16549* | 255 |
| 33. | Lysinibacillus fusiformis | BDNZ 63466 | NZ | | DSM-2898* | 254 |
| 34. | Novosphingobium rosa | BDNZ 65589 | NZ | | DSM-7285* | 258 |
| | | BDNZ 65619 | | | | 259 |
| 35. | Rhizobium miluonense | BDNZ 65070 | NZ | | | 256 |
| 36. | Stenotrophomonas chelatiphaga | BDNZ 54952 | NZ | | DSM-21508* | 243 |
| 37. | Stenotrophomonas chelatiphaga | BDNZ 47207 | NZ | | DSM-21508* | 232 |
| 38. | Stenotrophomonas chelatiphaga | BDNZ 64212 | NZ | | DSM-21508* | 253 |
| 39. | Stenotrophomonas chelatiphaga | BNDZ 64208 | NZ | | DSM-21508* | 305 |
| 40. | Stenotrophomonas chelatiphaga | BDNZ 58264 | NZ | | DSM-21508* | 247 |
| 41. | Stenotrophomonas rhizophila | BDNZ 50839 | NZ | | DSM-14405* | 236 |
| 42. | Stenotrophomonas rhizophila | BDNZ 48183 | NZ | | DSM-14405* | 233 |
| 43. | Stenotrophomonas rhizophila | BDNZ 45125 | NZ | | DSM-14405* | 228 |
| 44. | Stenotrophomonas rhizophila | BDNZ 46120 | NZ | | DSM-14405* | 230 |
| 45. | Stenotrophomonas rhizophila | BDNZ 46012 | NZ | | DSM-14405* | 229 |
| 46. | Stenotrophomonas rhizophila | BDNZ 51718 | NZ | | DSM-14405* | 237 |
| 47. | Stenotrophomonas rhizophila | BDNZ 56181 | NZ | | DSM-14405* | 245 |
| 48. | Stenotrophomonas rhizophila | BDNZ 54999 | NZ | | DSM-14405* | 244 |
| 49. | Stenotrophomonas rhizophila | BDNZ 54850 | NZ | | DSM-14405* | 242 |
| 50. | Stenotrophomonas rhizophila | BDNZ 54841 | NZ | | DSM-14405* | 241 |
| 51. | Stenotrophomonas rhizophila | BDNZ 66478 | NZ | | DSM-14405* | 268 |
| 52. | Stenotrophomonas rhizophila | BDNZ 46856 | NZ | | DSM-14405* | 231 |
| 53. | Stenotrophomonas rhizophila | BDNZ 65303 | NZ | | DSM-14405* | 257 |
| 54. | Stenotrophomonas terrae | BDNZ 68599 | NZ | | DSM-15236* | 271 |
| 55. | Stenotrophomonas terrae | BDNZ 68741 | NZ | | DSM-18941* | 272 |
| 56. | Achromobacter spanius | BCI 385 | US | | DSM-23806* | 137 |

TABLE 3-continued

| | Microbial Species | Strain | Origin | Budapest Treaty International Depositary Authority Accession No. & Date of Deposit | Representative Deposited Species Available to the Public | SEQ ID No. |
|---|---|---|---|---|---|---|
| 57. | *Acidovorax soli* | BCI 690 | US | NRRL B-67182 Dec. 29, 2015 | | 191 |
| 58. | *Arthrobacter cupressi* | BCI 59 | US | NRRL B-67183 Dec. 29, 2015 | | 166 |
| 59. | *Arthrobacter mysorens* | BCI 700 | US | | DSM-12798* | 195 |
| 60. | *Arthrobacter pascens* | BCI 682 | US | | DSM-20545* | 187 |
| 61. | *Bacillus oleronius* | BCI 1071 | US | | DSM-9356* | 42 |
| 62. | *Bacillus cereus* or *Bacillus thuringiensis* (In Taxonomic Flux) | BCI 715 | US | | DSM-2046* | 197 |
| 63. | *Chitinophaga terrae* | BCI 79 | US | NRRL B-67188 Dec. 29, 2015 | | 203 |
| 64. | *Delftia lacustris* | BCI 124 | US | NRRL B-67190 Dec. 29, 2015 | | 65 |
| 65. | *Duganella radicis* | BCI 105 | US | NRRL B-67192 Dec. 29, 2015 | | 39 |
| 66. | *Duganella radicis* | BCI 57 | US | | | 161 |
| 67. | *Duganella radicis* | BCI 31 | US | NRRL B-67166 Jan. 3, 2016 | | 21 |
| 68. | *Dyadobacter soli* | BCI 68 | US | NRRL B-67194 Dec. 29, 2015 | | 186 |
| 69. | *Exiguobacterium acetylicum* | BCI 23 | US | | DSM-20416* | 108 |
| 70. | *Exiguobacterium acetylicum* | BCI 83 | US | | DSM-20416* | 216 |
| 71. | *Exiguobacterium acetylicum* | BCI 125 | US | | DSM-20416* | 66 |
| 72. | *Exiguobacterium aurantiacum* | BCI 50 | US | NRRL B-67175 Dec. 18, 2015 | | 155 |
| 73. | *Exiguobacterium* sp. (In Taxonomic Flux) | BCI 81 | US | | DSM-27935* | 214 |
| 74. | *Exiguobacterium sibiricum* | BCI 116 | US | NRRL B-67167 Dec. 18, 2016 | | 16 |
| 75. | *Herbaspirillum chlorophenolicum* | BCI 58 | US | NRRL B-67236 Feb. 8, 2016 | DSM-17796* | 164 |
| 76. | *Kosakonia radicincitans* | BCI 107 | US | | DSM-16656* | 41 |
| 77. | *Massilia kyonggiensis* (*Massilia albidiflava*) | BCI 97 | US | NRRL B-67198 Dec. 29, 2015 | | 32 |
| 78. | *Microbacterium* sp. | BCI 688 | US | | DSM-16050* | 189 |
| 79. | *Microbacterium oleivorans* | BCI 132 | US | NRRL B-67170 Dec. 18, 2015 | | 78 |
| 80. | *Mucilaginibacter gossypii* | BCI 142 | US | | | 98 |
| 81. | *Novosphigobium lindaniclasticum* | BCI 684 | US | NRRL B-67201 Dec. 29, 2015 | | 188 |
| 82. | *Novosphingobium resinovorum* | BCI 557 | US | NRRL B-67202 Dec. 29, 2015 | | 160 |
| 83. | *Novosphingobium sediminicola* | BCI 136 | US | | DSM-27057* | 94 |
| 84. | *Novosphingobium sediminicola* | BCI 82 | US | | DSM-27057* | 215 |
| 85. | *Novosphingobium sediminicola* | BCI 130 | US | NRRL B-67168 Dec. 18, 2015 | | 28 |
| 86. | *Paenibacillus glycanilyticus* | BCI 418 | US | NRRL B-67204 Dec. 29, 2015 | | 141 |
| 87. | *Pedobacter rhizosphaerae* (*Pedobacter soli*) | BCI 598 | US | NRRL B-67205 Dec. 29, 2015 | | 169 |
| 88. | *Pedobacter terrae* | BCI 91 | US | NRRL B-67206 Dec. 29, 2015 | | 220 |
| 89. | *Pseudomonas jinjuensis* | BCI 804 | US | NRRL B-67207 Dec. 29, 2015 | | 209 |
| 90. | *Rhizobium grahamii* | BCI 691 | US | | | 192 |
| 91. | *Rhizobium lemnae* (taxonomic name changed December 2015 to *Rhizobium rhizoryzae*) | BCI 34 | US | NRRL B-67210 Dec. 29, 2015 | | 121 |
| 92. | *Agrobacterium fabrum* or *Rhizobium pusense* (In Taxonomic Flux) | BCI 106 | US | NRRL B-67212 Dec. 29, 2015 | DSM-22668* | 40 |
| 93. | *Agrobacterium fabrum* or *Rhizobium pusense* (In Taxonomic Flux) | BCI 11 | US | | DSM-22668* | 47 |

TABLE 3-continued

| | Microbial Species | Strain | Origin | Budapest Treaty International Depositary Authority Accession No. & Date of Deposit | Representative Deposited Species Available to the Public | SEQ ID No. |
|---|---|---|---|---|---|---|
| 94. | Agrobacterium fabrum or Rhizobium pusense (In Taxonomic Flux) | BCI 609 | US | | DSM-22668* | 175 |
| 95. | Ensifer adhaerens | BCI 131 | US | NRRL B-67169 Dec. 18, 2015 | | 72 |
| 96. | Sphingopyxis alaskensis | BCI 914 | US | NRRL B-67215 Dec. 29, 2015 | DSM-13593* | 221 |
| 97. | Variovorax ginsengisoil | BCI 137 | US | NRRL B-67216 Dec. 29, 2015 | | 97 |
| 98. | Bacillus niacini | BCI 4718 | US | NRRL B-67230 Feb. 8, 2016 | DSM-2923* | 153 |
| 99. | Exiguobacterium sibiricum | BCI 116 | US | NRRL B-67167 Dec. 18, 2015 | | 16 |
| 100. | Chryseobacterium daecheongense | BCI 45 | US | NRRL B-67172 Dec. 18, 2015 | | 1 |
| 101. | Achromobacter pulmonis | BCI 49 | | NRRL B-67174 Dec. 18, 2015 | | 15 |
| 102. | Acidovorax soli | BCI 648 | | NRRL B-67181 Dec. 29, 2015 | | 184 |
| 103. | Arthrobacter cupressi | BCI 62 | | NRRL B-67184 Dec. 29, 2015 | | 180 |
| 104. | Chininophaga terrae | BCI 109 | | NRRL B-67189 Dec. 29, 2015 | | 44 |
| 105. | Delftia lacustris | BCI 2350 | | NRRL B-67191 Dec. 29, 2015 | | 111 |
| 106. | Duganella violaceinigra | BCI 2204 | | NRRL B-67193 Dec. 29, 2015 | | 107 |
| 107. | Dyadobacter soli | BCI 96 | | NRRL B-67195 Dec. 29, 2015 | | 222 |
| 108. | Flavobacterium glacei | BCI 4005 | | NRRL B-67196 Dec. 29, 2015 | | 139 |
| 109. | Herbaspirillum chlorophenolicum | BCI 162 | | NRRL B-67197 Dec. 29, 2015 | | 101 |
| 110. | Novosphingobium lindaniclasticum | BCI 608 | | NRRL B-67200 Dec. 29, 2015 | | 30 |
| 111. | Nocosphingobium resinovorum | BCI 3709 | | NRRL B-67203 Dec. 29, 2015 | | 133 |
| 112. | Ramlibacter henchirensis | BCI 1959 | | NRRL B-67209 Dec. 29, 2015 | | 106 |
| 113. | Rhizobium rhizoryzae | BCI 661 | | NRRL B-67211 Dec. 29, 2015 | | 35 |
| 114. | Sinorhizobium chiapanecum (Ensifer adhaerens) | BCI 111 | | NRRL B-67213 Dec. 29, 2015 | | 48 |
| 115. | Sphingopyxis alaskensis | BCI 412 | | NRRL B-67214 Dec. 29, 2015 | | 140 |
| 116. | Variovorax ginsengisoli | BCI 3078 | | NRRL B-67217 Dec. 29, 2015 | | 119 |
| 117. | Kosakonia radicincitans | BCI 44 | | NRRL B-67171 Dec. 18, 2015 | | 142 |
| 118. | Pedobacter terrae | BCI 53 | | NRRL B-67176 Dec. 18, 2015 | DSM17933* | 20 |
| 119. | Agrobacterium fabrum or Rhizobium pusense (In Taxonomic Flux) (previously Rhizobium sp.) | BCI 46 | | NRRL B-67173 Dec. 18, 2015 | | 146 |

*Denotes a microbial species that has been deposited and is available to the public, but said species is not a deposit of the exact BCI or BDNZ strain.

TABLE 4

| Microbial Species | Strain | Origin | Budapest Treaty International Depositary Authority Accession No. & Date of Deposit | Representative Deposited Species Available to the Public | SEQ ID No. |
|---|---|---|---|---|---|
| 1. *Chryseobacterium daecheongense* | BCI 191 | US | NRRL B-67291 Jul. 14, 2016 | DSM15235* | 2 |
| 2. *Chryseobacterium rhizosphaerae* | BCI 597 | US | NRRL B-67288 Jul. 14, 2016 | | 3 |
| | BCI 615 | US | NRRL B-67287 Jul. 14, 2016 | | 4 |
| 3. *Frigidibacter albus* or *Defluviimonas denitrificans* (In Taxonomic Flux) | BCI 712 | US | NRRL B-67285 Jul. 14, 2016 | | 5 |
| | BCI 402 | US | NRRL B-67283 Jul. 14, 2016 | | 6 |
| | BCI 745 | US | NRRL B-67284 Jul. 14, 2016 | | 7 |
| 4. *Arthrobacter nicotinovorans* | BCI 717 | US | NRRL B-67289 Jul. 14, 2016 | DSM420* | 8 |
| | BCI 3189 | US | NRRL B-67290 Jul. 14, 2016 | | 9 |
| 5. *Pseudomonas helmanticensis* | BCI 616 | US | NRRL B-67295 Jul. 14, 2016 | DSM28442* | 10 |
| | BCI 2945 | US | NRRL B-67296 Jul. 14, 2016 | | 11 |
| | BCI 800 | US | NRRL B-67297 Jul. 14, 2016 | | 12 |
| 6. *Agrobacterium fabrum* or *Rhizobium pusense* (In Taxonomic Flux) (previously *Rhizobium sp.*) | BCI 958 | US | NRRL B-67286 Jul. 14, 2016 | D5M22668* | 14 |
| 7. *Exiguobacterium sibiricum* | BCI 718 | US | NRRL B-67294 Jul. 14, 2016 | DSM17290* | 17 |
| 8. *Exiguobacterium antarcticum* | BCI 63 | US | NRRL B-67292 Jul. 14, 2016 | D5M14480* | 18 |
| | BCI 225 | US | NRRL B-67293 Jul. 14, 2016 | | 19 |
| 9. *Leifsonia lichenia* | BDNZ 72243 | NZ | NRRL B-67298 Jul. 21, 2016 | | 22 |
| | BDNZ 72289 | NZ | NRRL B-67299 Jul. 21, 2016 | | 23 |
| 10. *Tumebacillus permanentifrigoris* | BDNZ 72229 | NZ | NRRL B-67302 Jul. 22, 2016 | D5M118773* | 24 |
| | BDNZ 74542 | NZ | NRRL B-67300 Jul. 21, 2016 | | 25 |
| | BDNZ 72366 | NZ | NRRL B-67303 Jul. 22, 2016 | | 26 |
| | BDNZ 72287 | NZ | NRRL B-67301 Jul. 21, 2016 | | 307 |
| 11. *Bacillus asahii* | BCI 928 | US | | | 27 |
| 12. *Novosphingobium sediminicola* | BDNZ 71628 | NZ | | DSM27057* | 29 |
| 13. *Novosphingobium lindaniclasticum* | BDNZ 71222 | NZ | | DSM25409* | 31 |
| 14. *Massilia kyonggiensis* | BCI 94 | US | | DSM101532* | 33 |
| | BDNZ 73021 | NZ | | | 34 |

*Denotes a microbial species that has been deposited and is available to the public, but said species is not a deposit of the exact BCI or BDNZ strain.

DETAILED DESCRIPTION

Definitions

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "microorganism" or "microbe" should be taken broadly. These terms are used interchangeably and include, but are not limited to, the two prokaryotic domains, Bacteria and Archaea, as well as eukaryotic fungi and protists. In some embodiments, the disclosure refers to the "microbes" of Tables 1-4, or the "microbes" of various other tables present in the disclosure. This characterization can refer to not only the identified taxonomic bacterial genera of the tables, but also the identified taxonomic species, as well as the various novel and newly identified bacterial strains of said tables.

The term "microbial consortia" or "microbial consortium" refers to a subset of a microbial community of individual microbial species, or strains of a species, which can be described as carrying out a common function, or can be described as participating in, or leading to, or correlating with, a recognizable parameter or plant phenotypic trait. The community may comprise two or more species, or strains of a species, of microbes. In some instances, the microbes coexist within the community symbiotically.

The term "microbial community" means a group of microbes comprising two or more species or strains. Unlike microbial consortia, a microbial community does not have to be carrying out a common function, or does not have to be participating in, or leading to, or correlating with, a recognizable parameter or plant phenotypic trait.

The term "accelerated microbial selection" or "AMS" is used interchangeably with the term "directed microbial selection" or "DMS" and refers to the iterative selection methodology that was utilized, in some embodiments of the disclosure, to derive the claimed microbial species or consortia of said species.

As used herein, "isolate," "isolated," "isolated microbe," and like terms, are intended to mean that the one or more microorganisms has been separated from at least one of the materials with which it is associated in a particular environment (for example soil, water, plant tissue).

Thus, an "isolated microbe" does not exist in its naturally occurring environment; rather, it is through the various techniques described herein that the microbe has been removed from its natural setting and placed into a non-naturally occurring state of existence. Thus, the isolated strain may exist as, for example, a biologically pure culture, or as spores (or other forms of the strain) in association with an agricultural carrier.

In certain aspects of the disclosure, the isolated microbes exist as isolated and biologically pure cultures. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g. In re Bergstrom, 427 F.2d 1394, (CCPA 1970)(discussing purified prostaglandins), see also, In re Bergy, 596 F.2d 952 (CCPA 1979)(discussing purified microbes); see also, *Parke-Davis & Co. v. H. K. Mulford & Co.*, 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co. v. Olin Mathieson Chemical Corp.*, 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

The term "growth medium" as used herein, is any medium which is suitable to support growth of a plant. By way of example, the media may be natural or artificial including, but not limited to: soil, potting mixes, bark, vermiculite, hydroponic solutions alone and applied to solid plant support systems, and tissue culture gels. It should be appreciated that the media may be used alone or in combination with one or more other media. It may also be used with or without the addition of exogenous nutrients and physical support systems for roots and foliage.

In one embodiment, the growth medium is a naturally occurring medium such as soil, sand, mud, clay, humus, regolith, rock, or water. In another embodiment, the growth medium is artificial. Such an artificial growth medium may be constructed to mimic the conditions of a naturally occurring medium; however, this is not necessary. Artificial growth media can be made from one or more of any number and combination of materials including sand, minerals, glass, rock, water, metals, salts, nutrients, water. In one embodiment, the growth medium is sterile. In another embodiment, the growth medium is not sterile.

The medium may be amended or enriched with additional compounds or components, for example, a component which may assist in the interaction and/or selection of specific groups of microorganisms with the plant and each other. For example, antibiotics (such as penicillin) or sterilants (for example, quaternary ammonium salts and oxidizing agents) could be present and/or the physical conditions (such as salinity, plant nutrients (for example organic and inorganic minerals (such as phosphorus, nitrogenous salts, ammonia, potassium and micronutrients such as cobalt and magnesium), pH, and/or temperature) could be amended.

As used herein, the term "plant" includes the whole plant or any parts or derivatives thereof, such as plant cells, plant protoplasts, plant cell tissue cultures from which plants can be regenerated, plant calli, embryos, pollen, ovules, fruit, flowers, leaves, seeds, roots, root tips and the like.

As used herein, the term "cultivar" refers to a variety, strain, or race, of plant that has been produced by horticultural or agronomic techniques and is not normally found in wild populations.

As used herein, the terms "dicotyledon," "dicot" and "dicotyledonous" refer to a flowering plant having an embryo containing two cotyledons. As used herein, the terms "monocotyledon," "monocot" and "monocotyledonous" refer to a flowering plant having an embryo containing only one cotyledon. There are of course other known differences between these groups, which would be readily recognized by one of skill in the art.

As used herein, "improved" should be taken broadly to encompass improvement of a characteristic of a plant, as compared to a control plant, or as compared to a known average quantity associated with the characteristic in question. For example, "improved" plant biomass associated with application of a beneficial microbe, or consortia, of the disclosure can be demonstrated by comparing the biomass of a plant treated by the microbes taught herein to the biomass of a control plant not treated. Alternatively, one could compare the biomass of a plant treated by the microbes taught herein to the average biomass normally attained by the given plant, as represented in scientific or agricultural publications known to those of skill in the art. In the present disclosure, "improved" does not necessarily demand that the data be statistically significant (i.e. $p<0.05$); rather, any quantifiable difference demonstrating that one value (e.g. the average treatment value) is different from another (e.g. the average control value) can rise to the level of "improved."

As used herein, "inhibiting and suppressing" and like terms should not be construed to require complete inhibition or suppression, although this may be desired in some embodiments.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment. The term "recombinant" refers to a plant having a new genetic makeup arising as a result of a recombination event.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed by the average person skilled in molecular-biological techniques.

As used herein, the term "trait" refers to a characteristic or phenotype. For example, in the context of some embodiments of the present disclosure, yield of a crop relates to the amount of marketable biomass produced by a plant (e.g., fruit, fiber, grain). Desirable traits may also include other plant characteristics, including but not limited to: water use efficiency, nutrient use efficiency, production, mechanical harvestability, fruit maturity, shelf life, pest/disease resistance, early plant maturity, tolerance to stresses, etc. A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment.

A dominant trait results in a complete phenotypic manifestation at heterozygous or homozygous state; a recessive trait manifests itself only when present at homozygous state.

In the context of this disclosure, traits may also result from the interaction of one or more plant genes and one or more microorganism genes.

As used herein, the term "homozygous" means a genetic condition existing when two identical alleles reside at a specific locus, but are positioned individually on corresponding pairs of homologous chromosomes in the cell of a diploid organism. Conversely, as used herein, the term "heterozygous" means a genetic condition existing when two different alleles reside at a specific locus, but are positioned individually on corresponding pairs of homologous chromosomes in the cell of a diploid organism.

As used herein, the term "phenotype" refers to the observable characteristics of an individual cell, cell culture, organism (e.g., a plant), or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) Molecular Cloning: A Laboratory Manual (2nd ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, a "plant promoter" is a promoter capable of initiating transcription in plant cells whether or not its origin is a plant cell, e.g. it is well known that *Agrobacterium* promoters are functional in plant cells. Thus, plant promoters include promoter DNA obtained from plants, plant viruses and bacteria such as *Agrobacterium* and *Bradyrhizobium* bacteria. A plant promoter can be a constitutive promoter or a non-constitutive promoter.

As used herein, a "constitutive promoter" is a promoter which is active under most conditions and/or during most development stages. There are several advantages to using constitutive promoters in expression vectors used in plant biotechnology, such as: high level of production of proteins used to select transgenic cells or plants; high level of expression of reporter proteins or scorable markers, allowing easy detection and quantification; high level of production of a transcription factor that is part of a regulatory transcription system; production of compounds that requires ubiquitous activity in the plant; and production of compounds that are required during all stages of plant development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues, such as stems, leaves, roots, or seeds.

As used herein, "inducible" or "repressible" promoter is a promoter which is under chemical or environmental factors control. Examples of environmental conditions that may effect transcription by inducible promoters include anaerobic conditions, or certain chemicals, or the presence of light.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related plant species to achieve efficient and reliable expression of transgenes in particular tissues. This is one of the main reasons for the large amount of tissue-specific promoters isolated from particular plants and tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

In some embodiments, the cell or organism has at least one heterologous trait. As used herein, the term "heterologous trait" refers to a phenotype imparted to a transformed host cell or transgenic organism by an exogenous DNA segment, heterologous polynucleotide or heterologous nucleic acid. Various changes in phenotype are of interest to the present disclosure, including but not limited to modifying the fatty acid composition in a plant, altering the amino acid content of a plant, altering a plant's pathogen defense mechanism, increasing a plant's yield of an economically important trait (e.g., grain yield, forage yield, etc.) and the like. These results can be achieved by providing expression of heterologous products or increased expression of endogenous products in plants using the methods and compositions of the present disclosure A "synthetic combination" can include a combination of a plant and a microbe of the disclosure. The combination may be achieved, for example, by coating the surface of a seed of a plant, such as an agricultural plant, or host plant tissue (root, stem, leaf, etc.), with a microbe of the disclosure. Further, a "synthetic combination" can include a combination of microbes of various strains or species. Synthetic combinations have at least one variable that distinguishes the combination from any combination that occurs in nature. That variable may be, inter alia, a concentration of microbe on a seed or plant tissue that does not occur naturally, or a combination of microbe and plant that does not naturally occur, or a combination of microbes or strains that do not occur naturally together. In each of these instances, the synthetic combination demonstrates the hand of man and possesses structural and/or functional attributes that are not present when the individual elements of the combination are considered in isolation.

In some embodiments, a microbe can be "endogenous" to a seed or plant. As used herein, a microbe is considered "endogenous" to a plant or seed, if the microbe is derived from the plant specimen from which it is sourced. That is, if the microbe is naturally found associated with said plant. In embodiments in which an endogenous microbe is applied to a plant, then the endogenous microbe is applied in an amount that differs from the levels found on the plant in nature. Thus, a microbe that is endogenous to a given plant can still form a synthetic combination with the plant, if the microbe is present on said plant at a level that does not occur naturally.

In some embodiments, a microbe can be "exogenous" (also termed "heterologous") to a seed or plant. As used herein, a microbe is considered "exogenous" to a plant or seed, if the microbe is not derived from the plant specimen from which it is sourced. That is, if the microbe is not naturally found associated with said plant. For example, a microbe that is normally associated with leaf tissue of a maize plant is considered exogenous to a leaf tissue of another maize plant that naturally lacks said microbe. In another example, a microbe that is normally associated with a maize plant is considered exogenous to a wheat plant that naturally lacks said microbe.

Microbes can also be "exogenously disposed" on a given plant tissue. This means that the microbe is placed upon a plant tissue that it is not naturally found upon. For instance, if a given microbe only naturally occurs on the roots of a given plant, then that microbe could be exogenously applied to the above-ground tissue of a plant and would thereby be "exogenously disposed" upon said plant tissue. As such, a microbe is deemed exogenously disposed, when applied on a plant that does not naturally have the microbe present or does not naturally have the microbe present in the number that is being applied The compositions and methods herein may provide for an improved "agronomic trait" or "trait of agronomic importance" to a host plant, which may include, but not be limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation.

Ability to Impart Beneficial Traits Upon a Given Plant Species by Microbes and Consortia of the Disclosure The present disclosure utilizes microbes to impart beneficial properties (or beneficial traits) to desirable plant species, such as agronomic species of interest. In the current disclosure, the terminology "beneficial property" or "beneficial trait" is used interchangeably and denotes that a desirable plant phenotypic or genetic property of interest is modulated, by the application of a microbe or microbial consortia as described herein. As aforementioned, in some aspects, it may very well be that a metabolite produced by a given microbe is ultimately responsible for modulating or imparting a beneficial trait to a given plant.

There are a vast number of beneficial traits that can be modulated by the application of microbes of the disclosure. For instance, the microbes may have the ability to impart one or more beneficial properties to a plant species, for example: increased growth, increased yield, increased nitrogen utilization efficiency, increased stress tolerance, increased drought tolerance, increased photosynthetic rate, enhanced water use efficiency, increased pathogen resistance, modifications to plant architecture that don't necessarily impact plant yield, but rather address plant functionality, causing the plant to increase production of a metabolite of interest, etc.

In aspects, the microbes taught herein provide a wide range of agricultural applications, including: improvements in yield of grain, fruit, and flowers, improvements in growth of plant parts, improved resistance to disease, improved survivability in extreme climate, and improvements in other desired plant phenotypic characteristics.

In some aspects, the isolated microbes, consortia, and/or agricultural compositions of the disclosure can be applied to a plant, in order to modulate or alter a plant characteristic such as altered oil content, altered protein content, altered seed carbohydrate composition, altered seed oil composition, altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome relative to a reference plant.

In some aspects, the isolated microbes, consortia, and/or agricultural compositions of the disclosure can be applied to a plant, in order to modulate in a negative way, a particular plant characteristic. For example, in some aspects, the microbes of the disclosure are able to decrease a phenotypic trait of interest, as this functionality can be desirable in some applications. For instance, the microbes of the disclosure may possess the ability to decrease root growth or decrease root length. Or the microbes may possess the ability to decrease shoot growth or decrease the speed at which a plant grows, as these modulations of a plant trait could be desirable in certain applications.

Isolated Microbes—Tables 1-4

In aspects, the present disclosure provides isolated microbes, including novel strains of identified microbial species, presented in Tables 1-4.

In other aspects, the present disclosure provides isolated whole microbial cultures of the species and strains identified in Tables 1-4. These cultures may comprise microbes at various concentrations.

In aspects, the disclosure provides for utilizing a microbe selected from Tables 1-4 in agriculture.

In some embodiments, the disclosure provides isolated microbial species belonging to genera of: *Achromobacter, Agrobacterium, Arthrobacter, Azotobacter, Azospirillum, Bacillus, Bosea, Caulobacter, Chryseobacterium, Defluviimonas, Duganella, Exiguobacterium, Flavobacterium, Frigidibacter, Herbaspirillum, Leifsonia, Luteibacter, Massilia, Mucilaginibacter, Novosphingobium, Pantoeo, Paenibacillus, Pedobacter, Polaromonas, Pseudoduganella, Pseudomonas, Rahnella, Ramlibacter, Rhizobium, Rhodococcus, Rhodoferax, Sphingobium, Stenotrophomonas* and *Tumebacillus*.

In some embodiments, the disclosure provides isolated microbial species belonging to genera of: *Achromobacter, Agrobacterium, Arthrobacter, Chryseobacterium, Defluviimonas, Exiguobacterium, Frigidibacter, Leifsonia, Massilia, Novosphingobium, Pedobacter, Pseudomonas*, and *Tumebacillus*.

In some embodiments, a microbe from the genus *Bosea* is utilized in agriculture to impart one or more beneficial properties to a plant species.

In some embodiments, the disclosure provides isolated microbial species, selected from the group consisting of: *Achromobacter pulmonis, Agrobacterium fabrum* (previously *Rhizobium pusense*), *Arthrobacter nicotinovorans, Azotobacter chroococcum, Chryseobacterium daecheongense, Chryseobacterium rhizosphaerae, Duganella radicis, Exiguobacterium antarcticum, Exiguobacterium sibiricum, Frigidibacter albus* (previously *Defluviimonas denitrificans*) *Leifsonia lichenia, Pantoea agglomerans* (recently reassigned to *Pantoea vagans*), *Pedobacter terrae, Pseudomonas fluorescens, Pseudomonas helmanticensis, Pseudomonas oryzihabitans, Pseudomonas putida, Rahnella aquatilis, Rhizobium etli, Rhodococcus erythropolis, Stenotrophomonas maltophilia* and *Tumebacillus permanentifrigoris*.

In some embodiments, the disclosure provides isolated microbial species, selected from the group consisting of: *Achromobacter pulmonis, Agrobacterium fabrum* (previously *Rhizobium pusense*), *Arthrobacter nicotinovorans, Chryseobacterium daecheongense, Chryseobacterium rhizosphaerae, Exiguobacterium antarcticum, Exiguobacterium sibiricum, Frigidibacter albus* (previously *Defluviimonas denitrificans*) *Leifsonia lichenia, Massilia kyonggiensis, Novosphingobium lindaniclasticum, Novosphingobium sediminicola, Pedobacter terrae, Pseudomonas helmanticensis*, and *Tumebacillus permanentifrigoris*.

In some embodiments, the disclosure provides novel isolated microbial strains of species, selected from the group consisting of: *Achromobacter, Agrobacterium, Arthrobacter, Azotobacter, Azospirillum, Bacillus, Bosea, Caulobacter, Chryseobacterium, Defluviimonas, Duganella, Exiguobacterium, Flavobacterium, Frigidibacter, Herbaspirillum, Leifsonia, Luteibacter, Massilia, Mucilaginibacter, Novosphingobium, Pantoeo, Paenibacillus, Pedobacter, Polaromonas, Pseudoduganella, Pseudomonas, Rahnella, Ramlibacter, Rhizobium, Rhodococcus, Rhodoferax, Sphingobium, Stenotrophomonas* and *Tumebacillus*. Particular novel strains of these aforementioned species can be found in Tables 1-4.

Furthermore, the disclosure relates to microbes having characteristics substantially similar to that of a microbe identified in Tables 1-4.

The isolated microbial species, and novel strains of said species, identified in the present disclosure, are able to impart beneficial properties or traits to target plant species.

For instance, the isolated microbes described in Tables 1-4, or consortia of said microbes, are able to improve plant health and vitality. The improved plant health and vitality can be quantitatively measured, for example, by measuring the effect that said microbial application has upon a plant phenotypic or genotypic trait.

Microbial Consortia—Tables 1-4

In aspects, the disclosure provides microbial consortia comprising a combination of at least any two microbes selected from amongst the microbes identified in Table 1.

In other aspects, the disclosure provides microbial consortia comprising a combination of at least any two microbes selected from amongst the microbes identified in Table 2.

In yet other aspects, the disclosure provides microbial consortia comprising a combination of at least any two microbes selected from amongst the microbes identified in Table 3.

In additional aspects, the disclosure provides microbial consortia comprising a combination of at least any two microbes selected from amongst the microbes identified in Table 4.

Also, the disclosure provides microbial consortia comprising a combination of at least any two microbes selected from amongst the microbes identified in Tables 1-4.

In certain embodiments, the consortia of the present disclosure comprise two microbes, or three microbes, or four microbes, or five microbes, or six microbes, or seven microbes, or eight microbes, or nine microbes, or ten or more microbes. Said microbes of the consortia are different microbial species, or different strains of a microbial species.

In some embodiments, the disclosure provides consortia, comprising: at least two isolated microbial species belonging to genera of: Achromobacter, Agrobacterium, Arthrobacter, Azotobacter, Azospirillum, Bacillus, Bosea, Caulobacter, Chryseobacterium, Delfulviimonas, Duganella, Exiguobacterium, Flavobacterium, Frigidibacter, Herbaspirillum, Leifsonia, Luteibacter, Massilia, Mucilaginibacter, Novosphingobium, Pantoeo, Paenibacillus, Pedobacter, Polaromonas, Pseudoduganella, Pseudomonas, Rahnella, Ramlibacter, Rhizobium, Rhodococcus, Rhodoferax, Sphingobium, Stenotrophomonas and Tumebacillus.

In some embodiments, the disclosure provides consortia, comprising: at least two isolated microbial species, selected from the group consisting of: Achromobacter pulmonis, Agrobacterium fabrum (previously Rhizobium pusense), Arthrobacter nicotinovorans, Azotobacter chroococcum, Chryseobacterium daecheongense, Chryseobacterium rhizosphaerae, Duganella radicis, Exiguobacterium antarcticum, Exiguobacterium sibiricum, Frigidibacter albus (previously Defluviimonas denitrificans) Leifsonia lichenia, Massilia kyonggiensis, Novosphingobium sediminicola, Novosphingobium lindaniclasticum, Pantoea agglomerans (recently reassigned to Pantoea vagans), Pedobacter terrae, Pseudomonas fluorescens, Pseudomonas helmanticensis, Pseudomonas oryzihabitans, Pseudomonas putida, Rahnella aquatilis, Rhizobium etli, Rhodococcus erythropolis, Stenotrophomonas maltophilia and Tumebacillus permanentifrigoris.

In some embodiments, the disclosure provides consortia, comprising: at least two novel isolated microbial strains of species, selected from the group consisting of: Achromobacter pulmonis, Agrobacterium fabrum (previously Rhizobium pusense), Arthrobacter nicotinovorans, Azotobacter chroococcum, Chryseobacterium daecheongense, Chryseobacterium rhizosphaerae, Duganella radicis, Exiguobacterium antarcticum, Exiguobacterium sibiricum, Frigidibacter albus (previously Defluviimonas denitrificans) Leifsonia lichenia, Massilia kyonggiensis, Novosphingobium sediminicola, Novosphingobium lindaniclasticum, Pantoea agglomerans (recently reassigned to Pantoea vagans), Pedobacter terrae, Pseudomonas fluorescens, Pseudomonas helmanticensis, Pseudomonas oryzihabitans, Pseudomonas putida, Rahnella aquatilis, Rhizobium etli, Rhodococcus erythropolis, Stenotrophomonas maltophilia and Tumebacillus permanentifrigoris. Particular novel strains of these aforementioned species can be found in Tables 1-4.

In some embodiments, the disclosure provides consortia, comprising: at least two isolated microbial species selected from Tables 1-4, and further comprising a Bradyrhizobium species.

In particular aspects, the disclosure provides microbial consortia, comprising species as grouped in Tables 5-11. With respect to Tables-5-11, the letters A through I represent a non-limiting selection of microbes of the present disclosure, defined as:

A=Rahnella aquatilis and associated novel strains identified in Table 1;

B=Bacillus megatarium and associated novel strains identified in Table 2;

C=Bacillus niacini and associated novel strains identified in Table 3;

D=Chryseobacterium rhizosphaerae and associated novel strains identified in Table 4;

E=Frigidibacter albus or Defluviimonas denitrificans (In Taxonomic Flux) and associated novel strains identified in Table 4;

F=Pedobacter terrae and associated novel strains identified in Table 4;

G=Leifsonia lichenia and associated novel strains identified in Table 4;

H=Tumebacillus permanentifrigoris and associated novel strains identified in Table 4; and I=Novosphingobium sediminicola and associated novel strains identified in Table 4.

TABLE 5

Eight and Nine Strain Consortia

| | | | | | |
|---|---|---|---|---|---|
| A, B, C, D, E, F, G, H | A, B, C, D, E, F,G, I | A, B, C, D, E, F, H, I | A, B, C, D, E, G, H, I | A, B, C, D, F, G, H, I | A, B, C, E, F, G, H, I |
| A, B, D, E, F, G, H, I | A, C, D, E, F, G, H, I | B, C, D, E, F, G, H, I | A, B, C, D, E, F, G, H, I | | |

TABLE 6

Seven Strain Consortia

| | | | | | |
|---|---|---|---|---|---|
| A, B, C, D, E, F, G | A, B, C, D, E, F, H | A, B, C, D, E, F, I | A, B, C, D, E, G, H | A, B, C, D, E, G, I | A, B, C, D, E, H, I |
| A, B, C, D, F, G, H | A, B, C, D, F, G, I | A, B, C, D, F, H, I | A, B, C, D, G, H, I | A, B, C, E, F, G, H | A, B, C, E, F, G, I |
| A, B, C, E, F, H, I | A, B, C, E, G, H, I | A, B, C, F, G, H, I | A, B, D, E, F, G, H | A, B, D, E, F,G, I | A, B, D, E, F, H, I |
| A, B, D, E, G, H, I | A, B, D, F, G, H, I | A, B, E, F, G, H, I | A, C, D, E, F, G, H | A, C, D, E, F, G, I | A, C, D, E, F, H, I |
| A, C, D, E, G, H, I | A, C, D, F, G, H, I | A, C, E, F, G, H, I | A, D, E, F, G, H, I | B, C, D, E, F, G, H | B, C, D, E, F, G, I |
| B, C, D, E, F, H, I | B, C, D, E, G, H, I | B, C, D, F, G, H, I | B, C, E, F, G, H, I | B, D, E, F, G, H, I | C, D, E, F, G, H, I |

TABLE 7

Six Strain Consortia

| | | | | | | |
|---|---|---|---|---|---|---|
| A, B, C, D, E, F | A, B, C, D, E, G | A, B, C, D, E, H | A, B, C, D, E, I | A, B, C, D, F, G | A, B, C, D, F, H | A, B, C, D, F, I |
| A, B, C, D, G, H | A, B, C, D, G, I | A, B, C, D, H, I | A, B, C, E, F, G | A, B, C, E, F, H | A, B, C, E, F, I | A, B, C, E, G, H |
| A, B, C, E, G, I | A, B, C, E, H, I | A, B, C, F, G, H | A, B, C, F, G, I | A, B, C, F, H, I | A, B, C, G, H, I | A, B, D, E, F, G |
| A, B, D, E, F, H | A, B, D, E, F, I | A, B, D, E, G, H | A, B, D, E, G, I | A, B, D, E, H, I | A, B, D, F, G, H | A, B, D, F, G, I |
| D, E, F, G, H, I | C, E, F, G, H, I | A, B, D, F, H, I | A, B, D, G, H, I | A, B, E, F, G, H | A, B, E, F, G, I | A, B, E, F, H, I |
| A, B, E, G, H, I | A, B, F, G, H, I | A, C, D, E, F, G | A, C, D, E, F, H | A, C, D, E, F, I | A, C, D, E, G, H | A, C, D, E, G, I |
| A, C, D, E, H, I | A, C, D, F, G, H | A, C, D, F, G, I | A, C, D, F, H, I | A, C, D, G, H, I | A, C, E, F, G, H | A, C, E, F, G, I |
| A, C, E, F, H, I | A, C, E, G, H, I | A, C, F, G, H, I | A, D, E, F, G, H | A, D, E, F, G, I | A, D, E, F, H, I | A, D, E, G, H, I |
| A, D, F, G, H, I | A, E, F, G, H, I | B, C, D, E, F, G | B, C, D, E, F, H | B, C, D, E, F, I | B, C, D, E, G, H | B, C, D, E, G, I |
| B, C, D, E, H, I | B, C, D, F, G, H | B, C, D, F, G, I | B, C, D, F, H, I | B, C, D, G, H, I | B, C, E, F, G, H | B, C, E, F, G, I |
| B, C, E, F, H, I | B, C, E, G, H, I | B, C, F, G, H, I | B, D, E, F, G, H | B, D, E, F, G, I | B, D, E, F, H, I | B, D, E, G, H, I |
| B, D, F, G, H, I | B, E, F, G, H, I | C, D, E, F, G, H | C, D, E, F, G, I | C, D, E, F, H, I | C, D, E, G, H, I | C, D, F, G, H, I |

TABLE 8

Five Strain Consortia

| | | | | | | | |
|---|---|---|---|---|---|---|---|
| A, B, C, D, E | A, B, C, D, F | A, B, C, D, G | A, B, C, D, H | A, B, C, D, I | A, B, C, E, F | A, B, C, E, G | A, B, C, E, H |
| A, B, C, F, H | A, B, C, F, G | A, B, C, F, I | A, B, C, G, H | A, B, C, G, I | A, B, C, H, I | A, B, D, E, F | A, B, D, E, G |
| A, B, D, E, I | A, B, D, F, G | A, B, D, F, H | A, B, D, F, I | A, B, D, G, H | A, B, D, G, I | A, B, D, H, I | A, B, E, F, G |
| A, B, E, F, I | A, B, E, G, H | A, B, E, G, I | A, B, E, H, I | A, B, F, G, H | A, B, F, G, I | A, B, F, H, I | A, B, G, H, I |
| A, C, D, E, G | A, C, D, E, H | A, C, D, E, I | A, C, D, F, G | A, C, D, F, H | A, C, D, F, I | A, C, D, G, H | A, C, D, G, I |
| A, C, E, F, G | A, C, E, F, H | A, C, E, F, I | A, C, E, G, H | A, C, E, G, I | A, C, E, H, I | A, C, F, G, H | A, C, F, G, I |
| A, C, G, H, I | A, D, E, F, G | A, D, E, F, H | A, D, E, F, I | A, D, E, G, H | A, D, E, G, I | A, D, E, H, I | A, D, F, G, H |
| A, D, F, H, I | A, D, G, H, I | A, E, F, G, H | A, E, F, G, I | A, E, F, H, I | A, E, G, H, I | A, F, G, H, I | B, C, D, E, F |
| B, C, D, E, H | B, C, D, E, I | B, C, D, F, G | B, C, D, F, H | B, C, D, F, I | B, C, D, G, H | B, C, D, G, I | B, C, D, H, I |
| B, C, E, F, H | B, C, E, F, I | B, C, E, G, H | B, C, E, G, I | B, C, E, H, I | B, C, F, G, H | B, C, F, G, I | B, C, F, H, I |
| B, D, E, F, G | B, D, E, F, H | B, D, E, F, I | B, D, E, G, H | B, D, E, G, I | B, D, E, H, I | B, D, F, G, H | B, D, F, G, I |
| B, D, G, H, I | B, E, F, G, H | B, E, F, G, I | B, E, F, H, I | B, E, G, H, I | B, F, G, H, I | C, D, E, F, G | C, D, E, F, H |
| C, D, E, G, H | C, D, E, G, I | C, D, E, H, I | C, D, F, G, H | C, D, F, G, I | C, D, F, H, I | C, D, G, H, I | C, E, F, G, H |
| C, E, F, H, I | C, E, G, H, I | C, F, G, H, I | D, E, F, G, H | D, E, F, G, I | D, E, F, H, I | D, E, G, H, I | D, F, G, H, I |
| A, B, C, E, I | A, B, D, E, H | A, B, E, F, H | A, C, D, E, F | A, C, D, H, I | A, C, F, H, I | A, D, F, G, I | B, C, D, E, G |
| B, C, E, F, G | B, C, G, H, I | B, D, F, H, I | C, D, E, F, I | C, E, F, G, I | E, F, G, H, I | | |

TABLE 9

Four Strain Consortia

| | | | | | | | |
|---|---|---|---|---|---|---|---|
| A, B, C, D | A, B, C, E | A, B, C, F | A, B, C, G | A, B, C, H | A, B, C, I | A, B, D, E | A, B, D, F | D, G, H, I |
| A, B, D, G | A, B, D, H | A, B, D, I | A, B, E, F | A, B, E, G | A, B, E, H | A, B, E, I | A, B, F, G | E, F, G, H |
| A, B, F, H | A, D, F, H | A, D, F, I | A, D, G, H | A, D, G, I | A, D, H, I | A, E, F, G | A, E, F, H | E, F, G, I |
| A, B, F, I | A, B, G, H | A, B, G, I | A, B, H, I | A, C, D, E | A, C, D, F | A, C, D, G | A, C, D, H | E, F, H, I |
| A, C, D, I | A, C, E, F | A, C, E, G | A, C, E, H | A, C, E, I | A, C, F, G | A, C, F, H | A, C, F, I | E, G, H, I |
| A, C, G, H | A, C, G, I | A, C, H, I | A, D, E, F | A, D, E, G | A, D, E, H | A, D, E, I | A, D, F, G | F, G, H, I |
| A, E, F, I | A, E, G, H | A, E, G, I | A, E, H, I | A, F, G, H | A, F, G, I | A, F, H, I | A, G, H, I | D, E, F, H |
| B, C, D, E | B, C, D, F | B, C, D, G | B, C, D, H | B, C, D, I | B, C, E, F | B, C, E, G | B, C, E, H | D, E, F, I |
| B, C, E, I | B, C, F, G | B, C, F, H | B, C, F, I | B, C, G, H | B, C, G, I | B, C, H, I | B, D, E, F | D, E, G, H |
| B, D, E, G | B, D, E, H | B, D, E, I | B, D, F, G | B, D, F, H | B, D, F, I | B, D, G, H | B, D, G, I | D, E, G, I |
| B, D, H, I | B, E, F, G | B, E, F, H | B, E, F, I | B, E, G, H | B, E, G, I | B, E, H, I | B, F, G, H | D, E, H, I |
| B, F, G, I | B, F, H, I | B, G, H, I | C, D, E, F | C, D, E, G | C, D, E, H | C, D, E, I | C, D, F, G | D, F, G, H |
| C, D, F, H | C, D, F, I | C, D, G, H | C, D, G, I | C, D, H, I | C, E, F, G | C, E, F, H | C, E, F, I | D, F, G, I |
| C, E, G, H | C, E, G, I | C, E, H, I | C, F, G, H | C, F, G, I | C, F, H, I | C, G, H, I | D, E, F, G | D, F, H, I |

TABLE 10

Three Strain Consortia

| | | | | | | | | | |
|---|---|---|---|---|---|---|---|---|---|
| A, B, C | A, B, D | A, B, E | A, B, F | A, B, G | A, B, H | A, B, I | A, C, D | A, C, E | G, H, I | E, F, H |
| A, C, F | A, C, G | A, C, H | A, C, I | A, D, E | A, D, F | A, D, G | A, D, H | A, D, I | F, H, I | E, F, G |
| A, E, F | A, E, G | A, E, H | A, E, I | A, F, G | A, F, H | A, F, I | A, G, H | A, G, I | F, G, I | D, H, I |
| A, H, I | B, C, D | B, C, E | B, C, F | B, C, G | B, C, H | B, C, I | B, D, E | B, D, F | F, G, H | D, G, I |
| B, D, G | B, D, H | B, D, I | B, E, F | B, E, G | B, E, H | B, E, I | B, F, G | B, F, H | E, H, I | E, F, I |
| B, F, I | B, G, H | B, G, I | B, H, I | C, D, E | C, D, F | C, D, G | C, D, H | C, D, I | E, G, I | D, G, H |

TABLE 10-continued

Three Strain Consortia

| | | | | | | | | | | |
|---|---|---|---|---|---|---|---|---|---|---|
| C, E, F | C, E, G | C, E, H | C, E, I | C, F, G | C, F, H | C, F, I | C, G, H | C, G, I | E, G, H | D, F, I |
| C, H, I | D, E, F | D, E, G | D, E, H | D, E, I | D, F, G | D, F, H | | | | |

TABLE 11

Two Strain Consortia

| | | | | | | | | | | | | | | | | |
|---|---|---|---|---|---|---|---|---|---|---|---|---|---|---|---|---|
| A, B | A, C | A, D | A, E | A, F | A, G | A, H | A, I | B, C | B, D | B, E | B, F | B, G | B, H | B, I | C, D |
| C, E | C, F | C, G | C, H | C, I | D, E | D, F | D, G | D, H | D, I | E, F | E, G | E, H | E, I | F, G | F, H |
| F, I | G, H | G, I | H, I | | | | | | | | | | | | |

In some embodiments, the microbial consortia may be selected from any member group from Tables 5-11.

Isolated Microbes—Source Material

The microbes of the present disclosure were obtained, among other places, at various locales in New Zealand and the United States.

Isolated Microbes—Microbial Culture Techniques

The microbes of Tables 1-4 were identified by utilizing standard microscopic techniques to characterize the microbes' phenotype, which was then utilized to identify the microbe to a taxonomically recognized species.

The isolation, identification, and culturing of the microbes of the present disclosure can be effected using standard microbiological techniques. Examples of such techniques may be found in Gerhardt, P. (ed.) Methods for General and Molecular Microbiology. American Society for Microbiology, Washington, D.C. (1994) and Lennette, E. H. (ed.) Manual of Clinical Microbiology, Third Edition. American Society for Microbiology, Washington, D.C. (1980), each of which is incorporated by reference.

Isolation can be effected by streaking the specimen on a solid medium (e.g., nutrient agar plates) to obtain a single colony, which is characterized by the phenotypic traits described hereinabove (e.g., Gram positive/negative, capable of forming spores aerobically/anaerobically, cellular morphology, carbon source metabolism, acid/base production, enzyme secretion, metabolic secretions, etc.) and to reduce the likelihood of working with a culture which has become contaminated.

For example, for isolated bacteria of the disclosure, biologically pure isolates can be obtained through repeated subculture of biological samples, each subculture followed by streaking onto solid media to obtain individual colonies. Methods of preparing, thawing, and growing lyophilized bacteria are commonly known, for example, Gherna, R. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages; herein incorporated by reference. Thus freeze dried liquid formulations and cultures stored long term at −70° C. in solutions containing glycerol are contemplated for use in providing formulations of the present inventions.

The bacteria of the disclosure can be propagated in a liquid medium under aerobic conditions. Medium for growing the bacterial strains of the present disclosure includes a carbon source, a nitrogen source, and inorganic salts, as well as specially required substances such as vitamins, amino acids, nucleic acids and the like. Examples of suitable carbon sources which can be used for growing the bacterial strains include, but are not limited to, starch, peptone, yeast extract, amino acids, sugars such as glucose, arabinose, mannose, glucosamine, maltose, and the like; salts of organic acids such as acetic acid, fumaric acid, adipic acid, propionic acid, citric acid, gluconic acid, malic acid, pyruvic acid, malonic acid and the like; alcohols such as ethanol and glycerol and the like; oil or fat such as soybean oil, rice bran oil, olive oil, corn oil, sesame oil. The amount of the carbon source added varies according to the kind of carbon source and is typically between 1 to 100 gram(s) per liter of medium. Preferably, glucose, starch, and/or peptone is contained in the medium as a major carbon source, at a concentration of 0.1-5% (W/V). Examples of suitable nitrogen sources which can be used for growing the bacterial strains of the present invention include, but are not limited to, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the type of nitrogen source, typically between 0.1 to 30 gram per liter of medium. The inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate can be used alone or in combination. The amount of inorganic acid varies according to the kind of the inorganic salt, typically between 0.001 to 10 gram per liter of medium. Examples of specially required substances include, but are not limited to, vitamins, nucleic acids, yeast extract, peptone, meat extract, malt extract, dried yeast and combinations thereof. Cultivation can be effected at a temperature, which allows the growth of the bacterial strains, essentially, between 20° C. and 46° C. In some aspects, a temperature range is 30° C.-37° C. For optimal growth, in some embodiments, the medium can be adjusted to pH 7.0-7.4. It will be appreciated that commercially available media may also be used to culture the bacterial strains, such as Nutrient Broth or Nutrient Agar available from Difco, Detroit, Mich. It will be appreciated that cultivation time may differ depending on the type of culture medium used and the concentration of sugar as a major carbon source.

In aspects, cultivation lasts between 24-96 hours. Bacterial cells thus obtained are isolated using methods, which are well known in the art. Examples include, but are not limited to, membrane filtration and centrifugal separation. The pH may be adjusted using sodium hydroxide and the like and the culture may be dried using a freeze dryer, until the water content becomes equal to 4% or less. Microbial co-cultures may be obtained by propagating each strain as described hereinabove. It will be appreciated that the microbial strains may be cultured together when compatible culture conditions can be employed.

Isolated Microbes—Microbial Strains

Microbes can be distinguished into a genus based on polyphasic taxonomy, which incorporates all available phenotypic and genotypic data into a consensus classification (Vandamme et al. 1996. Polyphasic taxonomy, a consensus approach to bacterial systematics. Microbiol Rev 1996, 60:407-438). One accepted genotypic method for defining species is based on overall genomic relatedness, such that strains which share approximately 70% or more relatedness using DNA-DNA hybridization, with 5° C. or less $\Delta T_m$ (the difference in the melting temperature between homologous and heterologous hybrids), under standard conditions, are considered to be members of the same species. Thus, populations that share greater than the aforementioned 70% threshold can be considered to be variants of the same species.

The 16S rRNA sequences are often used for making distinctions between species, in that if a 16S rRNA sequence shares less than a specified % sequence identity from a reference sequence, then the two organisms from which the sequences were obtained are said to be of different species.

Thus, one could consider microbes to be of the same species, if they share at least 80%, 85%, 90%, 95%, 97%, 98%, or 99% sequence identity across the 16S or 18S rRNA or rDNA sequence. In some aspects, a microbe could be considered to be the same species only if it shares at least 95% identity.

Further, one could define microbial strains of a species, as those that share at least 80%, 85%, 90%, 95%, 97%, 98%, or 99% sequence identity across the 16S rRNA sequence. Comparisons may also be made with 23S rRNA sequences against reference sequences. In some aspects, a microbe could be considered to be the same strain only if it shares at least 95% identity. In some embodiments, "substantially similar genetic characteristics" means a microbe sharing at least 95% identity.

In one embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs:1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, 32, 33, 34, or 307; or any one of SEQ ID NOs:35-306.

In one embodiment, microbes of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs:1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, 32, 33, 34, or 307; or any one of SEQ ID NOs:35-306.

In one embodiment, microbial consortia of the present disclosure include two or more microbes those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, 32, 33, 34, and/or 307; or any one of SEQ ID NOs:35-306.

Unculturable microbes often cannot be assigned to a definite species in the absence of a phenotype determination, the microbes can be given a candidatus designation within a genus provided their 16S rRNA sequences subscribes to the principles of identity with known species.

One approach is to observe the distribution of a large number of strains of closely related species in sequence space and to identify clusters of strains that are well resolved from other clusters. This approach has been developed by using the concatenated sequences of multiple core (housekeeping) genes to assess clustering patterns, and has been called multilocus sequence analysis (MLSA) or multilocus sequence phylogenetic analysis. MLSA has been used successfully to explore clustering patterns among large numbers of strains assigned to very closely related species by current taxonomic methods, to look at the relationships between small numbers of strains within a genus, or within a broader taxonomic grouping, and to address specific taxonomic questions. More generally, the method can be used to ask whether bacterial species exist—that is, to observe whether large populations of similar strains invariably fall into well-resolved clusters, or whether in some cases there is a genetic continuum in which clear separation into clusters is not observed.

In order to more accurately make a determination of genera, a determination of phenotypic traits, such as morphological, biochemical, and physiological characteristics are made for comparison with a reference genus archetype. The colony morphology can include color, shape, pigmentation, production of slime, etc. Features of the cell are described as to shape, size, Gram reaction, extracellular material, presence of endospores, flagella presence and location, motility, and inclusion bodies. Biochemical and physiological features describe growth of the organism at different ranges of temperature, pH, salinity and atmospheric conditions, growth in presence of different sole carbon and nitrogen sources. One of ordinary skill in the art would be reasonably apprised as to the phenotypic traits that define the genera of the present disclosure. For instance, colony color, form, and texture on a particular agar (e.g. YMA) was used to identify species of *Rhizobium*.

In one embodiment, the microbes taught herein were identified utilizing 16S rRNA gene sequences. It is known in the art that 16S rRNA contains hypervariable regions that can provide species/strain-specific signature sequences useful for bacterial identification. In the present disclosure, many of the microbes were identified via partial (500-1200 bp) 16S rRNA sequence signatures. In aspects, each strain represents a pure colony isolate that was selected from an agar plate. Selections were made to represent the diversity of organisms present based on any defining morphological characteristics of colonies on agar medium. The medium used, in embodiments, was R2A, PDA, Nitrogen-free semi-solid medium, or MRS agar. Colony descriptions of each of the 'picked' isolates were made after 24-hour growth and then entered into our database. Sequence data was subsequently obtained for each of the isolates.

Phylogenetic analysis using the 16S rRNA gene was used to define "substantially similar" species belonging to common genera and also to define "substantially similar" strains of a given taxonomic species. Further, we recorded physiological and/or biochemical properties of the isolates that can be utilized to highlight both minor and significant differences between strains that could lead to advantageous behavior on plants.

Agricultural Compositions

In some embodiments, the microbes of the disclosure are combined into agricultural compositions. In some embodiments, the agricultural compositions of the present disclosure include, but are not limited to: wetters, compatibilizing agents (also referred to as "compatibility agents"), antifoam agents, cleaning agents, sequestering agents, drift reduction agents, neutralizing agents and buffers, corrosion inhibitors, dyes, odorants, spreading agents (also referred to as "spreaders"), penetration aids (also referred to as "penetrants"), sticking agents (also referred to as "stickers" or "binders"), dispersing agents, thickening agents (also referred to as "thickeners"), stabilizers, emulsifiers, freezing point depressants, antimicrobial agents, and the like.

In some embodiments, the agricultural compositions of the present disclosure are solid. Where solid compositions are used, it may be desired to include one or more carrier materials with the active isolated microbe or consortia. In some embodiments, the present disclosure teaches the use of carriers including, but not limited to: mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or compositions of these.

In some embodiments, the agricultural compositions of the present disclosure are liquid. Thus in some embodiments, the present disclosure teaches that the agricultural compositions disclosed herein can include compounds or salts such as monoethanolamine salt, sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate.

In some embodiments, the present disclosure teaches that agricultural compositions can include binders such as: polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or compositions of these; lubricants such as magnesium stearate, sodium stearate, talc or polyethylene glycol, or compositions of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or compositions of these.

In some embodiments, the agricultural compositions comprise surface-active agents. In some embodiments, the surface-active agents are added to liquid agricultural compositions. In other embodiments, the surface-active agents are added to solid formulations, especially those designed to be diluted with a carrier before application. Thus, in some embodiments, the agricultural compositions comprise surfactants. Surfactants are sometimes used, either alone or with other additives, such as mineral or vegetable oils as adjuvants to spray-tank mixes to improve the biological performance of the microbes on the target. The types of surfactants used for bioenhancement depend generally on the nature and mode of action of the microbes. The surface-active agents can be anionic, cationic, or nonionic in character, and can be employed as emulsifying agents, wetting agents, suspending agents, or for other purposes. In some embodiments, the surfactants are non-ionics such as: alky ethoxylates, linear aliphatic alcohol ethoxylates, and aliphatic amine ethoxylates. Surfactants conventionally used in the art of formulation and which may also be used in the present formulations are described, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. In some embodiments, the present disclosure teaches the use of surfactants including alkali metal, alkaline earth metal or ammonium salts of aromatic sulfonic acids, for example, ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or compositions of these.

In some embodiments, the present disclosure teaches other suitable surface-active agents, including salts of alkyl sulfates, such as diethanolammonium lauryl sulfate; alkylarylsulfonate salts, such as calcium dodecylbenzenesulfonate; alkylphenol-alkylene oxide addition products, such as nonylphenol-Cis ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

In some embodiments, the agricultural compositions comprise wetting agents. A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank or other vessel to reduce the wetting time of wettable powders and to improve the penetration of water into water-dispersible granules. In some embodiments, examples of wetting agents used in the agricultural compositions of the present disclosure, including wettable powders, suspension concentrates, and water-dispersible granule formulations are: sodium lauryl sulphate; sodium dioctyl sulphosuccinate; alkyl phenol ethoxylates; and aliphatic alcohol ethoxylates.

In some embodiments, the agricultural compositions of the present disclosure comprise dispersing agents. A dispersing agent is a substance which adsorbs onto the surface of particles and helps to preserve the state of dispersion of the particles and prevents them from re-aggregating. In some embodiments, dispersing agents are added to agricultural compositions of the present disclosure to facilitate dispersion and suspension during manufacture, and to ensure the particles redisperse into water in a spray tank. In some embodiments, dispersing agents are used in wettable powders, suspension concentrates, and water-dispersible granules. Surfactants that are used as dispersing agents have the ability to adsorb strongly onto a particle surface and provide a charged or steric barrier to re-aggregation of particles. In some embodiments, the most commonly used surfactants are anionic, non-ionic, or mixtures of the two types.

In some embodiments, for wettable powder formulations, the most common dispersing agents are sodium lignosulphonates. In some embodiments, suspension concentrates provide very good adsorption and stabilization using polyelectrolytes, such as sodium naphthalene sulphonate formaldehyde condensates. In some embodiments, tristyrylphenol ethoxylate phosphate esters are also used. In some embodiments, such as alkylarylethylene oxide condensates and EO-PO block copolymers are sometimes combined with anionics as dispersing agents for suspension concentrates.

In some embodiments, the agricultural compositions of the present disclosure comprise polymeric surfactants. In some embodiments, the polymeric surfactants have very long hydrophobic 'backbones' and a large number of ethylene oxide chains forming the 'teeth' of a 'comb' surfactant. In some embodiments, these high molecular weight polymers can give very good long-term stability to suspension concentrates, because the hydrophobic backbones have many anchoring points onto the particle surfaces. In some embodiments, examples of dispersing agents used in agricultural compositions of the present disclosure are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

In some embodiments, the agricultural compositions of the present disclosure comprise emulsifying agents. An emulsifying agent is a substance, which stabilizes a suspension of droplets of one liquid phase in another liquid phase. Without the emulsifying agent the two liquids would separate into two immiscible liquid phases. In some embodiments, the most commonly used emulsifier blends include alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. In some embodiments, emulsion stability can sometimes be improved by the addition of a small amount of an EO-PO block copolymer surfactant.

In some embodiments, the agricultural compositions of the present disclosure comprise solubilizing agents. A solubilizing agent is a surfactant, which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

In some embodiments, the agricultural compositions of the present disclosure comprise organic solvents. Organic solvents are used mainly in the formulation of emulsifiable concentrates, ULV formulations, and to a lesser extent granular formulations. Sometimes mixtures of solvents are used. In some embodiments, the present disclosure teaches the use of solvents including aliphatic paraffinic oils such as kerosene or refined paraffins. In other embodiments, the present disclosure teaches the use of aromatic solvents such as xylene and higher molecular weight fractions of C9 and C10 aromatic solvents. In some embodiments, chlorinated hydrocarbons are useful as co-solvents to prevent crystallization of pesticides when the formulation is emulsified into water. Alcohols are sometimes used as co-solvents to increase solvent power.

In some embodiments, the agricultural compositions comprise gelling agents. Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. In some embodiments, the agricultural compositions comprise one or more thickeners including, but not limited to: montmorillonite, e.g. bentonite; magnesium aluminum silicate; and attapulgite. In some embodiments, the present disclosure teaches the use of polysaccharides as thickening agents. The types of polysaccharides most commonly used are natural extracts of seeds and seaweeds or synthetic derivatives of cellulose. Some embodiments utilize xanthan and some embodiments utilize cellulose. In some embodiments, the present disclosure teaches the use of thickening agents including, but are not limited to: guar gum; locust bean gum; carrageenam; alginates; methyl cellulose; sodium carboxymethyl cellulose (SCMC); hydroxyethyl cellulose (HEC). In some embodiments, the present disclosure teaches the use of other types of anti-settling agents such as modified starches, polyacrylates, polyvinyl alcohol, and polyethylene oxide. Another good anti-settling agent is xanthan gum.

In some embodiments, the presence of surfactants, which lower interfacial tension, can cause water-based formulations to foam during mixing operations in production and in application through a spray tank. Thus, in some embodiments, in order to reduce the tendency to foam, anti-foam agents are often added either during the production stage or before filling into bottles/spray tanks. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

In some embodiments, the agricultural compositions comprise a preservative.

Further, the individual microbes, or microbial consortia, or microbial communities, developed according to the disclosed methods can be combined with known actives available in the agricultural space, such as: pesticide, herbicide, bactericide, fungicide, insecticide, virucide, miticide, nemataicide, acaricide, plant growth regulator, rodenticide, anti-algae agent, biocontrol or beneficial agent. Further, the microbes, microbial consortia, or microbial communities developed according to the disclosed methods can be combined with known fertilizers. Such combinations may exhibit synergistic properties. Further still, the individual microbes, or microbial consortia, or microbial communities, developed according to the disclosed methods can be combined with inert ingredients. Also, in some aspects, the disclosed microbes are combined with biological active agents.

Metabolites Produced by Microbes and Consortia of the Disclosure

In some cases, the microbes of the present disclosure may produce one or more compounds and/or have one or more activities, e.g., one or more of the following: production of a metabolite, production of a phytohormone such as auxin, production of acetoin, production of an antimicrobial compound, production of a siderophore, production of a cellulase, production of a pectinase, production of a chitinase, production of a xylanase, nitrogen fixation, or mineral phosphate solubilization.

For example, a microbe of the disclosure may produce a phytohormone selected from the group consisting of an auxin, a cytokinin, a gibberellin, ethylene, a brassinosteroid, and abscisic acid.

Thus, a "metabolite produced by" a microbe of the disclosure, is intended to capture any molecule (small molecule, vitamin, mineral, protein, nucleic acid, lipid, fat, carbohydrate, etc.) produced by the microbe. Often, the exact mechanism of action, whereby a microbe of the disclosure imparts a beneficial trait upon a given plant species is not known. It is hypothesized, that in some instances, the microbe is producing a metabolite that is beneficial to the plant. Thus, in some aspects, a cell-free or inactivated preparation of microbes is beneficial to a plant, as the microbe does not have to be alive to impart a beneficial trait upon the given plant species, so long as the preparation includes a metabolite that was produced by said microbe and which is beneficial to a plant.

In one embodiment, the microbes of the disclosure may produce auxin (e.g., indole-3-acetic acid (IAA)). Production of auxin can be assayed. Many of the microbes described herein may be capable of producing the plant hormone auxin indole-3-acetic acid (IAA) when grown in culture. Auxin plays a key role in altering the physiology of the plant, including the extent of root growth.

Therefore, in an embodiment, the microbes of the disclosure are present as a population disposed on the surface or within a tissue of a given plant species. The microbes may produce a metabolite in an amount effective to cause a detectable increase in the amount of metabolite that is found on or within the plant, when compared to a reference plant not treated with the microbes or cell-free or inactive preparations of the disclosure. The metabolites produced by said microbial population may be beneficial to the plant species.

Plant Growth Regulators and Biostimulants

In some embodiments, the agricultural compositions of the present disclosure comprise plant growth regulators and/or biostimulants, used in combination with the taught microbes.

In some embodiments, the individual microbes, or microbial consortia, or microbial communities, developed according to the disclosed methods can be combined with known plant growth regulators in the agricultural space, such as: auxins, gibberellins, cytokinins, ethylene generators, growth inhibitors, and growth retardants.

For example, in some embodiments, the present disclosure teaches agricultural compositions comprising one or more of the following active ingredients including: ancymidol, butralin, alcohols, chloromequat chloride, cytokinin, daminozide, ethephohon, flurprimidol, giberrelic acid, gibberellin mixtures, indole-3-butryic acid (IBA), maleic hydrazide, mefludide, mepiquat chloride, mepiquat pentaborate, naphthalene-acetic acid (NAA), 1-napthaleneacetemide, (NAD), n-decanol, placlobutrazol, prohexadione calcium, trinexapac-ethyl, uniconazole, salicylic acid, abscisic acid, ethylene, brassinosteroids, jasmonates, polyamines, nitric oxide, strigolactones, or karrikins among others.

In some embodiments, the individual microbes, or microbial consortia, or microbial communities, developed according to the disclosed methods can be combined with seed inoculants known in the agricultural space, such as: QUICK-ROOTS®, VAULT®, RHIZO-STICK®, NODULATOR®, DORMAL®, SABREX®, among others. In some embodiments, a *Bradyrhizobium* inoculant is utilized in combination with any single microbe or microbial consortia disclosed here. In particular aspects, a synergistic effect is observed when one combines one of the aforementioned inoculants, e.g. QUICKROOTS® or *Bradyrhizobium*, with a microbe or microbial consortia as taught herein.

In some embodiments, the agricultural compositions of the present disclosure comprise a plant growth regulator, which contains: kinetin, gibberellic acid, and indole butyric acid, along with copper, manganese, and zinc.

In some aspects, the agricultural compositions comprising microbes of the disclosure (e.g. any microbe or combination thereof from Tables 1-4) and kinetin, gibberellic acid, and indole butyric acid, along with copper, manganese, and zinc, exhibit the ability to act synergistically together.

In some embodiments, the present disclosure teaches agricultural compositions comprising one or more commercially available plant growth regulators, including but not limited to: Abide®, A-Rest®, Butralin®, Fair®, Royaltac M®, Sucker-Plucker®, Off-Shoot®, Contact-85®, Citadel®, Cycocel®, E-Pro®, Conklin®, Culbac®, Cytoplex®, Early Harvest®, Foli-Zyme®, Goldengro®, Happygro®, Incite®, Megagro®, Ascend®, Radiate®, Stimulate®, Suppress®, Validate®, X-Cyte®, B-Nine®, Compress®, Dazide®, Boll Buster®, BollD®, Cerone®, Cotton Quik®, Ethrel®, Finish®, Flash®, Florel®, Mature®, MFX®, Prep®, Proxy®, Quali-Pro®, SA-50®, Setup®, Super Boll®, Whiteout®, Cutless®, Legacy®, Mastiff®, Topflor®, Ascend®, Cytoplex®, Ascend®, Early Harvest®, Falgro®, Florgib®, Foli-Zyme®, GA3®, GibGro®, Green Sol®, Incite®, N-Large®, PGR IV®, Pro-Gibb®, Release®, Rouse®, Ryzup®, Stimulate®, BVB®, Chrysal®, Fascination®, Procone®, Fair®, Rite-Hite®, Royal®, Sucker Stuff®, Embark®, Sta-Lo®, Pix®, Pentia®, DipN Grow®, Goldengro®, Hi-Yield®, Rootone®, Antac®, FST-7®, Royaltac®, Bonzi®, Cambistat®, Cutdown®, Downsize®, Florazol®, Paclo®, Paczol®, Piccolo®, Profile®, Shortstop®, Trimmit®, Turf Enhancer®, Apogee®, Armor Tech®, Goldwing®, Governor®, Groom®, Legacy®, Primeraone®, Primo®, Provair®, Solace®, T-Nex®, T-Pac®, Concise®, and Sumagic®.

In some embodiments, the present invention teaches a synergistic use of the presently disclosed microbes or microbial consortia with plant growth regulators and/or stimulants such as phytohormones or chemicals that influence the production or disruption of plant growth regulators.

In some embodiments, the present invention teaches that phytohormones can include: Auxins (e.g., Indole acetic acid IAA), Gibberellins, Cytokinins (e.g., Kinetin), Abscisic acid, Ethylene (and its production as regulated by ACC synthase and disrupted by ACC deaminase).

In some embodiments, the present invention teaches additional plant-growth promoting chemicals that may act in synergy with the microbes and microbial consortia disclosed herein, such as: humic acids, fulvic acids, amino acids, polyphenols and protein hydrolysates.

In some embodiments, the present disclosure teaches that the individual microbes, or microbial consortia, or microbial communities, developed according to the disclosed methods—including any single microorganism or combination of microorganisms disclosed in Tables 1-4 of the specification—can be combined with Ascend® or other similar plant growth regulators. Ascend® is described as comprising 0.090% cytokinin as kinetin, 0.030% gibberellic acid, 0.045% indole butyric acid, and 99.835% other ingredients.

Thus, in some embodiments, the disclosure provides for the application of the taught microbes in combination with Ascend® upon any crop. Further, the disclosure provides for the application of the taught microbes in combination with Ascend® upon any crop and utilizing any method or application rate.

In some embodiments, the present disclosure teaches agricultural compositions with biostimulants.

As used herein, the term "biostimulant" refers to any substance that acts to stimulate the growth of microorganisms that may be present in soil or other plant growing medium.

The level of microorganisms in the soil or growing medium is directly correlated to plant health. Microorganisms feed on biodegradable carbon sources, and therefore plant health is also correlated with the quantity of organic matter in the soil. While fertilizers provide nutrients to feed and grow plants, in some embodiments, biostimulants provide biodegradable carbon, e.g., molasses, carbohydrates, e.g., sugars, to feed and grow microorganisms. Unless clearly stated otherwise, a biostimulant may comprise a single ingredient, or a combination of several different ingredients, capable of enhancing microbial activity or plant growth and development, due to the effect of one or more of the ingredients, either acting independently or in combination.

In some embodiments, biostimulants are compounds that produce non-nutritional plant growth responses. In some embodiments, many important benefits of biostimulants are based on their ability to influence hormonal activity. Hormones in plants (phytohormones) are chemical messengers regulating normal plant development as well as responses to the environment. Root and shoot growth, as well as other growth responses are regulated by phytohormones. In some embodiments, compounds in biostimulants can alter the hormonal status of a plant and exert large influences over its growth and health. Thus, in some embodiments, the present disclosure teaches sea kelp, humic acids, fulvic acids, and B Vitamins as common components of biostimulants. In some embodiments, the biostimulants of the present disclosure enhance antioxidant activity, which increases the plant's defensive system. In some embodiments, vitamin C, vitamin E, and amino acids such as glycine are antioxidants contained in biostimulants.

In other embodiments, biostimulants may act to stimulate the growth of microorganisms that are present in soil or other plant growing medium. Prior studies have shown that when certain biostimulants comprising specific organic seed extracts (e.g., soybean) were used in combination with a microbial inoculant, the biostimulants were capable of stimulating growth of microbes included in the microbial inoculant. Thus, in some embodiments, the present disclosure teaches one or more biostimulants that, when used with a microbial inoculant, is capable of enhancing the population of both native microbes and inoculant microbes. For a review of some popular uses of biostimulants, please see Calvo et al., 2014, Plant Soil 383:3-41.

In some embodiments, the present disclosure teaches that the individual microbes, or microbial consortia, or microbial communities, developed according to the disclosed methods—including any single microorganism or combination of microorganisms disclosed in Tables 1-4 of the specification—can be combined with any plant biostimulant.

In some embodiments, the present disclosure teaches agricultural compositions comprising one or more commercially available biostimulants, including but not limited to: Vitazyme®, Diehard™ Biorush®, Diehard™ Biorush® Fe, Diehard™ Soluble Kelp, Diehard™ Humate SP, Phocon®, Foliar Plus™, Plant Plus™, Accomplish LM®, Titan®, Soil Builder™, Nutri Life, Soil Solution™, Seed Coat™ PercPlus™, Plant Power, CropKarb®, Thrust™, Fast2Grow®, Baccarat®, and Potente® among others.

In some embodiments, the present disclosure teaches that the individual microbes, or microbial consortia, or microbial communities, developed according to the disclosed methods—including any single microorganism or combination of microorganisms disclosed in Tables 1-4 of the specification—can be combined with ProGibb® or other similar plant growth regulators. ProGibb® is described as comprising 4.0% Gibberellic Acid and 96.00% other ingredients.

In some embodiments, the present disclosure teaches that the individual microbes, or microbial consortia, or microbial communities, developed according to the disclosed methods—including any single microorganism or combination of microorganisms disclosed in Tables 1-4 of the specification—can be combined with Release® or other similar plant growth regulators. Release® is described as comprising 10.0% Gibberellic Acid and 90.00% other ingredients.

In some embodiments, the present disclosure teaches that the individual microbes, or microbial consortia, or microbial communities, developed according to the disclosed methods—including any single microorganism or combination of microorganisms disclosed in Tables 1-4 of the specification—can be combined with RyzUp SmartGrass® or other similar plant growth regulators. RyzUp SmartGrass® is described as comprising 40.0% Gibberellin A3 and 60.00% other ingredients.

In some embodiments, the present disclosure teaches that the individual microbes, or microbial consortia, or microbial communities, developed according to the disclosed methods—including any single microorganism or combination of microorganisms disclosed in Tables 1-4 of the specification—can be combined with X-CYTE™ or other similar plant growth regulators. X-CYTE™ is described as comprising 0.04% Cytokinin, as kinetin and 99.96% other ingredients.

In some embodiments, the present disclosure teaches that the individual microbes, or microbial consortia, or microbial communities, developed according to the disclosed methods—including any single microorganism or combination of microorganisms disclosed in Tables 1-4 of the specification—can be combined with N-Large™ or other similar plant growth regulators. N-Large™ is described as comprising 4.0% Gibberellin A3 and 96.00% other ingredients.

In some embodiments, when the microbe or microbial consortia identified according to the taught methods is combined with an active chemical agent one witnesses an additive effect on a plant phenotypic trait of interest. In other embodiments, when the microbe or microbial consortia identified according to the taught methods is combined with an active chemical agent one witness a synergistic effect on a plant phenotypic trait of interest.

In some embodiments, when the microbe or microbial consortia identified according to the taught methods is combined with a fertilizer one witnesses an additive effect on a plant phenotypic trait of interest. In other embodiments, when the microbe or microbial consortia identified according to the taught methods is combined with a fertilizer one witness a synergistic effect on a plant phenotypic trait of interest.

In some embodiments, when the microbe or microbial consortia identified according to the taught methods is combined with a plant growth regulator, one witnesses an additive effect on a plant phenotypic trait of interest. In some embodiments, when the microbe or microbial consortia identified according to the taught methods is combined with a plant growth regulator, one witnesses a synergistic effect. In some aspects, the microbes of the present disclosure are combined with Ascend® and a synergistic effect is observed for one or more phenotypic traits of interest.

In some embodiments, when the microbe or microbial consortia identified according to the taught methods is combined with a biostimulant, one witnesses an additive effect on a plant phenotypic trait of interest. In some embodiments, when the microbe or microbial consortia identified according to the taught methods is combined with a biostimulant, one witnesses a synergistic effect.

The synergistic effect obtained by the taught methods can be quantified according to Colby's formula (i.e. (E)=X+Y−(X*Y/100). See Colby, R. S., "Calculating Synergistic and Antagonistic Responses of Herbicide Combinations," 1967 Weeds, vol. 15, pp. 20-22, incorporated herein by reference in its entirety. Thus, by "synergistic" is intended a component which, by virtue of its presence, increases the desired effect by more than an additive amount.

The isolated microbes and consortia of the present disclosure can synergistically increase the effectiveness of agricultural active compounds and also agricultural auxiliary compounds.

In other embodiments, when the microbe or microbial consortia identified according to the taught methods is combined with a fertilizer one witnesses a synergistic effect.

Furthermore, in certain embodiments, the disclosure utilizes synergistic interactions to define microbial consortia. That is, in certain aspects, the disclosure combines together certain isolated microbial species, which act synergistically, into consortia that impart a beneficial trait upon a plant, or which are correlated with increasing a beneficial plant trait.

The agricultural compositions developed according to the disclosure can be formulated with certain auxiliaries, in order to improve the activity of a known active agricultural compound. This has the advantage that the amounts of active ingredient in the formulation may be reduced while maintaining the efficacy of the active compound, thus allowing costs to be kept as low as possible and any official regulations to be followed. In individual cases, it may also possible to widen the spectrum of action of the active compound since plants, where the treatment with a particular active ingredient without addition was insufficiently successful, can indeed be treated successfully by the addition of certain auxiliaries along with the disclosed microbial isolates and consortia. Moreover, the performance of the active may be increased in individual cases by a suitable formulation when the environmental conditions are not favorable.

Such auxiliaries that can be used in an agricultural composition can be an adjuvant. Frequently, adjuvants take the form of surface-active or salt-like compounds. Depending on their mode of action, they can roughly be classified as modifiers, activators, fertilizers, pH buffers, and the like. Modifiers affect the wetting, sticking, and spreading properties of a formulation. Activators break up the waxy cuticle of the plant and improve the penetration of the active ingredient into the cuticle, both short-term (over minutes) and long-term (over hours). Fertilizers such as ammonium sulfate, ammonium nitrate or urea improve the absorption and solubility of the active ingredient and may reduce the antagonistic behavior of active ingredients. pH buffers are conventionally used for bringing the formulation to an optimal pH.

For further embodiments of agricultural compositions of the present disclosure, See "Chemistry and Technology of Agrochemical Formulations," edited by D. A. Knowles, copyright 1998 by Kluwer Academic Publishers, hereby incorporated by reference.

Seed Treatments

In some embodiments, the present disclosure also concerns the discovery that treating seeds before they are sown or planted with a combination of one or more of the microbes or agricultural compositions of the present disclosure can enhance a desired plant trait, e.g. plant growth, plant health, and/or plant resistance to pests.

Thus, in some embodiments, the present disclosure teaches the use of one or more of the microbes or microbial consortia as seed treatments. The seed treatment can be a seed coating applied directly to an untreated and "naked" seed. However, the seed treatment can be a seed overcoat that is applied to a seed that has already been coated with one or more previous seed coatings or seed treatments. The previous seed treatments may include one or more active compounds, either chemical or biological, and one or more inert ingredients.

The term "seed treatment" generally refers to application of a material to a seed prior to or during the time it is planted in soil. Seed treatment with microbes, and other agricultural compositions of the present disclosure, has the advantages of delivering the treatments to the locus at which the seeds are planted shortly before germination of the seed and emergence of a seedling.

In other embodiments, the present disclosure also teaches that the use of seed treatments minimizes the amount of microbe or agricultural composition that is required to successfully treat the plants, and further limits the amount of contact of workers with the microbes and compositions compared to application techniques such as spraying over soil or over emerging seedlings.

Moreover, in some embodiments, the present disclosure teaches that the microbes disclosed herein are important for enhancing the early stages of plant life (e.g., within the first thirty days following emergence of the seedling). Thus, in some embodiments, delivery of the microbes and/or compositions of the present disclosure as a seed treatment places the microbe at the locus of action at a critical time for its activity.

In some embodiments, the microbial compositions of the present disclosure are formulated as a seed treatment. In some embodiments, it is contemplated that the seeds can be substantially uniformly coated with one or more layers of the microbes and/or agricultural compositions disclosed herein, using conventional methods of mixing, spraying, or a combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists, or a combination thereof. Liquid seed treatments such as those of the present disclosure can be applied via either a spinning "atomizer" disk or a spray nozzle, which evenly distributes the seed treatment onto the seed as it moves though the spray pattern. In aspects, the seed is then mixed or tumbled for an additional period of time to achieve additional treatment distribution and drying.

The seeds can be primed or unprimed before coating with the microbial compositions to increase the uniformity of germination and emergence. In an alternative embodiment, a dry powder formulation can be metered onto the moving seed and allowed to mix until completely distributed.

In some embodiments, the seeds have at least part of the surface area coated with a microbiological composition, according to the present disclosure. In some embodiments, a seed coat comprising the microbial composition is applied directly to a naked seed. In some embodiments, a seed overcoat comprising the microbial composition is applied to a seed that already has a seed coat applied thereon. In some aspects, the seed may have a seed coat comprising, e.g. clothianidin and/or *Bacillus firmus*-I-1582, upon which the present composition will be applied on top of, as a seed overcoat. In some aspects, the taught microbial compositions are applied as a seed overcoat to seeds that have already been treated with PONCHO™ VOTiVO™. In some aspects, the seed may have a seed coat comprising, e.g. Metalaxyl, and/or clothianidin, and/or *Bacillus firmus*-I-1582, upon which the present composition will be applied on top of, as a seed overcoat. In some aspects, the taught microbial compositions are applied as a seed overcoat to seeds that have already been treated with ACCELERON™.

In some embodiments, the microorganism-treated seeds have a microbial spore concentration, or microbial cell concentration, from about: $10^3$ to $10^{12}$, $10^3$ to $10^{11}$, $10^3$ to $10^{10}$, $10^3$ to $10^9$, $10^3$ to $10^8$, $10^3$ to $10^7$, $10^3$ to $10^6$, $10^3$ to $10^5$, or $10^3$ to $10^4$ per seed.

In some embodiments, the microorganism-treated seeds have a microbial spore concentration, or microbial cell concentration, from about: $10^4$ to $10^{12}$, $10^4$ to $10^{11}$, $10^4$ to $10^{10}$, $10^4$ to $10^9$, $10^4$ to $10^8$, $10^4$ to $10^7$, $10^4$ to $10^6$, or $10^4$ to $10^5$ per seed.

In some embodiments, the microorganism-treated seeds have a microbial spore concentration, or microbial cell concentration, from about: $10^5$ to $10^{12}$, $10^5$ to $10^{11}$, $10^5$ to $10^{10}$, $10^5$ to $10^9$, $10^5$ to $10^8$, $10^5$ to $10^7$, or $10^5$ to $10^6$ per seed.

In some embodiments, the microorganism-treated seeds have a microbial spore concentration, or microbial cell concentration, from about: $10^5$ to $10^9$ per seed.

In some embodiments, the microorganism-treated seeds have a microbial spore concentration, or microbial cell concentration, of at least about: $1\times10^3$, or $1\times10^4$, or $1\times10^5$, or $1\times10^6$, or $1\times10^7$, or $1\times10^8$, or $1\times10^9$ per seed.

In some embodiments, the amount of one or more of the microbes and/or agricultural compositions applied to the seed depend on the final formulation, as well as size or type of the plant or seed utilized. In some embodiments, one or more of the microbes are present in about 2% w/w to about 80% w/w of the entire formulation. In some embodiments, the one or more of the microbes employed in the compositions is about 5% w/w to about 65% w/w, or 10% w/w to about 60% w/w by weight of the entire formulation.

In some embodiments, the seeds may also have more spores or microbial cells per seed, such as, for example about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, or $10^{17}$ spores or cells per seed.

In some embodiments, the seed coats of the present disclosure can be up to 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, 500 μm, 510 μm, 520 μm, 530 μm, 540 μm, 550 μm, 560 μm, 570 μm, 580 μm, 590 μm, 600 μm, 610 μm, 620 μm, 630 μm, 640 μm, 650 μm, 660 μm, 670 μm, 680 μm, 690 μm, 700 μm, 710 μm, 720 μm, 730 μm, 740 μm, 750 μm, 760 μm, 770 μm, 780 μm, 790 μm, 800 μm, 810 μm, 820 μm, 830 μm, 840 μm, 850 μm, 860 μm, 870 μm, 880 μm, 890 μm, 900 μm, 910 μm, 920 μm, 930 μm, 940 μm, 950 μm, 960 μm, 970 μm, 980 μm, 990 μm, 1000 μm, 1010 μm, 1020 μm, 1030 μm, 1040 μm, 1050 μm, 1060 μm, 1070 μm, 1080 μm, 1090 μm, 1100 μm, 1110 μm, 1120 μm, 1130 μm, 1140 μm, 1150 μm, 1160 μm, 1170 μm, 1180 μm, 1190 μm, 1200 μm, 1210 μm, 1220 μm, 1230 μm, 1240 μm, 1250 μm, 1260 μm, 1270 μm, 1280 μm, 1290 μm, 1300 μm, 1310 μm, 1320 μm, 1330 μm, 1340 μm, 1350 μm, 1360 μm, 1370 μm, 1380 μm, 1390 μm, 1400 μm, 1410 μm, 1420 μm, 1430 μm, 1440 μm, 1450 μm, 1460 μm, 1470 μm, 1480 μm, 1490 μm, 1500 μm, 1510 μm, 1520 μm, 1530 μm, 1540 μm, 1550 μm, 1560 μm, 1570 μm, 1580 μm, 1590 μm, 1600 μm, 1610 μm, 1620 μm, 1630 μm, 1640 μm, 1650 μm, 1660 μm, 1670 μm, 1680 μm, 1690 μm, 1700 μm, 1710 μm, 1720 μm, 1730 μm, 1740 μm, 1750 μm, 1760 μm, 1770 μm, 1780 μm, 1790 μm, 1800 μm, 1810 μm, 1820 μm, 1830 μm, 1840 μm, 1850 μm, 1860 μm, 1870 μm, 1880 μm, 1890 μm, 1900 μm, 1910 μm, 1920 μm, 1930 μm, 1940 μm, 1950 μm, 1960 μm, 1970 μm, 1980 μm, 1990 μm, 2000 μm, 2010 μm, 2020 μm, 2030 μm, 2040 μm, 2050 μm, 2060 μm, 2070 μm, 2080 μm, 2090 μm, 2100 μm, 2110 μm, 2120 μm, 2130 μm, 2140 μm, 2150 μm, 2160 μm, 2170 μm, 2180 μm, 2190 μm, 2200 μm, 2210 μm, 2220 μm, 2230 μm, 2240 μm, 2250 μm, 2260 μm, 2270 μm, 2280 μm, 2290 μm, 2300 μm, 2310 μm, 2320 μm, 2330 μm, 2340 μm, 2350 μm, 2360 μm, 2370 μm, 2380 μm, 2390 μm, 2400 μm, 2410 μm, 2420 μm, 2430 μm, 2440 μm, 2450 μm, 2460 μm, 2470 μm, 2480 μm, 2490 μm, 2500 μm, 2510 μm, 2520 μm, 2530 μm, 2540 μm, 2550 μm, 2560 μm, 2570 μm, 2580 μm, 2590 μm, 2600 μm, 2610 μm, 2620 μm, 2630 μm, 2640 μm, 2650 μm, 2660 μm, 2670 μm, 2680 μm, 2690 μm, 2700 μm, 2710 μm, 2720 μm, 2730 μm, 2740 μm, 2750 μm, 2760 μm, 2770 μm, 2780 μm, 2790 μm, 2800 μm, 2810 μm, 2820 μm, 2830 μm, 2840 μm, 2850 μm, 2860 μm, 2870 μm, 2880 μm, 2890 μm, 2900 μm, 2910 μm, 2920 μm, 2930 μm, 2940 μm, 2950 μm, 2960 μm, 2970 μm, 2980 μm, 2990 μm, or 3000 μm thick.

In some embodiments, the seed coats of the present disclosure can be 0.5 mm, 1 mm, 1.5 mm, 2 mm, 2.5 mm, 3 mm, 3.5 mm, 4 mm, 4.5 mm, or 5 mm thick.

In some embodiments, the seed coats of the present disclosure can be at least 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, 49.5%, or 50% of the uncoated seed weight.

In some embodiments, the microbial spores and/or cells can be coated freely onto the seeds or they can be formulated in a liquid or solid composition before being coated onto the seeds. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid microbial compositions of the present disclosure further contain functional agents e.g., activated carbon, nutrients (fertilizers), and other agents capable of improving the germination and quality of the products or a combination thereof.

Seed coating methods and compositions that are known in the art can be particularly useful when they are modified by the addition of one of the embodiments of the present disclosure. Such coating methods and apparatus for their application are disclosed in, for example: U.S. Pat. Nos. 5,916,029; 5,918,413; 5,554,445; 5,389,399; 4,759,945; 4,465,017, and U.S. patent application Ser. No. 13/260,310, each of which is incorporated by reference herein.

Seed coating compositions are disclosed in, for example: U.S. Pat. Nos. 5,939,356; 5,876,739, 5,849,320; 5,791,084, 5,661,103; 5,580,544, 5,328,942; 4,735,015; 4,634,587; 4,372,080, 4,339,456; and 4,245,432, each of which is incorporated by reference herein.

In some embodiments, a variety of additives can be added to the seed treatment formulations comprising the inventive compositions. Binders can be added and include those composed of an adhesive polymer that can be natural or synthetic without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

Any of a variety of colorants may be employed, including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. Other additives that can be added include trace nutrients such as salts of iron, manganese, boron, copper, cobalt, molybdenum and zinc.

A polymer or other dust control agent can be applied to retain the treatment on the seed surface.

In some specific embodiments, in addition to the microbial cells or spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrins; alginates; sugars; molasses; polyvinyl pyrrolidones; polysaccharides; proteins; fats; oils; gum arabics; gelatins; syrups; and starches. More examples can be found in, for example, U.S. Pat. No. 7,213,367, incorporated herein by reference.

Various additives, such as adherents, dispersants, surfactants, and nutrient and buffer ingredients, can also be included in the seed treatment formulation. Other conventional seed treatment additives include, but are not limited to: coating agents, wetting agents, buffering agents, and polysaccharides. At least one agriculturally acceptable carrier can be added to the seed treatment formulation such as water, solids, or dry powders. The dry powders can be derived from a variety of materials such as calcium carbonate, gypsum, vermiculite, talc, humus, activated charcoal, and various phosphorous compounds.

In some embodiments, the seed coating composition can comprise at least one filler, which is an organic or inorganic, natural or synthetic component with which the active components are combined to facilitate its application onto the seed. In aspects, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates.

In some embodiments, the seed treatment formulation may further include one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; chemical fertilizers; biological fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed, or alternatively may be added as part of the seed coating composition of the disclosure.

In some embodiments, the formulation that is used to treat the seed in the present disclosure can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation can be about 0.5% to about 99% by weight (w/w), or 5-40%, or as otherwise formulated by those skilled in the art.

As mentioned above, other conventional inactive or inert ingredients can be incorporated into the formulation. Such inert ingredients include, but are not limited to: conventional sticking agents; dispersing agents such as methylcellulose, for example, serve as combined dispersant/sticking agents for use in seed treatments; polyvinyl alcohol; lecithin, polymeric dispersants (e.g., polyvinylpyrrolidone/vinyl acetate); thickeners (e.g., clay thickeners to improve viscosity and reduce settling of particle suspensions); emulsion stabilizers; surfactants; antifreeze compounds (e.g., urea), dyes, colorants, and the like. Further inert ingredients useful in the present disclosure can be found in McCutcheon's, vol. 1, "Emulsifiers and Detergents," MC Publishing Company, Glen Rock, N.J., U.S.A., 1996, incorporated by reference herein.

The seed coating formulations of the present disclosure can be applied to seeds by a variety of methods, including, but not limited to: mixing in a container (e.g., a bottle or bag), mechanical application, tumbling, spraying, and immersion. A variety of active or inert material can be used for contacting seeds with microbial compositions according to the present disclosure.

In some embodiments, the amount of the microbes or agricultural composition that is used for the treatment of the seed will vary depending upon the type of seed and the type of active ingredients, but the treatment will comprise contacting the seeds with an agriculturally effective amount of the inventive composition.

As discussed above, an effective amount means that amount of the inventive composition that is sufficient to affect beneficial or desired results. An effective amount can be administered in one or more administrations.

In some embodiments, in addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the coating layer.

In some embodiments, the seed coating formulations of the present disclosure may be applied to the seeds using a variety of techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are known in the art.

In some embodiments, the microorganism-treated seeds may also be enveloped with a film overcoating to protect the coating. Such overcoatings are known in the art and may be applied using fluidized bed and drum film coating techniques.

In other embodiments of the present disclosure, compositions according to the present disclosure can be introduced onto a seed by use of solid matrix priming. For example, a quantity of an inventive composition can be mixed with a solid matrix material and then the seed can be placed into contact with the solid matrix material for a period to allow the composition to be introduced to the seed. The seed can then optionally be separated from the solid matrix material and stored or used, or the mixture of solid matrix material plus seed can be stored or planted directly. Solid matrix materials which are useful in the present disclosure include polyacrylamide, starch, clay, silica, alumina, soil, sand, polyurea, polyacrylate, or any other material capable of absorbing or adsorbing the inventive composition for a time and releasing that composition into or onto the seed. It is useful to make sure that the inventive composition and the solid matrix material are compatible with each other. For example, the solid matrix material should be chosen so that it can release the composition at a reasonable rate, for example over a period of minutes, hours, or days.

Microorganisms

As used herein the term "microorganism" should be taken broadly. It includes, but is not limited to, the two prokaryotic domains, Bacteria and Archaea, as well as eukaryotic fungi and protists.

By way of example, the microorganisms may include: Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma,* and *Acetobacterium*), Actinobacteria (such as *Streptomyces, Rhodococcus, Microbacterium,* and *Curtobacterium*), and the fungi Ascomycota (such as *Trichoderma, Ampelomyces, Coniothyrium, Paecoelomyces, Penicillium, Cladosporium, Hypocrea, Beauveria, Metarhizium, Verticullium, Cordyceps, Pichea,* and *Candida*, Basidiomycota (such as *Coprinus, Corticium,* and *Agaricus*) and Oomycota (such as *Pythium, Mucor,* and *Mortierella*).

In a particular embodiment, the microorganism is an endophyte, or an epiphyte, or a microorganism inhabiting the plant rhizosphere or rhizosheath. That is, the microorganism may be found present in the soil material adhered to the roots of a plant or in the area immediately adjacent a plant's roots. In one embodiment, the microorganism is a seed-borne endophyte.

Endophytes may benefit host plants by preventing pathogenic organisms from colonizing them. Extensive colonization of the plant tissue by endophytes creates a "barrier effect," where the local endophytes outcompete and prevent pathogenic organisms from taking hold. Endophytes may also produce chemicals which inhibit the growth of competitors, including pathogenic organisms.

In certain embodiments, the microorganism is unculturable. This should be taken to mean that the microorganism is not known to be culturable or is difficult to culture using methods known to one skilled in the art.

Microorganisms of the present disclosure may be collected or obtained from any source or contained within and/or associated with material collected from any source.

In an embodiment, the microorganisms are obtained from any general terrestrial environment, including its soils, plants, fungi, animals (including invertebrates) and other biota, including the sediments, water and biota of lakes and rivers; from the marine environment, its biota and sediments (for example sea water, marine muds, marine plants, marine invertebrates (for example sponges), marine vertebrates (for example, fish)); the terrestrial and marine geosphere (regolith and rock, for example crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, road surfaces).

In another embodiment the microorganisms are collected from a source likely to favor the selection of appropriate microorganisms. By way of example, the source may be a particular environment in which it is desirable for other plants to grow, or which is thought to be associated with terroir. In another example, the source may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the microorganisms may be collected from commercial crops grown in such environments, or more specifically from individual crop plants best displaying a trait of interest amongst a crop grown in any specific environment, for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste, or smell. The microorganisms may be collected from a plant of interest or any material occurring in the environment of interest, including fungi and other animal and plant biota, soil, water, sediments, and other elements of the environment as referred to previously. In certain embodiments, the microorganisms are individual isolates separated from different environments.

In one embodiment, a microorganism or a combination of microorganisms, of use in the methods of the disclosure may be selected from a pre-existing collection of individual microbial species or strains based on some knowledge of their likely or predicted benefit to a plant. For example, the microorganism may be predicted to: improve nitrogen fixation; release phosphate from the soil organic matter; release phosphate from the inorganic forms of phosphate (e.g. rock phosphate); "fix carbon" in the root microsphere; live in the rhizosphere of the plant thereby assisting the plant in absorbing nutrients from the surrounding soil and then providing these more readily to the plant; increase the number of nodules on the plant roots and thereby increase the number of symbiotic nitrogen fixing bacteria (e.g. *Rhizobium* species) per plant and the amount of nitrogen fixed by the plant; elicit plant defensive responses such as ISR (induced systemic resistance) or SAR (systemic acquired resistance) which help the plant resist the invasion and spread of pathogenic microorganisms; compete with microorganisms deleterious to plant growth or health by antagonism, or competitive utilization of resources such as nutrients or space; change the color of one or more part of the plant, or change the chemical profile of the plant, its smell, taste or one or more other quality.

In one embodiment a microorganism or combination of microorganisms is selected from a pre-existing collection of individual microbial species or strains that provides no knowledge of their likely or predicted benefit to a plant. For example, a collection of unidentified microorganisms isolated from plant tissues without any knowledge of their ability to improve plant growth or health, or a collection of microorganisms collected to explore their potential for producing compounds that could lead to the development of pharmaceutical drugs.

In one embodiment, the microorganisms are acquired from the source material (for example, soil, rock, water, air, dust, plant or other organism) in which they naturally reside. The microorganisms may be provided in any appropriate form, having regard to its intended use in the methods of the disclosure. However, by way of example only, the microorganisms may be provided as an aqueous suspension, gel, homogenate, granule, powder, slurry, live organism or dried material.

The microorganisms of the disclosure may be isolated in substantially pure or mixed cultures. They may be concentrated, diluted, or provided in the natural concentrations in which they are found in the source material. For example, microorganisms from saline sediments may be isolated for use in this disclosure by suspending the sediment in fresh water and allowing the sediment to fall to the bottom. The water containing the bulk of the microorganisms may be removed by decantation after a suitable period of settling and either applied directly to the plant growth medium, or concentrated by filtering or centrifugation, diluted to an appropriate concentration and applied to the plant growth medium with the bulk of the salt removed. By way of further example, microorganisms from mineralized or toxic sources may be similarly treated to recover the microbes for application to the plant growth material to minimize the potential for damage to the plant.

In another embodiment, the microorganisms are used in a crude form, in which they are not isolated from the source material in which they naturally reside. For example, the microorganisms are provided in combination with the source material in which they reside; for example, as soil, or the roots, seed or foliage of a plant. In this embodiment, the source material may include one or more species of microorganisms.

In some embodiments, a mixed population of microorganisms is used in the methods of the disclosure.

In embodiments of the disclosure where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

Whilst not essential, in one embodiment, the material containing the microorganisms may be pre-treated prior to the isolation process in order to either multiply all microorganisms in the material, or select portions of the microbial population, either by enriching the material with microbial nutrients (for example, by pasteurizing the sample to select for microorganisms resistant to heat exposure (for example, bacilli), or by exposing the sample to low concentrations of an organic solvent or sterilant (for example, household bleach) to enhance the survival of spore-forming or solvent-resistant microorganisms). Microorganisms can then be isolated from the enriched materials or materials treated for selective survival, as above.

In an embodiment of the disclosure, endophytic or epiphytic microorganisms are isolated from plant material. Any number of standard techniques known in the art may be used and the microorganisms may be isolated from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilization with an appropriate solution (e.g. 2% sodium hypochlorite), after which the plant material is placed on nutrient medium for microbial growth (See, for example, Strobel G and Daisy B (2003) Microbiology and Molecular Biology Reviews 67 (4): 491-502; Zinniel D K et al. (2002) Applied and Environmental Microbiology 68 (5): 2198-2208).

In one embodiment of the disclosure, the microorganisms are isolated from root tissue. Further methodology for isolating microorganisms from plant material are detailed hereinafter.

In one embodiment, the microbial population is exposed (prior to the method or at any stage of the method) to a selective pressure. For example, exposure of the microorganisms to pasteurisation before their addition to a plant growth medium (preferably sterile) is likely to enhance the probability that the plants selected for a desired trait will be associated with spore-forming microbes that can more easily survive in adverse conditions, in commercial storage, or if applied to seed as a coating, in an adverse environment.

In certain embodiments, as mentioned herein before, the microorganism(s) may be used in crude form and need not be isolated from a plant or a media. For example, plant material or growth media which includes the microorganisms identified to be of benefit to a selected plant may be obtained and used as a crude source of microorganisms for the next round of the method or as a crude source of microorganisms at the conclusion of the method. For example, whole plant material could be obtained and optionally processed, such as mulched or crushed. Alternatively, individual tissues or parts of selected plants (such as leaves, stems, roots, and seeds) may be separated from the plant and optionally processed, such as mulched or crushed. In certain embodiments, one or more part of a plant which is associated with the second set of one or more microorganisms may be removed from one or more selected plants and, where any successive repeat of the method is to be conducted, grafted on to one or more plant used in any step of the plant breeding methods.

Plants that are Able to Benefit from the Application of the Disclosed Microbes, Consortia, and Compositions Comprising the Same Any number of a variety of different plants, including mosses and lichens and algae, may be used in the methods of the disclosure. In embodiments, the plants have economic, social, or environmental value. For example, the plants may include those used as: food crops, fiber crops, oil crops, in the forestry industry, in the pulp and paper industry, as a feedstock for biofuel production, and as ornamental plants.

In other embodiments, the plants may be economically, socially, or environmentally undesirable, such as weeds. The following is a list of non-limiting examples of the types of plants the methods of the disclosure may be applied to:

Food Crops:

Cereals e.g maize, rice, wheat, barley, sorghum, millet, oats, rye, triticale, and buckwheat;

Leafy vegetables e.g. brassicaceous plants such as cabbages, broccoli, bok choy, rocket; salad greens such as spinach, cress, and lettuce;

Fruiting and flowering vegetables e.g. avocado, sweet corn, artichokes; curcubits e.g. squash, cucumbers, melons, courgettes, pumpkins; solanaceous vegetables/fruits e.g. tomatoes, eggplant, and capsicums;

Podded vegetables e.g. groundnuts, peanuts, peas, soybeans, beans, lentils, chickpea, okra;

Bulbed and stem vegetables e.g. asparagus, celery, *Allium* crops e.g garlic, onions, and leeks;

Roots and tuberous vegetables e.g. carrots, beet, bamboo shoots, cassava, yams, ginger, Jerusalem artichoke, parsnips, radishes, potatoes, sweet potatoes, taro, turnip, and wasabi;

Sugar crops including sugar beet (*Beta vulgaris*), sugar cane (*Saccharum officinarum*);

Crops grown for the production of non-alcoholic beverages and stimulants e.g. coffee, black, herbal, and green teas, cocoa, marijuana, and tobacco;

Fruit crops such as true berry fruits (e.g. kiwifruit, grape, currants, gooseberry, guava, feijoa, pomegranate), citrus fruits (e.g. oranges, lemons, limes, grapefruit), epigynous fruits (e.g. bananas, cranberries, blueberries), aggregate fruit (blackberry, raspberry, boysenberry), multiple fruits (e.g. pineapple, fig), stone fruit crops (e.g. apricot, peach, cherry, plum), pip-fruit (e.g. apples, pears) and others such as strawberries, sunflower seeds;

Culinary and medicinal herbs e.g. rosemary, basil, bay laurel, coriander, mint, dill, *Hypericum*, foxglove, alovera, rosehips, and cannabis;

Crop plants producing spices e.g. black pepper, cumin cinnamon, nutmeg, ginger, cloves, saffron, cardamom, mace, paprika, masalas, star anise;

Crops grown for the production of nuts e.g. almonds and walnuts, Brazil nut, cashew nuts, coconuts, chestnut, macadamia nut, pistachio nuts; peanuts, pecan nuts;

Crops grown for production of beers, wines and other alcoholic beverages e.g grapes, and hops;

Oilseed crops e.g. soybean, peanuts, cotton, olives, sunflower, sesame, lupin species and brassicaeous crops (e.g. canola/oilseed rape); and, edible fungi e.g. white mushrooms, Shiitake and oyster mushrooms;

Plants Used in Pastoral Agriculture:

Legumes: *Trifolium* species, *Medicago* species, and *Lotus* species; White clover (*T. repens*); Red clover (*T. pratense*); Caucasian clover (*T. ambigum*); subterranean clover (*T. subterraneum*); Alfalfa/Lucerne (*Medicago sativum*); annual medics; barrel medic; black medic; Sainfoin (*Onobrychis viciifolia*); Birdsfoot trefoil (*Lotus corniculatus*); Greater Birdsfoot trefoil (*Lotus pedunculatus*);

Seed legumes/pulses including Peas (*Pisum sativum*), Common bean (*Phaseolus vulgaris*), Broad beans (*Vicia faba*), Mung bean (*Vigna radiata*), Cowpea (*Vigna unguiculata*), Chick pea (*Cicer arietum*), Lupins (*Lupinus* species); Cereals including Maize/corn (*Zea mays*), Sorghum (*Sorghum* spp.), Millet (*Panicum miliaceum, P. sumatrense*), Rice (*Oryza sativa indica, Oryza sativa japonica*), Wheat (*Triticum sativa*), Barley (*Hordeum vulgare*), Rye (*Secale cereale*), Triticale (*Triticum×Secale*), Oats (*Avena sativa*);

Forage and Amenity grasses: Temperate grasses such as *Lolium* species; *Festuca* species; *Agrostis* spp., Perennial ryegrass (*Lolium perenne*); hybrid ryegrass (*Lolium hybridum*); annual ryegrass (*Lolium multiflorum*), tall fescue (*Festuca arundinacea*); meadow fescue (*Festuca pratensis*); red fescue (*Festuca rubra*); *Festuca ovina*; Festuloliums (*Lolium×Festuca* crosses); Cocksfoot (*Dactylis glomerata*); Kentucky bluegrass *Poa pratensis; Poa palustris; Poa nemoralis; Poa trivialis; Poa compresa; Bromus* species; *Phalaris* (*Phleum* species); *Arrhenatherum elatius; Agropyron* species; *Avena strigosa; Setaria* italic;

Tropical grasses such as: *Phalaris* species; *Brachiaria* species; *Eragrostis* species; *Panicum* species; Bahai grass (*Paspalum notatum*); *Brachypodium* species; and, grasses used for biofuel production such as Switchgrass (*Panicum virgatum*) and *Miscanthus* species; Fiber crops:

Cotton, hemp, jute, coconut, sisal, flax (*Linum* spp.), New Zealand flax (*Phormium* spp.); plantation and natural forest species harvested for paper and engineered wood fiber products such as coniferous and broadleafed forest species; Tree and shrub species used in plantation forestry and bio-fuel crops:

Pine (*Pinus* species); Fir (*Pseudotsuga* species); Spruce (*Picea* species); Cypress (*Cupressus* species); Wattle (*Acacia* species); Alder (*Alnus* species); Oak species (*Quercus* species); Redwood (*Sequoiadendron* species); willow (*Salix* species); birch (*Betula* species); Cedar (*Cedurus* species); Ash (*Fraxinus* species); Larch (*Larix* species); *Eucalyptus* species; Bamboo (*Bambuseae* species) and Poplars (*Populus* species).

Plants Grown for Conversion to Energy, Biofuels or Industrial Products by Extractive. Biological. Physical or Biochemical Treatment:

Oil-producing plants such as oil palm, jatropha, soybean, cotton, linseed; Latex-producing plants such as the Para Rubber tree, *Hevea brasiliensis* and the Panama Rubber Tree *Castilla elastica*; plants used as direct or indirect feedstocks for the production of biofuels i.e. after chemical, physical (e.g. thermal or catalytic) or biochemical (e.g. enzymatic pre-treatment) or biological (e.g. microbial fermentation) transformation during the production of biofuels, industrial solvents or chemical products e.g. ethanol or butanol, propane dials, or other fuel or industrial material including sugar crops (e.g. beet, sugar cane), starch producing crops (e.g. C3 and C4 cereal crops and tuberous crops), cellulosic crops such as forest trees (e.g. Pines, Eucalypts) and Graminaceous and Poaceous plants such as bamboo, switch grass, miscanthus; crops used in energy, biofuel or industrial chemical production via gasification and/or microbial or catalytic conversion of the gas to biofuels or other industrial raw materials such as solvents or plastics, with or without the production of biochar (e.g. biomass crops such as coniferous, eucalypt, tropical or broadleaf forest trees, graminaceous and poaceous crops such as bamboo, switch grass, miscanthus, sugar cane, or hemp or softwoods such as poplars, willows; and, biomass crops used in the production of biochar;

Crops Producing Natural Products Useful for the Pharmaceutical. Agricultural Nutraceutical and Cosmeceutical Industries:

Crops producing pharmaceutical precursors or compounds or nutraceutical and cosmeceutical compounds and materials for example, star anise (shikimic acid), Japanese knotweed (resveratrol), kiwifruit (soluble fiber, proteolytic enzymes);

Floricultural, Ornamental and Amenity Plants Grown for their Aesthetic or Environmental Properties:

Flowers such as roses, tulips, chrysanthemums;

Ornamental shrubs such as *Buxus, Hebe, Rosa, Rhododendron, Hedera*

Amenity plants such as *Platanus, Choisya, Escallonia, Euphorbia, Carex*

Mosses such as sphagnum moss

Plants Grown for Bioremediation:

*Helianthus, Brassica, Salix, Populus, Eucalyptus*

Hybrid and GM Plant Improvement

In certain aspects, the microbes of the present disclosure are applied to hybrid plants to increase beneficial traits of said hybrids. In other aspects, the microbes of the present disclosure are applied to genetically modified plants to increase beneficial traits of said GM plants. The microbes taught herein are able to be applied to hybrids and GM plants and thus maximize the elite genetics and trait technologies of these plants.

It should be appreciated that a plant may be provided in the form of a seed, seedling, cutting, propagule, or any other plant material or tissue capable of growing. In one embodiment the seed may be surface-sterilised with a material such as sodium hypochlorite or mercuric chloride to remove surface-contaminating microorganisms. In one embodiment, the propagule is grown in axenic culture before being placed in the plant growth medium, for example as sterile plantlets in tissue culture.

Methods of Application

The microorganisms may be applied to a plant, seedling, cutting, propagule, or the like and/or the growth medium containing said plant, using any appropriate technique known in the art.

However, by way of example, an isolated microbe, consortia, or composition comprising the same may be applied to a plant, seedling, cutting, propagule, or the like, by spraying or dusting.

In another embodiment, the isolated microbe, consortia, or composition comprising the same may applied directly to a plant seed prior to sowing.

In another embodiment, the isolated microbe, consortia, or composition comprising the same may applied directly to a plant seed, as a seed coating.

In one embodiment of the present disclosure, the isolated microbe, consortia, or composition comprising the same is supplied in the form of granules, or plug, or soil drench that is applied to the plant growth media.

In other embodiments, the isolated microbe, consortia, or composition comprising the same are supplied in the form of a foliar application, such as a foliar spray or liquid composition. The foliar spray or liquid application may be applied to a growing plant or to a growth media, e.g. soil.

In another embodiment, the isolated microbe, consortia, or composition comprising the same may be formulated into granules and applied alongside seeds during planting. Or the granules may be applied after planting. Or the granules may be applied before planting.

In some embodiments, the isolated microbe, consortia, or composition comprising the same are administered to a plant or growth media as a topical application and/or drench application to improve crop growth, yield, and quality. The topical application may be via utilization of a dry mix or powder or dusting composition or may be a liquid based formulation.

In embodiments, the isolated microbe, consortia, or composition comprising the same can be formulated as: (1) solutions; (2) wettable powders; (3) dusting powders; (4) soluble powders; (5) emulsions or suspension concentrates; (6) seed dressings or coatings, (7) tablets; (8) water-dispersible granules; (9) water soluble granules (slow or fast release); (10) microencapsulated granules or suspensions; and (11) as irrigation components, among others. In certain aspects, the compositions may be diluted in an aqueous medium prior to conventional spray application. The compositions of the present disclosure can be applied to the soil, plant, seed, rhizosphere, rhizosheath, or other area to which it would be beneficial to apply the microbial compositions. Further still, ballistic methods can be utilized as a means for introducing endophytic microbes.

In aspects, the compositions are applied to the foliage of plants. The compositions may be applied to the foliage of plants in the form of an emulsion or suspension concentrate, liquid solution, or foliar spray. The application of the compositions may occur in a laboratory, growth chamber, greenhouse, or in the field.

In another embodiment, microorganisms may be inoculated into a plant by cutting the roots or stems and exposing the plant surface to the microorganisms by spraying, dipping, or otherwise applying a liquid microbial suspension, or gel, or powder.

In another embodiment, the microorganisms may be injected directly into foliar or root tissue, or otherwise inoculated directly into or onto a foliar or root cut, or else into an excised embryo, or radicle, or coleoptile. These inoculated plants may then be further exposed to a growth media containing further microorganisms; however, this is not necessary.

In other embodiments, particularly where the microorganisms are unculturable, the microorganisms may be transferred to a plant by any one or a combination of grafting, insertion of explants, aspiration, electroporation, wounding, root pruning, induction of stomatal opening, or any physical, chemical or biological treatment that provides the opportunity for microbes to enter plant cells or the intercellular space. Persons of skill in the art may readily appreciate a number of alternative techniques that may be used.

In one embodiment, the microorganisms infiltrate parts of the plant such as the roots, stems, leaves and/or reproductive plant parts (become endophytic), and/or grow upon the surface of roots, stems, leaves and/or reproductive plant parts (become epiphytic) and/or grow in the plant rhizosphere. In one embodiment, the microorganisms form a symbiotic relationship with the plant.

EXAMPLES

I. Increased Yield in Agriculturally Important Crops

In certain embodiments of the disclosure, the present methods aim to increase the yields for a given crop.

The methodologies presented herein—based upon utilizing the disclosed isolated microbes, consortia, and compositions comprising the same—have the potential to increase the yield of important agricultural crops. These yield increases can be realized without the need for further fertilizer addition.

Example 1: Increasing Ryegrass Biomass with Isolated Microbes and Microbial Consortia A. Seed Treatment with Isolated Microbe In this example, an isolated microbe from Tables 1-4 will be applied as a seed coating to seeds of ryegrass (*Lolium perenne*). Upon applying the isolated microbe as a seed coating, the ryegrass will be planted and cultivated in the standard manner.

A control plot of ryegrass seeds, which did not have the isolated microbe applied as a seed coating, will also be planted.

It is expected that the ryegrass plants grown from the seeds treated with the seed coating will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

B. Seed Treatment with Microbial Consortia

In this example, a microbial consortium, comprising at least two microbes from Tables 1-4 will be applied as a seed coating to seeds of ryegrass (*Lolium perenne*). Upon applying the microbial consortium as a seed coating, the ryegrass will be planted and cultivated in the standard manner.

A control plot of ryegrass seeds, which did not have the microbial consortium applied as a seed coating, will also be planted.

It is expected that the ryegrass plants grown from the seeds treated with the seed coating will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

C. Treatment with Agricultural Composition Comprising Isolated Microbe

In this example, an isolated microbe from Tables 1-4 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

D. Treatment with Agricultural Composition Comprising Microbial Consortia

In this example, a microbial consortium, comprising at least two microbes from Tables 1-4 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

Example 2: Increasing Maize Biomass with Isolated Microbes and Microbial Consortia A. Seed Treatment with Isolated Microbe In this example, an isolated microbe from Tables 1-4 will be applied as a seed coating to seeds of corn (Zea mays). Upon applying the isolated microbe as a seed coating, the corn will be planted and cultivated in the standard manner.

A control plot of corn seeds, which did not have the isolated microbe applied as a seed coating, will also be planted.

It is expected that the corn plants grown from the seeds treated with the seed coating will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

B. Seed Treatment with Microbial Consortia

In this example, a microbial consortium, comprising at least two microbes from Tables 1-4 will be applied as a seed coating to seeds of corn (Zea mays). Upon applying the microbial consortium as a seed coating, the corn will be planted and cultivated in the standard manner.

A control plot of corn seeds, which did not have the microbial consortium applied as a seed coating, will also be planted.

It is expected that the corn plants grown from the seeds treated with the seed coating will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

C. Treatment with Agricultural Composition Comprising Isolated Microbe

In this example, an isolated microbe from Tables 1-4 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

D. Treatment with Agricultural Composition Comprising Microbial Consortia

In this example, a microbial consortium, comprising at least two microbes from Tables 1-4 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

Example 3: Increasing Soybean Biomass with Isolated Microbes and Microbial Consortia A. Seed Treatment with Isolated Microbe In this example, an isolated microbe from Tables 1-4 will be applied as a seed coating to seeds of soybean (*Glycine max*). Upon applying the isolated microbe as a seed coating, the soybean will be planted and cultivated in the standard manner.

A control plot of soybean seeds, which did not have the isolated microbe applied as a seed coating, will also be planted.

It is expected that the soybean plants grown from the seeds treated with the seed coating will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

B. Seed Treatment with Microbial Consortia

In this example, a microbial consortium, comprising at least two microbes from Tables 1-4 will be applied as a seed coating to seeds of soybean (*Glycine max*). Upon applying the microbial consortium as a seed coating, the soybean will be planted and cultivated in the standard manner.

A control plot of soybean seeds, which did not have the microbial consortium applied as a seed coating, will also be planted.

It is expected that the soybean plants grown from the seeds treated with the seed coating will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

C. Treatment with Agricultural Composition Comprising Isolated Microbe

In this example, an isolated microbe from Tables 1-4 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

D. Treatment with Agricultural Composition Comprising Microbial Consortia

In this example, a microbial consortium, comprising at least two microbes from Tables 1-4 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

Example 4: Modifying Wheat Seedling Biomass with Isolated Microbes

A. Seed Treatment with Isolated Microbe

Figure 5:
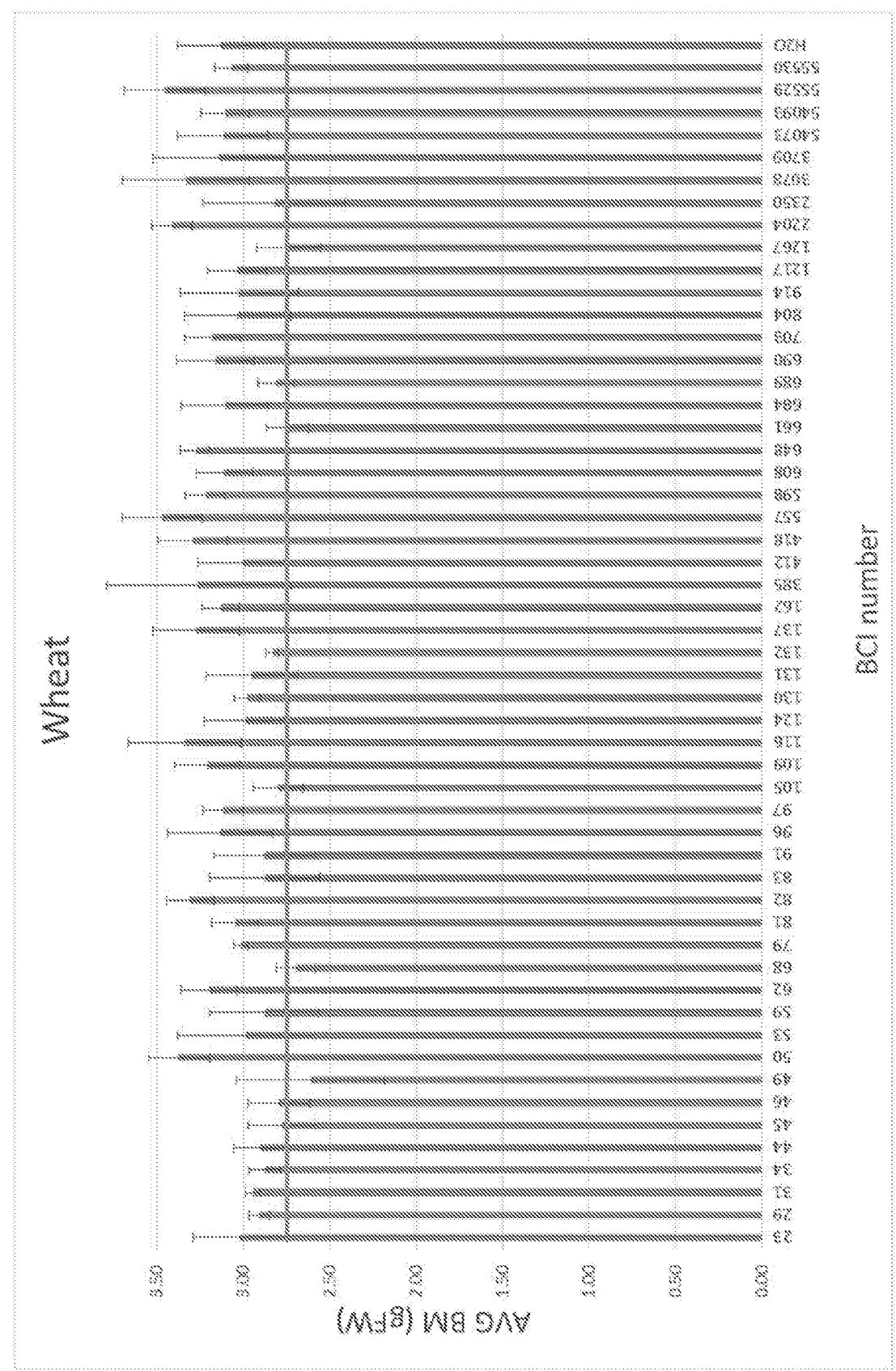
FIG. 5 shows a graphic representation of the average total biomass of wheat, in grams of fresh weight, at seven days post inoculation with individual microbial strains (BCI).

In this example, wheat seeds were inoculated with individual microbial strains (BCIs), and allowed to germinate (FIG. 5).

The seeds were inoculated and placed on wet paper towels and rolled. The rolls were then incubated at 25° C. in plastic bins covered with wet towels. Each strain appearing in FIG. 5 was tested in triplicate, with 20 seeds per replicate test.

Total biomass was measured at seven days post treatment. An uninoculated 'water' control treatment was run and measured simultaneously. The solid line parallel to the x axis and bisecting the bars near the top of the y-axis of FIG. 5 represents uninoculated control seeds. Some of the inoculated strains revealed relative increases in biomass at seven days post inoculation (DPI) compared to untreated control in vitro.

Table 12 provides a breakout of the biomass increase in wheat having been inoculated as described above, relative to a water-only treatment control (H2O) and an untreated (Unt) control. The two columns immediately to the right of the species reflect the percentage increase over control (% IOC) for the water-only treatment control and the untreated control. Both increases and decreases in the biomasses are reflected in the data of table 12. A smaller plant reflects potential for in-field conservation of nutrients and water where these resources may be limited by drought or local conditions, thus decreases are hypothesized to be yield relevant.

The results demonstrated that ~19 strains caused a relative increase in total biomass of wheat at seven days post inoculation (DPI) compared to the water-only and untreated controls in vitro. Eight strains showed greater than a 5% increase over both controls, whereas 19 strains showed greater than a 5% decrease in biomass over the water control.

TABLE 12

| Strain | Species | % IOC UNT | % IOC H2O |
|---|---|---|---|
| 557 | Novosphingobium resinovorum | 26.2 | 10.9 |
| 55529 | Pantoea vagans | 25.7 | 10.4 |
| 2204 | Duganella violaceinigra | 24.3 | 9.2 |
| 50 | Exiguobacterium aurantiacum | 22.7 | 7.8 |
| 116 | Exiguobacterium sibiricum | 21.5 | 6.7 |
| 3078 | Variovorax ginsengisoli | 21.3 | 6.6 |
| 82 | Novosphingobium sediminicola | 20.4 | 5.7 |
| 418 | Paenibacillus glycanilyticus | 19.9 | 5.3 |
| 648 | Acidovorax soli | 19.3 | 4.8 |
| 137 | Variovorax ginsengisoli | 19.0 | 4.6 |
| 385 | Achromobacter spanius | 18.6 | 4.1 |
| 598 | Pedobacter rhizosphaerae | 17.2 | 3.0 |
| 109 | Chitinophaga terrae | 16.7 | 2.5 |
| 62 | Arthrobacter cupressi | 16.4 | 2.2 |
| 703 | Bosea thiooxidans | 15.8 | 1.7 |
| 690 | Acidovorax soli | 15.2 | 1.2 |
| 3709 | Novosphingobium resinovorum | 14.2 | 0.3 |
| 96 | Dyadobacter soli | 14.1 | 0.2 |
| 162 | Herbaspirillum chlorophenolicum | 13.9 | 0.1 |
| H2O | | 13.8 | 0.0 |
| 97 | Massilia albidiflava | 13.5 | −0.3 |
| 54073 | Stenotrophomonas maltophilia | 13.5 | −0.3 |
| 608 | Novosphingobium lindaniclasticum | 13.2 | −0.5 |
| 684 | Novosphingobium lindaniclasticum | 13.1 | −0.7 |
| 54093 | Rhodococcus erythropolis | 13.0 | −0.8 |
| 55530 | Pseudomonas oryzihabitans | 11.6 | −1.9 |
| 81 | Exiguobacterium sp. | 10.9 | −2.6 |
| 804 | Pseudomonas jinjuensis | 10.4 | −3.0 |
| 1217 | Massilia niastensis | 10.4 | −3.0 |
| 914 | Sphingopyxis alaskensis | 10.1 | −3.3 |
| 23 | Exiguobacterium acetylicum | 9.8 | −3.5 |
| 79 | Chitinophaga terrae | 9.7 | −3.6 |
| 412 | Sphingopyxis alaskensis | 9.3 | −4.0 |
| 124 | Delftia lacustris | 8.7 | −4.5 |
| 53 | Pedobacter terrae | 8.6 | −4.6 |
| 130 | Novosphingobium sediminicola | 8.4 | −4.8 |
| 131 | Ensifer adhaerens | 7.4 | −5.7 |
| 31 | Duganella radicis | 7.3 | −5.8 |
| 29 | Rahnella aquatilis | 5.7 | −7.2 |
| 44 | Kosakonia radicincitans | 5.6 | −7.3 |
| 59 | Arthrobacter cupressi | 4.7 | −8.0 |
| 83 | Exiguobacterium acetylicum | 4.7 | −8.0 |
| 91 | Pedobacter terrae | 4.7 | −8.0 |
| 34 | Rhizobium rhizoryzae | 4.7 | −8.1 |
| 132 | Microbacterium oleivorans | 3.0 | −9.5 |
| 2350 | Delftia lacustris | 2.8 | −9.7 |

TABLE 12-continued

| Strain | Species | % IOC UNT | % IOC H2O |
|---|---|---|---|
| 689 | Bosea robiniae | 2.3 | −10.1 |
| 105 | Duganella radicis | 1.9 | −10.5 |
| 46 | Agrobacterium fabrum or Rhizobium pusense (In Taxonomic Flux) (previously Rhizobium sp.) | 1.7 | −10.7 |
| 45 | Chryseobacterium daecheongense | 1.2 | −11.1 |
| UNT | | 0.0 | −12.2 |
| 661 | Rhizobium rhizoryzae | −0.3 | −12.4 |
| 1267 | Bosea eneae | −0.4 | −12.5 |
| 68 | Dyadobacter soli | −1.8 | −13.8 |
| 49 | Achromobacter pulmonis | −5.0 | −16.5 |

Figure 6A:
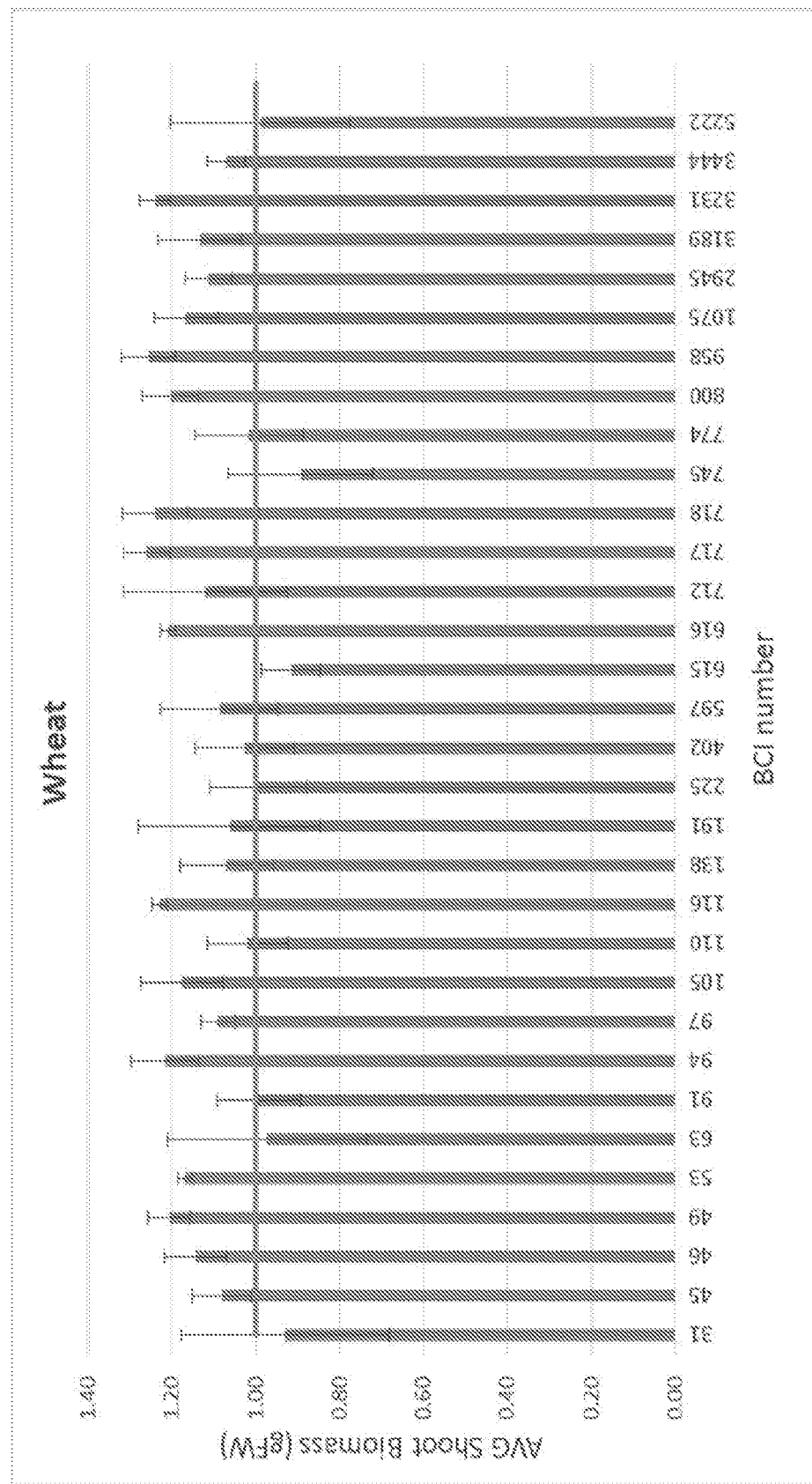
FIG. 6A and FIG. 6B shows a graphic representation of the average wheat shoot (A) and root (B) biomass, in grams of fresh weight, at six days post inoculation (DPI) with individual microbial strains. Seeds were inoculated, placed on wet germination paper and rolled. Rolls were incubated at 25° C. in sealed plastic bins. Each individual strain was tested in triplicates of 30 seeds each. The horizontal red line represents the water control.
Figure 6:
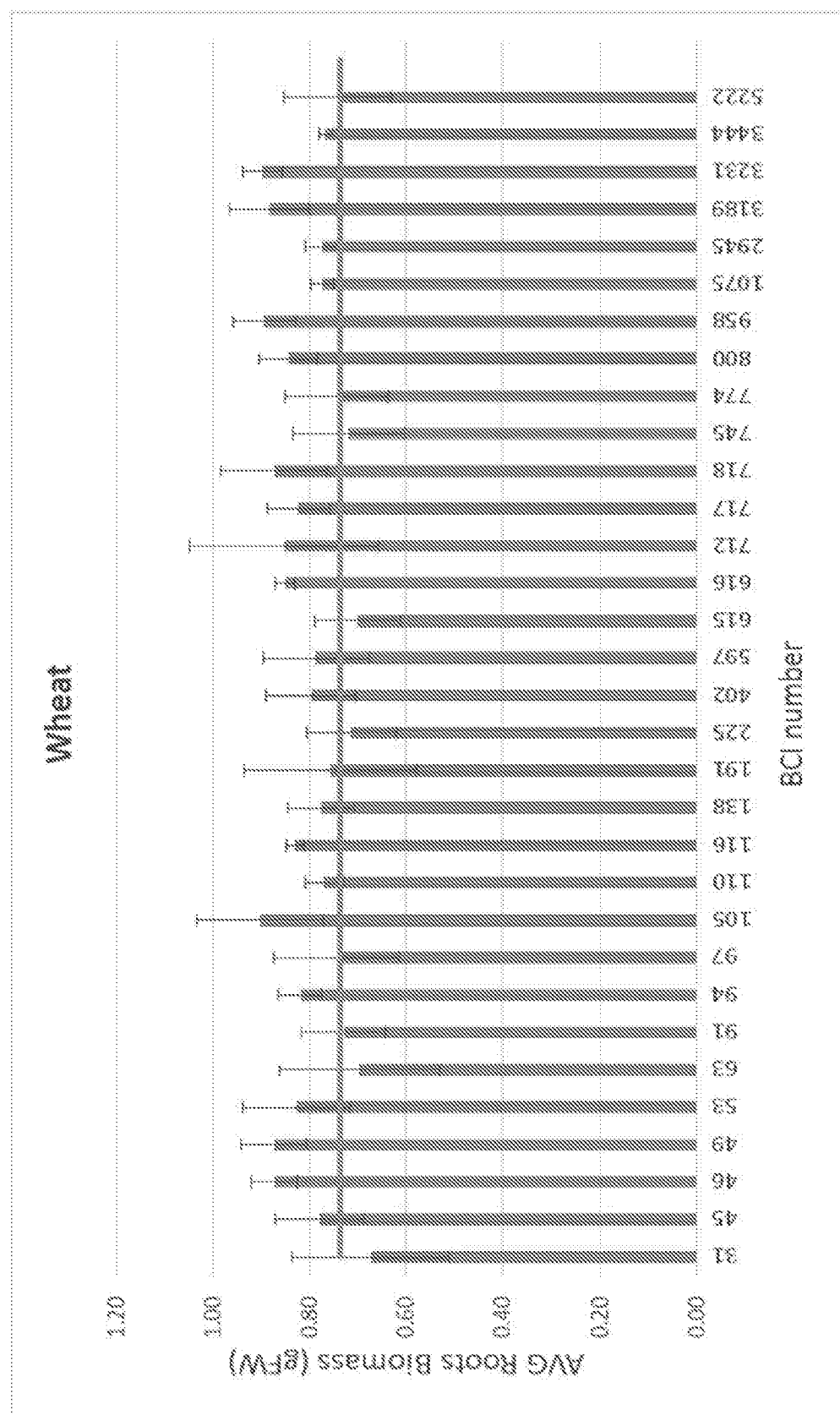

Example 5: Modifying Wheat Seedling Shoot and Root Biomass with Isolated Microbes A. Seed Treatment with Isolated Microbe In this example, wheat seeds were inoculated with individual microbial strains (BCIs), and subjected to a germination test (FIG. 6 A and FIG. 6 B).

The seeds were inoculated, placed on wet germination paper, and rolled. The rolls were then incubated at 25° C. in plastic bins. Each strain in FIG. 6 was tested in triplicate, with 30 seeds per replicate.

Shoot and root biomass was measured at six days post treatment. An uninoculated 'water' control treatment was run and measured simultaneously. The solid line parallel to the x axis and bisecting the bars near the top of the y-axis in each figure represents the average of values for the water-treated control seeds. Some of the inoculated strains revealed relative increases in shoot and/or root biomass at six days post inoculation (DPI) compared to untreated control in vitro.

Table 13 provides a breakout of the shoot and root biomass increase in wheat having been inoculated and treated as described above, relative to a water-only control (H2O). The two columns immediately to the right of the species reflect the percentage increase over control (% IOC). Both increases and decreases in biomass are reflected in the data of table 13. A smaller plant reflects potential for in-field conservation of nutrients and water where these resources may be limited by drought or local conditions, thus decreases are hypothesized to be yield relevant.

The results demonstrated that 16 strains caused a relative increase in shoot biomass of wheat at six days post inoculation (DPI) compared to the water-only controls in vitro. Twelve strains showed greater than a 5% increase over water control, whereas 10 strains showed greater than a 5% decrease in shoot biomass over the water control.

The results demonstrated that 26 strains caused a relative increase in root biomass of wheat at six days post inoculation (DPI) compared to the water-only control in vitro. Eighteen strains showed greater than a 5% increase over control, whereas 2 strains showed greater than a 5% decrease in biomass relative to the water control.

TABLE 13

| BCI Strain # | Crop | Species | Shoot Biomass % IOC Control | Root Biomass % IOC Control |
|---|---|---|---|---|
| 49 | Wheat | Achromobacter pulmonis | 9.03 | 18.55 |
| 46 | Wheat | Agrobacterium fabrum or Rhizobium pusense (In Taxonomic Flux) (previously Rhizobium sp.) | 3.31 | 18.55 |
| 958 | Wheat | Agrobacterium fabrum or Rhizobium pusense (In Taxonomic Flux) (previously Rhizobium sp.) | 13.55 | 21.26 |
| 5222 | Wheat | Agrobacterium fabrum or Rhizobium pusense (In Taxonomic Flux) (previously Rhizobium sp.) | −10.54 | 0.90 |
| 717 | Wheat | Arthrobacter nicotinovorans | 13.85 | 11.76 |
| 3189 | Wheat | Arthrobacter nicotinovorans | 2.41 | 19.90 |
| 3444 | Wheat | Arthrobacter nicotinovorans | −3.32 | 4.07 |
| 45 | Wheat | Chryseobacterium doecheongense | −2.41 | 5.88 |
| 191 | Wheat | Chryseobacterium doecheongense | −3.92 | 2.71 |
| 774 | Wheat | Chryseobacterium doecheongense | −8.14 | 0.90 |
| 597 | Wheat | Chryseobacterium rhizosphaerae | −1.81 | 6.78 |
| 615 | Wheat | Chryseobacterium rhizosphaerae | −17.17 | −4.98 |
| 1075 | Wheat | Chryseobacterium rhizosphaerae | 5.42 | 4.97 |
| 402 | Wheat | Frigidibacter albus or Defulviimonas dentrificans (In Taxonomic Flux) | −7.23 | 8.14 |
| 745 | Wheat | Frigidibacter albus or Defulviimonas dentrificans (In Taxonomic Flux) | −19.28 | −2.27 |
| 31 | Wheat | Duganella radicis | −15.97 | −8.60 |
| 105 | Wheat | Duganella radicis | 6.32 | 22.62 |
| 63 | Wheat | Exiguobacterium antarcticum | −6.03 | −5.43 |
| 718 | Wheat | Exiguobacterium sibircum or antarcticum | 12.04 | 18.55 |
| 116 | Wheat | Exiguobacterium sibiricum | 11.14 | 12.66 |
| 225 | Wheat | Exiguobacterium soli | −10.24 | −3.17 |
| 712 | Wheat | Frigidibacter albus | 1.20 | 15.83 |
| 3231 | Wheat | Massilia kyonggiensis | 12.04 | 21.71 |
| 94 | Wheat | Massilia kyonggiensis | 9.94 | 11.31 |
| 97 | Wheat | Massilia kyonggiensis | −1.51 | 0.90 |
| 138 | Wheat | Novosphingobium sediminicola | −3.32 | 5.43 |
| 53 | Wheat | Pedobacter terrae | 5.72 | 12.21 |
| 91 | Wheat | Pedobacter terrae | −10.24 | −0.91 |
| 110 | Wheat | Pedobacter terrae | −7.83 | 4.52 |
| 616 | Wheat | Pseudomonas helmanticensis | 9.33 | 15.38 |
| 800 | Wheat | Pseudomonas helmanticensis | 8.73 | 14.47 |
| 2945 | Wheat | Pseudomonas helmanticensis | 0.60 | 4.97 |

Figure 7A:
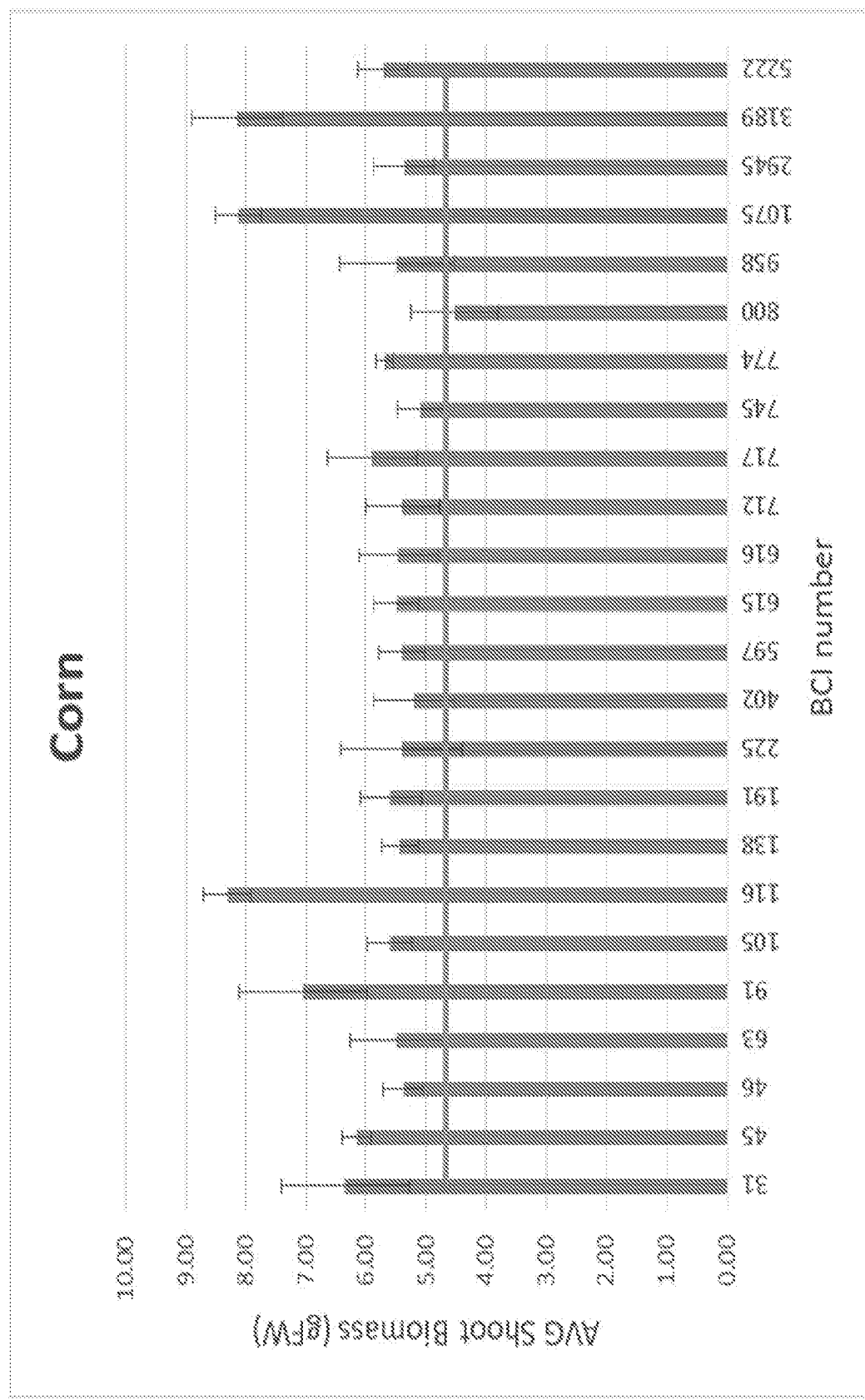
FIG. 7A and FIG. 7B shows a graphic representation of average corn shoot biomass, in grams of fresh weight, at six days post inoculation (DPI) with individual microbial strains. Seeds were inoculated, placed on wet germination paper and rolled. Rolls were incubated at 25° C. in sealed plastic bins. Each individual strain was tested in triplicates of 30 seeds each. Due to the amount of samples tested, rolls were placed in two independent bins with a respective water control, represented individually in FIG. 7 by graphs A and B. The horizontal red line represents the water control.
Figure 7B:
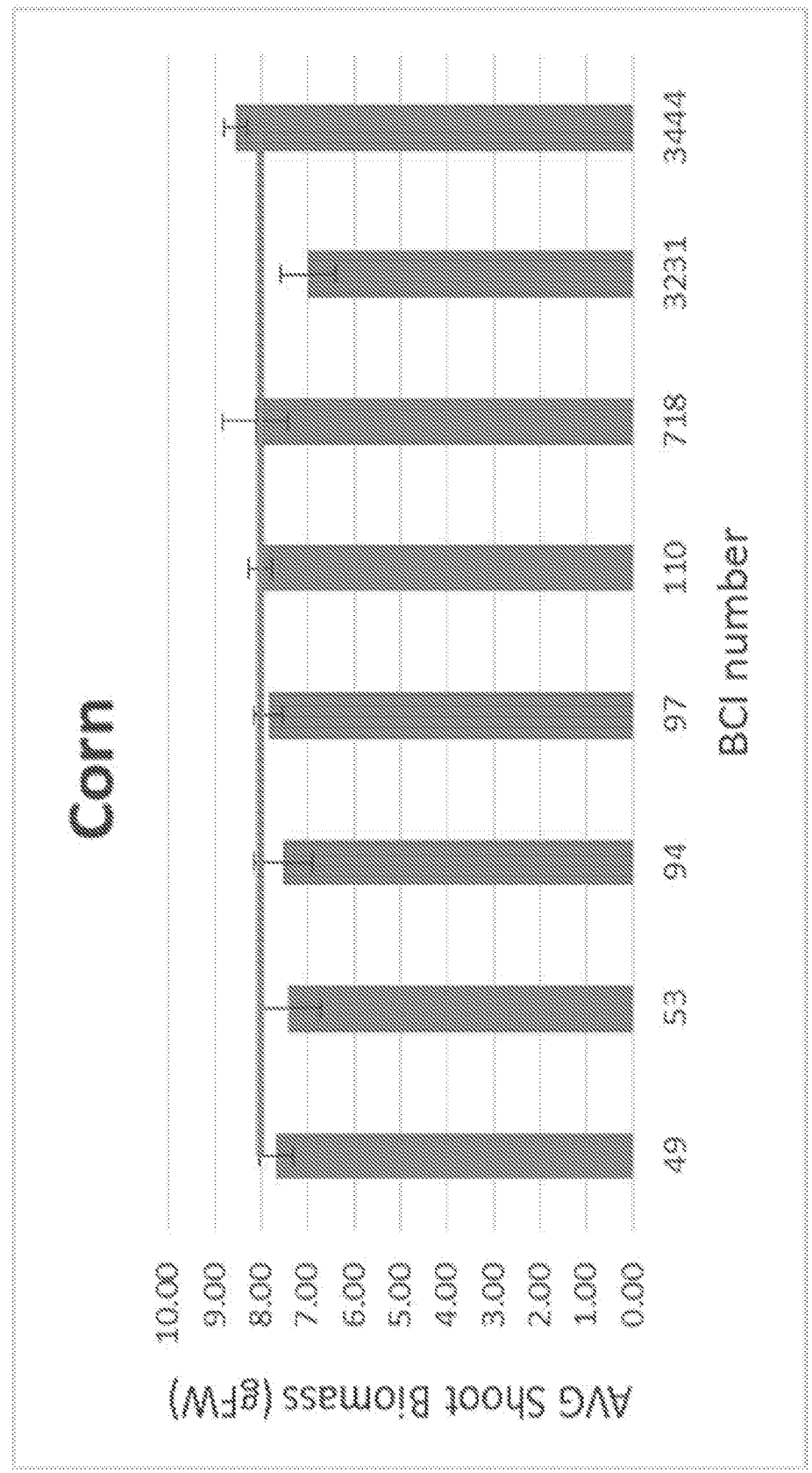
Figure 8A:
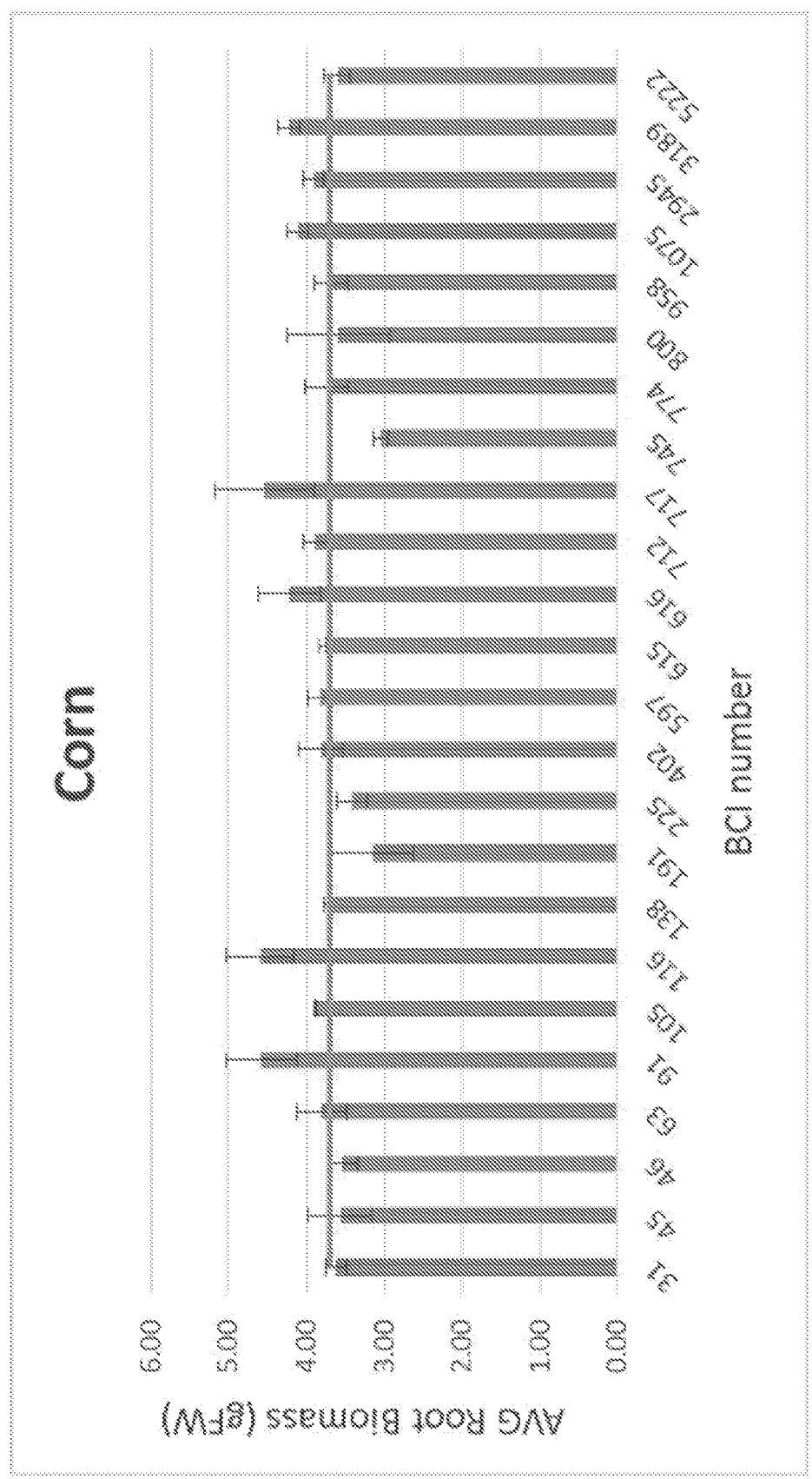
FIG. 8A and FIG. 8B shows a graphic representation of average corn root biomass, in grams of fresh weight, at six days post inoculation (DPI) with individual microbial strains. Seeds were inoculated, placed on wet germination paper and rolled. Rolls were incubated at 25° C. in sealed plastic bins. Each individual strain was tested in triplicates of 30 seeds each. Due to the amount of samples tested, rolls were placed in two independent bins with a respective water control, represented individually in FIG. 8 by graphs A and B. The horizontal red line represents the water control.
Figure 8:
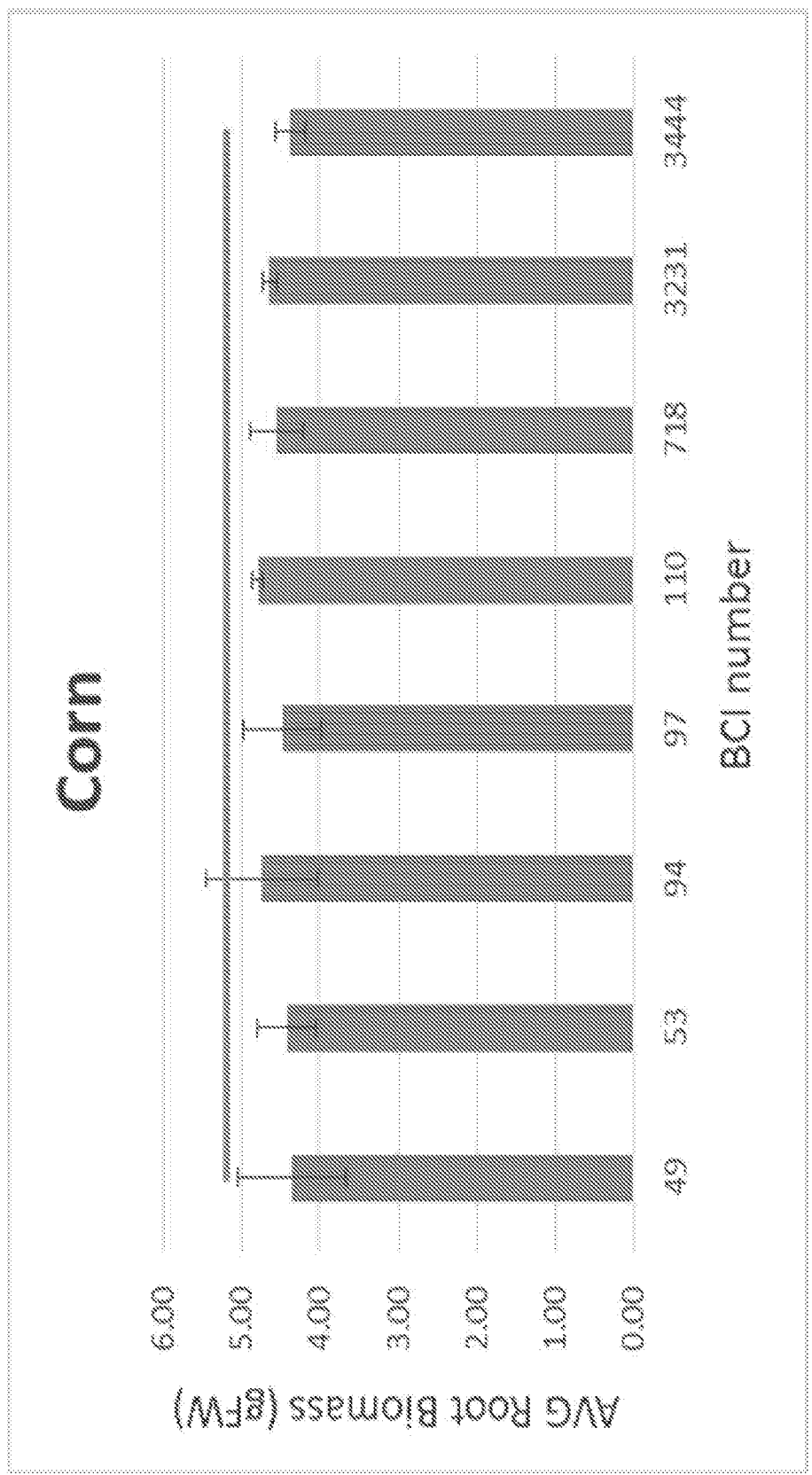

Example 6: Modifying Corn Seedling Shoot and Root Biomass with Isolated Microbes A. Seed Treatment with Isolated Microbe In this example, corn seeds were inoculated with individual microbial strains (BCIs), and subjected to a germination test (FIGS. 7 A, 7 B, 8 A and 8 B).

The seeds were inoculated, placed on wet germination paper, and rolled. The rolls were then incubated at 25° C. in plastic bins. Each strain appearing in FIGS. 7 A, 7 B, 8 A and 8 B was tested in triplicates, with 30 seeds per replicate test. Due to the amount of samples tested, rolls were placed in two independent bins with a respective water control, represented individually in FIGS. 7 A, 7 B, 8 A and 8 B.

Shoot and root biomass was measured at six days post treatment. An uninoculated 'water' control treatment was run and measured simultaneously. The solid line parallel to the x axis and bisecting the bars near the top of the y-axis in each figure represents the average of values for the water-treated control seeds. Some of the inoculated strains revealed relative increases in shoot and/or root biomass at six days post inoculation (DPI) compared to untreated control in vitro.

Table 14 provides a breakout of the shoot and root biomass changes in corn having been inoculated and treated as described above, relative to a water-only control (H2O). The two columns immediately to the right of the species reflect the percentage increase over control (% IOC). Both increases and decreases in the biomasses are reflected in the data of table 14. A smaller plant reflects potential for in-field conservation of nutrients and water where these resources may be limited by drought or local conditions, thus decreases are hypothesized to be yield relevant.

The results demonstrated that 25 strains caused a relative increase in shoot biomass of corn at six days post inoculation (DPI) compared to the water-only control in vitro. Twenty-two strains showed greater than a 10% increase, whereas 7 strains caused a decrease in biomass relative the water control.

The results demonstrated that 15 strains caused a relative increase in root biomass of corn at six days post inoculation (DPI) compared to the water-only control in vitro. Eight strains showed greater than a 5% increase over water control, whereas 11 strains showed greater than a 5% decrease in root biomass over the water control.

Results demonstrated that a number of strains isolated from superior plants caused a significant increase over the water control in root and/or shoot biomass ($p<0.05$ Dunnett's Multiple Comparisons Test). Statistically significant results are labeled with an asterisk. In one embodiment, superior plants are defined as a subset of individual plants observed in an AMS process to exhibit a phenotype of interest that is improved relative to the plurality of plants screened in the same assay. Phenotypes of interest may be screened in the absence or presence of biotic or abiotic stress and include early vigor, as manifested by improved germination rate, foliar and or root biomass; chlorophyll content; leaf canopy temperature; and water use efficiency.

TABLE 14

| BCI Strain # | Crop | Species | Shoot Biomass % IOC Control | Root Biomass % IOC Control |
|---|---|---|---|---|
| 49 | Corn | Achromobacter pulmonis | −4.28 | −16.12 |
| 46 | Corn | Agrobacterium fabrum or Rhizobium pusense (In Taxonomic Flux) (previously Rhizobium sp.) | 15.10 | −4.41 |
| 958 | Corn | Agrobacterium fabrum or Rhizobium pusense (In Taxonomic Flux) (previously Rhizobium sp.) | 17.31 | −0.63 |
| 5222 | Corn | Agrobacterium fabrum or Rhizobium pusense (In Taxonomic Flux) (previously Rhizobium sp.) | 22.22 | −2.52 |
| 717 | Corn | Arthrobacter nicotinovorans | 26.21 | 22.61* |
| 3189 | Corn | Arthrobacter nicotinovorans | 74.15* | 14.05 |
| 3444 | Corn | Arthrobacter nicotinovorans | 6.48 | −15.54 |
| 45 | Corn | Chryseobacterium doecheongense | 31.48 | −3.60 |
| 191 | Corn | Chryseobacterium doecheongense | 19.44 | −14.86 |
| 774 | Corn | Chryseobacterium doecheongense | 21.58 | 1.17 |
| 597 | Corn | Chryseobacterium rhizosphaerae | 15.53 | 3.15 |
| 615 | Corn | Chryseobacterium rhizosphaerae | 17.52 | 1.89 |
| 1075 | Corn | Chryseobacterium rhizosphaerae | 73.79* | 11.26 |
| 402 | Corn | Frigidibacter albus or Defluviimonas denitrificans (In Taxonomic Flux) | 11.25 | 2.976 |
| 745 | Corn | Frigidibacter albus or Defluviimonas denitrificans (In Taxonomic Flux) | 8.76 | −17.75 |
| 31 | Corn | Duganella radicis | 35.68* | −2.07 |
| 105 | Corn | Duganella radicis | 19.73 | 5.05 |
| 63 | Corn | Exiguobacterium antarcticum | 17.17 | 2.61 |

TABLE 14-continued

| BCI Strain # | Crop | Species | Shoot Bio-mass % IOC Control | Root Bio-mass % IOC Control |
|---|---|---|---|---|
| 718 | Corn | Exiguobacterium sibircum or antarcticum | 1.29 | −12.27 |
| 116 | Corn | Exiguobacterium sibiricum | 77.56* | 24.05* |
| 225 | Corn | Exiguobacterium soli | 15.67 | −7.75 |
| 138 | Corn | Exiguobacterium sp. | 16.31 | 0.81 |
| 712 | Corn | Frigidibacter albus | 15.24 | 4.77 |
| 3231 | Corn | Massilia kyonggiensis | −12.84 | −10.53 |
| 94 | Corn | Massilia kyonggiensis | −6.44 | −8.54 |
| 97 | Corn | Massilia kyonggiensis | −2.29 | −13.74 |
| 53 | Corn | Pedobacter terrae | −7.90 | −14.58 |
| 91 | Corn | Pedobacter terrae | 50.64* | 23.87* |
| 110 | Corn | Pedobacter terrae | −0.17 | −7.64 |
| 616 | Corn | Pseudomonas helmanticensis | 16.67 | 14.05 |
| 800 | Corn | Pseudomonas helmanticensis | −3.21 | −2.88 |
| 2945 | Corn | Pseudomonas helmanticensis | 14.60 | 5.58 |

*Statistically significant results

Example 7: Increasing Root and Shoot Length of Maize, Wheat, and Tomato with Isolated Microbes A. Seed Treatment with Isolated Microbe In this example, seeds of maize, wheat, and tomato were inoculated with individual microbial strains (BDNZ strains), and allowed to germinate.

The seeds were inoculated, placed on wet paper towels and rolled. The rolls were then incubated at 25° C. in sealed plastic bags. Each strain appearing in table 15 was tested in germination tests in duplicate, with 30 seeds per replicate test for wheat and maize and 50 seeds for tomato.

Root length and shoot length (RL and SL) were measured at four days post treatment. Some of the inoculated strains revealed relative increases in root and/or shoot length at four days point inoculation (DPI) compared to untreated control.

Figure 9:
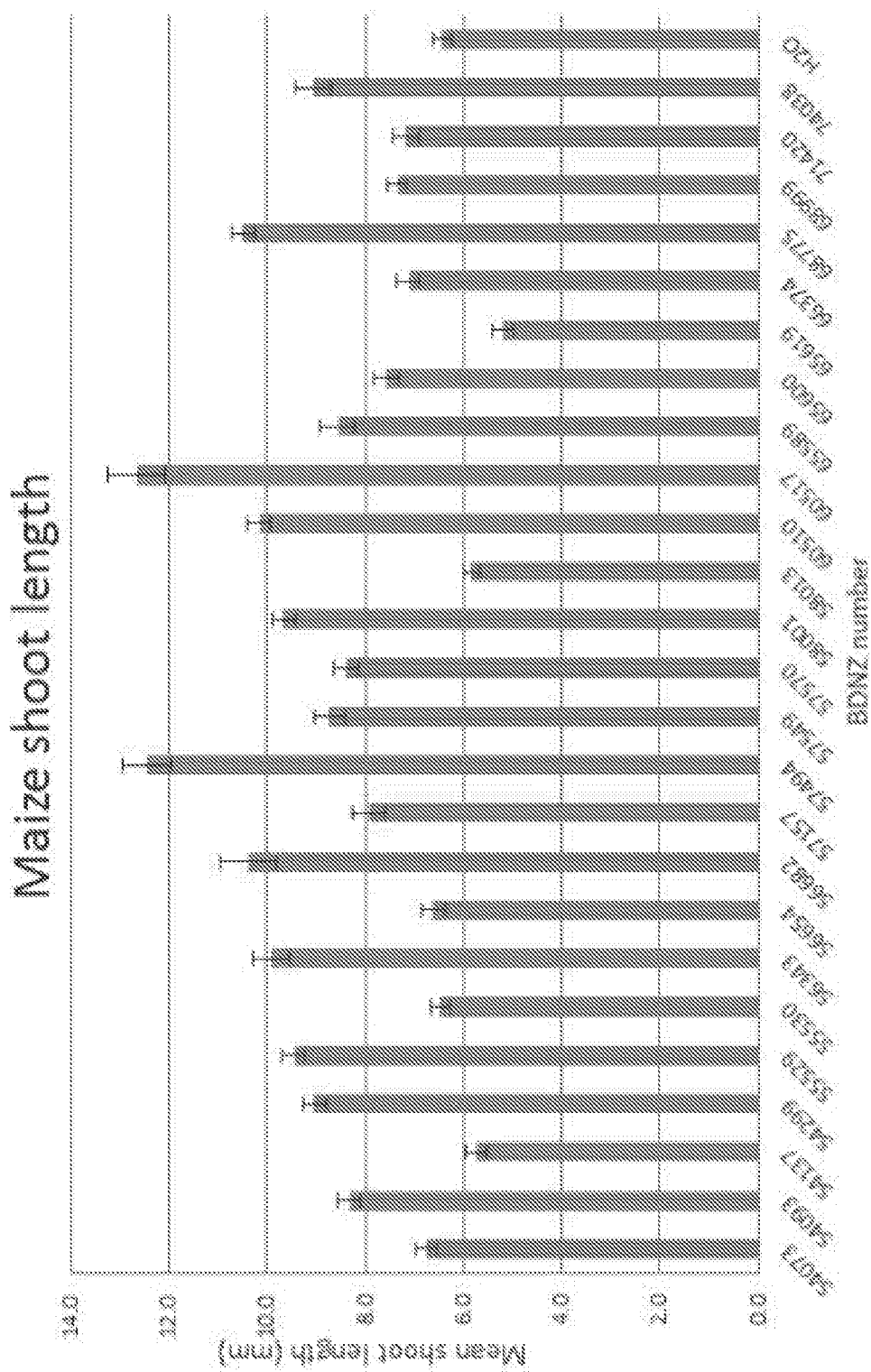
FIG. 9 shows a graphic representation of the average shoot length, in millimeters, of maize at 4 days post treatment with individual microbial strains. Maize seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 30 seeds each. Shoot length was measured at 4 days post inoculation (DPI). Standard error bars are shown. Results show that while germination rates were good for all strains tested, some strains caused a relative increase in shoot length at 4 days post inoculation (DPI) compared to the water control in vivo.
Figure 10:
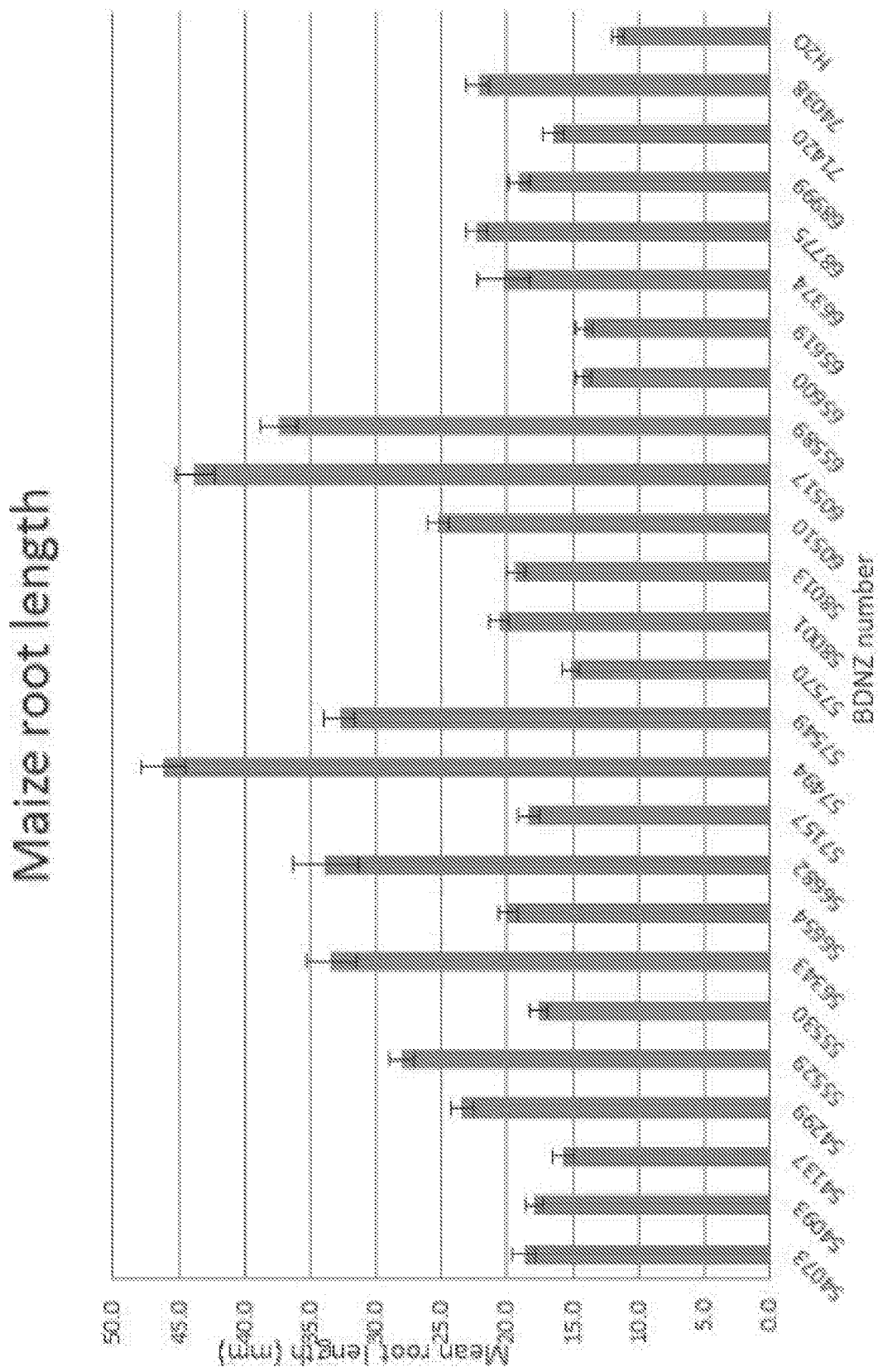
FIG. 10 shows a graphic representation of the average root length, in millimeters, of maize at 4 days post treatment with individual microbial strains. Maize seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 30 seeds each. Root length was measured at 4 days post inoculation (DPI). Standard error bars are shown. Results show that while germination rates were good for all strains tested, some strains caused a relative increase in root length at 4 days post inoculation (DPI) compared to the water control in vivo.

Each strain applied to maize seed was tested in duplicates of 30 seeds each. Results show that while germination rates were good for all strains tested, some strains caused a relative increase in root and/or shoot length at 4 days post inoculation (DPI) compared to the water control in vitro (See FIGS. 9 and 10).

Figure 11:
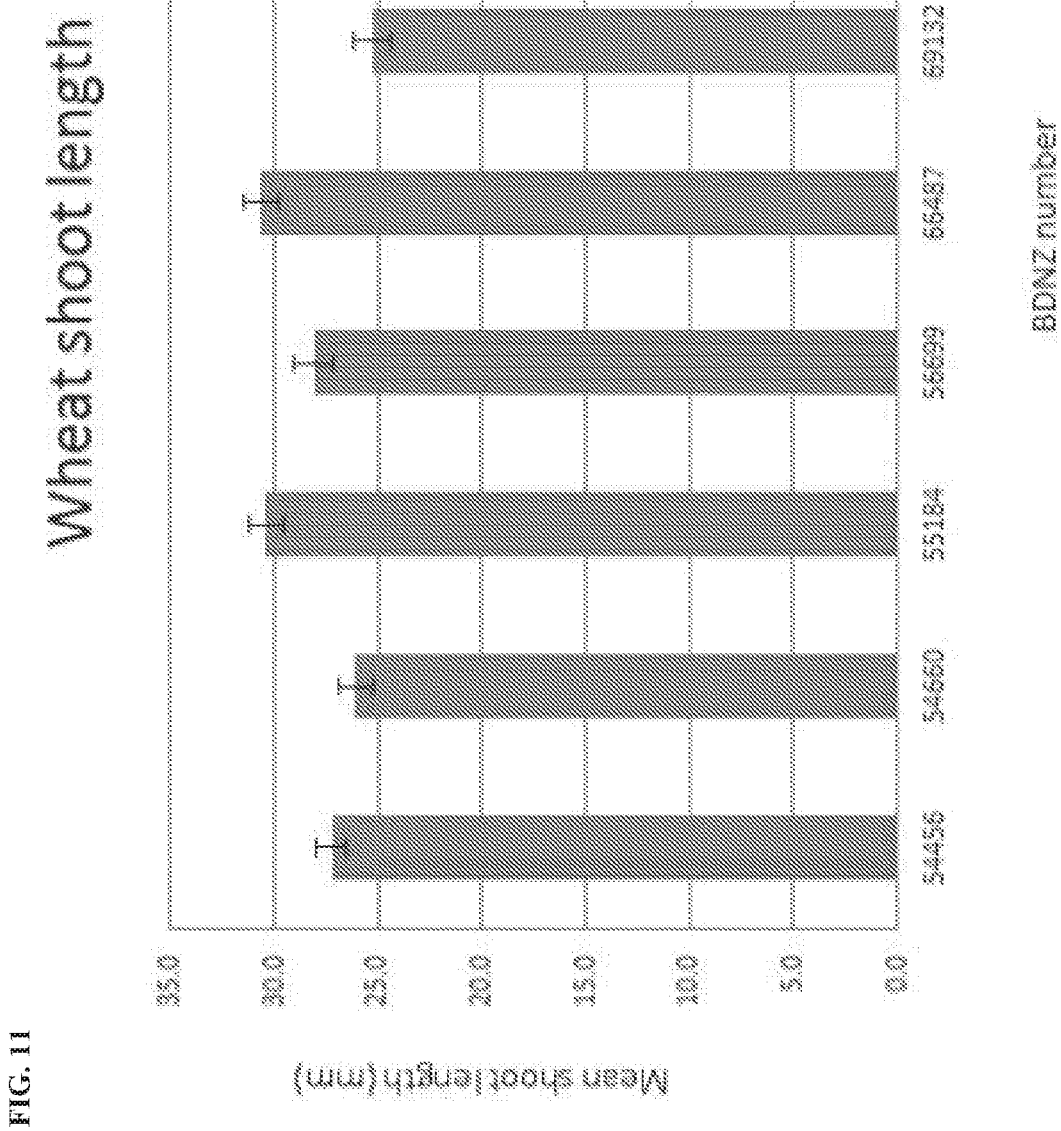
FIG. 11 shows a graphic representation of the average shoot length, in millimeters, of wheat at 4 days post treatment with individual microbial strains. Wheat seeds were inoculated with individual microbial strains (BDNZ numbers) and subjected to a germination test. Seed were inoculated, placed on wet paper towels and rolled. Rolls were incubated in sealed plastic bags at 25° C. Each individual strain was tested in duplicates of 30 seeds each. Shoot length was measured at 4 days post treatment. Results show that germination rates were good for all strains tested (>90%) and some strains caused a relative increase in shoot length at 4 days post inoculation (DPI) compared to the water control in vitro.
Figure 12:
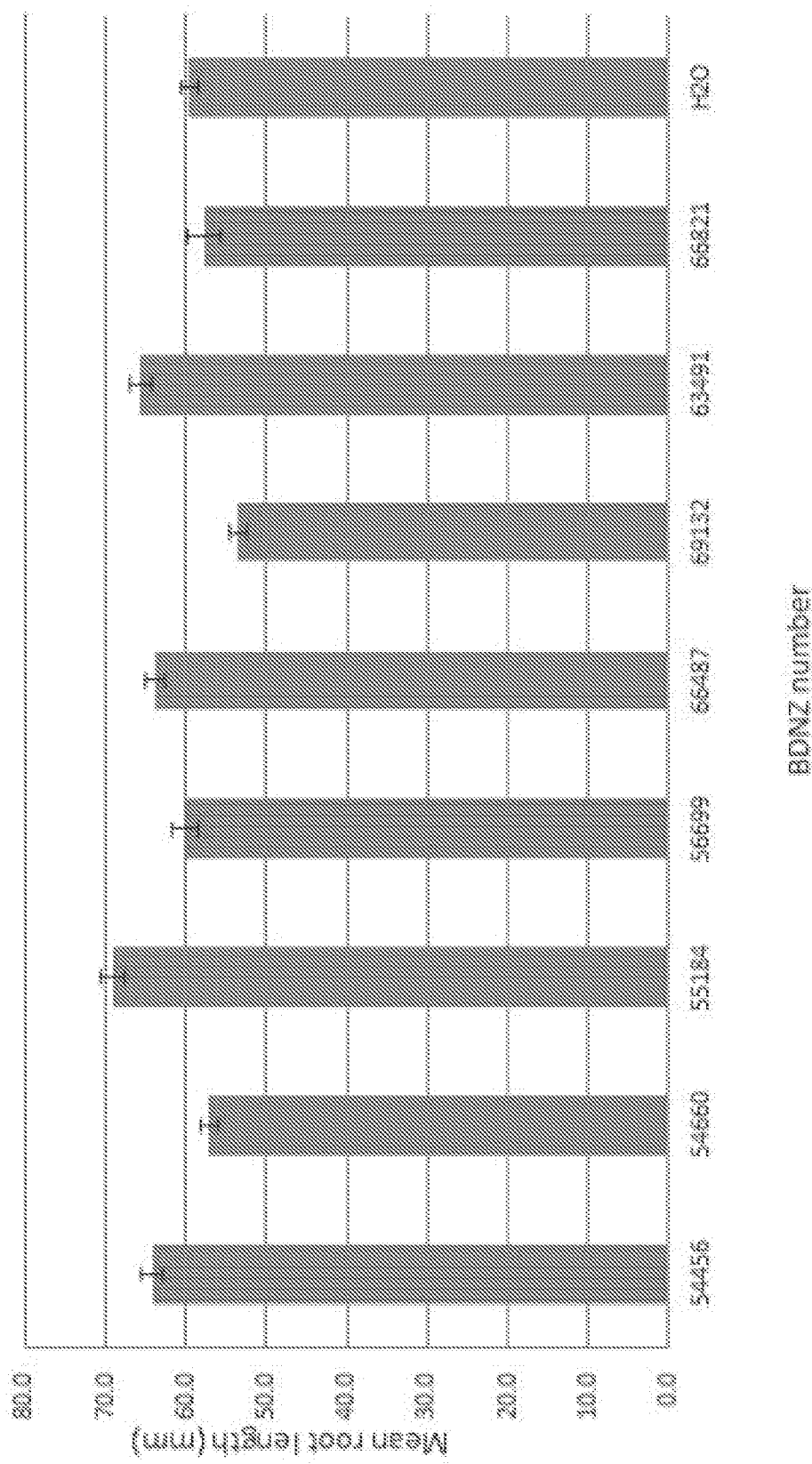
FIG. 12 shows a graphic representation of the average root length, in millimeters, of wheat at 4 days post treatment with individual microbial strains. Wheat seeds were inoculated with individual microbial strains (BDNZ numbers) and subjected to a germination test. Seed were inoculated, placed on wet paper towels and rolled. Rolls were incubated in sealed plastic bags at 25° C. Each individual strain was tested in duplicates of 30 seeds each. Root length was measured at 4 days post treatment. Results show that germination rates were good for all strains tested (>90%) and some strains caused a relative increase in root length at 4 days post inoculation (DPI) compared to the water control in vitro.

Each strain applied to wheat seed was tested in duplicates of 30 seeds each. Root and shoot length were measured at 4 days post treatment. Results show that germination rates were good for all strains tested (>90%), and some strains caused a relative increase in root and/or shoot length at 4 days post inoculation (DPI) compared to the water control in vitro (See FIGS. 11 and 12).

Figure 13:
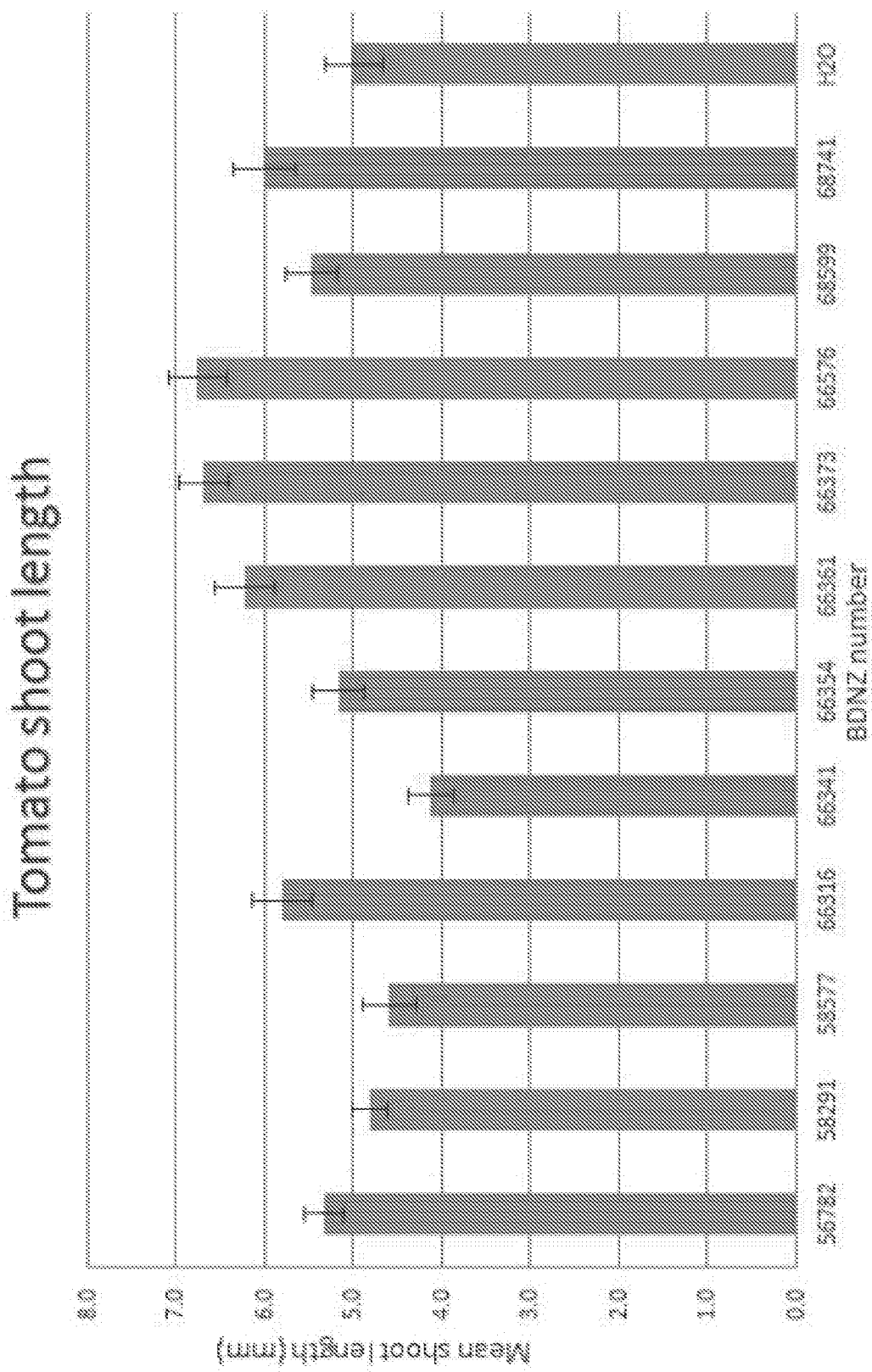
FIG. 13 shows a graphic representation of the average shoot length, in millimeters, of tomato at 4 days post treatment with individual microbial strains. Tomato seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 50 seeds each. Shoot length was measured at 4 days post treatment. The mean length of shoots of the water control seed can be seen in the far right bar labelled "H2O". Results show that germination rates were good for all strains tested and some strains caused a relative increase in shoot length at 4 days post inoculation (DPI) compared to the water control in vitro.
Figure 14:
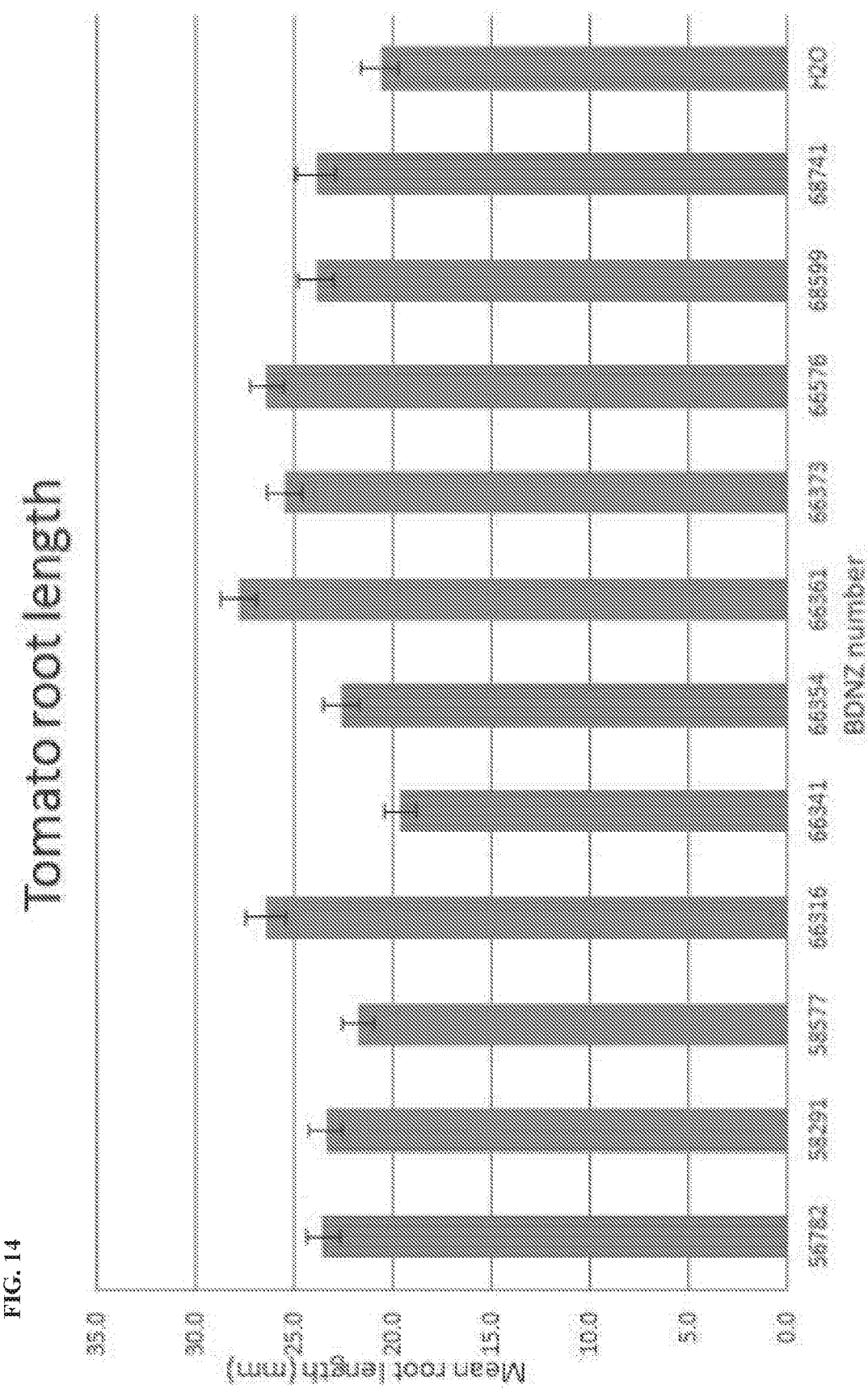
FIG. 14 shows a graphic representation of the average root length, in millimeters, of tomato at 4 days post treatment with individual microbial strains. Tomato seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 50 seeds each. Root length was measured at 4 days post treatment. The mean length of roots of the water control seed can be seen in the far right bar labelled "H2O". Results show that germination rates were good for all strains tested and some strains caused a relative increase in root length at 4 days post inoculation (DPI) compared to the water control in vitro.

Each strain applied to tomato seed was tested in duplicates of 50 seeds each. Root and shoot length were measured at 4 days post inoculation (DPI). Results show that germination rates were good for all strains tested, and some strains caused a relative increase in root and/or shoot length at 4 days post inoculation (DPI) compared to the water control in vitro (See FIGS. 13 and 14).

Table 15 provides a breakout of the root and shoot length increase (in mm) after inoculation and treatment as described above, relative to a water-only control (H2O). The columns immediately to the right of the species reflect the percentage increase over control (% IOC) for the water-only control. Both increases and decreases are reflected in the data. A smaller plant reflects potential for in-field conservation of nutrients and water where these resources may be limited by drought or local conditions, thus decreases are hypothesized to be yield relevant.

The results demonstrated that a number of strains isolated from superior plants caused a significant increase over the water control in root and/or shoot length (p<0.1, Fisher's LSD) at four days post inoculation (DPI). Twenty strains isolated from superior plants caused a significant increase over the water control in maize root length and 19 caused a significant increase in maize shoot length. Four strains caused a significant increase over control in root and shoot length of wheat. Four strains caused a significant increase over control in root and shoot length of tomato.

TABLE 15

| BDNZ Strain # | Crop | Species | % IOC RL | % IOC SL |
|---|---|---|---|---|
| 54073 | Maize | Stenotrophomonas maltophilia | 61.8 | 5 |
| 54093 | Maize | Rhodococcus erythropolis | 54.6 | 29.7 |
| 54137 | Maize | Pantoea agglomerans | 36.1 | −10.5 |
| 54299 | Maize | Rhodococcus erythropolis | 102.7 | 40.7 |
| 55529 | Maize | Pantoea agglomerans | 142.4 | 47.3 |
| 55530 | Maize | Pseudomonas oryzihabitans | 52.3 | 0.6 |
| 56343 | Maize | Chitinophaga arvensicola | 188.6 | 54.3 |
| 56654 | Maize | Paenibacillus chondroitinus | 72.1 | 3.1 |
| 56682 | Maize | Paenibacillus chondroitinus | 192.5 | 61.8 |
| 57157 | Maize | Rahnella aquatilis | 58.5 | 23.2 |
| 57494 | Maize | Bosea minatitlanensis | 298.9 | 93.8 |
| 57549 | Maize | Luteibacter yeojuensis | 183 | 35.9 |
| 57570 | Maize | Caulobacter henricii | 30.5 | 30.6 |
| 58001 | Maize | Stenotrophomonas maltophilia | 78 | 50.5 |
| 58013 | Maize | Rahnella aquatilis | 67 | −9 |
| 60510 | Maize | Dyella ginsengisoli | 118 | 58.2 |
| 60517 | Maize | Frateuria sp. | 278.5 | 96.9 |
| 65589 | Maize | Novosphingobium rosa | 223 | 33.2 |
| 65600 | Maize | Herbaspirillum huttiense | 23 | 18 |
| 65619 | Maize | Novosphingobium rosa | 22.4 | −19.3 |
| 66374 | Maize | Albidiferax sp. | 75.3 | 10.9 |
| 68775 | Maize | Rhodoferax ferrireducens | 93 | 63.1 |
| 68999 | Maize | Chitinophaga arvensicola | 65.4 | 14.5 |
| 71420 | Maize | Luteibacter yeojuensis | 42.3 | 11.6 |
| 74038 | Maize | Pseudomonas oryzihabitans | 92.2 | 40.7 |
| 54456 | Wheat | Janthinobacterium sp. | 7.7 | 0.5 |
| 54660 | Wheat | Paenibacillus amylolyticus | −4 | −3.9 |
| 55184 | Wheat | Massilia niastensis | 16.1 | 12.2 |
| 56699 | Wheat | Massilia niastensis | 0.8 | 3.6 |
| 66487 | Wheat | Flavobacterium saccharophilum | 7.2 | 13 |
| 69132 | Wheat | Flavobacterium glaciei | −10.2 | −6.8 |
| 63491 | Wheat | Janthinobacterium sp. | 10.2 | 13.9 |
| 66821 | Wheat | Polaromonas ginsengisoli | −3.1 | 11.1 |
| 56782 | Tomato | Sphingobium quisquiliarum | 14.1 | 7 |
| 58291 | Tomato | Duganella violaceinigra | 13.4 | −3.5 |
| 58577 | Tomato | Ramlibacter sp. | 5.6 | −8 |
| 66316 | Tomato | Paenibacillus amylolyticus | 28.1 | 16.2 |
| 66341 | Tomato | Caulobacter henricii | −4.8 | −17.4 |
| 66354 | Tomato | Bosea minatitlanensis | 9.4 | 3.4 |
| 66361 | Tomato | Duganella violaceinigra | 34.9 | 24.6 |
| 66373 | Tomato | Polaromonas ginsengisoli | 23.5 | 34 |
| 66576 | Tomato | Sphingobium quisquiliarum | 28.1 | 35.4 |
| 68599 | Tomato | Stenotrophomonas terrae | 15.9 | 9.6 |
| 68741 | Tomato | Stenotrophomonas terrae | 15.8 | 20.3 |

In table 15, the root and shoot length were assessed to evaluate the effect of the microbe treatments on early plant development. Both increases and decreases in biomass have been noted to reflect the possibility that decreases are hypothesized to be yield relevant; for example a smaller plant reflects potential for in-field conservation of nutrients and water where these may be limited by drought or local conditions. Results show that of all strains tested, some 40 strains caused a relative increase in root length at 4 days post inoculation (DPI) and 35 strains caused a relative increase in shoot length compared to water controls in vitro. Four tomato strains, three wheat strains and 17 maize strains caused a significant increase in both shoot length and root length (p<0.1, Fishers least squared difference).

Example 8: Modifying Root and Shoot Length of Corn with Isolated Microbes

A. Seed Treatment with Isolated Microbe

In this example, corn seeds were inoculated with individual microbial strains and allowed to germinate (FIGS. 15A, 15B, 16A and 16B).

The seeds were inoculated, placed on wet germination paper, and rolled. The rolls were then incubated at 25° C. in plastic bins. Each strain appearing in FIGS. 15 and 16 was tested in germination tests in triplicates, with 30 seeds per replicate. Due to the amount of samples tested, rolls were placed in two independent bins with a respective water control, represented individually in FIGS. 15 and 16 by graphs A and B.

Figure 15A:
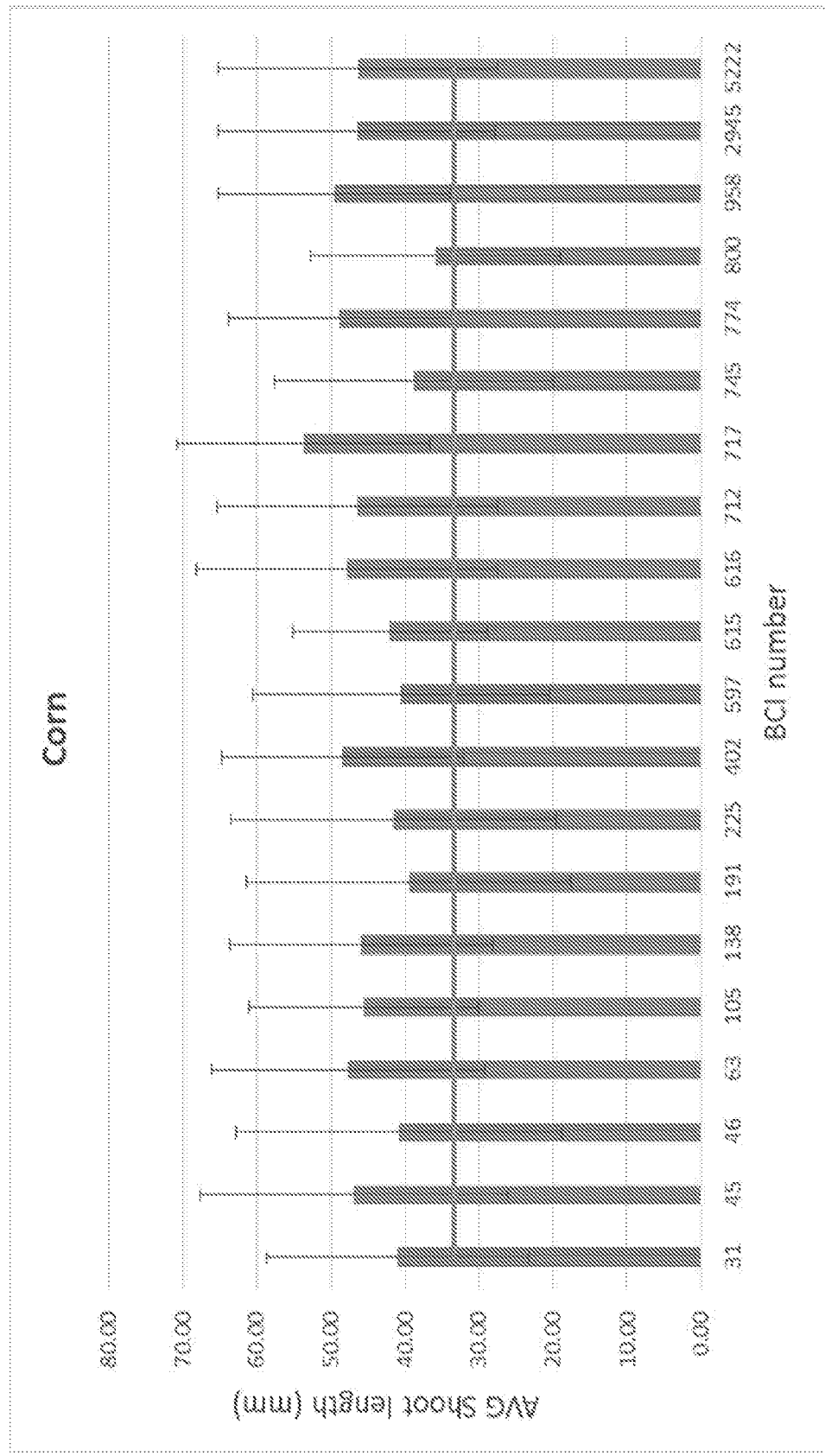
FIG. 15A and FIG. 15B shows a graphic representation of average corn shoot length, in millimeters, at six days post inoculation (DPI) with individual microbial strains. Seeds were inoculated, placed on wet germination paper and rolled. Rolls were incubated at 25° C. in sealed plastic bins. Each individual strain was tested in triplicates of 30 seeds each. Due to the amount of samples tested, rolls were placed in two independent bins with a respective water control, represented individually in FIG. 15 by graphs A and B. The horizontal red line represents the water control.
Figure 15:
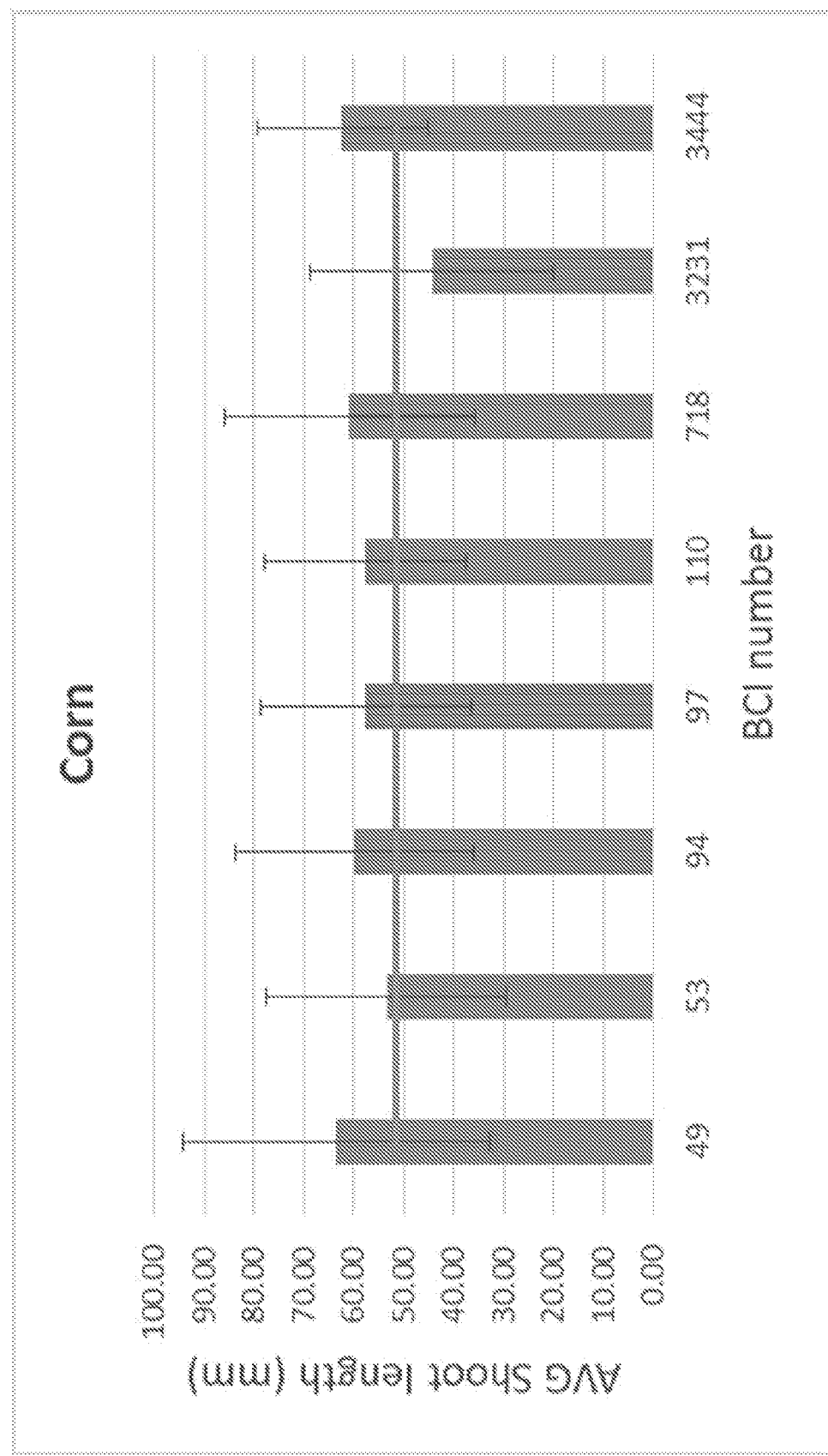
Figure 16A:
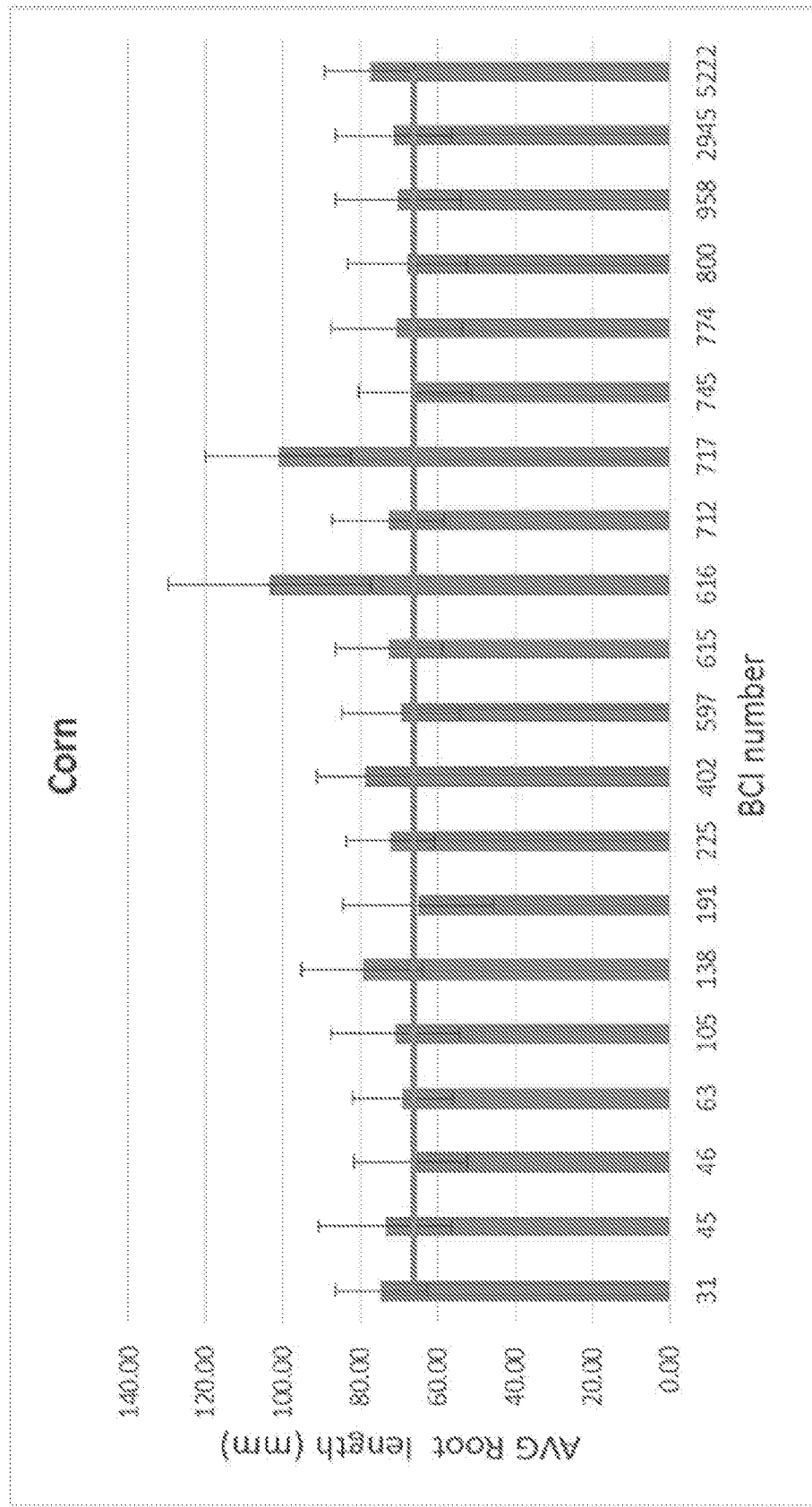
FIG. 16A and FIG. 16 B shows a graphic representation of average corn root length, in millimeters, at six days post inoculation (DPI) with individual microbial strains. Seeds were inoculated, placed on wet germination paper and rolled. Rolls were incubated at 25° C. in sealed plastic bins. Each individual strain was tested in triplicates of 30 seeds each. Due to the amount of samples tested, rolls were placed in two independent bins with a respective water control, represented individually in FIG. 16 by graphs A and B. The horizontal red line represents the water control.
Figure 16:
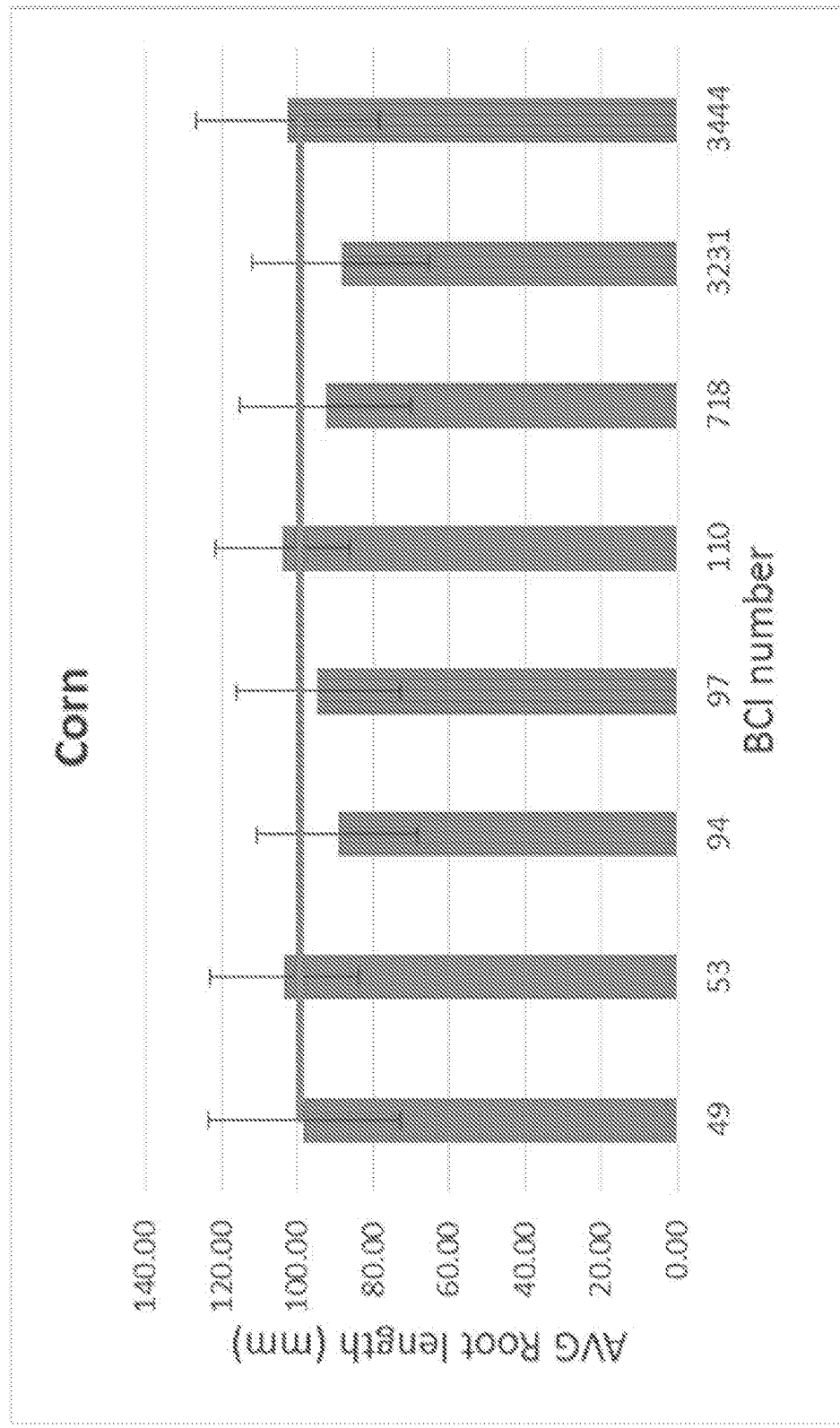

Root length and shoot length (RL and SL) were measured at six days post treatment. A control treatment was included comprising seeds treated with water in the absence of a microbial inoculant of the present disclosure. Some of the inoculated strains revealed relative increases in root and/or shoot length at six days point inoculation (DPI) compared to untreated control (FIGS. 15 and 16).

Table 16 provides a breakout of the root and shoot length increase (in mm) after inoculation and treatment as described above, relative to a water-only control (H2O). The columns immediately to the right of the species reflect the percentage increase over control (% IOC). Both increases and decreases are reflected in the data. A smaller plant reflects potential for in-field conservation of nutrients and water where these resources may be limited by drought or local conditions, thus decreases are hypothesized to be yield relevant.

Results demonstrated that a number of strains listed in Table 16 which were originally isolated from superior plants caused a significant increase, over the water-only control, in root and/or shoot length (p<0.05, Fisher's LSD) at six days post inoculation (DPI). Statistically significant results are labeled with an asterisk. Ten strains isolated from superior plants caused a significant increase over the water control in corn shoot length and 5 caused a significant increase in corn root length.

TABLE 16

| Strain | Crop | Species | % IOC SL | % IOC RL |
|---|---|---|---|---|
| 49 | Corn | Achromobacter pulmonis | 23.30 | −0.84 |
| 46 | Corn | Agrobacterium fabrum or Rhizobium pusense (In Taxonomic Flux) (previously Rhizobium sp.) | 21.79 | 1.56 |
| 958 | Corn | Agrobacterium fabrum or Rhizobium pusense (In Taxonomic Flux) (previously Rhizobium sp.) | 47.76* | 6.25 |
| 5222 | Corn | Agrobacterium fabrum or Rhizobium pusense (In Taxonomic Flux) (previously Rhizobium sp.) | 38.31* | 17.55* |
| 717 | Corn | Arthrobacter nicotinovorans | 60.20* | 53.32* |
| 3189 | Corn | Arthrobacter nicotinovorans | N/A | N/A |
| 3444 | Corn | Arthrobacter nicotinovorans | 21.04 | 3.36 |
| 45 | Corn | Chryseobacterium daecheongense | 39.99* | 11.43 |
| 191 | Corn | Chryseobacterium daecheongense | 17.91 | −1.62 |
| 774 | Corn | Chryseobacterium daecheongense | 45.65* | 6.84 |
| 597 | Corn | Chryseobacterium rhizosphaerae | 20.90 | 5.29 |
| 615 | Corn | Chryseobacterium rhizosphaerae | 25.57 | 9.98 |
| 1075 | Corn | Chryseobacterium rhizosphaerae | N/A | N/A |
| 402 | Corn | Frigidibacter albus or Defluviimonas denitrificans (In Taxonomic Flux) | 44.78* | 18.96* |
| 745 | Corn | Frigidibacter albus or Defluviimonas denitrificans (In Taxonomic Flux) | 15.92 | −0.36 |
| 31 | Corn | Duganella radicis | 22.39 | 12.81 |
| 105 | Corn | Duganella radicis | 36.02 | 7.51 |
| 63 | Corn | Exiguobacterium antarcticum | 42.29* | 4.59 |
| 718 | Corn | Exiguobacterium sibircum or antarcticum | 18.12 | −6.56 |
| 116 | Corn | Exiguobacterium sibiricum | N/A | N/A |
| 225 | Corn | Exiguobacterium soli | 23.88 | 9.48 |
| 138 | Corn | Exiguobacterium sp. | 37.11 | 20.56* |
| 712 | Corn | Frigidibacter albus | 38.81* | 10.24 |
| 3231 | Corn | Massilia kyonggiensis | −13.92 | −10.76 |
| 94 | Corn | Massilia kyonggiensis | 16.50 | −9.92 |
| 97 | Corn | Massilia kyonggiensis | 11.72 | −4.68 |
| 53 | Corn | Pedobacter terrae | 3.88 | 4.33 |
| 91 | Corn | Pedobacter terrae | N/A | N/A |
| 110 | Corn | Pedobacter terrae | 12.30 | 4.87 |
| 616 | Corn | Pseudomonas helmanticensis | 42.79* | 56.95* |
| 800 | Corn | Pseudomonas helmanticensis | 6.97 | 2.62 |
| 2945 | Corn | Pseudomonas helmanticensis | 38.81* | 8.22 |

*Statistically significant results

In table 16, the root and shoot length were assessed to evaluate the effect of the microbe treatments on early plant development. Both increases and decreases have been noted to reflect the possibility that decreases are hypothesized to be yield relevant; for example a smaller plant reflects potential for in-field conservation of nutrients and water where these may be limited by drought or local conditions. Results show that of all strains tested, some 21 strains caused a relative increase in root length at six days post inoculation (DPI) and 27 strains caused a relative increase in shoot length compared to water controls in vitro. A total of six strains tested on corn caused a significant increase in both shoot length and root length (p<0.1, Fishers least squared difference). Asterisks show significance (p<0.1, Dunnette's Multiple-Comparison Test).

Example 9: Biochemical Characterization of Microbial Isolates

A. In Vitro Analysis of Plant Beneficial Properties of a Microbe in US Trials

In this example, isolated microbes from Table 4 were grown on minimal or nutrient-deficient agar plates supplemented with insoluble nutrient substrates to determine biochemical activity (Table 17).

Isolates were tested, in triplicate, for phosphate, potassium, and zinc solubilization, siderophore production and the ability to grow on low nitrogen media. Plates were incubated at 25° C. for six days.

Table 17 provides a summary of the growth response of each isolate, having been grown as described above. Tests are abbreviated as follows: Mica (K solubilization)—isolates were grown on modified Alexandrov medium supplemented with Mica (Parmar and Sindhu 2013); PO4—isolates were grown on NBRIP media (Nautiyal, 1999) containing insoluble tri-calcium phosphate as the sole source of P; ZnO and ZnO3 (Zn solubilization)—isolates were grown on minimal media supplemented with insoluble Zn as described by Goteti et al., (2013); NfA—isolates were grown on Nfb media (Dobereiner et al., 1976) without Bromothymol blue, solidified with 12.5% agar; CAS agar—isolates were grown on Chrome Azurol-s agar for detection of iron chelation according to the method of Perez-Miranda et al (2007).

Within table 17, a (+) symbol represents an isolates ability to grow under the test conditions and solubilize the respective element, (−) symbol represents a lack of solubilization, (N/A) represents no isolate growth observed on the respective media.

Results show that microbes on table 4 exhibit a broad spectrum of known plant-beneficial biochemical activities (Rana et al., 2012, Rodriguez and Reynaldo, 1999) including solubilization of mineral nutrients and chelation of micronutrients. By enhancing nutrient availability for plant growth promotion, the microbes exhibit a potential for increasing plant yields.

TABLE 17

| Strain BCI # | Species | Mica (K) | PO4 | ZnO | ZnCO3 | NfA | CAS agar |
|---|---|---|---|---|---|---|---|
| 49 | *Achromobacter pulmonis* | N/A | + | + | + | + | − |
| 46 | *Agrobacterium fabrum* or *Rhizobium pusense* | − | − | + | − | + | − |
| 958 | *Agrobacterium fabrum* or *Rhizobium pusense* | − | − | + | + | + | − |
| 717 | *Arthrobacter nicotinovorans* | − | + | + | + | + | − |
| 3189 | *Arthrobacter nicotinovorans* | − | + | + | + | + | − |
| 3444 | *Arthrobacter nicotinovorans* | − | + | + | + | + | − |
| 774 | *Chryseobacterium daecheongense* | − | N/A | N/A | N/A | N/A | − |
| 615 | *Chryseobacterium rhizosphaerae* | N/A | N/A | N/A | N/A | N/A | + |
| 1075 | *Chryseobacterium rhizosphaerae* | N/A | N/A | N/A | N/A | N/A | + |
| 597 | *Chryseobacterium rhizosphaerae* | N/A | N/A | N/A | N/A | N/A | + |
| 402 | *Frigidibacter albus* or *Defluviimonas denitrificans* (In Taxonomic Flux) | − | − | N/A | N/A | + | − |
| 745 | *Frigidibacter albus* or *Defluviimonas denitrificans* (In Taxonomic Flux) | − | − | N/A | N/A | + | − |
| 31 | *Duganella radicis* | − | N/A | + | + | + | − |
| 105 | *Duganella radicis* | − | N/A | + | + | + | − |
| 712 | *Frigidibacter albus* | − | − | N/A | N/A | + | − |
| 3231 | *Massilia kyonggiensis* | − | + | N/A | N/A | + | − |
| 94 | *Massilia kyonggiensis* | − | + | + | + | + | − |
| 97 | *Massilia kyonggiensis* | − | − | N/A | N/A | N/A | + |
| 53 | *Pedobacter terrae* | − | N/A | + | + | + | − |
| 91 | *Pedobacter terrae* | − | − | + | + | + | − |
| 110 | *Pedobacter terrae* | − | − | + | + | + | − |
| 616 | *Pseudomonas helmanticensis* | + | + | N/A | N/A | + | − |
| 800 | *Pseudomonas helmanticensis* | + | + | N/A | N/A | + | − |

TABLE 17-continued

| Strain BCI # | Species | Mica (K) | PO4 | ZnO | ZnCO3 | NfA | CAS agar |
|---|---|---|---|---|---|---|---|
| 2945 | *Pseudomonas helmanticensis* | + | + | N/A | + | + | + |
| 5222 | *Agrobacterium fabrum* or *Rhizobium pusense* | − | − | + | + | + | − |

B. In Vitro Analysis of Plant Beneficial Properties of a Microbe on New Zealand Trials Microbes from Table 18 were grown on minimal or nutrient-deficient agar plates supplemented with insoluble nutrient substrates to determine biochemical activity.

Phosphate solubilization was determined using NBRIP media containing 5 g/L tri-calcium phosphate according to the method Islam et al., (2007). The ability to use phytate as the sole source of phosphorus for growth was assessed using media containing (g/L): phytic acid (10) $NaNO_3$ (3); KCl (0.5); $FeSO_4 \cdot 7H_2O$ (0.01); $MgSO_4 \cdot 7H_2O$ (0.5); glucose (10) and noble agar (15), pH 7.5. Growth on low-nitrogen media (Low N) was assessed using NfA media as described above.

Within table 18, a (+) symbol represents an isolates ability to grow under the test conditions and solubilize the respective element, (−) symbol represents a lack of solubilization.

TABLE 18

| Strain BDNZ | Species | low N | Tri Ca (P) | Phytic (P) |
|---|---|---|---|---|
| 74542 | *Tumebacillus permanentifrigoris* | − | − | − |
| 72366 | *Tumebacillus permanentifrigoris* | + | + | + |
| 72229 | *Tumebacillus permanentifrigoris* | + | − | + |
| 72287 | *Tumebacillus permanentifrigoris* | + | − | − |
| 72243 | *Leifsonia lichenia* | + | − | + |
| 72289 | *Leifsonia lichenia* | + | − | + |
| 73021 | *Massilia kyonggiensis* | + | − | − |
| 71222 | *Novosphingobium lindaniclasticum* | + | + | + |
| 71628 | *Novosphingobium sediminicola* | + | − | + |

II. Increased Drought Tolerance and $H_2O$ Use Efficiency in Agriculturally Important Crops In certain embodiments of the disclosure, the present methods aim to increase the drought tolerance and water use efficiency for a given crop.

The methodologies presented herein—based upon utilizing the disclosed isolated microbes, consortia, and compositions comprising the same—have the potential to increase the drought tolerance and water use efficiency of important agricultural crops. This will enable a more sustainable agricultural system and increase the regions of the world that are suitable for growing important crops.

Example 1: Increasing Ryegrass Drought Tolerance and $H_2O$ Use Efficiency with Isolated Microbes and Microbial Consortia A. Seed Treatment with Isolated Microbe In this example, an isolated microbe from Tables 1-4 will be applied as a seed coating to seeds of ryegrass (*Lolium perenne*). Upon applying the isolated microbe as a seed coating, the ryegrass will be planted and cultivated in the standard manner.

A control plot of ryegrass seeds, which did not have the isolated microbe applied as a seed coating, will also be planted.

It is expected that the ryegrass plants grown from the seeds treated with the seed coating will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

B. Seed Treatment with Microbial Consortia

In this example, a microbial consortium, comprising at least two microbes from Tables 1-4 will be applied as a seed coating to seeds of ryegrass (*Lolium perenne*). Upon applying the microbial consortium as a seed coating, the ryegrass will be planted and cultivated in the standard manner.

A control plot of ryegrass seeds, which did not have the microbial consortium applied as a seed coating, will also be planted.

It is expected that the ryegrass plants grown from the seeds treated with the seed coating will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

C. Treatment with Agricultural Composition Comprising Isolated Microbe

In this example, an isolated microbe from Tables 1-4 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the with the agricultural composition will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

D. Treatment with Agricultural Composition Comprising Microbial Consortia

In this example, a microbial consortium, comprising at least two microbes from Tables 1-4 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the with the agricultural composition will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

Example 2: Increasing Maize Drought Tolerance and $H_2O$ Use Efficiency with Isolated Microbes and Microbial Consortia A. Seed Treatment with Isolated Microbe In this example, an isolated microbe from Tables 1-4 will be applied as a seed coating to seeds of corn (*Zea mays*). Upon applying the isolated microbe as a seed coating, the corn will be planted and cultivated in the standard manner.

A control plot of corn seeds, which did not have the isolated microbe applied as a seed coating, will also be planted.

It is expected that the corn plants grown from the seeds treated with the seed coating will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

B. Seed Treatment with Microbial Consortia

In this example, a microbial consortium, comprising at least two microbes from Tables 1-4 will be applied as a seed coating to seeds of corn (*Zea mays*). Upon applying the microbial consortium as a seed coating, the corn will be planted and cultivated in the standard manner.

A control plot of corn seeds, which did not have the microbial consortium applied as a seed coating, will also be planted.

It is expected that the corn plants grown from the seeds treated with the seed coating will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

C. Treatment with Agricultural Composition Comprising Isolated Microbe

In this example, an isolated microbe from Tables 1-4 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the with the agricultural composition will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

D. Treatment with Agricultural Composition Comprising Microbial Consortia

In this example, a microbial consortium, comprising at least two microbes from Tables 1-4 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the with the agricultural composition will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

Example 3: Increasing Soybean Drought Tolerance and $H_2O$ Use Efficiency with Isolated Microbes and Microbial Consortia A. Seed Treatment with Isolated Microbe In this example, an isolated microbe from Tables 1-4 will be applied as a seed coating to seeds of soybean (*Glycine max*). Upon applying the isolated microbe as a seed coating, the soybean will be planted and cultivated in the standard manner.

A control plot of soybean seeds, which did not have the isolated microbe applied as a seed coating, will also be planted.

It is expected that the soybean plants grown from the seeds treated with the seed coating will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

B. Seed Treatment with Microbial Consortia

In this example, a microbial consortium, comprising at least two microbes from Tables 1-4 will be applied as a seed coating to seeds of soybean (*Glycine max*). Upon applying the microbial consortium as a seed coating, the soybean will be planted and cultivated in the standard manner.

A control plot of soybean seeds, which did not have the microbial consortium applied as a seed coating, will also be planted.

It is expected that the soybean plants grown from the seeds treated with the seed coating will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

C. Treatment with Agricultural Composition Comprising Isolated Microbe

In this example, an isolated microbe from Tables 1-4 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the with the agricultural composition will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

D. Treatment with Agricultural Composition Comprising Microbial Consortia

In this example, a microbial consortium, comprising at least two microbes from Tables 1-4 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the with the agricultural composition will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

III. Increased Nitrogen Use Efficiency in Agriculturally Important Crops

In certain embodiments of the disclosure, the present methods aim to decrease the amount of nitrogen that must be deposited into a given agricultural system and yet achieve the same or better yields for a given crop.

The methodologies presented herein-based upon utilizing the disclosed isolated microbes, consortia, and compositions comprising the same—have the potential to reduce the amount of nitrogen fertilizer that is lost by farmers every year due to nitrogen leaching into the air, soil, and waterways. This will enable a more sustainable agricultural system that is still able to produce yield results consistent with today's agricultural expectations.

Example 1: Increasing Ryegrass NUE with Isolated Microbes and Microbial Consortia A. Seed Treatment with Isolated Microbe In this example, an isolated microbe from Tables 1-4 will be applied as a seed coating to seeds of ryegrass (*Lolium perenne*). Upon applying the isolated microbe as a seed coating, the ryegrass will be planted and cultivated in the standard manner.

A control plot of ryegrass seeds, which did not have the isolated microbe applied as a seed coating, will also be planted.

It is expected that the ryegrass plants grown from the seeds treated with the seed coating will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

B. Seed Treatment with Microbial Consortia

In this example, a microbial consortium, comprising at least two microbes from Tables 1-4 will be applied as a seed coating to seeds of ryegrass (*Lolium perenne*). Upon applying the microbial consortium as a seed coating, the ryegrass will be planted and cultivated in the standard manner.

A control plot of ryegrass seeds, which did not have the microbial consortium applied as a seed coating, will also be planted.

It is expected that the ryegrass plants grown from the seeds treated with the seed coating will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

C. Treatment with Agricultural Composition Comprising Isolated Microbe

In this example, an isolated microbe from Tables 1-4 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

D. Treatment with Agricultural Composition Comprising Microbial Consortia

In this example, a microbial consortium, comprising at least two microbes from Tables 1-4 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

Example 2: Increasing Maize NUE with Isolated Microbes and Microbial Consortia

A. Seed Treatment with Isolated Microbe

In this example, an isolated microbe from Tables 1-4 will be applied as a seed coating to seeds of corn (Zea mays). Upon applying the isolated microbe as a seed coating, the corn will be planted and cultivated in the standard manner.

A control plot of corn seeds, which did not have the isolated microbe applied as a seed coating, will also be planted.

It is expected that the corn plants grown from the seeds treated with the seed coating will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

B. Seed Treatment with Microbial Consortia

In this example, a microbial consortium, comprising at least two microbes from Tables 1-4 will be applied as a seed coating to seeds of corn (Zea mays). Upon applying the microbial consortium as a seed coating, the corn will be planted and cultivated in the standard manner.

A control plot of corn seeds, which did not have the microbial consortium applied as a seed coating, will also be planted.

It is expected that the corn plants grown from the seeds treated with the seed coating will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

C. Treatment with Agricultural Composition Comprising Isolated Microbe

In this example, an isolated microbe from Tables 1-4 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

D. Treatment with Agricultural Composition Comprising Microbial Consortia

In this example, a microbial consortium, comprising at least two microbes from Tables 1-4 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

Example 3: Increasing Soybean NUE with Isolated Microbes and Microbial Consortia A. Seed Treatment with Isolated Microbe In this example, an isolated microbe from Tables 1-4 will be applied as a seed coating to seeds of soybean (*Glycine max*). Upon applying the isolated microbe as a seed coating, the soybean will be planted and cultivated in the standard manner.

A control plot of soybean seeds, which did not have the isolated microbe applied as a seed coating, will also be planted.

It is expected that the soybean plants grown from the seeds treated with the seed coating will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

B. Seed Treatment with Microbial Consortia

In this example, a microbial consortium, comprising at least two microbes from Tables 1-4 will be applied as a seed coating to seeds of soybean (*Glycine max*). Upon applying the microbial consortium as a seed coating, the soybean will be planted and cultivated in the standard manner.

A control plot of soybean seeds, which did not have the microbial consortium applied as a seed coating, will also be planted.

It is expected that the soybean plants grown from the seeds treated with the seed coating will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

C. Treatment with Agricultural Composition Comprising Isolated Microbe

In this example, an isolated microbe from Tables 1-4 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

D. Treatment with Agricultural Composition Comprising Microbial Consortia

In this example, a microbial consortium, comprising at least two microbes from Tables 1-4 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

IV. Increased Metabolite Expression in Agriculturally Important Crops

In certain embodiments of the disclosure, the present methods aim to increase the production of a metabolite of interest for a given crop.

The methodologies presented herein—based upon utilizing the disclosed isolated microbes, consortia, and compositions comprising the same—have the potential to increase the production of a metabolite of interest for a given crop.

Example 1: Increasing Sugar Content in Basil with Isolated Microbes and Microbial Consortia A. Seed Treatment with Isolated Microbe In this example, an isolated microbe from Tables 1-4 will be applied as a seed coating to seeds of basil (*Ocium basilicum*). Upon applying the isolated microbe as a seed coating, the basil will be planted and cultivated in the standard manner.

A control plot of basil seeds, which did not have the isolated microbe applied as a seed coating, will also be planted.

It is expected that the basil plants grown from the seeds treated with the seed coating will exhibit a quantifiable increase in water-soluble carbohydrate content, as compared to the control basil plants.

B. Seed Treatment with Microbial Consortia

In this example, a microbial consortium, comprising at least two microbes from Tables 1-4 will be applied as a seed coating to seeds of basil (*Ocium basilicum*). Upon applying the microbial consortium as a seed coating, the basil will be planted and cultivated in the standard manner.

A control plot of basil seeds, which did not have the microbial consortium applied as a seed coating, will also be planted.

It is expected that the basil plants grown from the seeds treated with the seed coating will exhibit a quantifiable increase in water-soluble carbohydrate content, as compared to the control basil plants.

V. Synergistic Effect Achievable with Combination of Microbes and Ascend®

A. Seed Treatment with Isolated Microbe Combined with Ascend®

In this example, an isolated microbe from Tables 1-4 will be combined with Ascend® and applied as a seed coating to seeds of a plant. Upon applying the isolated microbe/Ascend® combination as a seed coating, the plant will be planted and cultivated in the standard manner.

A control plot of plant seeds, which did not have the isolated microbe/Ascend® combination applied as a seed coating, will also be planted.

It is expected that the plants grown from the seeds treated with the seed coating will exhibit a quantifiable increase in a phenotypic trait of interest, as compared to the control plants. It is expected that a synergistic effect may be observed for the phenotypic trait of interest.

B. Seed Treatment with Microbial Consortia Combined with Ascend®

In this example, a microbial consortium, comprising at least two microbes from Tables 1-4 will be combined with Ascend® and then applied as a seed coating to seeds of a plant. Upon applying the microbial consortium/Ascend® combination as a seed coating, the plant will be planted and cultivated in the standard manner.

A control plot of plant seeds, which did not have the microbial consortium/Ascend® combination applied as a seed coating, will also be planted.

It is expected that the plants grown from the seeds treated with the seed coating will exhibit a quantifiable increase in a phenotypic trait of interest, as compared to the control plants. It is expected that a synergistic effect may be observed for the phenotypic trait of interest.

VI. Microbial Consortia

The microbial consortia utilized in the examples are presented in Table 18 in a non-limiting matter, while recognizing that the microbial consortia may comprise any one or more microbes presented in tables 1-4.

TABLE 19

Consortia Compositions

| ID | Microbes | ID | Microbes |
|---|---|---|---|
| D1 | *Stenotrophomonas maltophilia* BDNZ 54073<br>*Rhodococcus erythropolis* BDNZ 54093<br>*Pantoea vagans* BDNZ 55529<br>*Pseudomonas oryzihabitans* BDNZ 55530 | D2 | *Rhodococcus erythropolis* BDNZ 54093<br>*Pseudomonas oryzihabitans* BDNZ 55530<br>*Rahnella aquatilis* BDNZ 56532 |
| D3 | *Stenotrophomonas maltophilia* BDNZ 54073<br>*Rhodococcus erythropolis* BDNZ 54093<br>*Pantoea vagans* BDNZ 55529<br>*Rahnella aquatilis* BDNZ 56532 | D4 | *Stenotrophomonas maltophilia* BDNZ 54073<br>*Rhodococcus erythropolis* BDNZ 54093<br>*Pseudomonas fluorescens* BDNZ 56530<br>*Pantoea agglomerans* BDNZ 57547 |
| D5 | *Rhodococcus erythropolis* BDNZ 54093<br>*Pseudomonas fluorescens* BDNZ 56530<br>*Pantoea agglomerans* BDNZ 57547 | D6 | *Rahnella aquatilis* BDNZ 57157<br>*Rahnella aquatilis* BDNZ 58013<br>*Rhizobium etli* BDNZ 60473 |
| D7 | *Stenotrophomonas maltophilia* BDNZ 54073<br>*Rhodococcus erythropolis* BDNZ 54093<br>*Pantoea vagans* BDNZ 55529<br>*Pseudomonas oryzihabitans* BDNZ 55530<br>*Rahnella aquatilis* BDNZ 56532 | D8 | *Stenotrophomonas maltophilia* BDNZ 54073<br>*Rhodococcus erythropolis* BDNZ 54093<br>*Pantoea vagans* BDNZ 55529<br>*Pseudomonas oryzihabitans* BDNZ 55530<br>*Rahnella aquatilis* BDNZ 57157<br>*Rahnella aquatilis* BDNZ 58013<br>*Rhizobium etli* BDNZ 60473 |
| D9 | *Rahnella aquatilis* BDNZ 56532 | D10 | *Rhodococcus erythropolis* BDNZ 54093<br>*Pantoea vagans* BDNZ 55529<br>*Pseudomonas oryzihabitans* BDNZ 55530<br>*Rahnella aquatilis* BDNZ 56532 |
| D11 | *Exiguobacterium aurantiacum* BCI 50<br>*Duganella radicis* BCI 105 | D12 | *Rahnella aquatilis* BCI 29<br>*Duganella radicis* BCI 31<br>*Exiguobacterium sibiricum* |

TABLE 19-continued

Consortia Compositions

| ID | Microbes | ID | Microbes |
|---|---|---|---|
| | *Rhizobium pusense* BCI 106<br>*Kosakonia radicincitans* BCI 107<br>*Delftia lacustris* BCI 124 | | BCI 116<br>*Novosphingobium sediminicola* BCI 130<br>*Ensifer* sp. BCI 131<br>*Microbacterium oleivorans* BCI 132 |
| D13 | *Chitinophaga terrae* BCI 79<br>*Exiguobacterium* sp. BCI 81<br>*Novosphingobium sediminicola* BCI 82<br>*Exiguobacterium acetylicum* BCI 83<br>*Variovorax ginsengisoli* BCI 137 | D14 | *Exiguobacterium acetylicum* BCI 23<br>*Rahnella aquatilis* BCI 29<br>*Rhizobium lemnae* BCI 34<br>*Achromobacter spanius* BCI 385 |
| D15 | *Dyadobacter soli* BCI 68<br>*Chitinophaga terrae* BCI 79<br>*Pedobacter terrae* BCI 91<br>*Massilia albidiflava* BCI 97<br>*Novosphingobium sediminicola* BCI 136 | D16 | *Rhodococcus erythropolis* BDNZ 54093<br>*Pantoea vagans* BDNZ 55529<br>*Pseudomonas oryzihabitans* BDNZ 55530 |
| D17 | *Rhodococcus erythropolis* BDNZ 54093<br>*Rahnella aquatilis* BDNZ 56532<br>*Rahnella aquatilis* BDNZ 58013<br>*Rhizobium etli* BDNZ 60473 | D18 | *Exiguobacterium acetylicum* BCI125<br>*Bacillus megaterium* BCI 255<br>*Paenibacillus glycanilyticus* BCI 418 |
| D19 | *Agrobacterium fabrum* BCI 608<br>*Acidovorax soli* BCI 690<br>*Rhizobium grahamii* BCI 691<br>*Bacillus subtilis* BCI 989 | D20 | *Arthrobacter pascens* BCI 682<br>*Novosphingobium lindaniclasticum* BCI 684<br>*Bosea robiniae* BCI 688<br>*Microbacterium maritypicum* BCI 689<br>*Sphingopyxis alaskensis* BCI 914 |
| D21 | *Chryseobacterium rhizosphaerae* BCI 615<br>*Hydrogenophaga atypica* BCI 687<br>*Bosea robiniae* BCI 689<br>*Microbacterium maritypicum* BCI 688<br>*Agrobacterium fabrum* BCI 958 | D22 | *Novosphingobium resinovorum* BCI 557<br>*Arthrobacter mysorens* BCI 700<br>*Bosea thiooxidans* BCI 703<br>*Bacillus oleronius* BCI 1071 |
| D23 | *Pedobacter rhizosphaerae* BCI 598<br>*Bacillus* sp. BCI 715<br>*Pseudomonas jinjuensis* BCI 804<br>*Pseudomonas putida* BCI 805 | D24 | *Novosphingobium sediminicola* BCI 130<br>*Ensifer* sp. BCI 131<br>*Microbacterium oleivorans* BCI 132 |
| D25 | *Arthrobacter cupressi* BCI 59<br>*Dyadobacter soli* BCI 68 | D26 | *Bosea robiniae* BCI 689<br>*Bosea thiooxidans* BCI 703<br>*Bosea eneae* BCI 1267 |
| D27 | *Pseudomonas helmanticensis* BCI 616<br>*Arthrobacter pascens* BCI 682<br>*Bosea robiniae* BCI 689<br>*Pseudomonas putida* BCI 791<br>*Agrobacterium fabrum* BCI 958 | D28 | *Chryseobacterium rhizosphaerae* BCI 597<br>*Defluviimonas denitrificans* BCI 712<br>*Arthrobacter nicotinovorans* BCI 717<br>*Pseudomonas putida* BCI 802 |
| D29 | *Pseudomonas florescens* BDNZ 71627<br>*Novosphingobium sediminicola* BDNZ 71628<br>*Microbacterium azadirachtae* BDNZ 71629 | D30 | *Rhodococcus erythropolis* BDNZ 74552<br>*Tumebacillus permanentifrigoris* BDNZ 74542 |
| D31 | *Tumebacillus permanentifrigoris* BDNZ 72229 | D32 | *Rhodococcus erythropolis* BNDZ 72250<br>*Bacillus megaterium* BDNZ 72242<br>*Leifsonia lichenia* BDNZ 72243 |
| D33 | *Bacillus megatarium* BDNZ 72242<br>*Leifsonia lichenia* BDNZ 72243<br>*Bacillus aryabhattai* BDNZ 72259 | D34 | *Novosphingobium lindaniclasticum* BDNZ 71222 |
| D35 | *Rhodococcus erythropolis* BDNZ 71221<br>*Novosphingobium lindaniclasticum* BDNZ 71222<br>*Microbacterium azadirachtae* BDNZ 71663 | D36 | *Bacillus cereus* BDNZ 71220<br>*Rhodococcus erythropolis* BNDZ 71221<br>*Novosphingobium lindaniclasticum* BDNZ 71222 |
| D37 | *Massilia kyonggiensis* BDNZ 73021<br>*Microbacterium azadirachtae* BDNZ 72996<br>*Rhizobium tibeticum* BDNZ 72135 | D38 | *Variovorax paradoxus* BDNZ 72150<br>*Tumebacillus permanentifrigoris* BDNZ 72366 |
| D39 | *Tumebacillus permanentifrigoris* BDNZ 72287<br>*Bacillus megatarium* BDNZ 72255 | | |
| A1 | *Stenotrophomonas maltophilia* BDNZ 54073<br>*Rhodococcus erythropolis* BDNZ 54093<br>*Pantoea vagans* BDNZ 55529<br>*Pseudomonas oryzihabitans* BDNZ55530 | A2 | *Flavobacterium glaciei* BDNZ 66487<br>*Massilia niastensis* BDNZ 55184<br>*Pseudomonas fluorescens* BDNZ 54480 |
| A3 | *Azospirillum lipoferum* BDNZ 57661<br>*Herbaspirillum huttiense* BDNZ 54487<br>*Pantoea agglomerans* BDNZ 54499<br>*Pseudomonas fluorescens* BDNZ 54480 | A4 | *Janthinobacterium* sp. BDNZ 54456<br>*Mucilaginibacter dorajii* BDNZ 66513<br>*Pseudomonas psychrotolerans* BDNZ 54517 |
| A5 | *Janthinobacterium* sp. BDNZ 54456<br>*Mucilaginibacter dorajii* BDNZ 66513<br>*Pseudomonas psychrotolerans* BDNZ 54517 | A6 | *Rhizobium etli* BDNZ 61443<br>*Caulobacter henrici* BDNZ 66341<br>*Duganella violaceinigra* BDNZ 66361 |
| A7 | *Duganella violaceinigra* BDNZ 66361 | A8 | *Ramlibacter henchirensis* BDNZ 66331<br>*Rhizobium pisi* BDNZ 66326<br>*Mucilaginibacter gosypii* BDNZ 66321<br>*Paenibacillus amylolyticus* BDNZ 66316 |
| A9 | *Polaromonas ginsengisoli* BDNZ 66373 | A10 | *Sphingobium quisquiliarum* BDNZ 66576<br>*Bacillus subtilis* BDNZ 66347<br>*Azospirillum lipoferum* BDNZ 66297 |
| A11 | *Rhodoferax ferrireducens* BDNZ 66374<br>*Mucilaginibacter gosypii* BDNZ 66321<br>*Paenibacillus amylolyticus* BDNZ 66316<br>*Azospirillum lipoferum* BDNZ66315 | A12 | *Rhodococcus erythropolis* BDNZ 54093<br>*Pseudomonas oryzihabitans* BDNZ 55530<br>*Rahnella aquatilis* BDNZ 56532 |
| A13 | *Rhodococcus erythropolis* BDNZ 54093<br>*Rahnella aquatilis* BDNZ 57157<br>*Azotobacter chroococcum* BDNZ57597 | A14 | *Rhodococcus erythropolis* BDNZ54299<br>*Rahnella aquatilis* BDNZ58013<br>*Herbaspirillum huttiense* BDNZ 65600 |

TABLE 19-continued

Consortia Compositions

| ID | Microbes | ID | Microbes |
|----|----------|----|----------|
| A15 | Rhodococcus erythropolis BDNZ 54093 Pseudomonas oryzihabitans BDNZ 55530 Rahnella aquatilis BDNZ 56532 | | |

VII. Effects of Microbial Consortia on Plant Phenotypes

Example 1: Evaluation of Phenotype of Plants Exposed to Microbial Consortia in U.S. Trials Plants disclosed in Table 20 were grown in a controlled environment in a rooting volume of 167 ml and typically in a soil substrate. The chamber photoperiod was set to 16 hours for all experiments on all species. The light intensity ranged from 180 μmol PAR $m^{-2}$ $s^{-1}$ to approximately 200 μmol PAR $m^{-2}$ $s^{-1}$ as plant height increased during experiments.

The air temperature was typically 28° C. during the photoperiod, decreasing to 23° C. during the night for Zea mays, Glycine max, and Sorghum bicolor experiments. Air temperature was typically 24° C. during the photoperiod, decreasing to 20° C. during the night for Triticum aestivum experiments.

Phenotypes were measured during early vegetative growth, typically before the V3 developmental stage.

Leaf chlorophyll content was measured midway along the youngest fully-expanded leaf, non-destructively using a meter providing an index of leaf chlorophyll content (CCM-200, Opti Sciences, Hudson, N.H., US).

Whole plant, shoot, and root dry weight was measured after plants had been dried to a constant weight in a drying oven set to 80° C. At least 10 replicate plants were measured for each phenotype measured in each experiment.

For evaluations on Glycine max, the number of nodules were counted.

A control treatment of uninoculated seeds was run in each experiment for comparison with plants grown from seeds inoculated with microbial consortia.

TABLE 20

| | | | | Controlled Environment Efficacy (%) | | | | | |
|---|---|---|---|---|---|---|---|---|---|
| Consortia | Crop | Assay | Evaluations | Plant | Shoot | Root | Chlorophyll | T leaf | Nodulation |
| D1 | Zea mays | early vigor | 21 | | | 74 | | 25 | |
| D6 | Zea mays | early vigor | 15 | | | 36 | 36 | 22 | |
| D7 | Zea mays | early vigor | 15 | 72 | 63 | 65 | 25 | 0 | |
| D11 | Zea mays | early vigor | 17 | | | 60 | | 20 | |
| D13 | Zea mays | early vigor | 12 | | 40 | | 33 | 0 | |
| D14 | Zea mays | early vigor | 15 | 62 | 69 | | 22 | 10 | |
| D15 | Zea mays | early vigor | 12 | | | 70 | 25 | 0 | |
| D25 | Zea mays | early vigor | 13 | | | 63 | 22 | 0 | |
| D2 | Zea mays | early vigor | 5/4* | 100 | 100 | 100* | 60 | — | |
| D3 | Zea mays | early vigor | 5/4* | 80 | 100 | 75* | 60 | — | |
| D4 | Zea mays | early vigor | 5/4* | 80 | 80 | 75* | 60 | — | |
| D5 | Zea mays | early vigor | 5/4* | 60 | 80 | 100* | 80 | — | |
| D8 | Zea mays | early vigor | 5/4* | 60 | 80 | 75* | 40 | — | |
| D12 | Zea mays | early vigor | 3 | 100 | 100 | 100 | 66 | — | |
| D24 | Zea mays | early vigor | 2 | 100 | 100 | 100 | 0 | 0 | |
| D1 | Sorghum bicolor | early vigor | 5 | 60 | 80 | 80 | 40 | 20 | |
| D11 | Sorghum bicolor | early vigor | 3 | 60 | 80 | 80 | 40 | 20 | |
| D13 | Sorghum bicolor | early vigor | 5 | 80 | 60 | 80 | 60 | 40 | |
| D14 | Sorghum bicolor | early vigor | 5 | 80 | 80 | 100 | 40 | 20 | |
| D15 | Sorghum bicolor | early vigor | 3 | 100 | 66 | 100 | 33 | 0 | |
| D6 | Sorghum bicolor | early vigor | 3 | 100 | 100 | 100 | 33 | 66 | |
| D7 | Sorghum bicolor | early vigor | 3 | 33 | 33 | 33 | 33 | 66 | |
| D25 | Sorghum bicolor | early vigor | 3 | 66 | 100 | 66 | 33 | 66 | |
| D9 | Triticum aestivum | early vigor | 8/6* | | 38 | 63 | 33* | — | |
| D10 | Triticum aestivum | early vigor | 8/6* | 63 | 38 | 63 | | — | |
| D16 | Triticum aestivum | early vigor | 8/6* | | | 63 | 33* | — | |
| D17 | Triticum aestivum | early vigor | 8/6* | 76 | 63 | 75 | 33* | — | |
| D18 | Triticum aestivum | early vigor | 8/6* | | 50 | 50 | 33* | — | |
| D26 | Triticum aestivum | early vigor | 8/6* | | 66 | 66 | 0* | — | |
| D19 | Glycine max | early vigor | 2 | 0 | 0 | 0 | | — | |
| D20 | Glycine max | early vigor | 2 | 100 | 100 | 100 | 0 | — | |
| D21 | Glycine max | early vigor | 2 | 0 | 0 | 0 | 0 | — | |
| D22 | Glycine max | early vigor | 2 | | | 0 | | — | |
| D23 | Glycine max | early vigor | 2 | | 100 | | | — | |
| D27 | Glycine max | cold tolerance | 3 | | 100 | | | | |
| D28 | Glycine max | cold tolerance | 12/3* | | | | 67* | | 75 |
| A1 | Zea mays | early vigor | 5 | — | 80 | 80 | — | — | |
| A2 | Triticum aestivum | cold tolerance | 4 | — | 75 | 75 | — | — | |
| A3 | Triticum aestivum | cold tolerance | 4 | — | 75 | 75 | — | — | |
| A4 | Triticum aestivum | cold tolerance | 2 | — | 100 | 100 | — | — | |
| A5 | Triticum aestivum | early vigor | 2 | — | 50 | 50 | — | — | |
| A6 | Solanum sp. | early vigor | 2 | — | 100 | 100 | — | — | |
| A7 | Solanum sp. | early vigor | 3 | — | 100 | 100 | — | — | |
| A8 | Solanum sp. | early vigor | 3 | — | 100 | 66 | — | — | |
| A9 | Solanum sp. | early vigor | 3 | — | 66 | 100 | — | — | |
| A10 | Solanum sp. | early vigor | 3 | — | 66 | 66 | — | — | |
| A11 | Solanum sp. | early vigor | 3 | — | 100 | 66 | — | — | |

TABLE 20-continued

| | | | | Controlled Environment Efficacy (%) | | | | | |
|---|---|---|---|---|---|---|---|---|---|
| Consortia | Crop | Assay | Evaluations | Plant | Shoot | Root | Chlorophyll | T leaf | Nodulation |
| A12 | *Solanum* sp. | early vigor | 2 | — | 100 | 50 | — | — | |
| A13 | *Triticum aestivum* | early vigor | 2 | — | 0 | 0 | — | — | |
| A14 | *Triticum aestivum* | early vigor | 2 | — | | | — | — | |

The data presented in table 20 describes the percentage of time (efficiency) a particular consortium changed a phenotype of interest relative to a control run in the same experiment. The measured phenotypes were whole plant dry weight (plant), shoot dry weight (shoot), root dry weight (root), leaf chlorophyll content (chlorophyll), leaf temperature (Tleaf), and nodulation.

The data presented is averaged across the number of times a specific consortium was tested against a control (evaluations). For consortia where different phenotypes were measured in a different number of evaluations, an asterisk was placed next to data points to match the phenotype with the number of evaluations. Evaluations have been broken down and displayed for specific crop species (crop).

The presented data identifies consortia that have increased a phenotype of interest in greater than 60% of evaluations (hit rate >59) and consortia that decreased a phenotype of interest in greater than 60% of evaluations (hit rate<41). Both increases and decreases in a phenotype of interest were recorded to reflect the possibility that decreases in select phenotypes of interest are yield relevant. Improvement in canopy photosynthesis through decreased leaf chlorophyll, and improvement in drought tolerance through decreased shoot biomass constitute two examples.

Example 2: Evaluation of Phenotype of Plants Exposed to Microbial Consortia in New Zealand Trials A. Seed Treatment with Microbial Consortia The inoculants were prepared from isolates grown as spread plates on R2A incubated at 25° C. for 48 to 72 hours. Colonies were harvested by blending with sterile distilled water (SDW) which was then transferred into sterile containers. Serial dilutions of the harvested cells were plated and incubated at 25° C. for 24 hours to estimate the number of colony forming units (CFU) in each suspension. Dilutions were prepared using individual isolates or blends of isolates (consortia) to deliver ~1×10$^5$ cfu/microbe/seed and seeds inoculated by either imbibition in the liquid suspension or by overtreatment with 5% vegetable gum and oil.

Seeds corresponding to the plants of table 21 were planted within 24 to 48 hours of treatment in agricultural soil, potting media or inert growing media. Plants were grown in small pots (28 mL to 200 mL) in either a controlled environment or in a greenhouse. Chamber photoperiod was set to 16 hours for all experiments on all species. Air temperature was typically maintained between 22-24° C.

Unless otherwise stated, all plants were watered with tap water 2 to 3 times weekly. Growth conditions were varied according to the trait of interest and included manipulation of applied fertilizer, watering regime and salt stress as follows:

Low N—seeds planted in soil potting media or inert growing media with no applied N fertilizer Moderate N—seeds planted in soil or growing media supplemented with commercial N fertilizer to equivalent of 135 kg/ha applied N Insol P—seeds planted in potting media or inert growth substrate and watered with quarter strength Pikovskaya's liquid medium containing tri-calcium phosphate as the only form phosphate fertilizer.

Cold Stress—seeds planted in soil, potting media or inert growing media and incubated at 10° C. for one week before being transferred to the plant growth room.

Salt stress—seeds planted in soil, potting media or inert growing media and watered with a solution containing between 100 to 200 mg/L NaCl.

Untreated (no applied microbe) controls were prepared for each experiment. Plants were randomized on trays throughout the growth environment. Between 10 and 30 replicate plants were prepared for each treatment in each experiment. Phenotypes were measured during early vegetative growth, typically before the V3 developmental stage and between 3 and 6 weeks after sowing. Foliage was cut and weighed. Roots were washed, blotted dry and weighed. Results indicate performance of treatments against the untreated control.

TABLE 21

| Microbe sp. | Strain ID | Crop | Assay | Shoot IOC (%) | Root IOC (%) |
|---|---|---|---|---|---|
| *Bosea thiooxidans* overall | 1 | 2 | 3 | Efficacy 100% | Efficacy 100% |
| *Bosea thiooxidans* | 54522 | Wheat | Early vigor-insol P | 30-40 | — |
| *Bosea thiooxidans* | 54522 | Ryegrass | Early vigor | 50-60 | 50-60 |
| *Bosea thiooxidans* | 54522 | Ryegrass | Early vigor-moderate P | 0-10 | 0-10 |
| *Duganella violaceinigra* overall | 1 | 1 | 1 | Efficacy 100% | Efficacy 100% |
| *Duganella violaceinigra* | 66361 | Tomato | Early vigor | 0-10 | 0-10 |
| *Duganella violaceinigra* | 66361 | Tomato | Early vigor | 30-40 | 40-50 |
| *Duganella violaceinigra* | 66361 | Tomato | Early vigor | 20-30 | 20-30 |

TABLE 21-continued

| Microbe sp. | Strain ID | Crop | Assay | Shoot IOC (%) | Root IOC (%) |
|---|---|---|---|---|---|
| *Herbaspirillum huttiense* overall | 2 | 2 | 2 | Efficacy 100% | — |
| *Herbaspirillum huttiense* | 54487 | Wheat | Early vigor-insol P | 30-40 | — |
| *Herbaspirillum huttiense* | 60507 | Maize | Early vigor-salt stress | 0-10 | 0-10 |
| *Janthinobacterium* sp. Overall | 2 | 2 | 2 | Efficacy 100% | — |
| *Janthinobacterium* sp. | 54456 | Wheat | Early vigor-insol P | 30-40 | — |
| *Janthinobacterium* sp. | 54456 | Wheat | Early vigor-insol P | 0-10 | — |
| *Janthinobacterium* sp. | 63491 | Ryegrass | Early vigor-drought stress | 0-10 | 0-10 |
| *Massilia niastensis* overall | 1 | 1 | 2 | Efficacy 80% | Efficacy 80% |
| *Massilia niastensis* | 55184 | Wheat | Early vigor-salt stress | 0-10 | 20-30 |
| *Massilia niastensis* | 55184 | Winter wheat | Early vigor-cold stress | 0-10 | 10-20 |
| *Massilia niastensis* | 55184 | Winter wheat | Early vigor-cold stress | 20-30 | 20-30 |
| *Massilia niastensis* | 55184 | Winter wheat | Early vigor-cold stress | 10-20 | 10-20 |
| *Massilia niastensis* | 55184 | Winter wheat | Early vigor-cold stress | <0 | <0 |
| *Novosphingobium rosa* overall | 2 | 1 | 1 | Efficacy 100% | Efficacy 100% |
| *Novosphingobium rosa* | 65589 | Maize | Early vigor-cold stress | 0-10 | 0-10 |
| *Novosphingobium rosa* | 65619 | Maize | Early vigor-cold stress | 0-10 | 0-10 |
| *Paenibacillus amylolyticus* overall | 1 | 1 | 1 | Efficacy 100% | Efficacy 100% |
| *Paenibacillus amylolyticus* | 66316 | Tomato | Early vigor | 0-10 | 0-10 |
| *Paenibacillus amylolyticus* | 66316 | Tomato | Early vigor | 10-20 | 10-20 |
| *Paenibacillus amylolyticus* | 66316 | Tomato | Early vigor | 0-10 | 0-10 |
| *Pantoea agglomerans* | 3 | 2 | 3 | Efficacy 33% | Efficacy 50% |
| *Pantoea agglomerans* | 54499 | Wheat | Early vigor-insol P | 40-50 | — |
| *Pantoea agglomerans* | 57547 | Maize | Early vigor-low N | <0 | 0-10 |
| *Pantoea vagans* (formerly *P. agglomerans*) | 55529 | Maize | Early vigor | <0 | <0 |
| *Polaromonas ginsengisoli* | 1 | 1 | 1 | Efficacy 66% | Efficacy 100% |
| *Polaromonas ginsengisoli* | 66373 | Tomato | Early vigor | 0-10 | 0-10 |
| *Polaromonas ginsengisoli* | 66373 | Tomato | Early vigor | 20-30 | 30-40 |
| *Polaromonas ginsengisoli* | 66373 | Tomato | Early vigor | <0 | 10-20 |
| *Pseudomonas fluorescens* | 1 | 2 | 2 | Efficacy 100% | — |
| *Pseudomonas fluorescens* | 54480 | Wheat | Early vigor-insol P | >100 | — |
| *Pseudomonas fluorescens* | 56530 | Maize | Early vigor-moderate N | 0-10 | — |
| *Rahnella aquatilis* | 3 | 3 | 4 | Efficacy 80% | Efficacy 63% |
| *Rahnella aquatilis* | 56532 | Maize | Early vigor-moderate N | 10-20 | — |
| *Rahnella aquatilis* | 56532 | Maize | Early vigor-moderate N | 0-10 | 0-10 |
| *Rahnella aquatilis* | 56532 | Wheat | Early vigor-cold stress | 0-10 | 10-20 |
| *Rahnella aquatilis* | 56532 | Wheat | Early vigor-cold stress | <0 | 0-10 |
| *Rahnella aquatilis* | 56532 | Wheat | Early vigor-cold stress | 10-20 | <0 |
| *Rahnella aquatilis* | 57157 | Ryegrass | Early vigor | <0 | — |
| *Rahnella aquatilis* | 57157 | Maize | Early vigor-low N | 0-10 | 0-10 |
| *Rahnella aquatilis* | 57157 | Maize | Early vigor-low N | 0-10 | <0 |
| Rahnella aquatilis | 58013 | Maize | Early vigor | 0-10 | 10-20 |
| *Rahnella aquatilis* | 58013 | Maize | Early vigor-low N | 0-10 | <0 |

TABLE 21-continued

| Microbe sp. | Strain ID | Crop | Assay | Shoot IOC (%) | Root IOC (%) |
|---|---|---|---|---|---|
| Rhodococcus erythropolis | 3 | 1 | 3 | Efficacy 66% | — |
| Rhodococcus erythropolis | 54093 | Maize | Early vigor-low N | 40-50 | — |
| Rhodococcus erythropolis | 54299 | Maize | Early vigor-insol P | >100 | — |
| Rhodococcus erythropolis | 54299 | Maize | Early vigor | <0 | <0 |
| Stenotrophomonas chelatiphaga | 6 | 1 | 1 | Efficacy 60% | Efficacy 60% |
| Stenotrophomonas chelatiphaga | 54952 | Maize | Early vigor | 0-10 | 0-10 |
| Stenotrophomonas chelatiphaga | 47207 | Maize | Early vigor | <0 | 0 |
| Stenotrophomonas chelatiphaga | 64212 | Maize | Early vigor | 0-10 | 10-20 |
| Stenotrophomonas chelatiphaga | 64208 | Maize | Early vigor | 0-10 | 0-10 |
| Stenotrophomonas chelatiphaga | 58264 | Maize | Early vigor | <0 | <0 |
| Stenotrophomonas maltophilia | 6 | 1 | 2 | Efficacy 43% | Efficacy 66% |
| Stenotrophomonas maltophilia | 54073 | Maize | Early vigor-low N | 50-60 | — |
| Stenotrophomonas maltophilia | 54073 | Maize | Early vigor | <0 | 0-10 |
| Stenotrophomonas maltophilia | 56181 | Maize | Early vigor | 0-10 | <0 |
| Stenotrophomonas maltophilia | 54999 | Maize | Early vigor | 0-10 | 0-10 |
| Stenotrophomonas maltophilia | 54850 | Maize | Early vigor | 0 | 0-10 |
| Stenotrophomonas maltophilia | 54841 | Maize | Early vigor | <0 | 0-10 |
| Stenotrophomonas maltophilia | 46856 | Maize | Early vigor | <0 | <0 |
| Stenotrophomonas rhizophila | 8 | 1 | 1 | Efficacy 12.5% | Efficacy 37.5% |
| Stenotrophomonas rhizophila | 50839 | Maize | Early vigor | <0 | <0 |
| Stenotrophomonas rhizophila | 48183 | Maize | Early vigor | <0 | <0 |
| Stenotrophomonas rhizophila | 45125 | Maize | Early vigor | <0 | <0 |
| Stenotrophomonas rhizophila | 46120 | Maize | Early vigor | <0 | 0-10 |
| Stenotrophomonas rhizophila | 46012 | Maize | Early vigor | <0 | <0 |
| Stenotrophomonas rhizophila | 51718 | Maize | Early vigor | 0-10 | 0-10 |
| Stenotrophomonas rhizophila | 66478 | Maize | Early vigor | <0 | <0 |
| Stenotrophomonas rhizophila | 65303 | Maize | Early vigor | <0 | 0-10 |
| Stenotrophomonas terrae | 2 | 2 | 1 | Efficacy 50% | Efficacy 50% |
| Stenotrophomonas terrae | 68741 | Maize | Early vigor | <0 | <0 |
| Stenotrophomonas terrae | 68599 | Maize | Early vigor | <0 | 0-10 |
| Stenotrophomonas terrae | 68599 | Capsicum * | Early vigor | 20-30 | 20-30 |
| Stenotrophomonas terrae | 68741 | Capsicum * | Early vigor | 10-20 | 20-30 |

The data presented in table 21 describes the efficacy with which a microbial species or strain can change a phenotype of interest relative to a control run in the same experiment. Phenotypes measured were shoot fresh weight and root fresh weight for plants growing either in the absence of presence of a stress (assay). For each microbe species, an overall efficacy score indicates the percentage of times a strain of that species increased a both shoot and root fresh weight in independent evaluations. For each species, the specifics of each independent assay is given, providing a strain ID (strain) and the crop species the assay was performed on (crop). For each independent assay the percentage increase in shoot and root fresh weight over the controls is given.

B. Seed Treatment with Microbial Consortia

The inoculants were prepared from isolates grown as spread plates on R2A incubated at 25° C. for 48 to 72 hours. Colonies were harvested by blending with sterile distilled water (SDW) which was then transferred into sterile containers. Serial dilutions of the harvested cells were plated and incubated at 25° C. for 24 hours to estimate the number of colony forming units (CFU) in each suspension. Dilutions were prepared using individual isolates or blends of isolates (consortia) to deliver ~$1 \times 10^5$ cfu/microbe/seed and seeds inoculated by either imbibition in the liquid suspension or by overtreatment in combination with 0.1-1% vegetable gum.

Seeds corresponding to the plants of table 22 were planted within 24 to 48 hours of treatment in agricultural soil, potting media or inert growing media. Plants were grown in small pots (28 mL) in a controlled environment. The chamber photoperiod was set to 16 hours for all experiments on all species. Air temperature was typically maintained between 22-24° C.

All plants were watered with tap water 2 to 3 times weekly. Plants were subjected to either no stress (NS) or limited nitrogen to investigate nitrogen use efficiency (NUE). Growth conditions were varied according to the trait of interest and included manipulation of applied fertilizer as follows:

Low N—seeds planted in soil potting media or inert growing media with no applied N fertilizer Moderate N—seeds planted in soil or growing media supplemented with commercial N fertilizer to equivalent of 135 kg/ha applied N Untreated (no applied microbe) controls were prepared for each experiment. Plants were randomized on trays throughout the growth environment. Between 10 and 30 replicate plants were prepared for each treatment in each experiment. Phenotypes were measured during early vegetative growth, typically before the V3 developmental stage and between 3 and 6 weeks after sowing. Fresh foliar weight was measured 18 h after watering substrate to saturation. Dry root weight was measured after drying to a constant weight at 80° C. Results indicate performance of treatments against the untreated control.

TABLE 22

| Consortia | Crop | Assay | Evaluations | Controlled Environment Efficacy (%) | |
|---|---|---|---|---|---|
| | | | | Foliar Weight | Root Weight |
| D29 | Wheat | NS | 7 | 71 | 57 |
| D36 | Wheat | NS | 1 | 100 | 100 |
| D32 | Wheat | NS | 8 | 88 | 63 |
| D33 | Wheat | NS | 9 | 78 | 33 |
| D35 | Wheat | NS | 1 | 100 | 100 |
| D34 | Wheat | NS | 1 | 100 | 100 |
| D37 | Wheat | NS | 1 | 100 | 100 |
| D38 | Wheat | NS | 1 | 100 | 100 |
| D39 | Wheat | NS | 6 | 67 | 50 |
| D39 | Wheat | NUE | 8 | 100 | 75 |
| D31 | Wheat | NS | 7 | 71 | 43 |
| D31 | Wheat | NUE | 8 | 75 | 50 |
| D30 | Tomato | NS | 6 (FW) 3 RW | 50 | 33 |

The data presented in table 22 describes the percentage of time a particular consortium changed a phenotype of interest relative to an inert-only control run in the same experiment. The measured phenotypes were fresh shoot weight, measured 18 hours after watering to saturation, and dry root weight, measured after drying to a constant state at 80 degrees Celsius.

The presented data identifies consortia that have increased a phenotype of interest in greater than 60% of evaluations (hit rate >59) and consortia that decreased a phenotype of interest in greater than 60% of evaluations (hit rate<41). Both increases and decreases in a phenotype of interest were recorded to reflect the possibility that decreases in select phenotypes of interest are yield relevant.

Example 3: Evaluation of Yield Effect of Maize Exposed to Microbial Consortia in U.S. Field Trials The data presented in Table 23 summarizes the changes in final yield relative to a control for six consortia tested in eight locations in the mid-West of the United States. Also presented is final yield data from two drought trials performed in California in the United States. Data is expressed as the percentage of trials in which a yield effect in bushels per acre of a particular magnitude was observed. All field trials were run in accordance with standard agronomic practices.

TABLE 23

| Consortia | Trials | Field Trial Yield Increases (%) | | |
|---|---|---|---|---|
| | | >6 bu ac | 0-6 bu ac | <0 bu ac |
| D1 | 8 Yield | 62.5 | 25 | 12.2 |
| D6 | 8 Yield | 25 | 25 | 50 |
| D7 | 8 Yield | 25 | 37.5 | 37.5 |
| D2 | 8 Yield | 25 | 37.5 | 37.5 |
| D3 | 8 Yield | 25 | 25 | 50 |
| D4 | 8 Yield | 25 | 37.5 | 37.5 |
| D5 | 8 Yield | 25 | 50 | 25 |
| D12 | 2 Drought | 100 | — | — |

Example 4: Evaluate Yield Effect of Maize Exposed to Microbial Consortia in New Zealand Field Trials The data presented in Table 24 summarizes the results of New Zealand field trials for select consortia. The presented data describes the number of trials in which a particular consortia has been tested relative to a control, and the number of trials in which the consortia treatment increased the final yield relative to the control treatment. All field trials were run in accordance with standard agronomic practices.

TABLE 24

| Consortia | Trials | Trials with yield > control |
|---|---|---|
| A1 | 3 | 3 |
| D6 | 2 | 1 |
| A13 | 2 | 1 |
| A14 | 1 | 1 |
| A15 | 3 | 3 |

Example 5: Microbes Deposited with the ARS Culture Collection (NRRL)

In one experimental embodiment, the inventors utilized the following microbial species in applications of the present disclosure. Table 25 details microbial species of the present disclosure which have been deposited with the United States Department of Agriculture ARS Culture Collection (NRRL).

TABLE 25

| | Taxonomy | BCI (US) | BDNZ (NZ) | Deposited date | Accession number | USDA Viability Date |
|---|---|---|---|---|---|---|
| 1 | Acidovorax soli | 648 | | Dec. 29, 2015 | NRRL B-67181 | Jan. 4, 2016 |
| 2 | Acidovorax soli | 690 | | Dec. 29, 2015 | NRRL B-67182 | Jan. 4, 2016 |
| 3 | Arthrobacter cupressi | 59 | | Dec. 29, 2015 | NRRL B-67183 | Jan. 4, 2016 |
| 4 | Arthrobacter cupressi | 62 | | Dec. 29, 2015 | NRRL B-67184 | Jan. 4, 2016 |
| 5 | Bosea eneae | 1267 | | Dec. 29, 2015 | NRRL B-67185 | Jan. 4, 2016 |
| 6 | Bosea robiniae | 689 | | Dec. 29, 2015 | NRRL B-67186 | Jan. 4, 2016 |
| 7 | Bosea thiooxidans | 703 | | Dec. 29, 2015 | NRRL B-67187 | Jan. 4, 2016 |
| 8 | Chitinophaga terrae | 79 | | Dec. 29, 2015 | NRRL B-67188 | Jan. 4, 2016 |

TABLE 25-continued

| | Taxonomy | BCI (US) | BDNZ (NZ) | Deposited date | Accession number | USDA Viability Date |
|---|---|---|---|---|---|---|
| 9 | Chitinophaga terrae | 109 | | Dec. 29, 2015 | NRRL B-67189 | Jan. 4, 2016 |
| 10 | Delftia lacustris | 124 | | Dec. 29, 2015 | NRRL B-67190 | Jan. 4, 2016 |
| 11 | Delftia lacustris | 2350 | | Dec. 29, 2015 | NRRL B-67191 | Jan. 4, 2016 |
| 12 | Duganella radicis | 105 | | Dec. 29, 2015 | NRRL B-67192 | Jan. 4, 2016 |
| 13 | Duganella violaceinigra | 2204 | | Dec. 29, 2015 | NRRL B-67193 | Jan. 4, 2016 |
| 14 | Dyadobacter soli | 68 | | Dec. 29, 2015 | NRRL B-67194 | Jan. 4, 2016 |
| 15 | Dyadobacter soli | 96 | | Dec. 29, 2015 | NRRL B-67195 | Jan. 4, 2016 |
| 16 | Flavobacterium glacei | 4005 | | Dec. 29, 2015 | NRRL B-67196 | Jan. 4, 2016 |
| 17 | Herbaspirillum chlorophenolicum | 162 | | Dec. 29, 2015 | NRRL B-67197 | Jan. 4, 2016 |
| 18 | Massilia kyonggiensis (deposited as Massilia albidiflava | 97 | | Dec. 29, 2015 | NRRL B-67198 | Jan. 4, 2016 |
| 19 | Massilia niastensis | 1217 | | Dec. 29, 2015 | NRRL B-67199 | Jan. 4, 2016 |
| 20 | Novosphingobium lindaniclasticum | 684 | | Dec. 29, 2015 | NRRL B-67201 | Jan. 4, 2016 |
| 21 | Novosphingobium lindaniclasticum | 608 | | Dec. 29, 2015 | NRRL B-67200 | Jan. 4, 2016 |
| 22 | Novosphingobium resinovorum | 557 | | Dec. 29, 2015 | NRRL B-67202 | Jan. 4, 2016 |
| 23 | Novosphingobium resinovorum | 3709 | | Dec. 29, 2015 | NRRL B-67203 | Jan. 4, 2016 |
| 24 | Paenibacillus glycanilyticus | 418 | | Dec. 29, 2015 | NRRL B-67204 | Jan. 4, 2016 |
| 25 | Pedobacter rhizosphaerae (deposited as Pedobacter soli) | 598 | | Dec. 29, 2015 | NRRL B-67205 | Jan. 4, 2016 |
| 26 | Pedobacter terrae | 91 | | Dec. 29, 2015 | NRRL B-67206 | Jan. 4, 2016 |
| 27 | Pseudomonas jinjuensis | 804 | | Dec. 29, 2015 | NRRL B-67207 | Jan. 4, 2016 |
| 28 | Ramlibacter henchirensis | 739 | | Dec. 29, 2015 | NRRL B-67208 | Jan. 4, 2016 |
| 29 | Ramlibacter henchirensis | 1959 | | Dec. 29, 2015 | NRRL B-67209 | Jan. 4, 2016 |
| 30 | Rhizobium rhizoryzae (previously R. lemnae) | 34 | | Dec. 29, 2015 | NRRL B-67210 | Jan. 4, 2016 |
| 31 | Rhizobium rhizoryzae (previously R. lemnae) | 661 | | Dec. 29, 2015 | NRRL B-67211 | Jan. 4, 2016 |
| 32 | Rhizobium sp. | 106 | | Dec. 29, 2015 | NRRL B-67212 | Jan. 4, 2016 |
| 33 | Sinorhizobium Chiapanecum (now Ensifer adhaerens) | 111 | | Dec. 29, 2015 | NRRL B-67213 | Jan. 4, 2016 |
| 34 | Sphingopyxis alaskensis | 412 | | Dec. 29, 2015 | NRRL B-67214 | Jan. 4, 2016 |
| 35 | Sphingopyxis alaskensis | 914 | | Dec. 29, 2015 | NRRL B-67215 | Jan. 4, 2016 |
| 36 | Variovorax ginsengisoli | 137 | | Dec. 29, 2015 | NRRL B-67216 | Jan. 4, 2016 |
| 37 | Variovorax ginsengisoli | 3078 | | Dec. 29, 2015 | NRRL B-67217 | Jan. 4, 2016 |
| 38 | Achromobacter pulmonis | 49 | | Dec. 18, 2015 | NRRL B-67174 | Dec. 21, 2015 |
| 39 | Chryseobacterium daecheongense | 45 | | Dec. 18, 2015 | NRRL B-67172 | Dec. 21, 2015 |
| 40 | Duganella radicis | 31 | | Jan. 13, 2016 | NRRL B-67166 | Jan. 15, 2016 |
| 41 | Exiguobacterium aurantiacum | 50 | | Dec. 18, 2015 | NRRL B-67175 | Dec. 21, 2015 |
| 42 | Exiguobacterium sibiricum | 116 | | Dec. 18, 2015 | NRRL B-67167 | Dec. 21, 2015 |
| 43 | Kosakonia radicincitans | 44 | | Dec. 18, 2015 | NRRL B-67171 | Dec. 21, 2015 |
| 44 | Microbacterium oleivorans | 132 | | Dec. 18, 2015 | NRRL B-67170 | Dec. 21, 2015 |
| 45 | Novosphingobium sediminicola | 130 | | Dec. 18, 2015 | NRRL B-67168 | Dec. 21, 2015 |
| 46 | Pedobacter terrae | 53 | | Dec. 18, 2015 | NRRL B-67176 | Dec. 21, 2015 |
| 47 | Rahnella aquatilis | 29 | | Dec. 18, 2015 | NRRL B-67165 | Dec. 21, 2015 |
| 48 | Agrobacterium fabrum or Rhizobium pusense (In Taxonomic Flux) (previously Rhizobium sp.) | 46 | | Dec. 18, 2015 | NRRL B-67173 | Dec. 21, 2015 |
| 49 | Sinorhizobium chiapanecum (Ensifer adhaerens - current classification) | 131 | | Dec. 18, 2015 | NRRL B-67169 | Dec. 21, 2015 |
| 50 | Pantoea vagans | | 55529 | Jan. 29, 2016 | NRRL B-67224 | Feb. 4, 2016 |
| 51 | Pseudomonas oryzihabitans | | 55530 | Jan. 29, 2016 | NRRL B-67225 | Feb. 4, 2016 |
| 52 | Stenotrophomonas maltophilia | | 54073 | Jan. 29, 2016 | NRRL B-67226 | Feb. 4, 2016 |
| 53 | Rahnella aquatilis | | 58013 | Jan. 29, 2016 | NRRL B-67229 | Feb. 4, 2016 |
| 54 | Rahnella aquatilis | | 56532 | Jan. 29, 2016 | NRRL B-67228 | Feb. 4, 2016 |
| 55 | Rhodococcus erythropolis | | 54093 | Jan. 29, 2016 | NRRL B-67227 | Feb. 4, 2016 |
| 56 | Herbaspirillum chlorophenolicum | 58 | | Feb. 8, 2016 | NRRL B-67236 | Feb. 10, 2016 |
| 57 | Bacillus niacini | 4718 | | Feb. 8, 2016 | NRRL B-67230 | Feb. 10, 2016 |
| 58 | Polaromonas ginsengisoli | | 66373 | Feb. 8, 2016 | NRRL B-67231 | Feb. 10, 2016 |
| 59 | Polaromonas ginsengisoli | | 66821 | Feb. 8, 2016 | NRRL B-67234 | Feb. 10, 2016 |
| 60 | Duganella violaceinigra | | 66361 | Feb. 8, 2016 | NRRL B-67232 | Feb. 10, 2016 |
| 61 | Duganella violaceinigra | | 58291 | Feb. 8, 2016 | NRRL B-67233 | Feb. 10, 2016 |
| 62 | Massilia niastensis | | 55184 | Feb. 8, 2016 | NRRL B-67235 | Feb. 10, 2016 |
| 63 | Agrobacterium fabrum or Rhizobium pusense | 958 | | Jul. 14, 2016 | NRRL B-67286 | Jul. 17, 2016 |
| 64 | Arthrobacter nicotinovorans | 717 | | Jul. 14, 2016 | NRRL B-67289 | Jul. 17, 2016 |
| 65 | Arthrobacter nicotinovorans | 3189 | | Jul. 14, 2016 | NRRL B-67290 | Jul. 17, 2016 |
| 66 | Chryseobacterium daecheongense | 191 | | Jul. 14, 2016 | NRRL B-67291 | Jul. 17, 2016 |
| 67 | Chryseobacterium rhizosphaerae | 597 | | Jul. 14, 2016 | NRRL B-67288 | Jul. 17, 2016 |
| 68 | Chryseobacterium rhizosphaerae | 615 | | Jul. 14, 2016 | NRRL B-67287 | Jul. 17, 2016 |
| 69 | Frigidibacter albus or Defluviimonas denitrificans (In Taxonomic Flux) | 712 | | Jul. 14, 2016 | NRRL B-67285 | Jul. 17, 2016 |
| 70 | Frigidibacter albus or Defluviimonas denitrificans (In Taxonomic Flux) | 402 | | Jul. 14, 2016 | NRRL B-67283 | Jul. 17, 2016 |

TABLE 25-continued

| | Taxonomy | BCI (US) | BDNZ (NZ) | Deposited date | Accession number | USDA Viability Date |
|---|---|---|---|---|---|---|
| 71 | Frigidibacter albus or Defluviimonas denitrificans (In Taxonomic Flux) | 745 | | Jul. 14, 2016 | NRRL B-67284 | Jul. 17, 2016 |
| 72 | Exiguobacterium antarcticum | 63 | | Jul. 14, 2016 | NRRL B-67292 | Jul. 17, 2016 |
| 73 | Exiguobacterium antarcticum | 225 | | Jul. 14, 2016 | NRRL B-67293 | Jul. 17, 2016 |
| 74 | Exiguobacterium sibiricum | 718 | | Jul. 14, 2016 | NRRL B-67294 | Jul. 17, 2016 |
| 75 | Pseudomonas helmanticensis | 616 | | Jul. 14, 2016 | NRRL B-67295 | Jul. 17, 2016 |
| 76 | Pseudomonas helmanticensis | 2945 | | Jul. 14, 2016 | NRRL B-67296 | Jul. 17, 2016 |
| 77 | Pseudomonas helmanticensis | 800 | | Jul. 14, 2016 | NRRL B-67297 | Jul. 17, 2016 |
| 78 | Leifsonia lichenia | | 72243 | Jul. 21, 2016 | NRRL B-67298 | Jul. 22, 2016 |
| 79 | Leifsonia lichenia | | 72289 | Jul. 21, 2016 | NRRL B-67299 | Jul. 22, 2016 |
| 80 | Tumebacillus permanetifrigoris | | 72229 | Jul. 21, 2016 | NRRL B-67302 | In process |
| 81 | Tumebacillus permanetifrigoris | | 74542 | Jul. 21, 2016 | NRRL B-67300 | In process |
| 82 | Tumebacillus permanetifrigoris | | 72366 | Jul. 21, 2016 | NRRL B-67303 | In process |
| 83 | Tumebacillus permanetifrigoris | | 72287 | Jul. 21, 2016 | NRRL B-67301 | In process |

*In process notes that viability testing has been conducted and outcome is awaiting transmittal Example 6: Novel Microbial Species Deposited with the ARS Culture Collection (NRRL)

In one experimental embodiment, the inventors utilized the following microbial species in applications of the present disclosure.

TABLE 26

| Taxonomy | BCI (US) | BDNZ (NZ) |
|---|---|---|
| Achromobacter pulmonis | 49 | |
| Acidovorax soli | 648 | |
| Acidovorax soli | 690 | |
| Agrobacterium fabrum or Rhizobium pusense (in Taxonomix flux) | 46 | |
| Agrobacterium fabrum or Rhizobium pusense (in Taxonomix flux) | 958 | |
| Arthrobacter cupressi | 59 | |
| Arthrobacter cupressi | 62 | |
| Arthrobacter nicotinovorans | 717 | |
| Arthrobacter nicotinovorans | 3189 | |
| Bacillus niacini | 4718 | |
| Bosea eneae | 1267 | |
| Bosea robiniae | 689 | |
| Bosea thiooxidans | 703 | |
| Chitinophaga terrae | 79 | |
| Chitinophaga terrae | 109 | |
| Chryseobacterium daecheongense | 45 | |
| Chryseobacterium daecheongense | 191 | |
| Chryseobacterium rhizospaerae | 597 | |
| Chryseobacterium rhizospaerae | 615 | |
| Delftia lacustris | 124 | |
| Delftia lacustris | 2350 | |
| Frigidibacter albus or Defluviimonas denitrificans (In Taxonomic Flux) | 712 | |
| Frigidibacter albus or Defluviimonas denitrificans (In Taxonomic Flux) | 402 | |
| Frigidibacter albus or Defluviimonas denitrificans (In Taxonomic Flux) | 745 | |
| Duganella radicis | 105 | |
| Duganella radicis | 31 | |
| Duganella violaceinigra | 2204 | |
| Duganella violaceinigra | | 66361 |
| Duganella violaceinigra | | 58291 |
| Dyadobacter soli | 68 | |
| Dyadobacter soli | 96 | |
| Exiguobacterium antarcticum | 63 | |
| Exiguobacterium antarcticum | 225 | |
| Exiguobacterium aurantiacum | 50 | |
| Exiguobacterium sibiricum | 116 | |
| Exiguobacterium sibiricum | 718 | |
| Flavobacterium glacei | 4005 | |
| Herbaspirillum chlorophenolicum | 162 | |
| Herbaspirillum chlorophenolicum | 58 | |
| Kosakonia radicincitans | 44 | |
| Leifsonia lichenia | | 72243 |
| Leifsonia lichenia | | 72289 |
| Massilia kyonggiensis (deposited as Massilia albidiflava; new taxonomy is kyonggiensis) | 97 | |
| Massilia niastensis | 1217 | |
| Massilia niastensis | | 55184 |
| Microbacterium oleivorans | 132 | |
| Novosphingobium lindaniclasticum | 684 | |
| Novosphingobium lindaniclasticum | 608 | |
| Novosphingobium resinovorum | 557 | |
| Novosphingobium resinovorum | 3709 | |
| Novosphingobium sediminicola | 130 | |
| Paenibacillus glycanilyticus | 418 | |
| Pantoea vagans | | 55529 |
| Pedobacter rhizosphaerae (deposited as Pedobacter soli) | 598 | |
| Pedobacter terrae | 91 | |
| Pedobacter terrae | 53 | |
| Polaromonas ginsengisoli | | 66373 |
| Polaromonas ginsengisoli | | 66821 |
| Pseudomonas helmanticensis | 616 | |
| Pseudomonas helmanticensis | 2945 | |
| Pseudomonas helmanticensis | 800 | |
| Pseudomonas jinjuensis | 804 | |
| Pseudomonas oryzihabitans | | 55530 |
| Rahnella aquatilis | 29 | |
| Rahnella aquatilis | | 58013 |
| Rahnella aquatilis | | 56532 |
| Ramlibacter henchirensis | 739 | |
| Ramlibacter henchirensis | 1959 | |
| Rhizobium rhizoryzae | 34 | |
| Rhizobium rhizoryzae | 661 | |
| Rhizobium sp. | 106 | |
| Rhodococcus erythropolis | | 54093 |
| Sinorhizobium chiapanecum (now Ensifer adhaerens) | 131 | |
| Sinorhizobium Chiapanecum (now Ensifer adhaerens) | 111 | |
| Sphingopyxis alaskensis | 412 | |
| Sphingopyxis alaskensis | 914 | |
| Stenotrophomonas maltophilia | | 54073 |
| Tumebacillus permanentifrigoris | | 72229 |
| Tumebacillus permanentifrigoris | | 74542 |

TABLE 26-continued

| Taxonomy | BCI (US) | BDNZ (NZ) |
|---|---|---|
| *Tumebacillus permanentifrigoris* | | 72366 |
| *Tumebacillus permanentifrigoris* | | 72287 |
| *Variovorax ginsengisoli* | 137 | |
| *Variovorax ginsengisoli* | 3078 | |

Example 7: Deposited Microbial Species Novel to Agriculture

In one experimental embodiment, the inventors utilized the following microbial species in applications of the present disclosure. Table 27 notes microbial organisms of the present disclosure which have been deposited with the NRRL, ATCC, and/or DSMZ depositories with the respective accession numbers.

TABLE 27

| Species novel to Agriculture (in Tables 1, 2, 3, 4 and 25) | NRRL # | DSMZ # | ATTC # |
|---|---|---|---|
| *Achromobacter pulmonis* | NRRL B-67174 | DSM29617 | |
| *Acidovorax soli* | NRRL B-67181 | | |
|  | NRRL B-67182 | | |
| *Agrobacterium fabrum* or *Rhizobium pusense* (In Taxonomic Flux) (previously *Rhizobium* sp.) | NRRL B-67173 | DSM22668 | |
|  | NRRL B-67286 | | |
| *Arthrobacter cupressi* | NRRL B-67183 | | |
|  | NRRL B-67184 | | |
| *Arthrobacter nicotinovorans* | NRRL B-67289 | DSM420 | 49919 |
|  | NRRL B-67290 | | |
| *Bosea eneae* | NRRL B-67185 | | |
| *Bosea minatitlanensis* | | DSM-13099 | 700918 |
| *Bosea robinae* | NRRL B-67186 | | |
| *Caulobacter henricii* | | DSM-4730 | 15253 |
| *Chitinophaga arvensicola* | | DSM-3695 | 51264 |
| *Chitinophaga terrae* | NRRL B-67188 | | |
| *Chryseobacterium daecheongense* | NRRL B-67172 | DSM15235 | |
|  | NRRL B-67291 | | |
| *Chryseobacterium rhizophaerae* | NRRL B-67288 | | |
|  | NRRL B-67287 | | |
| *Delftia lacustris* | NRRL B-67190 | | |
|  | NRRL B-67191 | | |
| *Frigidibacter albus* or *Defluviimonas denitrificans* (In Taxonomic Flux) | NRRL B-67285 | | |
|  | NRRL B-67283 | | |
|  | NRRL B-67284 | | |
| *Duganella radicis* | NRRL B-67192 | | |
|  | NRRL B-67166 | | |
| *Duganella violaceinigra* (*Pseudoduganella violaceinigra*) | NRRL B-67193 | | |
|  | NRRL B-67232 | | |
|  | NRRL B-67233 | | |
| *Dyadobacter soli* | NRRL B-67193 | | |
|  | NRRL B-67194 | | |
| *Exiguobacterium antarcticum* | NRRL B-67292 | DSM14480 | |
|  | NRRL B-67293 | | |
| *Exiguobacterium sibiricum* | NRRL B-67167 | DSM17290 | |
|  | NRRL B-67294 | | |
| *Flavobacterium glaciei* | NRRL B-67196 | | |
| *Frateuria aurantia* | | DSM-6220 | |
| *Frateuria terrea* | | DSM-26515 | |
| *Herbaspirillum chlorophenolicum* | NRRL B-67197 | | |
|  | NRRL B-67236 | | |
| *Janthinobacterium agaricidamnosum* | | DSM-9628 | |
| *Janthinobacterium lividum* | | DSM-1522 | |
| *Leifsonia lichenia* | NRRL B-67298 | | |
|  | NRRL B-67299 | | |
| *Luteibacter yeojuensis* | | DSM-17673 | |
| *Massilia kyongggiensis* (previously *Massilia albidiflava*) | NRRL B-67198 | DSM101532 | |
| *Massilia niastensis* | NRRL B-67199 | | |
|  | NRRL B-67235 | | |
| *Microbacterium* sp. (OLIEVORANS DEPOSITED) | | DSM-16050 | 31001 |
| *Novosphingobium lindaniclasticum* | NRRL B-67201 | DSM25409 | |
|  | NRRL B-67200 | | |
| *Novosphingobium resinovorum* | NRRL B-67202 | | |
|  | NRRL B-67203 | | |
| *Novosphingobium rosa* | | DSM-7285 | 51837 |
| *Novosphingobium sediminicola* | NRRL B-67168 | DSM 27057 | |
| *Paenibacillus amylolyticus* | | DSM-11730 | 9995 |
| *Paenibacillus chondroitinus* | | DSM-5051 | 51184 |
| *Paenibacillus glycanilyticus* | NRRL B-67204 | | |
| *Pedobacter rhizosphaerae* (*Pedobacter soli*) | NRRL B-67205 | | |
| *Pedobacter terrae* | NRRL B-67206 | | |
|  | NRRL B-67176 | | |
| *Polaromonas ginsengisoli* | NRRL B-67231 | | |
|  | NRRL B-67234 | | |
| *Pseudomonas helmanticensis* | NRRL B-67295 | DSM28442 | |
|  | NRRL B-67296 | | |
|  | NRRL B-67297 | | |
| *Pseudomonas jinjuensis* | NRRL B-67207 | | |
| *Ramlibacter henchirensis* | NRRL B-67208 | | |
| *Rhizobium rhizoryzae* | NRRL B-67210 | | |
|  | NRRL B-67211 | | |
| *Rhodoferax ferrireducens* | | DSM-15236 | BAA-621 |
| *Sinorhizobium chiapanecum* (*Ensifer adhaerens*) | NRRL B-67213 | | |
|  | NRRL B-67169 | | |
| *Sphingobium quisquiliarum* | | DSM-24952 | |
| *Sphingopyxis alaskensis* | NRRL B-67214 | | |
|  | NRRL B-67215 | | |
| *Stenotrophomonas terrae* | | DSM-18941 | |
| *Tumebacillus permanentifrigoris* | NRRL B-67302 | DSM118773 | |
|  | NRRL B-67300 | | |
|  | NRRL B-67303 | | |
|  | NRRL B-67301 | | |
| *Variovorax ginsengisoli* | NRRL B-67216 | | |
|  | NRRL B-67217 | | |

Example 8: Microbial Consortia Embodiments

In one experimental embodiment, the inventors utilized the following microbial consortia in applications of the present disclosure. Table 28 notes microbial consortia D12, D21, D27, D28, D30, D31, D32, D33, and D34 of the present disclosure. Underneath each of the consortia designations are the specific strain numbers that identify the microbes present in each of the consortia.

TABLE 28

| Strain BCI# | Strain BDNZ# | Microbe identity | D12 | D21 | D27 | D28 | D30 | D31 | D32 | D33 | D34 |
|---|---|---|---|---|---|---|---|---|---|---|---|
| 31 | | Duganella radicis (31) | 31 | | — | — | | | | | |
| 116 | | Exiguobacterium sibiricum (116) | 116 | | — | — | | | | | |
| 130 | | Novosphingobium sediminicola (130) | 130 | | — | — | | | | | |
| 958 | | Agrobacterium fabrum or Rhizobium pusense (ini taxonomix flux) | | 958 | 958 | — | | | | | |
| 616 | | Pseudomonas helmanticensis (616) | | | — | 616 | | | | | |
| 615 | | Chryseobacterium rhizosphaerae (615) | | 615 | | | | | | | |
| | 74542 | Tumebacillus permanentifrigoris (74542) | | | — | — | 74542 | | | | |
| | 72229 | Tumebacillus permanentifrigoris (72229) | | | — | — | | 72229 | | | |
| | 72243 | Leifsonia lichenia (72243) | | | — | — | | | 72243 | 72243 | |
| 597 | | Chryseobacterium rhizosphaerae (597) | | | — | — | 597 | | | | |
| 712 | | Frigidibacter albus or Defluviimonas denitrificans (In Taxonomic Flux) (712) | | | — | — | 712 | | | | |
| 717 | | Arthrobacter nicotinovorans (717) | | | — | — | 717 | | | | |
| | 71222 | Novosphingobium lindaniclasticum (71222) | | | | | | | | | 71222 |

Example 9: Microbial Strain and Microbial Species Embodiments

In one experimental embodiment, the inventors utilized the following microbial species and/or strains in applications of the present disclosure. Table 29 notes specific microbial species and strains utilized in experimental studies which are novel to agriculture and have exhibited positive results in controlled environment screening experiments of the present disclosure.

TABLE 29

| Individual species of note Species | Strain BDNZ# | Strain BCI# | Individual strains of note Species | Strain BDNZ# | Strain BCI# |
|---|---|---|---|---|---|
| Duganella violoceinigra | 66361 | | Arthrobacter nicotinovorans | | 3189 |
| Bosea thiooxidans | 54522 | 703 | Chryseobacterium | | 45 |
| Massilia niastensis | 55184 | 1217 | daecheongense | | |
| Polaromonas ginsengisoli | 66373 | | Chryseobacterium daecheongense | | 191 |
| Novosphingobium resinovorum | | 557 | Chryseobacterium rhizosphaerae | | 597 |
| Duganella violoceinigra | | 2204 | Chryseobacterium rhizosphaerae | | 615 |
| Exiguobacterium aurantiocum | | 50 | Frigidibacter albus or Defluviimonas denitrificans (In Taxonomic Flux) | | 712 |
| Exiguobacterium sibiricum | | 116 | Frigidibacter albus or Defluviimonas denitrificans (In Taxonomic Flux) | | 402 |
| Variovorox ginsengisoli | | 3078 | | | |
| Pedobacter rhizosphaerae | | 598 | Frigidibacter albus or Defluviimonas denitrificans (In Taxonomic Flux) | | 745 |
| Duganella radicis | | 31 | | | |
| Paenibacillus glycanilyticus | | 418 | Exiguobacterium antarcticum | | 63 |
| Bacillus niacin | | 1718 | Exiguobacterium antarcticum | | 225 |
| Stenotrophomonas maltophilia | 54073 | | Exiguobacterium sibiricum | | 116 |
| Rhodococcus erythropolis | 54093 | | Exiguobacterium sibiricum | | 718 |
| Pantoea vagans | 55529 | | Leifsonia lichenia | 72243 | |
| Pseudomonas oryzihabitans | 55530 | | Leifsonia lichenia | 72289 | |
| Achromobacter pulmonis | | 49 | Pedobacter terrae | — | 53 |
| | | | Pseudomonas helmanticensis | | 616 |
| | | | Pseudomonas helmanticensis | | 2945 |
| | | | Pseudomonas helmanticensis | | 800 |
| | | | Tumebacillus permanentifrigoris | 72229 | |
| | | | Tumebacillus permanentifrigoris | 74542 | |

TABLE 29-continued

| Individual species of note Species | Strain BDNZ# | Strain BCI# | Individual strains of note Species | Strain BDNZ# | Strain BCI# |
|---|---|---|---|---|---|
| *Agrobacterium fabrum* or *Rhizobium pusense* (In Taxonomic Flux) (previously *Rhizobium sp.*) | | 46 | *Turnebacillus permanentifrigoris* *Tumebacillus permanentifrigoris* | 72366 72287 | |
| *Agrobacterium fabrum* or *Rhizobium pusense* (In Taxonomic Flux) (previously *Rhizobium sp.*) | 958 | | | | |
| *Arthrobacter nicotinovorans* | | 717 | | | |

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

Ascend® plant growth regulator product sheet. EPA reg. No. 9776-335
Calvo, P., Nelson, L., Kloepper, J. W., 2014 Agricultural uses of plant biostimulants. Plant soil 383, 3-41.
"Chemistry and Technology of Agrochemical Formulations," edited by D. A. Knowles, copyright 1998 by Kluwer Academic Publishers.
Colby, R. S., "Calculating Synergistic and Antagonistic Responses of Herbicide Combinations, 1967 Weeds, vol. 15, pp. 20-22.
Current Protocols in Molecular Biology (F. M. Ausubel et al., eds., 1987).
Crameri et al. (1997) Nature Biotech. 15:436-438.
Crameri et al. (1998) Nature 391:288-291.
De Almeida et al., (1989) Mol. Gen. Genetics 218:78-86).
Dobereiner J, Marriel E and Nery M 1976 Ecological distribution of *Spirillum lipoferum* Beijerinck. Can. J. Microbiol. 22, 1464-1473.
Fahraeus, G. (1957). *J. Gen Microbiol.* 16: 374-381.
Gerhardt, P. (ed.) Methods for General and Molecular Microbiology. American Society for Microbiology, Washington, D.C. (1994).
Gherna, R. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages.
Goteti, P. K. et al., (2013). International Journal of Microbiology 2013: 1-7 Article ID 869697.
Hartmann A., Baldani J. I. The genus *Azospirillum*//The Prokaryotes, V. 5: Proteobacteria Alpha and Beta Subclasses//Eds. M. Dworkin, S. Falkow, E. Rosenberg, K. H. Schleifer, E. Stackebrandt.—Springer Verlag, New York, USA, 2006. p. 115-140.
Innis et al., eds. (1990) PCR Protocols: A Guide to Methods and Applications (Academic Press, New York).
Innis and Gelfand, eds. (1995) PCR Strategies (Academic Press, New York).
In re Bergstrom, 427 F.2d 1394, (CCPA 1970).
In re Bergy, 596 F.2d 952 (CCPA 1979).
Islam, M. T., Deora, A., Hashidoko, Y., Rahman, A., Ito, T., and Tahara, S. (2007) Isolation and Identification of Potential Phosphate Solubilizing Bacteria from the Rhizoplane of *Oryza sativa* L. cv. BR29 of Bangladesh. Zeitschrift fur Naturforschung C 62(1-2):103-10.
Jones et al., (1985) EMBO J. 4:2411-2418.
Lennette, E. H. (ed.) Manual of Clinical Microbiology, Third Edition. American Society for Microbiology, Washington, D.C. (1980).
McCutcheon's Detergents and Emulsifiers Annual, MC Publishing Corp., Ridgewood, N.J., 1998, and in *Encyclopedia of Surfactants*, Vol. I-III, Chemical Publishing Co., New York, 1980-81.
McCutcheon's, vol. 1, "Emulsifiers and Detergents," MC Publishing Company, Glen Rock, N.J., U.S.A., 1996.
Merck & Co. v. Olin Mathieson Chemical Corp., 253 F.2d 156 (4th Cir. 1958).
Miche, L and Balandreau, J (2001). Effects of rice seed surface sterilisation with hypochlorite on inoculated *Burkholderia vietamiensis*. Appl. Environ. Microbiol. 67(7): p 3046-3052.
Moore et al. (1997) J. Mol. Biol. 272:336-347.
Nautiyal, C. S. (1999), FEMS Microbiology Letters 170 (1999) 265-270.
N-Large™ plant growth regulator product sheet. EPA Reg. No. 57538-18.
Parke-Davis & Co. v. H.K. Mulford & Co., 189 F. 95 (S.D.N.Y. 1911).
Parmar, P. and Sindhu, S. S. (2013) Potassium Solubilization by Rhizosphere Bacteria: Influence of Nutritional and Environmental Conditions. Journal of Microbiology Research, 3(1): 25-31.
PCT/NZ2012/000041, published on Sep. 20, 2012, as International Publication No. WO 2012125050 A1.
PCT/NZ2013/000171, published on Mar. 27, 2014, as International Publication No. WO 2014046553 A1.
Perez-Miranda, S. et al., (2007). Journal of Microbiological Methods 70: 127-131.
Pikovskaya R I (1948). Mobilization of phosphorus in soil connection with the vital activity of some microbial species. *Microbiologia* 17:362-370.
ProGibb® plant growth regulator product sheet. EPA Reg. No. 73049-15.
Rana, A. et al. (2012) Enhancing Micronutrient Uptake and Yield of Wheat Through Bacterial PGPR Consortia, Soil Science and Plant Nutrition, 58:5, 573-582.

Release® plant growth regulator product sheet. EPA Reg. No. 73049-6.
Rodriguez, H. and Reynaldo, F. (1999). Phosphate Solubilizing Bacteria and their Role in Plant Growth Promotion. Biotechnology Advances. 17. 319-339.
Ruth Eckford, R., Cook, F. D., Saul, D., Aislabie J., and J. Foght (2002) Free-living Heterotrophic Bacteria Isolated from Fuel-Contaminated Antarctic Soils. *Appl. Environ. Microbiol* 68(10):5181.
RyzUp SmartGrass® plant growth regulator product sheet. EPA Reg. No. 73049-1.
Sambrook et al. (1989) Molecular Cloning: A Laboratory Manual (2nd ed., Cold Spring Harbor Laboratory Press, Plainview, N.Y.).
Shanware, A. S. et al., 2014 Int. J. Curr. Microbiol. App. Sci 3(9) 622-629.
Stemmer (1994) Nature 370:389-391.
Stemmer (1994) PNAS 91:10747-10751.
Strobel G and Daisy B (2003) Microbiology and Molecular Biology Reviews 67 (4): 491-502.
U.S. Pat. No. 8,652,490 "Pasteuria Strain" issued Feb. 18, 2014.
U.S. Pat. No. 8,383,097 "Bacteria Cultures and Compositions Comprising Bacteria Cultures" issued Feb. 26, 2013.
Vandamme et al. 1996. Polyphasic taxonomy, a consensus approach to bacterial systematics. *Microbiol Rev* 1996, 60:407-438.
Bergey's Manual of Systematic Bacteriology $2^{nd}$ Edition Volume 1 (2001) The Archaea and the deeply branching and phototrophic Bacteria. Editor-in-Chief: George M. Garrity. Editors: David R. Boone and Richard W. Castenholz. ISBN 0-387-98771-1.
Bergey's Manual of Systematic Bacteriology $2^{nd}$ Edition Volume 2 (2005) The Proteobacteria. Editor-in-Chief: George M. Garrity. Editors: Don J. Brenner, Noel R. Krieg and James T. Staley. ISBN 0-387-95040-0.
Bergey's Manual of Systematic Bacteriology $2^{nd}$ Edition Volume 3 (2009) The Firmicutes. Editors: Paul De Vos, George Garrity, Dorothy Jones, Noel R. Krieg, Wolfgang Ludwig, Fred A. Rainey, Karl-Heinz Schleifer and William B. Whitman. ISBN 0-387-95041-9.
Bergey's Manual of Systematic Bacteriology $2^{nd}$ Edition Volume 4 (2011) The Bacteroidetes, Spirochaetes, Tenericutes (Mollicutes), Acidobacteria, Fibrobacteres, Fusobacteria, Dictyoglomi, Gemmatimonadetes, Lentisphaerae, Verrucomicrobia, Chlamydiae, and Planctomycetes. Editors: Noel R. Krieg, James T. Staley, Daniel R. Brown, Brian P. Hedlund, Bruce J. Paster, Naomi L. Ward, Wolfgang Ludwig and William B. Whitman. ISBN 0-387-95042-6
Bergey's Manual of Systematic Bacteriology $2^{nd}$ Edition Volume 5 (2012) The Actinobacteria. Editors: Michael Goodfellow, Peter Kampfer, Hans-Juirgen Busse, Martha E. Trujillo, Ken-ichiro Suzuki, Wolfgang Ludwig and William B. Whitman. ISBN 0-387-95042-7.
Yemm and Willis (Biochem. J. 1954, 57: 508-514).
X-CYTE™ plant growth regulator product sheet. EPA Reg. No. 57538-15.
Zhang et al. (1997) PNAS 94:4504-4509.
Zinniel D K et al. (2002) Applied and Environmental Microbiology 68 (5): 2198-2208).
Pikovskaya R I (1948). Mobilization of phosphorus in soil connection with the vital activity of some microbial species. *Microbiologia* 17:362-370.

What is claimed is:

1. A method of increasing biomass of a plant species, comprising:
   applying an isolated bacterial species to a plant, or to a growth medium in which the plant is located, wherein the isolated bacterial species is *Frigidibacter albus* (also known as *Defluviimonas denitrificans*).

2. The method of claim 1, wherein the method comprises applying a microbial consortium which comprises the isolated bacterial species and further comprises at least one other isolated bacterial species selected from the group consisting of: *Arthrobacter nicotinovorans, Chryseobacterium daecheongense, Chryseobacterium rhizosphaerae, Exiguobacterium antarcticum, Exiguobacterium sibiricum, Leifsonia lichenia, Massilia kyonggiensis, Novosphingobium lindaniclasticum, Novosphingobium sediminicola, Pseudomonas helmanticensis*, and *Tumebacillus permanentifrigoris*.

3. The method of claim 1, wherein the isolated bacterial species is formulated in an agricultural composition with one or more of the following:
   an agriculturally acceptable carrier, a pesticide, a plant growth regulator, a beneficial agent, and a biologically active agent.

4. The method of claim 3, wherein the isolated bacterial species is present in the agricultural composition at about $1\times10^3$ to about $1\times10^{12}$ bacterial cells per gram.

5. The method of claim 1, wherein the applying step occurs by: coating a plant seed with the isolated bacterial species thereby resulting in a bacterial seed coating, coating a plant part with the bacteria, spraying the bacteria onto a plant part, spraying the bacteria into a furrow into which a plant or seed will be placed, drenching the bacteria onto a plant part or into an area into which a plant will be placed, spreading the bacteria onto a plant part or into an area into which a plant will be placed, broadcasting the bacteria onto a plant part or into an area into which a plant will be placed, combining the bacteria with a fertilizer or other agricultural composition, or combinations thereof.

6. The method of claim 5, wherein the bacterial seed coating comprises the isolated bacterial species at a concentration of about $1\times10^5$ to about $1\times10^9$ bacterial cells per seed.

7. A method of increasing biomass of a plant species, the method comprising:
   applying an isolated bacterial species to a plant or to a growth medium having a plant, wherein the bacterial species is *Frigidibacter albus* (also known as *Defluviimonas denitrificans*) deposited as NRRL Accession Deposit Nos. NRRL B-67285, NRRL B-67283 or NRRL B-67284.

\* \* \* \* \*